US008759614B2

(12) United States Patent
Yu et al.

(10) Patent No.: US 8,759,614 B2
(45) Date of Patent: Jun. 24, 2014

(54) USE OF RICE POLYPEPTIDES FOR THE ENHANCEMENT OF GRAIN SIZE

(75) Inventors: Su-May Yu, Taipei (TW); Swee-Suak Ko, Kaoshiung County (TW); Yue-Ie C. Hsing, Taipei (TW); Tuan-Hua David Ho, Chesterfield, MO (US); Shuen-Fang Lo, Taichung County (TW)

(73) Assignee: Academia Sinica, Taipei (TW)

( * ) Notice: Subject to any disclaimer, the term of this patent is extended or adjusted under 35 U.S.C. 154(b) by 537 days.

(21) Appl. No.: 12/990,418

(22) PCT Filed: May 1, 2009

(86) PCT No.: PCT/US2009/042529

§ 371 (c)(1), (2), (4) Date: Dec. 15, 2010

(87) PCT Pub. No.: WO2009/135130

PCT Pub. Date: Nov. 5, 2009

(65) Prior Publication Data

US 2011/0126316 A1 May 26, 2011

Related U.S. Application Data

(60) Provisional application No. 61/049,501, filed on May 1, 2008.

(51) Int. Cl.
*A01H 1/00* (2006.01)
*C12N 15/82* (2006.01)
*C12N 15/87* (2006.01)

(52) U.S. Cl.
USPC ........................ 800/290; 536/23.6; 435/320.1

(58) Field of Classification Search
USPC ........................................................ 800/290
See application file for complete search history.

(56) References Cited

U.S. PATENT DOCUMENTS

| | | | | |
|---|---|---|---|---|
| 7,365,185 B2 * | 4/2008 | Boukharov et al. | .......... | 536/24.1 |
| 2001/0051713 A1 | 12/2001 | An et al. | | |
| 2004/0034888 A1 | 2/2004 | Liu et al. | | |
| 2004/0123343 A1 * | 6/2004 | La Rosa et al. | ............... | 800/278 |
| 2004/0214272 A1 | 10/2004 | La Rosa et al. | | |
| 2007/0011783 A1 | 1/2007 | Liu et al. | | |
| 2007/0020621 A1 | 1/2007 | Boukharov | | |
| 2007/0039076 A1 | 2/2007 | Boukharov | | |
| 2007/0118921 A1 | 5/2007 | Boukharov | | |
| 2008/0010703 A1 | 1/2008 | Creelman et al. | | |
| 2008/0040973 A1 | 2/2008 | Nelson et al. | | |
| 2009/0094717 A1 | 4/2009 | Troukhan et al. | | |

FOREIGN PATENT DOCUMENTS

| | | |
|---|---|---|
| WO | 00/63417 | 10/2000 |
| WO | 2008/034648 | 3/2008 |
| WO | 2009/091518 | 7/2009 |

OTHER PUBLICATIONS

Tanabe et al (2005) Plant Cell 17(3): 776-790.*
Waksman Institute—Rutgers University. The Rice Chromosomes 11 and 12 Sequencing Consortia (2005). BMC Biology 3:20.*
Stratton, M. (2008) Nature Biotechnology 26(1): 65-66.*
Guo et al (2004) PNAS 101(25): 9205-9210.*
Komatsu et al (2003) Development 130: 3841-3850.*
Tanabe, et al., "A novel cytochrome P450 is implicated in brassinosteroid biosynthesis via the characterization of a rice dwarf mutant, dwarf1 1, with reduced seed length." In Plant Cell. vol. 17(3):776-790 (Mar. 2005.
XP002679401 Database UniProt (online) "Subname: Full=Expressed protein; subname: Full=Os11g0497350 protein" (2006).
XP-002663313 , "SubName: Full=Putative cullin protein," retrieved from EBI accession No. UNIPROT: Q6F3B6, Aug. 16, 2004.

* cited by examiner

*Primary Examiner* — Li Zheng
(74) *Attorney, Agent, or Firm* — Cesari and McKenna, LLP

(57) ABSTRACT

A method of making a transgenic plant by transforming into a host plant a recombinant DNA construct that expresses in the transgenic plant a rice polypeptide and the transgenic plant thus produced.

5 Claims, No Drawings

USE OF RICE POLYPEPTIDES FOR THE ENHANCEMENT OF GRAIN SIZE

CROSS REFERENCE TO RELATED APPLICATIONS

This application is a National Stage of International Application No. PCT/US2009/042529, filed on May 1, 2009, which claims the priority of U.S. Provisional Application No. 61/049,501, filed on May 1, 2008, the contents of both of the foregoing applications are hereby incorporated by reference in their entirety.

BACKGROUND OF THE INVENTION

It is of great interest to identify plant polypeptides that contribute to desired properties, e.g. high yields or improved tolerance to environmental stresses. When introducing their encoding genes into a host plant, such polypeptides impart the desired traits to the host plant.

SUMMARY OF THE INVENTION

This invention is based on the discovery of a number of rice polypeptides that contribute to various important properties in rice, e.g., seed weight/size and panicle size/density, as well as their encoding polynucleotides.

Accordingly, this invention features a method of producing a transgenic plant by transforming a host plant with a recombinant DNA construct that expresses in a plant cell a polypeptide containing an amino acid sequence at least 80% identical (e.g., 85%, 90%, 95%, 98%, 99%, or 100%) to an amino acid sequence selected from SEQ ID NOs:1-49, 99-114, and 149. The recombinant DNA construct can include a nucleotide sequence selected from SEQ ID NOs:50-98, 115-148, 150, and 151, and a promoter sequence functional in a plant cell. The promoter sequence is operably linked to the nucleotide sequence.

The resultant transgenic plant exhibits one or more of the following properties relative to the host plant: (a) improved tolerance to an environmental stress, e.g., drought, cold, heat, salt, low fertilizer intensity, a plant disease, a herbicide, an extreme osmotic condition, a pathogen or pest, (b) elevated plant cell growth, (c) improved or decreased production of galactomannan, lignin, cellulose, flavonoid, or a plant growth regulator, (d) increased yields by modification of photosynthesis, carbohydrate use and/or uptake, nitrogen use and/or uptake, phosphorus use and/or uptake, mineral use and/or uptake, (e) increased yields of seed oil, starch and/or protein, and (f) increased rate of homologous recombination, (g) increased seed size or weight, (h) increased panicle length or density, (i) increased flowering, pollination or fertilization efficiency, and (j) elevated rate of seed development and maturation.

A transgenic plant is a plant whose genome has been altered by incorporation of foreign genetic material or additional copies of native genetic material, e.g., by transforming or recombination.

In another aspect, this invention provides a method of inhibiting expression of one of the above-described polypeptides in a plant cell or a plant by introducing into the plant cell or the plant a DNA construct containing a promoter operably linked to a polynucleotide that includes a nucleotide sequence complementary to a portion of a polynucleotide sequence encoding the polypeptide. The DNA construct expresses an RNA molecule in the plant cell or plant, which inhibits expression of the polypeptide. The RNA molecule can be an antisense RNA or an interfering RNA.

Also within the scope of this invention is any of the recombinant DNA constructs described above and a host plant cell or a transgenic plant containing the DNA construct.

The details of one or more embodiments of the invention are set forth in the description below. Other features or advantages of the present invention will be apparent from the following detailed description of several embodiments, and also from the appending claims.

DETAILED DESCRIPTION OF THE INVENTION

Described herein are 66 isolated rice polypeptides (SEQ ID NOs:1-49, 99-114, and 149), and their functional variants, i.e., a polypeptide having a sequence identity of at least 65% (e.g., 70%, 75%, 80%, 85%, 90%, 95%, 98%, or 99%) to one of SEQ ID NOs:1-49, 99-114, and 149 and possessing the same function as that polypeptide.

The term "isolated polypeptide" used herein refers to a polypeptide substantially free from naturally associated molecules, i.e., the naturally associated molecules constituting at most 20% by dry weight of a preparation containing the polypeptide. Purity can be measured by any appropriate method, e.g., column chromatography, polyacrylamide gel electrophoresis, and HPLC.

The sequence identity of two amino acid sequences can be determined using the algorithm described in Karlin and Altschul, *Proc, Natl. Acad. Sci. USA* 87:2264-2268, 1990, modified as described in Karlin and Altschul, *Proc, Natl. Acad. Sci. USA* 5873-5877, 1993. Such an algorithm is incorporated into the NBLAST and XBLAST programs of Altschul et al., *J. Mol. Biol.* 215:403-410, 1990. BLAST nucleotide searches are performed with the NBLAST program, score=100, wordlength=12, to obtain nucleotide sequences homologous to a nucleic acid molecule of the invention. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Altschul et al., *Nucleic Acids Res.* 25:3389-3402, 1997. When utilizing the BLAST and Gapped BLAST programs, the default parameters of the respective programs (e.g., XBLAST and NBLAST) are used.

Tables 1 and 2 below list the GenBank accession numbers, amino acid sequences and encoding nucleotide sequences of the 49 rice polypeptides mentioned above. Also listed in Table 1 are functions of these polypeptides.

TABLE 1

Rice Polypeptides That Are Involved in Seed Yield or Panicle Formation

| Proteins | Phenotype | Taiwan Rice International Mutants (TRIM) line | Gene Locus | Gene of Interest (GOI) | Protein | cDNA | GenBank Accession No. |
|---|---|---|---|---|---|---|---|
| 1 | high seed yield | M0015163 | LOC_Os03g57 90 | cullin | SEQ ID NO: 1 | SEQ ID NO: 50 | AAT75245 |

TABLE 1-continued

Rice Polypeptides That Are Involved in Seed Yield or Panicle Formation

| Proteins | Phenotype | Taiwan Rice International Mutants (TRIM) line | Gene Locus | Gene of Interest (GOI) | Protein | cDNA | GenBank Accession No. |
|---|---|---|---|---|---|---|---|
| 2 | high seed yield; drought tolerant | M0019261 | LOC_OS_01g61420 | ring finger protein 5 | SEQ ID NO: 2 | SEQ ID NO: 51 | BAD73632 |
| 3 | high seed yield; drought tolerant | | LOC_Os01g61430 | unk zinc finger HIT | SEQ ID NO: 3 | SEQ ID NO: 52 | NP_194611.2 |
| 4 | seed yield | M0025978 | LOC_Os01g52790 | cytochrome P450 | SEQ ID NO: 4 | SEQ ID NO: 53 | NP_916754 |
| 5 | | | LOC_Os01g52800 | cytochrome P450 | SEQ ID NO: 5 | SEQ ID NO: 54 | BAD86930 |
| 6 | | | LOC_Os01g52810 | PP2C | SEQ ID NO: 6 | SEQ ID NO: 55 | NP_567145 (ara) |
| 7 | | | LOC_Os01g52830 | unk | SEQ ID NO: 7 | SEQ ID NO: 56 | NP_916757 (ara) |
| 8 | long panicle | M0038751 | LOC_Os03g64150 | MatE efflux family | SEQ ID NO: 8 | SEQ ID NO: 57 | XP_470497 |
| 9 | long panicle, big seed | M0046723 | LOC_Os04g58180 | WD domain Gbeta | SEQ ID NO: 9 | SEQ ID NO: 58 | XP_474358 |
| 10 | | | LOC_Os04g58190 | dof28 | SEQ ID NO: 10 | SEQ ID NO: 59 | XP_474359 |
| 11 | big seed | M0022658 | LOC_Os02g28970 | | SEQ ID NO: 11 | SEQ ID NO: 60 | NP_001046872.1 |
| 12 | big seed | M0024255 | LOC_Os07g10110 | | SEQ ID NO: 12 | SEQ ID NO: 61 | NP_001044695.1 |
| 13 | big seed | M0034189 | LOC_Os04g39430 ?? | p450, dwarf4 | SEQ ID NO: 13 | SEQ ID NO: 62 | NP_001053047.1 |
| 14 | big seed | M0034642-1 | LOC_Os10g42820 | DUF221/ERD | SEQ ID NO: 14 | SEQ ID NO: 63 | NP_001065504.1 |
| 15 | big seed | M0039539 | LOC_Os04g55690 | unk | SEQ ID NO: 15 | SEQ ID NO: 64 | NP_001054091.1 |
| 16 | big seed | M0040296 | LOC_Os07g14890 | unk | SEQ ID NO: 16 | SEQ ID NO: 65 | NP_001059304.1 |
| 17 | | | LOC_Os07g14910 | unk | SEQ ID NO: 17 | SEQ ID NO: 66 | NP_001059305.1 |
| 18 | dense panicle | M0033394 | LOC_Os02g56250 | putative GATA | SEQ ID NO: 18 | SEQ ID NO: 67 | CT828966, not predicted, NP_001048448.1 |
| 19 | dense panicle | M0038155 | LOC_Os02g32504 | unk | SEQ ID NO: 19 | SEQ ID NO: 68 | NP_001046996.1 |
| 20 | dense panicle | M0039100 | LOC_Os06g50818 | unk | SEQ ID NO: 20 | SEQ ID NO: 69 | NP_001058607.1 |
| 21 | | | LOC_Os06g50830 | putative TF bzip | SEQ ID NO: 21 | SEQ ID NO: 70 | NP_001058608.1 |
| 22 | dense panicle | M0039314 | LOC_Os08g41950 | MADS, MADS7, MADS45 | SEQ ID NO: 22 | SEQ ID NO: 71 | NP_001062335.1 |
| 23 | | | LOC_Os08g41960 | mads unpredicted AGL72 | SEQ ID NO: 23 | SEQ ID NO: 72 | NP_001062336.1 |
| 24 | dense panicle | M0039419 | LOC_Os02g47430 | unk not predicted, peptidase M20, | SEQ ID NO: 24 | SEQ ID NO: 73 | NP_001058304.1 |
| 25 | | | LOC_Os02g47440 | putative syntaxin | SEQ ID NO: 25 | SEQ ID NO: 74 | NP_001047853.1 |
| 26 | dense panicle | M0039485 | LOC_Os12g15222 | unk | SEQ ID NO: 26 | SEQ ID NO: 75 | NP_001066501.1 |
| 27 | dense panicle | M0043153 | LOC_Os06g46240 | ARM repeat | SEQ ID NO: 27 | SEQ ID NO: 76 | |
| 28 | | | LOC_Os06g46250 | unk, proteophos-phoglycan precursor | SEQ ID NO: 28 | SEQ ID NO: 77 | NP_001058344.1 |
| 29 | dense panicle | M0050559 | LOC_Os12g43720 | put RXW8, DUF221, ERD | SEQ ID NO: 29 | SEQ ID NO: 78 | NP_001067352.1 |
| 30 | | | LOC_Os12g43730 | unpredicted, cyclin like Fbox | SEQ ID NO: 30 | SEQ ID NO: 79 | NP_001052038.1 |
| 31 | | | LOC_Os12g43740 | short chain dehydrogenase | SEQ ID NO: 31 | SEQ ID NO: 80 | BAF30371.1 |
| 32 | large grain | M0027918 | LOC_Os10g01700 | unk expressed, HSR201 | SEQ ID NO: 32 | SEQ ID NO: 81 | |
| 33 | large grain | M0028590-1 | LOC_Os03g55430 | 2 proteins in 2 frames ? | SEQ ID NO: 33 | SEQ ID NO: 82 | |
| 34 | | | | 2 proteins in 2 frames | SEQ ID NO: 34 | SEQ ID NO: 83 | NP_001051361.1 |
| 35 | | | LOC_Os03g55450 | unk | SEQ ID NO: 35 | SEQ ID NO: 84 | NP_001051362.1 |
| 36 | large grain | M0063563 | LOC_Os08g32930 | unk | SEQ ID NO: 36 | SEQ ID NO: 85 | NP_001061837.1 |

TABLE 1-continued

Rice Polypeptides That Are Involved in Seed Yield or Panicle Formation

| Proteins | Phenotype | Taiwan Rice International Mutants (TRIM) line | Gene Locus | Gene of Interest (GOI) | Protein | cDNA | GenBank Accession No. |
|---|---|---|---|---|---|---|---|
| 37 | large grain | M0063736 | LOC_Os08g31130 | unk integral mb prot DUF6 family MtN21 ara like | SEQ ID NO: 37 | SEQ ID NO: 86 | NP_001061761.1 |
| 38 | | | LOC_Os08g31120 | unk partial | SEQ ID NO: 38 | SEQ ID NO: 87 | NP_001066824.1 |
| 39 | large grain | M0063992 | LOC_Os04g47890 | Myb-like DNA-binding region, SHAQKYF class | SEQ ID NO: 39 | SEQ ID NO: 88 | NP_001053582.1 |
| 40 | | | LOC_Os04g47900 | | SEQ ID NO: 40 | SEQ ID NO: 89 | |
| 41 | large grain | M0064512 | LOC_Os12g01916 | DS RNA binding | SEQ ID NO: 41 | SEQ ID NO: 90 | NP_001065960.1 |
| 42 | | | LOC_Os12g01922 | WD like, raptor like | SEQ ID NO: 42 | SEQ ID NO: 91 | NP_001065961.1 |
| 43 | long panicle | M0066298-1 | LOC_Os10g40140 | VAMP associated protein, sperm protein | SEQ ID NO: 43 | SEQ ID NO: 92 | NP_001065309.1 |
| 44 | large grain | M0067806 | LOC_Os08g01580 | Disease resistance protein family protein | SEQ ID NO: 44 | SEQ ID NO: 93 | NP_001060794.1 |
| 45 | | | LOC_Os08g01590 | unk | SEQ ID NO: 45 | SEQ ID NO: 94 | NP_001060795.1 |
| 46 | large grain | M0068164 | LOC_Os03g52640 | unk protein 95 family | SEQ ID NO: 46 | SEQ ID NO: 95 | NP_001051193.1 |
| 47 | | | LOC_Os03g52650 | syntaxin 111 like | SEQ ID NO: 47 | SEQ ID NO: 96 | NP_001051194.1 |
| 48 | large grain | M0068730 | LOC_Os03g08330 | ZIM domain containing protein | SEQ ID NO: 48 | SEQ ID NO: 97 | NP_001049168.1 |
| 49 | large grain | M0069991 | LOC_Os03g14980 | CTLH, C-terminal to LisH motif domain containing protein, TOPLESS | SEQ ID NO: 49 | SEQ ID NO: 98 | NP_001049587.1 |
| 50 | large grains; drought tolerant | BASF 163 (M0028590-2) | LOC_Os03g55460 | | SEQ ID NO: 99 | SEQ ID NO: 115 | |
| 51 | large grains | BASF 162-1 (M0066298-2) | LOC_Os03g18000 | Phosphoinositide-specific phospholipase C | SEQ ID NO: 100 | SEQ ID NO: 116 | |
| 52 | large grains | BASF 162-2 (M0066298-3) | LOC_Os03g18010 | Phosphoinositide-specific phospholipase C | SEQ ID NO: 101 | SEQ ID NO: 117 | |
| 53 | large grains | BASF 162-3 (M0066298-4) | LOC_Os03g18020 | Rhodanese like protein | SEQ ID NO: 102 | SEQ ID NO: 118 | |
| 54 | large grains | BASF 148-1 (M0037341-1) | Os11g30430 | | SEQ ID NO: 103 | SEQ ID NO: 119 | |
| 55 | large grains | BASF 148-2 (M0037341-2) | Os11g30484 | ZOS11-03-C2H2 zinc finger protein | SEQ ID NO: 104 | SEQ ID NO: 120 | |
| 56 | large grains | BASF 148-3 (M0037341-3) | Os11g30410 | ThiF family domain containing protein | SEQ ID NO: 105 | SEQ ID NO: 121 | |
| 57 | large grains; taller plant; long panicles | BASF 7-1 (M0034642-2) | LOC_Os03g48820 | | SEQ ID NO: 106 | SEQ ID NO: 122 | |
| 58 | large grains; taller plant; long panicles | BASF 7-2 (M0037341-3) | LOC_Os03g48830 | | SEQ ID NO: 107 | SEQ ID NO: 123 | |
| 59 | large grains | BASF142 | LOC_Os03g12930 | | SEQ ID NO: 108 | SEQ ID NO: 124 | |
| 60 | large grains | BASF 143 | LOC_Os03g12940 | helix-loop-helix DNA-binding domain containing protein | SEQ ID NO: 109 | SEQ ID NO: 125 | |
| 61 | high seed yield; drought tolerant | BASF 10-1 | LOC_Os08g03600 | metal ion transporter | SEQ ID NO: 110 | SEQ ID NO: 126 | |
| 62 | high seed yield; drought tolerant | BASF 10-2 | LOC_Os08g03610 | LSD1 | SEQ ID NO: 111 | SEQ ID NO: 127 | |
| 63 | large grains | BASF 12 | LOC_Os04g39420 | 6-phosphofruc-tokinase 2 | SEQ ID NO: 112 | SEQ ID NO: 128 | |
| 64 | high seed yield | BASF 165-1 | LOC_Os10g33540 | alcohol oxidase | SEQ ID NO: 113 | SEQ ID NO: 129 | |
| 65 | high seed yield | BASF 165-2 | LOC_Os10g33550 | oxidoreductase | SEQ ID NO: 114 | SEQ ID NO: 130 | |
| 66 | high seed yield, large grains | | LOC_Os08g41940 | Putative glume architecture 1 (SPL16) | SEQ ID NO: 149 | SEQ ID NO: 150 | |

TABLE 2

| Amino Acid and Nucleotide Sequences of Rice Polypeptides | |
|---|---|
| SEQ ID NO: 1 | MKKAKFPGSSSSSSSSAAAPGVTEKNGLHVDPTAAAARTGGRTNGEEDAEMVLADQEELAAPSASAPAGVAANLERKKAT<br>LPQPSAARKPLRIKIGQPKLPTNFEEDTWAILKDAITAIFLKQKLSCDVEKLYQAAGDLCLHKLGANLYERIKKECEVH<br>ISAKISALVGQSPDLVVFLSLVQRTWQDFCDQMLIIRGIALLLDVKYVKNVANICSVWDMGLKLFRKHLSLSPEIEHKT<br>VTGLLRLIESERLGEAIDRTLLSHLLKMFTALGMYSESFEKPFLECTSEFYATEGVKYLQQSDIPDYLKHVETRLQEEH<br>ERCILYLEANTRKPLITATEKQLLQRHTSAILEKGFTMLMEANRVKDLSRMYTLFQRVDAIELLKQALSSYIRGTGQGI<br>IMDEEKDKELVPFLLEFKASLDRILEESFAKNEAFSNTIKESFEHLINLRQISSSPFFQQNRPAELIAKFLDEKLRAGN<br>KGTSEEELEGILDKVLVLFRFIQGKDVFEAFYKKDLAKRLLLGKSASIDAEKSMITKLKTECGSQFTNKLEGMFKDIEL<br>SKEINESFKQSSQARTKLPSGIEMSVHVLTTGYWPTYPPMDVKLPHELNVYQDIFKEFYLSKYSGRRLMWQNSLGHCVL<br>KAEFPKGKKELAVSLFQSVVLMLFNDAQKLSFLDIKESTGIEDKELRRTLQSLACGKVRVLQKMPKGRDVEDKDEFVFN<br>EEFSAPLYRIKVNAIQMKETVEENTSTTERVFQDRQYQVDAAIVRIMKTRKTLSHTLLITELFQQLKFPIKPSDIKKRI<br>ESLIDREYLERDRSNPQIYNYLA |
| SEQ ID NO: 2 | MDADEAAGSSRRMDLNLYLGLPRAPRPRRSDLGSDLALSTPMPSSPSSSAASVDAPPPPPELSHPPYSPSHADLSPPLQ<br>EVYSLYNPDDPPASETHLPPYAPPPAPVVSELPDDLEFGLHPPPPLVRASELLGWEDRPSSSTASSSFLPDTAARYWRL<br>LEQTGSRWLRARRFRSDLPPLSSEAYPAGRDAAAVPVLQHEPMNDTVEHNKVAADGAEVGASEESEEQGRSAATFECNI<br>CFDMASEPVVTSCGHLFCWPCLYQWLNVYSNHKECPVCKGEVTEANITPIYGRGNSCLDAEKAVEGGKQTGPTIPPRPH<br>GNRLESFRQQFHHLRPISRRLGEAHGLLSSWRRLLDQQIMNTASRFEGPPESAVQEMVDTAHAQHTSRLSRLASRMRAR<br>RLLREADNPNPPDGGSTSPDSGLIRNNASDPSRNGPSSLLPDGIDWLRGLTLLGYEDTERFASAMSDFRRITGPSQYGA<br>SASSSNPPNLESTFDRTHVVAAPSADQASNSSTAAVIQGDAGISESAGEPSNAGSSRSLRRRGRSSALGSLDADGGGLQ<br>RNKRRRIN |
| SEQ ID NO: 3 | MCPRATQTCEICEKVVSKYKCPSCLVPYCSLGCFKIHKETPCAKPSDPSSTEEKPAASPAKEVPVKRPEEANDVVEKTQ<br>QKASAASPAKEIPVARPIIVEEEKYILEKTQFEAIASSSEIREALKDEPLQKLIYSIDSSSNPLQELDEAMGIEAFREF<br>TDKILSNISKSNDEQ |
| SEQ ID NO: 4 | MLGEAASPWSLAGAGAAVALLWLCAWTLQWAWWTPRRLERALRAQGLRGTRYRLFIGDVAENGRLNREAASRPLPLGSH<br>DVVPRVMPFFCNVLKEHGKLSFVWTGPKPFVIIRDPDLAREILSNKSGNFAKQTTAGIAKFVVGGVVTYEGEKWAKHRR<br>ILNPAFHQEKIKRMLPVFLACCTKMITRWVNSMSSEGISELDVWDEFQNLTGDVISRTAFGSSYQEGWRIFQLQEEQAK<br>RVLKAFQRIFIPGYWYLPIENNRRIREIDQEIRTILRGIIVKRDKAVRNGEGSNDDLLGLLVESNMRQSNEKEDVGMSI<br>EDMIEECKLFYAAGSETTSMLLTWTLILLSMHPEWQEQAREEVMHHFGRTTPDHDGLSRLKIVTMILHEVLRLYPPVVF<br>LQRTTHKEIELGGIKYPEGVNFTLPVLSIHHDPSIWGQDAIKFNPERFANGVSKATKFQTAFFSFAWGPRICLGQSFAI<br>LEAKMALATILQSFSFELSPSYTHAPHTVLTLQPQYGSPIKLKKL |
| SEQ ID NO: 5 | MAKDHVKIVLKAYILGPIKYILSLESLYHNCGGLVVTMILHEVIRLYPSGIFLQRTTRKEIELGGIKYPEGANFTLPVP<br>SIHHDPSIWGGDASEFNLERFANGVSKATKFKTAFFMFGWGFSDLPWTELCNAGSQDGARHHPPELLL |
| SEQ ID NO: 6 | MCCSAVAVMKWEALLPNDTFLIVASSDGVFEKVTMQDVCDLMLYVKLGVKQELGSFALTQQNLADYVVDLSL |
| SEQ ID NO: 7 | MSSSDQNPSPTPASGTGTSVPPPGRATTVSSQLLDMGAQAVQALKPVRQMKQHACSFALYAHDLSRQVEVHHFVSRLNQ<br>DVLQCAVYDSDKPSARLIGVEYIVSDAIFESLPPEEQKLWHSHAYEVKAGLWTDVGVPEPLQSSEMARMAKTYGKLWCT<br>WQVDRGDALPLGAPALMVSPQAVEPGRVRAELVHGRDERYKIDSSAQGLKGARVEMDEPEWINPNADYWRLHGKGFAID<br>VTATEMKRHAPFP* |
| SEQ ID NO: 8 | MTPPPPSPPHERKTWAESVASEFRAQRGIAFPLIAMNLTWFAKLAVTTAFLGRLGDLQLAAGTLGFSFANVTGFAVLTG<br>LCAAMDPICGQAHGASNGKLLRKTLVMATILLLGASIPIAFLWLHVDAVLLRFGQQADMSSNARSYVVCLLPDLAVTSF<br>VNPLKSYLSAQGVTLPTLFASALALALHVPLTMWMARTRGIQGVATAVWVSDLAVAVMLAGYVLVSERRRKAGGGGGWV<br>EQTRGEWVRLLRLAVPSCLNTCLEWWCYEILVLLTGRLPDARRTVAVMAVTLNFDYLLFAGMLSLSVSASVRVSNELGA<br>GEAWAARRAGMVSIVGGAVGGVGGGVAMVAARRAWGSIYSSDAGVREGVGRAMEVMAVLEVVNFPLNVCGGIVRGTARP<br>AVGMYAVVAGFYVLALPLGVALAFKARLGIQGLLLGFLVGAAASLAVLLTFIARMDWPAEAQKARTRTTATVAQFHQHD<br>EVVQP |
| SEQ ID NO: 9 | MPEAAAAAAGHMDPVGDEAAERREMEEKEEEEEEEEEEDEEFYESLDRILSSSCSSTSASDDDDQQHRARRRHHPQPQQL<br>SSSATFSAYEVWISEPTSVEERRRVLLRRLGLAHDSEPLPHPSPRVSSSSPRSPTPSPPSSSPPRPAPVVAAAEEPRSS<br>GHGKPPLARNPSGGAEQCRIRNLDDGTEFEVGEVHDEVVREVGTGRQLTFEEFELCIGRSPIVQELMRRATTAASSSTS<br>DHAAPASKPRRKPGGWLRGIRHLAGSVAYGRSSTDERDKEKEKEKKEREARRLSSATDDSLDGNGSRNAGRVRVRQYGK<br>ACKELTGLFMTQELAAHSGSIWCINFSLDGRYLASAGEDRVIHVWEVSEGERKGELLGEGTVARENGGGCSPFLAAVGN<br>GSPELATLSLSCADGGFVEKKRRPRMQSSRKSVGSDHLVVPECVGGFRDKPVCSLLGHAADVLDLSWSKSQYLLSSSMD<br>KTVKLWDITTSTCLKTFSHTDYVTCIQFNPVDDNFFISGSLDEKVRIWNVHDRKIEDWNDLHEMVTAACYSPDGQVALV<br>GSHKGSCHLFDTTEKKLQYKSQIELRIRKKKSGQKKITGFQFAPGSSSEVLITSADSRIRVVNGDELVHKFKGFRNTSS<br>QISASVAPNGKYVVCASEDSHVYVWRHDNTSHPSRSRSAVDVTNSYEHFHCHDVTVAITWPGAESRGSFGSRSSRNSDS<br>DDAVMNTGRDAPVENSEHDLNGTVNRCTKRPVCEGVASTSNPPADGVSTSWPDEKQSSAKSSPGHCSSDLCIGALDVQR<br>RSAWGLVIVTAGRGGEIRVFQNFGFPVQV |
| SEQ ID NO: 10 | MAPAVASSPSLVLSAAAATASNKRPADSDASPPHQGDRTGQQEKKQQQLECPRCRSTNTKFCYYNNYSTSQPRHFCRAC<br>RRYWTHGGTLRDVPVGGASRRGGGGKRRRVSADADPSSASPPPPTTSTTDAYADLPAGFPPLSDGAFLPQFGLAGVAPA<br>AFSWASAVPDLYNCGIAPWDDGTAVTGAAWDNFADIAGLDLSWPPPGN |
| SEQ ID NO: 11 | MALLFRISLLLLLVPLIPTAAASHHHSPAGGGGAAVPLHPRRHHRSVANTATALFYPAPSMHQNHIEAEEGQLLHVLAD<br>PFAAAPAAAEAPSGETAIAAVGAAAEEATPTLIDDSPQQAAAASPPPPPPPPPPPPPPLFAKPDLDSTAPPQPKEEGVDG<br>YGSTTATATVTAAPPLDEPAAATATTTTTTTTTTLPLPRYSHVASPPPPPVHAGVAGLGDEQRLEQLARVLSSLGYNEMA<br>SAALLLANSALLAAWPGSITVFAAPDVFLRASCPMCSRRHVLLEHIALGYFPYTELAAASTAKLPSASPGLCLNLASDH<br>GPFAIHHVRLYVDGVEVSHPELYNDGRYVVHGLHGFLPPLSHGSCSHGSNHRHHYHYQYHHHHHHIIASSAASSAATAA<br>SVVRIMIREAIARLRDSGYGFVALAMRVKFAELERLANMTVFALDDQAIFVGGGHDYVSAVRFHVVPGHRLTHADLQRL<br>HPGTMLPTLAGEGQNLVVTQGASGSGSGPRDVRINYIPIKDPDVVINSRIALHGVYVTFPRLHLANLAAAVALASSNQ<br>INATCGVFGDCASAAATSTTVPAAHRYGEGQ |

TABLE 2-continued

| Amino Acid and Nucleotide Sequences of Rice Polypeptides | |
|---|---|
| SEQ ID NO: 12 | MDADEAAGSSRRMDLNLYLGLPRAPRPRRSDLGSDLALSTPMPSSPSSSAASVDAPPPPPELSHPPYSPSHADLSPPLQ<br>EVYSLYNPDDPPASETHLPPYAPPPAPVVSELPDDLEFGLHPPPPLPVTGGFSSRLEADGSVRGGLGRTFRHSVLKLTQ<br>LGVMLPQSQNGPSSLLPDGIDWLRGLTLLGYEDTERFASAMSDFRRITGPSQYGASASSSNPPNLESTFDRTHVVAAPS<br>ADQASNSSTAAVIQGDAGISESAGEPSNAGSSRSLRRRGRSSALGSLDADGGGLQRNKRRRIN |
| SEQ ID NO: 13 | MVGGELVLAALVILLALLLTLVLSHFLPLLLNPKAPKGSFGWPLLGETLRFLSPHASNTLGSFLEDHCSRYGRVFKSHL<br>FCTPTIVSCDQELNHFILQNEERLFQCSYPRPIHGILGKSSMLVVLGEDHKRLRNLALALVTSTKLKPSYLGDIEKIAL<br>HIVGSWHGKSKDKGMVNVIAFCEEARKFAFSVIVKQVLGLSPEEPVTAMILEDFLAFMKGLISFPLYIPGTPYAKAVQA<br>RARISSTVKGIIEERRNAGSSNKGDFLDVLLSSNELSDEEKVSFVLDSLLGGYETTSLLISMVVYFLGQSAQDLELVKR<br>EHEGIRSKKEKDEFLSSEDYKKMEYTQHVINEALRCGNIVKFVHRKALKDVRYKEYLIPSGWKVLPVFSAVHLNPLLHG<br>NAQQFQPCRWEGASQGTSKKFTPFGGGPRLCPGSELAKVEAAFFLHHLVLNYRWRIDGDDIPMAYPYVEFQRGLPIEIE<br>PLCSES |
| SEQ ID NO: 14 | MATLPDLGVSAFINILGAFVFLLIFAALRLQPINDRVYFPKLYLTGQRRHHPHPHGFVNLDLCSYLRFLAWVPGALRMS<br>QPDLIHHAGLDSAVYLRIYTLGLKIFLPIMTVALLVLIPVNVSGGTLLNLRKEIVFSDIDKLSISNVNPGSNRFFIHLL<br>MAYVFTFWTCFMLYKEYSNVAFMRLHFLASQKRCADQFTVIVRNIPHVSSHSTSETVDEFFRRNHPDHYLGQQAVYNAN<br>RYAKLVKKKERLQNWLDYYQLKFERHPGKRPIGRTGCLGFCGREVDQIDYYRARISELDKKLASERQRVLNDPKAVMPV<br>AFVTFDSRWGAAVCAQTQQSKNPTQWLTDWAPEPRDVYWQNLAIPFFSLSIRKFLISIAVFALVFFYMIPIAFVQSLAN<br>LEGIEKVAPFLRPVIDTPVVKSFLQGFLPGLALKIFLYILPTVLMIMSKVEGYVSLSSLERRAASKYYYFMLVNVFLGS<br>IIAGTAFEQLNAFFHQPPSQIPRTIGVAIPMKATFFMTYIMVDGWAGIANEILRVKPLVIYHLKNMFIVKTERDRERA<br>MDPGSIGLAENLPSLQLYFLLGLVYAVVTPILLPFIIIFFAFAFLVYRHQIINVYNQEYESAAAFWPQVHSRIIASLLI<br>SHVTLFGLMSTMKAAYSTPLLIFLPLLTIWFHKYCKSRFEPAFRKYPLEEAMEKDNLERTSEPNLNLKSYLQNAYLHPI<br>FHMFEQQQQQEQEQQREEKVEVRIDKAQQHHHRQVEEEEEESKSSQATTHYYHHHHEQTTTTTHHHYHQHEHMSHYHMG<br>PSDTADSPSPPHFVYHYGVDP |
| SEQ ID NO: 15 | MEMTRSLTLVPLPATLRPASAACRRRRARRGLPFGALFSPSPPSNQQQQEMHIRALQPRQDWVGEWVRSNDTLVRGLPI<br>LGGGASLLAVLLNRAVSGIAAVADASSSQSRADILTLALSVTDILAGLVWLSIRPKSISPVVPRGVECKRVGTGVLDSA<br>LRELLWTWDSLTTATCCKSLVVVYGGNCVLQIGVAAGSPEDGNAVMVDAQKFMQGSLYRSAMESKKQSYLANLALYPGR<br>TELPFLPANTQALILQPIGDKGIAVIGGDTIRGFTNLDQAWIAMIADKLDATLSKS |
| SEQ ID NO: 16 | MASSVAGSVTRRPPPVLLACRSRPNNRRLIRLLPLLFAVVVLLALLPPCVHGARALNDAKEAKVAEASDQTTTTTHAAA<br>AAVARWSVTVREGGGGGGHGSGHAGAGHGHGSGHGRPEPAEHHTGRRSAAAGSVRPPMAASCAALLVAAVVALLRF |
| SEQ ID NO: 17 | MESAKRSCLAISLILLLLLVPSIHGARHVAAAIKGTGADSEMVVTERTAGGGGGHGRGYTSHRSHNPNNPNDGGSGTPV<br>VDPHNVATRGHHHRGAATRTAAGGDPRLAACMLRLGATFFLLVLG |
| SEQ ID NO: 18 | MAGVGFVEDMLREQSLLEATCGDLFDHIDDLLDFPKEESAADVLLLDAPAPGSPLSSRIIGGHATMAAAPPPPPQMMAL<br>PPPPAPAKDDASALFDAAGALGAEVFDRKDAHIGPCDELDMDMAQLEWLSGLFDDGTIPHEPSFPGVNCAAPIKASALT<br>ANAGVVLPDKAEEALFRSSSPISVLEHSGFNVATNGGSSSSSSSSSPSPWTWTWTAV |
| SEQ ID NO: 19 | MIIVDDAGAFLPALNHSPWDGVTIADFVMPFFLFMVGISLTLAYKRVPDKLEATKKAVLRALKLFCLGLVLQGGFFHGV<br>RSLTFGVDITKIRLMGILQRIAIAYLLAAICEIWLKGDDDVDCGLDVIRRYRYQLVVALLLSTMYTVILNGVYVPDWEY<br>QISGPGSTEKSFSVRCGVRGDTGPACNAVGMLDRTILGIDHLYRRPVYARTKQCSINYPQNGPLPPDAPSWCQAPFDPE<br>GLLSSVMAIVTCLIGLQFGHIIIHFEKHKGRIINWLIPSFSMLALAFSMDFIGIRMNKPLYTISYALATSGAAGLLFAG<br>IYTLVDVYGFRKLTIPMEWMGKHALMIYVLVACNILPIFIHGFYWREPKNNLLKFIGVGA |
| SEQ ID NO: 20 | MAATGGAAGEKTASSLLLGVRGYTSTLKNASTASCRLSAGHPIEVTLWEASPPALSHFSVHCPDLPSFNGNLLGAPKAI<br>AAAVDDADGQLLLLLRVPIDQLGAPHDNDYLVYHPDPPSPKLDLLPNPPPPTLGDHQLAILSCGDDRYVVAALHVWSEF<br>TSTLRLYRSSCSSGSWTSEEVSVEEPVRDRLCPIPDSAKRQLYHVTTKTITLGGAKGTVGWVDLWRGILLCDVLDEMSP<br>RKLRDMPLPWPAKGNWRMYLNGDVSFCRDIAISQHKDSIKYLEMEIVSPRTVTTTIPTSTSADPTSYLEWVRRSREPQP<br>TRRRSVFHPGSWRITTWSMPIPVTSWDDWRRDCTAESREVHLDTNPSHHYELLHSLMLSNSGDEHREEAQGQGATSSLS<br>LGRLRLCYPALSCIDDDVVYLLGNAAGRGAKTGGMMVAVDVRNKELRGVAKLDPEKNTLYSMRCYLATGISKRLNTTTD<br>TRVGRPEEDAEAAE |
| SEQ ID NO: 21 | MANYHHQEYYQMAAAAAVAWPREPDSPQLSIMSGCSSLFSISTLRDDDDGGGVRLAGAALPATPVSLAGIAGGASTPGG<br>DEVDMEVRQQSGGSGDDRRTIRMMRNRESALRSRARKRAYVEELEKEVRRLVDDNLNLKKQCKELKQEVAALVMPTKSS<br>LRRTSSTQF |
| SEQ ID NO: 22 | MAEKKKKKKKKKPQSLLVLTSWRSIGMGRGRVELKRIENKINRQVTFAKRRNGLLKKAYELSVLCDAEVALIIFSNRGK<br>LYEFCSTQSMTKTLEKYQKCSYAGPETAVQNRESEQLKASRNEYLKLKARVENLQRTQRQYYKSKHRLCLVRSKVWNLV<br>KIRDDVTEKLCMYERNLLGEDLDSLGIKELESLEKQLDSSLKHVRTTRTKHLVDQLTELQRKEQMVSEANRCLRRKLEE<br>SNHVRGQQVWEQGCNLIGYERQPEVQQPLHGGNGFFHPLDAAGEPTLQIGYPAEHHEAMNSACMNTYMPPWLP |
| SEQ ID NO: 23 | MEGGGRRRKRGKVELRRIEDRTSRQVRFSKRRSGLFKKAYELSVLCDAQVALLVFSPAGRLYEFASSTS |
| SEQ ID NO: 24 | MALLLSYPRRHPSIHLLILSAYALFLLPILDGLELGGDGLYREILRDETVLRLKELGKISDGEGYLERTFLSPASIRAS<br>AVIISWMKDAGLTTWIDQMGNIHGRFEPTNSTKEALLIGSHMDTVIDAGMYDGALGIISAISALKVLKVTGRLQRLTRP<br>VEVIAFSDEEGVRFQTTFLGSAAVAGTLPESILQVSDKSGTTVQDVLKLNSLEGTANALGEVRYSPESVGSYVEVHIEQ<br>GPVLEALRYPLGVVKGIAGQTRLKVIINGSQGHAGTVPMKLRRDPMVAAAELVLTLETLCKEPNKFLTYDEECGCFTEE<br>SLAGLVCTVGELLTWPSASNVIPGQVNFTVDIRAMDDKVRETIVTSFSRLVLQRCDDRLVDCAVEQKHAAAATPCDAEL<br>TSRLERATRSTISSMAAGVRRAGGETPVLMSGAGHDAMAMARLTKVGMLFVRCRGGVSHSPEESVMDDDVWAAGLALVN<br>FIDQNAVDAAAATAAES |
| SEQ ID NO: 25 | MSFADLEAGAVRAPRRARGPDATRALVFQITTAVASYRRLLNSLGTPKDTPALRDQLQKTSHNILQLAKDAKEKLRRAA<br>EADKNADTSADKRVADMKLAKDFATTMEEYGKLQNLAIQREMAYKPVVPQTSQPNYTTGGIEARDSGKIPEQHALLAES<br>KRQEVLQLDNEIVFNEAIIEEREQAIQDIQQQIGEVHEAFKDLATLVHIQGVTIEEIDTNIENSAAATKEAKTELAKAS<br>KTQKSNSSLLCILLVIFGVVLLIVIIVLAT |

TABLE 2-continued

| Amino Acid and Nucleotide Sequences of Rice Polypeptides | |
|---|---|
| SEQ ID NO: 26 | MQLYMTYQACPMGDLQMGDSVVSTIDIRALYCNKSPGKSSSSSMYGASSSSKRKACELNHGDGGSAHDDVRDYGVDHVD<br>DNGEYYGDDHDDVMHG |
| SEQ ID NO: 27 | MRAAAAASKAAGKEKSRRKGGGGGAGGGGGEQLLTDQVLSLRARLHLALALGLAKSDGGPKKWQSTDAGIQSHVLKAA<br>SAFLGCLTNEMLRLPPIKESISDILIALEGILQSKNVSVLIQATDVSLKLVSSVGNLARQYPVLEIVTCLASQLSANQ<br>ITIAVSSASTLNCILNTLATARSSIHAEIWEALEKTDAVTSVIGALQNYSPDVHPLNYLMEMMSLLRIILWIWPSSRY<br>HVWSNCNLMGKLAQYCVASEMDVAVRVLKLYAALALCGNGAMVLLNNEDLMAKVGALLGKSNPSIARIEALKFYQILL<br>RSSKGCDLLMAAHYQHIIEGTINAMSRDDERLLTIEGCRTALLVLRYAGDHHRLFWSHAIDDVLYKILTGGCTSSHKA<br>NQILCHDKLFNMVSENFMDIHSYVWDILGNLAVHCKNEYLSVRKGQDSALQALIHCICSLAADAMQKSNTMKLSKDVH<br>EPALRAVLMMLLSPSGYILSEASSKLLHVLPLGDDCLNILFTSLESNTTRSITASFDNVKIMSNLMSLAGMSINFVCI<br>HCKRNLDVGIVCNDCRDHYSEGLIRVLQNASCQNLSPGPKLYISRILSLFGLCGFPSKLGGKMRRALDDNELADLELL<br>LSNGESLKAHTAIISVRCPKLLPSAKSLGSDGKITDEWGRSFYHVRMSDRVDSCGLKKILEYTYTNSVMVDDDNIKPR<br>TLAKYCHLKSLQEMLQKEQPRWNSDCPRYDLTAALEPVKCSFSFSEVINVPLGWQALNKLIHWFYSGELPKIDPDCRW<br>RNLNSEEQLSQLRPYAELSSLSEFWFLEGVKEESLSVVTSCLSSTSTAASVEFVVFAAQLGQWEMVEAAVGSVAHLYP<br>KLRDSGQLEQLDDDVLNMLRTEYVRRTQRTGVGSAAAQAGARVVTAVYRRGQRADYWQSGGFGDNWNFQMVILNASEE<br>HCRESKFDTIGVCKARFLYGKVSRGFRLRTSGINKEGGPRGGTVIYSRSSGGLPPWCGAGSHDALAAVRWPSLPGLES<br>HQTAQVIRRGAGRRGEGRDVNVTKQSNAPMRPPETMQREQPQSRARANGRKWPPPRRWRSGIREEQGVPSAKAWQEKR<br>KRTQQQRCALPAAIAASRLQL |
| SEQ ID NO: 28 | MASAVASNLPAAAPAAVMPFGGWHGPRVSFSRDAAGAEEAAAVVVCSSPLAAAAAVATTTTPEPAISKDFIDFEFSLGG<br>SATMLPADELFADGKLLPLRKAAAVPEMDAAAPRPPQPEAMPAPSEPMKPLRAATAAVDAADPYVFSPKAPSCSSRWRE<br>LLGLKRAAAQSPKPSPSSAPARTPGRAMNSTAARSLKLLLQRNNGRSSGASASELASAPLLRDSSDSEASLSLASSRFS<br>LSSSSSSSGHDHDDIPRLSLDSAADPNPPRIRLVRSSHRHSTSSSSSSRAGRSPARRRPSPPPPPRCLSVDSPRMNSSG<br>KIVFQGLERSSSSPCTLHAAAKPRSRAVDRSYSSGVRVAPVVLNVPVCSRPVFGFFKDKKDAAAKDAMAARTRSSLGRK<br>TTAAPQG WSGELGRSCG |
| SEQ ID NO: 29 | MKISGLLTSAGINIALSVLFISLYSVLRKQPANVRVYFGRRIAEEHNRLREAFILERFVPSTGWIVKALQCTEEEILAA<br>AGLDAVVFNRILVFSLRIFSLAAILCVFGILPLNYFGQDIHHVRIPSESLDIFTIGNVKVRSRWLWVHCVALYIISGVA<br>CILLYLEYKHIARLRLRHLTCAMPNPSHFTVLVRGIPKETKESCSNAIDDFFTKYHGSSYLFHQVVYKVGKVQKIMTGA<br>KKAYRKFKHFTDSTIDQRCRAISYRCCLCGASSNSFQLLATGLEQNQGKSDLQDSSLKLDDQECAAAFVYFRTRYAALV<br>ASEILQTSNPMKWVTDLAPEPDDVYWSNLWLPYKQLWIRRIATLLGSIVFMLFFLIPVTFIQGLSQLEQLQQRLPFLKG<br>ILEKKYMSQLVTGYLPSVILQIFLYAVAPIMILFSTLEGPISHSERKRSACCKVLYFTVWNIFFGNVLSGTVISQLNVL<br>SSPKDIPVQLARAIPVQATFFITYVLTSGWASLSSELMQLFGLIWNFVRKYILRMPEDTEFVPSFPYHTEVPKVLLFGL<br>LGFTCSVLAPLILPFLLVYFFLGYIVYRNQLLNVYRTRYDTGGLYWPIAHNAVIFSLVLTQIICLGVFGLKESPVAAGF<br>TIPLIILTLLFNQYCRNRLLPLFRTTPAQDLIDMDREDERSGRMDEIHHRLHSAYCQFHDTEDIPLEKIQTVGSDEEQG<br>CSSDKSNGKESFEEPRAELSHPTLNGLPVSRLRHAVK SITFLVRLQKRGLSE |
| SEQ ID NO: 30 | MAILREFGTIEGMENLLPEDVLSNIIHRLAPRYLAISRCVCKTWCTIIEAHNLLHVDLLPRPLCGIFINFNELSMSEFF<br>SRPSKGPTVSGNFDYLPCSSCIIDHCNGLLLFHKYVVNPATRQSAPLPPCPYMVVEHIFHREYLVFDPTLSPHFEVFMI<br>PEIRRSNVWYNMLNSDDKLDPAIEELEWPPSPCILHVFSSRTKVWEERSFVREGEAAGNVSDMRLDHPYVPDTSVYVPD<br>TSVYCRGVLYVYCQNKYVMRISLSNGKYQVIKPPSDCEGMAYTNLYLGKSMKGVYCAVRHLASRFLIYILDESSDRMEW<br>VCKDSCSIQPCQIIDGPGPWTLQDINNQERGFEYEDGNNEAVVEDRFEWDSDNDNVIETNSRGSGGYINFLVDTTRRGR<br>YNSGGYIDFLGFHPYKEVIFLSDSLRRGLAYHLNSSKIQDLGSLRPTNYGTEVGIQPFIQKFFPYSPWMGRFPEDN |
| SEQ ID NO: 31 | MKISGLLTSAGINIALSVLFISLYSVLRKQPANVRVYFGRRIAEEHNRLREAFILERFVPSTGWIVKALQCTEEEILAA<br>AGLDAVVFNRILVFSLRIFSLAAILCVFGILPLNYFGQDIHHVRIPSESLDIFTIGNVKVRSRWLWVHCVALYIISGVA<br>CILLYLEYKHIARLRLRHLTCAMPNPSHFTVLVRGIPKETKESCSNAIDDFFTKYHGSSYLFHQVVYKVGKVQKIMTGA<br>KKAYRKFKHFTDSTIDQRCRAISYRCCLCGASSNSFQLLATGLEQNQGKSDLQDSSLKLDDQECAAAFVYFRTRYAALV<br>ASEILQTSNPMKWVTDLAPEPDDVYWSNLWLPYKQLWIRRIATLLGSIVFMLFFLIPVTFIQGLSQLEQLQQRLPFLKG<br>ILEKKYMSQLVTGYLPSVILQIFLYAVAPIMILFSTLEGPISHSERKRSACCKVLYFTVWNIFFGNVLSGTVISQLNVL<br>SSPKDIPVQLARAIPVQATFFITYVLTSGWASLSSELMQLFGLIWNFVRKYILRMPEDTEFVPSFPYHTEVPKVLLFGL<br>LGFTCSVLAPLILPFLLVYFFLGYIVYRNQLLNVYRTRYDTGGLYWPIAHNAVIFSLVLTQIICLGVFGLKESPVAAGF<br>TIPLIILTLLFNQYCRNRLLPLFRTTPAQDLIDMDREDERSGRMDEIHHRLHSAYCQFHDTEDIPLEKIQTVGSDEEQG<br>CSSDKSNGKESFEEPRAELSHPTLNGLPVSRLRHAVKSITFLVRLQKRGLSE |
| SEQ ID NO: 32 | MVELSIADASASDLCGGTLGQMVELVCEARLRVREEYVRSTVDLMALLRGRGMVFDGVYVVSNLTRLFAELDFGRGEWV<br>VSGMAQPMLATFLVTCRNGDDEDAVAASMLLPPPVKLRFAEELAGLMMSMPHGGAALCPAPASTYLPLSMRGRRWLHIP<br>EGYYGNALAYSITDASASDLCGATLAQMMELVCEARLRVTEEYGRSTVDLMASLRGHDTVFDGVYVVSDLGAGSGWSAA<br>WPSRCWRRSW |
| SEQ ID NO: 33 | MNQQHQRSIEHCSIGCFLASPPPRFFPARTRSAPGELRMKLVVFLIRGCPGEVLLRPIVPAKEGLRTRIKWHILQRFCK<br>LEIISIETETMITISSRSIIKSRCKKSNKKILVFFLSMSVKFLLITTRRSLSVQKRSSTFSQLLH |
| SEQ ID NO: 34 | MCMDRAAVPVKRVWLGLAARLGLRRTSGLGKLKKEVRTCEYHDVHIMWEMLRKTDAPVPMAEKEAAAAAAVAAAAGARR<br>RKAAWRRFLYYCCAF |
| SEQ ID NO: 35 | MATSRKLARVDIAELKQRLVKRLGRQRAGQYFAHLTRLLNLKLTKVEFDKLCYATIGRENIALHNALIRGIISNALSGV<br>PPPSRQAVTGQSGTTTAPSGQCVGIALQSARNVGAVVDSGDGDFARERAVAGKVLSVEDGEEVEQVRSAPCVQSRSPIT<br>APLGISTTPTYGARTWRLDDPMVSCYDSHHLLDTGSLFKGLQRRLESDGIGVSVQGVEVLNRGLDEFLRRLIKPCMELS<br>RSRSSGRRVTKGNAMFAARMNGLQQANHGHCTTLQDFAVAMESDPHLLGTNWPTQLEKIQATSFGE |
| SEQ ID NO: 36 | MASPRCAAVALLHPAGVAAGGGARRRVLLLDQERPLWGTEVRRRRRRRFSSLETPPRCSKMYVPGFGEGSPEKKAARNL<br>QHFFNYIAVRVVLTQLESYNREAYGELMDFVNRNSLNDADTFCKKLIRESPRHKQLAMRILEVRSAYVKHDFEWDNLKR<br>LSFKMVDEANTKLMRDYVLETSHIEDDN* |
| SEQ ID NO: 37 | MDITGAGAMGGGSTAATAAAAAGAGWKTPVSMVLVQLFITGQILLSKVSIGGGMLIFVLLAYNSFFAVVFLLPFALIFE<br>RGKWRDMDWGAFGWIFLNAFIGYSVPMSLYYYGLKDTTSSYSVIFLNITPLFTFILSLMFRLEAFKLRSIPGVLKIASI |

TABLE 2-continued

| Amino Acid and Nucleotide Sequences of Rice Polypeptides | |
|---|---|
| | LLSIGGTMLISLYKGKSLHLWDSIIQHQNEHKSATNQLRGTILLVGSSFTFACWFLIQSKILKVYPYKYWSSMVTCLVG VFQTALVGIILRRDKSAWELGWNLNLVTIVYTGALATAGKYILNSWAITKRGPTYPTMFSPLSVVFTVVLDSVLLGNDI TIGSLLGTALVIVGLYLFLWAKAREIPKKST* |
| SEQ ID NO: 38 | MARRAAEKEAALRQGLTAGDGEARRTGALWRTDAWRQRAAASAAAASVVRTWPSSAPWLRFELDPWRRVCGEQDLQTAA CGGGDGAVGLSFETHHGGSVAPSPEFAACAASSCSAELMVLLVLQRGELLVRHDRPSHHHRRRFPTPQPAEAAAAVEVG WGFQNPRDAMTCLCKGL* |
| SEQ ID NO: 39 | MGSGGGGCGRNGAVRQYIRSKVPRLRWTGELHCSFVQAIEFLGGQDKATPKLILQLMGVKGLTISHVKSHLQMYRCSRL GSHGTGRRSEMQPQLQRKHSCGADEQVPREFLCPPLKRTRMGTEATYKGMQGSQGISEMRTTGTQYCIDDYMQAMAMER RIKEEGLRWQRDAAAAAAADGGAAASNLQTVGCSVQESDPFKIIKPEVHHLGPVLKLQCSKVENSGFISSSTGTAARDQ PEPPPLEKCSLSLSLGPDPKCMPAIASSPSESSCILSSSSRSFSDCSGNSGCLVAPGVNLELSMSICGS* |
| SEQ ID NO: 40 | MAAADQPAYGDRRPSRRTYKPDQPEGLTISFRELYDLPTSPEFLFHEEALRSRRTCGEDLTFYTGCGYLVGRAAGAAAG LKRAAEEAERGESMKLRGQPRPQPVRLPRARVRQPARRRRAALRGDREHRGGPPRRRRLGQHRRRRDRYRRALRRGCRP AGGDRRQLRRGAHGRRGGRGEASADEIRA* |
| SEQ ID NO: 41 | MDMPPTPLPPETANTSPAPNGATAGIRVENCYVFKSRLQEYAQKTGLQTPEYHTFKEGPSHEPVFKSTVVINNTSYDSL PGFFNRKAAEQSAAEVALMEIVKSIPANANIPAVQETGLCKNLLQEYAQKMNYAIPSYICTKSASGLAPFICTVEIGGI QYIGAAARTKKDAEIKAARTALLAIQGQSEGSANGATKYIVVPGKRVGKEVEKRPIETPKPLKVKKGGFKKKWNKRKFM KKDGQAVDVEKDEARVAGDAHDSDVLMQPTVITQEASCGTLFLQPCEEAKRVEAEPPRDIEMVQPDKENQHSDAALVQP DDEARVEQEPSRDISVVQPNEEAISGKQEPSIDAAILQPKEEASSVKQEPFIDTAMLQACKEAGSVELGPARDTVISQL NEQDRAVKQEPAGDIVVPQPDVHARVVKE* |
| SEQ ID NO: 42 | MALGDLMASRLVHSSSSSAAPSAALPNHHTNHLVDDHLPVENGPDPRRDVPDEEPPPPPPPQVALLPQVVVLCEQRHEG FDEAAAAAAGPSTSGPVSKWRPKDRMKTGCVALVLCLNISVDPPDVIKISPCARKECWIDPFSMAPPKALETIGKTLHS QYERWQPKARYKLQLDPTLEEVKKLCNTCRKFARTERVLFHYNGHGVPKPTANGEIWVFNKSYTQYIPLPITDLDSWLK TPSIYVFDCSAAGMIVKAFLERLDWSSSSSASSSKDCILLAACEAHQTLPQSAEFPADVFTACLTTPIKMALHWFCNRS LLRDSMEHNLIDQIPGRQNDRKTLLGELNWIFTAITDTIAWNVLPHDLFQRLFRQDLLVASLFRNFLLAERIMRSANCS PISYPLLPPTHQHHMWDAWDMAAEICLSKLPQLIADPNAEFQPSPFFTEQLTAFEVWLDHGSEDKKPPEQLPIVLQVLL SQSHRFRALVLLGRFLDMGPWAVDLALSVGIFPYVLKLLQTSAMELRQILVFIWTKILSLDKSCQVDLVKDGGHAYFIR FLDSLDAYPEQRAMAAFVLAVIVDGHRIGQEACANAGLIDVCLRHLQPENPNDAQTEPLLLQWLCLCLGKLWEDFPEAQ LLGLQSNAPEIVICLLSEPQPEVRASAVFALGNLVDIGSPSLNGADDDSDDDEKVRAEINVVRSLLQISSDGSPLVRSE VAVALTRFAMGHNKHIKSVAAEYWKPQTNSLLKSLPSLANINSSNVYSPSSLIQGSSGLASHIGPVLRVGSDNSATARD GRISTSSPIATNSIMHGSPQSDDSSQHSDSGILLRENASNGGLNYSRSRPIDNGIYSQFIATMCNVAKDPYPRIASIGK RALSLIGVEQVSMRNSRLSNGGAHPGETSVPPSSNFGMARSSSWFDMNSGNFSVAFRTPPVSPPQHDYLTGLRRVCSME FRPHVLNSPDGLADPLLSSSAAPSNMGLYILPQSLIYRWSCGHFSRPLLTGSDDNEEANARREERERIAMDCIAKCQRS SCKMTSQIASWDTRFELGTKASLLLPFSPIVVAADENEQIRVWNYDDALPVNTFENHKLSDRGLSKLLLINELDDSLLL VGSSDGNVRIWRNYTQKGGQKLVTAFSSVQGYRSAGRSIVFDWQQQSGYLYASGDMSSILVWDLDKEQVNTIQSTADSG ISALSASQVRCGQFAAGFLDASVRIFDVRTPDRLVYTARPHAPRSEKVVGIGFQPGFDPYKIVSASQAGDIQFLDVRRA SEPYLTIEAHRGSLTALAVHRHAPVIASGSAKQMIKVFSLEGEQLTIIRYQPSFMGQRIGSVNCLSFHRYKSLLAAGAG DNALVSIYAEDNYQVR* |
| SEQ ID NO: 43 | MGASGRLISIYPEDLTFLFELDKPCYCNLKVVNNSEHHVAFKVKTTSPRKYFVRPNASIIQPWDSCTITITLQAQKEYP PDMQCKDKFLIQSTKVAASTDMDEIPPNTFNKEVDKVIEEMKLKVVYTVPSGSSDDSGITSLGSRSFKLGSDDLTMLKN ASIEKIQTIQRLKDERDTTLQQNQQMQRELDVIRRRRSRKSDAGFSLTFAAFAGLIGVLIGLLMSLIFPRPQAAA* |
| SEQ ID NO: 44 | MGVMNPLMAKLTTLMGDEYKKLKGLRKQVSFLKDELTTMSAFLEKLALMDDDDDGELDPLAKDWRNHVREMAYDMEDCI DDYFTSHLDHRYSSSDAGLIRKIARRLRALRVRHRIASQINELKARVVEANERRVRYRLDDCNNKHGVSANPAIDPRIT SLYQNAGSLVGIDGPSQELIQLLSLDRDTDQRQLKVVSVVGFGGLGKTTLAKYVYDKIGHQFDCTAFVSVSHKPDITRI LSSIQSKLDIGGTSQACDDVQQLIDDIRAYLEHERYIIIVDDLWKQEAWVIISCAFPNNGKGSRVIVTTRVKDVARLAC GKDGQIYKIQPLNNKDSRKLFFDRVFRPEDSCVLQYEEISTEILKKCSGLPLAIVTVGSLLACRPRTMEEWKSIRDSLG APFDKNKSLEGMRNILNLSYKNLPLHLKTCLLYIGKYPEDYEIGRDELVTEWIAEGIMGNPHGENLEATGNGYFSELIN RGLIQPESTGYGGEVLSCKVHDMMLDLILIKCAEDNFVSVAHSCKDYMRMAMHHERSCNKVRRLSLQCKAARSDCAIEG SVISTSMARARSVSVFGECSRGLPFLMLSKYIRVVHIELEGHGGQVDLTAISHVLQLRYLRVETPGCEIDLPSKICGLV HLETLSIFSHKAVSRLPSDISSLPRLSVLSLVVPWATRLPNKLNKLKGSLRSLTILFNPPDALGMEAIGELKNLRDLNI SVNRWRDDEILSLYALGSSIGKLDELRSLQIHVPPATLGDVDLLGSLPIFPQSIERLILHGWCFSKVPRWINGTLRNLQ HVLLEVSETSSSEVDLLGELPSLADLELRVGLKTRDVIAFGGTRASLFPALLKLKLRVGEHVASRLQFQAGVMPKLQSL HLWFRNCESGIHVTPEGMQHLLSLQSICVEIYLRDEELKATYPWDAMERAFREITGANPNRPSFKFVKQV* |
| SEQ ID NO: 45 | MECEPEELQFLGMVGIYREAASILRAHRPLFARIAAAFVLPLSLLFLLHIAISHALFSHIDSDDSALDSAAPGTPAQRR LLHRLADDWLALLLFKAAYLLALLLFSLLSTAAAVFSVASVYSAKHDALSFPRVLSVVPRVWRRLAATFLAAFLLLFAY HLLFVAVFVALLVAADSGSGLAALLAFLLALAYIAGLVYLSVVWHLASVVSVLEDYKGFEAMRKSKALIQGKLWTASAI FFVLNVVFIVVEVAFRAWVVRGATHGLGAGSRLLLGLAMLAALCAVVMLALVVQTVVYLVCKSYHHESIDKSNLSDHLE VYLGEYVPLKASDVQMEQFNL* |
| SEQ ID NO: 46 | MASSSALASSPFLPPLSTPNPRALSLRLPARRLPVASSAAPSGAAAAASARERRRFLERYGLNPDDFEDDAEAEPREER RRDRRNRRSGRGEAEDAPAKAAAEPRETHKMLQVLGGKVRRRKLLSPKDRNVRPMMEVVRGAAFDILQSAGGFPASLRP GRWLDLYSGTGSVGIEAMSRGCSEAHFVEMDPWVVSEVLKPNLECTGFLDVSHIHMIRVENFLANAEKSSGKYPSFDYI SVTPPYLEVNYSTLLDQLARSPLVGEDCFILVEYPLKTDMAESCGSLIKVADRRFGRTNLLIYGPTWAEKKRRS* |
| SEQ ID NO: 47 | MNDLMTKSFMSYVDLKKAAMKDLEAGGDGVELPEVGVTDERLKGFFQETEAVEEEMAAIRDALARLNAANEEGKSLHQP DALRALRGRVNADIIAVLRRARDIRARLEAMDRANAAQRRLSAGCREGTPLDRTRTALTAALRKKLKDLMLDFQALRQR IMSEYKDTVERRYYTLTGEVPEEEVIERIISEGRSEELLCAAVAEHGKGAVLATVHEIQDRHDAAREVERSLLELHQVF LDMAVVVESQGEQLDDIERHVNSATTYVQGGNKELRKAREHQRSSRKWLCIGIIILLLLVLLVIVPIATSFKRS* |

TABLE 2-continued

| Amino Acid and Nucleotide Sequences of Rice Polypeptides | |
|---|---|
| SEQ ID NO: 48 | MAMEGKSRRFAVACGVLSQYVRAEQKMAAAAGAAPARAVTTLSLMPGAEVVVEEEERREVGEEEAGPATAPAAPLTIFY<br>GGRMVVFEDFPADKAAEVMRMASSGMAAAPAQREGAALADMPIMRKASLQRFFAKRKDRLAATTPYARPSPAETKASEP<br>EEKKTPTSWLDLAASASAAARRDSLTIAL* |
| SEQ ID NO: 49 | MSSLSRELVFLILQFLDEEKFKETVHKLEQESGFYFNMKYFEDEVINGNWDEVERYLGGFTKVDDNRYSMKIFFEIRKQ<br>KYLEALDKHDRSKAVEILVKDLKVFASFNEELFKEITQLLTLENFRENEQLSKYGDTKSARAIMLVELKKLIEANPLFR<br>DKLQFPNLKSSRLRTLINQSLNWQHQLCKNPRPNPDIKTLFVDHSCGQPNGARAPSPANNPLLGSIPKPGGFPPLGAHA<br>PFQPAPTPVPPLAGWMSNPPAVTHPAVSGGAIGFGTPTNPAAILKHPRTPTTANPSMDYPSGDSDHVSKRTRPVGMSEE<br>VNLPVNMLPVTYPQSHSYPQDDFHKNVARTLSQGSTPMSMDFHPVQQTLLLVGTNVGDIGLWDVGTKERLVLRNFKVWD<br>LTKCSMALQASLVKDPTVSVNRIIWSPDGTLFGVAYSRHIVQIYSYHGGDDIRQHLEIDAHVGGVNDIAFAHPNKQLCI<br>ITCGDDKTIKVWEATSGAKQFTFEGHEAPVYSVCPHYKENIQFIFSTALDGKIKAWLYDNLGSRVDYDAPGHWCTTMAY<br>SADGSRLFSCGTSKDGESHLVEWNESEGAVKRTYQGFRKRSMGVVQFDTTRNRFLAAGDEFLIKIWDMDNTSLLTTIDA<br>DGGLPASPRVRFNKEGTLLAVSTHENGIKILANADGVRLLRTLENRSFDASRSASETVTKPLMNPLTAAAAAAASAAAA<br>GTSSGNAAPPAITALNGDSRSLVDVKPRIADEPLDKSKVWKLMEITESSQCRSLKLTDNMRTSKISRLIYTNSGVAILA<br>LASNAVHLLWKWPRNDRNSSGKATASVSPQLWQPPSGILMTNDITDNPEEAVHCFALSKNDSYVMSASGGKISLFNMMT<br>FKTMTTFMPPPPAATFLAFHPQDNNIIAIGMDDSTIQIYNVRIDEVKSKLRGHSKKITGLAFSNVLNVLVSSGADAQIC<br>VWSTDGWDKLKSRMLQIPSSRPSSIILDTRVQFHQDQLHFLVVHETQIAIYETTKLEPVKQWPVRENSSPITHAMFSCD<br>SQLIYASFLDATVCIFNASSLRLQCRILPASYLPQNISSNVYPVVVAAHPSEANQFALGLTDGGVYVLEPLESERKWGN<br>PPPAENGSTSALSTPPNGASSSDQPER* |
| SEQ ID NO: 50 | ATGTCTCACCCCCACGCCACCGCCCCCAAGCGCCCCGGCCACTTCTCCTCCTCCGCCGCCGCCTCCTCCCCGACC<br>TCCCCCGCGCAGCCGCACATGAAGAAGGCCAAGTTCCCCGGCTCCTCCTCCTCCTCCTCCTCCGCCGCCGCCCCCGGG<br>GTCACCGAGAAGAACGGGCTCCACGTCGATCCCACGGCCGCCGCCGCCCGGACCGGTGGGCGCACCAACGGCGAGGAG<br>GATGCGGAGATGGTGCTCGCCGACCAGGAGGAGCTCGCCGCTCCGAGCGCATCGGCCCCGGCGGGGGTCGCCGCCAAC<br>CTCTTCCGGAAGAAGGCCACACTCCCCCAGCCATCCGCCGCCCGCAAGCCCCTCCGAATCAAAATAGGTCAGCCAAAA<br>TTGCCAACAAACTTTGAGGAGGATACATGGGCTATTTTGAAAGATGCTATTACAGCTATATTTCTAAAACAGAAACTT<br>TCGTGCGATGTTGAAAAACTTTACCAGGCTGCAGGTGACCTTTGTCTACACAAGCTAGGCGCAAATCTATACGAACGC<br>ATAAAGAAAGAATGTGAAGTACACATATCGGCAAAAATATCAGCATTAGTGGGTCAAAGTCCAGATTTAGTAGTATTT<br>TTGTCTCTGGTGCAAAGAACATGGCAAGATTTTTGCGATCAGATGTTGATTATTCGTGGTATTGCTTTACTTCTTGAT<br>GTAAAATATGTCAAGAATGTTGCAAACATTTGTTCAGTGTGGGACATGGGGTTGAAGCTATTCCGCAAGCATCTTTCA<br>CTGTCTCCGGAGATTGAACACAAAACTGTTACTGGTCTTCTAAGATTAATTGAGAGTGAGAGGCTTGGTGAAGCAATA<br>GACAGGACATTACTTAGTCATCTTCTGAAGATGTTTACTGCTCTTGGAATGTATTCTGAGAGTTTTGAAAAGCCCTTT<br>CTGGAGTGTACATCTGAATTTTATGCTACTGAAGGTGTTAAATATTTGCAGCAGTCTGATATTCCAGACTATCTCAAG<br>CATGTGGAGACAAGGTTGCAAGAAGAACATGAAAGGTGTATTCTATATTTGGAAGCTAACACTAGGAAGCCGCTTATA<br>ACAGCTACAGAAAAGCAATTATTGCAGCGGCACACATCTGCAATTCTTGAGAAGGGATTCACAATGCTTATGGAAGCA<br>AATCGTGTAAAAGACCTCTCGAGGATGTACACACTCTTCCAGAGGGTTGATGCCATTGAGTTGCTAAAGCAAGCACTT<br>AGTTCATATATTCGGGGCACAGGCCAGGGCATTATCATGGATGAAGAAAAGGACAAAGAACTGGTGCCCTTTCTTCTG<br>GAATTTAAGGCATCGCTTGATAGAATATTGGAGGAAAGTTTTGCCAAAAATGAGGCTTTCTCCAATACAATAAAAGAG<br>TCATTCGAACATCTTATCAATTTACGCCAGAATCGACCTGCTGAATTGATTGCGAAGTTTCTTGATGAGAAACTTCGA<br>GCTGGAAATAAAGGTACCTCCGAAGAAGAGCTGGAGGGAATATTGGATAAAGTTTTGGTTCTGTTCCGATTTATACAA<br>GGAAAAGATGTATTTGAGGCATTCTACAAGAAGGATCTGGCTAAGAGGTTGCTGCTGGGGAAGAGTGCATCGATAGAT<br>GCTGAAAAATCAATGATAACAAAGCTCAAAACTGAGTGTGGAAGTCAATTTACCAACAAGCTGGAGGGAATGTTCAAG<br>GACATTGAATTATCCAAAGAAATAAATGAGTCTTTCAAGCAATCATCTCAAGCAAGGACAAAGCTTCCATCTGGCATT<br>GAAATGAGTGTTCACGTGCTTACAACAGGCTATTGGCCAACATATCCACCAATGGATGTGAAACTCCCCCATGAACTT<br>AATGTCTATCAGGATATATTTAAAGAATTCTATTTGAGCAAGTATAGTGGAAGGCGTTTGATGTGGCAAAACTCATTG<br>GGTCACTGTGTATTAAAAGCAGAGTTCCCAAAAGGTAAAAAGGAACTTGCGGTGTCACTATTTCAGAGTGTGGTTTTG<br>ATGTTGTTCAATGATGCACAAAAACTAAGCTTCCTCGATATCAAGGAATCGACTGGTATTGAGGATAAAGAATTGCGA<br>AGAACGCTGCAATCACTTGCATGCGGTAAAGTTCGGGTTCTCCAAAAGATGCCAAAAGGGCGAGACGTAGAAGATAAG<br>GACGAATTTGTATTTAATGAAGAATTTAGTGCCCCTCTCTATCGCATAAAGGTGAATGCTATTCAGATGAAGGAGACG<br>GTTGAAGAAAACACAAGCACAACTGAGAGAGTATTCCAGGACAGACAGTATCAGGTGGATGCTGCCATAGTTCGAATA<br>ATGAAGACACGTAAAACCCTCAGCCACACGCTTCTAATAACTGAGCTTTTTCAGCAGCTCAAGTTCCCAATCAAGCCA<br>TCGGATATCAAGAAAAGAATAGAGAGCCTAATCGACAGGGAGTACCTGGAGAGAGACAGGAGTAACCCCCAGATCTAC<br>AATTACCTGGCTTGA |
| SEQ ID NO: 51 | ATGGACGCCGATGAGGCCGCGGGGAGTAGCAGGAGGATGGATCTGAACCTCTACCTTGGCCTCCCACGCGCCCCGC<br>GCCCGCGCCGCTCCGACCTCGGCTCCGACCTCGCCCTCAGCACCCCGATGCCCTCCTCCCCGTCCTCCTCCGCAGC<br>CTCCGTCGACGCGCCGCCGCCACCGCCCGAGCTGTCGCATCCCCCGTACTCCCCCTCTCACGCCGACCTTTCCCCT<br>CCGCTGCAGGAGGTCTACTCCCTGTACAACCCCGACGACCCGCCTGCTTCCGAGACGCACCTGCCGCCGTATGCGC<br>CGCCTCCGGCTCCGGTGGTCTCGGAGCTCCCTGACGACCTCGAGTTTGGCCTCCACCCCCCGCCGCCGCTGGTGCG<br>TGCCAGCGAACTGCTAGGTTGGGAGGACCGGCCGTCTTCGTCGACGGCATCGTCCTCTTTCCTCCCTGACACCGCA<br>GCCCGTTACTGGCGGCTTCTCGAGCAGACTGGAAGCAGATGGCTCCGTGCGAGGCGGTTTAGGTCGGACCTTCCGC<br>CACTCAGTTCTGAAGCTTACCCAGCTGGGCGTGATGCTGCCGCAGTCCCAGTGCTGCAGCATGAACCGATGAATGA<br>TACTGTTGAACATAATAAGGTAGCTGCCGATGGCGCGGAAGTAGGCGCCTCCGAGGAATCGGAGGAGCAGGGCAGG<br>AGCGCTGCCACATTTGAGTGTAATATATGCTTCGATATGGCCAGCGAGCCGGTGGTCACCTCTTGTGGCCATCTCT<br>TCTGCTGGCCTTGCTTGTACCAATGGCTCAATGTTTATTCCAATCACAAGGAATGCCCAGTCTGCAAAGGCGAGGT<br>GACTGAGGCGAATATTACTCCGATCTATGGGAGAGGGAATTCATGTTTGGATGCCGAGAAGGCTGTGGAAGGTGGG<br>AAACAAACAGGTCCTACTATCCCACCAAGACCACATGGAAATCGGCTCGAAAGCTTCAGGCAGCAGTTTCACCATT<br>TGCGACCGATCTCAAGAAGGCTTGGTGAGGCTCATGGGTTATTGTCATCATGGAGGCGCCTTCTGGACCAACAGAT<br>TATGAATACTGCGAGTAGGTTTGAAGGTCCGCCTGAATCAGCTGTGCAGGAAATGGTTGACACTGCTCACGCTCAG<br>CACACCAGTCGCCTAAGTAGATTGGCGTCAAGGATGAGAGCAAGACGGTTGCTGAGAGAAGCAGACAACCCTAACC<br>CTCCCGATGGCGGATCCACTTCCCCTGACAGTGGTTTGATCAGAAACAATGCATCGGATCCATCCAGAAATGGTCC<br>GAGCTCATTATTACCAGATGGAATTGACTGGTTGCGTGGACTTACCCTTCTTGGGTATGAAGACACGGAAAGATTT<br>GCATCTGCCATGAGTGATTTTAGAAGGATAACTGGACCAAGCCAATATGGTGCATCGGCTTCATCATCGAATCCTC<br>CAAATCTCGAGTCAACATTTGACAGAACTCATGTTGTTGCAGCACCTTCTGCAGACCAAGCATCTAACTCAAGCAC<br>TGCTGCAGTGATACAGGGGGATGCTGGTATCTCTGAGAGTGCAGGAGAACCAAGTAACGCGGGGTCATCAAGATCC<br>CTGAGGAGGAGAGGGAGGAGCAGTGCCCTGGGTTCTTTGGATGCTGATGGCGGGGGCCTCCAACGGAACAAGAGGC<br>GAAGGATAAACTGA |

TABLE 2-continued

| Amino Acid and Nucleotide Sequences of Rice Polypeptides | |
|---|---|
| SEQ ID NO: 52 | ATGGCTGGTGGGAGCTGCGACGTGTGCAAGGAGGCGCCGTCCAAGTACAAGTGCTCCGCTTGCCGCACGCCATATTG CTCGGTGGCATGCTTTAAAAATCACAAAGATAAATTTTGCCAGAAGACAATACCTCTGGAAGAAGTTAGCAAGTCAT CTCTTCAGGAGGAAATTTCAAGGAACTCTAGGTCACTGGAAGAAGCAACAAATTGTCCTAATGACAAGGATCAAACC CCGTCTTTATTATCGGACACGACTTGTCCCACACAATATCCAAACACATTGCACTCTGCAAAATCTCTTGAAGTTGA GGATCCAAGCTGGCTTGTTGACAAGAATGGATTAAGATCTTTAGCGGAATCTAATGAGATCCGAGATGCTCTGAAAG ATTGTAAGCTTCAGCAAATGCTACTTAAGATTGATGGCTCTGCAGAGCCAGAAAAGGAATTAGAGAAATTGATGGAA GGACAAGTTTTTCAACAGTTCACCAATAAGATTCTTGACATTGTTAGCCCACAACAATGA |
| SEQ ID NO: 53 | ATGCTGGGAGAGGCCGCCTCACCGTGGAGCCTGGCCGGCGCGGGCGCGGCCGTGGCGCTGCTGTGGCTGTGCGCCT GGACGCTGCAGTGGGCGTGGTGGACGCCGCGGCGGCTGGAGCGGGCCCTGCGGGCGCAGGGCCTCCGGGGCACCAG GTACCGCCTCTTCATCGGCGACGTGGCCGAGAACGGCCGGCTCAACAGAGAGGCCGCGTCAAGGCCGCTGCCGCTC GGCTCGCACGACGTCGTCCCGCGCGTCATGCCCTTCTTCTGCAACGTCCTGAAAGAGCACGGGAAACTGTCGTTCG TTTGGACTGGCCCAAAGCCATTCGTGATTATCAGAGACCCTGACTTAGCGAGGGAGATTTTGTCCAACAAGTCTGG CAATTTCGCCAAGCAAACGACCGCGGGTATTGCTAAGTTCGTAGTTGGCGGAGTTGTAACGTATGAAGGTGAGAAA TGGGCAAAACATCGGAGAATTCTCAACCCTGCCTTCCACCAGGAGAAAATAAAGCGGATGCTGCCAGTGTTTTTAG CATGTTGCACCAAAATGATCACTAGATGGGTGAATTCAATGTCTTCAGAAGGAATATCTGAGTTAGACGTTTGGGA TGAATTTCAAAATCTTACTGGAGATGTCATCTCAAGAACGGCATTTGGGAGCAGCTACCAGGAGGGGTGGAGAATT TTTCAGTTACAAGAAGAGCAAGCTAAACGCGTACTTAAAGCTTTTCAGAGAATCTTTATCCCAGGCTACTGGTACT TACCAATCGAAAACAACAGAAGGATCAGGGAAATTGATCAAGAAATCCGCACAATTCTGCGAGGAATAATAGTAAA AAGAGACAAGGCAGTTAGAAATGGTGAAGGTAGCAATGATGATTTGTTGGGATTATTGGTGGAATCGAATATGAGG CAATCAAATGAAAAAGAAGATGTGGGAATGAGTATAGAAGATATGATTGAGGAATGCAAGTTATTTTACGCTGCTG GTTCGGAGACAACATCAATGTTGCTCACTTGGACTTTAATTCTGCTAAGCATGCACCCTGAATGGCAAGAGCAGGC AAGAGAGGAAGTGATGCACCATTTGGAAGAACCACACCAGATCATGATGGCTTGAGTCGTCTAAAGATTGTAACG ATGATTCTCCACGAGGTTCTTAGGTTGTACCCACCGGTGGTATTCCTCCAAAGAACAACACACAAGGAAATAGAGC TTGGTGGCATCAAATACCCTGAAGGAGTGAACTTCACATTGCCTGTTCTATCCATTCACCACGATCCTAGCATCTG GGGACAAGATGCAATCAAATTCAACCCGGAAAGGTTCGCCAACGGAGTCTCCAAGGCAACGAAGTTTCAGACCGCG TTCTTTTCGTTTGCATGGGGTCCTCGGATCTGCCTTGGCCAGAGCTTTGCAATTCTGGAAGCCAAGATGGCGCTCG CCACCATCCTCCAGAGCTTCTCCTTCGAGCTCTCGCCGTCATACACCCACGCACCACACACCGTGCTAACTCTCCA ACCACAGTACGGTTCTCCAATTAAATTGAAGAAGCTCTAG |
| SEQ ID NO: 54 | ATGGCTAAAGATCACGTGAAGATTGTGTTAAAAGCTTACATTTTAGGACCTATAAAGTATATTTTAAGTTTAGAAT CTTTGTACCATAATTGTGGTGGACTGGTGGTAACAATGATTCTCCACGAAGTTATTAGGTTATACCCATCGGGGAT CTTCCTCCAAAGAACAACACGCAAGGAAATAGAGCTTGGTGGCATCAAATACCCTGAAGGAGCAAACTTCACATTG CCCGTTCCATCTATCCACCATGATCCCAGCATCTGGGGAGGAGATGCAAGCGAGTTCAACCTGGAGAGGTTTGCCA ACGGAGTCTCCAAGGCAACGAAGTTTAAGACCGCATTCTTTATGTTTGGATGGGGTTCTCGGATCTGCCTTGGAC AGAACTTTGCAATGCTGGAAGCCAAGATGGCGCTCGCCACCATCCTCCAGAGCTTCTCCTTTGA |
| SEQ ID NO: 55 | ATGTGCTGTTCAGCTGTTGCTGTTATGAAGTGGGAAGCTCTATTACCAAATGATACCTTTCTTATTGTTGCCTCCT CTGATGGCGTATTTGAGAAAGTGACTATGCAGGATGTCTGTGATCTGATGTTGTACGTGAAACTTGGTGTTAAGCA AGAATTAGGATCCTTTGCATTAACACAACAGAATTTGGCAGATTATGTTGTTGATCTTTCTTTATAG |
| SEQ ID NO: 56 | ATGTCCTCTAGCGATCAGAACCCATCGCCAACACCGGCGTCCGGCACCGGCACGTCCGTGCCGCCGCCAGGCAGGG CGACGACGGTATCCTCGCAGCTCCTGGACATGGGCGCGCAAGCGGTGCAGGCGCTGAAGCCCGTGCGCCAGATGAA GCAGCACGCGTGCAGCTTCGCGCTGTACGCTCACGACCTGAGCCGCCAGGTCGAGGTCCACCACTTCGTCTCCCGC CTCAACCAGGACGTCCTCCAGTGCGCCGTCTACGACTCCGACAAGCCCTCGGCCCGCCTCATCGGCGTGGAGTACA TCGTGTCGGACGCCATCTTCGAGAGCCTGCCTCCGGAGGAGCAGAAGCTGTGGCACTCGCACGCGTACGAGGTGAA GGCCGGGCTGTGGACCGACGTCGGCGTGCCGGAGCCGCTGCAGAGCTCGGAGATGGCGAGGATGGCCAAGACGTAC GGCAAGCTCTGGTGCACCTGGCAGGTGGACCGCGGCGACGCGCTGCCCCTGGGCGCGCCGGCGCTCATGGTGTCGC CGCAGGCCGTGGAGCCCGGGCGGGTGCGCGCCGAGCTCGTGCACGGCCGCGACGAGAGGTACAAGATCGACAGCTC GGCGCAGGGGCTGAAGGGGGCCAGGGTTGAGATGGACGAGCCGGAGTGGATCAACCCGAACGCCGACTACTGGCGC CTACACGGCAAGGGGTTCGCCATCGACGTCACCGCCACCGAGATGAAGCGCCACGCGCCCTTCCCGTGA |
| SEQ ID NO: 57 | ATGACGCCTCCACCGCCGTCGCCGCCGCACGAGAGGAAAACGTGGGCGGAGTCGGTGGCCAGCGAGTTTCGGGCGC AGCGCGGCATCGCGTTCCCTCTCATCGCCATGAACCTCACCTGGTTCGCCAAGCTGGCCGTCACCACCGCCTTCCT CGGCCGCCTCGGCGACCTCCAGCTCGCCGCCGGCACCCTCGGCTTCAGCTTCGCCAATGTCACCGGCTTCGCCGTC CTCACCGGCCTCTGCGCCGCCATGGACCCCATCTGCGGGCAGGCGCACGGCGCCAGCAACGGGAAGCTCCTCCGCA AGACGCTGGTGATGGCCACCATCCTGCTGCTGGGCGCGTCCATCCCCATCGCCTTCCTGTGGCTGCACGTGGACGC CGTCCTCCTCCGGTTCGGACAGCAGGCGGACATGAGCAGCAACGCACGCAGCTACGTGGTGTGCCTCCTCCCGGAC CTCGCCGTCACCTCCTTCGTCAACCCGCTCAAGTCGTACCTGAGCGCGCAGGGGGTGACGCTCCCCACGCTGTTCG CCTCCGCCCCTGGCCCTGGCGCTCCACGTCCCCCTCACCATGTGGATGGCCAGGACCAGGGGCATCCAGGGCGTCGC CACCGCCGTGTGGGTCAGCGACCTGGCCGTGGCCGTCATGCTCGCCGGCTACGTGCTCGTCTCGGAGCGACGACGG AAGGCGGGAGGGGGCGGCGGATGGGTGGAGCAGACGAGGGGTGAGTGGGTCCGGCTCCTCCGGCTGGCCGTTCCCA GCTGCCTCAACACCTGCCTGGAGTGGTGGTGCTACGAGATACTGGTGCTCCTGACGGGACGCCTCCCGGACGCCCG GCGCACGGTGGCGGTGATGGCCGTGACGCTCAACTTCGACTACCTGCTGTTCGCGGGGATGCTGTCCCTGTCGGTG AGCGCGTCGGTGCGCGTGTCGAACGAGCTGGGCGCGGGGGAGGCGTGGGCGGCGAGGCGCGCGGGCATGGTGTCGA TCGTGGGCGGCGCGGTGGGCGGGGTGGGCGGCGGGGTGGCGATGGTGGCGGCGCGGCGGGCGTGGGGGAGCATATA CAGCTCAGACGCCGGGGTGCGGGAGGGGGTGGGGAGGGCGATGGAGGTGATGGCGGTGCTGGAGGTGGTGAACTTC CCGCTGAACGTGTGCGGGGGGATAGTGCGAGGGACGGCGAGGCCGGCGGTGGGGATGTACGCCGTGGTGGCCGGCT TCTACGTGCTGGCGCTGCCGCTCGGGGTCGCGCTCGCCTTCAAGGCCAGACTTGGGATCCAGGGCCTCCTCCTGGG CTTCCTGGTGGGCGCCGCGGCCAGCTTGGCGGTGCTCCTCACCTTCATCGCGCGCATGGATTGGCCCGCCGAGGCC CAAAAGGCGCGGACTAGAACCACAGCAACCGTGGCCCAATTCCACCAACACGACGAGGTCGTCCAGCCTTGA |
| SEQ ID NO: 58 | ATGCCGGAGGCTGCGGCGGCGGCGGCGGGCCACATGGATCCGGTTGGCGACGAGGCGGCGGAGAGGAGGGAGATGG AGGAGAAGGAGGAGGAGGAGGAGGAGGAGGAGGAGGATGAGGAGTTCTACGAGTCGCTGGATCGGATCCTGTCGTC GTCGTGCTCGTCCACGTCCGCCTCCGACGACGACGACCAGCAGCACCGGCGGAGGCGGCGGCACCACCCGCAGCCG CAGCAGCTGTCGTCGTCCGCGACGTTCTCCGCGTACGAGGTCTGGATCTCCGAGCCGACATCCGTCGAGGAGCGCC GCCGCGTGCTGCTGCGTCGGCTCGGCCTCGCCCACGACTCCGAGCCCCTGCCGCACCCGTCCCCACGCGTATCATC CTCCTCCCCTCGTTCGCCGACCCCTTCCCCCCCGTCCTCGTCGCCGCCTCGGCCGGCTCCCGTGGTGGCCGCCGCG |

TABLE 2-continued

| Amino Acid and Nucleotide Sequences of Rice Polypeptides | |
|---|---|
| | GAGGAGCCCAGATCCAGCGGCCACGGGAAGCCGCCGCTTGCGAGGAACCCGAGCGGCGGCGCGGAGCAATGCCGGA<br>TCCGGAACCTGGACGACGGTACGGAGTTCGAGGTCGGGGAGGTTCACGATGAGGTGGTCCGGGAGGTCGGCACTGG<br>CCGGCAGCTCACCTTCGAGGAGTTCGAGCTCTGCATTGGCCGCTCCCCGATCGTCCAAGAGCTCATGCGCCGGGCC<br>ACCACAGCCGCATCATCCTCCACCTCCGACCACGCCGCCCCAGCATCCAAGCCACGGAGGAAGCCTGGAGGCTGGC<br>TGCGTGGCATCCGGCACCTGGCGGGAAGCGTTGCATACGGGCGCAGCAGCACCGATGAGAGGGACAAGGAGAAGGA<br>GAAGGAGAAGAAGGAGAGGGAAGCGCGGCGCCTGAGCTCCGCCACCGATGACAGCCTTGACGGCAACGGCTCGCGC<br>AATGCAGGGAGGGTCAGGGTGCGGCAGTATGGGAAGGCGTGCAAGGAGCTCACCGGGCTGTTCATGACACAAGAAT<br>TGGCTGCCCATTCGGGCTCAATCTGGTGTATCAACTTCAGCTTGGATGGACGATACCTTGCAAGCGCTGGCGAGGA<br>CCGTGTCATCCATGTGTGGGAGGTATCAGAGGGAGAAAGAAAGGGAGAATTGCTCGGGGAAGGTACGGTGGCAAGG<br>GAGAACGGTGGTGGCTGCAGCCCGTTTCTTGCAGCTGTTGGGAATGGATCGCCGGAGCTGGCAACATTGTCATTGA<br>GCTGTGCTGACGGGGGTTTTGTGGAGAAGAAGAGGAGGCCAAGGATGCAAAGCAGCCGGAAGTCTGTTGGCTCTGA<br>TCATCTAGTTGTGCCTGAATGTGTGTTTGGGTTCAGAGATAAACCAGTATGCTCTCTATTGGGTCACGCCGCCGAT<br>GTTCTTGATCTATCATGGTCCAAATCTCAGTACTTGCTTTCATCCTCAATGGACAAAACTGTTAAACTATGGGACA<br>TTACTACTAGTACCTGTCTGAAAACATTTTCACACACAGACTATGTGACTTGCATCCAGTTCAATCCCGTGGATGA<br>TAACTTCTTCATTAGTGGATCACTGGATGAAAAAGTACGCATTTGGAATGTACATGATCGTAAGATTGAGGATTGG<br>AATGATCTTCATGAGATGGTCACTGCTGCGTGTTACTCCCCTGATGGACAGGTTGCACTGGTGGGATCACACAAGG<br>GAAGCTGTCATTTATTTGATACAACTGAAAAGAAGCTTCAGTACAAAAGTCAGATAGAACTAAGAATCAGGAAGAA<br>GAAGTCTGGCCAGAAGAAGATAACTGGCTTCCAGTTTGCTCCTGGAAGCTCGTCGGAAGTCCTGATTACCTCTGCA<br>GATTCAAGAATCCGTGTTGTTAATGGTGATGAACTCGTTCACAAATTTAAAGGGTTCCGAAATACAAGTAGCCAAA<br>TATCCGCTTCTGTAGCTCCAAACGGGAAATATGTGGTCTGTGCCAGTGAGGACTCCCACGTGTATGTCTGGAGGCA<br>TGACAATACTTCCCATCCGAGCAGAAGCAGGAGTGCAGTTGATGTAACCAACTCATATGAGCATTTCCATTGCCAT<br>GATGTCACTGTGGCTATCACATGGCCCGGCGCTGAATCCCGTGGCTCATTCGGGTCCCGTAGCAGCAGAAACAGTG<br>ATTCAGACGATGCAGTGATGAACACGGGTCGGGATGCCCCTGTAGAGAACAGTGAGCATGATCTGAATGGCACTGT<br>CAATAGATGCACCAAGCGCCCAGTTTGTGAAGGTGTTGCAAGCACAAGCAATCCTCCAGCGGATGGAGTATCAACG<br>TCCTGGCCTGACGAGAAACAATCGTCTGCCAAGAGCAGTCCTGGTCACTGCTCATCCGACCTTTGCATTGGAGCTT<br>TGGATGTTCAGCGCCGGTCAGCTTGGGGATTGGTGATTGTCACTGCAGGAAGGGGTGGTGAAATTAGGGTGTTCCA<br>GAATTTCGGCTTCCCGGTTCAAGTGTAA |
| SEQ ID NO: 59 | ATGGCTCCTGCGGTTGCCTCCTCCCCGTCACTCGTGCTCTCCGCCGCCGCCGCCACCGCCTCCAACAAGCGCCCGG<br>CCGATTCCGACGCCTCGCCGCCGCACCAGGGAGATCGCACGGGGCAGCAGGAGAAGAAGCAGCAGCAGCTGGAGTG<br>CCCGCGCTGCCGATCCACCAACACCAAGTTCTGCTACTACAACAACTACAGCACGTCGCAGCCGCGCCACTTCTGC<br>CGCGCCTGCCGCCGCTACTGGACGCACGGGGGCACGCTCCGCGACGTGCCGGTGGGCGGCGCCTCTCGCCGCGGCG<br>GCGGCGGCAAGCGCCGCAGGGTCTCCGCCGACGCCGACCCTTCCTCGGCGTCGCCGCCGCCACCCACGACTTCCAC<br>CACGGACGCGTACGCCGACCTCCCAGCCGGCTTCCCGTTCCTCAGTGACGGCGCCTTCCTGCCGCAGTTCGGCCTC<br>GCCGGCGTTGCGCCGGCCGCGTTCTCTTGGGCATCGGCTGTCCCTGACTTGTACAACTGCGGGATCGCGCCGTGGG<br>ACGATGGAACGGCGGTCACCGGCGCGGCGTGGGACAACTTCGCCGACATCGCCGGCCTTGATCTCAGCTGGCCGCC<br>GCCGGGTAACTGA |
| SEQ ID NO: 60 | ATGTCTCACCCCCACGCCACCGCCCCCAAGCGCCCCGGCCACTTCTCCTCCTCCTCCGCCGCCGCCTCCTCCCCGAC<br>CTCCCCCGCGCAGCCGCACATGAAGAAGGCCAAGTTCCCCGGCTCCTCCTCCTCCTCCTCCTCCGCCGCCGCCCCCG<br>GGGTCACCGAGAAGAACGGGCTCCACGTCGATCCCACGGCCGCCGCCGCCCGGACCGGTGGGCGCACCAACGGCGAG<br>GAGGATGCGGAGATGGTGCTCGCCGACCAGGAGGAGCTCGCCGCTCCGAGCGCATCGGCCCCGGCGGGGGTCGCCGC<br>CAACCTCTTCCGGAAGAAGGCCACACTCCCCCAGCCATCCGCCGCCCGCAAGCCCCTCCGAATCAAAATAGGTCAGC<br>CAAAATTGCCAACAAACTTTGAGGAGGATACATGGGCTATTTTGAAAGATGCTATTACAGCTATATTTCTAAAACAG<br>AAACTTTCGTGCGATGTTGAAAAACTTTACCAGGCTGCAGGTGACCTTTGTCTACACAAGCTAGGCGCAAATCTATA<br>CGAACGCATAAAGAAAGAATGTGAAGTACACATATCGGCAAAAATATCAGCATTAGTGGGTCAAAGTCCAGATTTAG<br>TAGTATTTTTGTCTCTGGTGCAAAGAACATGGCAAGATTTTTGCGATCAGATGTTGATTATTCGTGGTATTGCTTTA<br>CTTCTTGATGTAAAATATGTCAAGAATGTTGCAAACATTTGTTCAGTGTGGGACATGGGGTTGAAGCTATTCCGCAA<br>GCATCTTTCACTGTCTCCGGAGATTGAACACAAAACTGTTACTGGTCTTCTAAGATTAATTGAGAGTGAGAGGCTTG<br>GTGAAGCAATAGACAGGACATTACTTAGTCATCTTCTGAAGATGTTTACTGCTCTTGGAATGTATTCTGAGAGTTTT<br>GAAAAGCCCTTTCTGGAGTGTACATCTGAATTTTATGCTACTGAAGGTGTTAAATATTTGCAGCAGTCTGATATTCC<br>AGACTATCTCAAGCATGTGGAGACAAGGTTGCAAGAAGAACATGAAAGGTGTATTCTATATTTGGAAGCTAACACTA<br>GGAAGCCGCTTATAACAGCTACAGAAAAGCAATTATTGCAGCGGCACACATCTGCAATTCTTGAGAAGGGATTCACA<br>ATGCTTATGGAAGCAAATCGTGTAAAAGACCTCTCGAGGATGTACACACTCTTCCAGAGGGTTGATGCCATTGAGTT<br>GCTAAAGCAAGCACTTAGTTCATATATTCGGGGCACAGGCCAGGGCATTATCATGGATGAAGAAAAGGACAAAGAAC<br>TGGTGCCCTTTCTTCTGGAATTTAAGGCATCGCTTGATAGAATATTGGAGGAAAGTTTTGCCAAAAATGAGGCTTTC<br>TCCAATACAATAAAAGAGTCATTCGAACATCTTATCAATTTACGCCAGAATCGACCTGCTGAATTGATTGCGAAGTT<br>TCTTGATGAGAAACTTCGAGCTGGAAATAAAGGTACCTCCGAAGAAGAGCTGGAGGGAATATTGGATAAAGTTTTGG<br>TTCTGTTCCGATTTATACAAGGAAAAGATGTATTTGAGGCATTCTACAAGAAGGATCTGGCTAAGAGGTTGCTGCTG<br>GGGAAGAGTGCATCGATAGATGCTGAAAAATCAATGATAACAAAGCTCAAAACTGAGTGTGGAAGTCAATTTACCAA<br>CAAGCTGGAGGGAATGTTCAAGGACATTGAATTATCCAAAGAAATAAATGAGTCTTTCAAGCAATCATCTCAAGCAA<br>GGACAAAGCTTCCATCTGGCATTGAAATGAGTGTTCACGTGCTTACAACAGGCTATTGGCCAACATATCCACCAATG<br>GATGTGAAACTCCCCCATGAACTTAATGTCTATCAGGATATATTTAAAGAATTCTATTTGAGCAAGTATAGTGGAAG<br>GCGTTTGATGTGGCAAAACTCATTGGGTCACTGTGTATTAAAAGCAGAGTTCCCAAAAGGTAAAAAGGAACTTGCGG<br>TGTCACTATTTCAGAGTGTGGTTTTGATGTTGTTCAATGATGCACAAAAACTAAGCTTCCTCGATATCAAGGAATCG<br>ACTGGTATTGAGGATAAAGAATTGCGAAGAACGCTGCAATCACTTGCATGCGGTAAAGTTCGGGTTCTCCAAAAGAT<br>GCCAAAAGGGCGAGACGTAGAAGATAAGGACGAATTTGTATTTAATGAAGAATTTAGTGCCCCTCTCTATCGCATAA<br>AGGTGAATGCTATTCAGATGAAGGAGACGGTTGAAGAAAACACAAGCACAACTGAGAGAGTATTCCAGGACAGACAG<br>TATCAGGTGGATGCTGCCATAGTTCGAATAATGAAGACACGTAAAACCCTCAGCCACACGCTTCTAATAACTGAGCT<br>TTTTCAGCAGCTCAAGTTCCCAATCAAGCCATCGGATATCAAGAAAAGAATAGAGAGCCTAATCGACAGGGAGTACC<br>TGGAGAGAGACAGGAGTAACCCCCAGATCTACAATTACCTGGCTTGA |
| SEQ ID NO: 61 | ATGGACGCCGATGAGGCCGCGGGGAGTAGCAGGAGGATGGATCTGAACCTCTACCTTGGCCTCCCACGCGCCCCGCG<br>CCCGCGCCGCTCCGACCTCGGCTCCGACCTCGCCCTCAGCACCCCGATGCCCTCCTCCCCGTCCTCCTCCGCAGCCT<br>CCGTCGACGCGCCGCCGCCACCGCCCGAGCTGTCGCATCCCCCGTACTCCCCCTCTCACGCCGACCTTTCCCCTCCG<br>CTGCAGGAGGTCTACTCCCTGTACAACCCCGACGACCCGCCTGCTTCCGAGACGCACCTGCCGCCGTATGCGCCGCC<br>TCCGGCTCCGGTGGTCTCGGAGCTCCCTGACGACCTCGAGTTTGGCCTCCACCCCCCGCCGCCGCTGGTGCGTGCCA<br>GCGAACTGCTAGGTTGGGAGGACCGGCCGTCTTCGTCGACGGCATCGTCCTCTTTCCTCCCTGACACCGCAGCCCGT |

TABLE 2-continued

| Amino Acid and Nucleotide Sequences of Rice Polypeptides | |
|---|---|
| | TACTGGCGGCTTCTCGAGCAGACTGGAAGCAGATGGCTCCGTGCGAGGCGGTTTAGGTCGGACCTTCCGCCACTCAG TTCTGAAGCTTACCCAGCTGGGCGTGATGCTGCCGCAGTCCCAGTGCTGCAGCATGAACCGATGAATGATACTGTTG AACATAATAAGGTAGCTGCCGATGGCGCGGAAGTAGGCGCCTCCGAGGAATCGGAGGAGCAGGGCAGGAGCGCTGCC ACATTTGAGTGTAATATATGCTTCGATATGGCCAGCGAGCCGGTGGTCACCTCTTGTGGCCATCTCTTCTGCTGGCC TTGCTTGTACCAATGGCTCAATGTTTATTCCAATCACAAGGAATGCCCAGTCTGCAAAGGCGAGGTGACTGAGGCGA ATATTACTCCGATCTATGGGAGAGGGAATTCATGTTTGGATGCCGAGAAGGCTGTGGAAGGTGGGAAACAAACAGGT CCTACTATCCCACCAAGACCACATGGAAATCGGCTCGAAAGCTTCAGGCAGCAGTTTCACCATTTGCGACCGATCTC AAGAAGGCTTGGTGAGGCTCATGGGTTATTGTCATCATGGAGGCGCCTTCTGGACCAACAGATTATGAATACTGCGA GTAGGTTTGAAGGTCCGCCTGAATCAGCTGTGCAGGAAATGGTTGACACTGCTCACGCTCAGCACACCAGTCGCCTA AGTAGATTGGCGTCAAGGATGAGAGCAAGACGGTTGCTGAGAGAAGCAGACAACCCTAACCCTCCCGATGGCGGATC CACTTCCCCTGACAGTGGTTTGATCAGAAACAATGCATCGGATCCATCCAGAAATGGTCCGAGCTCATTATTACCAG ATGGAATTGACTGGTTGCGTGGACTTACCCTTCTTGGGTATGAAGACACGGAAAGATTTGCATCTGCCATGAGTGAT TTTAGAAGGATAACTGGACCAAGCCAATATGGTGCATCGGCTTCATCATCGAATCCTCCAAATCTCGAGTCAACATT TGACAGAACTCATGTTGTTGCAGCACCTTCTGCAGACCAAGCATCTAACTCAAGCACTGCTGCAGTGATACAGGGGG ATGCTGGTATCTCTGAGAGTGCAGGAGAACCAAGTAACGCGGGGTCATCAAGATCCCTGAGGAGGAGAGGGAGGAGC AGTGCCCTGGGTTCTTTGGATGCTGATGGCGGGGGCCTCCAACGGAACAAGAGGCGAAGGATAAACTGA |
| SEQ ID NO: 62 | ATGGTGGGAGGAGAGCTTGTGCTGGCTGCTCTGGTGATCCTGCTTGCTTTGCTGCTGACCCTGGTGCTGAGCCACTT CCTGCCTTTGCTCCTGAATCCCAAGGCTCCCAAGGGAAGCTTTGGGTGGCCTCTCCTTGGTGAGACGCTGAGGTTCC TCAGTCCTCATGCTAGCAACACCCTGGGCAGCTTCCTGGAGGATCACTGCTCCAGGTATGGGAGGGTGTTTAAGTCC CATCTGTTCTGCACCCCCACCATAGTGTCCTGTGACCAGGAGCTGAACCACTTCATCCTTCAGAATGAGGAGAGGCT GTTTCAGTGCAGCTACCCCAGGCCAATTCATGGCATTCTGGGCAAGTCCTCCATGTTAGTGGTCCTAGGGGAGGACC ACAAGAGGCTCAGGAACCTTGCTCTAGCACTGGTCACCTCCACAAAGCTCAAGCCCAGCTACCTTGGCGACATTGAG AAGATTGCACTGCATATAGTTGGGTCATGGCATGGCAAGAGCAAGGACAAGGGGATGGTCAATGTCATCGCCTTCTG CGAGGAGGCAAGAAAGTTTGCATTCAGTGTAATAGTGAAGCAGGTGCTGGGGCTATCACCAGAGGAGCCGGTCACTG CCATGATACTTGAAGATTTCCTCGCCTTCATGAAGGGTCTCATCTCTTTCCCTCTCTACATCCCAGGGACGCCCTAT GCCAAAGCTGTGCAGGCCAGAGCGAGGATATCAAGCACTGTGAAGGGTATTATTGAGGAGAGGAGGAATGCTGGCTC CAGCAACAAGGGTGATTTCCTTGATGTGCTGCTTTCAAGCAATGAGCTCTCTGATGAGGAGAAAGTGAGCTTTGTGC TGGATTCCTTACTGGGAGGATATGAGACCACCTCACTCTTGATCTCCATGGTTGTGTATTTCCTTGGGCAGTCAGCT CAAGATCTGGAACTAGTGAAGAGGGAGCATGAAGGCATAAGATCGAAGAAAGAGAAGGACGAGTTCTTGAGCTCTGA AGACTATAAGAAGATGGAATATACCCAACATGTTATCAATGAGGCACTGAGATGTGGCAACATTGTCAAGTTTGTCC ACAGGAAGGCTCTCAAAGATGTCAGATACAAAGAGTATCTGATTCCTTCTGGTTGGAAGGTCCTACCTGTTTTCAGT GCTGTTCATTTGAACCCCTTACTTCATGGAAATGCCCAACAATTTCAGCCCTGCAGATGGGAGGGTGCAAGCCAAGG GACAAGCAAGAAGTTTACGCCGTTCGGCGGTGGCCCCCGGCTCTGCCCTGGATCAGAGCTTGCAAAAGTAGAGGCTG CTTTCTTCCTCCATCACCTTGTGCTCAATTATAGATGGAGAATCGATGGCGATGACATTCCGATGGCATACCCGTAC GTGGAGTTCCAGAGAGGTCTGCCCATAGAAATCGAGCCACTTTGCTCTGAATCCTGA |
| SEQ ID NO: 63 | ATGGCGACGCTGCCGGACCTGGGTGTGTCCGCCTTCATCAACATCTTGGGCGCCTTCGTCTTCCTCCTCATCTTCGC CGCCCTCCGCCTCCAGCCCATCAACGACCGCGTCTACTTCCCCAAGCTCTACCTCACTGGCCAGCGACGCCACCACC CTCACCCTCATGGCTTCGTCAACCTCGACCTCTGCTCCTACCTCCGCTTCCTCGCCTGGGTCCCCGGCGCCCTCCGC ATGTCCCAGCCCGACCTCATCCACCACGCCGGCCTCGACTCCGCCGTCTACCTCCGAATCTACACGCTCGGCCTCAA GATATTTTTGCCCATCATGACTGTCGCCTTGCTGGTTCTTATTCCAGTTAATGTCTCTGGTGGCACGTTACTTAATT TACGAAAAGAAATTGTCTTTAGTGATATTGATAAGCTTTCCATATCAAATGTCAACCCTGGATCCAACAGGTTCTTT ATCCATCTATTAATGGCATATGTGTTCACTTTTTGGACTTGCTTTATGCTATACAAAGAGTATAGCAATGTGGCATT TATGAGATTGCACTTCCTGGCTTCTCAGAAGCGTTGTGCTGATCAGTTCACTGTGATTGTTAGAAACATACCTCATG TTTCAAGCCATTCAACATCTGAAACAGTGGATGAATTCTTCCGTAGGAATCATCCAGACCACTATCTTGGTCAGCAG GCTGTTTATAACGCAAACAGGTATGCTAAACTTGTGAAGAAAAAAGAGAGGCTTCAAAACTGGTTGGATTACTACCA GCTGAAGTTTGAAAGGCATCCTGGAAAAAGACCAATTGGAAGGACAGGGTGCCTTGGTTTCTGCGGTAGAGAAGTGG ATCAAATCGACTATTACCGTGCTAGAATCAGCGAGCTTGATAAGAAGCTTGCATCTGAGCGTCAAAGAGTTCTCAAT GACCCAAAAGCTGTTATGCCAGTTGCTTTTGTGACATTTGACTCGAGATGGGGAGCTGCTGTATGTGCACAGACACA ACAGTCAAAGAATCCTACCCAATGGCTAACTGATTGGGCTCCTGAACCGCGGGATGTATATTGGCAGAATCTTGCCA TTCCATTTTTCTCTCTCAGTATCCGCAAGTTCCTGATATCCATTGCAGTTTTTGCTCTGGTGTTCTTCTACATGATA CCTATAGCTTTTGTGCAATCACTTGCCAATCTTGAGGGTATTGAAAAAGTTGCACCTTTCCTAAGGCCTGTGATAGA CACACCAGTGGTGAAATCCTTCCTGCAGGGTTTCCTTCCGGGTTTGGCTTTGAAGATTTTTCTGTATATCCTCCCAA CGGTTTTGATGATTATGTCAAAGGTTGAAGGTTATGTGTCTTTATCATCTCTGGAAAGGAGGGCTGCTTCAAAATAT TACTACTTCATGCTGGTGAATGTATTTCTTGGAAGCATAATCGCTGGCACAGCTTTTGAACAGCTAAATGCATTTTT CCATCAGCCACCTTCACAAATACCAAGGACCATTGGAGTAGCTATACCAATGAAAGCTACATTTTTTATGACATACA TAATGGTTGACGGGTGGGCTGGCATCGCGAACGAGATTCTTCGAGTGAAGCCGCTGGTGATATACCACCTGAAGAAC ATGTTTATTGTGAAGACGGAGCGGGACAGGGAGAGGGCAATGGATCCGGGCAGCATTGGGCTTGCAGAGAACCTCCC ATCACTGCAGCTGTATTTTCTTCTTGGGCTTGTGTATGCTGTGGTCACCCCCATTCTCCTCCCTTTCATTATCATCT TCTTTGCCTTCGCTTTCCTCGTGTACAGACACCAGATCATCAACGTGTACAACCAAGAATACGAGAGTGCTGCTGCG TTTTGGCCTCAGGTGCACTCTCGCATAATAGCGAGCTTGCTGATCTCGCATGTAACTCTGTTTGGGCTGATGAGCAC CATGAAGGCTGCCTACTCCACCCCGCTGCTTATCTTTCTGCCACTCCTCACCATATGGTTCCACAAGTACTGCAAGA GCCGTTTCGAGCCTGCTTTCCGCAAGTACCCTCTAGAGGAAGCGATGGAGAAGGACAATCTGGAGCGCACGTCGGAG CCAAACCTGAACCTCAAATCGTACCTGCAGAACGCTTACCTGCACCCCATTTTCCACATGTTTGAGCAGCAGCAGCA GCAGGAGCAGGAGCAGCAACGGGAGGAGAAGGTAGAGGTGCGAATCGACAAGGCGCAGCAACATCATCATCGGCAGG TAGAGGAGGAAGAGGAGGAGAGCAAGAGCAGCCAGGCTACAACACACTACTACCACCATCACCATGAGCAGACCACA ACGACGACACACCACCATTACCATCAGCATGAGCATATGAGCCACTACCACATGGGCCCCTCCGACACAGCTGACTC ACCCTCGCCGCCGCACTTTGTCTACCATTATGGCGTCGACCCTTGA |
| SEQ ID NO: 64 | ATGGAGATGACCAGAAGCCTTACGCTCGTGCCGCTCCCGGCGACGCTCCGGCCGGCATCCGCGGCCTGTCGCCGGC GGCGGAGGCGGCGAGGGCTTCCCTTCGGTGCACTCTTCTCACCATCGCCTCCTTCGAACCAGCAGCAGCAGGAAAT GCACATCAGGGCGCTGCAGCCGCGGCAGGATTGGGTGGGGGAGTGGGTCCGGAGCAACGACACGCTAGTCCGCGGC CTGCCCATCCTCGGCGGCGGCGCCTCCCTGCTCGCCGTCCTCCTCAACCGTGCGGTTTCCGGCATTGCAGCTGTCG CCGACGCCTCCAGTTCGCAGTCAAGGGCTGACATACTGACTCTTGCTCTCTCCGTAACTGATATTCTTGCTGGCCT TGTTTGGTTGTCCATCCGGCCGAAATCCATTTCTCCTGTTGTTCCTCGAGGTGTCGAGTGCAAACGGGTAGGAACG GGTGTATTGGACTCGGCTCTTCGTGAACTACTTTGGACATGGGATTCCCTTACAACTGCAACTTGTTGCAAATCCT TGGTTGTTGTGTATGGAGGTAATTGTGTTCTTCAAATTGGGGTTGCTGCTGGCTCTCCAGAGGATGGTAATGCAGT |

TABLE 2-continued

| Amino Acid and Nucleotide Sequences of Rice Polypeptides | |
|---|---|
| | TATGGTGGATGCACAGAAGTTCATGCAAGGTTCCCTTTATAGAAGTGCCATGGAATCCAAGAAGCAATCTTACCTA GCAAATCTTGCCTTATATCCTGGAAGGACTGAACTACCATTCTTGCCAGCTAACACGCAGGCCCTAATATTGCAAC CAATTGGTGATAAAGGAATTGCAGTTATTGGTGGTGACACTATAAGGGGGTTCACTAATCTTGATCAGGCATGGAT TGCAATGATAGCAGATAAACTGGATGCTACATTGTCAAAGTCGTAA |
| SEQ ID NO: 65 | ATGGCATCATCAGTTGCAGGCTCAGTGACTCGTCGTCCTCCTCCCGTGCTGCTGGCTTGCCGATCGCGACCAAATAA TCGTCGCCTCATCAGATTGTTACCGCTCCTCTTCGCCGTCGTCGTCTTGCTTGCTCTTCTTCCACCATGCGTTCATG GAGCTCGTGCTCTGAATGATGCCAAAGAAGCCAAAGTTGCAGAGGCCAGCGACCAGACGACGACGACGACGCACGCC GCGGCGGCGGCGGTGGCTCGGTGGTCTGTCACCGTGAGGGAAGGAGGAGGTGGTGGTGGTCACGGCAGCGGCCATGC CGGCGCCGGCCACGGCCACGGCAGCGGCCACGGCAGGCCGGAGCCAGCCGAGCACCACACGGGCAGGCGCAGCGCGG CGGCCGGATCCGTGCGCCCTCCCATGGCGGCCTCCTGCGCCGCCCTCCTTGTCGCCGCCGTCGTCGCTCTGCTTCGC TTCTGA |
| SEQ ID NO: 66 | ATGGAGAGTGCAAAGAGATCTTGCCTTGCTATCTCCCTCATCCTACTCCTACTCCTTGTTCCAAGTATCCATGGAGC AAGGCATGTTGCTGCAGCTATCAAGGGTACAGGCGCCGACAGCGAGATGGTGGTGACGGAGAGGACGGCCGGCGGCG GCGGCGGACATGGACGCGGTTACACAAGCCACCGGTCGCACAACCCCAACAATCCCAACGACGGTGGCTCCGGCACG CCGGTGGTGGACCCGCACAATGTCGCCACCAGGGGCCACCACCACCGCGGCGCGGCGACGAGGACGGCCGCCGGCGG CGACCCCCGCCTGGCAGCCTGCATGCTTCGTCTGGGAGCGACCTTCTTCCTGCTGGTTCTTGGCTGA |
| SEQ ID NO: 67 | ATGGCGGGCGTTGGATTCGTGGAGGACATGCTGCGGGAGCAGAGCCTCCTGGAGGCGACCTGCGGCGACCTCTTCGAC CACATCGACGACCTGCTCGACTTCCCCAAGGAGGAGTCGGCCGCCGACGTGCTCCTGCTCGACGCGCCGGCGCCAGGG AGCCCGCTGTCCTCGCGCATCATCGGCGGCCACGCCACCATGGCGGCGGCGCCGCCACCGCCGCCGCAGATGATGGCG CTCCCCCCGCCGCCGGCCCCCGCGAAGGACGACGCGTCGGCGCTGTTCGACGCGGCCGGCGCGCTCGGCGCCGAGGTG TTCGACCGCAAGGACGCCCACATTGGCCCGTGTGATGAGCTGGACATGGACATGGCGCAGCTGGAGTGGCTGTCGGGG CTGTTCGACGATGGAACCATCCCGCACGAGCCGAGTTTTCCGGGCGTCAACTGCGCGGCGCCGATCAAGGCGTCGGCG CTGACGGCGAACGCCGGCGTCGTGCTGCCGGACAAGGCGGAGGAGGCGCTGTTCCGCAGCTCCAGCCCCATCTCCGTG CTGGAGCACAGCGGCTTCAACGTGGCAACCAATGGGGGCTCCTCCTCGTCGTCCTCCTCGTCGGCGTCCTCCTCGTCG GAGTCGTTCTCCGGCAGCGGCCGCGCGTGGTCCGCGCCCGTGTCGCCGCGCCCGGAGCCGCCCGTGCTCGTCATCCCG GCGCGCGCGCGCAGCAAACGGTCTAGGCCGTCCGCGTTCCCGGCTGTCCGCGGCGCGCCGGCGGCGACGGAGACCACC ATCCTGGTGCCGACGCCAATGTACTCGTCCACCTCGTCGCACTCGGATCCCGAGAGCATTGCCGAGTCCAACCCGCAC CCGCCGCCGATGAAGAAGAAGAAGAAGGCCAAGAAGCCGGCCGCTCCGGCCGCCGCCTCTGACGCCGAGGCCGACGCC GACGCGGCGGACGCCGACTACGAGGAAGGCGGCGCGCTCGCGCTCCCGCCGGGCACCGTGCGGCGGTGCACGCATTGC CAGATCGAGAAGACGCCGCAGTGGCGCGCGGGCCCGCTCGGCCCCAAGACGCTCTGCAACGCGTGCGGCGTCCGCTAC AAGTCCGGCCGCCTCTTCCCGGAGTACCGCCCGGCGGCGAGCCCCACCTTCATGCCGTCCATCCATTCCAACTCCCAC AAGAAGGTGGTGGAGATGCGCCAGAAGGCAACCCGGACCGCCGACCCGTCCTGCGACCTCCTGCAGTACATCCGCCGC CGGGATTAA |
| SEQ ID NO: 68 | ATGGGCGGGTACGAGCTCGTCAGGAGCGACGACGCCGCGGCGGCCGGCCCGCCAGATCTCGAGCTCGGCGGCAGCGGC AGCTGCAACGGCGGCGGCGTCTCGGCCAAGTCCCGGCCTCCGTCATCGCCGCCGTCGCAGGGCGGCGCGCGGCAGCGG CTCGTCTCCCTCGACGTCTTCCGCGGGATCACCGTGCTGCTTATGATCATTGTCGATGATGCTGGAGCTTTTCTCCCA GCACTGAACCACTCTCCATGGGACGGCGTAACCATTGCAGATTTCGTCATGCCATTCTTCCTTTTCATGGTTGGGATC TCTCTAACGCTCGCGTACAAGAGGGTGCCGGACAAATTGGAGGCTACTAAGAAGGCTGTACTACGTGCCCTCAAGTTG TTCTGCCTTGGCCTTGTTCTCCAAGGCGGTTTTTTCCATGGTGTCCGCAGTCTCACTTTTGGTGTTGATATTACAAAA ATACGGTTGATGGGTATACTTCAGAGAATTGCTATAGCTTATCTTTTGGCTGCAATCTGTGAAATTTGGCTCAAGGGA GATGATGATGTAGATTGTGGACTCGATGTGATACGGAGATACCGTTACCAATTGGTTGTAGCATTGCTCCTGTCAACC ATGTATACTGTTATTTTAAACGGTGTCTACGTTCCAGACTGGGAATACCAGATATCAGGTCCTGGTTCCACAGAGAAA TCATTCTCTGTGAGATGTGGAGTAAGAGGAGACACTGGTCCAGCTTGCAATGCCGTTGGAATGGTTGACCGTACAATC TTGGGGATCGATCATCTCTACAGACGACCGGTTTATGCGCGTACAAAGCAATGTAGTATAAACTATCCGCAAAATGGG CCCCTTCCACCTGATGCTCCATCATGGTGTCAGGCTCCATTTGATCCTGAAGGCCTCCTCAGCTCTGTTATGGCAATT GTCACATGCTTGATTGGGCTGCAGTTTGGACATATAATTATACATTTTGAGAAACACAAGGGAAGGATAATAAATTGG CTAATTCCTTCCTTCAGCATGTTAGCACTGGCCTTCTCAATGGACTTCATTGGGATTCGTATGAACAAGCCGCTGTAC ACGATAAGTTACGCCTTGGCTACCTCTGGTGCTGCAGGGCTTCTTTTTGCTGGGATCTACACACTGGTGGACGTGTAT GGATTCAGGAAACTTACCATCCCCATGGAGTGGATGGGTAAGCACGCGCTGATGATCTACGTGCTAGTGGCATGCAAC ATCCTGCCCATTTTCATCCATGGTTTCTATTGGAGGGAGCCCAAGAACAACCTTTTGAAGTTCATCGGAGTTGGGGCA TGA |
| SEQ ID NO: 69 | ATGGCCGCGACTGGCGGCGCCGCCGGGGAGAAGACGGCCAGCAGCCTCCTGCTCGGCGTCCGGGGCTACACGTCCA CCCTCAAGAACGCCTCCACCGCCAGCTGCAGGTTGAGCGCCGGCCATCCCATCGAGGTGACTTTGTGGGAGGCGTC CCCGCCTGCCCTCTCCCACTTCTCCGTCCACTGCCCCGATCTCCCATCCTTCAATGGCAATCTGCTTGGCGCGCCT AAAGCCATCGCCGCCGCCGTCGACGACGCCGACGGCCAGCTCCTCCTCCTCCTCCGAGTCCCCATCGATCAGCTTG GTGCCCCGCATGACAACGACTACTTGGTCTACCATCCGGATCCCCCGTCTCCGAAACTGGATCTGCTCCCCAACCC GCCTCCCCCTACCCTCGGTGACCACCAGCTCGCCATACTCAGCTGCGGCGACGACCGCTACGTCGTGGCCGCCCTC CACGTCTGGAGTGAGTTCACTTCCACGCTGCGCCTGTACAGATCTTCTTGTTCGTCTGGGAGTTGGACATCGGAGG AGGTGTCCGTGGAGGAGCCGGTGAGGGACAGGCTGTGCCCGATCCCGGACTCAGCCAAGAGGCAGCTGTACCACGT CACCACCAAGACCATCACGCTCGGAGGTGCGAAGGGCACCGTGGGCTGGGTTGATCTCTGGCGCGGCATCCTCCTC TGCGACGTGCTCGACGAAATGTCTCCAAGGAAGCTCCGCGACATGCCGCTGCCGTGGCCGGCCAAGGGCAATTGGA GGATGTACCTCAATGGAGATGTGTCCTTTTGTCGGGACATCGCCATCAGCCAACACAAGGATTCCATCAAGTATCT GGAGATGGAGATCGTTTCACCAAGAACGGTGACCACCACCATACCCACCTCCACCTCTGCAGATCCTACTTCATAC CTTGAATGGGTTCGCCGCAGCAGAGAACCTCAGCCGACACGGCGACGCTCCGTGTTCCACCCTGGTTCGTGGAGAA TCACTACATGGAGCATGCCTATCCCGGTCACTTCATGGGACGACTGGCGCCGTGACTGCACTGCTGAATCGCGTGA AGTCCATCTTGACACCAACCCAAGTCACCATTACGAGTTGCTTCATAGCCTCATGCTCAGCAACAGCGGTGATGAA CACAGGGAGGAGGCTCAAGGTCAAGGGGCAACCTCTTCCTTGTCCCTAGGTCGCCTGCGTTTGTGTTACCCGGCCT TGAGTTGCATCGATGATGATGTTGTTTACCTCTTGGGCAACGCTGCTGGCAGGGGTGCTAAGACGGGAGGAATGAT GGTCGCTGTTGACGTCAGGAACAAGGAGCTGCGAGGAGTGGCCAAGCTTGACCCCGAAAAGAACACCCTCTACTCC ATGCGATGCTACCTTGCAACTGGGATCTCCAAACGCCTCAACACTACCACAGACACAAGAGTTGGACGACCTGAGG AGGATGCAGAAGCCGCCGAGTAG |

TABLE 2-continued

| Amino Acid and Nucleotide Sequences of Rice Polypeptides | |
|---|---|
| SEQ ID NO: 70 | ATGGCGAACTACCACCACCAGGAGTACTACCAGATGGCGGCGGCGGCAGCGGTGGCGTGGCCGAGGGAGCCGGACAG CCCGCAGCTGAGCATCATGAGCGGCTGCAGCTCCCTCTTCTCCATCTCCACCCTGAGGGACGACGACGACGGCGGCG GCGTCCGCCTCGCCGGCGCCGCGCTGCCCGCCACGCCGGTGTCGCTCGCCGGGATCGCCGGCGGCGCCAGTACCCCC GGCGGCGACGAGGTGGACATGGAGGTGCGGCAGCAGAGCGGCGGCAGCGGCGACGACCGGAGGACCATCCGGATGAT GAGGAACCGGGAGTCCGCGCTTCGCTCCAGGGCGCGCAAGAGGGCGTACGTTGAAGAGCTAGAGAAAGAGGTTCGCC GGCTGGTGGATGACAACTTGAATCTCAAGAAGCAGTGCAAAGAGCTGAAACAGGAGGTTGCTGCACTGGTGATGCCT ACAAAGAGCTCACTGCGACGAACTTCATCAACTCAATTCTGA |
| SEQ ID NO: 71 | ATGGCAGAGAAAAAGAAGAAGAAGAAGAAGAAGAAGCCGCAATCACTCCTAGTCCTTACAAGCTGGAGATCGATCGGG ATGGGGAGGGGTCGGGTGGAGCTGAAGAGGATCGAGAACAAGATCAACCGGCAGGTGACGTTCGCCAAGCGCAGGAAT GGCCTGCTCAAGAAGGCGTACGAGCTCTCCGTCCTCTGCGACGCCGAGGTCGCCCTCATCATCTTCTCCAACCGCGGC AAGCTCTACGAGTTCTGCAGCACCCAGAGCATGACTAAAACGCTTGAGAAGTATCAGAAATGCAGTTACGCAGGACCC GAAACAGCTGTCCAAAATAGAGAAAGTGAGCAATTGAAAGCTAGCCGCAATGAATACCTCAAACTGAAGGCAAGGGTT GAAAATTTACAACGGACTCAAAGGCAATACTACAAATCTAAACATAGGCTGTGTTTAGTTCGGTCCAAAGTTTGGAAT TTGGTTAAAATTAGAGACGATGTGACTGAAAAGTTGTGTATGTATGAAAGAAATTTGCTGGGTGAAGATCTTGATTCA TTAGGCATAAAAGAGCTCGAGAGCCTAGAGAAGCAGCTTGATTCATCCCTGAAGCACGTCAGAACTACAAGGACAAAA CATCTGGTTGACCAACTGACGGAGCTTCAGAGAAAGGAACAAATGGTTTCTGAAGCAAATAGATGCCTTAGGAGAAAA CTGGAGGAAAGCAACCATGTTCGCGGGCAGCAAGTGTGGGAGCAGGGCTGCAACTTAATTGGCTATGAACGTCAGCCT GAAGTGCAGCAGCCTCTTCACGGCGGCAATGGGTTCTTCCATCCACTTGATGCTGCTGGTGAACCCACCCTTCAGATT GGGTACCCTGCAGAGCATCATGAGGCGATGAACAGTGCGTGCATGAACACCTACATGCCCCCATGGCTACCATGA |
| SEQ ID NO: 72 | ATGGAGGGAGGAGGGAGGAGGAGGAAGAGGGGGAAGGTGGAGCTGCGGCGGATAGAGGACCGGACGAGCCGGCAGGTGC GATTCTCGAAGCGGCGGAGCGGGCTGTTCAAGAAGGCGTACGAGCTGTCCGTGCTCTGCGACGCCCAGGTCGCCCTCCT CGTCTTCTCCCCCGCCGGCCGCCTCTACGAGTTCGCCTCTTCCACCTCCAGCATTGATACAATTTTTGGTCGGTATTGG GACCTTCTGGACACAACAATTGATCTCAATATTGAAGCAAGGGAATCTCGGGTTGATTGCAATATACAGGTCTGGATAC GGAGACAAATCGTCCACGGAGGGCTAGCTCCTTTGTTGGTTGGAGATGCAGCTCCTCCATTTAGGGGTGTTGGTGTGGC TCCTCGCCTAGCCCTTTGTATTTATGACGACACTCCACCTAGGATCAAGGTGGCAAAAGCTGGTGGCATGGAAGGTGGC ATGATGGACGTCAATGATGGGTTGCAAGAGTTTGGGCTGCATCTCATGATTGCCTTAGTGTGGTATTTTATGCGACAAG GCTCGTTAGGCAACAAAGGATCAATCTCTGGCACGACGATCATCAAAGTTTCTAAGTAA |
| SEQ ID NO: 73 | ATGGGTTTGAGGTGGGACAAGGCGGAGAGGTCAACGAGAAGGGCAAGGAGCGCACCGACGAGGGAGAAGAGGCCGGAGA AGGGGAAGTCCCGCCAGAGGCGTCGCGTGGCAACGACGCAGTCGGCGGCGGCGGCACTGCCAAGCGTGCGCCGCGCTGG CGGTGAGACGCCGGTGCTGATGAGCGGCACGAGGCACGACGCGATGGCGATGGTGAGGCTGACAAAGGTCAGGATGCTG TTCGTGCGGTGCGGTGGCAGCGTGAGGCACTCGTCGGAGGAGTCTGTGTTGGACGACGACATCTGGGCCGCCGCGAGGA AGAAGGGGAAAAGAAAAGAAGAGAGAGAGAGGAAGAACAGTGTCAAAGGTGGGCGGGCTAAGGTGAGATCAAGGCTAAG ACGAGAGTGCCATCAAACGTCGAATTCTTCGTCTGGCTAG |
| SEQ ID NO: 74 | ATGAGCTTCGCGGATCTGGAGGCCGGCGCGGTGCGGGCGCCCAGGAGGGCGCGGGGCCCCGACGCCACGCGCGCGC TCGTCTTCCAGATCACCACCGCCGTGGCCTCCTACCGCCGCCTCCTCAACTCGCTCGGGACGCCCAAGGACACCCC CGCCCTTCGTGACCAGCTGCAGAAGACTAGTCATAACATTCTTCAATTGGCAAAGGATGCGAAGGAGAAGCTCAGG AGAGCTGCTGAGGCAGACAAGAACGCCGATACTAGTGCAGACAAGAGGGTTGCTGACATGAAGCTTGCCAAGGATT TTGCCACGACGATGGAGGAGTATGGAAAACTTCAAAATCTTGCGATTCAAAGGGAGATGGCATATAAGCCAGTTGT TCCCCAGACATCTCAGCCAAACTATACTACAGGTGGTATAGAAGCCAGGGATTCTGGTAAAATTCCTGAACAGCAT GCGCTACTCGCAGAATCAAAGAGGCAAGAGGTGCTGCAATTGGATAATGAAATTGTTTTCAATGAAGCTATCATTG AGGAAAGGGAGCAAGCTATTCAAGATATTCAACAACAGATTGGTGAAGTACATGAAGCATTTAAGGATCTTGCTAC ACTTGTGCATATTCAAGGAGTTACAATCGAGGAAATCGATACAAACATTGAGAATTCTGCAGCAGCAACCAAAGAG GCAAAGACAGAACTCGCGAAAGCGTCCAAGACTCAGAAATCGAATTCATCACTGCTCTGCATTCTTCTGGTGATCT TCGGGGTTGTCTTGCTAATTGTGATAATAGTTTTGGCAACTTGA |
| SEQ ID NO: 75 | ATGTGTGTGCTCGCACAAGAGAAAGAGAGAAGAGGTAACAATGCACTTGCTGCAGAATGGTTTCCAGCAAGGATAT TATGCATGTACTGGAGTACACCAAGTTTCAGGAAGATGTCAATGCGTGGCAAGGAGAATCGGTTGGTAGGAGGTAA CACTGTATACCATCGTAGCGGATCACGTGGCTTATTAGGGACTCGACAATTCCTAAAGACCAAAAATGGAGTTGAT CCTGGGCAGGCAGGAGCATGGCATCATCAACACCGAATGGAACATGACGGGCCAAGAGGGCTCTGCTGTGAGAAAA CTGCTATTTTTTAG |
| SEQ ID NO: 76 | ATGCGTGCGGCGGCGGCGGCCTCCAAGGCGGCGGGGAAGGAGAAGAGCAGGAGGAAGGGCGGCGGCGGAGGAGCAGGA GGAGGAGGAGGCGAGCAGCTGCTCACCGACCAGGTCCTCTCCCTCCCGCGCCCGCCTCCACCTCGCCCTCGCGCTCGGC CTCGCCAAGTCTGATGGAGGTCCAAAGAAATGGCAGTCTACTGATGCTGGAATACAGTCTCATGTGCTCAAAGCAGCA TCAGCCTTTCTTGGCTGTTTGACCAATGAGATGCTGCGGCTTCCTCCTATAAAGGAGTCAATTTCGGATATACTCATA GCACTGGAAGGTATTCTTCAGTCCAAGAATGTGTCGGTTCTGATCCAAGCAACTGATGTTAGCTTGAAGTTAGTTTCC AGTGTAGGAAATTTAGCTCGCCAATACCCGGTTTTAGAGATCGTTACATGCCTCGCGAGTCAGCTTTCTGCAAACCAG ATAACTATAGCTGTCTCATCTGCAAGTACATTGAACTGCATACTGAACACCCTAGCAACAGCGAGAAGTTCGATTCAT GCAGAAATTTGGGAAGCTTTGGAGAAAACCGATGCAGTTACAAGTGTCATTGGAGCTCTGCAGAATTACTCCCCTGAT GTCCATCCATTAAACTATCTGATGGAAATGATGTCTCTGCTAAGAATTATACTGTGGATTTGGCCTTCTTCGAGATAC CATGTATGGAGTAACTGCAACTTGATGGGGAAGCTAGCACAATACTGTGTTGCCTCTGAAATGGATGTTGCTGTTAGA GTCCTCAAGCTATATGCTGCTTTAGCTTTATGTGGGAATGGTGCAATGGTCCTTCTGAATAATGAAGACTTGATGGCT AAGGTTGGTGCGCTTTTGGGGAAGTCAAATCCATCTATTGCTAGAATTGAAGCATTGAAATTCTATCAGATTCTTTTG CGATCTTCAAAAGGGTGCGATCTGTTAATGGCTGCACACTATCAACACATTATTGAAGGCACAATCAACGCAATGTCT AGAGATGATGAAAGATTGTTAACAATAGAGGGCTGCCGCACTGCACTGCTGGTCCTTCGTTATGCTGGGGATCATCAT CGGCTCTTTTGGTCTCATGCTATTGATGATGTATTATATAAGATTCTTACTGGTGGCTGCACCTCTTCACATAAAGCC AATCAGATTTTGTGCCACGACAAGCTTTTTAATATGGTTTCCGAGAACTTTATGGATATACATTCTTATGTGTGGGAT ATACTTGGAAATCTAGCAGTACATTGCAAAAATGAGTATCTCTCTGTTAGGAAAGGGCAAGACTCTGCCTTGCAGGCA CTAATACATTGTATTTGCTCACTTGCAGCAGATGCTATGCAGAAAAGCAACACCATGAAATTATCCAAGGATGTGCAT GAGCCAGCTTTGAGGGCTGTTCTGATGATGCTTCTCTCACCCAGTGGATACATTTTGTCTGAGGCAAGTTCTAAACTC TTACATGTTTTACCTTTAGGTGATGACTGTTTGAATATTCTGTTCACGTCGTTAGAATCAAATACTACAAGAAGCATT ACTGCATCTTTTGACAATGTCAAAATTATGTCCAACCTCATGAGCCTAGCGGGCATGAGCATCAATTTTGTTTGTATC CACTGTAAAAGGAATTTGGATGTGGGGATTGTGTGCAATGATTGCAGAGATCATTATAGTGAAGGTCTGATTAGAGTT CTTCAAAATGCGTCATGTCAAAACTTGAGCCCAGGACCGAAGTTGTACATTTCACGTATACTGAGTTTGTTTGGCCTA |

TABLE 2-continued

| Amino Acid and Nucleotide Sequences of Rice Polypeptides | |
|---|---|
| | TGCGGTTTTCCAAGCAAGTTGGGAGGAAAGATGAGAAGGGCCTTAGATGATAATGAGCTAGCTGATCTGGAACTGTTG<br>CTTTCAAATGGTGAATCTTTAAAAGCTCATACAGCCATCATTTCAGTAAGGTGTCCAAAGTTGTTGCCATCTGCAAAA<br>TCCCTTGGTAGTGATGGAAAAATTACTGATGAATGGGGCAGATCATTTTATCATGTTCGAATGTCTGATCGTGTTGAT<br>AGTTGTGGCTTGAAGAAAATTTTGGAATACACATACACAAATTCTGTCATGGTAGATGATGACAACATTAAGCCAGTA<br>AGGACACTTGCGAAGTATTGTCACTTGAAATCATTACAAGAGATGCTTCAAAAAGAGCAGCCTAGGTGGAACTCTGAT<br>TGTCCTAGATATGATCTTACTGCAGCACTTGAACCAGTTAAATGTTCATTCTCCTTCTCAGAAGTTATCAATGTTCCA<br>CTGGGGTGGCAAGCGCTGAACAAACTGATCCACTGGTTCTACTCAGGCGAGCTACCCAAGATCGACCCCGATTGCCGA<br>TGGCGAAACCTGAACAGCGAGGAGCAGCTTTCTCAGCTGCGGCCTTACGCCGAGCTGTCATCCCTGTCTGAATTCTGG<br>TTCCTGGAGGGAGTGAAGGAGGAGAGCCTGTCAGTGGTCACCTCCTGCCTGAGTTCCACCAGCACGGCCGCCTCCGTC<br>GAGTTCGTCGTCTTCGCGGCGCAGCTGGGTCAGTGGGAGATGGTGGAGGCCGCCGTCGGCAGCGTCGCCCATCTGTAC<br>CCCAAGCTGCGGGACTCCGGTCAGCTGGAGCAGCTTGATGATGATGTGCTCAACATGCTGCGGACAGAGTATGTCAGA<br>CGCACGCAAAGAACGGGAGTTGGCTCGGCGGCGGCGCAGGCGGGGGCCAGAGTGGTGACGGCGGTGTACAGGCGGGGG<br>CAGAGGGCAGATTATTGGCAAAGTGGTGGTTTTGGAGATAATTGGAATTTTCAAATGGTGATTCTTAATGCCTCGGAA<br>GAGCATTGCCGGGAGTCCAAATTTGATACAATTGGAGTTTGTAAAGCTCGTTTCTTGTACGGGAAGGTTTCTAGGGGA<br>TTTAGATTGCGTACCTCGGGTATAAACAAAGAGGGAGGCCCAAGAGGGGGTACAGTAATTTATAGCAGGTCGTCAGGA<br>GGGCTGCCTCCCTGGTGTGGTGCAGGAAGTCACGACGCATTGGCAGCCGTCAGATGGCCGTCACTTCCAGGCTTGGAG<br>TCGCATCAGACGGCGCAGGTGATAAGGCGAGGCGCAGGGCGCAGAGGCGAGGGGAGAGACGTAAACGTAACCAAGCAA<br>AGCAACGCGCCCATGCGGCCGCCCGAGACGATGCAACGCGAGCAGCCGCAGAGCAGAGCAAGAGCCAACGGTAGGAAA<br>TGGCCACCACCACGACGATGGAGATCCGGAATTCGCGAGGAGCAGGGGGTGCCAAGTGCAAAGGCGTGGCAGGAGAAG<br>AGGAAGAGGACACAGCAACAGCGTTGCGCACTGCCTGCTGCCATTGCTGCCTCGCGTTTACAGCTATAG |
| SEQ ID NO: 77 | ATGGCCTCCGCCGTCGCGAGTAACTTGCCTGCAGCTGCGCCCGCGGCTGTCATGCCGTTCGGTGGATGGCATGGTC<br>CGCGTGTCTCGTTCAGCCGCGACGCCGCCGGGGCTGAGGAGGCTGCCGCGGTGGTCGTGTGTTCTTCGCCCCTGGC<br>CGCCGCGGCGGCGGTGGCGACGACGACGACGCCGGAGCCGGCGATATCCAAGGACTTCATCGACTTCGAGTTCAGC<br>CTCGGGGGCTCCGCCACCATGCTCCCGGCGGACGAGCTCTTTGCCGACGGGAAGCTGCTCCCGCTTCGGAAGGCGG<br>CGGCTGTGCCGGAGATGGATGCGGCGGCGCCACGGCCGCCGCAGCCTGAGGCAATGCCGGCGCCTTCGGAGCCGAT<br>GAAGCCACTACGGGCGGCTACCGCCGCGGTTGACGCCGCCGACCCGTACGTTTTCTCTCCTAAGGCGCCCAGCTGC<br>TCGAGCCGGTGGCGGGAGTTGCTCGGGCTGAAGAGAGCGGCAGCGCAGAGCCCGAAGCCATCGCCGTCGTCTGCGC<br>CCGCGAGAACCCCCGGGAGAGCGATGAACTCGACGGCGGCGAGGTCGCTGAAGCTGCTGCTCCAACGGAACAACGG<br>CCGCTCGTCCGGGGCCTCCGCGTCGGAGCTCGCCTCTGCGCCGCTCCTCCGCGACAGCTCCGACTCGGAGGCGTCT<br>CTCTCCCTCGCCTCCTCCCGCTTCTCCCTCTCGTCGTCGTCGTCTTCCTCCGGCCACGACCACGACGACATCCCGC<br>GCCTCTCCCTCGACTCCGCCGCTGACCCCAACCCGCCCCGCATCCGCCTCGTCCGTTCCTCCCACCGCCACTCCAC<br>CTCCTCATCCTCCTCATCCCGCGCCGGCCGJAGCCCCGCGCGCCGCCGCCCCTCCCCGCCGCCGCCGCCGCGCTGC<br>CTCTCCGTCGACTCCCCGCGCATGAACTCCTCCGGCAAGATCGTGTTCCAGGGCCTGGAGCGCAGCTCCAGCTCAC<br>CGTGCACCCTCCACGCCGCGGCGAAGCCACGCTCCCGCGCCGTCGACCGGTCATACTCCTCCGGCGTCCGCGTGGC<br>GCCGGTGGTGCTGAACGTGCCGGTGTGCTCGCGGCCGGTGTTCGGGTTCTTCAAGGACAAGAAGGACGCGGCGGCG<br>AAGGACGCCATGGCGGCGAGGACGAGGTCGTCGCTGGGGCGGAAGACGACGGCGGCGCCGCAAGGGTGGAGCGGCG<br>AGCTGGGGAGATCTTGTGGGTAA |
| SEQ ID NO: 78 | ATGAAAATCAGCGGACTTCTGACCTCTGCTGGCATCAATATCGCTCTTTCTGTGCTGTTTATATCGCTCTATTCTGT<br>TCTGAGGAAGCAGCCAGCCAATGTCAGGGTCTACTTTGGGAGGAGGATTGCCGAGGAGCATAATCGGCTCCGAGAAG<br>CTTTTATCTTGGAGAGATTTGTAGCATCTACTGGCTGGATAGTAAAAGCCCTGCAGTGTACCGAGGAAGAGATCTTG<br>GCTGCTGCTGGGCTAGATGCTGTTGTTTTCAATAGAATTCTAGTATTCAGCTTACGCATCTTCTCTCTAGCTGCCAT<br>TCTGTGTGTGTTTGGAATTCTACCACTGAACTACTTTGGGCAAGATATACATCATGTTCGGATTCCTTCAGAATCAT<br>TGGATATCTTTACAATTGGGAATGTGAAAGTGAGATCAAGATGGCTTTGGGTCCATTGTGTAGCCTTGTACATAATA<br>TCAGGAGTAGCTTGCATTCTCCTATATCTTGAGTACAAGCACATTGCTAGGCTGAGGCTCCGTCATCTTACTTGTGC<br>AATGCCCAATCCAAGCCATTTTACTGTCCTTGTTCGTGGAATACCAAAGGAAACCAAAGAATCATGCAGTAATGCTA<br>TTGATGATTTCTTCACCAAGTACCATGGATCAAGCTACCTGTTCCATCAAGTTGTTTACAAAGTTGGAAAAGTTCAG<br>AAGATAATGACTGGTGCTAAGAAGGCATACAGGAAATTCAAACATTTTACAGACAGCACTATTGATCAGAGGTGTCG<br>AGCAATTTCATACCGGTGCTGTCTGTGCGGAGCCTCATCTAATTCTTTCCAGCTGTTGGCAACTGGGCTTGAGCAGA<br>ATCAGGGGAAATCTGACCTTCAAGATTCCAGCTTGAAACTAGATGATCAGGAATGTGCAGCTGCTTTTGTATATTTC<br>AGAACTCGGTATGCTGCTCTTGTTGCCTCAGAAATACTCCAAACATCTAACCCTATGAAATGGGTTACTGATCTAGC<br>TCCAGAACCAGATGATGTGTATTGGTCAAATCTTTGGCTACCTTATAAGCAGCTTTGGATTCGCCGAATAGCTACGC<br>TCCTTGGTTCAATTGTTTTTATGTTATTCTTTCTGATACCAGTGACATTTATACAAGGACTATCTCAGCTAGAGCAG<br>TTGCAGCAGAGGCTTCCTTTCCTGAAGGGGATACTGGAGAAGAAATACATGAGCCAGCTTGTAACTGGGTACCTTCC<br>CAGTGTCATACTGCAAATATTTTTATATGCCGTTGCACCGATAATGATATTATTTTCTACATTAGAGGGGCCTATAT<br>CTCACAGTGAAAGGAAGAGGAGTGCTTGCTGTAAAGTGCTGTACTTCACTGTTTGGAACATATTCTTTGGAAATGTA<br>CTATCTGGTACTGTCATAAGCCAATTGAATGTGTTATCAAGCCCAAAGGACATCCCTGTCCAGCTTGCTAGAGCTAT<br>ACCTGTCCAGGCTACCTTCTTTATCACCTATGTTCTGACATCAGGATGGGCCAGTTTATCATCTGAACTTATGCAAT<br>TATTTGGTTTAATATGGAACTTTGTGAGGAAATATATTCTACGTATGCCAGAAGACACAGAGTTTGTTCCCTCATTC<br>CCATATCACACAGAAGTGCCAAAAGTTTTGCTGTTCGGACTACTGGGCTTCACATGCTCTGTACTGGCACCTTTGAT<br>CTTACCTTTTCTGTTAGTGTACTTCTTCCTTGGTTACATCGTGTACCGCAATCAGTTGCTCAATGTTTACCGCACAA<br>GATATGACACAGGGGGTTTGTACTGGCCAATCGCACACAACGCAGTGATATTCTCTCTCGTGCTCACACAGATTATC<br>TGCCTTGGTGTATTTGGCCTGAAAGAATCACCAGTAGCTGCAGGCTTCACCATACCTCTTATCATCCTCACTCTGTT<br>ATTCAATCAGTATTGCAGAAATCGACTTCTCCCATTATTCAGAACTACCCCAGCACAGGATTTAATTGACATGGACA<br>GGGAAGACGAACGGTCAGGAAGAATGGATGAAATTCACCACCGGCTTCATTCTGCCTATTGTCAGTTCCACGACACT<br>GAAGATATACCCTTGGAGAAAATTCAGACTGTCGGGAGCGATGAGGAACAAGGGTGTAGCTCTGATAAGTCGAATGG<br>AAAAGAAAGCTTCGAGGAACCCAGAGCGGAGTTGTCTCACCCAACACTGAATGGACTCCCAGTTAGCCGTCTTCGGC<br>ATGCTGTGAAGTCGATTACTTTCCTTGTCAGATTGCAGAAAAGAGGTTTGTCAGAATAG |
| SEQ ID NO: 79 | ATGGCGGGGGCGGCGGAGGGAGGGAGAGCGAACCCTACCACGAGGCGCCACCAGAGGACGGCGATCAACATATCTCC<br>TCCTCCACGGCATGGCGTGGTGGCGCCTCGCCGGAGTGCGCGGCGGCGCGTAGGCGTAGCAGCTCAGCTTAGGCTTC<br>GCCCTAACTCTCGATCCCAATCCCCATGCGGCGTCTCTACCTCTACCAATCAGGTCAGGCTCCGATCCCCATTCGCT<br>CGTGCTCTCGTCGGCGTGGAACAACAGGTGCAAGAAGCTGGGCAGGCTGGCCAAGATGTCCAGCGCCGACGTGGAAG<br>GGGCCGAGAAGGCTTAGATGGGCCTGAGTGGGAATGCGACTCTCTCTTCTGGTTGGGCCAGAACAGTATCAATGACA<br>TACATGCGGCCCATATTTATTGGGCCGGAACGGGATTGCTACTTCGTGCGGCGGTCGCGCTCCTCCCAAACCATCTC<br>CGCGGCCTCTTCGTCTGCCTCAATGAATCGTGCCTCCATGGCTTCTTCGCCCGTCCCTCGCCGCCGGCCACCATCCC<br>CGGCATCGACCTCGACTACGACCTGGACGACGATGCCACCATCGAAGTCCACTGCAACGGCCTCCTCTTGCTCGATC |

TABLE 2-continued

| Amino Acid and Nucleotide Sequences of Rice Polypeptides | |
|---|---|
| | GCCACATCGTCAACCCGGCCACACGCCAGTGGATGCGTCTACCTCCTGTCCCCCCGTACGCCTCACTGCCCAACATA<br>ATGTACGGTGATCGGGGCCTCGTCTTCGACCCAGCAGCGTCACCACACTACGACGTCCTCTGGATGCCCTACCTGAT<br>TCTTCATCGACTCCCTGCTGCGTCTCTGTCGGATCAGTGGCCGCCGTCGCCGTTCATCCTGCACGTCTTCTCCTCCA<br>CGACGGGGCGATGGGAGGAGAAGTCGTTTCTCCGGGAAGGCGACGCCACCATGGGCACCATGGCTGATGTATCCTTG<br>GCAAGGGTACCTTACCACTGCAAGACTCACTCCGTCTACCTCCGGGGAGCGCTCTACATGCATTGCCAGAATGATTG<br>CGTCATCAAGATCACACTTAACGACCACAAGTATCGGGTCATCAGATTGCCTGGCGACTCTGCATCAAACAGAAAGA<br>CTAGGGACCCTTTCCTAGGAAAATCAAAAGACAGAGTGTGCTACGTATTGGTCACCGGTCTAAGTCGACTCCAAATT<br>TGGCTCCTCAACGAAACTTCTTCTTCTTCTTCTTCTTCTTCATACGACGACAACGAGTGGGTGCTCAAGCATGG<br>TGTTGACCTAGGGCCAATAATACAAAGCTACCCCTGCAACCATGGTCGTCAGCAATGGATATGGCATAATGCTGACA<br>CTAAACAAGACAAAACCAGGGAATTACCAGCTGTAAATGATATGGAGGAATTTGAATGGGCTATCGATAAGGACTCT<br>GATGACATTATTAGTGGTGCCAATGAAAGCATCCACCATAATGGAGAATACATCTCCGCTGTACTCGGATTTCATCC<br>TTTTAAAGACATCGTCTTCTTGCACGATACAAATTTAAGAGTTGTTGCATATGACTACAACAAGGCAAAGGTTCAAG<br>ACTTGGGTATGATGTTCCTATACCATAATACAGATAGAGTGCCGTCGGATGGAAAGGCTCAGGGTTCACAGCACGTG<br>AGGCCCATGTCACCTTCCTCCTCCCATCTCATTCTCATCTCACCATCCCACGCTTTTGGACTCCCAAACGACGCTGT<br>TGCCTTTCGTCAACCCCCACTTCTCCTTCCCCGCCGCCGCCGCTCGCCGCCCGCCCGCCCGCCCGCCATGGATGAGG<br>AGTACGACGTGATCGTGCTGGGGACGGGCCTCATGGAGTGCATCCTCAGCGGCCTCCTCTCCGTCGACGGCCTCAAG<br>CCGCACTCGGATGAGCTGCTGCTGGTTGCTTTTTTTTTTTTACCTCGCCATTTGATCGCTGCACAGAGATCGAAGGG<br>AGGGCCTGCCATGGCCGCTCAACGTACTCCCGCCCCCTCTCCGCCCTCCACTGCCTTCTACACATCGGCTCCTCCCT<br>CTCCACTCCCCCGCTTTTGCACCCACCACCGCATCCCCCGCCCGGAGACCGGCAACGACGGAGGGTTAGCTTCGACG<br>AGCGACCGACCACGAGATATGATATGA |
| SEQ ID NO: 80 | ATGGCGCCGCCTAATGACGCCGGAGATGGCGACGACGACAAGCCCGAGATGCCGGTGGTGCTCATCACCGGCTGCGC<br>CAACGGCGGCATCGGCTACGAGTACTGCAAGGCCTTCGCCTCCCTCGGCTGCCGCGTCGTCGCCACCGACGTCCCCG<br>ACCGCGTGCCCGACCTCGCCGGCCTCGACGCCGACCACCTCCCGCTCGACGTCACCTCCGACGAGAGCGTCGAGGGC<br>GCCGTGGCGCGCGTCCTCGCCGAGCACGGGCGCGTCGACGTGCTGGTGAACAACGCCGGCATCGGGTGCACCGGCCC<br>GCTCGCCGAGCTCCGCGGCGAGGCCGTGCGTCGCGCCATGGACGTCAACTTCCTCGGCCAGCTCCGGATGGTGCGCG<br>CCGTGGCGCCGCACATGGCGTCGCGGCGTTCCGGGCGCGTGGTGAACGTGGGCAGCGTGGTGGGCACGGCGGCGACG<br>CCGTGGGCCGGCCCCTACTGCGCGTCGAAGGCGGCGGTGCACGCGGCGACGGACGCGCTGCGGGTGGAGCTGCGGCC<br>GTTCGGCGTGCACGTGGTGAAGGTGGTGCCCCGCCGCGGCGAGGTCCGGGCTGGGCCACGCCAACACGGCGCAGCTC<br>GCCGGAGGGCAGGCGGAGTGGCGGCTGTACCGGGAGTTCGCGGCGGCGATCGCGGAGAGGGCGCGGGCGTCGCAGGC<br>GGGGGGCGCGACGGACGGCGGCGTGTTCGCGGCGCACGTGGCTCGGCGGGTGATGAGCGCGCGGCCGCCGCGGGAGA<br>TCGTGTACGGGAACATGACGTTGCTGTTCGCGGCGCTGGCGGCGGCGCCGCTGTGGGCGCGCGACGCCTTCTTCGCC<br>AAGCGCTTCGGCCTCGACAAGATGCTACCACCGCGCTAGAGAAGAAGAAGAAGCCATCATGA |
| SEQ ID NO: 81 | ATGGTGGAGCTCTCTATCGCCGACGCCAGCGCCAGTGATCTGTGCGGCGGCACGCTGGGGCAGATGGTGGAGCTCG<br>TCTGCGAGGCGAGGCTACGAGTGAGGGAGGAGTATGTGAGATCAACAGTGGACTTGATGGCGTTGCTGCGTGGGCG<br>CGGCATGGTGTTCGACGGGGTGTACGTGGTGTCGAACCTGACGCGGCTCTTCGCGGAGCTGGACTTTGGGCGCGGG<br>GAGTGGGTGGTTAGCGGCATGGCACAGCCGATGCTGGCAACGTTCCTGGTGACGTGCAGGAACGGCGACGACGAGG<br>ACGCGGTGGCGGCATCGATGCTGTTGCCGCCTCCGGTGAAGTTGAGGTTTGCAGAGGAGCTTGCTGGGCTGATGAT<br>GAGCATGCCGCACGGCGGCGCTGCCCTATGCCCCGCACCGGCGAGTACGTACCTCCCTCTTAGCATGCGTGGAAGA<br>CGGTGGCTACACATCCCGGAGGGGTACTACGGCAACGCACTCGCATACTCCATCACCGATGCCAGTGCCAGCGATC<br>TGTGCGGCGCGACGCTGGCCCAGATGATGGAGCTGGTCTGCGAGGCGAGGCTACGGGTGACGGAGGAGTACGGGAG<br>ATCGACAGTGGACTTGATGGCGTCGCTCCGTGGGCACGACACGGTGTTCGATGGGGTGTACGTGGTGTCGGACCTG<br>GGTGCGGGGAGTGGGTGGTCAGCGGCATGGCCTAGCCGATGCTGGCGACGTTCCTGGTGA |
| SEQ ID NO: 82 | ATGAATCAACAACACCAAAGATCAATCGAGCACTGCTCGATCGGTTGCTTTCTGGCCTCGCCGCCGCCTCGGTTCT<br>TCCCAGCTCGGACTCGATCGGCTCCCGGCGAGCTTCGAATGAAGCTCGTCGTGTTCTTGATTCGAGGCTGTCCCGG<br>CGAAGTTTTGCTGAGACCAATCGTCCCGGCAAAAGAGGGGCTGCGAACCAGAACGAAATGGCACATATTGCAGAGG<br>TTTTGCAAACTTGAAATAATAAGTATAGAGACAGAAACGATGATCACGATCTCGAGTCGATCGATCATCAAATCGA<br>GATGTAAAAAGTCAAATAAAAAGATTTTGGTTTTCTTTTTATCTATGTCAGTGAAATTTCTGCTCATCACAACCAG<br>AAGATCTTTGTCAGTACAGAAGAGATCTTCCACGTTCTCCCAACTTTTGCATTAG |
| SEQ ID NO: 83 | ATGTGCATGGACCGAGCTGCCGTGCCGGTGAAGAGGGTGTGGCTCGGCCTCGCCGCGCGCCTCGGCCTCCGGCGAA<br>CCAGCGGGCTGGGGAAGCTGAAGAAGGAGGTGAGGACGTGCGAGTACCACGACGTGCACATCATGTGGGAGATGCT<br>GAGGAAGACGGACGCGCCGGTGCCCATGGCGGAGAAGGAGGCCGCCGCCGCCGCGGCCGTCGCGGCGGCCGCCGGC<br>GCCCGGAGGAGGAAGGCGGCGTGGAGACGGTTCCTCTACTACTGCTGCGCGTTCTAA |
| SEQ ID NO: 84 | ATGGCGACGTCCCGCAAGCTGGCCCGCGTCGACATCGCCGAGCTGAAGCAGCGGCTGGTGAAGCGGCTGGGGCGGC<br>AGCGCGCCGGGCAGTACTTCGCGCACCTCACCAGGCTGCTGAATCTGAAGCTCACCAAGGTGGAGTTCGACAAGCT<br>CTGCTACGCCACCATCGGGAGGGAAAACATCGCTCTGCACAACGCCCTGATTAGGGGGATCATCAGCAATGCGCTG<br>TCCGGGGTGCCCCCGCCCAGCCGCCAGGCGGTGACGGGGCAGTCCGGGACGACCACGGCTCCCAGCGGGCAGTGCG<br>TCGGCATCGCGCTACAGAGCGCCCGAAATGTAGGGGCCGTGGTGGATTCGGGCGATGGGGACTTTGCGAGGGAACG<br>GGCGGTTGCCGGCAAGGTGTTGTCGGTGGAGGATGGGGAGGAGGTGGAGCAGGTTAGGTCTGCTCCATGTGTGCAG<br>AGCCGAAGCCCGATAACTGCCCCATTGGGGATTTCGACTACGCCAACCTATGGTGCAAGGACATGGAGGTTGGATG<br>ATCCAATGGTGTCGTGTTACGATTCCCACCATCTGCTGGACACTGGTTCTCTGTTCAAGGGTTTGCAGCGTCGGTT<br>GGAGAGTGATGGCATTGGAGTGTCGGTGCAGGGTGTTGAAGTTTTAAATCGTGGATTAGATGAGTTTTTGCGGAGG<br>TTGATTAAACCATGCATGGAATTGTCCAGGTCAAGGTCCAGCGGTAGAAGAGTTACCAAAGGCAATGCTATGTTTG<br>CAGCTAGGATGAATGGCTTGCAACAAGCCAATCATGGTCATTGTACAACACTACAAGATTTTGCTGTCGCTATGGA<br>ATCTGATCCACATTTGCTTGGGACCAATTGGCCTACACAGCTTGAAAAGATACAGGCAACGTCGTTTGGTGAATGA |
| SEQ ID NO: 85 | ATGGCGTCTCCTCGCTGCGCCGCCGTCGCCCTCCTCCATCCCGCCGGAGTCGCCGCCGGCGGCGGAGCTCGCCGGC<br>GTGTCCTCCTCCTCGACCAAGAGCGGCCGTTGTGGGGGACTGAGGTGCGCCGGCGCCGGCGCCGGCGTTTCTCGAG<br>CCTCGAGACGCCGCCGCGGTGCAGCAAGATGTACGTACCCGGCTTCGGAGAGGGATCGCCGGAGAAGAAGGCAGCA<br>AGAAACCTGCAGCACTTCTTCAACTACATTGCTGTCAGGGTTGTGCTCACACAGCTTGAGAGTTACAACCGGGAAG<br>CATATGGTGAGCTGATGGATTTCGTGAACCGAAACTCCCTCAACGACGCTGATACTTTCTGCAAGAAGTTGATCCG<br>CGACTCTCCAAGGCACAAGCAGCTAGCAATGAGGATCTTGGAGGTCCGATCTGCTTATGTCAAGCATGATTTCGAG<br>TGGGATAATCTGAAAAGGTTATCTTTCAAGATGGTTGATGAGGCCAACACAAAGCTCATGAGGGACTATGTCTTGG<br>AGACCAGCCACATCGAAGACGATAACTGA |

TABLE 2-continued

| Amino Acid and Nucleotide Sequences of Rice Polypeptides | |
|---|---|
| SEQ ID NO: 86 | ATGGACATCACCGGCGCGGGCGCTATGGGAGGAGGATCCACGGCCGCCACCGCCGCCGCGGCGGCGGGGGCCGGGT GGAAGACGCCGGTGTCGATGGTGCTGGTGCAGCTGTTCATCACGGGGCAGATCCTGCTGTCCAAGGTGTCCATCGG CGGTGGCATGTTGATCTTCGTGCTGCTTGCGTACAACAGCTTCTTCGCCGTCGTCTTCCTCCTCCCCTTCGCGCTC ATCTTCGAGAGAGGCAAGTGGAGGGACATGGATTGGGGTGCATTCGGATGGATCTTTCTCAATGCGTTCATTGGGT ACTCTGTGCCAATGAGCCTCTACTACTATGGCCTCAAGGATACCACATCATCCTATTCCGTTATCTTTCTTAATAT AACTCCCCTGTTCACCTTCATCCTCTCACTTATGTTCAGGTTGGAGGCATTCAAACTTAGAAGCATACCTGGAGTA CTGAAAATAGCGAGCATACTGCTTTCCATTGGAGGGACAATGCTTATAAGCCTTTACAAAGGCAAGTCATTGCATC TCTGGGATTCTATCATACAACACCAAAATGAACACAAGTCAGCAACCAATCAGCTAAGAGGAACAATTCTATTGGT TGGCAGCAGCTTCACCTTTGCTTGCTGGTTTCTTATTCAGTCAAAGATTCTCAAAGTGTATCCATACAAATATTGG TCGTCCATGGTGACATGCTTGGTTGGAGTATTTCAAACCGCATTGGTCGGAATCATATTAAGGAGAGACAAGAGTG CATGGGAGCTAGGATGGAATCTCAACCTTGTTACCATCGTGTACAGGGGGGCACTTGCAACAGCCGGGAAATATAT ATTGAATTCATGGGCAATAACTAAGCGAGGCCCAACCTATCCCACAATGTTCAGTCCATTATCAGTCGTCTTCACT GTTGTGTTGGATTCAGTCCTTCTAGGAAATGATATTACAATTGGAAGTCTTCTAGGCACAGCATTGGTGATTGTCG GGCTCTACCTTTTTCTCTGGGCCAAAGCACGAGAAATACCTAAGAAGTCAACATAG |
| SEQ ID NO: 87 | ATGGCTCGGCGCGCTGCGGAAAAAGAGGCGGCGCTCCGCCAGGGTCTCACCGCCGGTGACGGCGAGGCGCGACGGA CAGGTGCATTGTGGCGGACAGATGCGTGGCGGCAGCGGGCAGCTGCTAGTGCGGCTGCAGCGTCGGTGGTGCGGAC TTGGCCGAGCTCTGCGCCGTGGCTGCGGTTTGAGCTGGATCCATGGCGACGGGTCTGTGGAGAACAGGACCTGCAG ACCGCGGCCTGCGGCGGCGGCGACGGCGCCGTGGGGCTCAGCTTCGAGACGCACCACGGCGGCAGCGTGGCGCCTT CGCCGGAGTTCGCGGCGTGCGCGGCGAGCTCTTGCAGCGCGGAACTCATGGTCTTGCTGGTCCTGCAGCGCGGCGA GCTCCTGGTGCGCCATGACCGGCCGAGCCATCACCACCGCCGTCGCTTCCCAACGCCGCAACCAGCCGAAGCCGCC GCCGCAGTTGAAGTTGGATGGGGATTTCAGAATCCCAGAGATGCAATGACTTGCCTTTGTAAAGGCTTATAA |
| SEQ ID NO: 88 | ATGGGCAGCGGCGGCGGTGGCTGCGGCAGGAACGGCGCTGTGAGGCAGTACATCAGGTCCAAGGTGCCGAGGCTGA GGTGGACCGGGGAGCTCCACTGCAGCTTCGTCCAAGCCATCGAATTCCTCGGTGGCCAAGACAAGGCTACACCTAA GCTCATTCTTCAGCTCATGGGGGTGAAGGGGCTGACCATATCTCATGTCAAGAGCCACCTCCAGATGTACAGATGC TCCAGGCTCGGCTCCCATGGCACGGGAAGGAGATCAGAGATGCAACCACAGCTGCAAAGGAAGCACTCATGTGGTG CTGATGAGCAAGTCCCCAGAGAATTCCTGTGCCCCCCTCTGAAAAGGACCAGGATGGGGACAGAAGCCACATACAA AGGCATGCAAGGAAGCCAAGGAATCAGTGAGATGAGGACTACTGGCACCCAGTACTGCATTGATGATTACATGCAA GCCATGGCAATGGAGAGGAGAATAAAGGAGGAGGGCCTCAGATGGCAGAGGGATGCTGCTGCTGCTGCTGCTGCAG ATGGTGGTGCTGCTGCTTCCAACCTCCAAACCGTGGGATGTTCGGTGCAAGAATCTGACCCCTTTAAGATCATCAA ACCAGAAGTGCACCATCTTGGTCCCGTGTTGAAGCTGCAATGCTCCAAGGTGGAGAACAGTGGATTCATCTCCAGC AGCACCGGCACGGCTGCAAGGGATCAACCGGAGCCGCCGCCGCTGGAGAAATGTTCGCTGTCACTCTCCCTCGGTC CAGACCCCAAATGCATGCCGGCGATCGCCTCGTCGCCGAGCGAAAGCAGCTGCATCCTCTCGTCGTCGTCCAGGAG CTTCAGCGACTGCTCCGGGAACTCAGGTTGTCTTGTTGCCCCGGGTGTGAACTTGGAACTCTCCATGTCCATCTGT GGATCTTAG |
| SEQ ID NO: 89 | ATGGCTGCCGCCGACCAGCCCGCCTACGGCGATCGCCGGCCGTCCCGGCGCACGTACAAGCCGGACCAGCCGGAGG GCCTCACCATCTCGTTCCGCGAGCTCTACGACCTGCCGACCTCGCCGGAGTTCCTGTTCCACGAGGAGGCGCTCCG CAGCCGCCGCACCTGTGGCGAGGACCTCACGTTCTACACCGGCTGCGGCTACCTCGTCGGCCGGGCGGCGGGGGCG GCCGCGGGGCTGAAGCGCGCGGCGGAGGAGCGGAGCGCGGCGAGTCGATGAAGCTGCGGGGGCAGCCGCGTCCTC AACCAGTGCGGCTCCCTCGGGCGCGCGTACGGCAACCGGCTCGGCGTCGTCGCGCTGCTCTTCGTGGGGATCGAGA GCACCGTGGGCGGCCTCCGCGACGCCGACGGCTGGGCCAACACCGTCGCCGCCGGGATCGGTACCGGCGCGCTCTA CCGCGCGGCTGCCGGCCCGCGGGCGGCGATCGTCGGCAGCTCCGTCGGGGGGCTCATGGCCGGCGCGGTGGTCGTG GGGAGGCAAGCGCTGACGAGATACGCGCCTAA |
| SEQ ID NO: 90 | ATGGACATGCCGCCCACGCCCCTTCCGCCGGAGACCGCCAACACCTCGCCCGCTCCCAACGGCGCCACCGCCGGAA TCCGGGTTGAGAACTGCTACGTCTTCAAGAGCCGGCTGCAAGAGTATGCACAGAAAACCGGCCTCCAGACTCCAGA GTATCATACCTTCAAGGAGGGACCTTCCCACGAGCCTGTCTTCAAGTCCACAGTGGTGATTAATAATACCAGCTAT GACTCCCTGCCCGGATTCTTCAACAGAAAGGCTGCAGAACAGTCTGCTGCTGAAGTTGCCCTCATGGAAATTGTCA AGTCCATACCAGCCAACGCAAATATCCCAGCTGTTCAAGAGACTGGGCTGTGCAAGAATCTTCTTCAGGAGTATGC ACAGAAGATGAATTATGCCATTCCATCTTATATTTGCACCAAATCAGCCTCAGGCTTAGCTCCTTTCATATGCACT GTAGAGATTGGTGGAATACAATATATTGGTGCTGCAGCCAGGACAAAGAAAGATGCAGAGATAAAAGCTGCCCGAA CTGCTCTTCTGGCAATCCAAGGTCAATCAGAGGGTTCGGCAAATGGTGCAACAAAATATATTGTAGTTCCTGGTAA AAGGGTAGGTAAGGAGGTAGAGAAAAGGCCAATTGAAACACCGAAACCACTTAAAGTAAAGAAAGGTGGTTTCAAG AAGAAATGGAACAAGAGGAAATTCATGAAGAAGGATGGTCAAGCTGTTGATGTGGAAAAGGATGAAGCTAGAGTGG CTGGAGATGCTCACGATTCTGATGTCCTAATGCAGCCAACAGTAATAACACAGGAGGCATCTTGTGGCACTCTGTT CCTGCAACCTTGTGAGGAAGCTAAAAGAGTAGAAGCTGAGCCACCTAGAGATATTGAAATGGTACAGCCTGATAAG GAGAACCAACACAGTGACGCTGCATTGGTGCAACCTGATGATGAAGCTAGAGTAGAACAGGAGCCATCCAGAGATA TTTCAGTGGTGCAACCTAATGAGGAAGCTATAAGTGGTAAGCAGGAACCATCCATCGATGCTGCAATTCTGCAACC TAAAGAGGAAGCTTCAAGTGTAAAGCAGGAGCCATTCATCGATACTGCAATGCTGCAAGCTTGTAAGGAAGCTGGA AGTGTAGAACTTGGGCCAGCCAGAGATACTGTAATTTCCCAACTTAATGAGCAAGATAGGGCTGTAAAGCAGGAGC CAGCTGGTGACATTGTAGTGCCACAACCTGACGTGCACGCTAGGGTCGTAAAGGAGTAG |
| SEQ ID NO: 91 | ATGGCATTGGGGGATCTCATGGCCTCCAGGCTCGTCCACTCCTCCTCCTCCTCCGCCGCGCGCCATCCGCCGCCCCTGC CCAATCACCATACCAACCACCTCGTCGATGACCACCTCCCCGTGGAGAATGGACCGGACCCCAGGAGGGACGTGCC CGACGAGGAGCCGCCGCCCCCGCCGCCGCCGCAGGTCGCCTTGCTGCCCCAGGTGGTCGTGCTGTGCGAGCAGCGG CACGAGGGGTTCGACGAGGCCGCCGCTGCGGCGGCCGGGCCCTCCACCAGCGGGCCCGTCTCCAAATGGCGCCCCA AAGACCGGATGAAAACTGGCTGTGTGGCACTTGTGTTGTGTTTAAACATTAGTGTTGATCCGCCGGATGTGATCAA AATCTCCCCTTGTGCAAGAAAGGAGTGCTGGATAGATCCATTTTCTATGGCACCTCCAAAAGCCCTTGAAACTATT GGGAAAACATTACACTCACAATATGAGCGCTGGCAGCCAAAGGCTCGTTACAAGCTTCAGCTGGATCCGACATTAG AGGAAGTTAAGAAGCTATGTAATACTTGCCGTAAATTTGCTAGAACAGAGAGAGTCCTTTTTCATTACAATGGTCA TGGTGTACCAAAGCCTACAGCTAATGGGGAGATTTGGGTATTTAACAAGAGTTACACACAGTATATTCCGCTTCCT ATTACTGATCTTGATTCATGGCTGAAAACACCCTCTATATATGTTTTTGACTGCTCAGCAGCTGGAATGATCGTGA AAGCTTTTCTGGAGCGCCTAGACTGGAGTTCTAGCTCGTCTGCATCTTCATCGAAGGACTGCATTCTCCTTGCGGC CTGTGAGGCACATCAAACTCTCCCACAGAGCGCAGAATTTCCTGCTGATGTGTTCACAGCTTGCCTCACCACACCC ATCAAAATGGCACTGCACTGGTTTTGTAACCGATCGTTACTCCGTGATTCCATGGAACACAATCTTATCGACCAAA |

TABLE 2-continued

| Amino Acid and Nucleotide Sequences of Rice Polypeptides | |
|---|---|
| | TTCCTGGAAGGCAAAATGACCGCAAAACTCTTCTAGGGGAGTTGAACTGGATTTTCACTGCTATCACAGACACTAT TGCATGGAATGTTCTTCCTCATGATCTATTCCAAAGACTTTTCAGGCAGGATCTTTTGGTTGCTAGTCTCTTTCGC AACTTCTTACTTGCTGAGAGAATCATGCGGTCCGCAAATTGTTCCCCAATTTCATACCCTTTGTTGCCACCAACTC ATCAGCACCATATGTGGGATGCATGGGACATGGCTGCAGAGATCTGCCTTTCTAAGCTTCCTCAATTAATTGCTGA TCCTAATGCAGAGTTTCAGCCGAGTCCATTTTTCACGGAGCAATTGACAGCATTTGAAGTTTGGCTTGATCATGGC TCTGAAGACAAGAAACCCCCAGAACAGCTACCTATTGTTCTTCAGGTTTTGCTTAGTCAGTCACACAGATTTAGAG CACTTGTTCTGCTTGGAAGATTTCTTGACATGGGACCTTGGGCAGTTGATTTGGCTTTGTCCGTTGGCATCTTCCC TTATGTACTTAAACTGCTTCAAACAAGTGCAATGGAGTTGCGCCAAATTCTTGTGTTCATATGGACAAAAATTCTC TCTCTTGATAAGTCATGCCAGGTTGACTTGGTGAAAGATGGAGGGCATGCATACTTTATCAGGTTTCTTGACAGTT TGGATGCTTACCCAGAGCAGCGTGCAATGGCTGCTTTCGTTTTAGCCGTTATTGTGGATGGGCATAGGATTGGTCA AGAGGCTTGTGCTAATGCAGGGCTTATAGATGTCTGCCTGAGACATCTGCAACCTGAAAATCCGAATGATGCTCAG ACAGAGCCTTTGCTCTTGCAATGGCTTTGTTTATGCCTTGGCAAACTTTGGGAAGATTTCCCTGAGGCTCAGTTAC TTGGTCTGCAATCAAACGCACCGGAAATTGTTATATGCTTATTGTCAGAGCCTCAACCTGAAGTCAGAGCTTCTGC TGTTTTTGCACTTGGAAATCTTGTGGATATTGGATCTCCATCACTGAATGGAGCTGACGACGATTCTGATGATGAT GAAAAGGTGAGAGCTGAAATAAATGTTGTCCGAAGCCTTCTGCAGATCTCTTCAGATGGTAGCCCTCTTGTTAGAT CTGAGGTTGCCGTAGCGCTTACCCGCTTTGCAATGGGGCACAATAAACATATCAAATCTGTTGCCGCCGAGTACTG GAAACCTCAAACCAATTCACTGCTCAAGTCATTACCATCGTTGGCTAATATTAATTCGAGCAATGTTTACAGTCCC AGCAGCTTAATACAAGGTAGCAGTGGCCTTGCCTCACATATTGGTCCTGTTTTAAGGGTTGGCAGTGATAACAGTG CCACTGCTCGTGATGGAAGAATCTCTACGAGCAGCCCGATTGCAACAAATAGCATCATGCATGGTTCTCCACAGTC AGATGATTCTTCCCAACACTCTGATTCAGGCATATTACTGAGAGAGAATGCAAGTAATGGTGGTCTCAACTACTCA AGATCGAGGCCTATTGATAATGGGATCTATTCCCAATTTATAGCAACTATGTGCAATGTTGCTAAAGATCCTTACC CAAGAATTGCAAGTATTGGGAAAAGGGCATTGTCCCTCATAGGTGTTGAGCAAGTAAGCATGAGAAACAGTAGACT TAGCAATGGAGGTGCACACCCAGGAGAGACATCTGTGCCCCCTTCATCAAACTTTGGAATGGCACGCTCCTCTTCC TGGTTTGATATGAACTCTGGAAATTTCTCGGTGGCCTTTAGGACTCCTCCTGTTAGTCCCCCTCAGCATGACTACC TCACAGGATTGCGCCGAGTGTGCTCGATGGAGTTCAGACCACATGTTTTGAACTCACCTGATGGCTTAGCTGATCC GCTTTTAAGCTCCAGTGCAGCCCCCAGCAACATGGGGCTCTATATACTTCCCCAATCATTAATTTACAGATGGAGT TGTGGTCACTTTTCTAGGCCACTTCTAACTGGTTCTGATGATAACGAGGAAGCAAATGCTAGAAGAGAAGAGCGAG AACGAATTGCAATGGATTGCATTGCTAAATGCCAACGATCATCTTGCAAGATGACCAGCCAAATTGCTAGCTGGGA TACGAGGTTTGAGTTGGGTACAAAAGCATCATTGTTGTTGCCATTTTCTCCTATTGTTGTTGCTGoGGATGAAAAT GAGCAAATACGAGTATGGAACTATGACGATGCGCTGCCAGTGAATACTTTTGAAAACCACAAGTTATCTGACAGAG GCCTATCTAAACTTTTGCTGATCAATGAGCTTGATGATAGCTTGTTGTTAGTTGGCTCAAGTGATGGAAATGTCCG CATATGGAGAAACTATACTCAAAAGGGAGGACAAAAACTTGTAACTGCTTTTTCATCAGTTCAAGGCTATCGAAGT GCTGGTCGCAGTATTGTATTTGATTGGCAGCAACAGTCGGGTTATCTGTATGCATCTGGTGACATGTCCTCTATCC TTGTATGGGATCTTGACAAGGAACAAGTCAACACCATCCAGTCAACTGCTGATAGCGGGATTTCAGCTCTTTCTGC ATCTCAGGTTCGATGTGGCCAATTCGCTGCTGGTTTTCTTGATGCATCTGTTAGGATATTTGACGTGCGTACACCT GATAGGCTAGTATATACAGCAAGACCACATGCCCCAAGATCAGAAAAGGTTGTTGGTATAGGATTTCAGCCTGGGT TTGATCCCTACAAGATTGTAAGTGCATCTCAAGCTGGAGACATTCAGTTCCTTGATGTTAGAAGGGCATCTGAACC CTACCTCACTATTGAAGCACATAGGGGTTCATTAACGGCATTAGCTGTTCATCGGCATGCCCCAGTTATTGCAAGC GGCTCAGCCAAGCAGATGATCAAAGTGTTTAGTCTTGAAGGAGAACAGTTGACAATAATTCGCTACCAGCCATCTT TTATGGGTCAACGAATAGGCAGCGTAAACTGCCTTTCTTTCCACCGATACAAATCACTCCTTGCCGCTGGTGCTGG TGATAATGCTCTTGTTTCTATCTACGCGGAGGACAATTACCAAGTACGATGA |
| SEQ ID NO: 92 | ATGGGTGCCAGCGGAAGGCTGATCTCCATTTACCCAGAGGATCTCACTTTCCTATTTGAGCTAGATAAGCCATGCT ATTGCAATCTCAAGGTGGTGAACAACAGCGAGCATCATGTTGCATTTAAGGTCAAGACGACATCACCGAGGAAGTA TTTTGTCCGGCCGAACGCGAGCATCATCCAGCCATGGGATTCTTGCACAATAACAATTACGCTCCAGGCGCAGAAA GAGTACCCACCAGATATGCAATGCAAGGATAAATTCTTGATCCAGAGCACCAAGGTAGCTGCCAGTACTGACATGG ACGAGATCCCCCCTAACACGTTCAACAAGGAAGTCGATAAGGTGATTGAGGAAATGAAGCTTAAGGTTGTTTATAC AGTTCCCAGTGGAAGTTCTGACGACTCTGGTATTACATCTTTAGGCAGCAGGAGCTTCAAATTGGGGTCTGACGAT CTCACGATGCTGAAGAATGCAAGCATTGAAAAGATACAGACAATACAACGCCTAAAAGACGAACGAGACACCACCC TGCAGCAAAATCAGCAAATGCAACGTGAATTGGATGTGATCAGGAGGCGTAGAAGCCGCAAAAGCGATGCGGGTTT CTCCTTAACGTTTGCTGCTTTTGCTGGGCTCATAGGTGTCCTGATTGGGCTCTTGATGAGCCTCATCTTCCCTCGC CCACAGGCTGCTGCTTAA |
| SEQ ID NO: 93 | ATGGGGGTGATGAACCCGCTGATGGCAAAGCTCACCACGCTCATGGGCGACGAGTACAAGAAGCTCAAGGGGCTCA GGAAGCAGGTCTCCTTCCTCAAGGATGAGCTCACCACCATGAGCGCTTTCCTCGAGAAGCTCGCGCTCATGGATGA TGATGATGATGGTGAGCTCGATCCTCTGGCCAAGGACTGGAGGAACCACGTCAGGGAGATGGCCTATGACATGGAA GACTGCATTGATGATTACTTCACAAGTCATCTTGATCATCGTTACTCTTCCTCAGATGCAGGGTTAATCCGCAAGA TAGCTCGCCGTCTCAGGGCATTGCGGGTGCGTCATCGCATAGCCAGCCAGATCAATGAGCTCAAGGCTCGTGTGGT CGAGGCAAATGAGCGTCGCGTGAGATACAGGCTTGATGACTGTAACAACAAACATGGTGTTTCTGCCAATCCTGCT ATAGATCCACGGATAACATCGCTCTACCAAAATGCCGGGAGTCTTGTGGGTATTGATGGCCCAAGCCAAGAACTAA TCCAGCTGTTGTCGTTAGATCGTGATACCGATCAACGACAACTCAAAGTGGTGTCCGTCGTGGGATTTGGAGGTCT CGGTAAAACAACTCTTGCAAAATATGTGTACGACAAGATCGGGCATCAATTCGATTGCACGGCATTCGTCTCAGTA TCCCACAAACCTGACATAACAAGGATCCTCAGTAGCATCCAATCCAAGCTTGACATAGGGGGCACGTCTCAAGCTT GCGACGACGTGCAACAACTCATCGACGACATACGAGCCTATCTGGAGCATGAAAGGTATATTATTATAGTCGATGA CCTGTGGAAACAAGAAGCATGGGTTATTATTAGTTGTGCCTTTCCAAACAATGGCAAAGGTAGCAGAGTGATAGTA ACCACACGAGTGAAAGATGTGGCCAGGTTGGCATGTGGCAAGGATGGACAAATTTACAAAATACAGCCTCTGAACA ATAAGGACTCAAGAAAGTTATTCTTCGATAGAGTATTTAGGCCTGAAGATAGTTGTGTCCTGCAGTATGAAGAAAT TTCAACTGAAATCTTAAAGAAGTGTAGTGGCTTGCCACTTGCAATTGTTACTGTAGGGAGCCTCTTAGCCTGTCGA CCAAGAACAATGGAAGAATGGAAGAGCATACGGGATTCTTTGGGTGCCCCGTTTGACAAAAACAAGAGCTTGGAAG GCATGAGGAATATTTTAAACCTGAGTTACAAGAATCTTCCTCTTCATCTCAAAACATGCCTCCTATATATTGGTAA ATATCCAGAGGACTATGAGATCGGGAGGGATGAACTAGTTACGGAGTGGATAGCTGAAGGTATTATGGGTAACCCT CATGGGGAAAACTTGGAGGCTACTGGTAATGGCTACTTCAGTGAGCTTATCAACAGGGGCTTGATTCAACCAGAGA GCACCGGCTATGGTGGGGAGGTGTTGAGTTGCAAGGTGCATGATATGATGCTTGATCTGATCCTCATCAAGTGTGC AGAAGATAATTTTGTCAGCGTTGCACACAGTTGTAAAGACTACATGCGCATGGCTATGCACCATGAGCGGAGTTGC AATAAGGTCCGTCGGCTATCCCTGCAGTGCAAGGCTGCAAGATCAGATTGCGCAATTGAGGGCAGCGTCATTTCTA CAAGCATGGCTCGTGCTCGATCAGTTTCAGTGTTTGGTGAGTGTTCACGTGGGCTCCCATTTCTGATGCTATCCAA GTATATACGGGTGGTGCACATCGAATTGGAAGGCCATGGCGGTCAAGTCGACCTCACTGCCATTAGCCATGTGCTT CAATTGAGGTATTTGAGAGTGGAGACGCCTGGTTGTGAGATAGATCTCCCCAGCAAAATATGTGGGCTCGTGCATT |

TABLE 2-continued

| Amino Acid and Nucleotide Sequences of Rice Polypeptides | |
|---|---|
| | TGGAGACATTGTCAATATTTTCCCATAAAGCTGTAAGTCGGCTCCCTTCAGATATTAGCAGTCTTCCCCGCTTGTC AGTCCTGTCCCTGGTGGTTCCATGGGCTACAAGGCTACCCAACAAGTTAAACAAGCTAAAAGGGTCACTACGCAGT CTCACCATACTATTCAATCCCCCGGATGCGTTAGGCATGGAGGCCATTGGTGAGCTGAAAAATCTAAGGGACCTAA ACATCTCTGTTAACAGGTGGCGGGACGATGAGATCCTTAGCCTTTATGCTCTGGGGTCTTCCATTGGAAAACTGGA TGAACTCAGGAGTTTGCAAATTCATGTCCCACCTGCTACCTTAGGTGATGTTGACCTGCTGGGCTCATTACCCATT TTTCCTCAAAGTATCGAGAGACTAATACTACACGGTTGGTGCTTCTCCAAAGTACCTCGATGGATCAACGGTACTC TCCGTAACCTCCAACATGTGTTGCTGGAGGTATCGGAGACATCGAGTAGCGAGGTTGACCTTCTTGGTGAACTACC CTCCCTCGCCGACCTCGAGCTGAGAGTAGGACTCAAGACAAGAGATGTCATCGCGTTCGGTGGCACTAGAGCATCA TTATTCCCTGCTCTCCTGAAACTCAAGCTGCGTGGGTGAACACGTTGCCTCAAGGCTGCAGTTCCAGGCAGGGG TGATGCCCAAGCTCCAAAGCCTCCATCTGTGGTTCCGGAATTGTGAGTCGGGCATTCACGTAACACCGGAGGGTAT GCAGCACCTCCTGAGCCTCCAAAGCATCTGCGTGGAGATATACCTCCGGGATGAGGAGCTGAAAGCAACTTATCCA TGGGACGCCATGGAGCGTGCGTTCAGGGAAATCACTGGAGCAAACCCCAACCGGCCTTCCTTCAAATTTGTCAAGC AAGTCTGA |
| SEQ ID NO: 94 | ATGGAGTGCGAGCCGGAGGAGCTGCAATTCCTGGGCATGGTGGGTATCTACAGGGAGGCGGCGTCCATCCTGCGCG CCCACCGGCCGCTCTTCGCCCGCATCGCCGCCGCCTTCGTCCTCCCGCTCTCCCTCCTCTTCCTCCTCCACATCGC CATCTCCCACGCCCTCTTCTCCCACATCGACTCCGACGACTCCGCCCTCGACTCCGCCGCCCCGGGCACCCCCGCC CAGCGCCGCCTCCTCCACCGCCTCGCCGACGACTGGCTCGCCCTCCTCCTCTTCAAGGCCGCCTACCTCCTCGCCC TCCTCCTCTTCTCCCTCCTCTCCACCGCCGCCGCCGTCTTCTCCGTCGCCTCCGTCTACTCCGCCAAGCACGACGC CCTCTCCTTCCCCAGGGTCCTCTCCGTCGTCCCCCGCGTCTGGCGCCGCCTCGCCGCCACCTTCCTCGCCGCCTTC CTCCTCCTCTTCGCCTACCACCTCCTCTTCGTCGCCGTCTTCGTCGCCCTCCTCGTCGCCGCCGACTCCGGATCGG GCCTCGCCGCGCTGCTCGCCTTCCTCCTCGCCCTCGCCTACATCGCGGGCCTCGTCTACCTCAGCGTCGTCTGGCA CCTCGCCAGCGTCGTCTCCGTCCTCGAGGACTACAAGGGATTCGAGGCCATGCGCAAGAGCAAGGCGCTCATACAG GGCAAGCTCTGGACCGCCTCCGCCATCTTCTTCGTCCTCAACGTCGTCTTCATCGTCGTCGAGGTCGCCTTCCGGG CGTGGGTGGTGCGCGGGGCCACCCACGGCCTCGGCGCCGGCTCAAGGCTCCTCCTGGGCCTCGCCATGCTCGCCGC GCTCTGCGCTGTCGTGATGCTGGCGCTCGTGGTGCAGACGGTGGTGTACCTGGTGTGCAAGAGCTACCACCACGAG AGCATCGACAAGAGCAACCTCTCCGACCACCTCGAGGTCTACCTCGGCGAGTACGTCCCGCTCAAGGCCAGCGACG TCCAGATGGAGCAATTCAACCTCTGA |
| SEQ ID NO: 95 | ATGGCGTCCTCCTCCGCCCTCGCTTCCTCCCCCTTCCTCCCGCCCCTCTCAACCCCAAACCCTAGGGCCCTCTCCC TCCGCCTCCCCGCTCGCCGCCTCCCCGTGGCGTCCTCCGCGGCTCCCTCGGGCGCTGCCGCTGCGGCGTCGGCGAG GGAGCGCCGCCGCTTCCTGGAGCGGTACGGCCTCAACCCCGACGACTTCGAGGACGATGCCGAGGCGGAACCCAGG GAAGAGAGGAGAAGGGATAGGCGGAACCGGCGGTCGGGTAGAGGGGAGGCGGAGGATGCTCCGGCGAAGGCGGCGG CTGAGCCTCGGGAGACGCATAAAATGCTTCAGGTGTTAGGAGGAAAAGTACGCAGAAGAAAATTACTTTCACCAAA AGATAGGAATGTTCGTCCAATGATGGAAGTTGTACGAGGGGCAGCCTTTGACATTTTACAGTCAGCTGGTGGTTTT CCGGCTTCGCTTAGACCTGGTCGATGGTTAGACTTGTATAGTGGTACTGGATCTGTTGGAATTGAGGCTATGAGCC GTGGATGTTCAGAGGCACATTTTGTTGAGATGGATCCTTGGGTTGTTTCTGAGGTCCTTAAACCGAATCTGGAGTG TACTGGATTTCTTGATGTTTCGCACATACATATGATCCGCGTCGAAAACTTCTTGGCCAATGCTGAAAAATCTAGT GGTAAATATCCTTCTTTTGATTATATTAGTGTAACACCGCCATATCTTGAGGTAAACTACAGTACACTACTCGATC AACTTGCAAGGTCACCATTGGTTGGAGAAGATTGCTTCATTCTCGTTGAATACCCACTGAAAACAGACATGGCCGA ATCATGTGGAAGCCTTATAAAAGTAGCTGACAGGAGGTTTGGTAGGACAAACTTGCTAATTTATGGGCCAACCTGG GCTGAGAAGAAGAGGAGATCTTGA |
| SEQ ID NO: 96 | ATGAACGACCTCATGACCAAGTCGTTCATGAGCTACGTCGACCTGAAGAAGGCGGCGATGAAGGACCTGGAGGCGG GCGGGGATGGCGTGGAGCTCCCCGAGGTGGGCGTCACCGACGAGCGCCTCAAGGGGTTCTTCCAGGAGACGGAGGC GGTGGAGGAGGAGATGGCCGCCATCCGCGACGCGCTGGCGAGGCTCAACGCCGCCAACGAGGAGGGCAAGTCGCTG CACCAGCCCGACGCCCTCCGCGCGCTCCGCGGCCGCGTCAACGCCGACATCATCGCCGTGCTCCGCCGCGCGCGCG ACATCCGCGCCAGGCTCGAGGCCATGGACCGCGCCAACGCGGCGCAGCGCAGGCTCTCCGCGGGCTGCCGCGAGGG CACCCCGCTCGACCGCACCCGCACCGCGCTCACCGCCGCGCTCCGGAAGAAGCTCAAGGACCTCATGCTCGACTTC CAGGCCCTGCGGCAGCGGATCATGTCCGAGTACAAGGACACCGTCGAGCGCCGCTACTACACCCTCACCGGCGAGG TCCCCGAGGAGGAGGTGATCGAGCGCATCATCTCCGAGGGACGCAGCGAGGAGCTCCTGTGCGCCGCCGTGGCGGA GCACGGCAAGGGCGCGGTGCTGGCCACGGTGCACGAGATCCAGGACCGCCACGACGCCGCCCGCGAGGTGGAGCGC AGCCTCCTGGAGCTCCACCAGGTGTTCCTCGACATGGCCGTGGTGGTGGAGTCCCAGGGGGAGCAGCTCGACGACA TCGAGCGCCACGTCAACAGCGCCACCACCTACGTCCAGGGCGGCAACAAGGAGCTACGCAAGGCCCGCGAGCACCA GCGCAGCAGCCGCAAGTGGCTCTGCATCGGCATCATCATCCTGCTGCTCCTCGTCCTCCTCGTCATCGTGCCCATC GCCACCAGCTTCAAGAGATCGTGA |
| SEQ ID NO: 97 | ATGGCGATGGAGGGGAAGAGCAGGAGGTTCGCGGTGGCGTGCGGGGTGCTCAGCCAGTACGTGAGGGCGGAGCAGA AGATGGCGGCGGCGGCGGGGGCGGCACCGGCGAGGGCGGTGACGACGCTGAGCCTGATGCCTGGGGCGGAGGTGGT CGTCGAGGAGGAGGAGCGGAGGGAGGTTGGGGAGGAGGAGGCGGGGCCAGCGACGGCGCCGGCCGCGCCGCTGACC ATCTTCTACGGTGGGAGGATGGTCGTCTTCGAGGACTTCCCCGCGGACAAGGCGGCGGAGGTGATGCGCATGGCCT CCTCCGGGATGGCGGCGGCGCCGGCTCAGCGGGAGGGCGCCGCGCTCGCGGACATGCCCATCATGAGGAAGGCGTC GCTGCAGCGGTTCTTCGCCAAGCGCAAGGACCGCCTCGCGGCGACCACCCCCTACGCCCGCCCGTCGCCGGCGGAG ACCAAGGCCTCCGAGCCGGAGGAGAAGAAGACGCCCACCTCATGGCTGGACCTCGCCGCCTCCGCCTCCGCCGCCG CGCGCCGTGACAGCCTCACCATCGCGCTGTGA |
| SEQ ID NO: 98 | ATGTCGTCGCTGAGCCGGGAGCTGGTATTCCTCATCCTGCAGTTCCTCGATGAGGAGAAGTTCAAGGAGACTGTTC ACAAGCTTGAGCAGGAGTCTGGGTTCTACTTCAACATGAAGTACTTCGAAGACGAGGTGATCAATGGGAATTGGGA TGAGGTTGAGCGCTACCTCGGTGGCTTTACCAAGGTTGATGACAACCGCTACTCGATGAAGATATTCTTTGAGATC CGCAAACAGAAGTATCTTGAGGCCCTTGATAAGCATGATCGCTTCGAAGGCGGTTGAAATCTTGGTCAAGGACCTGA AGGTCTTCGCGTCCTTTAACGAGGAGTTGTTTAAGGAGATCACACAGCTTTTGACGTTGGAAAACTTTAGGGAAAA TGAGCAACTCTCCAAATACGGTGATACAAAATCTGCCAGAGCAATAATGCTTGTTGAACTAAAGAAGCTGATTGAA GCTAATCCCTTGTTCCGTGACAAGCTTCAGTTTCCAAATCTGAAGAGCTCCAGATTGCGGACACTTATAAACCAGA GCTTAAACTGGCAGCACCAGCTTTGCAAAAATCCTAGACCTAACCCTGATATCAAGACTCTGTTTGTTGATCATTC TTGTGGACAACCAAATGGTGCTCGTGCTCCATCGCCAGCAAACAATCCATTACTTGGATCTATACCAAAACCTGGA GGTTTCCCCCCATTGGGTGCTCACGCGCCATTTCAACCTGCACCTACACCTGTCCCACCTCTGGCTGGCTGGATGT CAAACCCTCCAGCAGTAACACATCCTGCTGTGTCTGGTGGAGCTATTGGATTTGGTACTCCTACAAATCCTGCTGC TATATTAAAACATCCTAGAACACCAACAACTGCCAATCCTTCTATGGATTATCCATCAGGAGATTCTGATCACGTc |

TABLE 2-continued

| | Amino Acid and Nucleotide Sequences of Rice Polypeptides |
|---|---|
| | TCCAAGAGAACGAGACCAGTTGGGATGTCTGAGGAGGTGAATCTTCCAGTGAATATGTTACCTGTGACATATCCAC<br>AGAGTCATAGTTACCCGCAAGATGATTTTCATAAAAATGTTGCACGGACATTGAGCCAAGGATCAACTCCAATGAG<br>CATGGACTTCCATCCAGTTCAGCAAACTCTCCTTCTTGTTGGTACCAATGTTGGTGACATTGGATTATGGGATGTC<br>GGTACCAAGGAACGACTTGTTTTAAGAAACTTCAAGGTTTGGGATCTTACAAAATGCTCAATGGCCCTCCAGGCAT<br>CACTTGTCAAAGACCCTACTGTCTCAGTTAACCGCATAATATGGAGTCCTGATGGAACCTTGTTTGGTGTTGCTTA<br>TTCAAGGCATATTGTACAGATCTATTCATACCATGGCGGTGATGATATCAGGCAGCACTTGGAGATTGATGCGCAT<br>GTCGGTGGTGTAAATGACATTGCATTTGCCCATCCAAATAAGCAGCTATGTATAATAACCTGCGGAGATGACAAGA<br>CAATTAAGGTCTGGGAGGCCACTAGTGGAGCAAAGCAATTTACATTTGAAGGTCATGAAGCTCCTGTTTACTCTGT<br>TTGTCCACATTATAAGGAAAATATTCAGTTCATCTTCTCAACTGCTTTGGATGGAAAGATAAAGGCTTGGCTATAT<br>GATAATTTGGGATCCAGAGTTGACTATGATGCGCCAGGACATTGGTGCACAACAATGGCATATAGTGCAGATGGTT<br>CAAGGTTATTTTCTTGTGGGACTAGCAAGGATGGCGAATCACATCTAGTGGAATGGAATGAAAGTGAAGGAGCTGT<br>CAAGAGAACTTACCAGGGATTTCGCAAGCGATCGATGGGTGTTGTCCAATTTGATACCACACGGAACAGGTTTTTG<br>GCTGCTGGAGATGAATTCTTGATTAAGATATGGGACATGGACAACACAAGTCTTCTGACTACCATTGATGCCGATG<br>GTGGTCTTCCTGCAAGTCCACGGGTCCGATTCAACAAGGAAGGTACTCTGCTGGCTGTTTCTACCCATGAAAATGG<br>TATCAAGATCTTAGCAAATGCTGATGGAGTACGGTTGCTGCGCACATTGGAAAATCGTTCATTTGATGCTTCTCGG<br>AGTGCGTCTGAGACTGTAACAAAGCCCCTAATGAATCCATTGACTGCTGCTGCTGCTGCGGCGGCGTCAGCTGCTG<br>CTGCCGGGACTAGTTCAGGAAATGCTGCTCCACCGGCAATAACTGCACTGAATGGGGATAGCCGAAGCTTGGTTGA<br>TGTAAAGCCTAGAATAGCTGATGAGCCATTGGATAAATCAAAAGTCTGGAAACTTATGGAGATAACCGAGTCAAGT<br>CAGTGCAGATCATTGAAATTAACAGATAATATGAGGACAAGCAAGATTTCAAGACTTATTTACACAAATTCTGGTG<br>TCGCTATCTTGGCTTTAGCTTCAAATGCTGTTCATCTGCTCTGGAAATGGCCTCGCAATGACCGAAACTCAAGTGG<br>AAAGGCTACTGCAAGTGTTTCTCCTCAATTATGGCAACCTCCAAGCGGCATCCTCATGACTAATGACATAACTGAC<br>AACCCTGAAGAAGCTGTCCATTGCTTTGCTTTGTCAAAGAATGATTCATATGTCATGTCTGCATCTGGAGGGAAAA<br>TATCTCTGTTCAACATGATGACTTTTAAGACGATGACAACTTTTATGCCTCCGCCGCCGGCGGCAACGTTTCTTGC<br>TTTCCATCCTCAAGATAACAACATTATAGCAATTGGAATGGATGACTCAACCATCCAAATCTACAATGTTCGAATT<br>GATGAGGTCAAAAGCAAACTTCGAGGGCACTCTAAGAAAATTACTGGACTTGCTTTTCAAATGTATTAAATGTGT<br>TAGTCTCTTCTGGAGCTGATGCGCAGATATGTGTGTGGAGCACAGATGGGTGGGATAAATTAAAGAGCAGAATGTT<br>ACAGATACCATCAAGTCGTCCATCATCTATAATCTTAGACACACGTGTTCAGTTCCATCAGGATCAATTGCACTTT<br>CTTGTTGTGCATGAGACCCAGATTGCCATATATGAAACTACAAAATTAGAACCCGTGAAGCAGTGGCCTGTCCGGG<br>AGAACTCTTCTCCAATAACGCATGCCATGTTCTCCTGCGATAGTCAATTGATTTATGCAAGCTTTCTGGATGCCAC<br>TGTTTGCATATTTAATGCATCGAGTTTGAGACTCCAATGTCGAATTCTTCCAGCATCCTATCTTCCTCAGAATATC<br>AGCTCAAATGTTTATCCTGTCGTTGTGGCGGCACATCCTTCGGAAGCAAATCAGTTTGCTCTAGGCCTGACTGATG<br>GTGGTGTTTATGTATTGGAACCCTTGGAATCTGAGAGAAAATGGGGAAATCCTCCACCAGCAGAGAATGGATCAAC<br>CAGCGCTTTGTCCACACCTCCTAATGGAGCATCAAGTTCTGATCAACCAGAAAGATAA |
| SEQ ID NO: 99 | MPRHACLLQSDRIFFIATEECRRRRRQGGADAGAGGRGGGRRCWAEAAEAAHMAAAAAHRAAAVHRAACGSSTVAVGLR<br>ELHRRRLCSTCTGDGDGDRMLMQRNDSSNSKWMLSRRAFSPFHVSAKFAWEVQESLLDGGSTWFCLGSSAYFVAVKYDW<br>* |
| SEQ ID NO: 100 | MGTYKCCIFFTRRFALSDASTPGDVRMLFTRHAGGAPYMGIDELRRYLAASGEAHVDADTAERIIDRVLQERSRTPRFG<br>KPSLTIDDFQYFLFSEDLNPPICHSKEESFDAMEKLEV* |
| SEQ ID NO: 101 | MQVHHDMNAPLSHYFIYTGHNSYLTGNQLSSDCSDIPIIKALQIGVRVIELDMWPNSSKDDVDILHGRTLTAPVSLIKC<br>LKSIKEYAFVASPYPVIITLEDHLTSDLQAKVAKMVLEVFGDTLYYPESKHLQEFPSPEALRGRVILSTKPPKEYLESK<br>GGTMKDRDIEPQFSKGQNEEAVWGTEVPDIQDEMQTADKQHENDILYTQRDVEEDDEKKMCQHHPLEYKHLITIKAGKP<br>KGAVVDALKGDPDKVRRLSLSEQELAKVAAHHGRNIVSFTHKNLLRIYPKGTRFNSSNYNPFLGWVHGAQMVAFNMQGY<br>GRSLWLMHGFYKANGGCGYVKKPDFMMQTCPDGNVFDPKADLPVKKTLKVKVYMGEGWQSDFKQTYFDTYSPPDFYAKV<br>GIAGVPSDSVMQKTKAVEDSWVPVWEEEFVFPLTVPEIALLRVEVHEYDVSEDDFGGQTALPVSELRPGIRTVPLFDHK<br>GLKFKSVKLLMRFEFV* |
| SEQ ID NO: 102 | MAMGAAAAPWYGAIGGGGSRRARVRAQAAAPWAGGAEELVRSGAVRAVRAREAAGAMSAEGFRLLDVRPEWERARAAVR<br>GSAHAPLFVGDDDTGPVTLLKKWVHFGYIGLWTGQSFTKMNDRFLDDVAAAAGEGKDAKLLVACGEGLRSLIAVRMLYD<br>DGYKNLAWLAGGFSKCVDGDFADVEGESKLQYATVGGVSYIFLQILLLLRVVK* |
| SEQ ID NO: 103 | MAAAAQRRRSSSASPEFRFWPLDADPAASPSCADELFSGGVLLPLQPLPYPRRDADLSMSLAVADDDDDEDEEEEEVQP<br>GAAVASRAPPTAAVAASGGGGGGSKRWTDIFAKKQQQPAAEEKEKDQPTRRRRPAGGGGGSELNINIWPFSRSRSAGGG<br>GVGSSKPRPPPRKASSAPCSRSNSRGEAAAVASSLPPPPRRWAASPGRAGGGVPVGRSSPVWQIRRPPSPAAKHAAADR<br>RPPHHKDKPTGGAKKPHTTSATGGGGIRGINLSINSCIGYRHQVSCRRADAGVARASAGGGGGGGLFGIKGFFSKKVH* |
| SEQ ID NO: 104 | MQQKPAAEAMEEELKGEAVGPRRPGLGLWLAARRRLAPDDPFFAAGDMERELLAKQVALDLSEDERYQLERMEVASANA<br>LLCPISGCGAHLDCLENFEDHYRTRHTASCSVCWRVYPTSRLLSIHISEAHDSFFQAKVARGFPMYECLVEGCGVKLKS<br>YKSRQQHLLDKHQFPKSFEFFKKARPSQRQRNKNQKQRQTVHKGDETSETLMDVDGKKSSRYMNSRYRPKQHDGKESKE<br>NEHSSCKEAKNNEMEVDKQVDELASAVSRLSTADSTPSSISFGHRRSRGLAFVPRSIRQNKQVSQTEPK* |
| SEQ ID NO: 105 | MGGGGGAEEELTAQETALYDRQIRVWGVDAQKRLSKAHVLVCGMNGTTTEFCKNIVLAGVGSLSLMDDHLVTEDDLNAN<br>FLIPHDESIYGGRSRAEVCCESLKDFNPMVRVAVEKGDPSLIDGEFLDKFDIIVVSCAPIKTKLLINDNCRKRSKHIAF<br>YAIECKDSCGEIFVDLQNHSYVQKVGGEPKPKELAYPSLQEAISVPWKNLPRKTTKLYFAMRVLENYESSEGRNACEAS<br>LSDRPAVLALRKDMCDKMSLSESQIPTALLERLLAAGKKQHPPVCAILGGILGQEVIKSISGKGDPIKNFFYYDAADGK<br>GIAEDIPPLSSD* |
| SEQ ID NO: 106 | MAMPLPPPPPPRPPLGRGRLVGVGPAPAPATASQSNRPVPPLQLPRCRCHRSEGPWRTTAAANGRRRWWSDEDMEEEDD<br>EEGYGYDDGGAPGGSAQELFGEPWFSKLFRAYGYVLPLLLASMLVATGPRAFLMAMALPLAQSAISWVVSFFTTRSRRQ<br>QEEEESYGYDYDDDPAFQRREEDDDDGDYYDAGAWQWRSRSHQQSTESGSGFGGWDDLLYDDEEKKEQESSGKKRTPPE<br>PDTAAAAAAASDLGLGLRARRGPRRSNGGMSRGRSSSSMRYNQAPLLTRLLVALFPFLGSWFRIL* |
| SEQ ID NO: 107 | MRGSLEVHAIGRHAASPCALRLKALPALDMMRYQRLSPDCLPLANGGGGGSGSVTRKPASRSCKDDDGGMAVAADSSRL<br>SSYLPSSQLDSKPLRARAPQPSSSSAAAWSPARDHAHAHHNHHHHHHPSDSSDTASPSSNGAGTGGDVLLQWGHNKRSR<br>CRRDASSSANAAPSSSQRRQTASAAGKILRRSSAPAEKLMPPPPPSTTTGSYTRGSNLRSASSFPTRSAAAAAVGDAHH<br>HRSAVEERSGGGYKRSPDKAHKSALDAALHMDSKNNHHHHHHDSSVTANGGAGAGEKIGSERFELPRIYISLSRKEKED |

TABLE 2-continued

| Amino Acid and Nucleotide Sequences of Rice Polypeptides | |
|---|---|
| | DFLIMKGTKLPQRPKKRAKNVDKTLQYVFPGMWLSDLTRGRYEVREKKCVKKVYSTLHLAFSVHAFCVFLQTRRGKLPR<br>FRASVTQIGWV* |
| SEQ ID NO: 108 | MATTASLLPPLLPAPSSSPRHLHPSPRHLRPLPPIRLLRAARRRHPDAVVVVPDARPWVGDLSGAAASYRDGREEDDDD<br>AGEEDDENDDDDEDRSLDLLVRFLHSVFRKVSRRARRAARSVLPPSVPAELVKFSVNGVLVLTFLWVLKGLLEVVCTFG<br>SMVFVTILLVRGIWSGVTYIRENRYSYIRQIDNDDNRWSRVQTAG* |
| SEQ ID NO: 109 | MKLRLRSMDQRGGAGGAAETHRVQLPDTATLSDVKAFLATKLSAAQPVPAESVRLTLNRSEELLTPDPSATLPALGLAS<br>GDLLYFTLSPLPSPSPPPQPQPQAQPLPRNPNPDVPSIAGAADPTKSPVESGSSSSMPQALCTNRGLPVASDPHHPPPD<br>VVMAEAFAVIKSKSSLVVGDTREMENVGGADGTVICRLVVALHAALLDAGFLYANPVGSCLQLPQNWASGSFVPVSMKY<br>TLPELVEALPVVEEGMVAVLNYSLMGNFMMVYGHVPGATSGVRRLCLELPELAPLLYLDSDEVSTAEEREIHELWRVLK<br>DEMCLPLMISLCQLNNLSLPPCLMALPGDVKAKVLEFVPGVDLARVQCTCKELRDLAADDNLWKKKCEMEFNTQDTCGC<br>MMCKCIYSDQRKDIVLADKYTCGNYMQKPVTQPGRWLIILVYHSLLCQYITIGLSLLWYHLVDLVQDAPAAGIHFDCII<br>PLPINPYQLPPSAGACCSTTQASASAKDGGNMYSPPCSAAASSQGHCFAVGANQLASLDLAMDFDEPILFPVHNASLQE<br>GIQFYNPTGDTQLSRNMSIDKCLKGSKRKGSGEGSSSLHSQEETGEMPQRELSMEHAGEKAGDADASREEYVHVRAKRG<br>QATNSHSLAERFRREKINERMKLLQDLVPGCNKITGKAMMLDEIINYVQSLQRQVEFLSMKLSTISPELNSDLDLQDIL<br>CSQDARSAFLGCSPQLSNAHPNLYRAAQQCLSPPGLYGSVCVPNPADVHLARAGHLASFPQQRGLIWNEELRNIAPAGF<br>ASDAAGTSSLENSDSMKVE* |
| SEQ ID NO: 110 | MAAAAGAGEPSPYAEAAGSDLANARAPSPVVGKHLPSGAVPRHAYVFDGEGGFADAAWDVAAAAPGAFTWHHIELPRQQ<br>PGGAAAKPLHHAQALIELLCPPLTLQEILAFVATGPHCGVVDGGGGGGAGALLLRVSSPGPVGSAFALRLAARVTDSSV<br>VTVSVGGVPRLAFGTTQASLLSEVPLGVTASLSDEGHGGGRAVEGGVVIEERLLESLLAMNHADGAHTDNPVPRTVSNL<br>LVHVLGTHVDHVHDIVTRLEMELDSIELHLDKGGHFMRKLLLDGRRFPKMHLDLQRLLQVVSHGDQVFPRVKEKCASKS<br>WFASEDIVALEDLIGRLRRLKENLGFITNRVTTLQASLDSWQSEQINKSLYYLSFLSIIFLPLSIVTGVFGMNVGGVPW<br>TEQKNPANLDGFFNVMLICVVILLILLLCFLFPSLYSHVSAWRTRRALARSSSQNKRHLKLFKGHKDGYMRL* |
| SEQ ID NO: 111 | MQDQLICSGCRRVVQYRRGVAGVCCPGCNTLTAVNPSAVADMSELICSGCPTLLFYNRGASNIRCPSCNALNSTRSANQ<br>IAHLTCGQCRTTLMHPPGASTVQCATCRYVNHVRDARPQTVLVENPKTLDDKGKLVSNVVVGVTSWKR* |
| SEQ ID NO: 112 | MRGAVAIFNEFKRRGLNISITGIPKTVDNDIGIIDRSFGFQTAVEIAQQAIDAAHVEAVSAVNGIGLVKLMGRSTGHIA<br>LHATLSSRDVDCCLIPEVDFYLEGKGGLFEFLYERIKQKGHAVVVVAEGAGQELIPRTDDQKREQDESGNIVFLDVGPW<br>LKSELGKWWKREHPSELFTVKYIDPTYMIRAVPANATDNLYCTLLAHSAIHGIMAGYTGFVPGPINGNYSYIPLEDVAV<br>AKNPVDVNDHKWAWVRSVTNQPDFMKPKY* |
| SEQ ID NO: 113 | MVESASMVNENSENPYWKAIGYRVEEPRRDRAESMPSPSPSPVSRRPLDNGVVETRALTDTTLLRSLAAKGLAVRPGAS<br>DEHHTVRCDAVIVGSGCGGGVAAAVLASAGYKVVVVEKGDYFTKEDYSSIEGPSMERLFERGGVFCTSNVTTMIFTGAT<br>VGGGSAVNWSASIRTPAGVMQEWSREHGLAVFASPGYARAMDAVCERLGVTDACREEGFQNKVVRRGCDALGLRADAVP<br>RNSSEGHFCGSCNFGCPTGDKKGTDTTWLVDAVERGAVILTGCKAEHFIVESNGGGGGRSKRCVGLVATCMSNGITKKL<br>RVEAKVSISASGALMTPPLLRNSGLKNRHIGRNLHLHPVSMAWGYFPDNTPEPHIPGKCYEGGIITSMHRVTERTIIET<br>PALGPGAFAALVPWESGRDMKERMRRYARTAHAFALVRDRGAGSVDGEGRVRYAPSRDDAEELRAGLRRALRILVAAGA<br>AEVGTHRSDGARLRCKGARDADVEAFLDEVTVEKGPMHSTTDKWSVLCSAHQMGSCRMGASPRDGAVDVAGESWEAEGL<br>YVCDGSLLPTAVGVNPMITIQSIAYCVAKGIADSMAHGKEQR* |
| SEQ ID NO: 114 | MAPHPLLRGGARRGRKYAHGMHPAQMEALRAMCGALIPSLPVDADGGDGGRRPGDKDLERFYLASAADSSIPDEVAELL<br>VTRCIWEAVALTWVVLWALSTRAGTLLLCGRDSVAAVDGGGFPFVSVRRFADMPAARREAALWRWSGARWLFFPLRIAF<br>AIAKILCHYVFYSMILVSA* |
| SEQ ID NO: 115 | ATGCCCAGGCACGCATGTCTGCTGCAGTCTGACCGAATTTTTTTCATAGCCACTGAAGAGTGCAGACGGAGGCGACGCC<br>AAGGAGGTGCCGACGCCGGCGCTGGAGGCAGAGGCGGAGGGCGCCGGTGCTGGGCGGAGGCGGCGGAGGCGGCGCACAT<br>GGCGGCGGCGGCGGCGCATAGGGCGGCGGCGGTGCACAGGGCGGCCTGCGGTAGCTCCACCGTCGCCGTCGGGCTGCGG<br>GAGCTCCACCGGCGTCGTCTCTGCAGCACCTGCACGGGGGATGGGGATGGGGATAGGATGCTTATGCAGAGAAATGACA<br>GTAGCAATAGCAAATGGATGTTGTCACGGAGGGCATTTTCGCCTTTTCACGTGAGTGCTAAATTTGCATGGGAGGTACA<br>GGAATCGCTTCTGGATGGAGGGAGTACCTGGTTCTGTTTAGGATCTAGTGCGTACTTTGTCGCAGTCAAATACGATTGG<br>TGA |
| SEQ ID NO: 116 | ATGGGGACGTACAAGTGCTGCATCTTCTTCACCCGCAGGTTCGCGCTGAGCGACGCGTCCACGCCGGGCGACGTGCGCA<br>TGCTGTTCACCCGCCACGCCGGCGGCGCGCCCTACATGGGCATCGACGAGCTCCGGCGCTACCTCGCCGCCAGCGGGGA<br>GGCCCACGTCGACGCCGACACGGCGGAGCGGATCATCGACCGGGTCCTGCAGGAGCGCAGCCGCACCCCGCGCTTCGGG<br>AAGCCGTCGCTCACCATCGACGATTTCCAGTACTTCCTCTTCTCCGAGGACCTCAACCCGCCC<br>ATCTGCCATTCCAAGGAAGAAAGTTTTGATGCGATGGAAAAGTTGGAAGTTTGA |
| SEQ ID NO: 117 | ATGCAGGTCCATCACGACATGAATGCACCATTATCGCACTACTTCATATACACTGGACACAACTCGTATCTGACGGGCA<br>ATCAACTTAGCAGTGACTGCAGTGATATTCCCATCATTAAGGCACTGCAAATAGGCGTCCGTGTAATTGAACTGGACAT<br>GTGGCCAAATTCTTCTAAAGATGATGTTGATATTCTCCATGGAAGGACACTGACTGCCCCAGTATCACTTATCAAATGC<br>TTGAAATCCATCAAAGAATATGCCTTTGTTGCGTCTCCCTACCCTGTTATTATAACATTAGAAGACCACCTTACATCTG<br>ATCTTCAGGCGAAAGTAGCTAAGATGGTTCTTGAAGTATTTGGAGATACCCTATATTATCCCGAGTCAAAACATCTTCA<br>AGAATTTCCTTCACCCGAAGCACTGAGGGGACGTGTCATCCTCTCAACAAAACCCCCAAAGGAGTACCTTGAATCAAAA<br>GGTGGTACTATGAAAGACAGAGACATTGAGCCTCAGTTTAGCAAAGGACAAAATGAAGAAGCTGTCTGGGGAACAGAAG<br>TCCCAGATATTCAGGATGAGATGCAAACCGCCGACAAGCAGCATGAGAATGATATACTATACACCCAAAGAGATGTGGA<br>AGAAGATGATGAGAAGAAAATGTGCCAGCATCACCCACTAGAGTATAAACACCTTATTACTATTAAGGCAGGAAAGCCA<br>AAGGGTGCTGTAGTTGATGCCTTAAAGGGTGATCCAGATAAAGTTAGACGCCTCAGTTTGAGTGAGCAG<br>GAACTTGCAAAAGTGGCAGCGCATCATGGTCGTAACATCGTGAGCTTTACACATAAAAATCTTCTGAGAATATACCCAA<br>AGGGCACTCGCTTCAATTCTTCGAACTATAATCCGTTTCTTGGTTGGGTGCATGGTGCACAAATGGTGGCATTTAATAT<br>GCAGGGGTATGGAAGATCTCTTTGGCTAATGCACGGATTCTACAAGGCCAACGGTGGCTGCGGTTATGTGAAGAAGCCA<br>GATTTCATGATGCAAACTTGTCCAGATGGAAATGTTTTTGACCCGAAAGCAGATTTACCTGTGAAGAAAACACTCAAGG<br>TCAAAGTATACATGGGCGAAGGTTGGCAGAGCGACTTCAAGCAGACATACTTCGACACGTATTCCCCTCCAGACTTCTA<br>CGCAAAGGTGGGCATTGCCGGGGTTCCGTCGGACTCGGTGATGCAGAAGACGAAAGCCGTGGAGGACAGCTGGGTTCCC<br>GTGTGGGAGGAGGAGTTCGTGTTCCCGCTGACCGTCCCGGAGATCGCGCTGCTCCGCGTGGAGGTGCACGAGTACGACG |

TABLE 2-continued

| Amino Acid and Nucleotide Sequences of Rice Polypeptides | |
|---|---|
| | TGAGCGAGGACGACTTCGGCGGGCAGACGGCGCTCCCGGTGTCGGAGCTGCGGCCGGGGATCCGCACCGTGCCGCTCTTCGACCACAAGGGGCTCAAGTTCAAGAGCGTCAAGCTCCTCATGCGGTTCGAGTTCGTCTAG |
| SEQ ID NO: 118 | ATGGCGATGGGAGCCGCGGCGGCGCCATGGTACGGCGCCATCGGCGGCGGTGGCTCGCGGCGCGCGCGGGTGAGGGCGCAGGCGGCGGCGCCGTGGGCAGGAGGCGCGGAGGAGCTGGTGCGGTCGGGCGCGGTGCGGGCGGTGCGGGCGAGGGAGGCGGCGGGGGCGATGTCCGCGGAGGGGTTCCGGCTGCTGGACGTCCGGCCGGAGTGGGAGCGCGCGCGCGCCGCCGTGCGGGGCTCGGCGCACGCGCCGCTGTTCGTCGGGGACGACGACACGGGCCCCGTCACGCTGCTCAAGAAGTGGGTCCACTTCGGCTACATCGGCCTCTGGACCGGCCAGTCCTTCACCAAGATGAACGACCGCTTCCTCGACGACGTCGCCGCCGCCGCCGGCGAAGGCAAGGACGCCAAGCTGCTCGTCGCCTGCGGCGAAGGCCTCCGGTCGTTGATCGCGGTGAGGATGCTGTACGACGACGGGTACAAGAACCTGGCGTGGCTCGCCGGAGGGTTCAGCAAGTGCGTCGACGGCGACTTCGCCGACGTGGAGGGGGAGAGCAAGCTGCAGTATGCCACCGTGGGTGGGGTGTCCTACATCTTCCTCCAGATCCTGCTTCTGCTGCGGGTAGTCAAGTGA |
| SEQ ID NO: 119 | ATGGCCGCAGCAGCGCAGAGGCGGCGGAGGAGCAGCGCCTCCCCGGAGTTCCGCTTCTGGCCCCTCGACGCCGACCCCGCCGCATCCCCCTCCTGCGCCGACGAGCTCTTCTCCGGCGGCGTCCTCCTCCCCCTCCAACCCCTCCCCTACCCCCGCCGCGACGCCGACCTCTCCATGTCCCTCGCCGTCGCGGATGATGATGATGATGAGGACGAGGAGGAGGAGGAGGTGCAGCCTGGTGCGGCCGTCGCGTCCAGGGCGCCGCCCACTGCTGCGGTGGCGGCGTCGGGTGGTGGTGGTGGTGGGTCGAAGAGGTGGACGGATATATTCGCCAAGAAGCAGCAGCAGCCGGCGGCGGAGGAGAAGGAGAAGGATCAGCCGACGAGGCGGCGGAGACCGGCGGGAGGCGGAGGCGGATCGGAGCTGAACATTAACATCTGGCCGTTCTCCCGGAGCCGCTCCGCCGGCGGGGGCGGCGTGGGGTCGTCGAAGCCCCGCCCGCCGCCGCGGAAGGCCAGTAGCGCCCCGTGCTCCCGCAGCAACTCCCGCGGCGAGGCGGCGGCGGTGGCGTCGTCCCTTCCTCCTCCTCCTCGCCGCTGGGCCGCCAGCCCCGGCCGCGCAGGCGGCGGCGTGCCGGTGGGCCGGTCTAGCCCGGTCTGGCAGATCAGGCGCCCGCCATCGCCGGCGGCGAAGCACGCCGCCGCGGACAGGAGGCCGCCGCACCACAAGGACAAGCCAACCGGCGGCGCCAAGAAACCCCACACCACCTCCGCCACCGGCGGCGGCGGGATACGCGGCATCAACCTGAGCATCAACTCCTGCATCGGGTACCGCCACCAGGTGAGCTGCCGCCGCGCCGACGCCGGAGTCGCCCGCGCCTCCGCCGGCGGCGGCGGCGGCGGCGGGCTCTTCGGCATCAAGGGGTTCTTCTCCAAGAAGGTGCATTGA |
| SEQ ID NO: 120 | ATGCAGCAGAAGCCCGCGGCGGAGGCCATGGAGGAGGAGTTGAAGGGGGAGGCCGTGGGGCCCCGCCGCCCCGGGCTAGGGTTATGGTTGGCGGCGCGGCGGCGGCTGGCCCCCGACGACCCCTTCTTCGCCGCCGGGGACATGGAGCGCGAGCTCCTCGCCAAGCAAGTTGCTCTGGATCTCTCCGAAGATGAACGGTACCAGCTTGAGAGGATGGAAGTGGCGAGTGCCAATGCCCTTTTATGCCCAATTTCTGGCTGTGGTGCTCATCTAGATTGCCTGGAGAACTTTGAGGACCACTATCGCACCCGTCATACTGCTTCATGCTCTGTATGTTGGAGAGTGTATCCAACTTCAAGGCTGCTGAGTATTCATATTTCTGAGGCACATGATTCCTTTTTTCAAGCAAAAGTTGCCCGTGGTTTTCCAATGTATGAGTGTTTGGTGGAGGGTTGTGGGGTGAAGTTGAAGAGCTACAAAAGTCGGCAGCAGCATCTTCTTGATAAGCACCAGTTTCCCAAGTCATTTGAATTCTTCAAAAAAGCACGCCCTTCGCAACGCCAGCGGAACAAGAACCAGAAGCAACGGCAAACAGTTCACAAGGGAGACGAGACAAGCGAAACACTAATGGATGTTGATGGGAAGAAGAGCTCAAGGTACATGAATTCCAGATATCGGCCAAAGCAACATGATGGAAAAGAGTCAAAAGAAAATGAGCATAGTAGCTGTAAGGAGGCCAAGAACAACGAAATGGAGGTTGACAAGCAGGTTGATGAGCTTGCTTCGGCCGTATCAAGACTGAGCACAGCGGATTCAACTCCTTCTAGCATAAGCTTTGGTCATCGTCGCTCTCGCGGTCTTGCTTTTGTCCCTAGGTCGATTCGGCAAAACAAGCAGGTTTCTCAGACAGAACCAAAATGA |
| SEQ ID NO: 121 | ATGGGCGGCGGCGGCGGCGCGGAGGAGGAGCTGACGGCGCAGGAGACGGCGCTCTACGACCGCCAGATCCGCGTCTGGGGCGTTGACGCCCAGAAGAGGCTAAGTAAAGCTCATGTGCTCGTGTGCGGCATGAATGGTACTACTACTGAGTTCTGCAAGAATATTGTTCTAGCAGGAGTTGGCAGTTTATCCTTGATGGATGATCATTTAGTCACAGAGGATGATCTCAATGCAAATTTCTTAATTCCTCATGATGAGAGCATATATGGTGGTAGATCACGAGCTGAGGTTTGCTGTGAGTCCCTGAAAGATTTCAATCCAATGGTCCGAGTTGCAGTCGAAAAGGGTGATCCATCATTAATTGATGGAGAATTCCTTGACAAGTTTGACATAATTGTAGTTAGCTGTGCGCCTATTAAAACAAAGTTGTTAATTAACGACAACTGCCGGAAGAGAAGCAAGCATATTGCATTCTACGCCATTGAGTGCAAGGATTCCTGTGGTGAAATATTTGTTGATTTGCAGAACCATAGCTATGTTCAGAAGGTTGGAGGTGAACCCAAACCAAAGGAGTTGGCATATCCAAGTCTCCAGGAAGCTATCTCCGTACCCTGGAAGAATTTACCAAGAAAAACAACTAAACTGTACTTTGCCATGAGAGTACTGGAGAATTATGAGTCATCTGAAGGCCGCAATGCTTGTGAGGCATCACTTTCTGATCGACCTGCAGTTTTGGCTCTGAGGAAGGACATGTGTGATAAAATGTCTTTAAGTGAGTCTCAAATTCCTACTGCTCTCCTGGAACGGCTTTTAGCAGCTGGAAAGAAGCAACATCCTCCTGTATGTGCAATCCTTGGCGGCATTCTTGGTCAGGAGGTGATTAAGTCAATATCTGGTAAGGGTGATCCGATCAAGAATTTCTTCTATTACGACGCCGCTGATGGTAAAGGGATCGCTGAAGACATTCCTCCCCTTTCTTCAGACTGA |
| SEQ ID NO: 122 | ATGGCTATGCCGCTGCCGCCGCCGCCGCCGCCTCGTCCTCCTCTTGGACGGGGACGGCTCGTCGGAGTAGGACCAGCTCCAGCACCAGCAACGGCCTCCCAATCCAACCGCCCAGTGCCCCCCCTGCAGCTGCCTCGCTGCCGCTGCCATCGCTCGGAGGGACCCTGGAGGACGACGGCGGCGGCGAACGGGAGGAGGCGGTGGTGGTCCGACGAGGACATGGAGGAAGAGGACGACGAGGAGGGATACGGATACGACGACGGCGGCGCGCCAGGCGGGTCAGCGCAGGAGCTGTTCGGCGAGCCATGGTTTTCCAAGCTCTTCCGTGCGTACGGCTACGTGCTGCCGCTGCTGCTGGCGTCCATGCTGGTGGCCACGGGGCCCAGAGCTTTCCTCATGGCCATGGCGCTGCCGCTCGCCCAGTCCGCCATCTCCTGGGTCGTCTCCTTCTTCACCACCAGGAGTCGTCGGCAGCAGGAGGAGGAGGAGTCGTACGGATACGACTACGATGACGATCCCGCCTTCCAACGCCGAGAGGAAGACGACGACGACGGCGACTACTATGATGCCGGGGCATGGCAATGGCGGAGCAGGAGCCACCAGCAATCGACCGAATCCGGCTCCGGTTTTGGAGGATGGGATGACCTCCTCTACGACGATGAGGAGAAGAAGGAGCAGGAGAGCTCAGGGAAGAAGAGGACGCCACCGGAGCCCGACACGGCGGCGGCTGCTGCCGCCTCCGATCTGGGACTGGGATTGCGGGCGAGGAGAGGTCCACGACGCAGCAATGGCGGCATGTCGCGAGGAAGAAGCAGCAGCAGCATGAGGTATAACCAGGCGCCACTGCTGACGCGCCTTCTCGTGGCACTCTTCCCCTTCCTCGGCTCATGGTTCAGGATACTCTAA |
| SEQ ID NO: 123 | ATGCGTGGCTCCCTGGAGGTCCACGCGATTGGCAGACACGCCGCGTCGCCGTGCGCCCTGAGACTGAAAGCCCTCCCGGCATTGGACATGATGAGGTACCAAAGGCTTAGCCCGGACTGCCTCCCGCTAGCCAACGGCGGCGGCGGAGGAAGCGGTAGCGTGACACGGAAGCCGGCGTCGAGATCCTGCAAGGACGACGATGGCGGCATGGCCGTCGCCGCGGACAGCTCCCGCCTCTCGTCGTACCTCCCGTCGTCACAGCTCGATTCCAAGCCGCTGCGCGCTCGGGCGCCGCAGCCGTCGTCCTCGTCGGCCGCCGCCTGGAGCCCGGCGCGCGACCACGCGCACGCCCACCACAACCACCACCACCACCACCACCCGTCCGACTCCTCCGACACGGCCTCGCCGAGCTCCAACGGCGCGGGCACCGGTGGCGACGTGCTGCTGCAGTGGGGGCACAACAAGCGGTCCCGCTGCCGGCGCGACGCGTCCTCCTCGGCCAACGCGGCTCCCTCCTCCTCGCAGCGCCGCCAGACCGCCTCCGCCGCCGGCAAGATCCTGCGCCGCTCGTCGGCGCCGGCGGAGAAGCTCATGCCGCCGCCGCCCCCATCCACCACCACCACCGGGTCGTACACGCGCGGGTCCAACCTGAGGTCCGCTTCGTCCTTCCCGACGCGGTCCGCCGCCGCCGCCGCCGCCGTCGGAGACGCACACCACCACAGGTCCGCCGTGGAGGAGCGATCAGGCGGCGGGTACAAGCGGTCGCCGGACAAGGCGCACAAGTCCGCCCTGGACGCGGCGCTGCACATGGATTCCAAGAACAACCACCATCACCACCACCACGACTCGTCGGTGACCGCAAACGGCGGCGCCGGCGCCGGCGAGAAGATCGGCTCCGAGCGGTTTGAGCTGCCCCGGATCTACATCTCGCTGTCGCGCAAGGAGAAGGAGGAC |

TABLE 2-continued

| Amino Acid and Nucleotide Sequences of Rice Polypeptides | |
|---|---|
| | GACTTCTTGATCATGAAGGGCACCAAGCTGCCTCAGAGGCCCAAGAAGAGGGCCAAGAACGTGGACAAGACCCTCCAAT<br>ATGTATTCCCTGGGATGTGGCTTTCAGACTTGACGAGAGGACGGTATGAGGTGCGAGAGAAGAAATGTGTGAAGAAGGT<br>ATACTCCACTCTGCACCTGGCATTTTCAGTTCATGCATTCTGTGTATTTTTACAGACAAGAAGAGGAAAATTACCTAGA<br>TTTAGGGCATCAGTGACCCAGATTGGTTGGGTCTAA |
| SEQ ID NO: 124 | ATGGCGACCACCGCCTCCCTCCTCCCTCCTCTCCTCCCGGCCCCTTCCTCCTCCCCCCGCCACCTCCACCCCTCCCCTC<br>GCCACCTCCGCCCCTTGCCACCGATCCGCCTCCTCCGCGCCGCCCGCCGCCGCCACCCCGACGCCGTCGTCGTCGTCCC<br>GGACGCCCGCCCCTGGGTCGGCGACCTCTCGGGCGCCGCCGCGTCCTACCGGGACGGCAGGGAAGAGGACGACGACGAC<br>GCGGGGGAGGAGGATGACGAAAACGACGACGACGACGAGGACCGCAGCCTGGACCTCCTGGTCCGCTTCCTGCACTCGG<br>TGTTCAGGAAGGTCTCCCGCCGCGCGCGCCGCGCCGCCAGGTCCGTGCTGCCGCCTTCCGTCCCCGCTGAGCTGGTGAA<br>GTTCTCGGTCAACGGCGTGCTTGTTCTCACGTTTCTATGGGTCCTAAAGGGGCTACTTGAGGTGGTGTGCACATTTGGA<br>AGTATGGTGTTCGTGACCATCCTTCTTGTTCGTGGAATATGGTCTGGAGTGACTTACATAAGAGAAAACCGATATAGCT<br>ATATTCGCCAGATTGATAATGATGACAACCGATGGAGCAGAGTACAGACTGCTGGCTAA |
| SEQ ID NO: 125 | ATGAAGCTTCGGTTGCGATCCATGGACCAGCGCGGCGGCGCCGGCGGCGCCGCCGAGACCCACCGCGTGCAGCTGCCGG<br>ACACGGCCACGCTCTCCGACGTCAAGGCCTTCCTCGCCACCAAGCTGTCCGCGGCGCAGCCCGTGCCCGCCGAGTCGGT<br>GCGCCTCACCCTCAACCGCTCCGAGGAGCTCCTCACCCCCGACCCCTCCGCTACCCTCCCGGCCCTCGGGCTCGCGTCC<br>GGTGATCTCCTCTACTTCACGOTCTCCCCCTCCCGTCGCCCTCGCCTCCGCCGCAGCCGCAGCCACAGGCCCAACCCT<br>GCCCCGTAACCCTAACCCTGATGTCCCCTCGATCGCGGGAGCTGCTGACCCGACCAAATCTCCTGTGGAGTCTGGTAGT<br>CCTCGTCGATGCCGCAAGCTTTGTGCACGAATCCTGGCTTACCTGTCGCATCCGATCCGCATCATCCTCCACCGGATGT<br>GGTGATGGCGGAGGCCTTCGCCGTGATCAAGAGCAAGTCGAGTCTCGTCGTCGGGGATACGAAGAGAGAGATGGAGAAT<br>GTCGGTGGTGCGGATGGAACCGTCATCTGTCGCCTTGTCGTGGCGCTGCATGCGGCCTTGCTCGATGCCGGCTTCCTCT<br>ATGCAAACCCGGTGGGGTCTTGCCTTCAGCTGCCACAGAATTGGGCGTCAGGTTCTTTTGTCCCCGTATCGATGAAGTA<br>CACCCTGCCAGAGCTTGTAGAAGCGTTACCTGTGGTTGAGGAGGGGATGGTGGCAGTGCTGAACTACTCCTTGATGGGG<br>AATTTTATGATGGTGTATGGGCATGTGCCTGGGGCAACATCGGGGGTGCGAAGGTTGTGCTTGGAGCTGCCGGAGCTTG<br>CGCCTTTGTTGTACTTGGATAGTGATGAGGTGAGCACAGCAGAGGAGAGGGAAATTCATGAGCTGTGGAGGGTCCTGAA<br>GGATGAGATGTGCTTGCCTCTGATGATATCGTTGTGTCAACTGAACAATTTGAGCTTGCCACCGTGCTTGATGGCGCTG<br>CCAGGTGATGTCAAGGCAAAGGTCCTGGAGTTTGTTCCTGGGGTGGATCTTGCAAGGGTTCAATGCACGTGCAAGGAAT<br>TGAGGGATCTTGCTGCAGATGATAATCTTTGGAAGAAGAAGTGTGAGATGGAGTTCAATACTCAAGATACATGCGGTTG<br>TATGATGTGTAAATGCATTTACTCTGACCAAAGGAAGGATATCGTACTAGCTGATAAGTATACCTGTGGTAATTATATG<br>CAGAAGCCCGTCACACAACCTGGTAGGTGGCTTATTATATTAGTCTACCATTCCCTACTTTGCCAGTACATCACTATTG<br>GGTTGAGTTTGCTGTGGTATCATTTGGTTGATTTGGTTCAGGATGCTCCTGCAGCAGGCATTCACTTTGACTGTATTAT<br>TCCACTGCCAATCAATCCTTACCAGCTTCCCCCATCTGCTGGTGCCTGCTGCTCAACAACTCAAGCTTCAGCATCAGCA<br>AAAGATGGTGGCAATATGTATTCCCCTCCCTGCAGTGCTGCTGCAAGCAGCCAAGGGCATTGTTTCGCGGTCGGAGCTA<br>ACCAGCTTGCTTCGCTTGACCTTGCCATGGACTTCGACGAGCCTATCCTTTTTCCTGTGCATAATGCAAGTTTGCAAGA<br>GGGGATTCAGTTTTACAATCCTACCGGCGATACTCAGCTAAGTAGAAACATGAGCATTGACAAGTGTTTGAAGGGCAGT<br>AAAAGGAAGGGCTCAGGCGAGGGCAGTTCATCGCTACATTCCCAAGAGGAAACCGGTGAAATGCCTCAGAGAGAACTCA<br>GCATGGAGCATGCCGGAGAGAAGGCGGGTGATGCTGACGCTAGCAGGGAGGAGTACGTGCATGTCCGGGCAAAACGCGG<br>CCAGGCGACCAACAGCCACAGCCTTGCAGAAAGATTTCGAAGGGAGAAGATAAACGAAAGGATGAAGCTTCTGCAGGAC<br>CTCGTCCCAGGATGCAACAAGATTACAGGGAAGGCCATGATGCTCGACGAGATCATAAACTACGTCCAGTCTCTGCAGC<br>GACAGGTGGAGTTCCTCTCGATGAAGCTCTCGACAATCAGTCCTGAGTTGAACTCTGACCTCGACCTGCAAGATATCCT<br>TTGTTCACAAGATGCTCGCTCCGCATTTCTGGGATGCAGCCCGCAATTGAGCAATGCCCATCCTAACCTTTACAGGGCG<br>GCTCAGCAATGCCTCTCACCTCCTGGCTTGTACGGGAGTGTGTGTGTCCCAAATCCCGCAGATGTTCATTTGGCAAGGG<br>CCGGTCACTTGGCTTCGTTTCCTCAGCAGAGAGGCCTCATCTGGAACGAGGAACTTCGCAACATTGCTCCGGCCGGTTT<br>CGCTTCAGACGCCGCTGGCACCAGTAGCTTAGAGAACTCTGATTCGATGAAAGTGGAGTAG |
| SEQ ID NO: 126 | ATGGCGGCCGCGGCCGGCGCCGGCGAGCCGTCGCCGTACGCGGAGGCGGCGGGATCCGACCTCGCGAATGCGCGGGCGC<br>CGTCTCCCGTGGTCGGCAAGCACCTCCCGTCGGGCGCCGTGCCGCGCCACGCGTACGTGTTCGACGGCGAGGGGGGGTT<br>CGCCGACGCGGCGTGGGACGTCGCGGCGGCGGCGCCGGGGGCGTTCACGTGGCACCACATCGAGCTCCCGCGGCAGCAG<br>CCCGGGGGCGCCGCCGCGAAGCCGCTCCACCACGCGCAGGCGCTGATCGAGCTGCTCTGCCCGCCGCTCACGCTGCAGG<br>AGATCCTCGCGTTCGTCGCCACGGGCCCGCACTGCGGCGTCGTGGACGGCGGCGGCGGCGGCGGGGCGGGCGCGCTCCT<br>TCTCCGCGTGAGCTCGCCGGGGCCGGTGGGGAGCGCGTTCGCGCTCCGCCTCGCCGCGCGCGTCACGGACAGCTCCGTG<br>GTGACCGTGTCCGTGGGCGGCGTCCCGCGCCTCGCGTTCGGGACCACGCAGGCGTCGCTCCTCTCCGAGGTGCCGCTCG<br>GGGTGACCGCGTCGCTCTCCGACGAGGGCCACGGCGGCGGGCGCGCCGTCGAGGGCGGGGTGGTGATCGAGGAGCGGCT<br>GCTCGAGTCGCTGCTCGCCATGAACCACGCCGACGGCGCGCACACCGACAACCCCGTGCCGCGGACCGTGTCCAACCTC<br>CTCGTGCACGTCCTGGGAACGCACGTAGACCACGTCCACGACATCGTCACGCGCCTCGAGATGGAGCTCGACAGCATCG<br>AGCTGCATCTCCACAAGGGTGGTCACTTTATGAGGAAACTTTTGTTGGATGGAAGGAGATTCCCCAAAATGCATCTTGA<br>TCTACAGCGCCTGCTTCAGGTTGTTTCTCATGGTGACCAAGTATTCCCCCGTGTAAAGGAAAAATGTGCGAGCAAGAGT<br>TGGTTTGCGAGTGAAGATATTGTTGCTCTTGAAGATCTGATAGGCCGTCTTAGGAGGCTGAAGGAAAATCTTGGATTTA<br>TAACGAATAGGGTGACTACACTTCAAGCTAGTCTAGATAGCTGGCAATCTGAGCAGATAAACAAAAGCTTGTACTATCT<br>TTCATTTTTGTCCATAATATTCCTTCCTCTATCCATTGTCACTGGAGTTTTTGGGATGAATGTTGGTGGTGTGCCATGG<br>ACTGAGCAGAAAAACCCTGCAAATCTAGATGGCTTCTTCAATGTCATGTTAATATGCGTCGTGATCTTGTTGATCCTGC<br>TGCTTTGTTTCTTATTTCCTTCATTGTATTCACACGTGTCGGCATGGAGAACCCGCCGTGCACTGGCCCGGAGCAGTTC<br>TCAGAACAAGAGACATCTGAAACTCTTTAAGGGTCACAAAGATGGTTACATGCGCCTCTGA |
| SEQ ID NO: 127 | ATGCAGGACCAGCTGATCTGCAGCGGCTGCAGGCGCGTCGTCCAGTACAGGAGAGGGGTCGCCGGCGTCTGCTGCCCGG<br>GCTGCAACACGCTCACCGCCGTCAACCCGTCAGCGGTGGCCGACATGTCGGAGCTCATCTGCAGCGGCTGCCCCACGCT<br>GCTGTTCTACAACCGCGGCGCCTCCAACATCCGCTGCCCCAGCTGCAACAGGCTCAACTCCACCAGATCAGCCAACCAG<br>ATTGCACACCTGACATGCGGGCAGTGCCGGACGACTCTGATGCACCCACCTGGAGCCTCAACTGTGCAGTGTGCAACCT<br>GCAGATATGTTAACCATGTCAGGGATGCTCGGCCTCAAACTGTCCTTGTAGAGAATCCTAAGACACTGGATGATAAGGG<br>CAAGCTGGTGAGCAATGTGGTTGTTGGTGTCACCTCATGGAAAAGATGA |
| SEQ ID NO: 128 | ATGAGAGGAGCTGTGGCCATCTTCAACGAGTTTAAGCGCCGTGGTTTGAACATTTCTATTACAGGGATCCCGAAAACTG<br>TGGACAATGATATCGGCATCATAGACAGGTCATTTGGGTTCCAAACCGCAGTGGAGATTGCTCAGCAGGCAATCGACGC<br>AGCACATGTCGAGGCTGTGAGCGCCGTGAATGGCATTGGACTTGTCAAACTTATGGGCAGGAGCACAGGCCACATTGCT<br>CTTCATGCCACCCTGAGCAGCCGCGATGTTGACTGCTGTTTGATTCCTGAGGTTGATTTCTATCTTGAAGGAAAGGGGG<br>GCCTGTTTGAGTTCTTGTATGAAAGGATAAAACAGAAGGACATGCTGTTGTCGTTGTTGCTGAAGGTGCTGGTCAGGA<br>ATTGATTCCAAGGACTGACGATCAAAAGCGGGAGCAGGACGAGTCCGGCAACATTGTGTTCCTTGATGTGGGTCCCTGG |

TABLE 2-continued

| Amino Acid and Nucleotide Sequences of Rice Polypeptides | |
|---|---|
| | TTAAAATCTGAGCTGGGTAAATGGTGGAAGAGAGAACACCCAAGCGAGTTGTTCACTGTGAAGTATATCGATCCCACTT<br>ACATGATACGAGCTGTTCCAGCAAATGCCACTGACAATCTGTACTGTACATTGTTGGCACATTCGGCGATCCATGGGAT<br>CATGGCTGGGTACACTGGCTTCGTCCCTGGCCCGATTAATGGAAACTATAGCTACATACCGCTGGAAGATGTTGCTGTG<br>GCGAAGAACCCGGTGGATGTGAATGATCACAAATGGGCATGGGTTAGATCAGTCACAAACCAACCAGATTTCATGAAGC<br>CAAAATACTAA |
| SEQ ID NO: 129 | ATGGTTGAAAGTGCAAGCATGGTGAACGAGAACTCGGAGAATCCATACTGGAAAGCAATAGGATACAGAGTGGAAGAGC<br>CCCGACGTGATCGAGCAGAGTCGATGCCGTCGCCGTCGCCATCGCCGGTATCGCGGCGGCCACTGGACAACGGCGTCGT<br>GGAGACGAGGGCGCTGACGGACACCACCCTCCTCCGGTCGCTCGCGGCGAAGGGCCTCGCCGTGAGGCCCGGCGCGTCG<br>GACGAGCACCACACGGTGCGGTGCGACGCCGTCATCGTCGGCTCCGGCTGCGGCGGCGGCGTGGCCGCCGCGGTGCTCG<br>CGTCCGCCGGGTACAAGGTGGTCGTCGTCGAGAAGGGCGACTACTTCACCAAGGAGGATTACAGCTCGATCGAGGGCCC<br>GTCCATGGAGCGCCTCTTCGAGAGGGGCGGCGTCTTCTGCACGTCCAACGTCACGACGATGATATTCACCGGCGCGACG<br>GTCGGCGGCGGGTCGGCGGTGAACTGGTCGGCGAGCATCCGCACGCCGGCGGGCGTGATGCAGGAGTGGTCGCGCGAGC<br>ACGGGCTGGCGGTGTTCGCGAGCCCCGGGTACGCGCGGGCCATGGACGCGGTGTGCGAGCGCCTCGGTGTGACCGACGC<br>GTGCCGGGAGGAAGGGTTCCAGAACAAGGTGGTGCGCCGCGGGTGCGACGCGCTCGGGCTGCGCGCCGACGCCGTGCCG<br>CGCAACTCGTCGGAGGGGCACTTCTGCGGCAGCTGCAACTTCGGGTGCCCCACCGGCGACAAGAAGGGCACCGACACGA<br>CGTGGCTCGTCGACGCCGTCGAGCGCGGTGCGGTCATCCTGACCGGGTGCAAGGCCGAACACTTCATCGTCGAGAGCAA<br>CGGCGGTGGCGGCGGCCGGAGCAAGAGGTGCGTCGGCCTGGTGGCGACGTGCATGAGCAACGGCATCACCAAGAAGCTC<br>CGCGTCGAGGCGAAGGTGTCCATCTCGGCGAGCGGCGCGCTCATGACGCCGCCGCTGCTGCGCAACAGCGGGCTCAAGA<br>ACCGCCACATCGGCCGGAACCTGCACCTCCACCCGGTGTCCATGGCGTGGGGCTACTTCCCGGACAACACGCCGGAGCC<br>GCACATCCCGGGGAAGTGCTACGAGGGCGGCATCATCACCAGCATGCACCGCGTCACGGAGCGCACCATCATCGAGACG<br>CCAGCGCTCGGCCCGGGCGCCTTCGCCGCCCTGGTGCCCTGGGAGTCCGGCCGCGACATGAAGGAGCGGATGCGCCGGT<br>ACGCGCGCACGGCGCACGCGTTCGCGCTGGTGCGCGACCGCGGCGCCGGGTCCGTCGACGGCGAGGCCCGCGTCCGCTA<br>CGCCCCGAGCCGCGACGACGCCGAGGAGCTCCGCGCCGGCCTCCGCCGCGCGCTGCGCATCCTGGTGGCCGCCGGCGCC<br>GCCGAGGTGGGCACGCACCGCAGCGACGGGGCCCGCCTCCGATGCAAGGGCGCGCGCGACGCGGACGTGGAGGCGTTCC<br>TCGACGAGGTGACCGTGGAGAAGGGGCCGATGCACTCGACGACGGACAAGTGGTCGGTGCTCTGCTCGGCGCACCAGAT<br>GGGGAGCTGCCGGATGGGCGCGAGCCCCCGCGACGGCGCCGTCGACGTCGCCGGCGAGAGCTGGGAGGCGGAGGGGCTC<br>TACGTCTGCGACGGCAGCCTGCTCCCGACGGCGGTGGGCGTGAACCCGATGATCACCATACAGTCCATCGCCTACTGCG<br>TCGCCAAGGGCATAGCCGACTCGATGGCACACGGCAAGGAGCAGCGCTAG |
| SEQ ID NO: 130 | ATGGCGCCGCACCCGCTGCTGAGGGGAGGGGCGAGGCGGGGGAGGAAGTACGCGCACGGGATGCACCCCGCGCAGATGG<br>AGGCGCTGCGCGCCATGTGCGGCGCGCTCATCCCGTCGCTGCCCGTGGACGCGGACGGCGGCGACGGCGGGCGCCGCCC<br>CGGCGACAAGGACCTCGAGCGGTTCTACCTCGCCTCCGCCGCCGACTCCTCCATCCCCGACGAGGTGGCGGAGCTGCTG<br>GTGACGCGTTGCATATGGGAGGCGGTGGCGCTGACGTGGGTGGTGCTGTGGGCGCTGAGCACGCGGGCGGGCACGCTGC<br>TGCTGTGCGGCCGGGACAGCGTCGCCGCCGTCGACGGCGGCGGGTTCCCGTTCGTGTCCGTGCGCCGCTTCGCCGACAT<br>GCCGGCGGCGAGGCGGGAGGCGGCGCTGTGGCGGTGGAGCGGCGCGCGGTGGCTCTTCTTCCCGCTCCGCATCGCCTTC<br>GCCATCGCCAAGATCCTCTGCCACTACGTCTTCTACTCCATGATACTCGTATCAGCCTAA |
| SEQ ID NO: 149 | MEWDLKMPPAASWELADELENSGGGGVPAAVSSSSAAVGGGVNAGGGGRQECSVDLKLGGLGEFGGGGAQPRVAVAGEP<br>AKGKGPAAAATGAAAAASSAPAKRPRGAAAAGQQQCPSCAVDGCKEDLSKCRDYHRRHKVCEAHSKTPLVVVSGREMRF<br>CQQCSRFHLLQEFDEAKRSCRKRLDGHNRRRRKPQPDPMNSASYLASQQGARFSPFATPRPEASWTGMIKTEESPYYTH<br>HQIPLGISSRQQHFVGSTSDGGRRFPFLQEGEISFGTGAGAGGVPMDQAAAAAAASVCQPLLKTVAPPPPPHGGGGSGG<br>GKMFSDGGLTQVLDSDCALSLLSAPANSTAIDVGGGRVVVQPTEHIPMAQPLISGLQFGGGGGSSAWFAARPHHQAATG<br>AAATAVVVSTAGFSCPVVESEQLNTVLSSNDNEMNYNGMFHVGGEGSSDGTSSSLPFSWQ* |
| SEQ ID NO: 150 | ATGGAGTGGGATCTCAAGATGCCGCCGGCGGCGAGCTGGGAGCTAGCCGACGAGCTGGAGAACAGCGGCGGCGGGGGTG<br>TACCGGCGGCGGTATCGTCGTCATCGGCTGCGGTTGGTGGCGGCGTCAATGCGGGGGGTGGTGGCAGGCAGGAGTGCTC<br>GGTCGACCTCAAGCTCGGCGGGTTGGGGGAGTTCGGCGGCGGCGGCGCGCAGCCGCGGGTCGCCGTGGCGGGCGAGCCG<br>GCCAAGGGGAAGGGGCCAGCGGCCGCCGCCACGGGAGCAGCAGCAGCAGCGTCGTCGGCGCCGGCGAAGCGGCCGCGCG<br>GTGCGGCGGCGGCGGGGCAGCAGCAGTGCCCGTCGTGCGCGGTGGACGGGTGCAAGGAGGACCTGAGCAAGTGCCGCGA<br>CTACCATCGCCGGCACAAGGTGTGCGAGGCCCACTCCAAGACCCCCCTCGTCGTCGTCTCCGGCCGCGAGATGCGCTTC<br>TGCCAGCAGTGCAGCAGGTTTCACTTGCTTCAGGAGTTTGATGAGGCCAAGCGCAGCTGTAGAAAGCGACTAGATGGGC<br>ACAACCGTCGCCGCAGGAAGCCACAGCCAGATCCCATGAACTCTGCAAGTTATCTTGCAAGCCAACAAGGGGCAAGATT<br>CTCACCGTTCGCGACGCCGAGACCGGAGGCAAGCTGGACAGGGATGATCAAAACCGAGGAGAGCCCATACTACACGCAC<br>CACCAAATCCCTCTTGGCATCAGCAGCAGGCAGCAGCATTTCGTTGGCTCCACCTCTGACGGCGGCCGCCGCTTCCCTT<br>TCCTCCAGGAAGGCGAGATCAGCTTCGGCACCGGCGCCGGCGCCGGCGGCGTGCCAATGGATCAGGCAGCAGCTGCTGC<br>TGCTGCTTCAGTGTGCCAGCCACTTCTGAAGACGGTAGCTCCTCCTCCTCCTCCTCATGGCGGCGGCGGCAGCGGCGGC<br>GGCAAGATGTTCTCCGATGGTGGGTTGACACAAGTGCTCGACTCCGATTGTGCTCTCTCTCTTCTGTCAGCTCCGGCGA<br>ACTCCACGGCCATCGACGTCGGCGGTGGCCGGGTGGTCGTCCAGCCGACCGAGCACATCCCCATGGCGCAGCCTCTCAT<br>CTCTGGCCTTCAGTTCGGCGGCGGCGGCGGCAGCTCAGCCTGGTTCGCGGCGCGGCCGCATCATCAGGCGGCCACCGGC<br>GCCGCCGCCACCGCCGTCGTCGTCTCGACGGCCGGTTTCTCCTGCCCGGTGGTGGAGAGCGAGCAGCTGAACACAGTCC<br>TGAGCTCCAATGACAATGAGATGAACTACAATGGGATGTTTCACGTCGGCGGCGAAGGCTCATCGGATGGCACGTCGTC<br>GTCTCTGCCGTTCTCATGGCAGTAG |

TABLE 3

Genomic Sequences Encoding Certain Rice Polypeptides

| Protein | Genomic Sequence |
|---|---|
| 2 | ATTGCTGCTACTCTCTCTCCCCTTCTCTTCTCCGGTTCTCCCTCTCCTCCTCCCACCTCAGCCGCCGCTTACCGGCGGCGC<br>CGCCTGCTAATCTGCCGGCGTGAGCACCGGCGGAGATGTGTTACTGCTACCCAACCTATAACGCAGCTCTCCCGCGCAGTG<br>CCTCTGTCTCTAGCTAGGGTTTTCCTCTTGGGGGAGACGACCTACTATGGTAAGGTGGGGAGCTGAAGCCGGCGACCTGGT<br>GCTGTCCGGAGGAAGCTGGAGCTCGTCGCCGTCGGATGGACGCCGATGAGGCCGCGGGGAGTAGCAGGAGGATGGATCTGA<br>ACCTCTACCTTGGCCTCCCACGCGCCCCGCGCCCGCGCCGCTCCGACCTCGGCTCCGACCTCGCCCTCAGCACCCCGATGC |

TABLE 3-continued

Genomic Sequences Encoding Certain Rice Polypeptides

| Protein | Genomic Sequence |
| --- | --- |
| | CCTCCTCCCCGTCCTCCTCCGCAGCCTCCGTCGACGCGCCGCCGCCACCGCCCGAGCTGTCGCATCCCCCGTACTCCCCCT<br>CTCACGCCGACCTTTCCCCTCCGCTGCAGGAGGTCTACTCCCTGTACAACCCCGACGACCCGCCTGCTTCCGAGACGCACC<br>TGCCGCCGTATGCGCCGCCTCCGGCTCCGGTGGTCTCGGAGCTCCCTGACGACCTCGAGTTTGGCCTCCACCCCCCGCCGC<br>CGCTGGTGCGTGCCAGCGAACTGCTAGGTTGGGAGGACCGGCCGTCTTCGTCGACGGCATCGTCCTCTTTCCTCCCTGACA<br>CCGCAGCCCGTTACTGGCGGCTTCTCGAGCAGACTGGAAGGAGATGGCTCCGTGCGAGGCGGTTTAGGTCGGACCTTCCGC<br>CACTCAGTTCTGAAGCTTACCCAGCTGGGCGTGATGCTGCCGCAGTCCCAGTGCTGCAGCATGAACCGATGAATGATACTG<br>TTGAACATAATAAGGTAGCTGCCGATGGCGCGGAAGTAGGCGCCTCCGAGGAATCGGAGGAGGAGGGCAGGAGCGCTGCCA<br>CATTTGAGTGTAATATATGCTTCGATATGGCCAGCGAGCCGGTGGTCACCTCTTGTGGCCATCTCTTCTGCTGGCCTTGCT<br>TGTACCAATGGCTCAATGTTTATTCCAATCACAAGGAATGCCCAGTCTGCAAAGGCGAGGTGACTGAGGCGAATATTACTC<br>CGATCTATGGGAGAGGGAATTCATGTTTGGATGCCGAGAAGGCTGTGGAAGGTGGGAAACAAACAGGTCCTACTATCCCAC<br>CAAGACCACATGGAAATCGGCTCGAAAGCTTCAGGCAGCAGTTTCACCATTTGCGACCGATCTCAAGAAGGCTTGGTGAGG<br>CTCATGGGTTATTGTCATCATGGAGGCGCCTTCTGGACCAACAGATTATGAATACTGCGAGTAGGTTTGAAGGTCCGCCTG<br>AATCAGCTGTGCAGGAAATGGTTGACACTGCTCACGCTCAGCACACCAGTCGCCTAAGTAGATTGGCGTCAAGGATGAGAG<br>CAAGACGGTTGCTGAGAGAAGCAGACAACCCTAACCCTCCCGATGGCGGATCCACTTCCCCTGACAGTGGTTTGATCAGAA<br>ACAATGCATCGGATCCATCCAGAAATGGTCCGAGCTCATTATTACCAGATGGAATTGACTGGTTGCGTGGACTTACCCTTC<br>TTGGGTATGAAGACACGGAAAGATTTGCATCTGCCATGAGTGATTTAGAAGGATAACTGGACCAAGCCAATATGGTGCAT<br>CGGCTTCATCATCGAATCCTCCAAATCTCGAGTCAACATTTGACAGAACTCATGTTGTTGCAGCACCTTCTGCAGAGCAAG<br>CATCTAACTCAAGCACTGCTGCAGTGATACAGGGGGATGCTGGTATCTCTGAGAGTGCAGGAGAACCAAGTAACGCGGGGT<br>CATCAAGATCCCTGAGGAGGAGAGGGAGGAGCAGTGCCCTGGGTTCTTTGGATGCTGATGGCGGGGGCCTCCAACGGAACA<br>AGAGGCGAAGGATAAACTGAACATTCTGTGTTGTGGTGTTGATCTAAACTCTGCATGCCATGCTCGCTGATTTTCAACTAT<br>TGCATTTCATTTCTTCGGGTGATGTCTCCTGTGTTGTAGTGTAACATTTTTTCTTCTCTTTTCATTTTCCCCCGTAGGTTG<br>CACTGAAATGTTTATCTGTTTAGTTCTCATGTAGCCTGTACCTGTTTAATTTATGGAAAGTTATTGATCAAGACATTTTTG<br>CATTCGAAAGGTAATGAATGGTTCAACTGCATTTCCATGACAATAAATTGGATGCTGAAATGTGCATCCAACACAATGGTA<br>TTCTTGTGCATCAAATAATAGGCATAAACATTGTGTTTTTATTTGTGTCAATAAGCTCCTTCAGACATATAGAAAACTAAC<br>AGGTCAATAATGTAGTATATTGAAGTTGGAAGGAATACCCAGAGAATGGATCCATGGACACAATTGTCTTTTGTTGCTTGG<br>GAGAAGGTACATAGCCTGATCTTTAGTCCTTGTTTATCCTCCAATGAAAATACTCACGCATTGATTGTTTCAATAGACAAG<br>GTAAACTTTGCCATCGCCGTGAATTTTATGATCCATGGAAGCTGTTTCATTGAGCAGTGGTGGGTGTAACTGTGATAACCT<br>TTATATTACTTGCTTGCTTTTAAGGAATAGCACACTTTTTGTGGGGATGGGATTACTCCCCTTTTTGGAACTACATATTGA<br>GGAACGGATTTAACATAGAAAGAGCTTAATACATTTAAGTACTGATTGTGTGCATAGAAAGGGGTTTATTATTTGGAACAA<br>AATTGCTTAGCTCGTAGTAATAAGGAAGTTCATAGTATTGAACTTTATATGACATGTGAGTTATATATATCATGTTTGTCT<br>TTGGTCACTTCTATTTTATGACCATGTAACATTTATTTCATGTGGAACTTGGCAGAAGAGAATTTGAAGAGATTTCTTCTG<br>ATTGATTTCCATTTCGGACAAAATACAAAGCTCCCAGACCAGCTGTCACAAAGAGGTCTGGTTGATTTTCCAGATTTGTAT<br>GCCTGTCTCTAGCCGAGAGTAACAGGTATTTTTCTGCATCTATGACTGGCATGGATAGTAGATTGGCATATGGAAACAAAC<br>TCGGAAGGGTTTGGGTGGTGCTTAGGTGCTCTTGGCAGGGAAGGGAGACAACTCTGTGTTTTTGGGTTTTCAGTACATCTA<br>TCCTACATATCTTCCAAAAGCTCACACATAAGCCAGTTAATTGTTTTTTTTTTTGGCTTGCAGAATTACCTCAATAACTTC<br>CATGTAAATATTTTACTCTTTTGCAGTATTACATGAACAGATTCAATGCTATTTTTCTGCAGAACTGCCCCAAGATGTAAA<br>ATGAAAATGCATTGAGTCTGTTCAATTAGAAAACACAAGATCACTGTGTATACTGTTCAAAGAATGTGCTAAACATATTAT<br>AGAACCAAACACAGTTCATCTCAACATTGTTGCTTTTTGTCTTAGTTGTCACAACTATTTAAACGGATGAAACAGTGGAAT<br>CTCTAAGCAAAGCTGTGAAGAGCTTCAGGGCTACCTCCTGGCGCGAAATGAAGGTGCTATTGCAAGCTGCTGCAGCTCTACT<br>GGGTGAACAATTACTCACATGTCACCAGAACTCTAGCAATGAAGCAGCATATTGGAACCTGAAAAGATTTGGATCTCACCAA<br>TGTGGACAACGAGGCTCATGAGTTATGACTGCTATGATGATGATGATGAAGATCTGCTTCAGCAAGCTCATGTTATGGATGT<br>ACTACTTTAGTATGCTTTGCTTTGTTGATTGGGAGCTGCATCAGATCCTGTTTGACTGCTCAATCAATTGCACCATCTTACT<br>CTCACCTACTGTTGGATGAGGGTGGGGCTTTGCTGTATGCTCAATGTTCTTGAACTCTTGCATATGACAGTAATGATGTTCC<br>GTCCTTAAGAAATTGTACTTATGTAGTGCAGCAGTTGATCATCCAGGATTTAACCCAAGTTCTAGGTGATACAATATAGGTT<br>GTACATGACCTAATAAATTTCTAAATAGAAGGTAAATCCATGTTGATTTTCAGG (SEQ ID NO: 131) |
| 3 | TCGCATATCCCGTTACCTTTGCCGCCGCGGCGCCGCCGCCCTCTTCCGCTCGCCGCCGGCCGAGGGCGCCCGTCGCGCGCC<br>GTGGAGCGAGCCTAGCCGCACGAGCTGAAAGCACCTAAAAGGTCAGCGCGTCCCCTCCCCCTTTCCTCTCCTTTCGCCGCT<br>CCCGCAGCAGCCACAGGACACCTGAGACGGGTCTGGGGGTGCAGGTCGCGCCTGGAGGAATCCCTAGGGGCTAGGGGAGGT<br>GGCTGGAGATGGCTGGTGGGAGCTGCGACGTGTGCAAGGAGGCGCCGTCCAAGTACAAGTGCTCCGCTTGCCGCACGCCAT<br>AGTAAGTCCAGCCACCGGATATCTCCACCCTTCTGTGCTTACAGCTTCCATGGGTAGCGTCGTCGCATACCACTGTCCTTA<br>AAATTTGGGAAATCGCTTCGATCATGGTGCTCAGTAATGGCCTACTAGCTAGCATAACAATTGAATTGAAGAACACTTGTT<br>ACGGTTTTAGTGCAATGTCCTACTTGCTGTGTTCACATCGATTACTTCACTGCTTACTGCTTGAAAAGAGAGTACGGGTTT<br>GCTAGGTCAATAGAGTAGATTGATGATTAATGGTTGGAAGCATTAGCTTCTTTTTAGAATATGAGCCTACATCAGAATTAG<br>CTTGATATATTTTGGGTTTGACTCGGTAGCTTGCTGCTGGAGTGGTTTTGCATGAGTAAAAAAAAAAAAAAGGCAGCAGCAA<br>AACAAGACATGTAAACCTTTCTCCTGATATCTGGTGTCAGTGTTGGTTTTGGTACTAAGCTGTATTGAATTAGTATTCAGA<br>GGCAAACGTCCATCATTCAATAATCTGTAATACTTTGCTTATTTTTTCTTGAATACGCAAGAGAATTACATATCATACTTT<br>ATGACTTCTCTTGCACAATTGTTTCAAGGATGTAACCTTAGGATTGCCAAATATGATTATCTAAACAAACTGTTTTTCAAG<br>ATTCCCTGAAACTAAATGGACTACTGAACTAACATACCTGTTCAGCGATGCAATCACGGTTGGACATCTTCTATGTGTCCT<br>GTAGATTTGTTTGGTAAAATTGCTCTTTTGCCCTAAAGTTGAATGGCATTGGCTCATTTGCCACAGTCCGGTGTATGACAA<br>CTGGGGCCAGGGCTACATGTTATACACACATATGTGGCAAAAGAGCACATGTCATATTGTAGACCAATTAAGAGCATGGTC<br>CGTTCAATTTCTCTGGCTTCTTTTTCTCTATTGTGTAATGCAGTTGGGCCTTACAAACGGTTTCATTATCCCTTGCAGTTG<br>CTCGGTGGCATGCTTTAAAAATCACAAAGGTACTCAGTGCTATCCTTTGGTAGTTTCTAAATATAGCTCTAGTGCTGCGAT<br>CTGAAAGTAGCTCAAGTAGCGCGAGGGGGCTGTAGCAAACTGCCGTGTTCCCTCTGTTGCTTCTTAGTTGTGTATTTTAAA<br>TCAACAAGCTTCCCTGTACTGCCTTTTCTCTCTTTGGCCAGCGTTCTTTGCCAGCCGCATTTTTAAACATAGCTCAATAAA<br>CCAAACGTCTTAAAAAAATATAGCAAGTGATAAACTGCTTATCACACTCCAAGTGTCCAAGTCTGCGGGGGACCTTTTGTT<br>TTGAAATTTTGGCAATTTTACTATTGTACTTGGTTTGAGATTAGGGAAAGGCTGAACAGTACTAAACACAGCACAAATTAT<br>AACTATCATTTATGCATTGCCTTTATGCAAACAAAAATGGCCACCAAATATCTTCATCTCCCTTTTTTAGAGGAATATATT<br>TATTATCTTGATAGCCAGTATTTGTGCTAAATATCGTTTTGCCAACAGATAAATTTTGCCAGAAGACAATACCTCTGGAA<br>GAAGTTAGCAAGTCATCTCTTCAGGAGGAAATTTGTAAGTGCTCTAGCTTTTGGTGACTCAATACAGTTGTTTGCAACAGCT<br>ATATAGTCCTGCTATATATGGAAATTGAGTTGAAACCATGATCATTAAAATAGAGGGGTCCTACATAAAATTACATCAATAT<br>ACTGTAAATGAGCATTTGACTGTGTACACCTAAAAGTCCTGCAGGGCATGTACTTGCCCATATATAAGGGCCTGAATTATCT<br>TATCATATAGTCATTCATTAAATTGTCAATTGTTCTGTCCTACTAACATGTTTCTAAAATAATCTACTGGAATTTACAGTTG<br>TGCCTTCTATTGTTTTCAGCAAGGAACTCTAGGTCACTGGAAGAAGCAACAAATTGTCCTAATGACAAGGATCAAACCCCGT<br>CTTTATGTAAAAATGCACCATACTTATCTCTGTTGTTAACTCTCCATTTCTTCTATTTGGTTTTCACTAATAATTGATTGAA<br>CTCAAAACTTTATAGATCATGACTACCTTCAGTTGTAAACAATGTAACCATATGCTATCCTCGCAAAAAAAGAAGAAGAAGT |

TABLE 3-continued

Genomic Sequences Encoding Certain Rice Polypeptides

| Protein | Genomic Sequence |
| --- | --- |
| | AACCATATGCTATGCTTTTTAATCAATAATTTAAATTAGTTTCTCTAGAATTTATTATAAGGGCTATAATATTATTCATTGT<br>GAATCTTGAAGGCCAAGAAAATTTATGTTAAGCTCAATTTTTTGTCTGTAGTATCGGACACGACTTGTCCCACACAATATCC<br>AAACACATTGCACTCTGCAAAATCTCTTGAAGTTGAGGATCCAAGCTGGCTTGTTGACAAGAATGGATTAAGATCTTTAGGT<br>ATTGCCTATGTTTGACTATTTCATACCATGATTTGTGTTTTTTAAAAAGGAATCCTTTGCTTTTACTTGATTTCTGGCTTTA<br>TTTGTTAGCTGAAACAAATGTCTCCATGTTAGTATAGTCCAGCATTTCAACCCAAGAATATCGACTTCAATTTCATAATTAT<br>CTGAACCTAATCCCAATCCTACAGACCTACAGTATAGGAGTAAAATATTGGCATGCACATTTAGTAATGGGGAATTTAACTA<br>TTTGCCACTTTTATAAATGGCTACTCTCCGTTTGCCATTCTTACATTTCTCTACGGATTTGCCACCAGAGAGAAGGTTTCTT<br>AATCATTTGCCACTTTCACCTATTAAGCATGCTAGTGAGGACAGCCAATGTGGACAAGAGACACAAAAAGTCCATTTTACCC<br>ATGGCCCTTCCCTTGTGTTCCCCCCTCTCTCCCTTTCCTTTTCAGATTTGAGCTCACCTCCGCCGCTGTTTCTCGTCCATCT<br>TCTGCACTGCTGTGTAGTGACAAGCCATTAGGTAGCAGTAACACTTAGGTGCGTGCATGGATGTTCTTTGGCTGCTATTGAT<br>TGCGGATGTACCTTCTCCTTGTGGCTGTCGATGACAACCTTCAACCTTGCGGATGTACCTTCTCCTTGTACCTCAACGTGCT<br>CCTCACTTGCCGGCCTTGCCATCAATGAACCGCATGACGACCTGCACCGGGGTGCTCCGCCATCCTCCCAGTGAGTTTGAGG<br>GCCTCGCGGTTATCTGGCCTGCCGAAGAAGATGATGCAGATGCAGTGCACAACCTTCTTGCCGCTGACACATGATTGACGAG<br>GCTTGATGAGACAGCGTGGCTGGTGTGGCCGCGGATGGTCTCAATGAGGAGGTGACCCCGCAAGCAGGAAGCCAGAAGCATA<br>CGTGCACCGCTGTGGATGATCTCAATGAGATGAAGGGGAGTGGCAGGGGCAAAAAGGACATTCACGTCCTCAGTCCATGCTG<br>GTATGCCACATCGGTGAAAGGGGCAAATTGTTAAGAAAATTTCTCTCCGGTGGCAAAAATGTAAGGACAATCGTAAGTGGCA<br>TTTGGAGAGTGGTTATTCGTAAGAGTTGACAAATAGTTAGTAAGGATAGTACTGTAAGCAGAATATGGGCTTCATGCTAGTC<br>AATTTTGTATATTGGTTCCACATCCCTCCCTGTACAAATTTCATAACCTGCTAGCATTTCTACCTTATTTAATTAATCATAG<br>TAATACTCATCGTCTTGTCTCGCAAAAAGAAATAAACATCATCAATTAACTCATTGCTTGATTTTTGTATCCATGCCAGCGG<br>AATCTAATGAGATCCGAGATGCTCTGAAAGATTGTAAGCTTCAGCAAATGCTACTTAAGATTGATGGCTCTGCAGAGCCAGA<br>AAAGGTAATTCTCTACTCTTGTGATAACTGCAAGTTTATTTAACAAGTTAACTATGTTTGCAATTTCTGTCCGGCTGCTCAA<br>ATAACATGCACATAATATGCCAATACCTATTGAGGACAATGGTTTGCAGTAATGAACATTGTCACTGTTATAGTACAACACT<br>TCTGTTTCTTATTCCACCATCATGACTTCATTTTCCTACCAGTAGTTGAGAAGCTTCAAATGGGCACGTTCGATGAATTAAT<br>TCCTTTTACTATAGTCTGCTGAATACTGATACGAATATAACTTTTCTCACTTACATTTATTTTTTTCCTCTCTCTACCACCT<br>TTATTTTATGATGCCCACTCCCTCATTAATTCATCCTCAGGAATTAGAGAAATTGATGGAAGGACAAGTTTTTCAACAGTTC<br>ACCAATAAGGTTTCTCTTTCCGTTGCATTTGCTCTTCTATCCACAAGATATTCCTTGTTAACTCTAAGTTAATTAACCAGAC<br>ACTTGCACGTTTTTGTTTCCTCTGTGTTTGCAGATTCTTGACATTGTTAGCCCACAACAATGAACACCAACTTTCTGGTGGA<br>GCTATTCAGCAGAAGAGTGCACGCATCGGGGCAAATGACAACATGTAGAGCAACTTACCTCAGATGCTGTTTTCCTACCATG<br>ATGAGATTGCCTATACCCGTGACATTTCCTTCTACTACTTTGAGAAAGTTTTGTCGTCCAATATGGTGCTAGTATTTTACCA<br>TGGCATCTCTGGCTCAATCAACAACTGTTCAATTTGTCTACATCCGTGACATCTTCTTTGGCTAATGGCTACTGTGAGAGTT<br>TTGTTGTCCATTATGTTTTTTTTGTGGTATACTCCCTCCAGTTTTAGGTTTTGTTGTTCAGTTTTGTGGTTTACCAAAGTCA<br>AACTACTTTAAGTTTGACTAACGTTATAGACAAATACAATAATATTCACATTACCAAA (SEQ ID NO: 132) |
| 50 | ATGCCCAGGCACGCATGTCTGCTGCAGGTAGCCAAAACTGAAACTTAGAAATCCGTGTACGCGTCGCTTAAGTGCTTCGG<br>CTTAAGGATGGGCATTCGGTCAGGCTGAAAAATTCGGTCTCGGTTTTTAGTTTTTTGGTTAGTTCGGTTTTTGAAAACTC<br>AGGACCGAATTTCATCACAAAAATCTCATAACTGATAAATTCGGTCTCGGTTTCGGTCTCAGTCTGACCGAATTTTTTTC<br>ATAGCCACTGAAGAGTGCAGACGGAGGCGACGCCAAGGAGGTGCCGACGCCGGCGCTGGAGGCAGAGGCGGAGGGCGCCG<br>GTGCTGGGCGGAGGCGGCGGAGGCGGCGCACATGGCGGCGGCGGCGGCGCATAGGGCGGCGGCGGTGCACAGGGCGGCCT<br>GCGGTAGCTCCACCGTCGCCGTCGGGCTGCGGGAGCTCCACCGGCGTCGTCTCTGCAGCACCTGCACGGGGGATGGGGAT<br>GGGGATAGGGTATGGATGGAGAGATGCTTGTGGTGGTGGGTGGATAAGGTTTTTCTTTTGCTGTGGTCTGTGGAGGTATT<br>GGGCCTAATGGGCCAATGCAATATTTCGGTTTTTTGTCAATTCGGTTAACCGAGCCAAAAAAACCGAATTGACCGAACTAA<br>ATTTGGTTAGCTGAAACTGCTGACCGAATTTGTGACCGAATTTTTCAGTCTCGGTTAGTTCGGTTTCGGTCTCGGTTATT<br>TTGGTTCGGTTTTTCGGTTCGGCCTTTTTTCCCACCCCTACTGCGGAGAATGCAGCGCGATGGGCCTCCAATCTTTGTCC<br>TGCCTAGCTCGCGGCGGATGTGTAGTTGCATGATCCGAGGAGATTTGTCGTGGCGGCGTGCGGTCAATATCGGGATCAGC<br>GCAGTGGCCGACGGCGCGGACACCGGCAGAACGTAGCGGCCAGCGGGTTCGCGGTTGATCAAACGGCTGGGGGTGCCCGG<br>TCCACGTCTCTTTGACGGTATACGTACATATTCATAATATCATATATTTCATTTGATATTTTTCCCTCTGTTTCATATTA<br>TAATTCTATTTGACTCTTTTTTTAAAGTCATTTTTTTCTAAATTTGATTAAGTTTATGTAAAAATTTAGTAACATTTACA<br>ACACGAAATTAATTTCATTTAAACTAACATTTAATATATTTGATAATATTTATGTTTTATGTCAAAAATATTGTCAAATT<br>TTTCTATAAATTTAATCGTTCTTAAAAAAAATTAATTAGAAAAAAAATCAAAACAACTTAAAACGAAGTTTGAAACTGAG<br>GAAGTACATTATCATATTTTAAGACGGTAATAGTTACTACGAAAGAGCAGCCCGATTAACGGAAAAGCAATAGAGAAGA<br>ACGTACGAACGTCGCGTGCGCGAAAGGAGGACAGAAAGAAAGATCGATCGATCGATGGATCGGCCAACGCGAGCGAAAC<br>GTCGTACACATGTACACACAGATCACGAGTTCACGGCTCATGGGTGTCGGCCCTTCTTTTGTCGAAAAGAAAAATTGTT<br>GCGTGACTGAATGGAGATTTCAGATTTCTGCGTGCTCGGTTAGTTGATTACAAGTACTAGTTACTAGTATACGCAACAG<br>AGACGTACGTCGTCTGCTGCGATCTCAATATCTCATGCTCACGTTTGGTGGTGGTTGCTGTTCGATCGTCCAGGTATTA<br>ATTGTCGAGCCATGCATCCACGTGCACAGGGTATCATGTTTAATTCGTGACTTACATGTCCTTTATGGTTGATGTCTCA<br>TTGGATTGATCATTTTCCTGGGAGATAATTAATTACTTACTCCTACTCCCTCGGTCCCAGAAAGAGACGATTTCTGGAG<br>GGGAGGATTTGTCCAAAAAAAAGCAATTCCTCTACAGAAATCAAGAAAACTTCAAGTATATCGTATCATTATGGGCCCA<br>AGTGGATAGCGAATTCTTTTTCTCTCGTTCACATTCACCCCACAAGAATCTTATCGCCTGCCCGTCTCTCGCAGTCTCG<br>CATTTCTCTCTTTTTCTCTCACGTTTCTCTCCCGTTCCCAAATCGATTGCATCGATGTGGCGGCGGCGGAGGCGACGGG<br>GAGACGCGGCTTCGTCGGCGGCGGCGGAGACGCGGAGGCCACGAGGAGACGTGGCGTCGTCGGAGGCGGAGGCAACAAA<br>TGGATGCTGCTTCGTCGGCGGCGGGGGCTTGTATGCCTAACTGCTTATCATCCCCGGAAGAAGATCTGATGCGGTTGCC<br>TGATGCACGAGCTGCGTTGTTCTTGTGTTCATTGTGTTCATGCACTGCATTTCTTTTTCTTTGGGTTCTTGCCATGTTC<br>ATGCGTGCGTCAGATGCTTATGCAGAGAAATGACAGTAGCAATAGCAAATGGATGTTGTCACGGAGGGCATTTTCGCCT<br>TTTCACGTGAGTGCTAAATTTGCATGGGAGGTACAGGAATCGCTTCTGGATGGAGGGAGTACCTGGTTCTGTTTAGGAT<br>CTAGTGCGTACTTTGTCGCAGTCAAATACGATTGGTGA (SEQ ID NO: 133) |
| 51 | ATGGGGACGTACAAGTGCTGCATCTTCTTCACCCGCAGGTTCGCGCTGAGCGACGCGTCCACGCCGGGCGACGTGCGCA<br>TGCTGTTCACCCGCCACGCCGGCGGCGCGCCCTACATGGGCATCGACGAGCTCCGGCGCTACCTCGCCGCCAGCGGGGA<br>GGCCCACGTCGACGCCGACACGGCGGAGCGGATCATCGACCGGGTCCTGCAGGAGCGCAGCCGCACCCCGCGCTTCGGG<br>AAGCCGTCGCTCACCATCGACGATTTCCAGTACTTCCTCTTCTCCGAGGACCTCAACCCGCCCATCTGCCATTCCAAGG<br>AAGTAAGCAAACTACCCGCTCGATCCCCAATTTCCCAAATGCTGTTAGATTCATCGTCATTCCGTGATAATCCTGCCGT<br>TGCACAATGCGGTGAAATGGCGTAATTTGCTAGGATTCAGAAGGGGATTCTTGGGGTTTGTTTAGTTCACATTAAAATT<br>AAAAGTTTGGTTAAAATTGGAATGATGTGACGAAAAGTTAGAAGTTTGTGTGTGCAGGAAAGTTTTGATGCGATGGAAA<br>AGTTGGAAGTTTGA (SEQ ID NO: 134) |

TABLE 3-continued

Genomic Sequences Encoding Certain Rice Polypeptides

| Protein | Genomic Sequence |
|---|---|
| 52 | ATGCAGGTAATGAATTGAATTTCCATACAACATTCTGCTCTCCTAAGAAATTACGCTTACAAGTTCACTTGGATATTGC TAAACTCCATTTTGATATTACTTAGTGTGTACTGAATGATCTAAGATGTGAGTTGATGGTAGATCTCGTGCTCTCAGGT CCATCACGACATGAATGCACCATTATCGCACTACTTCATATACACTGGACACAACTCGTATCTGACGGGCAATCAACTT AGCAGTGACTGCAGTGATATTCCCATCATTAAGGCACTGCAAATAGGCGTCCGTGTAATTGAACTGGACATGTGGCCAA ATTCTTCTAAAGATGATGTTGATATTCTCCATGGAAGGTATGCATGAGAATTGCTCACTTGAAGACATTTTTGTTCTGC ACTGGAGGCCATTCGATATGCTATGACCTTATTCCAAACTATTTGCTTCTTTGGTAGGACACTGACTGCCCCAGTATCA CTTATCAAATGCTTGAAATCCATCAAAGAATATGCCTTTGTTGCGTCTCCCTACCCTGTTATTATAACATTAGAAGACC ACCTTACATCTGATCTTCAGGCGAAAGTAGCTAAGGTAATTGCATTTTCCTCGTATGATCAATAATTTGGTGCAGTTGA TTCTGTTGTAGCTAGTTATGAAATTTTCTTTAGATGGTTCTTGAAGTATTTGGAGATACCCTATATTATCCCGAGTCAA AACATCTTCAAGAATTTCCTTCACCCGAAGCACTGAGGGGACGTGTCATCCTCTCAACAAAACCCCCAAAGGAGTACCT TGAATCAAAAGGTGGTACTATGAAAGACAGAGAGATTGAGCCTCAGTTTAGCAAAGGACAAAATGAAGAAGCTGTCTGG GGAACAGAAGTCCCAGATATTCAGGATGAGATGCAAACCGCCGACAAGGTTCTACTGGTTTTAACATTTGTTGTTTCTT GTTTCTTAGCATATGGTGTATGTCCATCACTGTTGTATTGGCTTTATTCCCTAGCAGCATGAGAATGATATACTATACA CCCAAAGAGATGTGGAAGAAGATGATGAGAAGAAAATGTGCCAGCATCACCCACTAGAGTATAAACACCTTATTACTAT TAAGGCAGGAAAGCCAAAGGGTGCTGTAGTTGATGCCTTAAAGGGTGATCCAGATAAAGTTAGACGCCTCAGTTTGAGT GAGCAGGAACTTGCAAAAGTGGCAGCGCATCATGGTCGTAACATCGTGAGGTTCGTTTAGCAAATATACTGAATTTCGT AGCAAAGTATTTTCTATCATTGCACCAGAGCTCTCTATGTCCATTGACCTTAACTTCATTCTGTTTATTCAAAGCAGCT TTACACATAAAAATCTTCTGAGAATATACCCAAAGGGCACTCGCTTCAATTCTTCGAACTATAATCCGTTTCTTGGTTG GGTGCATGGTGCACAAATGGTGGCATTTAATATGCAGGTACATTTCTAACATGACACTCCTCTGCTACATCATATTGGC CTGAATGCCTGATACATTTTTCTTCGCAGGGGTATGGAAGATCTCTTTGGCTAATGCACGGATTCTACAAGGCCAACGG TGGCTGCGGTTATGTGAAGAAGCCAGATTTCATGATGCAAACTTGTCCAGATGGAAATGTTTTTGACCCGAAAGCAGAT TTACCTGTGAAGAAAACACTCAAGGTAGGTTTGTGGCATATGTTTCTTCCTTTCATTTTCATCTCTGAAATTCAGGAAT CGAGCTACTTACAGCTTGCCTGTTTGTCTACCAGGTCAAAGTATACATGGGCGAAGGTTGGCAGAGCGACTTCAAGCAG ACATACTTCGACACGTATTCCCCTCCAGACTTCTACGCAAAGGTACATCGAATTTTACGCTGATGCCAAACGCCAACAA ATTTGCAAATGCAAAACGGAGCTTTGAAAAAACATGTATATATGTATAACTTTTACATATGGAGTGAGATGAAGACAAA CTTTATATCAAAATTGTAGAGCTCCATGAGTTCTACGACGTTCTTATTGACTAGTCCATCGTTCCATCATCATAACAGG TGGGCATTGCCGGGGTTCCGTCGGACTCGGTGATGCAGAAGACGAAAGCCGTGGAGGACAGCTGGGTTCCCGTGTGGGA GGAGGAGTTCGTGTTCCCGCTGACCGTCCCGGAGATCGCGCTGCTCCGCGTGGAGGTGCACGAGTACGACGTGAGCGAG GACGACTTCGGCGGGCAGACGGCGCTCCCGGTGTCGGAGCTGCGGCCGGGGATCCGCACCGTGCCGCTCTTCGACCACA AGGGGCTCAAGTTCAAGAGCGTCAAGCTCCTCATCCGGTTCGAGTTCGTCTAGCAAATTCAGTAGGCATATCACTCGCT CATGTGTGTTGTATACTTAGCATGATGATCTATTTCTCTAGTAGCAAGATTAGATTTTTACTTATGTGTGTTGTATACG TAGTATGATGATATTTTCTAGCAAGATCAGAATTTTGGACTACCTGTTTTTCTAGGAAAAAACAGATTATTTGGACATC GGTGACCAGAATTTTGGACTAGCAAGATAGATTTGGACTGCTTTGATCTGCAGATCGGTGGACATTTTTCTAGCAAGAT TAGAATATTAGATTATGGTTTGATTAGATTTAAGAACTTGTTTTGGTCTCTATGTAGATCGGAGAATCAGTTCCATC (SEQ ID NO: 135) |
| 53 | ATGGCGATGGGAGCCGCGGCGGCGCCATGGTACGGCGCCATCGGCGGCGGTGGCTCGCGGCGCGCGCGGGTGAGGGCGC AGGCGGCGGCGCCGTGGGCAGGAGGCGCGGAGGAGCTGGTGCGGTCGGGCGCGGTGCGGGCGGTGCGGGCGAGGGAGGC GGCGGGGGCGATGTCCGCGGAGGGGTTCCGGCTGCTGGACGTCCGGCCGGAGTGGGAGCGCGCGCGCGCCGCCGTGCGG GGCTCGGCGCACGCGCCGCTGTTCGTCGGGGACGACGACACGGGCCCCGTCACGCTGCTCAAGAAGTGGGTCCACTTCG GCTACATCGGCCTCTGGACCGGCCAGTCCTTCACCAAGATGAACGACCGCTTCCTCGACGACGTCGCCGCCGCCGCCGG CGAAGGCAAGGACGCCAAGCTGCTCGTCGCCTGCGGCGAAGGCCTCCGGTAATTAATCTAATCACACTGAAGCTACTGA GAATTTTTATCTGTTTAGTGTGTAATACAACGTGGCAATTAAGCTTCTGGATCGGTTGCATGCATCCGAACTAGGGCTG CTTTCCGAACTACTAAACGGTGTGTTTTTTGTAAAAAAATTCTATAGGAAAGTTGTTTTAAAAAATCATATTAATCCAT TTTTAAAGTTTAAAATAATTAATACTCAATTAATCATGTACTAATGGCTCACCTCGTTTTACGTATCTTCCCAATCTCC TCTATCTCCTCCTCCTCAAACACAGGTCGTTGATCGCGGTGAGGATGCTGTACGACGACGGGTACAAGAACCTGGCGTG GCTCGCCGGAGGGTTCAGCAAGTGCGTCGACGGCGACTTCGCCGACGTGGAGGGGGAGAGCAAGCTGCAGTATGCCACC GTGGGTGGGGTGTCCTACATCTTCCTCCAGATCCTGCTTCTGCTGCGGGTAGTCAAGTGATGATCATGTAACATCAGGA CATGCATCCGAGTATCCGACCAATGTTGCAGTGGAATATGCTGCCAAGTCCCAAATATTCTCCC (SEQ ID NO: 136) |
| 54 | ATCTCCAAGAAGCAGTCTCCACGCCGATCCGAGATGGCCGCAGCAGCGCAGAGGCGGCGGAGCAGCAGCGCCTCCCCGG AGTTCCGCTTCTGGCCCCTCGACGCCGACCCCGCCGCATCCCCCTCCTGCGCCGACGAGCTCTTCTCCGGCGGCGTCCT CCTCCCCCTCCAACCCCTCCCCTACCCCCGCCGCGACGCCGACCTCTCCATGTCCCTCGCCGTCGCGGATGATGATGAT GATGAGGACGAGGAGGAGGAGGAGGTGCAGCCTGGTGCGGCCGTCGCGTCCAGGGCGCCGCCCACTGCTGCGGTGGCGG CGTCGGGTGGTGGTGGTGGTGGGTCGAAGAGGTGGACGGATATATTCGCCAAGAAGCAGCAGCAGCCGGCGGCGGAGGA GAAGGAGAAGGATCAGCCGACGAGGCGGCGGAGACCGGCGGGAGGCGGAGGCGGATCGGAGCTGAACATTAACATCTGG CCGTTCTCCCGGAGCCGCTCCGCCGGCGGGGGCGGCGTGGGGTCGTCGAAGCCCCGCCCGCCGCCGCGGAAGGCCAGTA GCGCCCCGTGCTCCCGCAGCAACTCCCGCGGCGAGGCGGCGGCGGTGGCGTCGTCCCTTCCTCCTCCTCCTCGCCGCTG GGCCGCCAGCCCCGGCCGCGCAGGCGGCGGCGTGCCGGTGGGCCGGTCTAGCCCGGTCTGGCAGATCAGGCGCCCGCCA TCGCCGGCGGCGAAGCACGCCGCCGCGGACAGGAGGCCGCCGCACCACAAGGACAAGCCAACCGGCGGCGCCAAGAAAC CCCACACCACCTCCGCCACCGGCGGCGGCGGGATACGCGGCATCAACCTGAGCATCAACTCCTGCATCGGGTACCGCCA CCAGGTGAGCTGCCGCCGCGCCGACGCCGGAGTCGCCCGCGCCTCCGCCGGCGGCGGCGGCGGCGGCGGGCTCTTCGGC ATCAAGGGGTTCTTCTCCAAGAAGGTGCATTGAGCCATGGAAGCCTTTCTTTCACCTTAGCTAGAGATCCAAATAACTT TTAATTTTCTCCTCTCTTTTTTACCCTCCTTTTTTTACTTTTCTTTTTTTTTTACCTTTTGTAACTTTTTTGTTTAAC CTTTGGGGTGCTTGTGATCATGATGATGATGATGATGGCTGTTAATTACATGTAATTAAGCCAATAACCTGTTTTTGTA A (SEQ ID NO: 137) |
| 55 | AAAAACGAAAAAAAAAAATCAAAATCCTTCCCCCTTTCAAATTCGAAATTTCGAATCAAACACGCGCACGCTCCTCTCT CCTCTCCCCTCTCGATCGAGGCACGCTTCTCCGCGGCGGCGGCGCGCGACCGGATCACGGCGGCGGGGGAGGGGAGGGG AGGGGAGGATGCAGCAGAAGCCCGCGGCGGAGGCCATGGAGGAGGAGTTGAAGGGGGAGGCCGTGGGGCCCCGCCGCCC CGGGCTAGGGTTATGGTTGGCGGCGCGGCGGCGGCTGGCCCCCGACGACCCCTTCTTCGCCGCCGGGGACATGGAGCGC GAGCTCCTCGCCAAGCAAGTGCGTTCTCTTCCCCTTTCACCTCCCTTCCTTCTGCTCGCTTAATTTGGGCGCTTTAGCT TCTTCGATTTTACGGGGATTTTTTTTGTTAGCTGTATTGAGCTGGAACCCGTGGAAAAGATGAAATAGAGATAGTAAAA TCAGCCATGATAACCTTTGATTTTGCAGAAATTCAGCTGTACTGTACATAAGAGGAAAAGCTTTTGCCCTTCTTTGAAA AAAAAAAGAGAGAAGAAATTCAGCTGCACTTAGCATCAGTTAGGTGGGAATTCCTTAATGCTCTGCAATACTTGTTTCT |

TABLE 3-continued

| Genomic Sequences Encoding Certain Rice Polypeptides | |
|---|---|
| Protein | Genomic Sequence |
| | TTGATTTCTTGAACGGATCATGGCCGATTAGCTCAGATACCCTGCCCTGATGTGAAAAGTGTAGATGAACTGTGCTTTT<br>ACTCAACAAGTCCCCTATACTCCACTGTTTTTTAGGTGTCTGATGTTTTCTTGTTTAGGTTGCTCTGGATCTCTCCGA<br>AGATGAACGGTACCAGCTTGAGAGGATGGAAGTGGCGAGTGCCAAGTAAGAGATTGATCTTTACTTATGCTTACTCTTT<br>GGATTGATGATTATTTATCCTTTCCGTTTCACGCCGAATTAGGGGGGGGGGGGGGTTAGTCCCTGTCACATCAGATGTT<br>TGGACACTAATTTGAAGTATTAAACGTAGACTATTGACAAAACCCACTCCATAACCTTGGACTAATTCGCGAGACGAAT<br>CTATTGAGCCAAATTAATCCATGATTAGCCTATGTGATGCTACAGTCAACATGTGCTAATTATGGATTAATTAGGCTTA<br>AAAAAAATTTCACGTGAATTAGCTCTCATTTATGTAATTAGTTTTGTAAGTAGTCTATGTTTAATACTCTAAGGGCCCC<br>TTTGAATCGTAGAAATGAAAAAACGGAGGAATAGGAAAAACATAGGATTCGACAGGAATATAAGTGTAAAACAGAGGAT<br>TGCAAAACACAGGGAAAACACATGAATGATCGTTTGATTGGACCAGAGGAAAAACACAAGAATCGGATGAGAGAGATAG<br>ACTCAAAGGATTTTTTCCAAGAGGTTGGACCTCTTGCTAAGTTTCCTCCAAAACCTATATGCCATAAGCCATTCCATAG<br>GAATTTTGTAGGATTTGGAAAACTTCAATCCTTTCAATCAAAGAGCTATATAGGAAAATTTCCTACAGGATTTCAATTC<br>TATGAAATTCCTTCATAATTTCATTTGATTCAAAGGGGCCCTTAATTAGTGTCTAAACATCCGATGTGCCAGGGACTAC<br>AGTTTAGTCCCTAGATCCAAACACCCCCTAACATACCCTCTCTACAGATTTAAAACAGCATGTTAATGTACTGTTTTTC<br>TGCATCCCCATAACACCATAAATTTCTTCGCTGTAGCTAAGGAAGTCCCTGAACCAGTGGTCCACACCCCACAGTGACT<br>AAAGTCTGAGAAAATGACAACTGGATGTCTTGAACTAAATTATTGTACGAGTTCTCTAGAACCTATAATTCAAAATGAT<br>TGGCGAGTATTCCATCCTGACACCTGCTAAATCATGTCACCTTTTGCAGTTGTATGTTCTCTGTGTTGTGTTAGTACTG<br>CAAGTTTTGGTCTCATTCTGTTTATTTGATCATATATACTACTGCAAGTTTATGTCACCTTTTGCAGTTGTATGTTCTT<br>TGTGTTGTGTTAGTACTGCAAGTTTTGGTCTCATTCTGTTTATTTGATCATATATACTACTGCAAGTTTTGGTCTTATC<br>TGTTCGATTTATTTGATCATATGTCTTAAGCTCTTGCAGTGCCCTTTTATGCCCAATTTCTGGCTGTGGTGCTCATCTA<br>GATTGCCTGGAGAACTTTGAGGACCACTATCGCACCCGTCATACTGCTTCATGCTCTGTATGTTGGAGAGTGTATCCAA<br>CTTCAAGGCTGCTGAGTATTCATATTTCTGAGGCACATGATTCCTTTTTTCAAGCAAAAGTTGCCCGTGGTTTTCCAAT<br>GGTAATAAATTCATAATCTATCCATGCCCCCAGTTCTTTAATTGGTTTAATTTTGTGGCATCATGCACACTAGCCAATT<br>TTATGCAAACCCAGAACTTCCAGTGGACTGTGCCTGCTGGCCAGTTTAAAATTACTACTCAATGTCTTAGCATTAGTTA<br>GCATTACATGGTTTTCTGGTCCCGCTAATGAAGCTTTCCAATTTCCACATGTCACCTTTACTGGCATCTGATTCTTGTA<br>TAAATTTACATAGTAGTAAGTGATACTTTTATATTCCCTCAACTTTCTATAGCAATTCACATTGTGTATGCTATTTTTG<br>AAACAGTATGAGTGTTTGGTGGAGGGTTGTGGGGTGAAGTTGAAGAGCTACAAAAGTCGGCAGCAGCATCTTCTTGATA<br>AGCACCAGTTTCCCAAGTCATTTGAATTCTTCAAAAAAGCACGCCCTTCGCAACGCCAGCGGAACAAGAACCAGAAGCA<br>ACGGCAAACAGTTCACAAGGGAGACGAGACAAGCGAAACACTAATGGATGTTGATGGGAAGAAGAGCTCAAGGTACATG<br>AATTCCAGATATCGGCCAAAGCAACATGATGGAAAAGAGTCAAAAGAAAATGAGCATAGTAGCTGTAAGGAGGCCAAGA<br>ACAACGAAATGGAGGTTGACAAGCAGGTTGATGAGCTTGCTTCGGCCGTATCAAGACTGAGCACAGCGGATTCAACTCC<br>TTCTAGCATAAGCTTTGGTCATCGTCGCTCTCGCGGTCTTGCTTTTGTCCCTAGGTCGATTCGGCAAAACAAGCAGGTT<br>TCTCAGACAGAACCAAAATGACAGCATTTGATACCATCTTTCTCTTCATTGCTGATCTCGGATGCATCAACAATCCTGA<br>ATGTGCTGTTTCCTGTACCTGGACATTCACCGAATCCACTAATATACATTCTTGTAGTTGTATCACGAGATATGTCTTC<br>TAGCTGGTTATCCTTGCTTATGGATGTACTGAGCTTCCTGTTACTGCCATGTAGTAGAACAATTTTTCTGAAGCGGCAA<br>ATATGAAGTGCAAAATACAAGACAGTTCTTGTGGTTGATCGATTT (SEQ ID NO: 138) |
| 56 | GAAAGCCATCATCTACTAGCAGCAGCGAAAGCCAAGAACGCCAAAAACCCTCGCTTTGCTGCTGCTCCTCCCCCTTCTC<br>CTTCGGCTGCTGATCGGATTCGCGGCGTCCCAGGCTAGGGATCCGGGCGGTGGCGGCGATGGGCGGCGGCGGCGGCGCG<br>GAGGAGGAGCTGACGGCGCAGGAGACGGCGCTCTACGACCGCCAGATCCGCGTCTGGGGCGTTGACGCCCAGAAGAGGT<br>ATCCCCGGCTCCGCCTCTCTCTCTCTCTCTCTCTCTCTCTCTCTCTCTCTCTCTCTCTCTCTTCCCCTAAAAGTCCCGG<br>GTTTTCTTTCGCTCTTCGCTTATGTGGAGGAAATTTTGTTGAGTTGATGCTTCTTCTTTTTCTTCTCTTTTAATCGCAG<br>GTTGTTTCTTGCAGAAAAGGAAGAAAAGAAAATCATTCTTTTGGGGGATTTCATGGTTTATGTTAGAACGAATGGCTGT<br>TGTTTGTTTCTTTAAAAGAAAAACTTGAGCCCGAAGTGTTTGTATTTTTGAAGTGAAGACAGAGATATCCGCTGTTTTC<br>GTATCTTGTGTCTGCTATTGAATTTTCCTAAATCTTTTTTTTTGAGCTTGTTTGGTGCTTTCCTTGAATTTCTCGTAAC<br>TTTCACCCCCAAATTATTCTTCCATTCCATCGTATTTGTTAGCTTCGGAACCAAAACTTTTGATGTCTTTCATCTGTTT<br>TTGACTACTGAATCTGTGCTGCTTGGAACAGGCTAAGTAAAGCTCATGTGCTCGTGTGCGGCATGAATGGTACTACTAC<br>TGAGGTAGGTATTTTAAGATTTTCCTCTCCAATTGTTGCGTTTTGTTTGTAGTTTACACCGCGTGGGCATTCAAAGCAT<br>TGAAACGAAGTTGCATTGAGTTATGGAGTAATAGGGGTTAGTTTCATGGGCCAAATTGCCCATGTTTACCTGTTGCTTT<br>TAGTTCGTTATTATAACTCATTAGTTTTCTGGGCATTTGATTATTGCTCTGTTGTTCTTGTAGACTTTCTAGTGCTATG<br>GATGCATTGCCTGCGAGATAAAATCTCAATGTTCTTATTTACTTTTTAGGCTGGCTTTTTCTCTTTTGTAGGACCCCTG<br>TTGTACCATCTGTTAAAGTTAATTGCTTTTAGTTCTCAACGTTTAGGCTCAATTTTCTGTAGATAAATTCTTTCATTTA<br>TTTATGCTAGCTTACGTTGTTCCAATATATGTCTATTTATCCTTTTCTTTTACAGTCATATCCCATGATTATCTGATCA<br>ATGCACTTCGCTTTGTTAAGAATATGATTGCTATTATACTATTTACTACTTCCTTCGTTTCATATTATAAGACTTTCTG<br>GCATTGCCTACATTCATATATATGTTAATGAATCTAGACATATATGTGTGCCTAGATTCATTAACATCTATATGAATAT<br>GGGCAATGCTAGAAAGTCTTATAACCTGAAACGGAGGTAGTAGTTAAAGTATATGCCTTAGAAACTAGATTTCTGTAGT<br>CATAGAGTATCATAAGCAGCTGCATCCTGACTCAATTGTATATTCATCTAGGTACTTAAGTACCTCAGTTCTTCTGGAT<br>ATATTGATAAAGCTTAACTCATAATCGAAGGCAGCCTTATACACTAAATGCCATTTCTCTCTTACCCTGTAGTTCTGCA<br>AGAATATTGTTCTAGCAGGAGTTGGCAGTTTATCCTTGATGGATGATCATTTAGTCACAGAGGATGATCTCAATGCAAA<br>TTTCTTAATTCCTCATGATGAGAGCATATATGGTGGTAGATCACGAGCTGAGGTTTGCTGTGAGTCCCTGAAAGATTTC<br>AATCCAATGGTCCGAGTTGCAGTCGAAAAGGGTGAGCCTAGTCTGGTTTTCTTCATTGGTTTGGGTGTCAGAATTAGAA<br>GTACATAAAGTAGGATGCCTTCTTGCATTCTTGAATTGCTCTCGTCCTAATGGTTAATCTTTGAATAAAATGTTAAAGA<br>AGAGATTCTATTTCAATTTGTAATCTTACACTTTTAGCTGCACTTTAACAAGGAAAGTTCTTGTAAGAAATCATTTAAT<br>TTTAGTAACAGGCACATGTTACTATAGTGTATCATTGTACCAAGAAATCAGCATATATGTTACTGAGAGAATTCTGATA<br>TATCTGTGGCCATAACAATGACTAATTCTTTGGATCTTCACAGCATATTCTAAAAACAAATTTCTTACTGTTTCTGCTA<br>TTTCCTTTAGGTGATCCATCATTAATTGATGGAGAATTCCTTGACAAGTTTGACATAATTGTAGTTAGCTGTGCGCCTA<br>TTAAAACAAAGGTGTGTATTCTTCTCCCGTTTAGTTCTTCATCCTATTGCAAGTTCCAAGTCACTCAGTGTCTTTTAAA<br>CTAAAATTCTGCAACAAATTTCTCTTTATTGCGCTCAGTTCTCACAACATTTCTGCATGTGTTGTACTGCTTTAGTTGT<br>TAATTAACGACAACTGCCGGAAGAGAAGCAAGCATATTGCATTCTACGCCATTGAGTGCAAGGATTCCTGTGGTGAAAT<br>ATTTGTTGATTTGCAGAACCATAGCTATGTTCAGGTATGGGCATATATGACATGCTATATGTTCTGTTGATTTTTCAGT<br>TTAATTTTTTTCCAGCAGTCCACATATATATCTGTAAGCACTAAGCATCGCGCAGATGTCTTAAATTGGTTTATTTTCT<br>CCATAATGTTTCTCATATACTGCTTCCAATATTCCTTCCTGTGTACATGCATGTGGTTTGTGTACTTGTTAGTACTTTT<br>CTTCATGTACTCTAGAGGCACTCATTTTTTTTCTATGATATGTTTGAACTCAAAATTGATGTCATTATGTCAGACTGTT<br>CATGTTAACATATTAAATCTGATGTACTTAGCCTGATGAAGGTGCCATTAAGGATGAGAATTGCAAAGGAGCACGTACT<br>TTTTTTTGGTAATAAAATGTAGTGTACTAATCTGCTCTCACTGACTGGTTTTCAACCAAGTTATTGTATCTGTTCCTTT<br>TCTGCATCATTGAAATGGTGATACAAAGAAAGGTTACTTAGTTTTGGTGCTTAAAATATGGTAATGTGACACTTTCTAG<br>CATATTAAGTTTTGTAATTTGTACCAAGGATTCATCTTGCAATGCTAGTTTTGGTTCAATCGCTATGAATATATAAGCA |

TABLE 3-continued

| Genomic Sequences Encoding Certain Rice Polypeptides | |
|---|---|
| Protein | Genomic Sequence |
| | CTTATGCTTTGGAAATCATGATCACTAGAATGTTTCAGGAATTATTTTCTTTGTTCAGTAGTTTGGGCCCTGGATACTT<br>TTTTGAAGGGGTATGTGTTTTTTTTTTTCTCAGAAGGTTGGAGGTGAACCCAAACCAAAGGAGTTGGCATATCCAAGTC<br>TCCAGGTAAATGACTTGTTAAGCTGATCTTTTTTTTATATGTTTGAGAGGAAGCTGATCCAACTTGAGATAACATCTTT<br>CATTTAATATTACATGTTTTGTATTGCCCCTGTAGTTTGTTCTCTCTTGGCTGCCATAAATGTAGCTGTGGAATATTTA<br>TGATGCACCTTATACAAGCTACATGGTATATATACATGAAAACCATTTAACCTGAAAAAATAAACAATTTGAATAGTGT<br>CTTCATGTTTTAATAATAGTAAACTTATGTTTTCCTCTGAAAAAAATGATTTTCTGTAAGACAAAAAAATAAATAGACA<br>AAATGCTTACTCTGCTGTTTTTTTGTTTTGACTATCAGAATGCCAGAGTGCTTATTTATTCGAATAAATGTGTATCATA<br>TATTATATTTTTACAATACTAAGAACAGTCATCTTCAATCTAAAACAAAGTAAAACCATATCAGCCGGCAATCTACATG<br>TATACATGTGCCAATTTGCAGTTAATCAAATCCTAAAAAGGACATACTTATTTACATAGATATTGACGGAGATCAGTGT<br>AGCATACCAACACCATCTCCTTACTCCTTTTAAGGAGTAGGTAAACTAAGTATGATTGACAATCTGGATAAGACTTGAA<br>TACGTAGATACATCTACAGAAGATTGATGTAGAGCACAGCAACACTATTACCAAATCCTCTTTTCACGGCATAGAAAAA<br>TACACTTATTTATGCTCATGTAGCCCAGCCTTACTATTGGAGGTCTTCATTTCATGTGGTAATTAAATTGGTTCCACAG<br>AAATCCCCTTTCTGGGTTATAGGTGTTTTTGGAATAATTTTGTAAGAGTTCAAATCTACACTAGACAATGTGCTGATGC<br>TTTCTGGTTTGTTCATTTTGCATACATCCCTAGAAGAATGGAGTAGCGTAGCATGTTGACCTTGACTTTTTAGCTTTCT<br>TTATGTGTATCATCACTTAAATATGTGTTCAATTTGTTGCCATATGCCACCATATATCACCATTTTGGATGCTTCAGTT<br>TGGAATGTTACAGTTTGTTTATCATTGGAAATGATCTTTTATACAGGAAGCTATCTCCGTACCCTGGAAGAATTTACCA<br>AGAAAAACAACTAAACTGTACTTTGCCATGAGAGGTGAGGATGTCAGACTTTTGCAGCACTGTTGAAGATTCATTAGTG<br>CAGTTTTATCTCCCCAAATACTCAAACAAATCAGCCAGCTTTCTAACTTGTTTTTCCCTGCCCCTGCGCATATGTCCTC<br>TTGAAATGTCCTTTTGCAGTACTGGAGAATTATGAGTCATCTGAAGGCCGCAATGCTTGTGAGGCATCACTTTCTGATC<br>GACCTGCAGTTTTGGCTCTGAGGAAGGACATGTGTGATAAAATGGTATATAAGTTTTTGTGTTCCTTAATTTCAATCAT<br>GTTCTTTAAGATTTTTTTCATGGTGTGGTAAATAAACTGCAGTCTTTAAGTGAGTCTCAAATTCCTACTGCTCTCCTGG<br>AACGGCTTTTAGCAGCTGGAAAGAAGCAACATCCTCCTGTATGTGCAATCCTTGGCGGCATTCTTGGTCAGGTAGGTAC<br>CAATGTTCCATTACTTGAATGTGAAAATTGAGTATATGTGGTTGAACTAGATGGCAATTAAGGATTTACCCTCTAGTAG<br>ATGGTAATTGAAGTAAACTACTAACTTCACAATAACCATTTCCCCCAAAAGAAAAAAATAAACTCCTCAACAAATACTA<br>TGCATCCACATTTTACTCCTGCAGTAATTCACTTAAACCACATTACTTGGGTCCATGAACTTAGGAACTACATATTAAG<br>GTCCTTAGTGGGTCTTTTCGGACATATTGAAAGACAACTTAATTTATAATCATGAATGATGGCCCCTGGCTGAGGGTGC<br>CTTGCTTGTCCTGGTTGTGGGTCTCACAGCCTCCAGGCCCAATTCCCATGACAGACACTTTGCCCAGACATGTGCTGAA<br>GTTTGACTATCCTTTTGCTACGTAAGATCGATGTAAAGCTAGCAGAAGTGCTGTGTCCTCTAATTATCAGTTATGATTC<br>CCTAGCTCAGCCATACAATTTTGGGAGCATGAATGTGTAGTTCTCAGTCCAGGGGCCCAAGATGCATACTTGGATATTG<br>TGTTGCCACAATTAGATGATAGTTACACATGGAATTGGATCGGTACTCTCACTGGACACCTTCAAAGATGTAAATATTT<br>TATCTACAGCCTTTTGGTGGAATACGGATTTTGTATTGATGGTTCAAGGAATTATACACAATGAAAGAACTAGCACAAG<br>AAAGATTTGAACATTCTGTAGCAATGTAAAATTTTCTGAATTATTTAGCAACCTCAACTCAGTGATGTCTGAAAGGAGT<br>CCAAAAGTAGTAATATTCCTTTTTTTGCCAAGAAAAGTATTCTGTACTTTGTCAAATGTTAATCTTCAAAAGCAGCAGG<br>AACTTAATTTTGTTCTGTTCCAAACAGGAATTTCATCTGTGTTTATGCACAGTTCTCATTGTTTTGCACTCTGTTTTTG<br>CCTAACAGGAGGTGATTAAGTCAATATCTGGTAAGGGTGATCCGATCAAGAATTTCTTCTATTACGACGCCGCTGATGG<br>TAAAGGGATCGCTGAAGACATTCCTCCCCTTTCTTCAGACTGAACCAGTTAACTGCTCGACTCCCATTCAGCCTGGCTT<br>CACTAATCCCTGTACCCATTAATTAGCTTCAAATTAGATTAGCAGTCAATTTAAGTCTGAGAGATACTTAGAACTCTAC<br>TATTTGTTATTTAAGTTGTGCCAGCTTAGAAATGGTATCAGATAGAAATTTTACATTTTGTGCCAACAATTTCAAAGCT<br>GAAACCAGGAAAGGTTTTGTGCTGATTGAAAGATTAAATGTGTTGCTCTGTATTCTCTTCCAATGATGTGCCTACAACT<br>ATGCCATGCCCGTGTACTAATCTACCCCTTTGTTCTAAAATATAATCATTTATGTGCGTTTTCCAATATCCAGAT<br>(SEQ ID NO: 139) |
| 57 | CTTCAAACTTCCAACTTTTCCATCACATCAAAACTTTCCTACATACATAAACTTCTAACATTTTCGTCACATCGTTCCA<br>ATTTCAATCAAACTTTCAATTTTAACGTGAACTAAACACACCAGTTGTGTTTGTTTGTAGACCCTGTTACAGCTGCTGC<br>ATTCTTGGTTCAAACTATTGGAAGGGAAAAATGTCAAGCTGATGCAAGGTTTGCTATATTTCGTTGTGATGAATTAGAG<br>CAGCGAAAAGACCTTACTAACCTCCTGCTTGTCTTGTCCACTCCAGTCCACACAGCCACTCGATCGTTATCCCTTGTCC<br>GTCTTGCCTTGCCTTGTCGTAAGCTAGGCAATGGCTATGCCGCTGCCGCCGCCGCCGCCTCGTCCTCCTCTTGGAC<br>GGGGACGGCTCGTCGGAGTAGGACCAGCTCCAGCACCAGCAACGGCCTCCCAATCCAACCGCCCAGTGCCCCCCCTGCA<br>GCTGCCTCGCTGCCGCTGCCATCGCTCGGAGGGACCCTGGAGGACGACGGCGGCGGCGAACGGGAGGAGGCGGTGGTGG<br>TCCGACGAGGACATGGAGGAAGAGGACGACGAGGAGGGATACGGATACGACGACGGCGGCGCGCCAGGCGGGTCAGCGC<br>AGGAGCTGTTCGGCGAGCCATGGTTTTCCAAGCTCTTCCGTGCGTACGGCTACGTGCTGCCGCTGCTGCTGGCGTCCAT<br>GCTGGTGGCCACGGGGCCCAGAGCTTTCCTCATGGCCATGGCGCTGCCGCTCGCCCAGTCCGCCATCTCCTGGGTCGTC<br>TCCTTCTTCACCACCAGGAGTCGTCGGCAGCAGGAGGAGGAGGAGTCGTACGGATACGACTACGATGACGATCCCGCCT<br>TCCAACGCCGAGAGGAAGACGACGACGACGGCGACTACTATGATGCCGGGGCATGGCAATGGCGGAGCAGGAGCCACCA<br>GCAATCGACCGAATCCGGCTCCGGTTTTGGAGGATGGGATGACCTCCTCTACGACGATGAGGAGAAGAAGGAGCAGGAG<br>AGCTCAGGGAAGAAGAGGACGCCACCGGAGCCCGACACGGCGGCGGCTGCTGCCGCCTCCGATCTGGGACTGGGATTGC<br>GGGCGAGGAGAGGTCCACGACGCAGCAATGGCGGCATGTCGCGAGGAAGAAGCAGCAGCAGCATGAGGTATAACCAGGC<br>GCCACTGCTGACGCGCCTTCTCGTGGCACTCTTCCCCTTCCTCGGCTCATGGTTCAGGATACTCTAAATTTGAGAAGAA<br>GAAGAAAAACTGAGAGATTTCAGCATTCAGAATGGATTGATTCATCGTCAGTTCGTCAGACTCTTATCACAATTTCCTT<br>CTCCCGGTCAGGTGCACTTTGCCTCTTTTTTGTCTTGGTCATGTTCACCTGACAATCACAACTCACAACTTCATGCAAA<br>TCAAAACAAAAAAAAAATCACTTGGTTTCTTCAGGAACCAAACCATGAAAATTGAGATGAAATTTCTGGCCTTGTTGTC<br>TACTGATAGCAAGAAGCATCAGACGCTGATGTGGACAGGCAGAAGAACTGACCTTCTTCTCCTTCTCCTTCTATTCCTT<br>CGCCGTGCTGGCGCTGTTGTTCTGCCTACTCTTT (SEQ ID NO: 140) |
| 58 | ATCGCCATTGCTGCCCTCCTCTCCGTCTTCCTCCTCCCTCCTCTGTCGCCTGTTCTTCTTCTTCTCACGATTTTTTTCC<br>CCTGTAAATTTCCCGGCGGCTTCTCGCATCTCGTTCATCGTCGTCGTCTGCTCGCGACTTGACGGACGAGGAGGAGGAA<br>GAAGGGAGCGATTGGTTTGGACGGTAAGAAAGGGAGGGACGCGCGGGCGGCCGGAGCCGGTGGCCGACGGCCATTTTTT<br>CATGCGTGGCTCCCTGGAGGTCCACGCGATTGGCAGACACGCCGCGTCGCCGTGCGCCCTGAGACTGAAAGCCCTCCCG<br>GCATTGGACATGATGAGGTAGACGGCAGATCTCCAGGCCCTCGAGCCTCTCGTCCTTGTTCGGTTGTTCCTGCGGTTCC<br>TCGTTTCTTGCTCTCTTCTGTGTCAGATCGCTATGTTGTTTCTATGGTTCGCGTTCGGTTTTGTTTTCCTCTTTCGGTT<br>TTTTGTTCGGCTGGTGAAGCGATTTGGTTGATTTGCTTGCCTGCCGGCCGGTGATGGCCGGCCTCCTTGTCGAATTGCT<br>GTCCTTTGTGATTCTACTTGTTAATCTGTCTGATGGTTTTGTTCTGTTCGTTTGATTTTTGGATTTCATGGTGTTGCTG<br>CTGTTGCGGTTCGATTGATCTCTACTTGACTGTTTCTATGCCGGTTTCGCTAATTCGCGTGGAATTCGTGCGTCTCGTT<br>TTGACCCGATTTCATTCTCTCCGTATTTCGCAGTCTTCTGCTCATAATCTCAGTATAATCGTCTTTTGCTTTTCTTGGT<br>TCCTCTCTGGCTGTTTTAGAGTCTGGGTACAAAAGCATCGGATCGTTTGGTCGTTTTGCAACCATGGGTACTCTTTCTG<br>GGATGATGAGAGCCATAGTTCATGTCAGTTTGTTCATGTTCTTTGTGGCCGTGTTCCCTTTCAAGAACTGGTTGGTTTG |

TABLE 3-continued

| Genomic Sequences Encoding Certain Rice Polypeptides | |
|---|---|
| Protein | Genomic Sequence |
| | TTGTCAAATTTTCGGTCATTTTGGTGCCTCCTGTTCAACCCTGCTTCTGTTGCATCTGCAGAGTTCGATCTGTTCGTTT TATTTCCATTCCATGTGATGGTCTGAGAAGGCCCGATTTGCGACTCGCATTTTGTAGCAGATCTCTTTCCTCCGATCAA ATCGCTAATCGGCGCGTTTTGATTCACTGCAGGTACCAAAGGCTTAGCCCGGACTGCCTCCCGCTAGCCAACGGCGGCG GCGGAGGAAGCGGTAGCGTGACACGGAAGCCGGCGTCGAGATCCTGCAAGGACGACGATGGCGGCATGGCCGTCGCCGC GGACAGCTCCCGCCTCTCGTCGTACCTCCCGTCGTCACAGCTCGATTCCAAGCCGCTGCGCGCTCGGGCGCCGCAGCCG TCGTCCTCGTCGGCCGCCGCCTGGAGCCCGGCGCGCGACCACGCGCACGCCCACCACAACCACCACCACCACCACCACC CGTCCGACTCCTCCGACACGGCCTCGCCGAGCTCCAACGGCGCGGGCACCGGTGGCGACGTGCTGCTGCAGTGGGGGCA CAACAAGCGGTCCCGCTGCCGGCGCGACGCGTCCTCCTCGGCCAACGCGGCTCCCTCCTCCTCGCAGCGCCGCCAGACC GCCTCCGCCGCCGGCAAGATCCTGCGCCGCTCGTCGGCGCCGGCGGAGAAGCTCATGCCGCCGCCGCCCCCATCCACCA CCACCGGGTCGTACACGCGCGGGTCCAACCTGAGGTCCGCTTCGTCCTTCCCGACGCGGTCCGCCGCCGCCGCCGCCGT CGGAGACGCACACCACCACAGGTAACACACGCCTCCTACCTCCTCCTCTCCGTCTCGTGTCATATCGATGTCGTGGGGA AGATGACGTCCTTCCTTTTTCCTCGCCTGCATTTCGCTCGGCGACTTTTTTCTGTTTCTCCGCTTTTGCCCCTCCGCGGA AACTACCGGGCCGCGCGCTCTCATATTCCTCGTTGGAGTCGTGGTGGCTCTTGCGTTTGTTTTGTTTTGTTGGGTTCGT GAGTTCGTGTCTTCGCCGCGTTATTTATTCGCTTCGGGTTTTTTTTGGGTCTTCGGGTTTGGGTCTCTTTTGTTTCTG AGCTGTACCGCTCCGTAGAGAGAAGGGTGGGTTGAGTTTGATAAAAGATTCTTTTCTCCTTTTTACTTCACACACTTTT GTTTCTATTAAAAAATTGGAGCAGGTTCTCACCTGATCTAGATCTCTTCGTCTCTCCCCGAATTTTCGTGGTATTTATA ACCCTTTTAATTTTTATTTACAATATTTTTCGGAGGATGTTGTGTGTCCGGATCTGGTGTGTGGTACATTGAGGTGGTA ACTTTACCTTCCTCTTCCTTGACTAATCTGTAACCCAAGTCGTAAGGTCATAGGCAGCAGCACCCGTATTTGTCACACG TTGCATGATGCATGGGGACCCCCATCGAGATCTCCATATCTCGCTGAAATTCGTTGATGGTCATGGTGGTACTCCTTGG TTAGGGCAGCTTTAATTTGGGAGGATCGTTTGGTCGATCTGGTTAATTTGGGGTGTTGGGATGATGATGATCATCATCA TATGAATTTGCAGCATCAAGAGGAGGGAGAGCTTGTAGTACTGCTTGTAGGGTAGATGGTTATAAATATATCCACATCA CAGCTCCCCTCTCTTTTCTTTCTGGGCATCAACAATAGTAGTATAGCTTTTGCTCATAGTGCATCCATCTTGTTGTGGT AGGAGTCTCCAGCAGACCAGTTGTACTACTAGTGAGTAACCAATCCACCCTACCCACCCCTTCTTCCCCTTTACCCTTT CTCTCAACCTCCCAACCACCTCCAAGTCCATCATCACCACCACTAGCACCTGCAACAATCCCCATGATTAACGTCTTGT TTTCTTTCTCTGGTGGTATGATCAGGTCCGCCGTGGAGGAGCGATCAGGCGGCGGGTACAAGCGGTCGCCGGACAAGGC GCACAAGTCCGCCCTGGACGCGGCGCTGCACATGGATTCCAAGAACAACCACCATCACCACCACCACGACTCGTCGGTG ACCGCAAACGGCGGCGCCGGCGCCGGCGAGAAGATCGGCTCCGAGCGGTTTGAGCTGCCCCGGATCTACATCTCGCTGT CGCGCAAGGAGAAGGAGGACGACTTCTTGATCATGAAGGGCACCAAGCTGCCTCAGAGGCCCAAGAAGAGGGCCAAGAA CGTGGACAAGACCCTCCAAGTATGCCAATCTTTGCTCCGCAAACCGGCCTGATCTTATCTGCTCCGATCCATTCTTGCA TCTGTTCTGATCACAGAGCTAACATGTGTCTCGTGTTGCCCCCGATGTGATGTGCAGTATGTATTCCCTGGGATGTGGC TTTCAGACTTGACGAGAGGACGGTATGAGGTGCGAGAGAAGAAATGTGTGAAGAAGGTATACTCCACTCTGCACCTGGC ATTTTCAGTTCATGCATTCTGTGTATTTTTACAGACAAGAAGAGGAAAATTACCTAGATTTAGGGCATCAGTGACCCAG ATTGGTTGGGTCTAATGCAAAAATAAAGCCGAAGAGTAGGTGAATTACTTGCCCTTTTCTTTTAGTTTGGCCCCTTCTC CCTCACATGGGGCCCATGACTCGTGATGCTCCGTGTCCTCATTGATGACGGCACGGCACTGATTTATTTGGCTCAGCTT TATTGCTGTGGACGTGGAGATGCAAGCGAACGATCATTCTATTGCCCTTACCTAAAGGAGTCTTCTTGTTCTACGTTTA GTTGGATCCATTCGTTCATCTTTCTACATTTGTCATGTGCTTTCCCAGGCAAATCTCATTCAAGAACACTACAGTCACA ACTCACAACAAACCAGAGTGTGCCACATGTCATAGCAGAAAGAACAAAAAAAAGTCTTGGCCTCTTTCAGTATGGGGCC CAGCTGTCAGCCTCTTATCGTCCTTAGCTAAGCATGAGAAAGAACTGTAGCATTATTACTACTTAGGTGGTGTTAGTTC AGTGCTTAGCTGCGGGTGCGAGATTGTTGACAACTTGATTATTCCGGACCTTGAAGGCTTGAATGCAAGTCGTCGTCGC TGACAAGTAGGGAAGGGCCAACGTGGAGACATGTATCTGTGTCTTTTGTTAGGACCACATGATAATGTCTGGATAGAGC TTGGAATCATAACCATCGAAAAAGAGAAGAAAAAGAAATGGTACAAAGGGTTGGAAAAGAAATTGTGGTGCTGTCTTTT GATCTACTAGTCTGTTTTTCACCTTTTCCGTGATAGGGTCTTCAACTCATTCCCTTTGTTATTAGGAGCATTCAAGCAT GCTGTAGTTTAATGAGCTCCTGTAACATACTAACATGCATATATTTTCCAATAGTAACAAGGCCAGCTCGAATCTTGTA ACATGAACTCTACTAGTATTGTTTAGCTGACTGGCAGCTATTAAAAACCCCTGATGGTTAGGTTGTGCTTGAGGGGTGC TAGATTCTCCACAAGAATTAGGCTCAGCACATGCACCTAATCACCTAGTAGTATCTCCATCCATCAAGGTTTCTGCTTA ATCTCGGGCACTAACCGAAAACTCCTGTTTCTGACTATGCAGAGGCGTAGAGGGCTGAAAGGGATGGAGAGCATGGACA GTGACTCGGAGTGACGGCAGCTGGAGGTCAAGCGAGGCACCCAAAGCGAAAGGAGCAATAAGATTGGAGTGGATGGAGA TTGGGCCATTGCAATCAAAGTGGATGGGGGGAGAAGAAGTAAGGGCAAGCCAAAGGGAAGGCGAAGGCGAAGAGTGTTT TTTGTGTAAATGGAGAGGAAAAAGAAGAGGAGGATGTGCCGAGGGCAGGAGGTGCACGCGTAACGCGTTTGCCTCACAC ACCCTCCTCGAGGCGCCCGGCCCAGCGGAAGTGGTGGCTTGAGACGACGACGACGACTATGCCCCGGGGTGAATTTTTT TCGTTTCTTTCGGGTTTTGTCAGAGCCGGCCACCTGCTCGCACGTCGTCGCAGCGGCGCACAACTTGGTGCCGCGTTTT TCTCCCCGCGAGAGGCCATTTTGTGGTGTAATTTTTTGGGTGGGCTCCGTTGGCCCGGCCGGCCTCGCCTTCCTGTGAG CTTTTGCGGTTTGGTTTGGTTGGAATGGTTACCCGGTGACTCTTGTGCATAGTTCTTTACTATTAGTACTAGTACCATT TTTTTTCTTCTTCTTTCTCCCATTCATTCACGTTGGGCAAGTCTTCGGAACACCAAAAGTATTCTGAAAAGGTTAAAAA AAAAAGAAAGAATCATTGTGCAGTCGCAATGAGGCAGGAGATTCTGAATGGATTCAGTATGGGCCAGGGCCAGGGCTGA TGGAGGCTGCTTCGATGGGCCTGGCGCGTCGCGGTCACCTGCAAAGTGCGGTAGTCCCTTGTGACGAGCTGACAAACGT TCGGCATGCCGGACGGACGGGGGCTGAGATATCTAACGAGGATCTTCTACGTCATATATGATGGAAGAATCTGTTACAG AAGTTTGGCATGGCTCGTCTATCAGCCGTGCGATTACACCGAATATTGGACACGTGTCGGCATCTCGCGTGATCAACTT GACCACTATTTCCTTTGGCTTCTTCCTTCGTCCATCAGTTGTGTGTACAGTACTGTTGTGGAAGAGGCGATGATTAAAC TCTCCAATCATGTATTCATGTGCTGATGCGTATATGTATGTGCACGTCACATGTGGGCGAGTATGGGAGGGCCGTGAGG GCGAGGAAAGCGTGGTTGAAAAACGCCAGCGACCACGATTTTCCATACGCAACGCCGGCCATTGCTGGTGAAGTAGCTC TTTTTTCCCCTTTTCTTTGGAAAACCCTGTACTACTCTTTACCCAGTTTGCAATATTTTAGGGTGGAGGAGTACTCCGT ATTTAGTTTAGGGGCGGAGAATTTGAGGCTTTGTTGTTCGGACATGGTACGAGTGGCGAACTGGCGGCGATGGCAGCCA TAAACAGGAACACAATTGTCTGTCTGTCTGTATGTTTACTACAGACTGTTTACGGTCTCATGTCCAGCTGTTTGAATTT TGTACCTGAATGTTTTTTTCTTTGGACAAAAAGATGGAGTATTTGAATA (SEQ ID NO: 141) |
| 59 | ACACCTGCTTTCCAATCGCAGCTGCCTCCCATGGCGACCACCGCCTCCCTCCTCCCTCCTCTCCTCCCGGCCCCTTCCT CCTCCCCCCGCCACCTCCACCCCTCCCCTCGCCACCTCCGCCCCTTGCCACCGATCCGCCTCCTCCGCGCCGCCCGCCG CCGCCACCCCGACGCCGTCGTCGTCGTCCCGGACGCCCGCCCCTGGGTCGGCGACCTCTCGGGCGCCGCCGCGTCCTAC CGGGACGGCAGGGAAGAGGACGACGACGACGCGGGGGAGGAGGATGACGAAAACGACGACGACGACGAGGACCGCAGCC TGGACCTCCTGGTCCGCTTCCTGCACTCGGTGTTCAGGAAGGTCTCCCGCCGCGCGCGCCGCGCCGCCAGGTCCGTGCT GCCGCCTTCCGTCCCCGCTGAGCTGGTCCGTTCAACCCTTCCGTTTCTCCCCTTTGGTTTCAATCTTCTTCTTGTTCAA ATTGAGCGGATCCTTCTCTGTATTGTGTGATCTGGCCTTGATATGTTTAGTTTATGCTTGTGCAGGTGAAGTTCTCGGT CAACGGCGTGCTTGTTCTCACGTTTCTATGGGTCCTAAAGGGGCTACTTGAGGTGAGCAATTCATTTGTCTGAGGCTTG TTTCAAAATTGTGAGCTGATTGTGATCATGCCCTTGATATGAACTACTAAGTGTTACACTGTGATACTATCCAGTGGAG GATTCAGGAATTTTCTTGAGCCTGGTCAAACCTAGTGATGTATAACAAGTACATAAAAAATCAGTATAGCTCCATACTT |

TABLE 3-continued

| Genomic Sequences Encoding Certain Rice Polypeptides | |
|---|---|
| Protein | Genomic Sequence |
| | CCATAGACCATATACTATGAACGCAAGCAAAACCGACAGCTGCCAAGTTGTGATTTAGGAAGAGCAAAACCAGTACGTA CGAGAGATTATATCGTTGAGATGATGGCTGTCTATTGCCAATGGGCTAGACTATGGGGCTATTATCATCCTGACAAATG TGGTGATGAGTGCTAGCTTAGAGTTGTGTCGGTTTGACCCTCGTGCAGCAAACATTCAAACCGGCATATCAAGTAGTTT GCTTGGTTGGTTTGGCTCCCATTCGAACCAGCAGATCAAGTAGTAATTGATGGAGTGCTGTCTTGCTCATGTGCTGATC GCAGAGCCTGGAGACCAGCCACAGTTGCTGGGGCTTGGCTCCTCCGCTGATACTAACAGTGACATATAATGGAATAACA TTATATGTCCAGAGAACAAACATTGTGCATGCTTCTGAATTTCATGTATGTCCAGAGAACAAATGGGTGTTCTACCTTC GTTGTCATTCGCTTAGAGAGTGAAGAAGACAATCAGTGTCTGATTACATGCTGATATGACACTTTTAAATGTTTGATTT GAGTTTTTTCCCTTCATTCTGATGTCTCGTAAATTTGGTTTTCAAATTTTGGTCAACCAAGTTTGATGAACATGGATGA GAACCAGACAAGTGTATATGATACCACAAAAAAGATTGTCCTTTTCTCTAACTGTCACGTGTAGATGAGAATCCTCACT TTGTTGAAGTGATGCCCTCTTTTCCCTTGTACTAGATGCTTGCTCCCAGTTTTGAGCATAAAACAAAAACATGTTCTAG TACAGAGTATATAATAATGTGCATATATACTCAGAGTAGGGAATGGTGCACATCAGCACATGGTTCAATCATTCCTTAT TGATTGTCTACTCTTTGATTGGAGTCATGCTTATGATCAATAAACAGTTATGCTTTCAATTCAGAAAATTATAAAAAAA AATTGTGATGAAATAACAAATACTCCACATGCATTACAAGTACAAGTTTGTTTCTGGGAGACATACAAGTAGTTTAGAA TCATGAGATTACTTAATGCTTATAATGGCGTTTTCGATGGATGAATTCAGACCAAATGAGAATGAATCTTGTATTCTTT TGCACTGACACTTTCAGCAAATTTCATTTCTTAGCATTCTGGTAGTTTGGTCATGTGATTTACCTCTGGTGCTTTTGGA ATACGAGTTTTTTATTCGTTGTAACATTTCCTATTGATAATAGATGGAAATGGTTCGTCTTATTAAGATGATTCTCTTT AGTGAAATTATGAATTCTGTTTAGTAGAGAAAGAGCCTACTGCTACTGCTGTCAAGTTTGATCCCATACCCACCCCAAC CCCCAGCGTCTGGCGGGCTTCCCCTTCTGGATGAGCTCGGTCCACCGCTATCCTCCACAAGGTCGTGCCATTGTCCTCC GTCGCTTCCCCTCCCTCCACTCCTGTCGCTTGCCTTCCCCTTCCTTCCGTCGATCTGAAGGCAGTGAGCAGAGAGGCCA AGGTGGTGGCTGCAAGGAGTAGATGGCGATGTCGCCTGGATCCAAGAGAGAGAGAAGGGGTAAGAAGGAATATATGCTG GCAAATGGGGACAGTCGGATTTTGTAAAATTATTTCATAATCTTGCTGAGTGGATTGCCATGTGACCAAATTAACACCA TGTAGTATCAAAACCACTCCGTTTTTTGCCAGGGGGGTAATTTGTCCAGATTCAATAGCTTGGAGGTGTCAAATGTCCG GTATTGTAGTGTAGTTCGCGCAGGGCGGGTGGGTGTGGGGTGTAAATCGTACGGTCCTAACCCTTATAATTGCATACAA GCTTAAACTACACCCTGGTTCTCAAGCAGGGCTACTGAGTACTGACTGTTACTCTCTTCAACTGACACCCCTACACACT GTCTTCTAGTGCCATGCCTTTCCTTCAGTAACTGTTTATATTGTTTGTGCTCAGGTGGTGTGCACATTTGGAAGTATGG TGTTCGTGACCATCCTTCTTGTTCGTGGAATATGGTCTGGAGTGACTTACATAAGAGAAAACCGATATAGCTATATTCG CCAGATTGATAATGATGACAACCGATGGAGCAGAGTACAGACTGCTGGCTAATCATTTGATTTCCTTGACTACATACAT ACACTTTGCACCAAAGGGATCATCAGTAAACCTTTCCTCACTGTTAAGACAGCATGCTACCAGTTCAGCACCAACTGCC AACAGCTGTTGCTATACAGCAGAGTTGAACAAGAACAAAAGGAATCCCATGTATTCGTCGAATAAGTGGAATTTTCTTC CTCTGCACAAATGCAGGAGGGATGGTTGAGCTGAACAAGATTAATACGCGTGTAAAACAATCCAGCACACTGATGAATG AGAGCTGCTGCTGTGATGCATTTTCTGCTACTCTTTTCTTGAAGAGATGTATCGGTCCTTATTAGTGTATGTATTGTTC CATGCTGTTACAACTAGCCGGTGTAGAAAAACTCATGTTTGTTGTATTGAAAGGTGGTGCACGATACCTTTTTGGTTAA AAAGTGAATATCATTTCGATTTCATTTGAA (SEQ ID NO: 142) |
| 60 | GGTAGACACCGCTTCAGCCTCTGCCCATCCAACTCGCAAAAATTCCCCACGATTCCACGAAAGTAGGAACCATGAAGCT TCGGTTGCGATCCATGGACCAGCGCGGCGGCGCCGGCGGCGCCGCCGAGACCCACCGCGTGCAGCTGCCGGACACGGCC ACGCTCTCCGACGTCAAGGCCTTCCTCGCCACCAAGCTGTCCGCGGCGCAGCCCGTGCCCGCCGAGTCGGTGCGCCTCA CCCTCAACCGCTCCGAGGAGCTCCTCACCCCCGACCCCTCCGCTACCCTCCCGGCCCTCGGGCTCGCGTCCGGTGATCT CCTCTACTTCACGCTCTCCCCCCTCCCGTCGGGCCCTCGCCTCCGCCGCAGCCGCAGCCACAGGCCCAACCCCTGCCCCGT AACCCTAACCCTGATGTCCCCTCGATCGCGGGAGCTGCTGACCCGACCAAATCTCCTGTGGAGTCTGGTAGCTCCTCGT CGATGCCGCAAGCTTTGTGCACGAATCCTGGCTTACCTGTCGCATCCGATCCGCATCATCCTCCACCGGATGTGGTGAT GGCGGAGGCCTTCGCCGTGATCAAGAGCAAGTCGAGTCTCGTCGTCGGGGATACGAAGAGAGAGATGGAGAATGTCGGT GGTGCGGATGGAACCGTCATCTGTCGCCTTGTCGTGGCGCTGCATGCGGCCTTGCTCGATGCCGGCTTCCTCTATGCAA ACCCGGTGGGGTCTTGCCTTCAGCTGCCACAGAATTGGGCGTCAGGTTCTTTTGTCCCCGTATCGATGAAGTACACCCT GCCAGAGCTTGTAGAAGCGTTACCTGTGGTTGAGGAGGGGGATGGTGGCAGTGCTGAACTACTCCTTGATGGGGAATTTT ATGATGGTGTATGGGCATGTGCCTGGGGCAACATCGGGGGTGCGAAGGTTGTGCTTGGAGCTGCCGGAGCTTGCGCCTT TGTTGTACTTGGATAGTGATGAGGTGAGCACAGCAGAGGAGAGGGAAATTCATGAGCTGTGGAGGGTCCTGAAGGATGA GATGTGCTTGCCTCTGATGATATCGTTGTGTCAACTGAACAATTTGAGCTTGCCACCGTGCTTGATGGCGCTGCCAGGT GATGTCAAGGCAAAGGTCCTGGAGTTTGTTCCTGGGGTGGATCTTGCAAGGGTTCAATGCACGTGCAAGGAATTGAGGG ATCTTGCTGCAGATGATAATCTTTGGAAGAAGAAGTGTGAGATGGAGTTCAATACTCAAGGTGAGAGTTCTCAGGTGGG CAGGAACTGGAAGGAAAGGTTTGGAGCAGCCTGGAAGGTTTCTAACAATAAGGGCCAGAAGAGGCCCAGTCCTTTTTTT AACTATGGCTGGGGTAATCCTTATAGTCCACATGGCTTTCCGGTGATTGGTGGGGATTCAGACATGCTCCCGTTTATCG GGCATCCCAATCTCCTTGGGCGCAGCTTTGGAAATCAGCGCAGGAACATCTCACCCAGCTGCAGTTTTGGTGGACACCA TCGCAACTTTCTTGGTTAAGTCATTTCGTGGGTTTTGCTAGTATGTTAAGAATATTTCATCTGAAAAGCTACATATAAC ATATTGTACATATTTTATAGTTGGCACTTTATGCATGTTCAGTTGTTAACTGTATTACTGTACTCGTAATCTTTTCTTT CTTTGTTGATATATCCTATATTTTCTTGTAGTACCAGTGTTATGCATGCCTTAATCATGGTAAAGTATCGTCTGTTTAA TTCTCTGTGCTACAATATGCATTTCAAACACTTGTAACTTGTAAGTCTCATTTGTTGGATGCCTTTAGTCAATCTGATT ATTTCATCCATCAACGGAGAAACAAGATACTGGTCATGTTATATACCATCATGATCTGCTGATGAGATTGAAACTGTCA CTTGTTTCTAAAGTTTGCGTGAAATAACTGGAAGCAGGTGGTGTCTTTCTTTGGTAAAAGAAAAGTATTGTCCTTATCA TCTCTTTGTTCTTTTCGTTTTATATGCTATGAAAAGATATATTCATCCCATATTCCGATAATTTGGAATACTTGCTTGC CTTTTGTGCTATGGCAACTTATGCATATTATTTTGTTATTTTTATGTTCGTGGGGGGTTGTAGCCTCACAGGTTGTAGC CTCCATACTGAATCGTGCAAAACTGCTATCCTACAAAGAAGGACAAACAAACTGGATAGGCTGTACTCATTAATCAATG TCTAAGCTAGTGCGATTAACTTGGGCAGCATATGGTCCGAAAACAAAGAAGGAAAAGGTGAACATATATCAGGAACAGA TCAATAGACTTATCACGAGACTATAACCACTGGTGCCAAACGAATTAGCAAACAGATAATACCTTAGAATTTTTGTATT TGGCAATAAAATCTAGTAAGAATTTGTTGAGCTGCACTACAAACATGTATAGATAAGAAATAGCATCCAAGGCGAGGAT GATATGTTGTTAAGACATACTATCGAGCAAATCCTGTGGCAGGTTTCTCTTACACCAGGTTTTACCTATGGTTTGTAAG TTTCTACCTGATTTTCATTGTATATATTATTTTGTGATTACACGAATCAATTGTTTCCTTCTATATATTGCTGAAACCG AGCTGCCCTGTTTAAATGCATTAGTTAATGTTATACGTTATCTGTGTTTGATAAAAAGCTTCTATGAAACTATGACCAC TGTTTGCTTTTGTTTTGATCAAGCTTTCAGTGCAAGGACTTTTGGTTGTGCACACGTATGTGACATTTAGTGGATTTTT TAAAATCAAATACATTATCAGTACTTGGGGCTGGAGCAATCTGTTCCCTGGGGATACTTTTAGCAGGAACATGACTGAA ACATTATCAGTTTAAAACAATATGACTGATTGTCATTTCCTTATTATTGTAATTGTATTTAGCAGGAACATGATTCTGA AACTTGTGTCTTGATGATCAGATACATGCGGTTGTATGATGTGTAAATGCATTTACTCTGACCAAAGGAAGGATATCGT ACTAGCTGATAAGTATACCTGTGGTAATTATATGCAGAAGCCCGTCACACAACCTGGTAGGTGAGTAATATATATAAGC ACTCTGGGGAACTATTTATTTCTTTCTAGAAATATTCTGAATAGTTGTTATGTTACCTGCATGCCTAAGTTAATTTCTT ATTCCCTTTGTGTCCTTTTTGTGTTTGTCTGTTACTTTATTTGTACAATGTTTCGCAGATCGTCAATATTCTCGTGGC TTGCATCTCAATTGGATTTCTCCAACTGATGCTTCCTCCTAACATATCCATTTTTGGTTGCGCGTACTTGTTTTATGAT |

TABLE 3-continued

Genomic Sequences Encoding Certain Rice Polypeptides

| Protein | Genomic Sequence |
|---|---|
| | AAAGGAGAATAAAGGAGTCATCCTTTTTTTTTTCACTTCGACTTACGAATATGGTTTATTTTCTTGGTTGTCGATGCAC<br>CACTTTATGAATCTGACTGTAGTATTTGCTTTTACTTTTATTTTTCCTTCGCAATAGGTGGCTTATTATATTAGTCTAC<br>CATTCCCTACTTTGCCAGTACATCACTATTGGGTTGAGTTTGCTGTGGTATCATTTGGTTGATTTGGTTCAGGTATAAT<br>TTTTTAAGAGATTTTAGTCTTTTGTCCTAAGTGAATATGGGTTGCAGGATCTATATGACAATAAAGTTCTTGATTTTAT<br>ACAGAAGCTTCACATTTACACTGCAGTCACTACTTGAATTATCAACATTTCTCACTATACATATATAATCAGCTGAACG<br>CCTGAACCTTTTGAGATATTTGAGTTATGACTAGAGGCAAAAATGGATAGTTTCTTTGTAAAACGATATATAACAATCA<br>ATAATGGTTTTTCATGGACTTCTGAAGCAACTCGACATTGATGTTCCCATACCATATTTTTCTTGAGGCTATGATGGTT<br>GAGTGAACCATATAGCTCTTCTCTCTCCATAGTCCATTGGAGTCTTAGACCTGGGGGGCCAAAGATTGCTCCATTTTCT<br>TAAAGTGGGCTTTATATTGACCGCAGGGAGAAATATCACTTTTTTGGTGTAGGCGTGCATCTATCTACTTTGCCTACAC<br>ATGTTCTATTGACTATTGGACTCATCTGTCTTTATGTTGCATAATTAAACCATGAAATATCTTTCATGAGATTTAACTT<br>TTTGATCACTTCTCTTTGGACTGAGACTGAACCACCGTTACGATACTCAAATGGGAGCTGTACGGAGTGTCACGGAGTC<br>CAAGAAAAGCTACAACTTTCAGTAAGGGGAGTACTCTTTGCTTGTGGCTTGGTGCACTGAAAAGATTGTGGGGGAAGGA<br>GTATGGGAAGAAAGAGTTTATAAATCCAAATGGGTAAGAATTTGAGTGTTTTACTGCCAGGATATCTCAATGCTATGAT<br>TGGTGATCTAAATTATGGTTAAACGTTACTCTGTGGTTCCATGAACTTTGGCTGCTCTATGAAAAGTATTTAGTTTCAG<br>TTCCGTGCCAAATACAGCATTTGAGTTTCAGTTATGTGGCAACTACCGTTCATACGCAGCCTTATATATTTTCCTCATT<br>GTTCCTTTTACCAATAGTCCTGTAAACCCGAATTCTTCTGTTTCACATTCAACTTTGTCCTGCATACAGTATGTTTTAC<br>GTTCTCAGCCTGTGCTATTATTGAAAGGCTATTGCATTGCAGTGGAGGACCTGAAGCGATACTGCATCCCAGCGACCCA<br>GCTCAATTCACGCATCCAGTTCTGTTAGCCTCGGAACAATAGTACTCCTACAGATAGCTGGCTGATACTGCACAAGCTA<br>CAGGCAGCCTCAGCGGAGTAAGTACAAGAATCCAATTCGCTGCCAACACACGTCTGCCTGCCGCTGGCAGGATGCTCCT<br>GCAGCAGGCATTCACTTTGACTGTATTATTCCACTGCCAATCAATCCTTACCAGCTTCCCCCATCTGCTGGTGCCTGCT<br>GCTCAACAACTCAAGCTTCAGCATCAGCAAAAGATGGTGGCAATGTACTCCAGATTCCAAAGCCTCTTGAAGTGAAACA<br>GCACAGTGATGAACTTCTATGATTGACACTTGGGCACCCTGCTTTGAGCTTTGCCTTTTGCTCTCTCATCTGCTACTAG<br>TAGCATGCTGGACCTTATCCTTATGCAACACAAGTAATATACTAACAGGTATTGCTTGTTGGAGAAGGCCTAACCAGGA<br>CCGATTTTTAAGCCAAGGTGGATAGGATAATCTTGTGGCAATTGAAATCTGCAAATGTGCAACTAGTCTTCTTCATGAA<br>GGGAAGTTGTACTTCTGCTATGCTTACACCGAGGTGTAATCAAATAAAGACACTGGGAAGCTGGTGGAAGCAGCAGTGG<br>TGGCCTTCTAGTATCTTTTATTTCACCCCTCCTGTCCTAGCCACATGTCTCTGCATGCAGCCACTACATGGTGAACACT<br>ATTCGTTCTACCATAGGCTGGTGAGTAACTAACACCTCTGATCAAGAGAGGTGGAGCAGAGAAAGTGGCAGCAGCCCTC<br>ACCCCCGACTGGTAATAAGAACTCTCCCCTTCCATCCTAAATATATATCTTGTTCAATATTTTCTACATCAATTTTATG<br>CATTTTGGCAGAATAGTTTCTTTGTAGACAGTGCATTGTTTTTTCCCTTGATGAAACTACAGCACAAGAACATTATTAG<br>CTGTTTGCTCATTAAGTGCCAACAGCCTTTTTACTGAACGGTTTCTGTGCTCCATCCAAGTCCTTTTGCCTCTCCTCAA<br>TCTACACATTAAAGAAAGGGGAGAAGTTTCAACGTTGTACTAACCCTTGTCCTTGCATCTGGGATCAATCAATTTCTCC<br>CTTCTGAATTTCGAGATAGCCCTTAAACTGTCATGGTAGAAGCTCTGAATTGGTGAGTAGTACGAAGTGTCGACAGCCT<br>GTGTAAAATCGGGCAGTCATTGTCGTGCTTGACAGATCATTTACAGTGCCAGCACCAAATTCGGATGATGGTATGTACG<br>ATACTCACTGTTGAGAGCCGAAGAATCCCTCTGCTTTGCTACTGATAACAATCAGCTCTCTTTTTAACTTTTATCGATC<br>ATAGAACCTAATCACTTCCCTGGTTTCTCTGATGATTTCATCGAAGCTTTGCACATTCTTAGCTGTTGCTGTCTTTGTT<br>GTTCTGTGGATCTGATTCTACAGAACGAACTTCTGACATTTCCATTCAGATTTCAGAGCGACAGTTTGAACTGTGTAAC<br>AACTAACCTTCTGTCCTTGTTACCTCTAGCCTCACATCCACCCCAGTGAATACGCAATCTGAGTCTTTGTGTTGGAGAT<br>TTCGTTTAATTACAAATTAAAAAGAGAGGACTAAGGTTTAGTCTGTAACATTAATTACCACACTTGAAACGACGCCTTA<br>CATCTAGGCACTGCCACTGAAAGGTGGGTTCCCTTTTCTCCTCTTATGCAAGAATTGTTGAACATGTTAAGAATAAGAC<br>TTTGAAACTAAAAACTTGTAAGTTGGGTTTATCAGAAAAAAATGGTGAAGAAGGGTATTAATCCAGTAGTACAAAATTT<br>AAGAGGGTTTAAGGCTTTAAGCAAAGATGGATCTGGTTCATTAATTAATCATTAACCTTATTCTGGGCTGGCCCATACA<br>GTGGATGACAATAGCATCTGTTCTTTGGTTTGGTCTTCATTTTACAGTACCACCTGCAATTTATCTTAATTCAGAGAAT<br>TTTATTCTGATTCATGGATGTGATCCAGCTGGTGCATGGTTGTTAGCAGTACCGACAATTCTATTCCAGGACTGTGGTT<br>TCCACCTTTGCCCTTGCGTTTGTCTATTGCATTAGGCTTACTTAACTTTTCACTTTGGACAATCTTTATGTAAGGCTGC<br>AAGGGTTAGTTGTTCCTTGTTGAGCCTTGCAAGAAATTGACTGCCACAGCTCCCGATCTACCCTACCCTTTAAGTAAAG<br>CCCATTCACTTGTCAAAGCTGACAATTTAGAAGGCCATCACGCATTTCTTAAAATGATTGCAATATCACCCTGAGATCA<br>AGTATCAGGCACAAGGTTGGTGGCTTGTTTAATTTCTTCATATGTATGTTCTTGGGAGTTGGGAACTAGCATCTATCTA<br>ATCTAGTACACACTAGATGACTTATCTCAGAGAGTTGTGATATAATGGTCATCATGTGATTGATCATCGTTTCTTCTGC<br>AGATGTATTCCCCTCCCTGCAGTGCTGCTGCAAGCAGCCAAGGGCATTGTTTCGCGGTCGGAGCTAACCAGCTTGCTTC<br>GCTTGACCTTGCCATGGACTTCGACGAGCCTATCCTTTTTCCTGTGCATAATGCAAGTTTGCAAGAGGGGATTCAGTTT<br>TACAATCCTACCGGCGGTATGTCTCTCTCGTTACCTATGTTCTATTTTCAAGGATAACCACAGTATCCTCCTCTCTTTT<br>TTTTTTTCAATTAGATAACCACAGTTTCTTAATTTGTGAAGTTCCTAACTATTACAGTTTCCGTGTTCCAACTCCCCAG<br>ATACTCAGCTAAGTAGAAACATGAGCATTGACAAGTGTTTGAAGGGCAGTAAAAGGAAGGGCTCAGGCGAGGGCAGTTC<br>ATCGCTACATTCCCAAGTAACAAGTTAATTAGAAGCTCTCTTTGCTTAGCTTCATCGGGTGGGAGCACGTTTCATCGTG<br>AAAATCGTACTACTGCAGGAGGAAACCGGTGAAATGCCTCAGAGAGAACTCAGCATGGAGCATGCCGGAGAGAAGGCGG<br>GTGATGCTGACGCTAGCAGGGAGGAGTACGTGCATGTCCGGGCAAAACGCGGCCAGGCGACCAACAGCCACAGCCTTGC<br>AGAAAGAGTAATTGATCTCTCCAACATTAATGGAAGATCTTTCTGTGTATAGATTTTCTTGCTCACACAGCTTCACCAT<br>CTGAATGCAGTTTCGAAGGGAGAAGATAAACGAAAGGATGAAGCTTCTGCAGGACCTCGTCCCAGGATGCAACAAGGTA<br>GCAACGAAATCAATAACTCTTTGAGTCTGTGATGGTGTGGTGTGCTCTAACCTGTGTGAACATGTTGCTCTTGACAAAG<br>CAGATTACAGGGAAGGCCATGATGCTCGACGAGATCATAAACTACGTCCAGTCTCTGCAGCGACAGGTGGAGGTAAGTG<br>TCCCGAAATTACACATCTTGTCAACAAGAATTTACACTTCTCAATGCCAATCACTGACTGAACTATCCATGAAGTGCTT<br>ATCCGTGCCGGGTTTTGCAGTTCCTCTCGATGAAGCTCTCGACAATCAGTCCTGAGTTGAACTCTGACCTCGACCTGCA<br>AGATGTAAGATGAAAAAACTCCAACTCTGAAGAACAAATAACTCATCTATCACCATTGCTACACCTTGATCCTTTCTTT<br>TTCACTGCCATACAGATCCTTTGTTCACAAGATGCTCGCTCCGCATTTCTGGGATGCAGCCCGCAATTGAGCAATGCCC<br>ATCCTAACCTTTACAGGGCGGCTCAGCAATGCCTCTCACCTCCTGGCTTGTACGGGAGTGTGTGTGTCCCAAATCCCGC<br>AGATGTTCATTTGGCAAGGGCCGGTCACTTGGCTTCGTTTCCTCAGGTCTACATCTAACTCCAGTGAATACAGTAGTTC<br>AAATCCTTCAGAACAGCCGAGAGTTATTCATGTTTTCTTTGCTGCAGCAGAGAGGCCTCATCTGGAACGAGGAACTTCG<br>CAACATTGCTCCGGCCGGTTTCGCTTCAGACGCCGCTGGCACCAGTAGCTTAGAGAACTCTGGTATTTTTCAGAGCTCC<br>ACTGCCCTACTTGCTTTTTTTAAATACATTTCTTCTGCAGCTGAAATTCTGGCGATCGTGATGCTGCAGATTCGATGAA<br>AGTGGAGTAGCTAGTCAGCAGCTGGTGATGAACAATTGACACGCCTGAAAGTCCTGAAATGATCGCGCGTTGGACTGCT<br>AATGGAGGGATGCACTCTTTCAGGTTTGCAAAGGCTGCACACAGGTTTCCATTGGGGTGAGCGAATTTGGTGGTCGTCG<br>AAGTTCTCGAGGAAAACTCTGTAGCCTAATCATTGTACAGTTTGACTAATCGAAAAGATGAAAGTTTGAGA<br>(SEQ ID NO: 143) |
| 61 | ATGGCGGCCGCGGCCGGCGCCGGCGAGCCGTCGCCGTACGCGGAGGCGGCGGATCCGACCTCGCGAATGCGCGGGCGC<br>CGTCTCCCGTGGTCGGCAAGCACCTCCCGTCGGGCGCCGTGCCGCGCCACGCGTACGTGTTCGACGGCGAGGGGGGGTT |

TABLE 3-continued

Genomic Sequences Encoding Certain Rice Polypeptides

| Protein | Genomic Sequence |
|---|---|
| | CGCCGACGCGGCGTGGGACGTCGCGGCGGCGGCGCCGGGGGCGTTCACGTGGCACCACATCGAGCTCCCGCGGCAGCAG<br>CCCGGGGGCGCCGCCGCGAAGCCGCTCCACCACGCGCAGGCGCTGATCGAGCTGCTCTGCCCGCCGCTCACGCTGCAGG<br>AGATCCTCGCGTTCGTCGCCACGGGCCCGCACTGCGGCGTCGTGGACGGCGGCGGCGGCGGCGGGGCGGGCGCGCTCCT<br>TCTCCGCGTGAGCTCGCCGGGGCCGGTGGGGAGCGCGTTCGCGCTCCGCCTCGCCGCGCGCGTCACGGACAGCTCCGTG<br>GTGACCGTGTCCGTGGGCGGCGTCCCGCGCCTCGCGTTCGGGACCACGCAGGCGTCGCTCCTCTCCGAGGTGCCGCTCG<br>GGGTGACCGCGTCGCTCTCCGACGAGGGCCACGGCGGCGGGCGCGCCGTCGAGGGCGGGGTGGTGATCGAGGAGCGGCT<br>GCTCGAGTCGCTGCTCGCCATGAACCACGCCGACGGCGCGCACACCGACAACCCCGTGCCGCGGACCGTGTCCAACCTC<br>CTCGTGCACGTCCTGGGAACGCACGTAGACCACGTCCACGACATCGTCACGCGCCTCGAGATGGAGCTCGACAGCATCG<br>AGCTGCATCTCGACAAGGGTAGGTGGAGGTTGCTTTCTTGACTAGTAATCGCATATAAACATAAATCAAATTATTAGGG<br>TTCTAAGAACATCTCCATTCGTTAGACAAAGTTGGTGCCCTTTTTTTCCCTTTTCTGGTGATGTTGTTAGGTAGGACGA<br>ACTAGCTTCTTCGTTACGTCTGTTGTTCATGATTATGCACGAGAGAAATTTATTGTGCTTTGCTTTGTTCTATGGGCTC<br>ATTGGATTACACTAAACTGGAAGTCTAAAAATTGGGAATTTGTCGAAAATTATCGATTCTGTTGTGATTGTCCATCCGC<br>ATTGGGGCGGCAACTTGATGAAAAACTCCTATGATTGGAAGGAGGTTGCTGATGCTATTGAATTGATTCTTGATTGTTA<br>CTGTTCCATGGAGAAGTTCCAATTCCATATTCGTGCTTAAATTGATTCTGAAGCGGTGTATTTCCTTTTAGAGGTGATT<br>TCGGGTGTCTTTAGTTCCCACCAAAATTGGAAGTTTGGTTGAAATTGGAACGATGTGACGGAAAAGTTGGAAGTTTGTA<br>TGTGTAGGAAAGTTTTGATGTGATGGAAAAGATGGAAGTTTGAAGAAAAACTTTGGAACTAAACCCAGCCAATAAATTA<br>TAAATTTGGGGTGAAGTAAGGTCAGAGAAGAAGGAAAGGTCATCAATTTATAGTTTGTTATGTATGGTGGAATGAAATT<br>TCTGAATGTCATGTTGGCAGCAACCGTATTTCCTGAAATGCCATGATTATATTGCTAGCTGTGATTCCAGATGGGATTC<br>ATTTCACATGATCAGTATGTGCAACAGAATATTTTCTGAGATGGATTTCTCACGTAGTCTATGGATATCTGTTCTACTT<br>CTACATAGGTTAATGTCAATGGAAGTCAATGTGAAGTCTAGTTTATTTACTACTAGCCAAACTTATGCTCAAATTTGTT<br>ATAGCATTCTGCAGATGTTATTCTTTCTCTTAATGGGCTTTGAAGGTATTTATGATATTTCTGTGAATCTTGCTTGCAG<br>GTGGTCACTTTATGAGGAAACTTTTGTTGGATGGAAGGAGATTCCCCAAAATGCATCTTGATCTACAGCGCCTGCTTCA<br>GGTATTTTCTGAGATTTATCTCAAATTGCTAAAATGGAGTTCAATGTATGAGTATGTTATTGTTCACTGGATCGGGAAC<br>GCATAATAGAAGTCATGGGCTTTAATGATTTCTTGCCTAGGTTGTTTCTCATGGTGACCAAGTATTCCCCCGTGTAAAG<br>GAAAAATGTGCGAGCAAGAGTTGGTTTGCGAGTGAAGATATTGTTGCTCTTGAAGATCTGATAGGCCGTCTTAGGAGGC<br>TGAAGGAAAATCTTGGATTTATAACGAATAGGGTGACTACACTTCAAGCTAGTCTAGATAGCTGGCAATCTGAGCAGAT<br>AAACAAAAGCTTGTACTATCTTTCATTTTTGTCCATAATATTCCTTCCTCTATCCATTGTCACTGGAGGTATGTTCCCA<br>TGCGTATTTCTGATGCCATTTATTGCTTAAGGTCTCCAATTTACATGATCTGCTGCAATGTTTGTGCAGTTTTTGGGAT<br>GAATGTTGGTGGTGTGCCATGGACTGAGCAGAAAAACCCTGCAAATCTAGATGGCTTCTTCAATGTCATGTTAATATGC<br>GTCGTGATCTTGTTGATCCTGCTGCTTTGTTTCTTATTTCCTTCATTGTATTCACACGTGTCGGCATGGAGAACCCGCC<br>GTGCACTGGCCCGGAGCAGTTCTCAGAACAAGAGACATCTGAAACTCTTTAAGGGTCACAAAGATGGTTACATGCGCCT<br>CTGA (SEQ ID NO: 144) |
| 62 | ACCGTGGAGCACTCGATCTCCAAGCTCATCTAGCTCTTCTTGCTTCAGCTTCTTCCTCTCTCTCACAGTTCATCACACTTGG<br>CTTTTTGAGTCAGGTGCTTGTTCTTCCTGCTGTTCTTGCCTTGGTAATGCTCTTGATCTCTTCTTAGATGTAATCTTGGGTT<br>AGCTAGCATGCAGTTCTTGGGGTTTATCTCATCTTTCTGTAGTTTAGTGTGTCAGGTTTAGTAGTAATTGTTCGTCGAGAAA<br>ACAAAATGATATATGGGTTGGATGAATGGAGAAGAATGTGGTTCAGTTCAGTGTGATCATCTTCTTGTTGTGGCTCTGAATC<br>GAATGAGCTGTGAATTTGGTGAATTTGCAGGCATATGCAGGACCAGCTGATCTGCAGCGGCTGCAGGCGCGTCGTCCAGTAC<br>AGGAGAGGGGTCGCCGGCGTCTGCTGCCCGGGCTGCAACACGCTCACCGCCGTCAACCCGTCAGCGGTGGCCGACATGTCGG<br>AGCTCATCTGCAGCGGCTGCCCCACGCTGCTGTTCTACAACCGCGGCGCCTCCAACATCCGCTGCCCCAGCTGCAACAGGCT<br>CAACTCCACCAGATCAGGTGAATGATCATATTTTTGCACATACTATATCTTTCTCTGAAAAGATCATATTTGCAGCTGATTC<br>AGAGCTGCAAATTGGGATGAAATTAATCTACTGAAATCTGAGCTGATCATGGATGGTTTTATTTGGTGGTTCAGCCAACCAG<br>ATTGCACACCTGACATGCGGGCAGTGCCGGACGACTCTGATGCACCCACCTGGAGCCTCAACTGTGCAGTGTGCAACCTGCA<br>GATATGTTAACCATGTCAGGGTATGTTCTCATCTCTGAATGTTTCTACCCTCTATATTTCTCGCATCGCGCATTCGCTCTCC<br>GGTTTCGCTCTCTGGTAGTAATCATCGTCGGCTCATCGGCTCGGTGATAACCAGGGTTGGAAATTCCGAAACGAAATTTCCG<br>AAATTTCGGACATTTTAGACCTCTCTGATATGATATTATTTCGGCCAAATTTTTTTATTTTTTTAATTTTTTCGTGAACTTT<br>GGTAATATTTGTTCAAATTCAACTAAATTTTATTCAAAATTTCGGAAATTTCAGACCGAAATTTCAAAAAATTTGGCATTTC<br>CATGAGGACCGATCAAATCGGCTAAACCGAAAGGTTTAACCCTGGTGATAAATAGTTAGTGTGTTCTTGAATGATCTTTCCA<br>CAACTGAACAGCAACCTGAGTTGATCAACTGGAAAGATGGAATAACCTTTTAACTTTGCCTAGAATATCAGTAGTCGGCACA<br>GGTTTTTCTGAAGCTGAAAATATGGAATTTTCAATTAGATTTTCTCATTTCTGTGAACAAAATTTCATGGGACCATTGACTG<br>AACAAACCAGCACTTGCTTTTATCTTTAATTTTGCATCAACTAGGGGATGCATATGGTTCTCCTCTTCTTAAAAAAGATGAC<br>AACTTTGGTAGGTTCAGCTTGCTCCATGGTTTTTCATGGAATCAGTTCTCAAAGTAGGCATGTACCTATGATTAGCCAGCAG<br>AACTCGATGCCTCGGCCAAGATTTTTATCTTCCAATTCCGTTATCAGGACAATGAAACTAAATGATGATGGTCCATTGGGAC<br>AAATGAAACAATCTGAATCTTATGTGATGTCAAATGTTCCATGATGACGATGCTAGCTTTGTTCTCTGAATTTCCTTTTCTT<br>TCTCCTACTTGCAGGATGCTCGGCCTCAAACTGTCCTTGTAGAGAATCCTAAGACACTGGATGATAAGGGCAAGCTGGTAAG<br>CCTCATCTCTAGGCTATATATCTCTACTATCTACTACTTTAAAAGACGCAGTCCTCCCATCCCACCCTACCGCACGCAGCAC<br>GAGAAAATCTTGTAATAAACCGAACCGGCCCACCCACCGCACCCTCCTTCCCGCACCGCGTGAGAGAAAAAAAAAGTGCACG<br>TCCGACTTCCATGTCGTCTTCTCGCTAGAAAAACCGAGTTTCAGTATCAGACAAAAATATGATAGTTGTTTTTATGGGTCCA<br>TTGCAACGCCTAGACATTTAACTAGTAGTACCCTAAAACCAAAATTTCCTTCTGAATTTTTTTCTTGGAATAGCAGAAAGTT<br>TCACTTCTGAAATGATAGCTGAAGAGTACATGTATTTCAGCTCTGAAATGTCCAGTTGATTGACTGTTCTGTTTTGTTATGG<br>TATAGGTGAGCAATGTGGTTGTTGGTGTCACCTCATGGAAAAGATGATGAACAGGGGCTCATCTAGGGTTTAATCCCAAGGG<br>TCTATGGATGATTGATACCCTTGGTGGATTTGTATCATTACTACAAAGCTATTGTTAAATCAAGTGTGTTTTGAAGCTTGAT<br>ATAAACAAGAGAAAAACAATAGGGCAAAAAATGAAGAAAAAAATATATCCGAAATGTGCCATGTTTGTGCTTCTTTTGTGAG<br>AAAAAAAAATGTAAATATGCTGGCTATGGTGCTAGCCTATGTGCTTTTTAGCAAAAAGGAATGGAAATGAGATGAGCAGCAT<br>TGTGTCCTGGAATTTTTAT (SEQ ID NO: 145) |
| 63 | CCCCTTCATTTTCTCGAAGCGCTTCCCTTCCCTTCGCTTCCCCGCACAATCTGCAAACGCGCCACCCGTCGCTCATAAA<br>CCCCTCTCCCTCTCTCTCTGGCCGACACATGGACCCCACCGCTCCCAACTCCGGCGACGCCAACGGCGGCGCGGCCGCC<br>GACGCCACCGCCCCGTCCAACACCACCGTCACCCTCCCGCCGCTCACCCTCCGAGACGTGCCCCTGCTCCCGTCGGCGG<br>CGGCGGCGACCGACACGATCCCCAACCCGATCTCCCGCCACCCCTACTTCCACCCGCCGGCCACCTTCTACATCTCCCC<br>GGGTGACGTCTCCCTCCGCCACGCCTTCTTCGACCTCGCCTCCGCGTCGCCGTCCCCGCTCGTCGCCTACCGCCCGCGC<br>GGGGCCGCGCGCGGGGGTCGCCGTGGACCCCGCCCGCGCGCGCGCCGCGGTCGTCACCTGCGGGGGGCTCTGCCCGGGC<br>CTCAACACCGTCCTCAGGGAGCTCGTCGTCGGCCTCCGGGAGCTCTACGGCGTCCGCGACGTCTTCGGCGTCGCCGCCG<br>GCTACCGCGGGTTCTACGGCCCCGACGCCGACCACGCCCGCCTGGACCTGGCCGCCGTCGACGACTGGCACAAGAAGGG<br>CGGCACCGTGCTCAAGACCACCCGTGGTGGCTTTGATCTCAACAAGATCGTTGACGGCATCGTCGCGCGCGGGTATACG<br>CAGGTGAGAGCAAACCCCTACCGTTTTTAGAGTTTTCAGGTTTTATGTATTTTTTTGGCAAATAGCTAAAGTTTAAACT |

TABLE 3-continued

Genomic Sequences Encoding Certain Rice Polypeptides

| Protein | Genomic Sequence |
|---|---|
| | GATCTCACAAATCATGTGCACGTGGAAACCCCTAAGCTTCTTTTTACGCCAAGCTGGCAAATGAAAGCTGGCCAATTTT<br>GTTAAGATTAGAAGCACAAGAAACATGTTACAGGTATTTGCAAGTGTACAATGTGTCATCTGAATTGGCAAGGATACTA<br>TCTTGGTGCTACAAATTTGCTTTAGACATTTTAGTATGTTGGTGTACAATCATGGGGGTTGTTCTGAATTGACATGGAG<br>TAGTACTTATTATGTTAGGTGTCATTATGGAAGAATTATCTCAAAGAATTTGTCTGTCCAGAATTTTTCTTTGTCAGTA<br>GAGTTTCTTTTTCCACCGGGCTCTTTGTCGGTTAGAGTGGTCAAGTACTCAAGTGGTTGAAGTCTTACTGATTTGATCG<br>ATCAGCGTTGAGTCGTCTTGCTAGTTCAACATGCTAATTTGTTTCAGTTATTGCTTGTATTTTGGCTTATTAAAGTGTC<br>TGACCTCAAACACTTTTTATCATGACTATATCTTGCTGAAGGTTTATGCAATTGGAGGGGATGGAACAATGAGAGGAGC<br>TGTGGCCATCTTCAACGAGTTTAAGCGCCGTGGTTTGAACATTTCTATTACAGGGATCCCGAAAACTGTGGACAATGAT<br>ATCGGCATCATAGACAGGTCATTTGGGTTCCAAACCGCAGTGGAGATTGCTCAGCAGGCAATCGACGCAGCACATGTCG<br>AGGCTGTGAGCGCCGTGAATGGCATTGGACTTGTCAAACTTATGGGCAGGAGCACAGGCCACATTGCTCTTCATGCCAC<br>CCTGAGCAGCCGCGATGTTGACTGCTGTTTGATTCCTGAGGTTGATTTCTATCTTGAAGGAAAGGGGGGCCTGTTTGAG<br>TTCTTGTATGAAAGGATAAAACAGAAGGGACATGCTGTTGTCGTTGTTGCTGAAGGTGCTGGTCAGGAATTGATTCCAA<br>GGACTGACGATCAAAAGCGGGAGCAGGACGAGTCCGGCAACATTGTGTTCCTTGATGTGGGTCCCTGGTTAAAATCTGA<br>GCTGGGTAAATGGTGGAAGAGAGAACACCCAAGCGAGTTGTTCACTGTGAAGTATATCGATCCCACTTACATGATACGA<br>GCTGTTCCAGCAAATGCCACTGACAATCTGTACTGTACATTGTTGGCACATTCGGCGATCCATGGGATCATGGCTGGGT<br>ACACTGGCTTCGTCCCTGGCCCGATTAATGGAAACTATAGCTACATACCGCTGGAAGATGTTGCTGTGGCGAAGAACCC<br>GGTGGATGTGAATGATCACAAATGGGCATGGGTTAGATCAGTCACAAACCAACCAGATTTCATGAAGCCAAAATACTAA<br>GACCAAAAGTGCTGTTACTGGACATGGTTGTATGACTTTTTCTCCCTGGAGCCTTGACACGTTAAGCTTGATTTCTTTC<br>TATCCAGTTTCTTCTCTTGTTATGCCGATCTATCTATAAGATGTTAGGTATTCTGATCTCCCTGGTTTGTGTTTGTGTG<br>CACTTGAAATCGTGTTAGCAGGTATTGCTGTAAATCTGTAGTACATAAATAAATGAAGTGGCAGGAAATGTTGTTCTCC<br>ATTGGCG (SEQ ID NO: 146) |
| 64 | ATGGTTGAAAGTGCAAGCATGGTAATTTGTGTGATTAAACAAATTTACACACTACGTTAGTACTCTCTCCATTTCACATTAT<br>AAGTCGTCTTGTAGGAGTACTAACTACTCCCTCCGTCCCAAAATATAAGAACTTAAAGACCATAAGGGATATTAGGAACTTA<br>AAGACCGGAAATGTCCCATCCGGTTCTAGATTCTTATATTTTGAGACGGAGAGAATAATATCTTATAATGTGAAACAGAGAA<br>AATACTTCTTCCTTAATGAAACAACTGTGCAAACTCTAAATTAATAACAAAAAAAAAGACCGATTAATATCTGAATGAATGA<br>TCAAAGAACAAATGTATCTGCAAATCAAACGATCATTTCTGTAACTTGCAAATTTCCTTTGTCCATCATGCAGGTGAACGAG<br>AACTCGGAGAATCCATACTGGAAAGCAATAGGATACAGAGTGGAAGAGCCCCGACGTGATCGAGCAGAGTCGATGCCGTCGC<br>CGTCGCCATCGCCGGTATCGCGGCGGCCACTGGACAACGGCGTCGTGGAGACGAGGGCGCTGACGGACACCACCCTCCTCCG<br>GTCGCTCGCGGCGAAGGGCCTCGCCGTGAGGCCCGGCGCGTCGGACGAGCACCACACGGTGCGGTGCGACGCCGTCATCGTC<br>GGCTCCGGCTGCGGCGGCGGCGTGGCCGCCGCGGTGCTCGCGTCCGCCGGGTACAAGGTGGTCGTCGTCGAGAAGGGCGACT<br>ACTTCACCAAGGAGGATTACAGCTCGATCGAGGGCCCGTCCATGGAGCGCCTCTTCGAGAGGGGCGGCGTCTTCTGCACGTC<br>CAACGTCACGACGATGATATTCACCGGCGCGACGGTCGGCGGCGGGTCGGCGGTGAACTGGTCGGCGAGCATCCGCACGCCG<br>GCGGGCGTGATGCAGGAGTGGTCGCGCGAGCACGGGCTGGCGGTGTTCGCGAGCCCCGGGTACGCGCGGGCCATGGACGCGG<br>TGTGCGAGCGCCTCGGTGTGACCGACGCGTGCCGGGAGGAAGGGTTCCAGAACAAGGTGGTGCGCCGCGGGTGCGACGCGCT<br>CGGGCTGCGCGCCGACGCCGTGCCGCGCAACTCGTCGGAGGGGCACTTCTGCGGCAGCTGCAACTTCGGGTGCCCCACCGGC<br>GACAAGAAGGGCACCGACACGACGTGGCTCGTCGACGCCGTCGAGCGCGGTGCGGTCATCCTGACCGGGTGCAAGGCCGAAC<br>ACTTCATCGTCGAGAGCAACGGCGGTGGCGGCGGCCGGAGCAAGAGGTGCGTCGGCCTGGTGGCGACGTGCATGAGCAACGG<br>CATCACCAAGAAGCTCCGCGTCGAGGCGAAGGTGTCCATCTCGGCGAGCGGCGCGCTCATGACGCCGCCGCTGCTGCGCAAC<br>AGCGGGCTCAAGAACCGCCACATCGGCCGGAACCTGCACCTCCACCCGGTGTCCATGGCGTGGGGCTACTTCCCGGACAACA<br>CGCCGGAGCCGCACATCCCGGGGAAGTGCTACGAGGGCGGCATCATCACCAGCATGCACCGCGTCACGGAGCGCACCATCAT<br>CGAGACGCCAGCGCTCGGCCCGGGCGCCTTCGCCGCCCTGGTGCCCTGGGAGTCCGGCCGCGACATGAAGGAGCGGATGCGC<br>CGGTACGCGCGCACGGCGCACGCGTTCGCGCTGGTGCGCGACCGCGGCGCCGGGTCCGTCGACGGCGAGGGCCGCGTCCGCT<br>ACGCCCCGAGCCGCGACGACGCCGAGGAGCTCCGCGCCGGCCTCCGCCGCGCGCTGCGCATCCTGGTGGCCGCCGGCGCCGC<br>CGAGGTGGGCACGCACCGCAGCGACGGGGCCCGCCTCCGATGCAAGGGCGCGCGCGACGCGGACGTGGAGGCGTTCCTCGAC<br>GAGGTGACCGTGGAGAAGGGGCCGATGCACTCGACGACGGACAAGTGGTCGGTGCTCTGCTCGGCGCACCAGATGGGGAGCT<br>GCCGGATGGGCGCGAGCCCCCGCGACGGCGCCGTCGACGTCGCCGGCGAGAGCTGGGAGGCGGAGGGGCTCTACGTCTGCGA<br>CGGCAGCCTGCTCCCGACGGCGGTGGGCGTGAACCCGATGATCACCATACAGTCCATCGCCTACTGCGTCGCCAAGGGCATA<br>GCCGACTCGATGGCACACGGCAAGGAGCAGCGCTAGTAAAATCTTTTTCCTCTTTTGTTCATGCATAAATTGCAAATTTGCA<br>ATGTCCCTGCTTGTTAATCAACTGTAATAGTGATGATAAATCACGAGCATATTTCAGCAGATGATTCATATGGGAAAATAAT<br>TCTAAGGGATTTAGAGATCTGTTTAGAGTCTTTCAGAGACGACATGGGCCTCAAGATAAATATGGTAAAGGTTCAAATGGCC<br>GGAATGAGAAGCTGAAATGTCTGCCCGTATTAA (SEQ ID NO: 147) |
| 65 | ATGGCGCCGCACCCGCTGCTGAGGGGAGGGGCGAGGCGGGGGAGGAAGTACGCGCACGGGATGCACCCCGCGCAGATGG<br>AGGCGCTGCGCGCCATGTGCGGCGCGCTCATCCCGTCGCTGCCCGTGGACGCGGACGGCGGCGACGGCGGGCGCCGCCC<br>CGGCGACAAGGACCTCGAGCGGTTCTACCTCGCCTCCGCCGCCGACTCCTCCATCCCCGACGAGGTCGGTCGGTCGGTC<br>GATCGGTCGAACACCCCATGCGCGCGAGTTCTTTCTTGTTTATAATCTCTAATCTGGCGGCGGCCGCGGCGACCGCGGC<br>GTGGCGTGGCGTGCAGGTGGCGGAGCTGCTGGTGACGCGTTGCATATGGGAGGCGGTGGCGCTGACGTGGGTGGTGCTG<br>TGGGCGCTGAGCACGCGGGCGGGCACGCTGCTGCTGTGCGGCCGGGACAGCGTCGCCGCCGTCGACGGCGGCGGGTTCC<br>CGTTCGTGTCCGTGCGCCGCTTCGCCGACATGCCGGCGGCGAGGCGGGAGGCGGCGCTGTGGCGGTGGAGCGGCGCGCG<br>GTGGCTCTTCTTCCCGCTCCGCATCGCCTTCGCCATCGCCAAGATCCTCTGCCACTACGTCTTCTACTCCATGGTACGT<br>ACGTCTCCTCTTCCTCCTCCTCCTCCTCCTCTCGACCGACTCACGAATCAGAATCACCATGCAGCAGCACGGCATCACA<br>TACCCCGTGCTTTTCAAATTTCAACCACATAAAAATCTGACAAATCTAAAATTCTGTAAGAAATCGATCAATTATCGTC<br>AAAATTTAGCAGAGATCGAATTTCCATACAAGTATACAACAGTCCTACACCGAAGCACGCAGGTGCACCATGTTAACAA<br>ACAACAGCAGGGTTTTTAATTTCGAAATTGGATTTTTTGGCAAGGGGGGACTGGAATTACTGAAATTTCGGAAATATCA<br>GTAATTTCGTTTTTTTTGCCAAAATTATTTGAAATTTTGACTATTTTGAATGAATTTGAATAAAATTTGATCAAATTCA<br>CAAAAAGTTGCAAAAAACCAAAAATTTCGGACGAGATTTGAGCATGCTGGTGGGGGGTGAAATCACCAAAATTTCAAAC<br>CCTGAACAACAGTACAAACACCAGCCAGTCACTCGCAGCAGCTGCACCGTAGACTTCTTGTTCTTGGAGCTACCTAGGA<br>ACCGGTTTAGAGAATTTTTTATTTATAATTCGTCTGTTTTCAGCATATGCGTATTCTGCATTTGTTCAAATTCAGATAC<br>TCGTATCAGCCTAA (SEQ ID NO: 148) |
| 66 | ACAGCTCAAGCTTACGCGGGAGCTAAGCTGAGCTACAGCGAGCGGCGGCGGCGGCCATGGAGTGGGATCTCAAGATGCC<br>GCCGGCGGCGAGCTGGGAGCTAGCCGACGAGCTGGAGAACAGCGGCGGCGGGGGTGTACCGGCGGCGGTATCGTCGTCA<br>TCGGCTGCGGTTGGTGGCGGCGTCAATGCGGGGGGTGGTGGCAGGCAGGAGTGCTCGGTCGACCTCAAGCTCGGCGGGT<br>TGGGGGAGTTCGGCGGCGGCGGCGCGCAGCCGCGGGTCGCCGTGGCGGGCGAGCCGGCCAAGGGGAAGGGGCCAGCGGC<br>CGCCGCCACGGGAGCAGCAGCAGCAGCGTCGTCGGCGCCGGCGAAGCGGCCGCGCGGTGCGGCGGCGGCGGGGCAGCAG |

TABLE 3-continued

Genomic Sequences Encoding Certain Rice Polypeptides

| Protein | Genomic Sequence |
| --- | --- |
| | CAGTGCCCGTCGTGCGCGGTGGACGGGTGCAAGGAGGACCTGAGCAAGTGCCGCGACTACCATCGCCGGCACAAGGTGT |
| | GCGAGGCCCACTCCAAGACCCCCCTCGTCGTCGTCTCCGGCCGCGAGATGCGCTTCTGCCAGCAGTGCAGCAGGTAACC |
| | CCCCCCCCCCCCCCCCAACCATTGTCTCCTTCCTTCCCGCCAAATTCACTGCAAAACAAAAAAAAAATCGTAGCCCAAA |
| | ACACCCCAAGACGTCATGGCAATTCGCATCAAGAACTGCATATATCAATTTCTCCACTTCTTTTCAGCGTCACTGTCTC |
| | TGATCATTCTCTTTGCTGAACAAAAGAAAAAGAAGATAAGCAAGAGTTTTTCTCTTTTTTTTGCTCCTTTTTTTTTTGG |
| | CTTTGCACAATCTCTTCTTGCTTCCAGTTGCAACTGACCATTGTGCAGTACATGCATCTGCATCTACTGATTCTAATTT |
| | CTACGCTACTTCGGATCAAAATTAATTCAGTACTGCAAAGCACAATTTCATTGATCCATTTCATCCAGCCTCGGACTTT |
| | GTTCATCATCATCTATCTGTCTCTTACTTCCTTTCCATTGGGAGCATACTATCCGGCTGTCTCGTTTCAGGGACGCACA |
| | GCTTTGCCTTTAATGGCATGCCTTTTCAGCCTTCCCTCATGCTATCCTTTAGCTCGGCAACTCGTATTACCCCAAATTA |
| | TTACCTCTTTGCTCGCCTTTAGATTTATTACTATCATCTTTTCTTTTCTTTTTTATATCTCTTCTTCACCAGTAGCTGC |
| | ACTGTTTTTGCACTGCTCAAGAGCAAAGCAGCTGCTGTAGTTGTTCAGTGTTTGTTGCTTACTGAGAAAAAAAAGTGAT |
| | AGAGACAGAAAAAAAAAGTGAGGGAGAGAAAAAAAAAAAAAACAGAACTGACGCCTGAATCTCATCAGCCAGAGATCACAT |
| | TAGGCAATTTACCACCAGACTGTTATGATATTATTTTCAGTGTCCTCCTGTCTGAATATGACCGTCTGCTTCCTCTAAC |
| | AAGAACAATAAATCAGCACCTAGTTCAGTACTAACTAATTTTCTCATGAATAAATAAATAAATATAGTCACTGTAATTA |
| | GTGACACTACTAGCACGGTAGCACCTGGTTTAGTGGTTAACAATACTTGGTTCTTGCACTTCTCCCTGTCGATGTTTTT |
| | TCGCGTGGGGGCTAGCTATCGATTGATTGATTCCTCAACTATGGCATCGAAACTGGAAGAACATATGCATACTGGGACA |
| | CACACCCTGCTTGCTTTCTGAATTTCTGATTTCTCCTCAAGGCAGCTGGCCTACCACATATATCTGACTGAGCTGTGCT |
| | GCTTCTTGCCATGAGAGCTAAGCTACCTTAGCTTAGCTACTACTACCACTTACTACGCCGTCTGTTTTGGAAGGGAAAG |
| | GCAGATGTGGATGCCCAAACCTAGAAAGATGGTTGTACCACTGAAAGAGAGAGTTTGTGGATGTGATCTGCACTAAAGC |
| | ACCCCTGTACAGGGAAAGGACCATGTAGCCCTACTACAAGTTCACCATTTACACCTCTGTTCCTAAGGTTGGGCCACAC |
| | ATATATGAAGCTTTTAATGTCTCGGTTTGTTGGAAAGGGTTTTGCATTGCCATTACAAGCCAGCACAGTGGATACAGAT |
| | AGCCAGGGTGCTCTCTATTGGAGAAGAAAAAAAATGGAGCCCTGAACACCCTGATTGGATCTCACTATTGCATGAAAGA |
| | ATGATGAGATTTCTTGTCTTATAATTTTTAAAGATTTTTTTTCTAAAGTCAGTCTTAGTTACATTCATTTGTTATATTC |
| | CAGTTTCAGACTTATTGGTACTAGGTTCTGTGAGATCTTTTTTTTTTTTTACATCGTTTGAGTATCATAGGGTGATTCA |
| | GTACCACCTTGACCCCTGTTTTTATCAGAGCTCTAAACTTCTAACACCACTTCTAACTTTTGAGCTAGTCTTCTAACCT |
| | TGCTGTTTTCTGAACAAAGATGTATACTCAAGATTGGTCATAGATGGAGATATTCTGTGAACAGAACTAACATAATAGC |
| | ACCAAATTAGTCAGACATACTCTTTACAAAATTACTTTGGAGTTTGTTGTCCACTCCTTGAACTAGTACAATATTGTCC |
| | TACTGAATGCCTTCCTGCCTTTCAACTTGAAAGTTCCCTATTTTATCTGTTAGTTCTTTTATAAAATGTAACTGCACAT |
| | TGTCAGAAGGATTTGCATCTTATTTCACTTTGCGCCAGTTTTAAGTAATACATGGTATATTGGCATAAGACCAGACTCT |
| | ACCATTTTTTATCTTGCAGAGACATAGCAAACAACTAAGTACTTTTTATTGTGGTGTGCTCCTTTACACAGTAGCACAA |
| | CTTGTAGGATGCTTATGTGATTGTCTCATCAATTATTCTCTTTATCTTTAAAAAGAGAATGATACAAAAAATCTCTTTA |
| | TCTGAGAATACACATTACCCAGTGGGGACAGTCTTTCAATGATTTGATTACTTCGTCAGTGTTTGCAAACTGGGAAGAT |
| | CATTATGCTGCTGCATGCAGACTTTATAAATTAAGTGATCTTCAGAGTCAGAACAAGATGTTAGCTTTCTATACCTATG |
| | GATCCACATCCACTGTATTGTGGTCCATGTACAAGTGGGGTTAAAATATTTTTCTGCCGTTGACAGAACTTCAGTTCAA |
| | TAAATTTATCTAAGATGAAGTATCCAAGCACGGAAAGAGCTAATTAACTGATGAAATTCCTGTGGTCCCTTGTGTTGGT |
| | ATATGAGTATTCTAAGAGAGAATATGGAGACAGTATATTAAATTATTCTGAGAATACTTATCCTGACGTTTCTTTAGTG |
| | AGAACTGTGGTGCATCGTTACAAAACTTCAGATCATGTTTCAGGAGTATTTTATCATGTAAGAATTTTAAAAAGACGTA |
| | CATCCTAGGTACAGTCATTTCTTAAGGTTTCATGGTACTGAATGATTAAATTACTTCTTCTGGATTGGGTTTCAAGCAT |
| | CATTTGGCTAATTTCAATGCAGTTAAATGATCATAAGCTTTTCTTTCTTCAGGTTTCACTTGCTTCAGGAGTTTGATGA |
| | GGCCAAGCGCAGCTGTAGAAAGCGACTAGATGGGCACAACCGTCGCCGCAGGAAGCCACAGCCAGATCCCATGAACTCT |
| | GCAAGTTATCTTGCAAGCCAACAAGGTATTTTCTTGTTTATTATTACCACTCTATGATATCGCAGTTCATATAAGATTA |
| | ACTGGGATATAGTCATTCAGACTTCCTAACTATTGTTAGACTAGGAAAAAAACTATGAAACATGCTAATAGCATAGATA |
| | AGTCATGGTAAAAAAAAAGTAAAAGAAAATGAAACTGTGGTTAAAAAAAAACGCAAATATTAGGGAATGACCTAATATC |
| | AAATAATTAGAAGGAGTGAGGCTTCGAACCCAGGTCGTCTAGCCCATCACCTTTTGAAGCTAGCCAGAAAACCCCTGGG |
| | CGTTTCTCAGAACTGTGGTTCAGCTATGACTCTGTTCTTTCAATCCTGACATCTTGTAACATGTAATGCATTCTAGTAT |
| | ACATCTAATGCATTGAACCATATCTTATGTACTAATTTGTGCTGATATATCAAACATCGCATCAAAATTCAGGGGCAAG |
| | ATTCTCACCGTTCGCGACGCCGAGACCGGAGGCAAGCTGGACAGGGATGATCAAAACCGAGGAGAGCCCATACTACACG |
| | CACCACCAAATCCCTCTTGGCATCAGCAGCAGGCAGCAGCATTTCGTTGGCTCCACCTCTGACGGCGGCCGCCGCTTCC |
| | CTTTCCTCCAGGAAGGCGAGATCAGCTTCGGCACCGGCGCCGGCGCCGGCGGCGTGCCAATGGATCAGGCAGCAGCTGC |
| | TGCTGCTGCTTCAGTGTGCCAGCCACTTCTGAAGACGGTAGCTCCTCCTCCTCCTCCTCATGGCGGCGGCGGCAGCGGC |
| | GGCGGCAAGATGTTCTCCGATGGTGGGTTGACACAAGTGCTCGACTCCGATTGTGCTCTCTCTCTTCTGTCAGCTCCGG |
| | CGAACTCCACGGCCATCGACGTCGGCGGTGGCCGGGTGGTCGTCCAGCCGACCGAGCACATCCCCATGGCGCAGCCTCT |
| | CATCTCTGGCCTTCAGTTCGGCGGCGGCGGCGGCAGCTCAGCCTGGTTCGCGGCGCGGCCGCATCATCAGGCGGCCACC |
| | GGCGCCGCCGCCACCGCCGTCGTCGTCTCGACGGCCGGTTTCTCCTGCCCGGTGGTGGAGAGCGAGCAGCTGAACACAG |
| | TCCTGAGCTCCAATGACAATGAGATGAACTACAATGGGATGTTTCACGTCGGCGGCGAAGGCTCATCGGATGGCACGTC |
| | GTCGTCTCTGCCGTTCTCATGGCAGTAGTTTTTTCAGTAACTGTATGTTGCTGCCTTAGTTTCAGTAGAGTTGGTTCTT |
| | CATTTCTTTTCAGTGATCAAATTATTGTTTCTGTTCTTTTCTGCCATGGTAAGTTCCTTTTTTTTTTCTTCTTCTTGCC |
| | TTCATTTGAGTTAATTACAGCATTGATTTGTGTGAACAAAATTCATCATAAATCAGTTCCTCGCGAGATCATTGGTCTC |
| | AACATGATGGTGCCAAGTGAGAACTGCAGTATTGTGCAGTTTTCAGTTTTGAGTCTAAGTTGTATAAACTTGCAG |
| | (SEQ ID NO: 151) |

The above-described polypeptides are involved in one or more important biological properties in plants, e.g., rice seed yields, panicle formation, and/or tolerance to environmental stresses. Such polypeptides can be produced in transgenic plants to provide plants having improved phenotypic properties or improved response to stressful environmental conditions.

Also described herein is an isolated nucleic acid that includes a polynucleotide (e.g., SEQ ID NOs: 50-98, 115-148, 150, and 151) encoding any of the polypeptides described above. An isolated nucleic acid refers to a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. In one example, the just-described isolated nucleic acid is a portion of a recombinant DNA construct, which preferably is an expression vector containing a promoter region operably linked to the just-mentioned nucleic acid. Upon introducing into a plant cell, this DNA construct expresses a polypeptide encoded by the polynucleotide.

The expression vector described above can be used to generate transgenic plants to provide for increased expression of the polypeptides also described above. As a result of such biotechnological applications, plants, particularly crop plants, having improved properties are obtained. Crop plants of interest in the present invention include, but are not limited to soy, cotton, canola, maize, wheat, sunflower, sorghum, alfalfa, barley, millet, rice, tobacco, fruit and vegetable crops, and turf grass.

In some cases, decreased expression of some of the above-described polypeptides are desired. Such decreased expression can be obtained by use of a recombinant DNA construct that expresses an RNA molecule containing a nucleotide sequence complementary to the nucleotide sequence of a gene that encodes one of the polypeptides. Such an RNA molecule can be an antisense RNA or an interfering RNA (e.g., a small interfering RNA). As used herein, the term "interfering RNA" means an RNA molecule capable of directing the degradation of an RNA transcript having a nucleotide sequence at least a portion of which is substantially the same as that of the interfering RNA, through the mechanism of RNA interference. An interfering RNA can be a small interfering RNA (siRNA), which includes two complementary single-stranded RNAs that form an intermolecular duplex. An interfering RNA can also be a short hairpin RNA (shRNA), which includes a single-stranded RNA with two self-complementary regions that allow the RNA to fold back upon itself and form a stem-loop structure with an intramolecular duplex region and an unpaired loop region. In some circumstances, interfering RNAs can be single-stranded antisense RNAs of 19 to 29 nucleotides that are complementary to a target sequence. See Martinez et al., Cell 110:563-574 (2002). In other instances, interfering RNAs are double-stranded RNAs that, upon cleavage in cells, produce siRNAs.

Any of the recombinant DNA constructs described above can be used to transform a host cell, e.g., an *E. coli*, a yeast, an insect, a plant, or a mammalian cell. The DNA construct and the transformed host cell can be used for producing a polypeptide of the invention or an RNA molecule that suppresses expression of the polypeptide.

The just-described DNA construct and a host plant cell transformed with the DNA construct can also be used for generating a transgenic plant containing the recombinant DNA construct described above to provide for increased or decreased expression of the polypeptides described herein. To generate a transgenic plant, one can (1) introduce into a plant cell a recombinant nucleic acid encoding one just-described heterologous polypeptide; (2) expressing the polypeptide in the cell, and (3) cultivating the cell to generate a plant. As a result of such biotechnological applications, plants, in particular, crop plants having one or more of the improved properties described below are obtained. Exemplary crop plants include, but are not limited to, soy, cotton, canola, maize, wheat, sunflower, sorghum, alfalfa, barley, millet, rice, tobacco, fruit and vegetable crops, and turf grass. The crop plants, when transformed with any of the DNA construct described herein have improved yields resulting from one or more of the following mechanisms:

(1) Improving Utilization of Key Biochemical Compounds, Such as Nitrogen, Phosphorous, Mineral, and Carbohydrate.

For example, a polypeptide of interest may improve nitrogen flow, sensing, uptake, storage and/or transport. Examples of such polypeptide include those involved in aspartate and glutamate biosynthesis, in aspartate and glutamate transport, associated with the TOR (Target of Rapamycin) pathway, nitrate transporters, ammonium transporters, chlorate transporters, or involved in tetrapyrrole biosynthesis. In another example, a polypeptide of interest effects on carbohydrate metabolism, for example by increasing sucrose production and/or transport, e.g., a polypeptide that plays a role in sucrose or starch metabolism, in carbon assimilation or carbohydrate transport (e.g., sucrose transporters or glucose/hexose transporters). Such a polypeptide can also be an enzyme involved in glycolysis/gluconeogenesis, the pentose phosphate cycle, or raffinose biosynthesis, or one that is involved in glucose signaling, such as SNF1 complex proteins. In yet another example, a polypeptide of interest, e.g., a phosphotase or phosphate transporter, is capable of increasing phosphorus uptake, transport or utilization.

(2) Improving Responses to Environmental Stresses, Such as Cold, Heat, Drought, Salt, Pestlpathogen, or Herbicide.

Polypeptides useful for improved stress tolerance under a variety of stress conditions include polypeptides involved in gene regulation, such as serine/threonine-protein kinases, MAP kinases, MAP kinase kinases, and MAP kinase kinase kinases; polypeptides that act as receptors for signal transduction and regulation, such as receptor protein kinases; intracellular signaling proteins, such as protein phosphatases, GTP binding proteins, and phospholipid signaling proteins; polypeptides involved in arginine biosynthesis; polypeptides involved in ATP metabolism, including for example ATPase, adenylate transporters, and polypeptides involved in ATP synthesis and transport; polypeptides involved in glycine betaine, jasmonic acid, flavonoid or steroid biosynthesis; and hemoglobin. Enhanced or reduced activity of such polypeptides in transgenic plants will provide changes in the ability of a plant to respond to a variety of environmental stresses, such as those mentioned above.

For example, polypeptides that improve plant tolerance to cold or freezing temperatures include those involved in biosynthesis of trehalose or raffinose, those encoded by cold induced genes, fatty acyl desaturases and others involved in glycerolipid or membrane lipid biosynthesis, which find use in modification of membrane fatty acid composition, alternative oxidase, calcium-dependent protein kinases, LEA proteins and uncoupling protein. Exemplary polypeptides capable of improving plant tolerance to heat include polypeptides involved in biosynthesis of trehalose, glycerolipid biosynthesis, or membrane lipid metabolism (for altering membrane fatty acid composition), e.g., heat shock proteins or mitochondrial NDK. Polypeptides that increase plant tolerance to extreme osmotic conditions are those that play roles in proline biosynthesis, and polypeptides that increase plant tolerance to drought are those involved in biosynthesis of trehalose, wax, LEA proteins or invertase, e.g., aquaporins. As to pest/pathogen tolerance, any of the following polypeptides contributes to this feature: proteases, a polypeptide involved in anthocyanin biosynthesis, a polypeptide involved in cell wall metabolism (e.g., cellulases, glucosidases, pectin methylesterase, pectinase, polygalacturonase, chitinase, chitosanase, or cellulose synthase), a polypeptide involved in biosynthesis of terpenoids or indole for production of bioactive metabolites to provide defense against herbivorous insects. Polypeptides contributing to plant herbicides tolerance include those involved in the shikimate pathway, which are of interest for providing glyphosate tolerant plants. Such polypeptides include polypeptides involved in biosynthesis of chorismate, phenylalanine, tyrosine and tryptophan.

(3) Modifying Plant Growth Rate or Cell Cycle.

Such polypeptides include those that encode cell cycle enzymes and regulators of the cell cycle pathway, e.g., cyclins and EIF5alpha pathway proteins, polypeptides involved in polyamine metabolism, polypeptides which act as regulators of the cell cycle pathway, including cyclin-dependent kinases (CDKs), CDK-activating kinases, CDK-inhibitors, Rb and Rb-binding proteins, and transcription factors that activate genes involved in cell proliferation and division, such as the E2F family of transcription factors, proteins involved in degradation of cyclins, such as cullins, and plant homologs of tumor suppressor polypeptides. They also include those involved in the biosynthesis of plant growth hormones, such as gibberellins, cytokinins, auxins, ethylene and abscisic acid, and other proteins involved in the activity and/or transport of such polypeptides, including for example, cytokinin oxidase, cytokinin/purine permeases, F-box proteins, G-proteins and phytosulfokines. These polypeptides are useful for manipulating growth rate in plants to provide early vigor and accelerated maturation leading to improved yield. Improvements in quality traits, such as seed oil content, may also be obtained by expression of cell cycle enzymes and cell cycle regulators.

(4) Modifying Photosynthesis Pathway.

Polypeptides useful for increasing the rate of photosynthesis include phytochrome, photosystem I and II proteins, electron carriers, ATP synthase, NADH dehydrogenase and cytochrome oxidase.

(5) Regulating Seed/Panicle Formation and Size/Weight.

Such polypeptides increase seed protein quantity/quality (e.g., polypeptides involved in the metabolism of amino acids in plants, and polypeptides involved in biosynthesis of methionine/cysteine and lysine, amino acid transporters, amino acid efflux carriers, seed storage proteins, proteases, and polypeptides involved in phytic acid metabolism), increase seed oil quantity and/or quality (e.g., polypeptides involved in fatty acid and glycerolipid biosynthesis, beta-oxidation enzymes, enzymes involved in biosynthesis of nutritional compounds, such as carotenoids and tocopherols, and polypeptides that increase embryo size or number or thickness of aleurone).

(6) Regulating Homologous Recombination.

Increasing the rate of homologous recombination in plants is useful for accelerating the introgression of transgenes into breeding varieties by backcrossing, and to enhance the conventional breeding process by allowing rare recombinants between closely linked genes in phase repulsion to be identified more easily. Polypeptides useful for expression in plants to provide increased homologous recombination include polypeptides involved in mitosis and/or meiosis, including for example, resolvases and polypeptide members of the RAD52 epistasis group.

The polypeptides described herein may also play roles in imparting improved disease resistance or increased reserve polysaccharides for use in food, pharmaceutical, cosmetic, paper and paint industries by improving production of galactomannans, to a transgenic plant carrying genes encoding such. They may also modify flavonoid/isoflavonoid metabolism in plants (e.g., cinnamate-4-hydroxylase, chalcone synthase), or affect lignin biosynthesis. Enhanced or reduced activity of such polypeptides in transgenic plants will provide changes in the quantity and/or speed of flavonoid metabolism in plants, improve disease resistance by enhancing synthesis of protective secondary metabolites or improving signaling pathways governing disease resistance, or increase plants' resistance to lodging and for increasing the usefulness of plant materials as biofuels.

In addition to the mechanisms set forth above, the polypeptides described herein may also affect flowering, pollination or fertilization efficiency or improve plant growth under undesirable conditions, e.g., low fertilizer concentration or environmental stresses.

Table 1 above lists the phenotypes that the polypeptides described herein contribute to. Other functions of these polypeptides can be determined by comparison of the amino acid sequence of the novel polypeptides to amino acid sequences of known polypeptides. A variety of homology based search algorithms are available to compare a query sequence to a protein database, including for example, BLAST, FASTA, and Smith-Waterman. In the present application, BLASTX and BLASTP algorithms are used to provide protein function information.

Also within the scope of this invention are a transgenic plant produced by the method described above.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of producing a transgenic plant, comprising transforming a host plant with a recombinant DNA construct containing a promoter sequence operably linked to a polynucleotide encoding a polypeptide having the amino acid sequence of SEQ ID NO:103, the promoter sequence being functional in a cell of the host plant, and identifying and selecting a transgenic plant that expresses the polypeptide and exhibits one or more of (a) increased grain size, (b) increased grain weight, and (c) increased panicle length relative to the untransformed host plant.

2. The method of claim 1, wherein the polynucleotide has the nucleotide sequence of SEQ ID NO: 119.

3. The method of claim 1, wherein the host plant is a crop.

4. The method of claim 3, wherein the host plant is a rice plant.

5. The method of claim 4, wherein the transgenic plant exhibits increased grain size, increased grain weight, and increased panicle length.

* * * * *

SEQUENCE LISTING

```
<160> NUMBER OF SEQ ID NOS: 151

<210> SEQ ID NO 1
<211> LENGTH: 813
<212> TYPE: PRT
<213> ORGANISM: Oryza sativa

<400> SEQUENCE: 1
```

```
Met Lys Lys Ala Lys Phe Pro Gly Ser Ser Ser Ser Ser Ser Ser Ala
1               5                   10                  15

Ala Ala Pro Gly Val Thr Glu Lys Asn Gly Leu His Val Asp Pro Thr
            20                  25                  30

Ala Ala Ala Ala Arg Thr Gly Gly Arg Thr Asn Gly Glu Glu Asp Ala
        35                  40                  45

Glu Met Val Leu Ala Asp Gln Glu Glu Leu Ala Ala Pro Ser Ala Ser
    50                  55                  60

Ala Pro Ala Gly Val Ala Ala Asn Leu Phe Arg Lys Lys Ala Thr Leu
65                  70                  75                  80

Pro Gln Pro Ser Ala Ala Arg Lys Pro Leu Arg Ile Lys Ile Gly Gln
                85                  90                  95

Pro Lys Leu Pro Thr Asn Phe Glu Glu Asp Thr Trp Ala Ile Leu Lys
            100                 105                 110

Asp Ala Ile Thr Ala Ile Phe Leu Lys Gln Lys Leu Ser Cys Asp Val
        115                 120                 125

Glu Lys Leu Tyr Gln Ala Ala Gly Asp Leu Cys Leu His Lys Leu Gly
    130                 135                 140

Ala Asn Leu Tyr Glu Arg Ile Lys Lys Glu Cys Glu Val His Ile Ser
145                 150                 155                 160

Ala Lys Ile Ser Ala Leu Val Gly Gln Ser Pro Asp Leu Val Val Phe
                165                 170                 175

Leu Ser Leu Val Gln Arg Thr Trp Gln Asp Phe Cys Asp Gln Met Leu
            180                 185                 190

Ile Ile Arg Gly Ile Ala Leu Leu Leu Asp Val Lys Tyr Val Lys Asn
        195                 200                 205

Val Ala Asn Ile Cys Ser Val Trp Asp Met Gly Leu Lys Leu Phe Arg
    210                 215                 220

Lys His Leu Ser Leu Ser Pro Glu Ile Glu His Lys Thr Val Thr Gly
225                 230                 235                 240

Leu Leu Arg Leu Ile Glu Ser Glu Arg Leu Gly Glu Ala Ile Asp Arg
                245                 250                 255

Thr Leu Leu Ser His Leu Leu Lys Met Phe Thr Ala Leu Gly Met Tyr
            260                 265                 270

Ser Glu Ser Phe Glu Lys Pro Phe Leu Glu Cys Thr Ser Glu Phe Tyr
        275                 280                 285

Ala Thr Glu Gly Val Lys Tyr Leu Gln Gln Ser Asp Ile Pro Asp Tyr
    290                 295                 300

Leu Lys His Val Glu Thr Arg Leu Gln Glu Glu His Glu Arg Cys Ile
305                 310                 315                 320

Leu Tyr Leu Glu Ala Asn Thr Arg Lys Pro Leu Ile Thr Ala Thr Glu
                325                 330                 335

Lys Gln Leu Leu Gln Arg His Thr Ser Ala Ile Leu Glu Lys Gly Phe
            340                 345                 350

Thr Met Leu Met Glu Ala Asn Arg Val Lys Asp Leu Ser Arg Met Tyr
        355                 360                 365

Thr Leu Phe Gln Arg Val Asp Ala Ile Glu Leu Leu Lys Gln Ala Leu
    370                 375                 380

Ser Ser Tyr Ile Arg Gly Thr Gly Gln Gly Ile Ile Met Asp Glu Glu
385                 390                 395                 400

Lys Asp Lys Glu Leu Val Pro Phe Leu Leu Glu Phe Lys Ala Ser Leu
                405                 410                 415

Asp Arg Ile Leu Glu Glu Ser Phe Ala Lys Asn Glu Ala Phe Ser Asn
```

```
            420                 425                 430

Thr Ile Lys Glu Ser Phe Glu His Leu Ile Asn Leu Arg Gln Ile Ser
        435                 440                 445

Ser Ser Pro Phe Phe Gln Gln Asn Arg Pro Ala Glu Leu Ile Ala Lys
    450                 455                 460

Phe Leu Asp Glu Lys Leu Arg Ala Gly Asn Lys Gly Thr Ser Glu Glu
465                 470                 475                 480

Glu Leu Glu Gly Ile Leu Asp Lys Val Leu Val Leu Phe Arg Phe Ile
                485                 490                 495

Gln Gly Lys Asp Val Phe Glu Ala Phe Tyr Lys Lys Asp Leu Ala Lys
            500                 505                 510

Arg Leu Leu Leu Gly Lys Ser Ala Ser Ile Asp Ala Glu Lys Ser Met
        515                 520                 525

Ile Thr Lys Leu Lys Thr Glu Cys Gly Ser Gln Phe Thr Asn Lys Leu
    530                 535                 540

Glu Gly Met Phe Lys Asp Ile Glu Leu Ser Lys Glu Ile Asn Glu Ser
545                 550                 555                 560

Phe Lys Gln Ser Ser Gln Ala Arg Thr Lys Leu Pro Ser Gly Ile Glu
                565                 570                 575

Met Ser Val His Val Leu Thr Thr Gly Tyr Trp Pro Thr Tyr Pro Pro
            580                 585                 590

Met Asp Val Lys Leu Pro His Glu Leu Asn Val Tyr Gln Asp Ile Phe
        595                 600                 605

Lys Glu Phe Tyr Leu Ser Lys Tyr Ser Gly Arg Arg Leu Met Trp Gln
    610                 615                 620

Asn Ser Leu Gly His Cys Val Leu Lys Ala Glu Phe Pro Lys Gly Lys
625                 630                 635                 640

Lys Glu Leu Ala Val Ser Leu Phe Gln Ser Val Val Leu Met Leu Phe
                645                 650                 655

Asn Asp Ala Gln Lys Leu Ser Phe Leu Asp Ile Lys Glu Ser Thr Gly
            660                 665                 670

Ile Glu Asp Lys Glu Leu Arg Arg Thr Leu Gln Ser Leu Ala Cys Gly
        675                 680                 685

Lys Val Arg Val Leu Gln Lys Met Pro Lys Gly Arg Asp Val Glu Asp
    690                 695                 700

Lys Asp Glu Phe Val Phe Asn Glu Glu Phe Ser Ala Pro Leu Tyr Arg
705                 710                 715                 720

Ile Lys Val Asn Ala Ile Gln Met Lys Glu Thr Val Glu Glu Asn Thr
                725                 730                 735

Ser Thr Thr Glu Arg Val Phe Gln Asp Arg Gln Tyr Gln Val Asp Ala
            740                 745                 750

Ala Ile Val Arg Ile Met Lys Thr Arg Lys Thr Leu Ser His Thr Leu
        755                 760                 765

Leu Ile Thr Glu Leu Phe Gln Gln Leu Lys Phe Pro Ile Lys Pro Ser
    770                 775                 780

Asp Ile Lys Lys Arg Ile Glu Ser Leu Ile Asp Arg Glu Tyr Leu Glu
785                 790                 795                 800

Arg Asp Arg Ser Asn Pro Gln Ile Tyr Asn Tyr Leu Ala
                805                 810
```

<210> SEQ ID NO 2
<211> LENGTH: 561
<212> TYPE: PRT
<213> ORGANISM: Oryza sativa

<400> SEQUENCE: 2

```
Met Asp Ala Asp Glu Ala Ala Gly Ser Ser Arg Arg Met Asp Leu Asn
1               5                   10                  15

Leu Tyr Leu Gly Leu Pro Arg Ala Pro Arg Pro Arg Arg Ser Asp Leu
            20                  25                  30

Gly Ser Asp Leu Ala Leu Ser Thr Pro Met Pro Ser Ser Pro Ser Ser
        35                  40                  45

Ser Ala Ala Ser Val Asp Ala Pro Pro Pro Pro Pro Glu Leu Ser His
    50                  55                  60

Pro Pro Tyr Ser Pro Ser His Ala Asp Leu Ser Pro Pro Leu Gln Glu
65                  70                  75                  80

Val Tyr Ser Leu Tyr Asn Pro Asp Asp Pro Pro Ala Ser Glu Thr His
                85                  90                  95

Leu Pro Pro Tyr Ala Pro Pro Pro Ala Pro Val Val Ser Glu Leu Pro
            100                 105                 110

Asp Asp Leu Glu Phe Gly Leu His Pro Pro Pro Pro Leu Val Arg Ala
        115                 120                 125

Ser Glu Leu Leu Gly Trp Glu Asp Arg Pro Ser Ser Ser Thr Ala Ser
    130                 135                 140

Ser Ser Phe Leu Pro Asp Thr Ala Ala Arg Tyr Trp Arg Leu Leu Glu
145                 150                 155                 160

Gln Thr Gly Ser Arg Trp Leu Arg Ala Arg Arg Phe Arg Ser Asp Leu
                165                 170                 175

Pro Pro Leu Ser Ser Glu Ala Tyr Pro Ala Gly Arg Asp Ala Ala Ala
            180                 185                 190

Val Pro Val Leu Gln His Glu Pro Met Asn Asp Thr Val Glu His Asn
        195                 200                 205

Lys Val Ala Ala Asp Gly Ala Glu Val Gly Ala Ser Glu Glu Ser Glu
    210                 215                 220

Glu Gln Gly Arg Ser Ala Ala Thr Phe Glu Cys Asn Ile Cys Phe Asp
225                 230                 235                 240

Met Ala Ser Glu Pro Val Val Thr Ser Cys Gly His Leu Phe Cys Trp
                245                 250                 255

Pro Cys Leu Tyr Gln Trp Leu Asn Val Tyr Ser Asn His Lys Glu Cys
            260                 265                 270

Pro Val Cys Lys Gly Glu Val Thr Glu Ala Asn Ile Thr Pro Ile Tyr
        275                 280                 285

Gly Arg Gly Asn Ser Cys Leu Asp Ala Glu Lys Ala Val Glu Gly Gly
    290                 295                 300

Lys Gln Thr Gly Pro Thr Ile Pro Pro Arg Pro His Gly Asn Arg Leu
305                 310                 315                 320

Glu Ser Phe Arg Gln Gln Phe His His Leu Arg Pro Ile Ser Arg Arg
                325                 330                 335

Leu Gly Glu Ala His Gly Leu Leu Ser Ser Trp Arg Arg Leu Leu Asp
            340                 345                 350

Gln Gln Ile Met Asn Thr Ala Ser Arg Phe Glu Gly Pro Pro Glu Ser
        355                 360                 365

Ala Val Gln Glu Met Val Asp Thr Ala His Ala Gln His Thr Ser Arg
    370                 375                 380

Leu Ser Arg Leu Ala Ser Arg Met Arg Ala Arg Arg Leu Leu Arg Glu
385                 390                 395                 400

Ala Asp Asn Pro Asn Pro Pro Asp Gly Gly Ser Thr Ser Pro Asp Ser
                405                 410                 415
```

```
Gly Leu Ile Arg Asn Asn Ala Ser Asp Pro Ser Arg Asn Gly Pro Ser
            420                 425                 430

Ser Leu Leu Pro Asp Gly Ile Asp Trp Leu Arg Gly Leu Thr Leu Leu
        435                 440                 445

Gly Tyr Glu Asp Thr Glu Arg Phe Ala Ser Ala Met Ser Asp Phe Arg
    450                 455                 460

Arg Ile Thr Gly Pro Ser Gln Tyr Gly Ala Ser Ala Ser Ser Ser Asn
465                 470                 475                 480

Pro Pro Asn Leu Glu Ser Thr Phe Asp Arg Thr His Val Val Ala Ala
                485                 490                 495

Pro Ser Ala Asp Gln Ala Ser Asn Ser Ser Thr Ala Ala Val Ile Gln
            500                 505                 510

Gly Asp Ala Gly Ile Ser Glu Ser Ala Gly Glu Pro Ser Asn Ala Gly
        515                 520                 525

Ser Ser Arg Ser Leu Arg Arg Arg Gly Arg Ser Ser Ala Leu Gly Ser
    530                 535                 540

Leu Asp Ala Asp Gly Gly Leu Gln Arg Asn Lys Arg Arg Arg Ile
545                 550                 555                 560

Asn


<210> SEQ ID NO 3
<211> LENGTH: 173
<212> TYPE: PRT
<213> ORGANISM: Arabidopsis thaliana

<400> SEQUENCE: 3

Met Cys Pro Arg Ala Thr Gln Thr Cys Glu Ile Cys Glu Lys Val Val
1               5                   10                  15

Ser Lys Tyr Lys Cys Pro Ser Cys Leu Val Pro Tyr Cys Ser Leu Gly
            20                  25                  30

Cys Phe Lys Ile His Lys Glu Thr Pro Cys Ala Lys Pro Ser Asp Pro
        35                  40                  45

Ser Ser Thr Glu Glu Lys Pro Ala Ala Ser Pro Ala Lys Glu Val Pro
    50                  55                  60

Val Lys Arg Pro Glu Glu Ala Asn Asp Val Val Glu Lys Thr Gln Gln
65                  70                  75                  80

Lys Ala Ser Ala Ala Ser Pro Ala Lys Glu Ile Pro Val Ala Arg Pro
                85                  90                  95

Ile Ile Val Glu Glu Glu Lys Tyr Ile Leu Glu Lys Thr Gln Phe Glu
            100                 105                 110

Ala Ile Ala Ser Ser Ser Glu Ile Arg Glu Ala Leu Lys Asp Glu Pro
        115                 120                 125

Leu Gln Lys Leu Ile Tyr Ser Ile Asp Ser Ser Ser Asn Pro Leu Gln
    130                 135                 140

Glu Leu Asp Glu Ala Met Gly Ile Glu Ala Phe Arg Glu Phe Thr Asp
145                 150                 155                 160

Lys Ile Leu Ser Asn Ile Ser Lys Ser Asn Asp Glu Gln
                165                 170


<210> SEQ ID NO 4
<211> LENGTH: 519
<212> TYPE: PRT
<213> ORGANISM: Oryza sativa

<400> SEQUENCE: 4

Met Leu Gly Glu Ala Ala Ser Pro Trp Ser Leu Ala Gly Ala Gly Ala
1               5                   10                  15
```

```
Ala Val Ala Leu Leu Trp Leu Cys Ala Trp Thr Leu Gln Trp Ala Trp
            20                  25                  30

Trp Thr Pro Arg Arg Leu Glu Arg Ala Leu Arg Ala Gln Gly Leu Arg
        35                  40                  45

Gly Thr Arg Tyr Arg Leu Phe Ile Gly Asp Val Ala Glu Asn Gly Arg
    50                  55                  60

Leu Asn Arg Glu Ala Ala Ser Arg Pro Leu Pro Leu Gly Ser His Asp
65                  70                  75                  80

Val Val Pro Arg Val Met Pro Phe Phe Cys Asn Val Leu Lys Glu His
                85                  90                  95

Gly Lys Leu Ser Phe Val Trp Thr Gly Pro Lys Pro Phe Val Ile Ile
            100                 105                 110

Arg Asp Pro Asp Leu Ala Arg Glu Ile Leu Ser Asn Lys Ser Gly Asn
        115                 120                 125

Phe Ala Lys Gln Thr Thr Ala Gly Ile Ala Lys Phe Val Val Gly Gly
    130                 135                 140

Val Val Thr Tyr Glu Gly Glu Lys Trp Ala Lys His Arg Arg Ile Leu
145                 150                 155                 160

Asn Pro Ala Phe His Gln Glu Lys Ile Lys Arg Met Leu Pro Val Phe
                165                 170                 175

Leu Ala Cys Cys Thr Lys Met Ile Thr Arg Trp Val Asn Ser Met Ser
            180                 185                 190

Ser Glu Gly Ile Ser Glu Leu Asp Val Trp Asp Glu Phe Gln Asn Leu
        195                 200                 205

Thr Gly Asp Val Ile Ser Arg Thr Ala Phe Gly Ser Ser Tyr Gln Glu
    210                 215                 220

Gly Trp Arg Ile Phe Gln Leu Gln Glu Glu Gln Ala Lys Arg Val Leu
225                 230                 235                 240

Lys Ala Phe Gln Arg Ile Phe Ile Pro Gly Tyr Trp Tyr Leu Pro Ile
                245                 250                 255

Glu Asn Asn Arg Arg Ile Arg Glu Ile Asp Gln Glu Ile Arg Thr Ile
            260                 265                 270

Leu Arg Gly Ile Ile Val Lys Arg Asp Lys Ala Val Arg Asn Gly Glu
        275                 280                 285

Gly Ser Asn Asp Asp Leu Leu Gly Leu Leu Val Glu Ser Asn Met Arg
    290                 295                 300

Gln Ser Asn Glu Lys Glu Asp Val Gly Met Ser Ile Glu Asp Met Ile
305                 310                 315                 320

Glu Glu Cys Lys Leu Phe Tyr Ala Ala Gly Ser Glu Thr Thr Ser Met
                325                 330                 335

Leu Leu Thr Trp Thr Leu Ile Leu Leu Ser Met His Pro Glu Trp Gln
            340                 345                 350

Glu Gln Ala Arg Glu Glu Val Met His His Phe Gly Arg Thr Thr Pro
        355                 360                 365

Asp His Asp Gly Leu Ser Arg Leu Lys Ile Val Thr Met Ile Leu His
    370                 375                 380

Glu Val Leu Arg Leu Tyr Pro Pro Val Val Phe Leu Gln Arg Thr Thr
385                 390                 395                 400

His Lys Glu Ile Glu Leu Gly Gly Ile Lys Tyr Pro Glu Gly Val Asn
                405                 410                 415

Phe Thr Leu Pro Val Leu Ser Ile His His Asp Pro Ser Ile Trp Gly
            420                 425                 430

Gln Asp Ala Ile Lys Phe Asn Pro Glu Arg Phe Ala Asn Gly Val Ser
```

```
        435                 440                 445

Lys Ala Thr Lys Phe Gln Thr Ala Phe Phe Ser Phe Ala Trp Gly Pro
    450                 455                 460

Arg Ile Cys Leu Gly Gln Ser Phe Ala Ile Leu Glu Ala Lys Met Ala
465                 470                 475                 480

Leu Ala Thr Ile Leu Gln Ser Phe Ser Phe Glu Leu Ser Pro Ser Tyr
                485                 490                 495

Thr His Ala Pro His Thr Val Leu Thr Leu Gln Pro Gln Tyr Gly Ser
            500                 505                 510

Pro Ile Lys Leu Lys Lys Leu
        515


<210> SEQ ID NO 5
<211> LENGTH: 147
<212> TYPE: PRT
<213> ORGANISM: Oryza sativa

<400> SEQUENCE: 5

Met Ala Lys Asp His Val Lys Ile Val Leu Lys Ala Tyr Ile Leu Gly
1               5                   10                  15

Pro Ile Lys Tyr Ile Leu Ser Leu Glu Ser Leu Tyr His Asn Cys Gly
            20                  25                  30

Gly Leu Val Val Thr Met Ile Leu His Glu Val Ile Arg Leu Tyr Pro
        35                  40                  45

Ser Gly Ile Phe Leu Gln Arg Thr Thr Arg Lys Glu Ile Glu Leu Gly
    50                  55                  60

Gly Ile Lys Tyr Pro Glu Gly Ala Asn Phe Thr Leu Pro Val Pro Ser
65                  70                  75                  80

Ile His His Asp Pro Ser Ile Trp Gly Gly Asp Ala Ser Glu Phe Asn
                85                  90                  95

Leu Glu Arg Phe Ala Asn Gly Val Ser Lys Ala Thr Lys Phe Lys Thr
            100                 105                 110

Ala Phe Phe Met Phe Gly Trp Gly Phe Ser Asp Leu Pro Trp Thr Glu
        115                 120                 125

Leu Cys Asn Ala Gly Ser Gln Asp Gly Ala Arg His His Pro Pro Glu
    130                 135                 140

Leu Leu Leu
145


<210> SEQ ID NO 6
<211> LENGTH: 72
<212> TYPE: PRT
<213> ORGANISM: Oryza sativa

<400> SEQUENCE: 6

Met Cys Cys Ser Ala Val Ala Val Met Lys Trp Glu Ala Leu Leu Pro
1               5                   10                  15

Asn Asp Thr Phe Leu Ile Val Ala Ser Ser Asp Gly Val Phe Glu Lys
            20                  25                  30

Val Thr Met Gln Asp Val Cys Asp Leu Met Leu Tyr Val Lys Leu Gly
        35                  40                  45

Val Lys Gln Glu Leu Gly Ser Phe Ala Leu Thr Gln Gln Asn Leu Ala
    50                  55                  60

Asp Tyr Val Val Asp Leu Ser Leu
65                  70


<210> SEQ ID NO 7
```

```
<211> LENGTH: 250
<212> TYPE: PRT
<213> ORGANISM: Oryza sativa

<400> SEQUENCE: 7

Met Ser Ser Ser Asp Gln Asn Pro Ser Pro Thr Pro Ala Ser Gly Thr
1               5                   10                  15

Gly Thr Ser Val Pro Pro Pro Gly Arg Ala Thr Thr Val Ser Ser Gln
            20                  25                  30

Leu Leu Asp Met Gly Ala Gln Ala Val Gln Ala Leu Lys Pro Val Arg
        35                  40                  45

Gln Met Lys Gln His Ala Cys Ser Phe Ala Leu Tyr Ala His Asp Leu
    50                  55                  60

Ser Arg Gln Val Glu Val His His Phe Val Ser Arg Leu Asn Gln Asp
65                  70                  75                  80

Val Leu Gln Cys Ala Val Tyr Asp Ser Asp Lys Pro Ser Ala Arg Leu
                85                  90                  95

Ile Gly Val Glu Tyr Ile Val Ser Asp Ala Ile Phe Glu Ser Leu Pro
            100                 105                 110

Pro Glu Glu Gln Lys Leu Trp His Ser His Ala Tyr Glu Val Lys Ala
        115                 120                 125

Gly Leu Trp Thr Asp Val Gly Val Pro Glu Pro Leu Gln Ser Ser Glu
    130                 135                 140

Met Ala Arg Met Ala Lys Thr Tyr Gly Lys Leu Trp Cys Thr Trp Gln
145                 150                 155                 160

Val Asp Arg Gly Asp Ala Leu Pro Leu Gly Ala Pro Ala Leu Met Val
                165                 170                 175

Ser Pro Gln Ala Val Glu Pro Gly Arg Val Arg Ala Glu Leu Val His
            180                 185                 190

Gly Arg Asp Glu Arg Tyr Lys Ile Asp Ser Ser Ala Gln Gly Leu Lys
        195                 200                 205

Gly Ala Arg Val Glu Met Asp Glu Pro Glu Trp Ile Asn Pro Asn Ala
    210                 215                 220

Asp Tyr Trp Arg Leu His Gly Lys Gly Phe Ala Ile Asp Val Thr Ala
225                 230                 235                 240

Thr Glu Met Lys Arg His Ala Pro Phe Pro
                245                 250


<210> SEQ ID NO 8
<211> LENGTH: 479
<212> TYPE: PRT
<213> ORGANISM: Oryza sativa

<400> SEQUENCE: 8

Met Thr Pro Pro Pro Pro Ser Pro Pro His Glu Arg Lys Thr Trp Ala
1               5                   10                  15

Glu Ser Val Ala Ser Glu Phe Arg Ala Gln Arg Gly Ile Ala Phe Pro
            20                  25                  30

Leu Ile Ala Met Asn Leu Thr Trp Phe Ala Lys Leu Ala Val Thr Thr
        35                  40                  45

Ala Phe Leu Gly Arg Leu Gly Asp Leu Gln Leu Ala Ala Gly Thr Leu
    50                  55                  60

Gly Phe Ser Phe Ala Asn Val Thr Gly Phe Ala Val Leu Thr Gly Leu
65                  70                  75                  80

Cys Ala Ala Met Asp Pro Ile Cys Gly Gln Ala His Gly Ala Ser Asn
                85                  90                  95
```

```
Gly Lys Leu Leu Arg Lys Thr Leu Val Met Ala Thr Ile Leu Leu Leu
            100                 105                 110

Gly Ala Ser Ile Pro Ile Ala Phe Leu Trp Leu His Val Asp Ala Val
        115                 120                 125

Leu Leu Arg Phe Gly Gln Gln Ala Asp Met Ser Ser Asn Ala Arg Ser
    130                 135                 140

Tyr Val Val Cys Leu Leu Pro Asp Leu Ala Val Thr Ser Phe Val Asn
145                 150                 155                 160

Pro Leu Lys Ser Tyr Leu Ser Ala Gln Gly Val Thr Leu Pro Thr Leu
                165                 170                 175

Phe Ala Ser Ala Leu Ala Leu Ala Leu His Val Pro Leu Thr Met Trp
            180                 185                 190

Met Ala Arg Thr Arg Gly Ile Gln Gly Val Ala Thr Ala Val Trp Val
        195                 200                 205

Ser Asp Leu Ala Val Ala Val Met Leu Ala Gly Tyr Val Leu Val Ser
    210                 215                 220

Glu Arg Arg Arg Lys Ala Gly Gly Gly Gly Gly Trp Val Glu Gln Thr
225                 230                 235                 240

Arg Gly Glu Trp Val Arg Leu Leu Arg Leu Ala Val Pro Ser Cys Leu
                245                 250                 255

Asn Thr Cys Leu Glu Trp Trp Cys Tyr Glu Ile Leu Val Leu Leu Thr
            260                 265                 270

Gly Arg Leu Pro Asp Ala Arg Arg Thr Val Ala Val Met Ala Val Thr
        275                 280                 285

Leu Asn Phe Asp Tyr Leu Leu Phe Ala Gly Met Leu Ser Leu Ser Val
    290                 295                 300

Ser Ala Ser Val Arg Val Ser Asn Glu Leu Gly Ala Gly Glu Ala Trp
305                 310                 315                 320

Ala Ala Arg Arg Ala Gly Met Val Ser Ile Val Gly Gly Ala Val Gly
                325                 330                 335

Gly Val Gly Gly Gly Val Ala Met Val Ala Ala Arg Arg Ala Trp Gly
            340                 345                 350

Ser Ile Tyr Ser Ser Asp Ala Gly Val Arg Glu Gly Val Gly Arg Ala
        355                 360                 365

Met Glu Val Met Ala Val Leu Glu Val Val Asn Phe Pro Leu Asn Val
    370                 375                 380

Cys Gly Gly Ile Val Arg Gly Thr Ala Arg Pro Ala Val Gly Met Tyr
385                 390                 395                 400

Ala Val Val Ala Gly Phe Tyr Val Leu Ala Leu Pro Leu Gly Val Ala
                405                 410                 415

Leu Ala Phe Lys Ala Arg Leu Gly Ile Gln Gly Leu Leu Leu Gly Phe
            420                 425                 430

Leu Val Gly Ala Ala Ala Ser Leu Ala Val Leu Leu Thr Phe Ile Ala
        435                 440                 445

Arg Met Asp Trp Pro Ala Glu Ala Gln Lys Ala Arg Thr Arg Thr Thr
    450                 455                 460

Ala Thr Val Ala Gln Phe His Gln His Asp Glu Val Val Gln Pro
465                 470                 475
```

<210> SEQ ID NO 9
<211> LENGTH: 819
<212> TYPE: PRT
<213> ORGANISM: Oryza sativa

<400> SEQUENCE: 9

```
Met Pro Glu Ala Ala Ala Ala Ala Ala Gly His Met Asp Pro Val Gly
1               5                   10                  15

Asp Glu Ala Ala Glu Arg Arg Glu Met Glu Glu Lys Glu Glu Glu Glu
            20                  25                  30

Glu Glu Glu Glu Glu Asp Glu Glu Phe Tyr Glu Ser Leu Asp Arg Ile
        35                  40                  45

Leu Ser Ser Ser Cys Ser Ser Thr Ser Ala Ser Asp Asp Asp Asp Gln
    50                  55                  60

Gln His Arg Arg Arg Arg Arg His His Pro Gln Pro Gln Gln Leu Ser
65                  70                  75                  80

Ser Ser Ala Thr Phe Ser Ala Tyr Glu Val Trp Ile Ser Glu Pro Thr
                85                  90                  95

Ser Val Glu Glu Arg Arg Arg Val Leu Leu Arg Arg Leu Gly Leu Ala
            100                 105                 110

His Asp Ser Glu Pro Leu Pro His Pro Ser Pro Arg Val Ser Ser Ser
        115                 120                 125

Ser Pro Arg Ser Pro Thr Pro Ser Pro Pro Ser Ser Ser Pro Pro Arg
    130                 135                 140

Pro Ala Pro Val Val Ala Ala Ala Glu Glu Pro Arg Ser Ser Gly His
145                 150                 155                 160

Gly Lys Pro Pro Leu Ala Arg Asn Pro Ser Gly Gly Ala Glu Gln Cys
                165                 170                 175

Arg Ile Arg Asn Leu Asp Asp Gly Thr Glu Phe Glu Val Gly Glu Val
            180                 185                 190

His Asp Glu Val Val Arg Glu Val Gly Thr Gly Arg Gln Leu Thr Phe
        195                 200                 205

Glu Glu Phe Glu Leu Cys Ile Gly Arg Ser Pro Ile Val Gln Glu Leu
    210                 215                 220

Met Arg Arg Ala Thr Thr Ala Ala Ser Ser Ser Thr Ser Asp His Ala
225                 230                 235                 240

Ala Pro Ala Ser Lys Pro Arg Arg Lys Pro Gly Gly Trp Leu Arg Gly
                245                 250                 255

Ile Arg His Leu Ala Gly Ser Val Ala Tyr Gly Arg Ser Ser Thr Asp
            260                 265                 270

Glu Arg Asp Lys Glu Lys Glu Lys Glu Lys Lys Glu Arg Glu Ala Arg
        275                 280                 285

Arg Leu Ser Ser Ala Thr Asp Asp Ser Leu Asp Gly Asn Gly Ser Arg
    290                 295                 300

Asn Ala Gly Arg Val Arg Val Arg Gln Tyr Gly Lys Ala Cys Lys Glu
305                 310                 315                 320

Leu Thr Gly Leu Phe Met Thr Gln Glu Leu Ala Ala His Ser Gly Ser
                325                 330                 335

Ile Trp Cys Ile Asn Phe Ser Leu Asp Gly Arg Tyr Leu Ala Ser Ala
            340                 345                 350

Gly Glu Asp Arg Val Ile His Val Trp Glu Val Ser Glu Gly Glu Arg
        355                 360                 365

Lys Gly Glu Leu Leu Gly Glu Gly Thr Val Ala Arg Glu Asn Gly Gly
    370                 375                 380

Gly Cys Ser Pro Phe Leu Ala Ala Val Gly Asn Gly Ser Pro Glu Leu
385                 390                 395                 400

Ala Thr Leu Ser Leu Ser Cys Ala Asp Gly Gly Phe Val Glu Lys Lys
                405                 410                 415

Arg Arg Pro Arg Met Gln Ser Ser Arg Lys Ser Val Gly Ser Asp His
            420                 425                 430
```

```
Leu Val Val Pro Glu Cys Val Phe Gly Phe Arg Asp Lys Pro Val Cys
        435                 440                 445

Ser Leu Leu Gly His Ala Ala Asp Val Leu Asp Leu Ser Trp Ser Lys
    450                 455                 460

Ser Gln Tyr Leu Leu Ser Ser Ser Met Asp Lys Thr Val Lys Leu Trp
465                 470                 475                 480

Asp Ile Thr Thr Ser Thr Cys Leu Lys Thr Phe Ser His Thr Asp Tyr
                485                 490                 495

Val Thr Cys Ile Gln Phe Asn Pro Val Asp Asp Asn Phe Phe Ile Ser
            500                 505                 510

Gly Ser Leu Asp Glu Lys Val Arg Ile Trp Asn Val His Asp Arg Lys
        515                 520                 525

Ile Glu Asp Trp Asn Asp Leu His Glu Met Val Thr Ala Ala Cys Tyr
    530                 535                 540

Ser Pro Asp Gly Gln Val Ala Leu Val Gly Ser His Lys Gly Ser Cys
545                 550                 555                 560

His Leu Phe Asp Thr Thr Glu Lys Lys Leu Gln Tyr Lys Ser Gln Ile
                565                 570                 575

Glu Leu Arg Ile Arg Lys Lys Lys Ser Gly Gln Lys Lys Ile Thr Gly
            580                 585                 590

Phe Gln Phe Ala Pro Gly Ser Ser Ser Glu Val Leu Ile Thr Ser Ala
        595                 600                 605

Asp Ser Arg Ile Arg Val Val Asn Gly Asp Glu Leu Val His Lys Phe
    610                 615                 620

Lys Gly Phe Arg Asn Thr Ser Ser Gln Ile Ser Ala Ser Val Ala Pro
625                 630                 635                 640

Asn Gly Lys Tyr Val Val Cys Ala Ser Glu Asp Ser His Val Tyr Val
                645                 650                 655

Trp Arg His Asp Asn Thr Ser His Pro Ser Arg Ser Arg Ser Ala Val
            660                 665                 670

Asp Val Thr Asn Ser Tyr Glu His Phe His Cys His Asp Val Thr Val
        675                 680                 685

Ala Ile Thr Trp Pro Gly Ala Glu Ser Arg Gly Ser Phe Gly Ser Arg
    690                 695                 700

Ser Ser Arg Asn Ser Asp Ser Asp Asp Ala Val Met Asn Thr Gly Arg
705                 710                 715                 720

Asp Ala Pro Val Glu Asn Ser Glu His Asp Leu Asn Gly Thr Val Asn
                725                 730                 735

Arg Cys Thr Lys Arg Pro Val Cys Glu Gly Val Ala Ser Thr Ser Asn
            740                 745                 750

Pro Pro Ala Asp Gly Val Ser Thr Ser Trp Pro Asp Glu Lys Gln Ser
        755                 760                 765

Ser Ala Lys Ser Ser Pro Gly His Cys Ser Ser Asp Leu Cys Ile Gly
    770                 775                 780

Ala Leu Asp Val Gln Arg Arg Ser Ala Trp Gly Leu Val Ile Val Thr
785                 790                 795                 800

Ala Gly Arg Gly Gly Glu Ile Arg Val Phe Gln Asn Phe Gly Phe Pro
                805                 810                 815

Val Gln Val
```

<210> SEQ ID NO 10
<211> LENGTH: 206
<212> TYPE: PRT
<213> ORGANISM: Oryza sativa

<400> SEQUENCE: 10

```
Met Ala Pro Ala Val Ala Ser Ser Pro Ser Leu Val Leu Ser Ala Ala
1               5                   10                  15

Ala Ala Thr Ala Ser Asn Lys Arg Pro Ala Asp Ser Asp Ala Ser Pro
            20                  25                  30

Pro His Gln Gly Asp Arg Thr Gly Gln Gln Glu Lys Lys Gln Gln Gln
        35                  40                  45

Leu Glu Cys Pro Arg Cys Arg Ser Thr Asn Thr Lys Phe Cys Tyr Tyr
    50                  55                  60

Asn Asn Tyr Ser Thr Ser Gln Pro Arg His Phe Cys Arg Ala Cys Arg
65                  70                  75                  80

Arg Tyr Trp Thr His Gly Gly Thr Leu Arg Asp Val Pro Val Gly Gly
                85                  90                  95

Ala Ser Arg Arg Gly Gly Gly Gly Lys Arg Arg Arg Val Ser Ala Asp
            100                 105                 110

Ala Asp Pro Ser Ser Ala Ser Pro Pro Pro Pro Thr Thr Ser Thr Thr
        115                 120                 125

Asp Ala Tyr Ala Asp Leu Pro Ala Gly Phe Pro Phe Leu Ser Asp Gly
    130                 135                 140

Ala Phe Leu Pro Gln Phe Gly Leu Ala Gly Val Ala Pro Ala Ala Phe
145                 150                 155                 160

Ser Trp Ala Ser Ala Val Pro Asp Leu Tyr Asn Cys Gly Ile Ala Pro
                165                 170                 175

Trp Asp Asp Gly Thr Ala Val Thr Gly Ala Ala Trp Asp Asn Phe Ala
            180                 185                 190

Asp Ile Ala Gly Leu Asp Leu Ser Trp Pro Pro Pro Gly Asn
        195                 200                 205
```

<210> SEQ ID NO 11
<211> LENGTH: 583
<212> TYPE: PRT
<213> ORGANISM: Oryza sativa

<400> SEQUENCE: 11

```
Met Ala Leu Leu Phe Arg Ile Ser Leu Leu Leu Leu Leu Val Pro Leu
1               5                   10                  15

Ile Pro Thr Ala Ala Ala Ser His His His Ser Pro Ala Gly Gly Gly
            20                  25                  30

Gly Ala Ala Val Pro Leu His Pro Arg Arg His His Arg Ser Val Ala
        35                  40                  45

Asn Thr Ala Thr Ala Leu Phe Tyr Pro Ala Pro Ser Met His Gln Asn
    50                  55                  60

His Ile Glu Ala Glu Glu Gly Gln Leu Leu His Val Leu Ala Asp Pro
65                  70                  75                  80

Phe Ala Ala Ala Pro Ala Ala Ala Glu Ala Pro Ser Gly Glu Thr Ala
                85                  90                  95

Ile Ala Ala Val Gly Ala Ala Ala Glu Glu Ala Thr Pro Thr Leu Ile
            100                 105                 110

Asp Asp Ser Pro Gln Gln Ala Ala Ala Ala Ser Pro Pro Pro Pro Pro
        115                 120                 125

Pro Pro Pro Pro Pro Pro Pro Pro Leu Phe Ala Lys Pro Asp Leu Asp
    130                 135                 140

Ser Thr Ala Pro Pro Gln Pro Lys Glu Glu Gly Val Asp Gly Tyr Gly
145                 150                 155                 160
```

```
Ser Thr Thr Ala Thr Ala Thr Val Thr Ala Ala Pro Pro Leu Asp Glu
                165                 170                 175

Pro Ala Ala Ala Thr Ala Thr Thr Thr Thr Thr Thr Thr Thr Thr Leu
            180                 185                 190

Pro Leu Pro Arg Tyr Ser His Val Ala Ser Pro Pro Pro Pro Pro Val
        195                 200                 205

His Ala Gly Val Ala Gly Leu Gly Asp Glu Gln Arg Leu Glu Gln Leu
    210                 215                 220

Ala Arg Val Leu Ser Ser Leu Gly Tyr Asn Glu Met Ala Ser Ala Ala
225                 230                 235                 240

Leu Leu Leu Ala Asn Ser Ala Leu Leu Ala Ala Trp Pro Gly Ser Ile
                245                 250                 255

Thr Val Phe Ala Ala Pro Asp Val Phe Leu Arg Ala Ser Cys Pro Met
            260                 265                 270

Cys Ser Arg Arg His Val Leu Leu Glu His Ile Ala Leu Gly Tyr Phe
        275                 280                 285

Pro Tyr Thr Glu Leu Ala Ala Ala Ser Thr Ala Lys Leu Pro Ser Ala
    290                 295                 300

Ser Pro Gly Leu Cys Leu Asn Leu Ala Ser Asp His Gly Pro Phe Ala
305                 310                 315                 320

Ile His His Val Arg Leu Tyr Val Asp Gly Val Glu Val Ser His Pro
                325                 330                 335

Glu Leu Tyr Asn Asp Gly Arg Tyr Val Val His Gly Leu His Gly Phe
            340                 345                 350

Leu Pro Pro Leu Ser His Gly Ser Cys Ser His Gly Ser Asn His Arg
        355                 360                 365

His His Tyr His Tyr Gln Tyr His His His His His His Ile Ile Ala
    370                 375                 380

Ser Ser Ala Ala Ser Ser Ala Ala Thr Ala Ala Ser Val Val Arg Ile
385                 390                 395                 400

Met Ile Arg Glu Ala Ile Ala Arg Leu Arg Asp Ser Gly Tyr Gly Phe
                405                 410                 415

Val Ala Leu Ala Met Arg Val Lys Phe Ala Glu Leu Glu Arg Leu Ala
            420                 425                 430

Asn Met Thr Val Phe Ala Leu Asp Asp Gln Ala Ile Phe Val Gly Gly
        435                 440                 445

Gly His Asp Tyr Val Ser Ala Val Arg Phe His Val Val Pro Gly His
    450                 455                 460

Arg Leu Thr His Ala Asp Leu Gln Arg Leu His Pro Gly Thr Met Leu
465                 470                 475                 480

Pro Thr Leu Ala Gly Glu Gly Gln Asn Leu Val Val Thr Gln Gly Ala
                485                 490                 495

Ser Gly Ser Gly Ser Gly Pro Arg Asp Val Arg Ile Asn Tyr Ile Pro
            500                 505                 510

Ile Lys Asp Pro Asp Val Val Ile Asn Ser Arg Ile Ala Leu His Gly
        515                 520                 525

Val Tyr Val Thr Phe Pro Arg Leu His Leu Ala Asn Leu Ala Ala Ala
    530                 535                 540

Val Ala Leu Ala Ser Ser Asn Gln Ile Asn Ala Thr Cys Gly Val Phe
545                 550                 555                 560

Gly Asp Cys Ala Ser Ala Ala Ala Thr Ser Thr Thr Val Pro Ala Ala
                565                 570                 575

His Arg Tyr Gly Glu Gly Gln
            580
```

<210> SEQ ID NO 12
<211> LENGTH: 300
<212> TYPE: PRT
<213> ORGANISM: Oryza sativa

<400> SEQUENCE: 12

```
Met Asp Ala Asp Glu Ala Ala Gly Ser Ser Arg Arg Met Asp Leu Asn
1               5                   10                  15

Leu Tyr Leu Gly Leu Pro Arg Ala Pro Arg Pro Arg Arg Ser Asp Leu
            20                  25                  30

Gly Ser Asp Leu Ala Leu Ser Thr Pro Met Pro Ser Ser Pro Ser Ser
        35                  40                  45

Ser Ala Ala Ser Val Asp Ala Pro Pro Pro Pro Pro Glu Leu Ser His
    50                  55                  60

Pro Pro Tyr Ser Pro Ser His Ala Asp Leu Ser Pro Pro Leu Gln Glu
65                  70                  75                  80

Val Tyr Ser Leu Tyr Asn Pro Asp Asp Pro Pro Ala Ser Glu Thr His
                85                  90                  95

Leu Pro Pro Tyr Ala Pro Pro Pro Ala Pro Val Val Ser Glu Leu Pro
            100                 105                 110

Asp Asp Leu Glu Phe Gly Leu His Pro Pro Pro Pro Leu Pro Val Thr
        115                 120                 125

Gly Gly Phe Ser Ser Arg Leu Glu Ala Asp Gly Ser Val Arg Gly Gly
    130                 135                 140

Leu Gly Arg Thr Phe Arg His Ser Val Leu Lys Leu Thr Gln Leu Gly
145                 150                 155                 160

Val Met Leu Pro Gln Ser Gln Asn Gly Pro Ser Ser Leu Leu Pro Asp
                165                 170                 175

Gly Ile Asp Trp Leu Arg Gly Leu Thr Leu Leu Gly Tyr Glu Asp Thr
            180                 185                 190

Glu Arg Phe Ala Ser Ala Met Ser Asp Phe Arg Arg Ile Thr Gly Pro
        195                 200                 205

Ser Gln Tyr Gly Ala Ser Ala Ser Ser Ser Asn Pro Pro Asn Leu Glu
    210                 215                 220

Ser Thr Phe Asp Arg Thr His Val Val Ala Ala Pro Ser Ala Asp Gln
225                 230                 235                 240

Ala Ser Asn Ser Ser Thr Ala Ala Val Ile Gln Gly Asp Ala Gly Ile
                245                 250                 255

Ser Glu Ser Ala Gly Glu Pro Ser Asn Ala Gly Ser Ser Arg Ser Leu
            260                 265                 270

Arg Arg Arg Gly Arg Ser Ser Ala Leu Gly Ser Leu Asp Ala Asp Gly
        275                 280                 285

Gly Gly Leu Gln Arg Asn Lys Arg Arg Arg Ile Asn
    290                 295                 300
```

<210> SEQ ID NO 13
<211> LENGTH: 480
<212> TYPE: PRT
<213> ORGANISM: Oryza sativa

<400> SEQUENCE: 13

```
Met Val Gly Gly Glu Leu Val Leu Ala Ala Leu Val Ile Leu Leu Ala
1               5                   10                  15

Leu Leu Leu Thr Leu Val Leu Ser His Phe Leu Pro Leu Leu Leu Asn
            20                  25                  30
```

```
Pro Lys Ala Pro Lys Gly Ser Phe Gly Trp Pro Leu Leu Gly Glu Thr
        35                  40                  45

Leu Arg Phe Leu Ser Pro His Ala Ser Asn Thr Leu Gly Ser Phe Leu
    50                  55                  60

Glu Asp His Cys Ser Arg Tyr Gly Arg Val Phe Lys Ser His Leu Phe
65                  70                  75                  80

Cys Thr Pro Thr Ile Val Ser Cys Asp Gln Glu Leu Asn His Phe Ile
                85                  90                  95

Leu Gln Asn Glu Glu Arg Leu Phe Gln Cys Ser Tyr Pro Arg Pro Ile
            100                 105                 110

His Gly Ile Leu Gly Lys Ser Ser Met Leu Val Val Leu Gly Glu Asp
        115                 120                 125

His Lys Arg Leu Arg Asn Leu Ala Leu Ala Leu Val Thr Ser Thr Lys
    130                 135                 140

Leu Lys Pro Ser Tyr Leu Gly Asp Ile Glu Lys Ile Ala Leu His Ile
145                 150                 155                 160

Val Gly Ser Trp His Gly Lys Ser Lys Asp Lys Gly Met Val Asn Val
                165                 170                 175

Ile Ala Phe Cys Glu Glu Ala Arg Lys Phe Ala Phe Ser Val Ile Val
            180                 185                 190

Lys Gln Val Leu Gly Leu Ser Pro Glu Glu Pro Val Thr Ala Met Ile
        195                 200                 205

Leu Glu Asp Phe Leu Ala Phe Met Lys Gly Leu Ile Ser Phe Pro Leu
    210                 215                 220

Tyr Ile Pro Gly Thr Pro Tyr Ala Lys Ala Val Gln Ala Arg Ala Arg
225                 230                 235                 240

Ile Ser Ser Thr Val Lys Gly Ile Ile Glu Glu Arg Arg Asn Ala Gly
                245                 250                 255

Ser Ser Asn Lys Gly Asp Phe Leu Asp Val Leu Leu Ser Ser Asn Glu
            260                 265                 270

Leu Ser Asp Glu Glu Lys Val Ser Phe Val Leu Asp Ser Leu Leu Gly
        275                 280                 285

Gly Tyr Glu Thr Thr Ser Leu Leu Ile Ser Met Val Val Tyr Phe Leu
    290                 295                 300

Gly Gln Ser Ala Gln Asp Leu Glu Leu Val Lys Arg Glu His Glu Gly
305                 310                 315                 320

Ile Arg Ser Lys Lys Glu Lys Asp Glu Phe Leu Ser Ser Glu Asp Tyr
                325                 330                 335

Lys Lys Met Glu Tyr Thr Gln His Val Ile Asn Glu Ala Leu Arg Cys
            340                 345                 350

Gly Asn Ile Val Lys Phe Val His Arg Lys Ala Leu Lys Asp Val Arg
        355                 360                 365

Tyr Lys Glu Tyr Leu Ile Pro Ser Gly Trp Lys Val Leu Pro Val Phe
    370                 375                 380

Ser Ala Val His Leu Asn Pro Leu Leu His Gly Asn Ala Gln Gln Phe
385                 390                 395                 400

Gln Pro Cys Arg Trp Glu Gly Ala Ser Gln Gly Thr Ser Lys Lys Phe
                405                 410                 415

Thr Pro Phe Gly Gly Gly Pro Arg Leu Cys Pro Gly Ser Glu Leu Ala
            420                 425                 430

Lys Val Glu Ala Ala Phe Phe Leu His His Leu Val Leu Asn Tyr Arg
        435                 440                 445

Trp Arg Ile Asp Gly Asp Asp Ile Pro Met Ala Tyr Pro Tyr Val Glu
    450                 455                 460
```

```
Phe Gln Arg Gly Leu Pro Ile Glu Ile Glu Pro Leu Cys Ser Glu Ser
465                 470                 475                 480


<210> SEQ ID NO 14
<211> LENGTH: 810
<212> TYPE: PRT
<213> ORGANISM: Oryza sativa

<400> SEQUENCE: 14

Met Ala Thr Leu Pro Asp Leu Gly Val Ser Ala Phe Ile Asn Ile Leu
1               5                   10                  15

Gly Ala Phe Val Phe Leu Leu Ile Phe Ala Ala Leu Arg Leu Gln Pro
            20                  25                  30

Ile Asn Asp Arg Val Tyr Phe Pro Lys Leu Tyr Leu Thr Gly Gln Arg
        35                  40                  45

Arg His His Pro His Pro His Gly Phe Val Asn Leu Asp Leu Cys Ser
    50                  55                  60

Tyr Leu Arg Phe Leu Ala Trp Val Pro Gly Ala Leu Arg Met Ser Gln
65                  70                  75                  80

Pro Asp Leu Ile His His Ala Gly Leu Asp Ser Ala Val Tyr Leu Arg
                85                  90                  95

Ile Tyr Thr Leu Gly Leu Lys Ile Phe Leu Pro Ile Met Thr Val Ala
            100                 105                 110

Leu Leu Val Leu Ile Pro Val Asn Val Ser Gly Gly Thr Leu Leu Asn
        115                 120                 125

Leu Arg Lys Glu Ile Val Phe Ser Asp Ile Asp Lys Leu Ser Ile Ser
    130                 135                 140

Asn Val Asn Pro Gly Ser Asn Arg Phe Phe Ile His Leu Leu Met Ala
145                 150                 155                 160

Tyr Val Phe Thr Phe Trp Thr Cys Phe Met Leu Tyr Lys Glu Tyr Ser
                165                 170                 175

Asn Val Ala Phe Met Arg Leu His Phe Leu Ala Ser Gln Lys Arg Cys
            180                 185                 190

Ala Asp Gln Phe Thr Val Ile Val Arg Asn Ile Pro His Val Ser Ser
        195                 200                 205

His Ser Thr Ser Glu Thr Val Asp Glu Phe Phe Arg Arg Asn His Pro
    210                 215                 220

Asp His Tyr Leu Gly Gln Gln Ala Val Tyr Asn Ala Asn Arg Tyr Ala
225                 230                 235                 240

Lys Leu Val Lys Lys Lys Glu Arg Leu Gln Asn Trp Leu Asp Tyr Tyr
                245                 250                 255

Gln Leu Lys Phe Glu Arg His Pro Gly Lys Arg Pro Ile Gly Arg Thr
            260                 265                 270

Gly Cys Leu Gly Phe Cys Gly Arg Glu Val Asp Gln Ile Asp Tyr Tyr
        275                 280                 285

Arg Ala Arg Ile Ser Glu Leu Asp Lys Lys Leu Ala Ser Glu Arg Gln
    290                 295                 300

Arg Val Leu Asn Asp Pro Lys Ala Val Met Pro Val Ala Phe Val Thr
305                 310                 315                 320

Phe Asp Ser Arg Trp Gly Ala Ala Val Cys Ala Gln Thr Gln Gln Ser
                325                 330                 335

Lys Asn Pro Thr Gln Trp Leu Thr Asp Trp Ala Pro Glu Pro Arg Asp
            340                 345                 350

Val Tyr Trp Gln Asn Leu Ala Ile Pro Phe Phe Ser Leu Ser Ile Arg
        355                 360                 365
```

```
Lys Phe Leu Ile Ser Ile Ala Val Phe Ala Leu Val Phe Phe Tyr Met
    370                 375                 380

Ile Pro Ile Ala Phe Val Gln Ser Leu Ala Asn Leu Glu Gly Ile Glu
385                 390                 395                 400

Lys Val Ala Pro Phe Leu Arg Pro Val Ile Asp Thr Pro Val Val Lys
                405                 410                 415

Ser Phe Leu Gln Gly Phe Leu Pro Gly Leu Ala Leu Lys Ile Phe Leu
            420                 425                 430

Tyr Ile Leu Pro Thr Val Leu Met Ile Met Ser Lys Val Glu Gly Tyr
        435                 440                 445

Val Ser Leu Ser Ser Leu Glu Arg Arg Ala Ala Ser Lys Tyr Tyr Tyr
    450                 455                 460

Phe Met Leu Val Asn Val Phe Leu Gly Ser Ile Ile Ala Gly Thr Ala
465                 470                 475                 480

Phe Glu Gln Leu Asn Ala Phe Phe His Gln Pro Pro Ser Gln Ile Pro
                485                 490                 495

Arg Thr Ile Gly Val Ala Ile Pro Met Lys Ala Thr Phe Phe Met Thr
            500                 505                 510

Tyr Ile Met Val Asp Gly Trp Ala Gly Ile Ala Asn Glu Ile Leu Arg
        515                 520                 525

Val Lys Pro Leu Val Ile Tyr His Leu Lys Asn Met Phe Ile Val Lys
    530                 535                 540

Thr Glu Arg Asp Arg Glu Arg Ala Met Asp Pro Gly Ser Ile Gly Leu
545                 550                 555                 560

Ala Glu Asn Leu Pro Ser Leu Gln Leu Tyr Phe Leu Leu Gly Leu Val
                565                 570                 575

Tyr Ala Val Val Thr Pro Ile Leu Leu Pro Phe Ile Ile Ile Phe Phe
            580                 585                 590

Ala Phe Ala Phe Leu Val Tyr Arg His Gln Ile Ile Asn Val Tyr Asn
        595                 600                 605

Gln Glu Tyr Glu Ser Ala Ala Ala Phe Trp Pro Gln Val His Ser Arg
    610                 615                 620

Ile Ile Ala Ser Leu Leu Ile Ser His Val Thr Leu Phe Gly Leu Met
625                 630                 635                 640

Ser Thr Met Lys Ala Ala Tyr Ser Thr Pro Leu Leu Ile Phe Leu Pro
                645                 650                 655

Leu Leu Thr Ile Trp Phe His Lys Tyr Cys Lys Ser Arg Phe Glu Pro
            660                 665                 670

Ala Phe Arg Lys Tyr Pro Leu Glu Glu Ala Met Glu Lys Asp Asn Leu
        675                 680                 685

Glu Arg Thr Ser Glu Pro Asn Leu Asn Leu Lys Ser Tyr Leu Gln Asn
    690                 695                 700

Ala Tyr Leu His Pro Ile Phe His Met Phe Glu Gln Gln Gln Gln Gln
705                 710                 715                 720

Glu Gln Glu Gln Gln Arg Glu Glu Lys Val Glu Val Arg Ile Asp Lys
                725                 730                 735

Ala Gln Gln His His His Arg Gln Val Glu Glu Glu Glu Glu Glu Ser
            740                 745                 750

Lys Ser Ser Gln Ala Thr Thr His Tyr Tyr His His His His Glu Gln
        755                 760                 765

Thr Thr Thr Thr Thr His His His Tyr His Gln His Glu His Met Ser
    770                 775                 780

His Tyr His Met Gly Pro Ser Asp Thr Ala Asp Ser Pro Ser Pro Pro
```

```
785                 790                 795                 800

His Phe Val Tyr His Tyr Gly Val Asp Pro
                805                 810


<210> SEQ ID NO 15
<211> LENGTH: 293
<212> TYPE: PRT
<213> ORGANISM: Oryza sativa

<400> SEQUENCE: 15

Met Glu Met Thr Arg Ser Leu Thr Leu Val Pro Leu Pro Ala Thr Leu
1               5                   10                  15

Arg Pro Ala Ser Ala Ala Cys Arg Arg Arg Arg Arg Arg Arg Gly Leu
            20                  25                  30

Pro Phe Gly Ala Leu Phe Ser Pro Ser Pro Pro Ser Asn Gln Gln Gln
        35                  40                  45

Gln Glu Met His Ile Arg Ala Leu Gln Pro Arg Gln Asp Trp Val Gly
    50                  55                  60

Glu Trp Val Arg Ser Asn Asp Thr Leu Val Arg Gly Leu Pro Ile Leu
65                  70                  75                  80

Gly Gly Gly Ala Ser Leu Leu Ala Val Leu Leu Asn Arg Ala Val Ser
                85                  90                  95

Gly Ile Ala Ala Val Ala Asp Ala Ser Ser Ser Gln Ser Arg Ala Asp
            100                 105                 110

Ile Leu Thr Leu Ala Leu Ser Val Thr Asp Ile Leu Ala Gly Leu Val
        115                 120                 125

Trp Leu Ser Ile Arg Pro Lys Ser Ile Ser Pro Val Val Pro Arg Gly
    130                 135                 140

Val Glu Cys Lys Arg Val Gly Thr Gly Val Leu Asp Ser Ala Leu Arg
145                 150                 155                 160

Glu Leu Leu Trp Thr Trp Asp Ser Leu Thr Thr Ala Thr Cys Cys Lys
                165                 170                 175

Ser Leu Val Val Val Tyr Gly Gly Asn Cys Val Leu Gln Ile Gly Val
            180                 185                 190

Ala Ala Gly Ser Pro Glu Asp Gly Asn Ala Val Met Val Asp Ala Gln
        195                 200                 205

Lys Phe Met Gln Gly Ser Leu Tyr Arg Ser Ala Met Glu Ser Lys Lys
    210                 215                 220

Gln Ser Tyr Leu Ala Asn Leu Ala Leu Tyr Pro Gly Arg Thr Glu Leu
225                 230                 235                 240

Pro Phe Leu Pro Ala Asn Thr Gln Ala Leu Ile Leu Gln Pro Ile Gly
                245                 250                 255

Asp Lys Gly Ile Ala Val Ile Gly Gly Asp Thr Ile Arg Gly Phe Thr
            260                 265                 270

Asn Leu Asp Gln Ala Trp Ile Ala Met Ile Ala Asp Lys Leu Asp Ala
        275                 280                 285

Thr Leu Ser Lys Ser
    290


<210> SEQ ID NO 16
<211> LENGTH: 155
<212> TYPE: PRT
<213> ORGANISM: Oryza sativa

<400> SEQUENCE: 16

Met Ala Ser Ser Val Ala Gly Ser Val Thr Arg Arg Pro Pro Pro Val
1               5                   10                  15
```

```
Leu Leu Ala Cys Arg Ser Arg Pro Asn Asn Arg Arg Leu Ile Arg Leu
            20                  25                  30

Leu Pro Leu Leu Phe Ala Val Val Val Leu Leu Ala Leu Leu Pro Pro
        35                  40                  45

Cys Val His Gly Ala Arg Ala Leu Asn Asp Ala Lys Glu Ala Lys Val
    50                  55                  60

Ala Glu Ala Ser Asp Gln Thr Thr Thr Thr Thr His Ala Ala Ala Ala
65                  70                  75                  80

Ala Val Ala Arg Trp Ser Val Thr Val Arg Glu Gly Gly Gly Gly Gly
                85                  90                  95

Gly His Gly Ser Gly His Ala Gly Ala Gly His Gly His Gly Ser Gly
            100                 105                 110

His Gly Arg Pro Glu Pro Ala Glu His His Thr Gly Arg Arg Ser Ala
        115                 120                 125

Ala Ala Gly Ser Val Arg Pro Pro Met Ala Ala Ser Cys Ala Ala Leu
    130                 135                 140

Leu Val Ala Ala Val Val Ala Leu Leu Arg Phe
145                 150                 155
```

<210> SEQ ID NO 17
<211> LENGTH: 124
<212> TYPE: PRT
<213> ORGANISM: Oryza sativa

<400> SEQUENCE: 17

```
Met Glu Ser Ala Lys Arg Ser Cys Leu Ala Ile Ser Leu Ile Leu Leu
1               5                   10                  15

Leu Leu Leu Val Pro Ser Ile His Gly Ala Arg His Val Ala Ala Ala
            20                  25                  30

Ile Lys Gly Thr Gly Ala Asp Ser Glu Met Val Val Thr Glu Arg Thr
        35                  40                  45

Ala Gly Gly Gly Gly Gly His Gly Arg Gly Tyr Thr Ser His Arg Ser
    50                  55                  60

His Asn Pro Asn Asn Pro Asn Asp Gly Gly Ser Gly Thr Pro Val Val
65                  70                  75                  80

Asp Pro His Asn Val Ala Thr Arg Gly His His His Arg Gly Ala Ala
                85                  90                  95

Thr Arg Thr Ala Ala Gly Gly Asp Pro Arg Leu Ala Ala Cys Met Leu
            100                 105                 110

Arg Leu Gly Ala Thr Phe Phe Leu Leu Val Leu Gly
        115                 120
```

<210> SEQ ID NO 18
<211> LENGTH: 215
<212> TYPE: PRT
<213> ORGANISM: Oryza sativa

<400> SEQUENCE: 18

```
Met Ala Gly Val Gly Phe Val Glu Asp Met Leu Arg Glu Gln Ser Leu
1               5                   10                  15

Leu Glu Ala Thr Cys Gly Asp Leu Phe Asp His Ile Asp Asp Leu Leu
            20                  25                  30

Asp Phe Pro Lys Glu Glu Ser Ala Ala Asp Val Leu Leu Leu Asp Ala
        35                  40                  45

Pro Ala Pro Gly Ser Pro Leu Ser Ser Arg Ile Ile Gly Gly His Ala
    50                  55                  60
```

```
Thr Met Ala Ala Ala Pro Pro Pro Pro Pro Gln Met Met Ala Leu Pro
65                  70                  75                  80

Pro Pro Pro Ala Pro Ala Lys Asp Asp Ala Ser Ala Leu Phe Asp Ala
                85                  90                  95

Ala Gly Ala Leu Gly Ala Glu Val Phe Asp Arg Lys Asp Ala His Ile
            100                 105                 110

Gly Pro Cys Asp Glu Leu Asp Met Asp Met Ala Gln Leu Glu Trp Leu
        115                 120                 125

Ser Gly Leu Phe Asp Asp Gly Thr Ile Pro His Glu Pro Ser Phe Pro
    130                 135                 140

Gly Val Asn Cys Ala Ala Pro Ile Lys Ala Ser Ala Leu Thr Ala Asn
145                 150                 155                 160

Ala Gly Val Val Leu Pro Asp Lys Ala Glu Glu Ala Leu Phe Arg Ser
                165                 170                 175

Ser Ser Pro Ile Ser Val Leu Glu His Ser Gly Phe Asn Val Ala Thr
            180                 185                 190

Asn Gly Gly Ser Ser Ser Ser Ser Ser Ser Ser Ser Pro Ser Pro Trp
        195                 200                 205

Thr Trp Thr Trp Thr Ala Val
    210                 215


<210> SEQ ID NO 19
<211> LENGTH: 376
<212> TYPE: PRT
<213> ORGANISM: Oryza sativa

<400> SEQUENCE: 19

Met Ile Ile Val Asp Asp Ala Gly Ala Phe Leu Pro Ala Leu Asn His
1               5                   10                  15

Ser Pro Trp Asp Gly Val Thr Ile Ala Asp Phe Val Met Pro Phe Phe
            20                  25                  30

Leu Phe Met Val Gly Ile Ser Leu Thr Leu Ala Tyr Lys Arg Val Pro
        35                  40                  45

Asp Lys Leu Glu Ala Thr Lys Lys Ala Val Leu Arg Ala Leu Lys Leu
    50                  55                  60

Phe Cys Leu Gly Leu Val Leu Gln Gly Gly Phe Phe His Gly Val Arg
65                  70                  75                  80

Ser Leu Thr Phe Gly Val Asp Ile Thr Lys Ile Arg Leu Met Gly Ile
                85                  90                  95

Leu Gln Arg Ile Ala Ile Ala Tyr Leu Leu Ala Ala Ile Cys Glu Ile
            100                 105                 110

Trp Leu Lys Gly Asp Asp Asp Val Asp Cys Gly Leu Asp Val Ile Arg
        115                 120                 125

Arg Tyr Arg Tyr Gln Leu Val Val Ala Leu Leu Leu Ser Thr Met Tyr
    130                 135                 140

Thr Val Ile Leu Asn Gly Val Tyr Val Pro Asp Trp Glu Tyr Gln Ile
145                 150                 155                 160

Ser Gly Pro Gly Ser Thr Glu Lys Ser Phe Ser Val Arg Cys Gly Val
                165                 170                 175

Arg Gly Asp Thr Gly Pro Ala Cys Asn Ala Val Gly Met Leu Asp Arg
            180                 185                 190

Thr Ile Leu Gly Ile Asp His Leu Tyr Arg Arg Pro Val Tyr Ala Arg
        195                 200                 205

Thr Lys Gln Cys Ser Ile Asn Tyr Pro Gln Asn Gly Pro Leu Pro Pro
    210                 215                 220
```

```
Asp Ala Pro Ser Trp Cys Gln Ala Pro Phe Asp Pro Glu Gly Leu Leu
225                 230                 235                 240

Ser Ser Val Met Ala Ile Val Thr Cys Leu Ile Gly Leu Gln Phe Gly
                245                 250                 255

His Ile Ile Ile His Phe Glu Lys His Lys Gly Arg Ile Ile Asn Trp
            260                 265                 270

Leu Ile Pro Ser Phe Ser Met Leu Ala Leu Ala Phe Ser Met Asp Phe
        275                 280                 285

Ile Gly Ile Arg Met Asn Lys Pro Leu Tyr Thr Ile Ser Tyr Ala Leu
    290                 295                 300

Ala Thr Ser Gly Ala Ala Gly Leu Leu Phe Ala Gly Ile Tyr Thr Leu
305                 310                 315                 320

Val Asp Val Tyr Gly Phe Arg Lys Leu Thr Ile Pro Met Glu Trp Met
                325                 330                 335

Gly Lys His Ala Leu Met Ile Tyr Val Leu Val Ala Cys Asn Ile Leu
            340                 345                 350

Pro Ile Phe Ile His Gly Phe Tyr Trp Arg Glu Pro Lys Asn Asn Leu
        355                 360                 365

Leu Lys Phe Ile Gly Val Gly Ala
    370                 375


<210> SEQ ID NO 20
<211> LENGTH: 488
<212> TYPE: PRT
<213> ORGANISM: Oryza sativa

<400> SEQUENCE: 20

Met Ala Ala Thr Gly Gly Ala Ala Gly Glu Lys Thr Ala Ser Ser Leu
1               5                   10                  15

Leu Leu Gly Val Arg Gly Tyr Thr Ser Thr Leu Lys Asn Ala Ser Thr
            20                  25                  30

Ala Ser Cys Arg Leu Ser Ala Gly His Pro Ile Glu Val Thr Leu Trp
        35                  40                  45

Glu Ala Ser Pro Pro Ala Leu Ser His Phe Ser Val His Cys Pro Asp
    50                  55                  60

Leu Pro Ser Phe Asn Gly Asn Leu Leu Gly Ala Pro Lys Ala Ile Ala
65                  70                  75                  80

Ala Ala Val Asp Asp Ala Asp Gly Gln Leu Leu Leu Leu Leu Arg Val
                85                  90                  95

Pro Ile Asp Gln Leu Gly Ala Pro His Asp Asn Asp Tyr Leu Val Tyr
            100                 105                 110

His Pro Asp Pro Pro Ser Pro Lys Leu Asp Leu Leu Pro Asn Pro Pro
        115                 120                 125

Pro Pro Thr Leu Gly Asp His Gln Leu Ala Ile Leu Ser Cys Gly Asp
    130                 135                 140

Asp Arg Tyr Val Val Ala Ala Leu His Val Trp Ser Glu Phe Thr Ser
145                 150                 155                 160

Thr Leu Arg Leu Tyr Arg Ser Ser Cys Ser Ser Gly Ser Trp Thr Ser
                165                 170                 175

Glu Glu Val Ser Val Glu Glu Pro Val Arg Asp Arg Leu Cys Pro Ile
            180                 185                 190

Pro Asp Ser Ala Lys Arg Gln Leu Tyr His Val Thr Thr Lys Thr Ile
        195                 200                 205

Thr Leu Gly Gly Ala Lys Gly Thr Val Gly Trp Val Asp Leu Trp Arg
    210                 215                 220
```

```
Gly Ile Leu Leu Cys Asp Val Leu Asp Glu Met Ser Pro Arg Lys Leu
225                 230                 235                 240

Arg Asp Met Pro Leu Pro Trp Pro Ala Lys Gly Asn Trp Arg Met Tyr
                245                 250                 255

Leu Asn Gly Asp Val Ser Phe Cys Arg Asp Ile Ala Ile Ser Gln His
            260                 265                 270

Lys Asp Ser Ile Lys Tyr Leu Glu Met Glu Ile Val Ser Pro Arg Thr
        275                 280                 285

Val Thr Thr Thr Ile Pro Thr Ser Thr Ser Ala Asp Pro Thr Ser Tyr
    290                 295                 300

Leu Glu Trp Val Arg Arg Ser Arg Glu Pro Gln Pro Thr Arg Arg Arg
305                 310                 315                 320

Ser Val Phe His Pro Gly Ser Trp Arg Ile Thr Thr Trp Ser Met Pro
                325                 330                 335

Ile Pro Val Thr Ser Trp Asp Asp Trp Arg Arg Asp Cys Thr Ala Glu
            340                 345                 350

Ser Arg Glu Val His Leu Asp Thr Asn Pro Ser His His Tyr Glu Leu
        355                 360                 365

Leu His Ser Leu Met Leu Ser Asn Ser Gly Asp Glu His Arg Glu Glu
    370                 375                 380

Ala Gln Gly Gln Gly Ala Thr Ser Ser Leu Ser Leu Gly Arg Leu Arg
385                 390                 395                 400

Leu Cys Tyr Pro Ala Leu Ser Cys Ile Asp Asp Asp Val Val Tyr Leu
                405                 410                 415

Leu Gly Asn Ala Ala Gly Arg Gly Ala Lys Thr Gly Gly Met Met Val
            420                 425                 430

Ala Val Asp Val Arg Asn Lys Glu Leu Arg Gly Val Ala Lys Leu Asp
        435                 440                 445

Pro Glu Lys Asn Thr Leu Tyr Ser Met Arg Cys Tyr Leu Ala Thr Gly
    450                 455                 460

Ile Ser Lys Arg Leu Asn Thr Thr Thr Asp Thr Arg Val Gly Arg Pro
465                 470                 475                 480

Glu Glu Asp Ala Glu Ala Ala Glu
                485


<210> SEQ ID NO 21
<211> LENGTH: 167
<212> TYPE: PRT
<213> ORGANISM: Oryza sativa

<400> SEQUENCE: 21

Met Ala Asn Tyr His His Gln Glu Tyr Tyr Gln Met Ala Ala Ala Ala
1               5                   10                  15

Ala Val Ala Trp Pro Arg Glu Pro Asp Ser Pro Gln Leu Ser Ile Met
            20                  25                  30

Ser Gly Cys Ser Ser Leu Phe Ser Ile Ser Thr Leu Arg Asp Asp Asp
        35                  40                  45

Asp Gly Gly Gly Val Arg Leu Ala Gly Ala Ala Leu Pro Ala Thr Pro
    50                  55                  60

Val Ser Leu Ala Gly Ile Ala Gly Gly Ala Ser Thr Pro Gly Gly Asp
65                  70                  75                  80

Glu Val Asp Met Glu Val Arg Gln Gln Ser Gly Gly Ser Gly Asp Asp
                85                  90                  95

Arg Arg Thr Ile Arg Met Met Arg Asn Arg Glu Ser Ala Leu Arg Ser
            100                 105                 110
```

```
Arg Ala Arg Lys Arg Ala Tyr Val Glu Glu Leu Glu Lys Glu Val Arg
        115                 120                 125

Arg Leu Val Asp Asp Asn Leu Asn Leu Lys Lys Gln Cys Lys Glu Leu
    130                 135                 140

Lys Gln Glu Val Ala Ala Leu Val Met Pro Thr Lys Ser Ser Leu Arg
145                 150                 155                 160

Arg Thr Ser Ser Thr Gln Phe
                165


<210> SEQ ID NO 22
<211> LENGTH: 310
<212> TYPE: PRT
<213> ORGANISM: Oryza sativa

<400> SEQUENCE: 22

Met Ala Glu Lys Lys Lys Lys Lys Lys Lys Lys Lys Pro Gln Ser Leu
1               5                   10                  15

Leu Val Leu Thr Ser Trp Arg Ser Ile Gly Met Gly Arg Gly Arg Val
            20                  25                  30

Glu Leu Lys Arg Ile Glu Asn Lys Ile Asn Arg Gln Val Thr Phe Ala
        35                  40                  45

Lys Arg Arg Asn Gly Leu Leu Lys Lys Ala Tyr Glu Leu Ser Val Leu
    50                  55                  60

Cys Asp Ala Glu Val Ala Leu Ile Ile Phe Ser Asn Arg Gly Lys Leu
65                  70                  75                  80

Tyr Glu Phe Cys Ser Thr Gln Ser Met Thr Lys Thr Leu Glu Lys Tyr
                85                  90                  95

Gln Lys Cys Ser Tyr Ala Gly Pro Glu Thr Ala Val Gln Asn Arg Glu
            100                 105                 110

Ser Glu Gln Leu Lys Ala Ser Arg Asn Glu Tyr Leu Lys Leu Lys Ala
        115                 120                 125

Arg Val Glu Asn Leu Gln Arg Thr Gln Arg Gln Tyr Tyr Lys Ser Lys
    130                 135                 140

His Arg Leu Cys Leu Val Arg Ser Lys Val Trp Asn Leu Val Lys Ile
145                 150                 155                 160

Arg Asp Asp Val Thr Glu Lys Leu Cys Met Tyr Glu Arg Asn Leu Leu
                165                 170                 175

Gly Glu Asp Leu Asp Ser Leu Gly Ile Lys Glu Leu Glu Ser Leu Glu
            180                 185                 190

Lys Gln Leu Asp Ser Ser Leu Lys His Val Arg Thr Thr Arg Thr Lys
        195                 200                 205

His Leu Val Asp Gln Leu Thr Glu Leu Gln Arg Lys Glu Gln Met Val
    210                 215                 220

Ser Glu Ala Asn Arg Cys Leu Arg Arg Lys Leu Glu Glu Ser Asn His
225                 230                 235                 240

Val Arg Gly Gln Gln Val Trp Glu Gln Gly Cys Asn Leu Ile Gly Tyr
                245                 250                 255

Glu Arg Gln Pro Glu Val Gln Gln Pro Leu His Gly Gly Asn Gly Phe
            260                 265                 270

Phe His Pro Leu Asp Ala Ala Gly Glu Pro Thr Leu Gln Ile Gly Tyr
        275                 280                 285

Pro Ala Glu His His Glu Ala Met Asn Ser Ala Cys Met Asn Thr Tyr
    290                 295                 300

Met Pro Pro Trp Leu Pro
305                 310
```

<210> SEQ ID NO 23
<211> LENGTH: 69
<212> TYPE: PRT
<213> ORGANISM: Oryza sativa

<400> SEQUENCE: 23

```
Met Glu Gly Gly Gly Arg Arg Arg Lys Arg Gly Lys Val Glu Leu Arg
1               5                   10                  15

Arg Ile Glu Asp Arg Thr Ser Arg Gln Val Arg Phe Ser Lys Arg Arg
            20                  25                  30

Ser Gly Leu Phe Lys Lys Ala Tyr Glu Leu Ser Val Leu Cys Asp Ala
        35                  40                  45

Gln Val Ala Leu Leu Val Phe Ser Pro Ala Gly Arg Leu Tyr Glu Phe
    50                  55                  60

Ala Ser Ser Thr Ser
65
```

<210> SEQ ID NO 24
<211> LENGTH: 491
<212> TYPE: PRT
<213> ORGANISM: Oryza sativa

<400> SEQUENCE: 24

```
Met Ala Leu Leu Leu Ser Tyr Pro Arg Arg His Pro Ser Ile His Leu
1               5                   10                  15

Leu Ile Leu Ser Ala Tyr Ala Leu Phe Leu Leu Pro Ile Leu Asp Gly
            20                  25                  30

Leu Glu Leu Gly Gly Asp Gly Leu Tyr Arg Glu Ile Leu Arg Asp Glu
        35                  40                  45

Thr Val Leu Arg Leu Lys Glu Leu Gly Lys Ile Ser Asp Gly Glu Gly
    50                  55                  60

Tyr Leu Glu Arg Thr Phe Leu Ser Pro Ala Ser Ile Arg Ala Ser Ala
65                  70                  75                  80

Val Ile Ile Ser Trp Met Lys Asp Ala Gly Leu Thr Thr Trp Ile Asp
                85                  90                  95

Gln Met Gly Asn Ile His Gly Arg Phe Glu Pro Thr Asn Ser Thr Lys
            100                 105                 110

Glu Ala Leu Leu Ile Gly Ser His Met Asp Thr Val Ile Asp Ala Gly
        115                 120                 125

Met Tyr Asp Gly Ala Leu Gly Ile Ile Ser Ala Ile Ser Ala Leu Lys
    130                 135                 140

Val Leu Lys Val Thr Gly Arg Leu Gln Arg Leu Thr Arg Pro Val Glu
145                 150                 155                 160

Val Ile Ala Phe Ser Asp Glu Glu Gly Val Arg Phe Gln Thr Thr Phe
                165                 170                 175

Leu Gly Ser Ala Ala Val Ala Gly Thr Leu Pro Glu Ser Ile Leu Gln
            180                 185                 190

Val Ser Asp Lys Ser Gly Thr Thr Val Gln Asp Val Leu Lys Leu Asn
        195                 200                 205

Ser Leu Glu Gly Thr Ala Asn Ala Leu Gly Glu Val Arg Tyr Ser Pro
    210                 215                 220

Glu Ser Val Gly Ser Tyr Val Glu Val His Ile Glu Gln Gly Pro Val
225                 230                 235                 240

Leu Glu Ala Leu Arg Tyr Pro Leu Gly Val Val Lys Gly Ile Ala Gly
                245                 250                 255

Gln Thr Arg Leu Lys Val Ile Ile Asn Gly Ser Gln Gly His Ala Gly
```

```
            260                 265                 270

Thr Val Pro Met Lys Leu Arg Arg Asp Pro Met Val Ala Ala Ala Glu
        275                 280                 285

Leu Val Leu Thr Leu Glu Thr Leu Cys Lys Glu Pro Asn Lys Phe Leu
    290                 295                 300

Thr Tyr Asp Glu Glu Cys Gly Cys Phe Thr Glu Glu Ser Leu Ala Gly
305                 310                 315                 320

Leu Val Cys Thr Val Gly Glu Leu Leu Thr Trp Pro Ser Ala Ser Asn
                325                 330                 335

Val Ile Pro Gly Gln Val Asn Phe Thr Val Asp Ile Arg Ala Met Asp
            340                 345                 350

Asp Lys Val Arg Glu Thr Ile Val Thr Ser Phe Ser Arg Leu Val Leu
        355                 360                 365

Gln Arg Cys Asp Asp Arg Leu Val Asp Cys Ala Val Glu Gln Lys His
    370                 375                 380

Ala Ala Ala Ala Thr Pro Cys Asp Ala Glu Leu Thr Ser Arg Leu Glu
385                 390                 395                 400

Arg Ala Thr Arg Ser Thr Ile Ser Ser Met Ala Ala Gly Val Arg Arg
                405                 410                 415

Ala Gly Gly Glu Thr Pro Val Leu Met Ser Gly Ala Gly His Asp Ala
            420                 425                 430

Met Ala Met Ala Arg Leu Thr Lys Val Gly Met Leu Phe Val Arg Cys
        435                 440                 445

Arg Gly Gly Val Ser His Ser Pro Glu Glu Ser Val Met Asp Asp Asp
    450                 455                 460

Val Trp Ala Ala Gly Leu Ala Leu Val Asn Phe Ile Asp Gln Asn Ala
465                 470                 475                 480

Val Asp Ala Ala Ala Ala Thr Ala Ala Glu Ser
                485                 490


<210> SEQ ID NO 25
<211> LENGTH: 267
<212> TYPE: PRT
<213> ORGANISM: Oryza sativa

<400> SEQUENCE: 25

Met Ser Phe Ala Asp Leu Glu Ala Gly Ala Val Arg Ala Pro Arg Arg
1               5                   10                  15

Ala Arg Gly Pro Asp Ala Thr Arg Ala Leu Val Phe Gln Ile Thr Thr
            20                  25                  30

Ala Val Ala Ser Tyr Arg Arg Leu Leu Asn Ser Leu Gly Thr Pro Lys
        35                  40                  45

Asp Thr Pro Ala Leu Arg Asp Gln Leu Gln Lys Thr Ser His Asn Ile
    50                  55                  60

Leu Gln Leu Ala Lys Asp Ala Lys Glu Lys Leu Arg Arg Ala Ala Glu
65                  70                  75                  80

Ala Asp Lys Asn Ala Asp Thr Ser Ala Asp Lys Arg Val Ala Asp Met
                85                  90                  95

Lys Leu Ala Lys Asp Phe Ala Thr Thr Met Glu Glu Tyr Gly Lys Leu
            100                 105                 110

Gln Asn Leu Ala Ile Gln Arg Glu Met Ala Tyr Lys Pro Val Val Pro
        115                 120                 125

Gln Thr Ser Gln Pro Asn Tyr Thr Thr Gly Gly Ile Glu Ala Arg Asp
    130                 135                 140

Ser Gly Lys Ile Pro Glu Gln His Ala Leu Leu Ala Glu Ser Lys Arg
```

```
145                 150                 155                 160

Gln Glu Val Leu Gln Leu Asp Asn Glu Ile Val Phe Asn Glu Ala Ile
                165                 170                 175

Ile Glu Glu Arg Glu Gln Ala Ile Gln Asp Ile Gln Gln Gln Ile Gly
            180                 185                 190

Glu Val His Glu Ala Phe Lys Asp Leu Ala Thr Leu Val His Ile Gln
        195                 200                 205

Gly Val Thr Ile Glu Glu Ile Asp Thr Asn Ile Glu Asn Ser Ala Ala
    210                 215                 220

Ala Thr Lys Glu Ala Lys Thr Glu Leu Ala Lys Ala Ser Lys Thr Gln
225                 230                 235                 240

Lys Ser Asn Ser Ser Leu Leu Cys Ile Leu Leu Val Ile Phe Gly Val
                245                 250                 255

Val Leu Leu Ile Val Ile Ile Val Leu Ala Thr
            260                 265


<210> SEQ ID NO 26
<211> LENGTH: 95
<212> TYPE: PRT
<213> ORGANISM: Oryza sativa

<400> SEQUENCE: 26

Met Gln Leu Tyr Met Thr Tyr Gln Ala Cys Pro Met Gly Asp Leu Gln
1               5                   10                  15

Met Gly Asp Ser Val Val Ser Thr Ile Asp Ile Arg Ala Leu Tyr Cys
            20                  25                  30

Asn Lys Ser Pro Gly Lys Ser Ser Ser Ser Ser Met Tyr Gly Ala Ser
        35                  40                  45

Ser Ser Ser Lys Arg Lys Ala Cys Glu Leu Asn His Gly Asp Gly Gly
    50                  55                  60

Ser Ala His Asp Asp Val Arg Asp Tyr Gly Val Asp His Val Asp Asp
65                  70                  75                  80

Asn Gly Glu Tyr Tyr Gly Asp Asp His Asp Asp Val Met His Gly
                85                  90                  95


<210> SEQ ID NO 27
<211> LENGTH: 1113
<212> TYPE: PRT
<213> ORGANISM: Oryza sativa

<400> SEQUENCE: 27

Met Arg Ala Ala Ala Ala Ala Ser Lys Ala Ala Gly Lys Glu Lys Ser
1               5                   10                  15

Arg Arg Lys Gly Gly Gly Gly Gly Ala Gly Gly Gly Gly Gly Glu Gln
            20                  25                  30

Leu Leu Thr Asp Gln Val Leu Ser Leu Arg Ala Arg Leu His Leu Ala
        35                  40                  45

Leu Ala Leu Gly Leu Ala Lys Ser Asp Gly Gly Pro Lys Lys Trp Gln
    50                  55                  60

Ser Thr Asp Ala Gly Ile Gln Ser His Val Leu Lys Ala Ala Ser Ala
65                  70                  75                  80

Phe Leu Gly Cys Leu Thr Asn Glu Met Leu Arg Leu Pro Pro Ile Lys
                85                  90                  95

Glu Ser Ile Ser Asp Ile Leu Ile Ala Leu Glu Gly Ile Leu Gln Ser
            100                 105                 110

Lys Asn Val Ser Val Leu Ile Gln Ala Thr Asp Val Ser Leu Lys Leu
        115                 120                 125
```

```
Val Ser Ser Val Gly Asn Leu Ala Arg Gln Tyr Pro Val Leu Glu Ile
    130                 135                 140

Val Thr Cys Leu Ala Ser Gln Leu Ser Ala Asn Gln Ile Thr Ile Ala
145                 150                 155                 160

Val Ser Ser Ala Ser Thr Leu Asn Cys Ile Leu Asn Thr Leu Ala Thr
                165                 170                 175

Ala Arg Ser Ser Ile His Ala Glu Ile Trp Glu Ala Leu Glu Lys Thr
            180                 185                 190

Asp Ala Val Thr Ser Val Ile Gly Ala Leu Gln Asn Tyr Ser Pro Asp
        195                 200                 205

Val His Pro Leu Asn Tyr Leu Met Glu Met Met Ser Leu Leu Arg Ile
    210                 215                 220

Ile Leu Trp Ile Trp Pro Ser Ser Arg Tyr His Val Trp Ser Asn Cys
225                 230                 235                 240

Asn Leu Met Gly Lys Leu Ala Gln Tyr Cys Val Ala Ser Glu Met Asp
                245                 250                 255

Val Ala Val Arg Val Leu Lys Leu Tyr Ala Ala Leu Ala Leu Cys Gly
            260                 265                 270

Asn Gly Ala Met Val Leu Leu Asn Asn Glu Asp Leu Met Ala Lys Val
        275                 280                 285

Gly Ala Leu Leu Gly Lys Ser Asn Pro Ser Ile Ala Arg Ile Glu Ala
    290                 295                 300

Leu Lys Phe Tyr Gln Ile Leu Leu Arg Ser Ser Lys Gly Cys Asp Leu
305                 310                 315                 320

Leu Met Ala Ala His Tyr Gln His Ile Ile Glu Gly Thr Ile Asn Ala
                325                 330                 335

Met Ser Arg Asp Asp Glu Arg Leu Leu Thr Ile Glu Gly Cys Arg Thr
            340                 345                 350

Ala Leu Leu Val Leu Arg Tyr Ala Gly Asp His His Arg Leu Phe Trp
        355                 360                 365

Ser His Ala Ile Asp Asp Val Leu Tyr Lys Ile Leu Thr Gly Gly Cys
    370                 375                 380

Thr Ser Ser His Lys Ala Asn Gln Ile Leu Cys His Asp Lys Leu Phe
385                 390                 395                 400

Asn Met Val Ser Glu Asn Phe Met Asp Ile His Ser Tyr Val Trp Asp
                405                 410                 415

Ile Leu Gly Asn Leu Ala Val His Cys Lys Asn Glu Tyr Leu Ser Val
            420                 425                 430

Arg Lys Gly Gln Asp Ser Ala Leu Gln Ala Leu Ile His Cys Ile Cys
        435                 440                 445

Ser Leu Ala Ala Asp Ala Met Gln Lys Ser Asn Thr Met Lys Leu Ser
    450                 455                 460

Lys Asp Val His Glu Pro Ala Leu Arg Ala Val Leu Met Met Leu Leu
465                 470                 475                 480

Ser Pro Ser Gly Tyr Ile Leu Ser Glu Ala Ser Ser Lys Leu Leu His
                485                 490                 495

Val Leu Pro Leu Gly Asp Asp Cys Leu Asn Ile Leu Phe Thr Ser Leu
            500                 505                 510

Glu Ser Asn Thr Thr Arg Ser Ile Thr Ala Ser Phe Asp Asn Val Lys
        515                 520                 525

Ile Met Ser Asn Leu Met Ser Leu Ala Gly Met Ser Ile Asn Phe Val
    530                 535                 540

Cys Ile His Cys Lys Arg Asn Leu Asp Val Gly Ile Val Cys Asn Asp
```

```
545                 550                 555                 560

Cys Arg Asp His Tyr Ser Glu Gly Leu Ile Arg Val Leu Gln Asn Ala
                565                 570                 575

Ser Cys Gln Asn Leu Ser Pro Gly Pro Lys Leu Tyr Ile Ser Arg Ile
            580                 585                 590

Leu Ser Leu Phe Gly Leu Cys Gly Phe Pro Ser Lys Leu Gly Gly Lys
        595                 600                 605

Met Arg Arg Ala Leu Asp Asp Asn Glu Leu Ala Asp Leu Glu Leu Leu
    610                 615                 620

Leu Ser Asn Gly Glu Ser Leu Lys Ala His Thr Ala Ile Ile Ser Val
625                 630                 635                 640

Arg Cys Pro Lys Leu Leu Pro Ser Ala Lys Ser Leu Gly Ser Asp Gly
                645                 650                 655

Lys Ile Thr Asp Glu Trp Gly Arg Ser Phe Tyr His Val Arg Met Ser
            660                 665                 670

Asp Arg Val Asp Ser Cys Gly Leu Lys Lys Ile Leu Glu Tyr Thr Tyr
        675                 680                 685

Thr Asn Ser Val Met Val Asp Asp Asp Asn Ile Lys Pro Arg Thr Leu
    690                 695                 700

Ala Lys Tyr Cys His Leu Lys Ser Leu Gln Glu Met Leu Gln Lys Glu
705                 710                 715                 720

Gln Pro Arg Trp Asn Ser Asp Cys Pro Arg Tyr Asp Leu Thr Ala Ala
                725                 730                 735

Leu Glu Pro Val Lys Cys Ser Phe Ser Phe Ser Glu Val Ile Asn Val
            740                 745                 750

Pro Leu Gly Trp Gln Ala Leu Asn Lys Leu Ile His Trp Phe Tyr Ser
        755                 760                 765

Gly Glu Leu Pro Lys Ile Asp Pro Asp Cys Arg Trp Arg Asn Leu Asn
    770                 775                 780

Ser Glu Glu Gln Leu Ser Gln Leu Arg Pro Tyr Ala Glu Leu Ser Ser
785                 790                 795                 800

Leu Ser Glu Phe Trp Phe Leu Glu Gly Val Lys Glu Glu Ser Leu Ser
                805                 810                 815

Val Val Thr Ser Cys Leu Ser Ser Thr Ser Thr Ala Ala Ser Val Glu
            820                 825                 830

Phe Val Val Phe Ala Ala Gln Leu Gly Gln Trp Glu Met Val Glu Ala
        835                 840                 845

Ala Val Gly Ser Val Ala His Leu Tyr Pro Lys Leu Arg Asp Ser Gly
    850                 855                 860

Gln Leu Glu Gln Leu Asp Asp Asp Val Leu Asn Met Leu Arg Thr Glu
865                 870                 875                 880

Tyr Val Arg Arg Thr Gln Arg Thr Gly Val Gly Ser Ala Ala Ala Gln
                885                 890                 895

Ala Gly Ala Arg Val Val Thr Ala Val Tyr Arg Arg Gly Gln Arg Ala
            900                 905                 910

Asp Tyr Trp Gln Ser Gly Gly Phe Gly Asp Asn Trp Asn Phe Gln Met
        915                 920                 925

Val Ile Leu Asn Ala Ser Glu Glu His Cys Arg Glu Ser Lys Phe Asp
    930                 935                 940

Thr Ile Gly Val Cys Lys Ala Arg Phe Leu Tyr Gly Lys Val Ser Arg
945                 950                 955                 960

Gly Phe Arg Leu Arg Thr Ser Gly Ile Asn Lys Glu Gly Gly Pro Arg
                965                 970                 975
```

```
Gly Gly Thr Val Ile Tyr Ser Arg Ser Ser Gly Gly Leu Pro Pro Trp
            980                 985                 990

Cys Gly Ala Gly Ser His Asp Ala  Leu Ala Ala Val Arg  Trp Pro Ser
        995                 1000                 1005

Leu Pro  Gly Leu Glu Ser His  Gln Thr Ala Gln Val  Ile Arg Arg
    1010                 1015                 1020

Gly Ala  Gly Arg Arg Gly Glu  Gly Arg Asp Val Asn  Val Thr Lys
    1025                 1030                 1035

Gln Ser  Asn Ala Pro Met Arg  Pro Pro Glu Thr Met  Gln Arg Glu
    1040                 1045                 1050

Gln Pro  Gln Ser Arg Ala Arg  Ala Asn Gly Arg Lys  Trp Pro Pro
    1055                 1060                 1065

Pro Arg  Arg Trp Arg Ser Gly  Ile Arg Glu Glu Gln  Gly Val Pro
    1070                 1075                 1080

Ser Ala  Lys Ala Trp Gln Glu  Lys Arg Lys Arg Thr  Gln Gln Gln
    1085                 1090                 1095

Arg Cys  Ala Leu Pro Ala Ala  Ile Ala Ala Ser Arg  Leu Gln Leu
    1100                 1105                 1110


<210> SEQ ID NO 28
<211> LENGTH: 412
<212> TYPE: PRT
<213> ORGANISM: Oryza sativa

<400> SEQUENCE: 28

Met Ala Ser Ala Val Ala Ser Asn Leu Pro Ala Ala Ala Pro Ala Ala
1               5                   10                  15

Val Met Pro Phe Gly Gly Trp His Gly Pro Arg Val Ser Phe Ser Arg
            20                  25                  30

Asp Ala Ala Gly Ala Glu Glu Ala Ala Ala Val Val Val Cys Ser Ser
        35                  40                  45

Pro Leu Ala Ala Ala Ala Ala Val Ala Thr Thr Thr Thr Pro Glu Pro
    50                  55                  60

Ala Ile Ser Lys Asp Phe Ile Asp Phe Glu Phe Ser Leu Gly Gly Ser
65                  70                  75                  80

Ala Thr Met Leu Pro Ala Asp Glu Leu Phe Ala Asp Gly Lys Leu Leu
                85                  90                  95

Pro Leu Arg Lys Ala Ala Ala Val Pro Glu Met Asp Ala Ala Ala Pro
            100                 105                 110

Arg Pro Pro Gln Pro Glu Ala Met Pro Ala Pro Ser Glu Pro Met Lys
        115                 120                 125

Pro Leu Arg Ala Ala Thr Ala Ala Val Asp Ala Ala Asp Pro Tyr Val
    130                 135                 140

Phe Ser Pro Lys Ala Pro Ser Cys Ser Ser Arg Trp Arg Glu Leu Leu
145                 150                 155                 160

Gly Leu Lys Arg Ala Ala Ala Gln Ser Pro Lys Pro Ser Pro Ser Ser
                165                 170                 175

Ala Pro Ala Arg Thr Pro Gly Arg Ala Met Asn Ser Thr Ala Ala Arg
            180                 185                 190

Ser Leu Lys Leu Leu Leu Gln Arg Asn Asn Gly Arg Ser Ser Gly Ala
        195                 200                 205

Ser Ala Ser Glu Leu Ala Ser Ala Pro Leu Leu Arg Asp Ser Ser Asp
    210                 215                 220

Ser Glu Ala Ser Leu Ser Leu Ala Ser Ser Arg Phe Ser Leu Ser Ser
225                 230                 235                 240
```

```
Ser Ser Ser Ser Ser Gly His Asp His Asp Asp Ile Pro Arg Leu Ser
                245                 250                 255

Leu Asp Ser Ala Ala Asp Pro Asn Pro Pro Arg Ile Arg Leu Val Arg
            260                 265                 270

Ser Ser His Arg His Ser Thr Ser Ser Ser Ser Ser Ser Arg Ala Gly
        275                 280                 285

Arg Ser Pro Ala Arg Arg Arg Pro Ser Pro Pro Pro Pro Pro Arg Cys
    290                 295                 300

Leu Ser Val Asp Ser Pro Arg Met Asn Ser Ser Gly Lys Ile Val Phe
305                 310                 315                 320

Gln Gly Leu Glu Arg Ser Ser Ser Ser Pro Cys Thr Leu His Ala Ala
                325                 330                 335

Ala Lys Pro Arg Ser Arg Ala Val Asp Arg Ser Tyr Ser Ser Gly Val
            340                 345                 350

Arg Val Ala Pro Val Val Leu Asn Val Pro Val Cys Ser Arg Pro Val
        355                 360                 365

Phe Gly Phe Phe Lys Asp Lys Lys Asp Ala Ala Ala Lys Asp Ala Met
    370                 375                 380

Ala Ala Arg Thr Arg Ser Ser Leu Gly Arg Lys Thr Thr Ala Ala Pro
385                 390                 395                 400

Gln Gly Trp Ser Gly Glu Leu Gly Arg Ser Cys Gly
                405                 410


<210> SEQ ID NO 29
<211> LENGTH: 763
<212> TYPE: PRT
<213> ORGANISM: Oryza sativa

<400> SEQUENCE: 29

Met Lys Ile Ser Gly Leu Leu Thr Ser Ala Gly Ile Asn Ile Ala Leu
1               5                   10                  15

Ser Val Leu Phe Ile Ser Leu Tyr Ser Val Leu Arg Lys Gln Pro Ala
            20                  25                  30

Asn Val Arg Val Tyr Phe Gly Arg Arg Ile Ala Glu Glu His Asn Arg
        35                  40                  45

Leu Arg Glu Ala Phe Ile Leu Glu Arg Phe Val Pro Ser Thr Gly Trp
    50                  55                  60

Ile Val Lys Ala Leu Gln Cys Thr Glu Glu Glu Ile Leu Ala Ala Ala
65                  70                  75                  80

Gly Leu Asp Ala Val Val Phe Asn Arg Ile Leu Val Phe Ser Leu Arg
                85                  90                  95

Ile Phe Ser Leu Ala Ala Ile Leu Cys Val Phe Gly Ile Leu Pro Leu
            100                 105                 110

Asn Tyr Phe Gly Gln Asp Ile His His Val Arg Ile Pro Ser Glu Ser
        115                 120                 125

Leu Asp Ile Phe Thr Ile Gly Asn Val Lys Val Arg Ser Arg Trp Leu
    130                 135                 140

Trp Val His Cys Val Ala Leu Tyr Ile Ile Ser Gly Val Ala Cys Ile
145                 150                 155                 160

Leu Leu Tyr Leu Glu Tyr Lys His Ile Ala Arg Leu Arg Leu Arg His
                165                 170                 175

Leu Thr Cys Ala Met Pro Asn Pro Ser His Phe Thr Val Leu Val Arg
            180                 185                 190

Gly Ile Pro Lys Glu Thr Lys Glu Ser Cys Ser Asn Ala Ile Asp Asp
        195                 200                 205
```

```
Phe Phe Thr Lys Tyr His Gly Ser Ser Tyr Leu Phe His Gln Val Val
    210                 215                 220

Tyr Lys Val Gly Lys Val Gln Lys Ile Met Thr Gly Ala Lys Lys Ala
225                 230                 235                 240

Tyr Arg Lys Phe Lys His Phe Thr Asp Ser Thr Ile Asp Gln Arg Cys
                245                 250                 255

Arg Ala Ile Ser Tyr Arg Cys Cys Leu Cys Gly Ala Ser Ser Asn Ser
            260                 265                 270

Phe Gln Leu Leu Ala Thr Gly Leu Glu Gln Asn Gln Gly Lys Ser Asp
        275                 280                 285

Leu Gln Asp Ser Ser Leu Lys Leu Asp Asp Gln Glu Cys Ala Ala Ala
    290                 295                 300

Phe Val Tyr Phe Arg Thr Arg Tyr Ala Ala Leu Val Ala Ser Glu Ile
305                 310                 315                 320

Leu Gln Thr Ser Asn Pro Met Lys Trp Val Thr Asp Leu Ala Pro Glu
                325                 330                 335

Pro Asp Asp Val Tyr Trp Ser Asn Leu Trp Leu Pro Tyr Lys Gln Leu
            340                 345                 350

Trp Ile Arg Arg Ile Ala Thr Leu Leu Gly Ser Ile Val Phe Met Leu
        355                 360                 365

Phe Phe Leu Ile Pro Val Thr Phe Ile Gln Gly Leu Ser Gln Leu Glu
    370                 375                 380

Gln Leu Gln Gln Arg Leu Pro Phe Leu Lys Gly Ile Leu Glu Lys Lys
385                 390                 395                 400

Tyr Met Ser Gln Leu Val Thr Gly Tyr Leu Pro Ser Val Ile Leu Gln
                405                 410                 415

Ile Phe Leu Tyr Ala Val Ala Pro Ile Met Ile Leu Phe Ser Thr Leu
            420                 425                 430

Glu Gly Pro Ile Ser His Ser Glu Arg Lys Arg Ser Ala Cys Cys Lys
        435                 440                 445

Val Leu Tyr Phe Thr Val Trp Asn Ile Phe Phe Gly Asn Val Leu Ser
    450                 455                 460

Gly Thr Val Ile Ser Gln Leu Asn Val Leu Ser Ser Pro Lys Asp Ile
465                 470                 475                 480

Pro Val Gln Leu Ala Arg Ala Ile Pro Val Gln Ala Thr Phe Phe Ile
                485                 490                 495

Thr Tyr Val Leu Thr Ser Gly Trp Ala Ser Leu Ser Ser Glu Leu Met
            500                 505                 510

Gln Leu Phe Gly Leu Ile Trp Asn Phe Val Arg Lys Tyr Ile Leu Arg
        515                 520                 525

Met Pro Glu Asp Thr Glu Phe Val Pro Ser Phe Pro Tyr His Thr Glu
    530                 535                 540

Val Pro Lys Val Leu Leu Phe Gly Leu Leu Gly Phe Thr Cys Ser Val
545                 550                 555                 560

Leu Ala Pro Leu Ile Leu Pro Phe Leu Leu Val Tyr Phe Phe Leu Gly
                565                 570                 575

Tyr Ile Val Tyr Arg Asn Gln Leu Leu Asn Val Tyr Arg Thr Arg Tyr
            580                 585                 590

Asp Thr Gly Gly Leu Tyr Trp Pro Ile Ala His Asn Ala Val Ile Phe
        595                 600                 605

Ser Leu Val Leu Thr Gln Ile Ile Cys Leu Gly Val Phe Gly Leu Lys
    610                 615                 620

Glu Ser Pro Val Ala Ala Gly Phe Thr Ile Pro Leu Ile Ile Leu Thr
625                 630                 635                 640
```

```
Leu Leu Phe Asn Gln Tyr Cys Arg Asn Arg Leu Leu Pro Leu Phe Arg
                645                 650                 655

Thr Thr Pro Ala Gln Asp Leu Ile Asp Met Asp Arg Glu Asp Glu Arg
            660                 665                 670

Ser Gly Arg Met Asp Glu Ile His His Arg Leu His Ser Ala Tyr Cys
        675                 680                 685

Gln Phe His Asp Thr Glu Asp Ile Pro Leu Glu Lys Ile Gln Thr Val
    690                 695                 700

Gly Ser Asp Glu Glu Gln Gly Cys Ser Ser Asp Lys Ser Asn Gly Lys
705                 710                 715                 720

Glu Ser Phe Glu Glu Pro Arg Ala Glu Leu Ser His Pro Thr Leu Asn
                725                 730                 735

Gly Leu Pro Val Ser Arg Leu Arg His Ala Val Lys Ser Ile Thr Phe
            740                 745                 750

Leu Val Arg Leu Gln Lys Arg Gly Leu Ser Glu
        755                 760


<210> SEQ ID NO 30
<211> LENGTH: 471
<212> TYPE: PRT
<213> ORGANISM: Oryza sativa

<400> SEQUENCE: 30

Met Ala Ile Leu Arg Glu Phe Gly Thr Ile Glu Gly Met Glu Asn Leu
1               5                   10                  15

Leu Pro Glu Asp Val Leu Ser Asn Ile Ile His Arg Leu Ala Pro Arg
            20                  25                  30

Tyr Leu Ala Ile Ser Arg Cys Val Cys Lys Thr Trp Cys Thr Ile Ile
        35                  40                  45

Glu Ala His Asn Leu Leu His Val Asp Leu Leu Pro Arg Pro Leu Cys
    50                  55                  60

Gly Ile Phe Ile Asn Phe Asn Glu Leu Ser Met Ser Glu Phe Phe Ser
65                  70                  75                  80

Arg Pro Ser Lys Gly Pro Thr Val Ser Gly Asn Phe Asp Tyr Leu Pro
                85                  90                  95

Cys Ser Ser Cys Ile Ile Asp His Cys Asn Gly Leu Leu Leu Phe His
            100                 105                 110

Lys Tyr Val Val Asn Pro Ala Thr Arg Gln Ser Ala Pro Leu Pro Pro
        115                 120                 125

Cys Pro Tyr Met Val Val Glu His Ile Phe His Arg Glu Tyr Leu Val
    130                 135                 140

Phe Asp Pro Thr Leu Ser Pro His Phe Glu Val Phe Met Ile Pro Glu
145                 150                 155                 160

Ile Arg Arg Ser Asn Val Trp Tyr Asn Met Leu Asn Ser Asp Asp Lys
                165                 170                 175

Leu Asp Pro Ala Ile Glu Glu Leu Glu Trp Pro Pro Ser Pro Cys Ile
            180                 185                 190

Leu His Val Phe Ser Ser Arg Thr Lys Val Trp Glu Glu Arg Ser Phe
        195                 200                 205

Val Arg Glu Gly Glu Ala Ala Gly Asn Val Ser Asp Met Arg Leu Asp
    210                 215                 220

His Pro Tyr Val Pro Asp Thr Ser Val Tyr Val Pro Asp Thr Ser Val
225                 230                 235                 240

Tyr Cys Arg Gly Val Leu Tyr Val Tyr Cys Gln Asn Lys Tyr Val Met
                245                 250                 255
```

```
Arg Ile Ser Leu Ser Asn Gly Lys Tyr Gln Val Ile Lys Pro Pro Ser
            260                 265                 270

Asp Cys Glu Gly Met Ala Tyr Thr Asn Leu Tyr Leu Gly Lys Ser Met
        275                 280                 285

Lys Gly Val Tyr Cys Ala Val Arg His Leu Ala Ser Arg Phe Leu Ile
    290                 295                 300

Tyr Ile Leu Asp Glu Ser Ser Asp Arg Met Glu Trp Val Cys Lys Asp
305                 310                 315                 320

Ser Cys Ser Ile Gln Pro Cys Gln Ile Ile Asp Gly Pro Gly Pro Trp
                325                 330                 335

Thr Leu Gln Asp Ile Asn Asn Gln Glu Arg Gly Phe Glu Tyr Glu Asp
            340                 345                 350

Gly Asn Asn Glu Ala Val Val Glu Asp Arg Phe Glu Trp Asp Ser Asp
        355                 360                 365

Asn Asp Asn Val Ile Glu Thr Asn Ser Arg Gly Ser Gly Gly Tyr Ile
    370                 375                 380

Asn Phe Leu Val Asp Thr Thr Arg Arg Gly Arg Tyr Asn Ser Gly Gly
385                 390                 395                 400

Tyr Ile Asp Phe Leu Gly Phe His Pro Tyr Lys Glu Val Ile Phe Leu
                405                 410                 415

Ser Asp Ser Leu Arg Arg Gly Leu Ala Tyr His Leu Asn Ser Ser Lys
            420                 425                 430

Ile Gln Asp Leu Gly Ser Leu Arg Pro Thr Asn Tyr Gly Thr Glu Val
        435                 440                 445

Gly Ile Gln Pro Phe Ile Gln Lys Phe Phe Pro Tyr Ser Pro Trp Met
    450                 455                 460

Gly Arg Phe Pro Glu Asp Asn
465                 470


<210> SEQ ID NO 31
<211> LENGTH: 763
<212> TYPE: PRT
<213> ORGANISM: Oryza sativa

<400> SEQUENCE: 31

Met Lys Ile Ser Gly Leu Leu Thr Ser Ala Gly Ile Asn Ile Ala Leu
1               5                   10                  15

Ser Val Leu Phe Ile Ser Leu Tyr Ser Val Leu Arg Lys Gln Pro Ala
            20                  25                  30

Asn Val Arg Val Tyr Phe Gly Arg Arg Ile Ala Glu Glu His Asn Arg
        35                  40                  45

Leu Arg Glu Ala Phe Ile Leu Glu Arg Phe Val Pro Ser Thr Gly Trp
    50                  55                  60

Ile Val Lys Ala Leu Gln Cys Thr Glu Glu Glu Ile Leu Ala Ala Ala
65                  70                  75                  80

Gly Leu Asp Ala Val Val Phe Asn Arg Ile Leu Val Phe Ser Leu Arg
                85                  90                  95

Ile Phe Ser Leu Ala Ala Ile Leu Cys Val Phe Gly Ile Leu Pro Leu
            100                 105                 110

Asn Tyr Phe Gly Gln Asp Ile His His Val Arg Ile Pro Ser Glu Ser
        115                 120                 125

Leu Asp Ile Phe Thr Ile Gly Asn Val Lys Val Arg Ser Arg Trp Leu
    130                 135                 140

Trp Val His Cys Val Ala Leu Tyr Ile Ile Ser Gly Val Ala Cys Ile
145                 150                 155                 160
```

```
Leu Leu Tyr Leu Glu Tyr Lys His Ile Ala Arg Leu Arg Leu Arg His
                165                 170                 175

Leu Thr Cys Ala Met Pro Asn Pro Ser His Phe Thr Val Leu Val Arg
            180                 185                 190

Gly Ile Pro Lys Glu Thr Lys Glu Ser Cys Ser Asn Ala Ile Asp Asp
        195                 200                 205

Phe Phe Thr Lys Tyr His Gly Ser Ser Tyr Leu Phe His Gln Val Val
    210                 215                 220

Tyr Lys Val Gly Lys Val Gln Lys Ile Met Thr Gly Ala Lys Lys Ala
225                 230                 235                 240

Tyr Arg Lys Phe Lys His Phe Thr Asp Ser Thr Ile Asp Gln Arg Cys
                245                 250                 255

Arg Ala Ile Ser Tyr Arg Cys Cys Leu Cys Gly Ala Ser Ser Asn Ser
            260                 265                 270

Phe Gln Leu Leu Ala Thr Gly Leu Glu Gln Asn Gln Gly Lys Ser Asp
        275                 280                 285

Leu Gln Asp Ser Ser Leu Lys Leu Asp Asp Gln Glu Cys Ala Ala Ala
    290                 295                 300

Phe Val Tyr Phe Arg Thr Arg Tyr Ala Ala Leu Val Ala Ser Glu Ile
305                 310                 315                 320

Leu Gln Thr Ser Asn Pro Met Lys Trp Val Thr Asp Leu Ala Pro Glu
                325                 330                 335

Pro Asp Asp Val Tyr Trp Ser Asn Leu Trp Leu Pro Tyr Lys Gln Leu
            340                 345                 350

Trp Ile Arg Arg Ile Ala Thr Leu Leu Gly Ser Ile Val Phe Met Leu
        355                 360                 365

Phe Phe Leu Ile Pro Val Thr Phe Ile Gln Gly Leu Ser Gln Leu Glu
    370                 375                 380

Gln Leu Gln Gln Arg Leu Pro Phe Leu Lys Gly Ile Leu Glu Lys Lys
385                 390                 395                 400

Tyr Met Ser Gln Leu Val Thr Gly Tyr Leu Pro Ser Val Ile Leu Gln
                405                 410                 415

Ile Phe Leu Tyr Ala Val Ala Pro Ile Met Ile Leu Phe Ser Thr Leu
            420                 425                 430

Glu Gly Pro Ile Ser His Ser Glu Arg Lys Arg Ser Ala Cys Cys Lys
        435                 440                 445

Val Leu Tyr Phe Thr Val Trp Asn Ile Phe Phe Gly Asn Val Leu Ser
    450                 455                 460

Gly Thr Val Ile Ser Gln Leu Asn Val Leu Ser Ser Pro Lys Asp Ile
465                 470                 475                 480

Pro Val Gln Leu Ala Arg Ala Ile Pro Val Gln Ala Thr Phe Phe Ile
                485                 490                 495

Thr Tyr Val Leu Thr Ser Gly Trp Ala Ser Leu Ser Ser Glu Leu Met
            500                 505                 510

Gln Leu Phe Gly Leu Ile Trp Asn Phe Val Arg Lys Tyr Ile Leu Arg
        515                 520                 525

Met Pro Glu Asp Thr Glu Phe Val Pro Ser Phe Pro Tyr His Thr Glu
    530                 535                 540

Val Pro Lys Val Leu Leu Phe Gly Leu Leu Gly Phe Thr Cys Ser Val
545                 550                 555                 560

Leu Ala Pro Leu Ile Leu Pro Phe Leu Leu Val Tyr Phe Phe Leu Gly
                565                 570                 575

Tyr Ile Val Tyr Arg Asn Gln Leu Leu Asn Val Tyr Arg Thr Arg Tyr
```

```
            580                 585                 590

Asp Thr Gly Gly Leu Tyr Trp Pro Ile Ala His Asn Ala Val Ile Phe
        595                 600                 605

Ser Leu Val Leu Thr Gln Ile Ile Cys Leu Gly Val Phe Gly Leu Lys
    610                 615                 620

Glu Ser Pro Val Ala Ala Gly Phe Thr Ile Pro Leu Ile Ile Leu Thr
625                 630                 635                 640

Leu Leu Phe Asn Gln Tyr Cys Arg Asn Arg Leu Leu Pro Leu Phe Arg
                645                 650                 655

Thr Thr Pro Ala Gln Asp Leu Ile Asp Met Asp Arg Glu Asp Glu Arg
            660                 665                 670

Ser Gly Arg Met Asp Glu Ile His His Arg Leu His Ser Ala Tyr Cys
        675                 680                 685

Gln Phe His Asp Thr Glu Asp Ile Pro Leu Glu Lys Ile Gln Thr Val
    690                 695                 700

Gly Ser Asp Glu Glu Gln Gly Cys Ser Ser Asp Lys Ser Asn Gly Lys
705                 710                 715                 720

Glu Ser Phe Glu Glu Pro Arg Ala Glu Leu Ser His Pro Thr Leu Asn
                725                 730                 735

Gly Leu Pro Val Ser Arg Leu Arg His Ala Val Lys Ser Ile Thr Phe
            740                 745                 750

Leu Val Arg Leu Gln Lys Arg Gly Leu Ser Glu
        755                 760


<210> SEQ ID NO 32
<211> LENGTH: 247
<212> TYPE: PRT
<213> ORGANISM: Oryza sativa

<400> SEQUENCE: 32

Met Val Glu Leu Ser Ile Ala Asp Ala Ser Ala Ser Asp Leu Cys Gly
1               5                   10                  15

Gly Thr Leu Gly Gln Met Val Glu Leu Val Cys Glu Ala Arg Leu Arg
            20                  25                  30

Val Arg Glu Glu Tyr Val Arg Ser Thr Val Asp Leu Met Ala Leu Leu
        35                  40                  45

Arg Gly Arg Gly Met Val Phe Asp Gly Val Tyr Val Val Ser Asn Leu
    50                  55                  60

Thr Arg Leu Phe Ala Glu Leu Asp Phe Gly Arg Gly Glu Trp Val Val
65                  70                  75                  80

Ser Gly Met Ala Gln Pro Met Leu Ala Thr Phe Leu Val Thr Cys Arg
                85                  90                  95

Asn Gly Asp Asp Glu Asp Ala Val Ala Ala Ser Met Leu Leu Pro Pro
            100                 105                 110

Pro Val Lys Leu Arg Phe Ala Glu Glu Leu Ala Gly Leu Met Met Ser
        115                 120                 125

Met Pro His Gly Gly Ala Ala Leu Cys Pro Ala Pro Ala Ser Thr Tyr
    130                 135                 140

Leu Pro Leu Ser Met Arg Gly Arg Arg Trp Leu His Ile Pro Glu Gly
145                 150                 155                 160

Tyr Tyr Gly Asn Ala Leu Ala Tyr Ser Ile Thr Asp Ala Ser Ala Ser
                165                 170                 175

Asp Leu Cys Gly Ala Thr Leu Ala Gln Met Met Glu Leu Val Cys Glu
            180                 185                 190

Ala Arg Leu Arg Val Thr Glu Glu Tyr Gly Arg Ser Thr Val Asp Leu
```

```
        195                 200                 205

Met Ala Ser Leu Arg Gly His Asp Thr Val Phe Asp Gly Val Tyr Val
    210                 215                 220

Val Ser Asp Leu Gly Ala Gly Ser Gly Trp Ser Ala Ala Trp Pro Ser
225                 230                 235                 240

Arg Cys Trp Arg Arg Ser Trp
                245


<210> SEQ ID NO 33
<211> LENGTH: 144
<212> TYPE: PRT
<213> ORGANISM: Oryza sativa

<400> SEQUENCE: 33

Met Asn Gln Gln His Gln Arg Ser Ile Glu His Cys Ser Ile Gly Cys
1               5                   10                  15

Phe Leu Ala Ser Pro Pro Pro Arg Phe Phe Pro Ala Arg Thr Arg Ser
            20                  25                  30

Ala Pro Gly Glu Leu Arg Met Lys Leu Val Val Phe Leu Ile Arg Gly
        35                  40                  45

Cys Pro Gly Glu Val Leu Leu Arg Pro Ile Val Pro Ala Lys Glu Gly
    50                  55                  60

Leu Arg Thr Arg Thr Lys Trp His Ile Leu Gln Arg Phe Cys Lys Leu
65                  70                  75                  80

Glu Ile Ile Ser Ile Glu Thr Glu Thr Met Ile Thr Ile Ser Ser Arg
                85                  90                  95

Ser Ile Ile Lys Ser Arg Cys Lys Lys Ser Asn Lys Lys Ile Leu Val
            100                 105                 110

Phe Phe Leu Ser Met Ser Val Lys Phe Leu Leu Ile Thr Thr Arg Arg
        115                 120                 125

Ser Leu Ser Val Gln Lys Arg Ser Ser Thr Phe Ser Gln Leu Leu His
    130                 135                 140


<210> SEQ ID NO 34
<211> LENGTH: 94
<212> TYPE: PRT
<213> ORGANISM: Oryza sativa

<400> SEQUENCE: 34

Met Cys Met Asp Arg Ala Ala Val Pro Val Lys Arg Val Trp Leu Gly
1               5                   10                  15

Leu Ala Ala Arg Leu Gly Leu Arg Arg Thr Ser Gly Leu Gly Lys Leu
            20                  25                  30

Lys Lys Glu Val Arg Thr Cys Glu Tyr His Asp Val His Ile Met Trp
        35                  40                  45

Glu Met Leu Arg Lys Thr Asp Ala Pro Val Pro Met Ala Glu Lys Glu
    50                  55                  60

Ala Ala Ala Ala Ala Ala Val Ala Ala Ala Ala Gly Ala Arg Arg Arg
65                  70                  75                  80

Lys Ala Ala Trp Arg Arg Phe Leu Tyr Tyr Cys Cys Ala Phe
                85                  90


<210> SEQ ID NO 35
<211> LENGTH: 303
<212> TYPE: PRT
<213> ORGANISM: Oryza sativa

<400> SEQUENCE: 35
```

```
Met Ala Thr Ser Arg Lys Leu Ala Arg Val Asp Ile Ala Glu Leu Lys
1               5                   10                  15

Gln Arg Leu Val Lys Arg Leu Gly Arg Gln Arg Ala Gly Gln Tyr Phe
            20                  25                  30

Ala His Leu Thr Arg Leu Leu Asn Leu Lys Leu Thr Lys Val Glu Phe
        35                  40                  45

Asp Lys Leu Cys Tyr Ala Thr Ile Gly Arg Glu Asn Ile Ala Leu His
    50                  55                  60

Asn Ala Leu Ile Arg Gly Ile Ile Ser Asn Ala Leu Ser Gly Val Pro
65                  70                  75                  80

Pro Pro Ser Arg Gln Ala Val Thr Gly Gln Ser Gly Thr Thr Thr Ala
                85                  90                  95

Pro Ser Gly Gln Cys Val Gly Ile Ala Leu Gln Ser Ala Arg Asn Val
            100                 105                 110

Gly Ala Val Val Asp Ser Gly Asp Gly Asp Phe Ala Arg Glu Arg Ala
        115                 120                 125

Val Ala Gly Lys Val Leu Ser Val Glu Asp Gly Glu Glu Val Glu Gln
    130                 135                 140

Val Arg Ser Ala Pro Cys Val Gln Ser Arg Ser Pro Ile Thr Ala Pro
145                 150                 155                 160

Leu Gly Ile Ser Thr Thr Pro Thr Tyr Gly Ala Arg Thr Trp Arg Leu
                165                 170                 175

Asp Asp Pro Met Val Ser Cys Tyr Asp Ser His His Leu Leu Asp Thr
            180                 185                 190

Gly Ser Leu Phe Lys Gly Leu Gln Arg Arg Leu Glu Ser Asp Gly Ile
        195                 200                 205

Gly Val Ser Val Gln Gly Val Glu Val Leu Asn Arg Gly Leu Asp Glu
    210                 215                 220

Phe Leu Arg Arg Leu Ile Lys Pro Cys Met Glu Leu Ser Arg Ser Arg
225                 230                 235                 240

Ser Ser Gly Arg Arg Val Thr Lys Gly Asn Ala Met Phe Ala Ala Arg
                245                 250                 255

Met Asn Gly Leu Gln Gln Ala Asn His Gly His Cys Thr Thr Leu Gln
            260                 265                 270

Asp Phe Ala Val Ala Met Glu Ser Asp Pro His Leu Leu Gly Thr Asn
        275                 280                 285

Trp Pro Thr Gln Leu Glu Lys Ile Gln Ala Thr Ser Phe Gly Glu
    290                 295                 300
```

<210> SEQ ID NO 36
<211> LENGTH: 186
<212> TYPE: PRT
<213> ORGANISM: Oryza sativa

<400> SEQUENCE: 36

```
Met Ala Ser Pro Arg Cys Ala Ala Val Ala Leu Leu His Pro Ala Gly
1               5                   10                  15

Val Ala Ala Gly Gly Gly Ala Arg Arg Arg Val Leu Leu Leu Asp Gln
            20                  25                  30

Glu Arg Pro Leu Trp Gly Thr Glu Val Arg Arg Arg Arg Arg Arg Arg
        35                  40                  45

Phe Ser Ser Leu Glu Thr Pro Pro Arg Cys Ser Lys Met Tyr Val Pro
    50                  55                  60

Gly Phe Gly Glu Gly Ser Pro Glu Lys Lys Ala Ala Arg Asn Leu Gln
65                  70                  75                  80
```

```
His Phe Phe Asn Tyr Ile Ala Val Arg Val Val Leu Thr Gln Leu Glu
                85                  90                  95

Ser Tyr Asn Arg Glu Ala Tyr Gly Glu Leu Met Asp Phe Val Asn Arg
            100                 105                 110

Asn Ser Leu Asn Asp Ala Asp Thr Phe Cys Lys Lys Leu Ile Arg Glu
        115                 120                 125

Ser Pro Arg His Lys Gln Leu Ala Met Arg Ile Leu Glu Val Arg Ser
    130                 135                 140

Ala Tyr Val Lys His Asp Phe Glu Trp Asp Asn Leu Lys Arg Leu Ser
145                 150                 155                 160

Phe Lys Met Val Asp Glu Ala Asn Thr Lys Leu Met Arg Asp Tyr Val
                165                 170                 175

Leu Glu Thr Ser His Ile Glu Asp Asp Asn
            180                 185


<210> SEQ ID NO 37
<211> LENGTH: 347
<212> TYPE: PRT
<213> ORGANISM: Oryza sativa

<400> SEQUENCE: 37

Met Asp Ile Thr Gly Ala Gly Ala Met Gly Gly Gly Ser Thr Ala Ala
1               5                   10                  15

Thr Ala Ala Ala Ala Ala Gly Ala Gly Trp Lys Thr Pro Val Ser Met
            20                  25                  30

Val Leu Val Gln Leu Phe Ile Thr Gly Gln Ile Leu Leu Ser Lys Val
        35                  40                  45

Ser Ile Gly Gly Gly Met Leu Ile Phe Val Leu Leu Ala Tyr Asn Ser
    50                  55                  60

Phe Phe Ala Val Val Phe Leu Leu Pro Phe Ala Leu Ile Phe Glu Arg
65                  70                  75                  80

Gly Lys Trp Arg Asp Met Asp Trp Gly Ala Phe Gly Trp Ile Phe Leu
                85                  90                  95

Asn Ala Phe Ile Gly Tyr Ser Val Pro Met Ser Leu Tyr Tyr Tyr Gly
            100                 105                 110

Leu Lys Asp Thr Thr Ser Ser Tyr Ser Val Ile Phe Leu Asn Ile Thr
        115                 120                 125

Pro Leu Phe Thr Phe Ile Leu Ser Leu Met Phe Arg Leu Glu Ala Phe
    130                 135                 140

Lys Leu Arg Ser Ile Pro Gly Val Leu Lys Ile Ala Ser Ile Leu Leu
145                 150                 155                 160

Ser Ile Gly Gly Thr Met Leu Ile Ser Leu Tyr Lys Gly Lys Ser Leu
                165                 170                 175

His Leu Trp Asp Ser Ile Ile Gln His Gln Asn Glu His Lys Ser Ala
            180                 185                 190

Thr Asn Gln Leu Arg Gly Thr Ile Leu Leu Val Gly Ser Ser Phe Thr
        195                 200                 205

Phe Ala Cys Trp Phe Leu Ile Gln Ser Lys Ile Leu Lys Val Tyr Pro
    210                 215                 220

Tyr Lys Tyr Trp Ser Ser Met Val Thr Cys Leu Val Gly Val Phe Gln
225                 230                 235                 240

Thr Ala Leu Val Gly Ile Ile Leu Arg Arg Asp Lys Ser Ala Trp Glu
                245                 250                 255

Leu Gly Trp Asn Leu Asn Leu Val Thr Ile Val Tyr Thr Gly Ala Leu
            260                 265                 270
```

```
Ala Thr Ala Gly Lys Tyr Ile Leu Asn Ser Trp Ala Ile Thr Lys Arg
        275                 280                 285

Gly Pro Thr Tyr Pro Thr Met Phe Ser Pro Leu Ser Val Val Phe Thr
    290                 295                 300

Val Val Leu Asp Ser Val Leu Leu Gly Asn Asp Ile Thr Ile Gly Ser
305                 310                 315                 320

Leu Leu Gly Thr Ala Leu Val Ile Val Gly Leu Tyr Leu Phe Leu Trp
                325                 330                 335

Ala Lys Ala Arg Glu Ile Pro Lys Lys Ser Thr
            340                 345


<210> SEQ ID NO 38
<211> LENGTH: 175
<212> TYPE: PRT
<213> ORGANISM: Oryza sativa

<400> SEQUENCE: 38

Met Ala Arg Arg Ala Ala Glu Lys Glu Ala Ala Leu Arg Gln Gly Leu
1               5                   10                  15

Thr Ala Gly Asp Gly Glu Ala Arg Arg Thr Gly Ala Leu Trp Arg Thr
            20                  25                  30

Asp Ala Trp Arg Gln Arg Ala Ala Ala Ser Ala Ala Ala Ala Ser Val
        35                  40                  45

Val Arg Thr Trp Pro Ser Ser Ala Pro Trp Leu Arg Phe Glu Leu Asp
    50                  55                  60

Pro Trp Arg Arg Val Cys Gly Glu Gln Asp Leu Gln Thr Ala Ala Cys
65                  70                  75                  80

Gly Gly Gly Asp Gly Ala Val Gly Leu Ser Phe Glu Thr His His Gly
                85                  90                  95

Gly Ser Val Ala Pro Ser Pro Glu Phe Ala Ala Cys Ala Ala Ser Ser
            100                 105                 110

Cys Ser Ala Glu Leu Met Val Leu Leu Val Leu Gln Arg Gly Glu Leu
        115                 120                 125

Leu Val Arg His Asp Arg Pro Ser His His His Arg Arg Arg Phe Pro
    130                 135                 140

Thr Pro Gln Pro Ala Glu Ala Ala Ala Ala Val Glu Val Gly Trp Gly
145                 150                 155                 160

Phe Gln Asn Pro Arg Asp Ala Met Thr Cys Leu Cys Lys Gly Leu
                165                 170                 175


<210> SEQ ID NO 39
<211> LENGTH: 306
<212> TYPE: PRT
<213> ORGANISM: Oryza sativa

<400> SEQUENCE: 39

Met Gly Ser Gly Gly Gly Gly Cys Gly Arg Asn Gly Ala Val Arg Gln
1               5                   10                  15

Tyr Ile Arg Ser Lys Val Pro Arg Leu Arg Trp Thr Gly Glu Leu His
            20                  25                  30

Cys Ser Phe Val Gln Ala Ile Glu Phe Leu Gly Gly Gln Asp Lys Ala
        35                  40                  45

Thr Pro Lys Leu Ile Leu Gln Leu Met Gly Val Lys Gly Leu Thr Ile
    50                  55                  60

Ser His Val Lys Ser His Leu Gln Met Tyr Arg Cys Ser Arg Leu Gly
65                  70                  75                  80

Ser His Gly Thr Gly Arg Arg Ser Glu Met Gln Pro Gln Leu Gln Arg
```

```
                85                  90                  95

Lys His Ser Cys Gly Ala Asp Glu Gln Val Pro Arg Glu Phe Leu Cys
            100                 105                 110

Pro Pro Leu Lys Arg Thr Arg Met Gly Thr Glu Ala Thr Tyr Lys Gly
        115                 120                 125

Met Gln Gly Ser Gln Gly Ile Ser Glu Met Arg Thr Thr Gly Thr Gln
    130                 135                 140

Tyr Cys Ile Asp Asp Tyr Met Gln Ala Met Ala Met Glu Arg Arg Ile
145                 150                 155                 160

Lys Glu Glu Gly Leu Arg Trp Gln Arg Asp Ala Ala Ala Ala Ala Ala
                165                 170                 175

Ala Asp Gly Gly Ala Ala Ala Ser Asn Leu Gln Thr Val Gly Cys Ser
            180                 185                 190

Val Gln Glu Ser Asp Pro Phe Lys Ile Ile Lys Pro Glu Val His His
        195                 200                 205

Leu Gly Pro Val Leu Lys Leu Gln Cys Ser Lys Val Glu Asn Ser Gly
    210                 215                 220

Phe Ile Ser Ser Ser Thr Gly Thr Ala Ala Arg Asp Gln Pro Glu Pro
225                 230                 235                 240

Pro Pro Leu Glu Lys Cys Ser Leu Ser Leu Ser Leu Gly Pro Asp Pro
                245                 250                 255

Lys Cys Met Pro Ala Ile Ala Ser Ser Pro Ser Glu Ser Ser Cys Ile
            260                 265                 270

Leu Ser Ser Ser Ser Arg Ser Phe Ser Asp Cys Ser Gly Asn Ser Gly
        275                 280                 285

Cys Leu Val Ala Pro Gly Val Asn Leu Glu Leu Ser Met Ser Ile Cys
    290                 295                 300

Gly Ser
305
```

<210> SEQ ID NO 40
<211> LENGTH: 187
<212> TYPE: PRT
<213> ORGANISM: Oryza sativa

<400> SEQUENCE: 40

```
Met Ala Ala Ala Asp Gln Pro Ala Tyr Gly Asp Arg Arg Pro Ser Arg
1               5                   10                  15

Arg Thr Tyr Lys Pro Asp Gln Pro Glu Gly Leu Thr Ile Ser Phe Arg
            20                  25                  30

Glu Leu Tyr Asp Leu Pro Thr Ser Pro Glu Phe Leu Phe His Glu Glu
        35                  40                  45

Ala Leu Arg Ser Arg Arg Thr Cys Gly Glu Asp Leu Thr Phe Tyr Thr
    50                  55                  60

Gly Cys Gly Tyr Leu Val Gly Arg Ala Ala Gly Ala Ala Ala Gly Leu
65                  70                  75                  80

Lys Arg Ala Ala Glu Glu Ala Glu Arg Gly Glu Ser Met Lys Leu Arg
                85                  90                  95

Gly Gln Pro Arg Pro Gln Pro Val Arg Leu Pro Arg Ala Arg Val Arg
            100                 105                 110

Gln Pro Ala Arg Arg Arg Arg Ala Ala Leu Arg Gly Asp Arg Glu His
        115                 120                 125

Arg Gly Gly Pro Pro Arg Arg Arg Arg Leu Gly Gln His Arg Arg Arg
    130                 135                 140

Arg Asp Arg Tyr Arg Arg Ala Leu Pro Arg Gly Cys Arg Pro Ala Gly
```

```
145                 150                 155                 160

Gly Asp Arg Arg Gln Leu Arg Arg Gly Ala His Gly Arg Arg Gly Gly
                165                 170                 175

Arg Gly Glu Ala Ser Ala Asp Glu Ile Arg Ala
            180                 185


<210> SEQ ID NO 41
<211> LENGTH: 424
<212> TYPE: PRT
<213> ORGANISM: Oryza sativa

<400> SEQUENCE: 41

Met Asp Met Pro Pro Thr Pro Leu Pro Pro Glu Thr Ala Asn Thr Ser
1               5                   10                  15

Pro Ala Pro Asn Gly Ala Thr Ala Gly Ile Arg Val Glu Asn Cys Tyr
            20                  25                  30

Val Phe Lys Ser Arg Leu Gln Glu Tyr Ala Gln Lys Thr Gly Leu Gln
        35                  40                  45

Thr Pro Glu Tyr His Thr Phe Lys Glu Gly Pro Ser His Glu Pro Val
    50                  55                  60

Phe Lys Ser Thr Val Val Ile Asn Asn Thr Ser Tyr Asp Ser Leu Pro
65                  70                  75                  80

Gly Phe Phe Asn Arg Lys Ala Ala Glu Gln Ser Ala Ala Glu Val Ala
                85                  90                  95

Leu Met Glu Ile Val Lys Ser Ile Pro Ala Asn Ala Asn Ile Pro Ala
            100                 105                 110

Val Gln Glu Thr Gly Leu Cys Lys Asn Leu Leu Gln Glu Tyr Ala Gln
        115                 120                 125

Lys Met Asn Tyr Ala Ile Pro Ser Tyr Ile Cys Thr Lys Ser Ala Ser
    130                 135                 140

Gly Leu Ala Pro Phe Ile Cys Thr Val Glu Ile Gly Gly Ile Gln Tyr
145                 150                 155                 160

Ile Gly Ala Ala Ala Arg Thr Lys Lys Asp Ala Glu Ile Lys Ala Ala
                165                 170                 175

Arg Thr Ala Leu Leu Ala Ile Gln Gly Gln Ser Glu Gly Ser Ala Asn
            180                 185                 190

Gly Ala Thr Lys Tyr Ile Val Val Pro Gly Lys Arg Val Gly Lys Glu
        195                 200                 205

Val Glu Lys Arg Pro Ile Glu Thr Pro Lys Pro Leu Lys Val Lys Lys
    210                 215                 220

Gly Gly Phe Lys Lys Lys Trp Asn Lys Arg Lys Phe Met Lys Lys Asp
225                 230                 235                 240

Gly Gln Ala Val Asp Val Glu Lys Asp Glu Ala Arg Val Ala Gly Asp
                245                 250                 255

Ala His Asp Ser Asp Val Leu Met Gln Pro Thr Val Ile Thr Gln Glu
            260                 265                 270

Ala Ser Cys Gly Thr Leu Phe Leu Gln Pro Cys Glu Glu Ala Lys Arg
        275                 280                 285

Val Glu Ala Glu Pro Pro Arg Asp Ile Glu Met Val Gln Pro Asp Lys
    290                 295                 300

Glu Asn Gln His Ser Asp Ala Ala Leu Val Gln Pro Asp Asp Glu Ala
305                 310                 315                 320

Arg Val Glu Gln Glu Pro Ser Arg Asp Ile Ser Val Val Gln Pro Asn
                325                 330                 335

Glu Glu Ala Ile Ser Gly Lys Gln Glu Pro Ser Ile Asp Ala Ala Ile
```

```
            340                 345                 350

Leu Gln Pro Lys Glu Glu Ala Ser Ser Val Lys Gln Glu Pro Phe Ile
        355                 360                 365

Asp Thr Ala Met Leu Gln Ala Cys Lys Glu Ala Gly Ser Val Glu Leu
    370                 375                 380

Gly Pro Ala Arg Asp Thr Val Ile Ser Gln Leu Asn Glu Gln Asp Arg
385                 390                 395                 400

Ala Val Lys Gln Glu Pro Ala Gly Asp Ile Val Val Pro Gln Pro Asp
                405                 410                 415

Val His Ala Arg Val Val Lys Glu
            420


<210> SEQ ID NO 42
<211> LENGTH: 1359
<212> TYPE: PRT
<213> ORGANISM: Oryza sativa

<400> SEQUENCE: 42

Met Ala Leu Gly Asp Leu Met Ala Ser Arg Leu Val His Ser Ser Ser
1               5                   10                  15

Ser Ser Ala Ala Pro Ser Ala Ala Leu Pro Asn His His Thr Asn His
            20                  25                  30

Leu Val Asp Asp His Leu Pro Val Glu Asn Gly Pro Asp Pro Arg Arg
        35                  40                  45

Asp Val Pro Asp Glu Glu Pro Pro Pro Pro Pro Pro Pro Gln Val Ala
    50                  55                  60

Leu Leu Pro Gln Val Val Val Leu Cys Glu Gln Arg His Glu Gly Phe
65                  70                  75                  80

Asp Glu Ala Ala Ala Ala Ala Ala Gly Pro Ser Thr Ser Gly Pro Val
                85                  90                  95

Ser Lys Trp Arg Pro Lys Asp Arg Met Lys Thr Gly Cys Val Ala Leu
            100                 105                 110

Val Leu Cys Leu Asn Ile Ser Val Asp Pro Pro Asp Val Ile Lys Ile
        115                 120                 125

Ser Pro Cys Ala Arg Lys Glu Cys Trp Ile Asp Pro Phe Ser Met Ala
    130                 135                 140

Pro Pro Lys Ala Leu Glu Thr Ile Gly Lys Thr Leu His Ser Gln Tyr
145                 150                 155                 160

Glu Arg Trp Gln Pro Lys Ala Arg Tyr Lys Leu Gln Leu Asp Pro Thr
                165                 170                 175

Leu Glu Glu Val Lys Lys Leu Cys Asn Thr Cys Arg Lys Phe Ala Arg
            180                 185                 190

Thr Glu Arg Val Leu Phe His Tyr Asn Gly His Gly Val Pro Lys Pro
        195                 200                 205

Thr Ala Asn Gly Glu Ile Trp Val Phe Asn Lys Ser Tyr Thr Gln Tyr
    210                 215                 220

Ile Pro Leu Pro Ile Thr Asp Leu Asp Ser Trp Leu Lys Thr Pro Ser
225                 230                 235                 240

Ile Tyr Val Phe Asp Cys Ser Ala Ala Gly Met Ile Val Lys Ala Phe
                245                 250                 255

Leu Glu Arg Leu Asp Trp Ser Ser Ser Ser Ser Ala Ser Ser Ser Lys
            260                 265                 270

Asp Cys Ile Leu Leu Ala Ala Cys Glu Ala His Gln Thr Leu Pro Gln
        275                 280                 285

Ser Ala Glu Phe Pro Ala Asp Val Phe Thr Ala Cys Leu Thr Thr Pro
```

-continued

```
    290                 295                 300

Ile Lys Met Ala Leu His Trp Phe Cys Asn Arg Ser Leu Leu Arg Asp
305                 310                 315                 320

Ser Met Glu His Asn Leu Ile Asp Gln Ile Pro Gly Arg Gln Asn Asp
                325                 330                 335

Arg Lys Thr Leu Leu Gly Glu Leu Asn Trp Ile Phe Thr Ala Ile Thr
            340                 345                 350

Asp Thr Ile Ala Trp Asn Val Leu Pro His Asp Leu Phe Gln Arg Leu
        355                 360                 365

Phe Arg Gln Asp Leu Leu Val Ala Ser Leu Phe Arg Asn Phe Leu Leu
    370                 375                 380

Ala Glu Arg Ile Met Arg Ser Ala Asn Cys Ser Pro Ile Ser Tyr Pro
385                 390                 395                 400

Leu Leu Pro Pro Thr His Gln His His Met Trp Asp Ala Trp Asp Met
                405                 410                 415

Ala Ala Glu Ile Cys Leu Ser Lys Leu Pro Gln Leu Ile Ala Asp Pro
            420                 425                 430

Asn Ala Glu Phe Gln Pro Ser Pro Phe Phe Thr Glu Gln Leu Thr Ala
        435                 440                 445

Phe Glu Val Trp Leu Asp His Gly Ser Glu Asp Lys Lys Pro Pro Glu
    450                 455                 460

Gln Leu Pro Ile Val Leu Gln Val Leu Leu Ser Gln Ser His Arg Phe
465                 470                 475                 480

Arg Ala Leu Val Leu Leu Gly Arg Phe Leu Asp Met Gly Pro Trp Ala
                485                 490                 495

Val Asp Leu Ala Leu Ser Val Gly Ile Phe Pro Tyr Val Leu Lys Leu
            500                 505                 510

Leu Gln Thr Ser Ala Met Glu Leu Arg Gln Ile Leu Val Phe Ile Trp
        515                 520                 525

Thr Lys Ile Leu Ser Leu Asp Lys Ser Cys Gln Val Asp Leu Val Lys
    530                 535                 540

Asp Gly Gly His Ala Tyr Phe Ile Arg Phe Leu Asp Ser Leu Asp Ala
545                 550                 555                 560

Tyr Pro Glu Gln Arg Ala Met Ala Ala Phe Val Leu Ala Val Ile Val
                565                 570                 575

Asp Gly His Arg Ile Gly Gln Glu Ala Cys Ala Asn Ala Gly Leu Ile
            580                 585                 590

Asp Val Cys Leu Arg His Leu Gln Pro Glu Asn Pro Asn Asp Ala Gln
        595                 600                 605

Thr Glu Pro Leu Leu Leu Gln Trp Leu Cys Leu Cys Leu Gly Lys Leu
    610                 615                 620

Trp Glu Asp Phe Pro Glu Ala Gln Leu Leu Gly Leu Gln Ser Asn Ala
625                 630                 635                 640

Pro Glu Ile Val Ile Cys Leu Leu Ser Glu Pro Gln Pro Glu Val Arg
                645                 650                 655

Ala Ser Ala Val Phe Ala Leu Gly Asn Leu Val Asp Ile Gly Ser Pro
            660                 665                 670

Ser Leu Asn Gly Ala Asp Asp Asp Ser Asp Asp Asp Glu Lys Val Arg
        675                 680                 685

Ala Glu Ile Asn Val Val Arg Ser Leu Leu Gln Ile Ser Ser Asp Gly
    690                 695                 700

Ser Pro Leu Val Arg Ser Glu Val Ala Val Ala Leu Thr Arg Phe Ala
705                 710                 715                 720
```

-continued

```
Met Gly His Asn Lys His Ile Lys Ser Val Ala Ala Glu Tyr Trp Lys
                725                 730                 735

Pro Gln Thr Asn Ser Leu Leu Lys Ser Leu Pro Ser Leu Ala Asn Ile
            740                 745                 750

Asn Ser Ser Asn Val Tyr Ser Pro Ser Ser Leu Ile Gln Gly Ser Ser
        755                 760                 765

Gly Leu Ala Ser His Ile Gly Pro Val Leu Arg Val Gly Ser Asp Asn
    770                 775                 780

Ser Ala Thr Ala Arg Asp Gly Arg Ile Ser Thr Ser Ser Pro Ile Ala
785                 790                 795                 800

Thr Asn Ser Ile Met His Gly Ser Pro Gln Ser Asp Asp Ser Ser Gln
                805                 810                 815

His Ser Asp Ser Gly Ile Leu Leu Arg Glu Asn Ala Ser Asn Gly Gly
            820                 825                 830

Leu Asn Tyr Ser Arg Ser Arg Pro Ile Asp Asn Gly Ile Tyr Ser Gln
        835                 840                 845

Phe Ile Ala Thr Met Cys Asn Val Ala Lys Asp Pro Tyr Pro Arg Ile
    850                 855                 860

Ala Ser Ile Gly Lys Arg Ala Leu Ser Leu Ile Gly Val Glu Gln Val
865                 870                 875                 880

Ser Met Arg Asn Ser Arg Leu Ser Asn Gly Gly Ala His Pro Gly Glu
                885                 890                 895

Thr Ser Val Pro Pro Ser Ser Asn Phe Gly Met Ala Arg Ser Ser Ser
            900                 905                 910

Trp Phe Asp Met Asn Ser Gly Asn Phe Ser Val Ala Phe Arg Thr Pro
        915                 920                 925

Pro Val Ser Pro Pro Gln His Asp Tyr Leu Thr Gly Leu Arg Arg Val
    930                 935                 940

Cys Ser Met Glu Phe Arg Pro His Val Leu Asn Ser Pro Asp Gly Leu
945                 950                 955                 960

Ala Asp Pro Leu Leu Ser Ser Ser Ala Ala Pro Ser Asn Met Gly Leu
                965                 970                 975

Tyr Ile Leu Pro Gln Ser Leu Ile Tyr Arg Trp Ser Cys Gly His Phe
            980                 985                 990

Ser Arg Pro Leu Leu Thr Gly Ser  Asp Asp Asn Glu Glu  Ala Asn Ala
        995                 1000                1005

Arg Arg  Glu Glu Arg Glu Arg  Ile Ala Met Asp Cys  Ile Ala Lys
    1010                1015                1020

Cys Gln  Arg Ser Ser Cys Lys  Met Thr Ser Gln Ile  Ala Ser Trp
    1025                1030                1035

Asp Thr  Arg Phe Glu Leu Gly  Thr Lys Ala Ser Leu  Leu Leu Pro
    1040                1045                1050

Phe Ser  Pro Ile Val Val Ala  Ala Asp Glu Asn Glu  Gln Ile Arg
    1055                1060                1065

Val Trp  Asn Tyr Asp Asp Ala  Leu Pro Val Asn Thr  Phe Glu Asn
    1070                1075                1080

His Lys  Leu Ser Asp Arg Gly  Leu Ser Lys Leu Leu  Leu Ile Asn
    1085                1090                1095

Glu Leu  Asp Asp Ser Leu Leu  Leu Val Gly Ser Ser  Asp Gly Asn
    1100                1105                1110

Val Arg  Ile Trp Arg Asn Tyr  Thr Gln Lys Gly Gly  Gln Lys Leu
    1115                1120                1125

Val Thr  Ala Phe Ser Ser Val  Gln Gly Tyr Arg Ser  Ala Gly Arg
    1130                1135                1140
```

```
Ser Ile  Val Phe Asp Trp Gln  Gln Gln Ser Gly Tyr  Leu Tyr Ala
    1145                 1150                 1155

Ser Gly  Asp Met Ser Ser Ile  Leu Val Trp Asp Leu  Asp Lys Glu
    1160                 1165                 1170

Gln Val  Asn Thr Ile Gln Ser  Thr Ala Asp Ser Gly  Ile Ser Ala
    1175                 1180                 1185

Leu Ser  Ala Ser Gln Val Arg  Cys Gly Gln Phe Ala  Ala Gly Phe
    1190                 1195                 1200

Leu Asp  Ala Ser Val Arg Ile  Phe Asp Val Arg Thr  Pro Asp Arg
    1205                 1210                 1215

Leu Val  Tyr Thr Ala Arg Pro  His Ala Pro Arg Ser  Glu Lys Val
    1220                 1225                 1230

Val Gly  Ile Gly Phe Gln Pro  Gly Phe Asp Pro Tyr  Lys Ile Val
    1235                 1240                 1245

Ser Ala  Ser Gln Ala Gly Asp  Ile Gln Phe Leu Asp  Val Arg Arg
    1250                 1255                 1260

Ala Ser  Glu Pro Tyr Leu Thr  Ile Glu Ala His Arg  Gly Ser Leu
    1265                 1270                 1275

Thr Ala  Leu Ala Val His Arg  His Ala Pro Val Ile  Ala Ser Gly
    1280                 1285                 1290

Ser Ala  Lys Gln Met Ile Lys  Val Phe Ser Leu Glu  Gly Glu Gln
    1295                 1300                 1305

Leu Thr  Ile Ile Arg Tyr Gln  Pro Ser Phe Met Gly  Gln Arg Ile
    1310                 1315                 1320

Gly Ser  Val Asn Cys Leu Ser  Phe His Arg Tyr Lys  Ser Leu Leu
    1325                 1330                 1335

Ala Ala  Gly Ala Gly Asp Asn  Ala Leu Val Ser Ile  Tyr Ala Glu
    1340                 1345                 1350

Asp Asn  Tyr Gln Val Arg
    1355
```

<210> SEQ ID NO 43
<211> LENGTH: 233
<212> TYPE: PRT
<213> ORGANISM: Oryza sativa

<400> SEQUENCE: 43

```
Met Gly Ala Ser Gly Arg Leu Ile Ser Ile Tyr Pro Glu Asp Leu Thr
1               5                   10                  15

Phe Leu Phe Glu Leu Asp Lys Pro Cys Tyr Cys Asn Leu Lys Val Val
            20                  25                  30

Asn Asn Ser Glu His His Val Ala Phe Lys Val Lys Thr Thr Ser Pro
        35                  40                  45

Arg Lys Tyr Phe Val Arg Pro Asn Ala Ser Ile Ile Gln Pro Trp Asp
    50                  55                  60

Ser Cys Thr Ile Thr Ile Thr Leu Gln Ala Gln Lys Glu Tyr Pro Pro
65                  70                  75                  80

Asp Met Gln Cys Lys Asp Lys Phe Leu Ile Gln Ser Thr Lys Val Ala
                85                  90                  95

Ala Ser Thr Asp Met Asp Glu Ile Pro Pro Asn Thr Phe Asn Lys Glu
            100                 105                 110

Val Asp Lys Val Ile Glu Glu Met Lys Leu Lys Val Val Tyr Thr Val
        115                 120                 125

Pro Ser Gly Ser Ser Asp Asp Ser Gly Ile Thr Ser Leu Gly Ser Arg
    130                 135                 140
```

```
Ser Phe Lys Leu Gly Ser Asp Asp Leu Thr Met Leu Lys Asn Ala Ser
145                 150                 155                 160

Ile Glu Lys Ile Gln Thr Ile Gln Arg Leu Lys Asp Glu Arg Asp Thr
                165                 170                 175

Thr Leu Gln Gln Asn Gln Gln Met Gln Arg Glu Leu Asp Val Ile Arg
            180                 185                 190

Arg Arg Arg Ser Arg Lys Ser Asp Ala Gly Phe Ser Leu Thr Phe Ala
        195                 200                 205

Ala Phe Ala Gly Leu Ile Gly Val Leu Ile Gly Leu Leu Met Ser Leu
    210                 215                 220

Ile Phe Pro Arg Pro Gln Ala Ala Ala
225                 230


<210> SEQ ID NO 44
<211> LENGTH: 939
<212> TYPE: PRT
<213> ORGANISM: Oryza sativa

<400> SEQUENCE: 44

Met Gly Val Met Asn Pro Leu Met Ala Lys Leu Thr Thr Leu Met Gly
1               5                   10                  15

Asp Glu Tyr Lys Lys Leu Lys Gly Leu Arg Lys Gln Val Ser Phe Leu
            20                  25                  30

Lys Asp Glu Leu Thr Thr Met Ser Ala Phe Leu Glu Lys Leu Ala Leu
        35                  40                  45

Met Asp Asp Asp Asp Asp Gly Glu Leu Asp Pro Leu Ala Lys Asp Trp
    50                  55                  60

Arg Asn His Val Arg Glu Met Ala Tyr Asp Met Glu Asp Cys Ile Asp
65                  70                  75                  80

Asp Tyr Phe Thr Ser His Leu Asp His Arg Tyr Ser Ser Ser Asp Ala
                85                  90                  95

Gly Leu Ile Arg Lys Ile Ala Arg Arg Leu Arg Ala Leu Arg Val Arg
            100                 105                 110

His Arg Ile Ala Ser Gln Ile Asn Glu Leu Lys Ala Arg Val Val Glu
        115                 120                 125

Ala Asn Glu Arg Arg Val Arg Tyr Arg Leu Asp Asp Cys Asn Asn Lys
    130                 135                 140

His Gly Val Ser Ala Asn Pro Ala Ile Asp Pro Arg Ile Thr Ser Leu
145                 150                 155                 160

Tyr Gln Asn Ala Gly Ser Leu Val Gly Ile Asp Gly Pro Ser Gln Glu
                165                 170                 175

Leu Ile Gln Leu Leu Ser Leu Asp Arg Asp Thr Asp Gln Arg Gln Leu
            180                 185                 190

Lys Val Val Ser Val Val Gly Phe Gly Gly Leu Gly Lys Thr Thr Leu
        195                 200                 205

Ala Lys Tyr Val Tyr Asp Lys Ile Gly His Gln Phe Asp Cys Thr Ala
    210                 215                 220

Phe Val Ser Val Ser His Lys Pro Asp Ile Thr Arg Ile Leu Ser Ser
225                 230                 235                 240

Ile Gln Ser Lys Leu Asp Ile Gly Gly Thr Ser Gln Ala Cys Asp Asp
                245                 250                 255

Val Gln Gln Leu Ile Asp Asp Ile Arg Ala Tyr Leu Glu His Glu Arg
            260                 265                 270

Tyr Ile Ile Ile Val Asp Asp Leu Trp Lys Gln Glu Ala Trp Val Ile
        275                 280                 285
```

```
Ile Ser Cys Ala Phe Pro Asn Asn Gly Lys Gly Ser Arg Val Ile Val
    290                 295                 300

Thr Thr Arg Val Lys Asp Val Ala Arg Leu Ala Cys Gly Lys Asp Gly
305                 310                 315                 320

Gln Ile Tyr Lys Ile Gln Pro Leu Asn Asn Lys Asp Ser Arg Lys Leu
                325                 330                 335

Phe Phe Asp Arg Val Phe Arg Pro Glu Asp Ser Cys Val Leu Gln Tyr
            340                 345                 350

Glu Glu Ile Ser Thr Glu Ile Leu Lys Lys Cys Ser Gly Leu Pro Leu
        355                 360                 365

Ala Ile Val Thr Val Gly Ser Leu Leu Ala Cys Arg Pro Arg Thr Met
    370                 375                 380

Glu Glu Trp Lys Ser Ile Arg Asp Ser Leu Gly Ala Pro Phe Asp Lys
385                 390                 395                 400

Asn Lys Ser Leu Glu Gly Met Arg Asn Ile Leu Asn Leu Ser Tyr Lys
                405                 410                 415

Asn Leu Pro Leu His Leu Lys Thr Cys Leu Leu Tyr Ile Gly Lys Tyr
            420                 425                 430

Pro Glu Asp Tyr Glu Ile Gly Arg Asp Glu Leu Val Thr Glu Trp Ile
        435                 440                 445

Ala Glu Gly Ile Met Gly Asn Pro His Gly Glu Asn Leu Glu Ala Thr
    450                 455                 460

Gly Asn Gly Tyr Phe Ser Glu Leu Ile Asn Arg Gly Leu Ile Gln Pro
465                 470                 475                 480

Glu Ser Thr Gly Tyr Gly Gly Glu Val Leu Ser Cys Lys Val His Asp
                485                 490                 495

Met Met Leu Asp Leu Ile Leu Ile Lys Cys Ala Glu Asp Asn Phe Val
            500                 505                 510

Ser Val Ala His Ser Cys Lys Asp Tyr Met Arg Met Ala Met His His
        515                 520                 525

Glu Arg Ser Cys Asn Lys Val Arg Arg Leu Ser Leu Gln Cys Lys Ala
    530                 535                 540

Ala Arg Ser Asp Cys Ala Ile Glu Gly Ser Val Ile Ser Thr Ser Met
545                 550                 555                 560

Ala Arg Ala Arg Ser Val Ser Val Phe Gly Glu Cys Ser Arg Gly Leu
                565                 570                 575

Pro Phe Leu Met Leu Ser Lys Tyr Ile Arg Val Val His Ile Glu Leu
            580                 585                 590

Glu Gly His Gly Gly Gln Val Asp Leu Thr Ala Ile Ser His Val Leu
        595                 600                 605

Gln Leu Arg Tyr Leu Arg Val Glu Thr Pro Gly Cys Glu Ile Asp Leu
    610                 615                 620

Pro Ser Lys Ile Cys Gly Leu Val His Leu Glu Thr Leu Ser Ile Phe
625                 630                 635                 640

Ser His Lys Ala Val Ser Arg Leu Pro Ser Asp Ile Ser Ser Leu Pro
                645                 650                 655

Arg Leu Ser Val Leu Ser Leu Val Val Pro Trp Ala Thr Arg Leu Pro
            660                 665                 670

Asn Lys Leu Asn Lys Leu Lys Gly Ser Leu Arg Ser Leu Thr Ile Leu
        675                 680                 685

Phe Asn Pro Pro Asp Ala Leu Gly Met Glu Ala Ile Gly Glu Leu Lys
    690                 695                 700

Asn Leu Arg Asp Leu Asn Ile Ser Val Asn Arg Trp Arg Asp Asp Glu
```

```
705                 710                 715                 720

Ile Leu Ser Leu Tyr Ala Leu Gly Ser Ser Ile Gly Lys Leu Asp Glu
                725                 730                 735

Leu Arg Ser Leu Gln Ile His Val Pro Pro Ala Thr Leu Gly Asp Val
            740                 745                 750

Asp Leu Leu Gly Ser Leu Pro Ile Phe Pro Gln Ser Ile Glu Arg Leu
        755                 760                 765

Ile Leu His Gly Trp Cys Phe Ser Lys Val Pro Arg Trp Ile Asn Gly
    770                 775                 780

Thr Leu Arg Asn Leu Gln His Val Leu Leu Glu Val Ser Glu Thr Ser
785                 790                 795                 800

Ser Ser Glu Val Asp Leu Leu Gly Glu Leu Pro Ser Leu Ala Asp Leu
                805                 810                 815

Glu Leu Arg Val Gly Leu Lys Thr Arg Asp Val Ile Ala Phe Gly Gly
            820                 825                 830

Thr Arg Ala Ser Leu Phe Pro Ala Leu Leu Lys Leu Lys Leu Arg Val
        835                 840                 845

Gly Glu His Val Ala Ser Arg Leu Gln Phe Gln Ala Gly Val Met Pro
    850                 855                 860

Lys Leu Gln Ser Leu His Leu Trp Phe Arg Asn Cys Glu Ser Gly Ile
865                 870                 875                 880

His Val Thr Pro Glu Gly Met Gln His Leu Leu Ser Leu Gln Ser Ile
                885                 890                 895

Cys Val Glu Ile Tyr Leu Arg Asp Glu Glu Leu Lys Ala Thr Tyr Pro
            900                 905                 910

Trp Asp Ala Met Glu Arg Ala Phe Arg Glu Ile Thr Gly Ala Asn Pro
        915                 920                 925

Asn Arg Pro Ser Phe Lys Phe Val Lys Gln Val
    930                 935


<210> SEQ ID NO 45
<211> LENGTH: 337
<212> TYPE: PRT
<213> ORGANISM: Oryza sativa

<400> SEQUENCE: 45

Met Glu Cys Glu Pro Glu Glu Leu Gln Phe Leu Gly Met Val Gly Ile
1               5                   10                  15

Tyr Arg Glu Ala Ala Ser Ile Leu Arg Ala His Arg Pro Leu Phe Ala
            20                  25                  30

Arg Ile Ala Ala Ala Phe Val Leu Pro Leu Ser Leu Leu Phe Leu Leu
        35                  40                  45

His Ile Ala Ile Ser His Ala Leu Phe Ser His Ile Asp Ser Asp Asp
    50                  55                  60

Ser Ala Leu Asp Ser Ala Ala Pro Gly Thr Pro Ala Gln Arg Arg Leu
65                  70                  75                  80

Leu His Arg Leu Ala Asp Asp Trp Leu Ala Leu Leu Leu Phe Lys Ala
                85                  90                  95

Ala Tyr Leu Leu Ala Leu Leu Leu Phe Ser Leu Leu Ser Thr Ala Ala
            100                 105                 110

Ala Val Phe Ser Val Ala Ser Val Tyr Ser Ala Lys His Asp Ala Leu
        115                 120                 125

Ser Phe Pro Arg Val Leu Ser Val Val Pro Arg Val Trp Arg Arg Leu
    130                 135                 140

Ala Ala Thr Phe Leu Ala Ala Phe Leu Leu Leu Phe Ala Tyr His Leu
```

```
145                 150                 155                 160

Leu Phe Val Ala Val Phe Val Ala Leu Leu Val Ala Ala Asp Ser Gly
                165                 170                 175

Ser Gly Leu Ala Ala Leu Leu Ala Phe Leu Leu Ala Leu Ala Tyr Ile
            180                 185                 190

Ala Gly Leu Val Tyr Leu Ser Val Val Trp His Leu Ala Ser Val Val
        195                 200                 205

Ser Val Leu Glu Asp Tyr Lys Gly Phe Glu Ala Met Arg Lys Ser Lys
    210                 215                 220

Ala Leu Ile Gln Gly Lys Leu Trp Thr Ala Ser Ala Ile Phe Phe Val
225                 230                 235                 240

Leu Asn Val Val Phe Ile Val Val Glu Val Ala Phe Arg Ala Trp Val
                245                 250                 255

Val Arg Gly Ala Thr His Gly Leu Gly Ala Gly Ser Arg Leu Leu Leu
            260                 265                 270

Gly Leu Ala Met Leu Ala Ala Leu Cys Ala Val Val Met Leu Ala Leu
        275                 280                 285

Val Val Gln Thr Val Val Tyr Leu Val Cys Lys Ser Tyr His His Glu
    290                 295                 300

Ser Ile Asp Lys Ser Asn Leu Ser Asp His Leu Glu Val Tyr Leu Gly
305                 310                 315                 320

Glu Tyr Val Pro Leu Lys Ala Ser Asp Val Gln Met Glu Gln Phe Asn
                325                 330                 335

Leu


<210> SEQ ID NO 46
<211> LENGTH: 311
<212> TYPE: PRT
<213> ORGANISM: Oryza sativa

<400> SEQUENCE: 46

Met Ala Ser Ser Ser Ala Leu Ala Ser Ser Pro Phe Leu Pro Pro Leu
1               5                   10                  15

Ser Thr Pro Asn Pro Arg Ala Leu Ser Leu Arg Leu Pro Ala Arg Arg
            20                  25                  30

Leu Pro Val Ala Ser Ser Ala Ala Pro Ser Gly Ala Ala Ala Ala Ala
        35                  40                  45

Ser Ala Arg Glu Arg Arg Arg Phe Leu Glu Arg Tyr Gly Leu Asn Pro
    50                  55                  60

Asp Asp Phe Glu Asp Asp Ala Glu Ala Glu Pro Arg Glu Glu Arg Arg
65                  70                  75                  80

Arg Asp Arg Arg Asn Arg Arg Ser Gly Arg Gly Glu Ala Glu Asp Ala
                85                  90                  95

Pro Ala Lys Ala Ala Ala Glu Pro Arg Glu Thr His Lys Met Leu Gln
            100                 105                 110

Val Leu Gly Gly Lys Val Arg Arg Arg Lys Leu Leu Ser Pro Lys Asp
        115                 120                 125

Arg Asn Val Arg Pro Met Met Glu Val Val Arg Gly Ala Ala Phe Asp
    130                 135                 140

Ile Leu Gln Ser Ala Gly Gly Phe Pro Ala Ser Leu Arg Pro Gly Arg
145                 150                 155                 160

Trp Leu Asp Leu Tyr Ser Gly Thr Gly Ser Val Gly Ile Glu Ala Met
                165                 170                 175

Ser Arg Gly Cys Ser Glu Ala His Phe Val Glu Met Asp Pro Trp Val
            180                 185                 190
```

Val Ser Glu Val Leu Lys Pro Asn Leu Glu Cys Thr Gly Phe Leu Asp
195 200 205

Val Ser His Ile His Met Ile Arg Val Glu Asn Phe Leu Ala Asn Ala
210 215 220

Glu Lys Ser Ser Gly Lys Tyr Pro Ser Phe Asp Tyr Ile Ser Val Thr
225 230 235 240

Pro Pro Tyr Leu Glu Val Asn Tyr Ser Thr Leu Leu Asp Gln Leu Ala
245 250 255

Arg Ser Pro Leu Val Gly Glu Asp Cys Phe Ile Leu Val Glu Tyr Pro
260 265 270

Leu Lys Thr Asp Met Ala Glu Ser Cys Gly Ser Leu Ile Lys Val Ala
275 280 285

Asp Arg Arg Phe Gly Arg Thr Asn Leu Leu Ile Tyr Gly Pro Thr Trp
290 295 300

Ala Glu Lys Lys Arg Arg Ser
305 310

<210> SEQ ID NO 47
<211> LENGTH: 311
<212> TYPE: PRT
<213> ORGANISM: Oryza sativa

<400> SEQUENCE: 47

Met Asn Asp Leu Met Thr Lys Ser Phe Met Ser Tyr Val Asp Leu Lys
1 5 10 15

Lys Ala Ala Met Lys Asp Leu Glu Ala Gly Gly Asp Gly Val Glu Leu
20 25 30

Pro Glu Val Gly Val Thr Asp Glu Arg Leu Lys Gly Phe Phe Gln Glu
35 40 45

Thr Glu Ala Val Glu Glu Glu Met Ala Ala Ile Arg Asp Ala Leu Ala
50 55 60

Arg Leu Asn Ala Ala Asn Glu Glu Gly Lys Ser Leu His Gln Pro Asp
65 70 75 80

Ala Leu Arg Ala Leu Arg Gly Arg Val Asn Ala Asp Ile Ile Ala Val
85 90 95

Leu Arg Arg Ala Arg Asp Ile Arg Ala Arg Leu Glu Ala Met Asp Arg
100 105 110

Ala Asn Ala Ala Gln Arg Arg Leu Ser Ala Gly Cys Arg Glu Gly Thr
115 120 125

Pro Leu Asp Arg Thr Arg Thr Ala Leu Thr Ala Ala Leu Arg Lys Lys
130 135 140

Leu Lys Asp Leu Met Leu Asp Phe Gln Ala Leu Arg Gln Arg Ile Met
145 150 155 160

Ser Glu Tyr Lys Asp Thr Val Glu Arg Arg Tyr Tyr Thr Leu Thr Gly
165 170 175

Glu Val Pro Glu Glu Glu Val Ile Glu Arg Ile Ile Ser Glu Gly Arg
180 185 190

Ser Glu Glu Leu Leu Cys Ala Ala Val Ala Glu His Gly Lys Gly Ala
195 200 205

Val Leu Ala Thr Val His Glu Ile Gln Asp Arg His Asp Ala Ala Arg
210 215 220

Glu Val Glu Arg Ser Leu Leu Glu Leu His Gln Val Phe Leu Asp Met
225 230 235 240

Ala Val Val Val Glu Ser Gln Gly Glu Gln Leu Asp Asp Ile Glu Arg
245 250 255

```
His Val Asn Ser Ala Thr Thr Tyr Val Gln Gly Gly Asn Lys Glu Leu
            260                 265                 270

Arg Lys Ala Arg Glu His Gln Arg Ser Ser Arg Lys Trp Leu Cys Ile
        275                 280                 285

Gly Ile Ile Ile Leu Leu Leu Leu Val Leu Leu Val Ile Val Pro Ile
    290                 295                 300

Ala Thr Ser Phe Lys Arg Ser
305                 310


<210> SEQ ID NO 48
<211> LENGTH: 187
<212> TYPE: PRT
<213> ORGANISM: Oryza sativa

<400> SEQUENCE: 48

Met Ala Met Glu Gly Lys Ser Arg Arg Phe Ala Val Ala Cys Gly Val
1               5                   10                  15

Leu Ser Gln Tyr Val Arg Ala Glu Gln Lys Met Ala Ala Ala Ala Gly
            20                  25                  30

Ala Ala Pro Ala Arg Ala Val Thr Thr Leu Ser Leu Met Pro Gly Ala
        35                  40                  45

Glu Val Val Val Glu Glu Glu Glu Arg Arg Glu Val Gly Glu Glu Glu
    50                  55                  60

Ala Gly Pro Ala Thr Ala Pro Ala Ala Pro Leu Thr Ile Phe Tyr Gly
65                  70                  75                  80

Gly Arg Met Val Val Phe Glu Asp Phe Pro Ala Asp Lys Ala Ala Glu
                85                  90                  95

Val Met Arg Met Ala Ser Ser Gly Met Ala Ala Ala Pro Ala Gln Arg
            100                 105                 110

Glu Gly Ala Ala Leu Ala Asp Met Pro Ile Met Arg Lys Ala Ser Leu
        115                 120                 125

Gln Arg Phe Phe Ala Lys Arg Lys Asp Arg Leu Ala Ala Thr Thr Pro
    130                 135                 140

Tyr Ala Arg Pro Ser Pro Ala Glu Thr Lys Ala Ser Glu Pro Glu Glu
145                 150                 155                 160

Lys Lys Thr Pro Thr Ser Trp Leu Asp Leu Ala Ala Ser Ala Ser Ala
                165                 170                 175

Ala Ala Arg Arg Asp Ser Leu Thr Ile Ala Leu
            180                 185


<210> SEQ ID NO 49
<211> LENGTH: 1133
<212> TYPE: PRT
<213> ORGANISM: Oryza sativa

<400> SEQUENCE: 49

Met Ser Ser Leu Ser Arg Glu Leu Val Phe Leu Ile Leu Gln Phe Leu
1               5                   10                  15

Asp Glu Glu Lys Phe Lys Glu Thr Val His Lys Leu Glu Gln Glu Ser
            20                  25                  30

Gly Phe Tyr Phe Asn Met Lys Tyr Phe Glu Asp Glu Val Ile Asn Gly
        35                  40                  45

Asn Trp Asp Glu Val Glu Arg Tyr Leu Gly Gly Phe Thr Lys Val Asp
    50                  55                  60

Asp Asn Arg Tyr Ser Met Lys Ile Phe Phe Glu Ile Arg Lys Gln Lys
65                  70                  75                  80
```

```
Tyr Leu Glu Ala Leu Asp Lys His Asp Arg Ser Lys Ala Val Glu Ile
                85                  90                  95

Leu Val Lys Asp Leu Lys Val Phe Ala Ser Phe Asn Glu Glu Leu Phe
            100                 105                 110

Lys Glu Ile Thr Gln Leu Leu Thr Leu Glu Asn Phe Arg Glu Asn Glu
        115                 120                 125

Gln Leu Ser Lys Tyr Gly Asp Thr Lys Ser Ala Arg Ala Ile Met Leu
    130                 135                 140

Val Glu Leu Lys Lys Leu Ile Glu Ala Asn Pro Leu Phe Arg Asp Lys
145                 150                 155                 160

Leu Gln Phe Pro Asn Leu Lys Ser Ser Arg Leu Arg Thr Leu Ile Asn
                165                 170                 175

Gln Ser Leu Asn Trp Gln His Gln Leu Cys Lys Asn Pro Arg Pro Asn
            180                 185                 190

Pro Asp Ile Lys Thr Leu Phe Val Asp His Ser Cys Gly Gln Pro Asn
        195                 200                 205

Gly Ala Arg Ala Pro Ser Pro Ala Asn Asn Pro Leu Leu Gly Ser Ile
    210                 215                 220

Pro Lys Pro Gly Gly Phe Pro Pro Leu Gly Ala His Ala Pro Phe Gln
225                 230                 235                 240

Pro Ala Pro Thr Pro Val Pro Pro Leu Ala Gly Trp Met Ser Asn Pro
                245                 250                 255

Pro Ala Val Thr His Pro Ala Val Ser Gly Gly Ala Ile Gly Phe Gly
            260                 265                 270

Thr Pro Thr Asn Pro Ala Ala Ile Leu Lys His Pro Arg Thr Pro Thr
        275                 280                 285

Thr Ala Asn Pro Ser Met Asp Tyr Pro Ser Gly Asp Ser Asp His Val
    290                 295                 300

Ser Lys Arg Thr Arg Pro Val Gly Met Ser Glu Glu Val Asn Leu Pro
305                 310                 315                 320

Val Asn Met Leu Pro Val Thr Tyr Pro Gln Ser His Ser Tyr Pro Gln
                325                 330                 335

Asp Asp Phe His Lys Asn Val Ala Arg Thr Leu Ser Gln Gly Ser Thr
            340                 345                 350

Pro Met Ser Met Asp Phe His Pro Val Gln Gln Thr Leu Leu Leu Val
        355                 360                 365

Gly Thr Asn Val Gly Asp Ile Gly Leu Trp Asp Val Gly Thr Lys Glu
    370                 375                 380

Arg Leu Val Leu Arg Asn Phe Lys Val Trp Asp Leu Thr Lys Cys Ser
385                 390                 395                 400

Met Ala Leu Gln Ala Ser Leu Val Lys Asp Pro Thr Val Ser Val Asn
                405                 410                 415

Arg Ile Ile Trp Ser Pro Asp Gly Thr Leu Phe Gly Val Ala Tyr Ser
            420                 425                 430

Arg His Ile Val Gln Ile Tyr Ser Tyr His Gly Gly Asp Asp Ile Arg
        435                 440                 445

Gln His Leu Glu Ile Asp Ala His Val Gly Gly Val Asn Asp Ile Ala
    450                 455                 460

Phe Ala His Pro Asn Lys Gln Leu Cys Ile Ile Thr Cys Gly Asp Asp
465                 470                 475                 480

Lys Thr Ile Lys Val Trp Glu Ala Thr Ser Gly Ala Lys Gln Phe Thr
                485                 490                 495

Phe Glu Gly His Glu Ala Pro Val Tyr Ser Val Cys Pro His Tyr Lys
            500                 505                 510
```

```
Glu Asn Ile Gln Phe Ile Phe Ser Thr Ala Leu Asp Gly Lys Ile Lys
        515                 520                 525

Ala Trp Leu Tyr Asp Asn Leu Gly Ser Arg Val Asp Tyr Asp Ala Pro
    530                 535                 540

Gly His Trp Cys Thr Thr Met Ala Tyr Ser Ala Asp Gly Ser Arg Leu
545                 550                 555                 560

Phe Ser Cys Gly Thr Ser Lys Asp Gly Glu Ser His Leu Val Glu Trp
                565                 570                 575

Asn Glu Ser Glu Gly Ala Val Lys Arg Thr Tyr Gln Gly Phe Arg Lys
            580                 585                 590

Arg Ser Met Gly Val Val Gln Phe Asp Thr Thr Arg Asn Arg Phe Leu
        595                 600                 605

Ala Ala Gly Asp Glu Phe Leu Ile Lys Ile Trp Asp Met Asp Asn Thr
    610                 615                 620

Ser Leu Leu Thr Thr Ile Asp Ala Asp Gly Gly Leu Pro Ala Ser Pro
625                 630                 635                 640

Arg Val Arg Phe Asn Lys Glu Gly Thr Leu Leu Ala Val Ser Thr His
                645                 650                 655

Glu Asn Gly Ile Lys Ile Leu Ala Asn Ala Asp Gly Val Arg Leu Leu
            660                 665                 670

Arg Thr Leu Glu Asn Arg Ser Phe Asp Ala Ser Arg Ser Ala Ser Glu
        675                 680                 685

Thr Val Thr Lys Pro Leu Met Asn Pro Leu Thr Ala Ala Ala Ala Ala
    690                 695                 700

Ala Ala Ser Ala Ala Ala Ala Gly Thr Ser Ser Gly Asn Ala Ala Pro
705                 710                 715                 720

Pro Ala Ile Thr Ala Leu Asn Gly Asp Ser Arg Ser Leu Val Asp Val
                725                 730                 735

Lys Pro Arg Ile Ala Asp Glu Pro Leu Asp Lys Ser Lys Val Trp Lys
            740                 745                 750

Leu Met Glu Ile Thr Glu Ser Ser Gln Cys Arg Ser Leu Lys Leu Thr
        755                 760                 765

Asp Asn Met Arg Thr Ser Lys Ile Ser Arg Leu Ile Tyr Thr Asn Ser
    770                 775                 780

Gly Val Ala Ile Leu Ala Leu Ala Ser Asn Ala Val His Leu Leu Trp
785                 790                 795                 800

Lys Trp Pro Arg Asn Asp Arg Asn Ser Ser Gly Lys Ala Thr Ala Ser
                805                 810                 815

Val Ser Pro Gln Leu Trp Gln Pro Pro Ser Gly Ile Leu Met Thr Asn
            820                 825                 830

Asp Ile Thr Asp Asn Pro Glu Glu Ala Val His Cys Phe Ala Leu Ser
        835                 840                 845

Lys Asn Asp Ser Tyr Val Met Ser Ala Ser Gly Gly Lys Ile Ser Leu
    850                 855                 860

Phe Asn Met Met Thr Phe Lys Thr Met Thr Thr Phe Met Pro Pro Pro
865                 870                 875                 880

Pro Ala Ala Thr Phe Leu Ala Phe His Pro Gln Asp Asn Asn Ile Ile
                885                 890                 895

Ala Ile Gly Met Asp Asp Ser Thr Ile Gln Ile Tyr Asn Val Arg Ile
            900                 905                 910

Asp Glu Val Lys Ser Lys Leu Arg Gly His Ser Lys Lys Ile Thr Gly
        915                 920                 925

Leu Ala Phe Ser Asn Val Leu Asn Val Leu Val Ser Ser Gly Ala Asp
```

```
    930                 935                 940

Ala Gln Ile Cys Val Trp Ser Thr Asp Gly Trp Asp Lys Leu Lys Ser
945                 950                 955                 960

Arg Met Leu Gln Ile Pro Ser Ser Arg Pro Ser Ser Ile Ile Leu Asp
                965                 970                 975

Thr Arg Val Gln Phe His Gln Asp Gln Leu His Phe Leu Val Val His
            980                 985                 990

Glu Thr Gln Ile Ala Ile Tyr Glu  Thr Thr Lys Leu Glu  Pro Val Lys
        995                 1000                1005

Gln Trp  Pro Val Arg Glu Asn  Ser Ser Pro Ile Thr  His Ala Met
    1010                 1015                 1020

Phe Ser  Cys Asp Ser Gln Leu  Ile Tyr Ala Ser Phe  Leu Asp Ala
    1025                 1030                 1035

Thr Val  Cys Ile Phe Asn Ala  Ser Ser Leu Arg Leu  Gln Cys Arg
    1040                 1045                 1050

Ile Leu  Pro Ala Ser Tyr Leu  Pro Gln Asn Ile Ser  Ser Asn Val
    1055                 1060                 1065

Tyr Pro  Val Val Val Ala Ala  His Pro Ser Glu Ala  Asn Gln Phe
    1070                 1075                 1080

Ala Leu  Gly Leu Thr Asp Gly  Gly Val Tyr Val Leu  Glu Pro Leu
    1085                 1090                 1095

Glu Ser  Glu Arg Lys Trp Gly  Asn Pro Pro Pro Ala  Glu Asn Gly
    1100                 1105                 1110

Ser Thr  Ser Ala Leu Ser Thr  Pro Pro Asn Gly Ala  Ser Ser Ser
    1115                 1120                 1125

Asp Gln  Pro Glu Arg
    1130
```

<210> SEQ ID NO 50
<211> LENGTH: 2511
<212> TYPE: DNA
<213> ORGANISM: Oryza sativa

<400> SEQUENCE: 50

```
atgtctcacc cccacgccac cgcccccaag cgccccggcc acttctcctc ctcctccgcc      60

gccgcctcct ccccgacctc ccccgcgcag ccgcacatga agaaggccaa gttccccggc     120

tcctcctcct cctcctcctc cgccgccgcc cccggggtca ccgagaagaa cgggctccac     180

gtcgatccca cggccgccgc cgcccggacc ggtgggcgca ccaacggcga ggaggatgcg     240

gagatggtgc tcgccgacca ggaggagctc gccgctccga gcgcatcggc cccggcgggg     300

gtcgccgcca acctcttccg gaagaaggcc acactccccc agccatccgc cgcccgcaag     360

cccctccgaa tcaaaatagg tcagccaaaa ttgccaacaa actttgagga ggatacatgg     420

gctattttga aagatgctat tacagctata tttctaaaac agaaactttc gtgcgatgtt     480

gaaaaacttt accaggctgc aggtgacctt tgtctacaca agctaggcgc aaatctatac     540

gaacgcataa agaaagaatg tgaagtacac atatcggcaa aaatatcagc attagtgggt     600

caaagtccag atttagtagt atttttgtct ctggtgcaaa gaacatggca agatttttgc     660

gatcagatgt tgattattcg tggtattgct ttacttcttg atgtaaaata tgtcaagaat     720

gttgcaaaca tttgttcagt gtgggacatg ggttgaagc tattccgcaa gcatctttca      780

ctgtctccgg agattgaaca caaaactgtt actggtcttc taagattaat tgagagtgag     840

aggcttggtg aagcaataga caggacatta cttagtcatc ttctgaagat gtttactgct     900

cttggaatgt attctgagag ttttgaaaag ccctttctgg agtgtacatc tgaattttat     960
```

```
gctactgaag gtgttaaata tttgcagcag tctgatattc cagactatct caagcatgtg   1020

gagacaaggt tgcaagaaga acatgaaagg tgtattctat atttggaagc taacactagg   1080

aagccgctta taacagctac agaaaagcaa ttattgcagc ggcacacatc tgcaattctt   1140

gagaagggat tcacaatgct tatggaagca aatcgtgtaa aagacctctc gaggatgtac   1200

acactcttcc agagggttga tgccattgag ttgctaaagc aagcacttag ttcatatatt   1260

cggggcacag gccagggcat tatcatggat gaagaaaagg acaaagaact ggtgcccttt   1320

cttctggaat ttaaggcatc gcttgataga atattggagg aaagttttgc caaaaatgag   1380

gctttctcca atacaataaa agagtcattc gaacatctta tcaatttacg ccagaatcga   1440

cctgctgaat tgattgcgaa gtttcttgat gagaaacttc gagctggaaa taaaggtacc   1500

tccgaagaag agctggaggg aatattggat aaagttttgg ttctgttccg atttatacaa   1560

ggaaaagatg tatttgaggc attctacaag aaggatctgg ctaagaggtt gctgctgggg   1620

aagagtgcat cgatagatgc tgaaaaatca atgataacaa agctcaaaac tgagtgtgga   1680

agtcaattta ccaacaagct ggagggaatg ttcaaggaca ttgaattatc caaagaaata   1740

aatgagtctt tcaagcaatc atctcaagca aggacaaagc ttccatctgg cattgaaatg   1800

agtgttcacg tgcttacaac aggctattgg ccaacatatc caccaatgga tgtgaaactc   1860

ccccatgaac ttaatgtcta tcaggatata tttaaagaat tctatttgag caagtatagt   1920

ggaaggcgtt tgatgtggca aaactcattg ggtcactgtg tattaaaagc agagttccca   1980

aaaggtaaaa aggaacttgc ggtgtcacta tttcagagtg tggttttgat gttgttcaat   2040

gatgcacaaa aactaagctt cctcgatatc aaggaatcga ctggtattga ggataaagaa   2100

ttgcgaagaa cgctgcaatc acttgcatgc ggtaaagttc gggttctcca aaagatgcca   2160

aaagggcgag acgtagaaga taaggacgaa tttgtattta atgaagaatt tagtgcccct   2220

ctctatcgca taaaggtgaa tgctattcag atgaaggaga cggttgaaga aaacacaagc   2280

acaactgaga gagtattcca ggacagacag tatcaggtgg atgctgccat agttcgaata   2340

atgaagacac gtaaaaccct cagccacacg cttctaataa ctgagctttt tcagcagctc   2400

aagttcccaa tcaagccatc ggatatcaag aaaagaatag agagcctaat cgacagggag   2460

tacctggaga gagacaggag taacccccag atctacaatt acctggcttg a            2511
```

<210> SEQ ID NO 51
<211> LENGTH: 1686
<212> TYPE: DNA
<213> ORGANISM: Oryza sativa

<400> SEQUENCE: 51

```
atggacgccg atgaggccgc ggggagtagc aggaggatgg atctgaacct ctaccttggc     60

ctcccacgcg ccccgcgccc gcgccgctcc gacctcggct ccgacctcgc cctcagcacc    120

ccgatgccct cctccccgtc ctcctccgca gcctccgtcg acgcgccgcc gccaccgccc    180

gagctgtcgc atcccccgta ctccccctct cacgccgacc tttcccctcc gctgcaggag    240

gtctactccc tgtacaaccc cgacgacccg cctgcttccg agacgcacct gccgccgtat    300

gcgccgcctc cggctccggt ggtctcggag ctccctgacg acctcgagtt tggcctccac    360

cccccgccgc cgctggtgcg tgccagcgaa ctgctaggtt gggaggaccg gccgtcttcg    420

tcgacggcat cgtcctcttt cctccctgac accgcagccc gttactggcg gcttctcgag    480

cagactggaa gcagatggct ccgtgcgagg cggtttaggt cggaccttcc gccactcagt    540

tctgaagctt acccagctgg gcgtgatgct gccgcagtcc cagtgctgca gcatgaaccg    600
```

```
atgaatgata ctgttgaaca taataaggta gctgccgatg gcgcggaagt aggcgcctcc    660
gaggaatcgg aggagcaggg caggagcgct gccacatttg agtgtaatat atgcttcgat    720
atggccagcg agccggtggt cacctcttgt ggccatctct tctgctggcc ttgcttgtac    780
caatggctca atgtttattc caatcacaag gaatgcccag tctgcaaagg cgaggtgact    840
gaggcgaata ttactccgat ctatgggaga gggaattcat gtttggatgc cgagaaggct    900
gtggaaggtg ggaaacaaac aggtcctact atcccaccaa gaccacatgg aaatcggctc    960
gaaagcttca ggcagcagtt tcaccatttg cgaccgatct caagaaggct tggtgaggct   1020
catgggttat tgtcatcatg gaggcgcctt ctggaccaac agattatgaa tactgcgagt   1080
aggtttgaag gtccgcctga atcagctgtg caggaaatgg ttgacactgc tcacgctcag   1140
cacaccagtc gcctaagtag attggcgtca aggatgagag caagacggtt gctgagagaa   1200
gcagacaacc ctaaccctcc cgatggcgga tccacttccc ctgacagtgg tttgatcaga   1260
aacaatgcat cggatccatc cagaaatggt ccgagctcat tattaccaga tggaattgac   1320
tggttgcgtg gacttaccct tcttgggtat gaagacacgg aaagatttgc atctgccatg   1380
agtgatttta gaaggataac tggaccaagc caatatggtg catcggcttc atcatcgaat   1440
cctccaaatc tcgagtcaac atttgacaga actcatgttg ttgcagcacc ttctgcagac   1500
caagcatcta actcaagcac tgctgcagtg atacaggggg atgctggtat ctctgagagt   1560
gcaggagaac caagtaacgc ggggtcatca agatccctga ggaggagagg gaggagcagt   1620
gccctgggtt ctttggatgc tgatggcggg ggcctccaac ggaacaagag gcgaaggata   1680
aactga                                                              1686
```

<210> SEQ ID NO 52
<211> LENGTH: 522
<212> TYPE: DNA
<213> ORGANISM: Oryza sativa

<400> SEQUENCE: 52

```
atggctggtg ggagctgcga cgtgtgcaag gaggcgccgt ccaagtacaa gtgctccgct     60
tgccgcacgc catattgctc ggtggcatgc tttaaaaatc acaaagataa attttgccag    120
aagacaatac ctctggaaga agttagcaag tcatctcttc aggaggaaat ttcaaggaac    180
tctaggtcac tggaagaagc aacaaattgt cctaatgaca aggatcaaac cccgtcttta    240
ttatcggaca cgacttgtcc cacacaatat ccaaacacat tgcactctgc aaaatctctt    300
gaagttgagg atccaagctg gcttgttgac aagaatggat taagatcttt agcggaatct    360
aatgagatcc gagatgctct gaaagattgt aagcttcagc aaatgctact taagattgat    420
ggctctgcag agccagaaaa ggaattagag aaattgatgg aaggacaagt tttcaacag    480
ttcaccaata agattcttga cattgttagc ccacaacaat ga                       522
```

<210> SEQ ID NO 53
<211> LENGTH: 1560
<212> TYPE: DNA
<213> ORGANISM: Oryza sativa

<400> SEQUENCE: 53

```
atgctgggag aggccgcctc accgtggagc ctggccggcg cgggcgcggc cgtggcgctg     60
ctgtggctgt gcgcctggac gctgcagtgg gcgtggtgga cgccgcggcg gctggagcgg    120
gccctgcggg cgcagggcct ccggggcacc aggtaccgcc tcttcatcgg cgacgtggcc    180
gagaacggcc ggctcaacag agaggccgcg tcaaggccgc tgccgctcgg ctcgcacgac    240
```

```
gtcgtcccgc gcgtcatgcc cttcttctgc aacgtcctga aagagcacgg gaaactgtcg    300

ttcgtttgga ctggcccaaa gccattcgtg attatcagag accctgactt agcgagggag    360

attttgtcca acaagtctgg caatttcgcc aagcaaacga ccgcgggtat tgctaagttc    420

gtagttggcg gagttgtaac gtatgaaggt gagaaatggg caaaacatcg gagaattctc    480

aaccctgcct tccaccagga gaaaataaag cggatgctgc cagtgttttt agcatgttgc    540

accaaaatga tcactagatg ggtgaattca atgtcttcag aaggaatatc tgagttagac    600

gtttgggatg aatttcaaaa tcttactgga gatgtcatct caagaacggc atttgggagc    660

agctaccagg aggggtggag aatttttcag ttacaagaag agcaagctaa acgcgtactt    720

aaagcttttc agagaatctt tatcccaggc tactggtact taccaatcga aaacaacaga    780

aggatcaggg aaattgatca agaaatccgc acaattctgc gaggaataat agtaaaaaga    840

gacaaggcag ttagaaatgg tgaaggtagc aatgatgatt tgttgggatt attggtggaa    900

tcgaatatga ggcaatcaaa tgaaaaagaa gatgtgggaa tgagtataga agatatgatt    960

gaggaatgca agttatttta cgctgctggt tcggagacaa catcaatgtt gctcacttgg   1020

actttaattc tgctaagcat gcaccctgaa tggcaagagc aggcaagaga ggaagtgatg   1080

caccattttg gaagaaccac accagatcat gatggcttga gtcgtctaaa gattgtaacg   1140

atgattctcc acgaggttct taggttgtac ccaccggtgg tattcctcca aagaacaaca   1200

cacaaggaaa tagagcttgg tggcatcaaa taccctgaag gagtgaactt cacattgcct   1260

gttctatcca ttcaccacga tcctagcatc tggggacaag atgcaatcaa attcaacccg   1320

gaaaggttcg ccaacggagt ctccaaggca acgaagtttc agaccgcgtt cttttcgttt   1380

gcatggggtc ctcggatctg ccttggccag agctttgcaa ttctggaagc caagatggcg   1440

ctcgccacca tcctccagag cttctccttc gagctctcgc cgtcatacac ccacgcacca   1500

cacaccgtgc taactctcca accacagtac ggttctccaa ttaaattgaa gaagctctag   1560
```

<210> SEQ ID NO 54
<211> LENGTH: 444
<212> TYPE: DNA
<213> ORGANISM: Oryza sativa

<400> SEQUENCE: 54

```
atggctaaag atcacgtgaa gattgtgtta aaagcttaca ttttaggacc tataaagtat     60

attttaagtt tagaatcttt gtaccataat tgtggtggac tggtggtaac aatgattctc    120

cacgaagtta ttaggttata cccatcgggg atcttcctcc aaagaacaac acgcaaggaa    180

atagagcttg gtggcatcaa ataccctgaa ggagcaaact tcacattgcc cgttccatct    240

atccaccatg atcccagcat ctggggagga gatgcaagcg agttcaacct ggagaggttt    300

gccaacggag tctccaaggc aacgaagttt aagaccgcat tctttatgtt tggatggggg    360

ttctcggatc tgccttggac agaactttgc aatgctggaa gccaagatgg cgctcgccac    420

catcctccag agcttctcct ttga                                           444
```

<210> SEQ ID NO 55
<211> LENGTH: 219
<212> TYPE: DNA
<213> ORGANISM: Oryza sativa

<400> SEQUENCE: 55

```
atgtgctgtt cagctgttgc tgttatgaag tgggaagctc tattaccaaa tgataccttt     60

cttattgttg cctcctctga tggcgtattt gagaaagtga ctatgcagga tgtctgtgat    120
```

ctgatgttgt acgtgaaact tggtgttaag caagaattag gatcctttgc attaacacaa 180
cagaatttgg cagattatgt tgttgatctt tctttatag 219

<210> SEQ ID NO 56
<211> LENGTH: 753
<212> TYPE: DNA
<213> ORGANISM: Oryza sativa

<400> SEQUENCE: 56
atgtcctcta gcgatcagaa cccatcgcca acaccggcgt ccggcaccgg cacgtccgtg 60
ccgccgccag gcagggcgac gacggtatcc tcgcagctcc tggacatggg cgcgcaagcg 120
gtgcaggcgc tgaagcccgt gcgccagatg aagcagcacg cgtgcagctt cgcgctgtac 180
gctcacgacc tgagccgcca ggtcgaggtc caccacttcg tctcccgcct caaccaggac 240
gtcctccagt gcgccgtcta cgactccgac aagccctcgg cccgcctcat cggcgtggag 300
tacatcgtgt cggacgccat cttcgagagc ctgcctccgg aggagcagaa gctgtggcac 360
tcgcacgcgt acgaggtgaa ggccgggctg tggaccgacg tcggcgtgcc ggagccgctg 420
cagagctcgg agatggcgag gatggccaag acgtacggca agctctggtg cacctggcag 480
gtggaccgcg gcgacgcgct gcccctgggc gcgccggcgc tcatggtgtc gccgcaggcc 540
gtggagcccg ggcgggtgcg cgccgagctc gtgcacggcc gcgacgagag gtacaagatc 600
gacagctcgg cgcaggggct gaagggggcc agggttgaga tggacgagcc ggagtggatc 660
aacccgaacg ccgactactg gcgcctacac ggcaaggggt tcgccatcga cgtcaccgcc 720
accgagatga agcgccacgc gcccttcccg tga 753

<210> SEQ ID NO 57
<211> LENGTH: 1440
<212> TYPE: DNA
<213> ORGANISM: Oryza sativa

<400> SEQUENCE: 57
atgacgcctc caccgccgtc gccgccgcac gagaggaaaa cgtgggcgga gtcggtggcc 60
agcgagtttc gggcgcagcg cggcatcgcg ttccctctca tcgccatgaa cctcacctgg 120
ttcgccaagc tggccgtcac caccgccttc ctcggccgcc tcggcgacct ccagctcgcc 180
gccggcaccc tcggcttcag cttcgccaat gtcaccggct tcgccgtcct caccggcctc 240
tgcgccgcca tggaccccat ctgcgggcag gcgcacggcg ccagcaacgg gaagctcctc 300
cgcaagacgc tggtgatggc caccatcctg ctgctgggcg cgtccatccc catcgccttc 360
ctgtggctgc acgtggacgc cgtcctcctc cggttcggac agcaggcgga catgagcagc 420
aacgcacgca gctacgtggt gtgcctcctc ccggacctcg ccgtcacctc cttcgtcaac 480
ccgctcaagt cgtacctgag cgcgcagggg gtgacgctcc ccacgctgtt cgcctccgcc 540
ctggccctgg cgctccacgt cccccctcacc atgtggatgg ccaggaccag gggcatccag 600
ggcgtcgcca ccgccgtgtg ggtcagcgac ctggccgtgg ccgtcatgct cgccggctac 660
gtgctcgtct cggagcgacg acggaaggcg ggagggggcg gcggatgggt ggagcagacg 720
aggggtgagt gggtccggct cctccggctg gccgttccca gctgcctcaa cacctgcctg 780
gagtggtggt gctacgagat actggtgctc ctgacgggac gcctcccgga cgcccggcgc 840
acggtggcgg tgatggccgt gacgctcaac ttcgactacc tgctgttcgc ggggatgctg 900
tccctgtcgg tgagcgcgtc ggtgcgcgtg tcgaacgagc tgggcgcggg ggaggcgtgg 960
gcggcgaggc gcgcgggcat ggtgtcgatc gtgggcggcg cggtgggcgg ggtgggcggc 1020

```
ggggtggcga tggtggcggc gcggcgggcg tgggggagca tatacagctc agacgccggg   1080

gtgcgggagg gggtggggag ggcgatggag gtgatggcgg tgctggaggt ggtgaacttc   1140

ccgctgaacg tgtgcggggg gatagtgcga gggacggcga ggccggcggt ggggatgtac   1200

gccgtggtgg ccggcttcta cgtgctggcg ctgccgctcg ggtcgcgct  cgccttcaag   1260

gccagacttg ggatccaggg cctcctcctg ggcttcctgg tgggcgccgc ggccagcttg   1320

gcggtgctcc tcaccttcat cgcgcgcatg gattggcccg ccgaggccca aaaggcgcgg   1380

actagaacca cagcaaccgt ggcccaattc caccaacacg acgaggtcgt ccagccttga   1440
```

```
<210> SEQ ID NO 58
<211> LENGTH: 2460
<212> TYPE: DNA
<213> ORGANISM: Oryza sativa

<400> SEQUENCE: 58

atgccggagg ctgcggcggc ggcggcgggc cacatggatc cggttggcga cgaggcggcg     60

gagaggaggg agatggagga gaaggaggag gaggaggagg aggaggagga ggatgaggag    120

ttctacgagt cgctggatcg gatcctgtcg tcgtcgtgct cgtccacgtc cgcctccgac    180

gacgacgacc agcagcaccg gcggaggcgg cggcaccacc cgcagccgca gcagctgtcg    240

tcgtccgcga cgttctccgc gtacgaggtc tggatctccg agccgacatc cgtcgaggag    300

cgccgccgcg tgctgctgcg tcggctcggc ctcgcccacg actccgagcc cctgccgcac    360

ccgtccccac gcgtatcatc ctcctcccct cgttcgccga cccccttcccc cccgtcctcg    420

tcgccgcctc ggccggctcc cgtggtggcc gccgcggagg agcccagatc cagcggccac    480

gggaagccgc cgcttgcgag gaacccgagc ggcggcgcgg agcaatgccg gatccggaac    540

ctggacgacg gtacggagtt cgaggtcggg gaggttcacg atgaggtggt ccgggaggtc    600

ggcactggcc ggcagctcac cttcgaggag ttcgagctct gcattggccg ctccccgatc    660

gtccaagagc tcatgcgccg ggccaccaca gccgcatcat cctccacctc cgaccacgcc    720

gccccagcat ccaagccacg gaggaagcct ggaggctggc tgcgtggcat ccggcacctg    780

gcgggaagcg ttgcatacgg gcgcagcagc accgatgaga gggacaagga gaaggagaag    840

gagaagaagg agagggaagc gcggcgcctg agctccgcca ccgatgacag ccttgacggc    900

aacggctcgc gcaatgcagg gagggtcagg gtgcggcagt atgggaaggc gtgcaaggag    960

ctcaccggcc tgttcatgac acaagaattg gctgcccatt cgggctcaat ctggtgtatc   1020

aacttcagct tggatggacg ataccttgca agcgctggcg aggaccgtgt catccatgtg   1080

tgggaggtat cagagggaga aagaaaggga gaattgctcg gggaaggtac ggtggcaagg   1140

gagaacggtg gtggctgcag cccgtttctt gcagctgttg ggaatggatc gccggagctg   1200

gcaacattgt cattgagctg tgctgacggg ggttttgtgg agaagaagag gaggccaagg   1260

atgcaaagca gccggaagtc tgttggctct gatcatctag ttgtgcctga atgtgtgttt   1320

gggttcagag ataaaccagt atgctctcta ttgggtcacg ccgccgatgt tcttgatcta   1380

tcatggtcca aatctcagta cttgctttca tcctcaatgg acaaaactgt taaactatgg   1440

gacattacta ctagtacctg tctgaaaaca ttttcacaca cagactatgt gacttgcatc   1500

cagttcaatc ccgtggatga taacttcttc attagtggat cactggatga aaaagtacgc   1560

atttggaatg tacatgatcg taagattgag gattggaatg atcttcatga gatggtcact   1620

gctgcgtgtt actcccctga tggacaggtt gcactggtgg gatcacacaa gggaagctgt   1680

catttatttg atacaactga aaagaagctt cagtacaaaa gtcagataga actaagaatc   1740
```

```
aggaagaaga agtctggcca gaagaagata actggcttcc agtttgctcc tggaagctcg   1800

tcggaagtcc tgattacctc tgcagattca agaatccgtg ttgttaatgg tgatgaactc   1860

gttcacaaat ttaaagggtt ccgaaataca agtagccaaa tatccgcttc tgtagctcca   1920

aacgggaaat atgtggtctg tgccagtgag gactcccacg tgtatgtctg gaggcatgac   1980

aatacttccc atccgagcag aagcaggagt gcagttgatg taaccaactc atatgagcat   2040

ttccattgcc atgatgtcac tgtggctatc acatggcccg gcgctgaatc ccgtggctca   2100

ttcgggtccc gtagcagcag aaacagtgat tcagacgatg cagtgatgaa cacgggtcgg   2160

gatgcccctg tagagaacag tgagcatgat ctgaatggca ctgtcaatag atgcaccaag   2220

cgcccagttt gtgaaggtgt tgcaagcaca agcaatcctc cagcggatgg agtatcaacg   2280

tcctggcctg acgagaaaca atcgtctgcc aagagcagtc ctggtcactg ctcatccgac   2340

ctttgcattg gagctttgga tgttcagcgc cggtcagctt ggggattggt gattgtcact   2400

gcaggaaggg gtggtgaaat tagggtgttc cagaatttcg gcttcccggt tcaagtgtaa   2460
```

```
<210> SEQ ID NO 59
<211> LENGTH: 621
<212> TYPE: DNA
<213> ORGANISM: Oryza sativa

<400> SEQUENCE: 59

atggctcctg cggttgcctc ctccccgtca ctcgtgctct ccgccgccgc cgccaccgcc     60

tccaacaagc gcccggccga ttccgacgcc tcgccgccgc accagggaga tcgcacgggg    120

cagcaggaga agaagcagca gcagctggag tgcccgcgct gccgatccac caacaccaag    180

ttctgctact acaacaacta cagcacgtcg cagccgcgcc acttctgccg cgcctgccgc    240

cgctactgga cgcacggggg cacgctccgc gacgtgccgg tgggcggcgc ctctcgccgc    300

ggcggcggcg gcaagcgccg cagggtctcc gccgacgccg acccttcctc ggcgtcgccg    360

ccgccaccca cgacttccac cacggacgcg tacgccgacc tcccagccgg cttcccgttc    420

ctcagtgacg gcgccttcct gccgcagttc ggcctcgccg gcgttgcgcc ggccgcgttc    480

tcttgggcat cggctgtccc tgacttgtac aactgcggga tcgcgccgtg ggacgatgga    540

acggcggtca ccggcgcggc gtgggacaac ttcgccgaca tcgccggcct tgatctcagc    600

tggccgccgc cgggtaactg a                                              621
```

```
<210> SEQ ID NO 60
<211> LENGTH: 2511
<212> TYPE: DNA
<213> ORGANISM: Oryza sativa

<400> SEQUENCE: 60

atgtctcacc cccacgccac cgcccccaag cgccccggcc acttctcctc ctcctccgcc     60

gccgcctcct ccccgacctc ccccgcgcag ccgcacatga agaaggccaa gttccccggc    120

tcctcctcct cctcctcctc cgccgccgcc cccggggtca ccgagaagaa cgggctccac    180

gtcgatccca cggccgccgc cgcccggacc ggtgggcgca ccaacggcga ggaggatgcg    240

gagatggtgc tcgccgacca ggaggagctc gccgctccga gcgcatcggc cccggcgggg    300

gtcgccgcca acctcttccg gaagaaggcc acactccccc agccatccgc cgcccgcaag    360

cccctccgaa tcaaaatagg tcagccaaaa ttgccaacaa actttgagga ggatacatgg    420

gctattttga aagatgctat tacagctata tttctaaaac agaaactttc gtgcgatgtt    480

gaaaaacttt accaggctgc aggtgacctt tgtctacaca agctaggcgc aaatctatac    540
```

```
gaacgcataa agaaagaatg tgaagtacac atatcggcaa aaatatcagc attagtgggt    600
caaagtccag atttagtagt atttttgtct ctggtgcaaa gaacatggca agatttttgc    660
gatcagatgt tgattattcg tggtattgct ttacttcttg atgtaaaata tgtcaagaat    720
gttgcaaaca tttgttcagt gtgggacatg ggttgaagc tattccgcaa gcatctttca    780
ctgtctccgg agattgaaca caaaactgtt actggtcttc taagattaat tgagagtgag    840
aggcttggtg aagcaataga caggacatta cttagtcatc ttctgaagat gtttactgct    900
cttggaatgt attctgagag ttttgaaaag ccctttctgg agtgtacatc tgaattttat    960
gctactgaag gtgttaaata tttgcagcag tctgatattc cagactatct caagcatgtg   1020
gagacaaggt tgcaagaaga acatgaaagg tgtattctat atttggaagc taacactagg   1080
aagccgctta taacagctac agaaaagcaa ttattgcagc ggcacacatc tgcaattctt   1140
gagaagggat tcacaatgct tatggaagca aatcgtgtaa aagacctctc gaggatgtac   1200
acactcttcc agagggttga tgccattgag ttgctaaagc aagcacttag ttcatatatt   1260
cggggcacag gccagggcat tatcatggat gaagaaaagg acaaagaact ggtgcccttt   1320
cttctggaat ttaaggcatc gcttgataga atattggagg aaagttttgc caaaaatgag   1380
gctttctcca atacaataaa agagtcattc gaacatctta tcaatttacg ccagaatcga   1440
cctgctgaat tgattgcgaa gtttcttgat gagaaacttc gagctggaaa taaaggtacc   1500
tccgaagaag agctggaggg aatattggat aaagttttgg ttctgttccg atttatacaa   1560
ggaaaagatg tatttgaggc attctacaag aaggatctgg ctaagaggtt gctgctgggg   1620
aagagtgcat cgatagatgc tgaaaaatca atgataacaa agctcaaaac tgagtgtgga   1680
agtcaattta ccaacaagct ggagggaatg ttcaaggaca ttgaattatc caaagaaata   1740
aatgagtctt tcaagcaatc atctcaagca aggacaaagc ttccatctgg cattgaaatg   1800
agtgttcacg tgcttacaac aggctattgg ccaacatatc caccaatgga tgtgaaactc   1860
ccccatgaac ttaatgtcta tcaggatata tttaaagaat tctatttgag caagtatagt   1920
ggaaggcgtt tgatgtggca aaactcattg ggtcactgtg tattaaaagc agagttccca   1980
aaaggtaaaa aggaacttgc ggtgtcacta tttcagagtg tggttttgat gttgttcaat   2040
gatgcacaaa aactaagctt cctcgatatc aaggaatcga ctggtattga ggataaagaa   2100
ttgcgaagaa cgctgcaatc acttgcatgc ggtaaagttc gggttctcca aaagatgcca   2160
aaagggcgag acgtagaaga taaggacgaa tttgtattta atgaagaatt tagtgcccct   2220
ctctatcgca taaaggtgaa tgctattcag atgaaggaga cggttgaaga aaacacaagc   2280
acaactgaga gagtattcca ggacagacag tatcaggtgg atgctgccat agttcgaata   2340
atgaagacac gtaaaaccct cagccacacg cttctaataa ctgagctttt tcagcagctc   2400
aagttcccaa tcaagccatc ggatatcaag aaaagaatag agagcctaat cgacagggag   2460
tacctggaga gagacaggag taacccccag atctacaatt acctggcttg a            2511
```

```
<210> SEQ ID NO 61
<211> LENGTH: 1686
<212> TYPE: DNA
<213> ORGANISM: Oryza sativa

<400> SEQUENCE: 61

atggacgccg atgaggccgc ggggagtagc aggaggatgg atctgaacct ctaccttggc      60
ctcccacgcg ccccgcgccc gcgccgctcc gacctcggct ccgacctcgc cctcagcacc     120
ccgatgccct cctccccgtc ctcctccgca gcctccgtcg acgcgccgcc gccaccgccc     180
```

```
gagctgtcgc atcccccgta ctccccctct cacgccgacc tttcccctcc gctgcaggag    240

gtctactccc tgtacaaccc cgacgacccg cctgcttccg agacgcacct gccgccgtat    300

gcgccgcctc cggctccggt ggtctcggag ctccctgacg acctcgagtt tggcctccac    360

cccccgccgc cgctggtgcg tgccagcgaa ctgctaggtt gggaggaccg gccgtcttcg    420

tcgacggcat cgtcctcttt cctccctgac accgcagccc gttactggcg gcttctcgag    480

cagactggaa gcagatggct ccgtgcgagg cggtttaggt cggaccttcc gccactcagt    540

tctgaagctt acccagctgg gcgtgatgct gccgcagtcc cagtgctgca gcatgaaccg    600

atgaatgata ctgttgaaca taataaggta gctgccgatg gcgcggaagt aggcgcctcc    660

gaggaatcgg aggagcaggg caggagcgct gccacatttg agtgtaatat atgcttcgat    720

atggccagcg agccggtggt cacctcttgt ggccatctct tctgctggcc ttgcttgtac    780

caatggctca atgtttattc caatcacaag gaatgcccag tctgcaaagg cgaggtgact    840

gaggcgaata ttactccgat ctatgggaga gggaattcat gtttggatgc cgagaaggct    900

gtggaaggtg ggaaacaaac aggtcctact atcccaccaa gaccacatgg aaatcggctc    960

gaaagcttca ggcagcagtt tcaccatttg cgaccgatct caagaaggct tggtgaggct   1020

catgggttat tgtcatcatg gaggcgcctt ctggaccaac agattatgaa tactgcgagt   1080

aggtttgaag gtccgcctga atcagctgtg caggaaatgg ttgacactgc tcacgctcag   1140

cacaccagtc gcctaagtag attggcgtca aggatgagag caagacggtt gctgagagaa   1200

gcagacaacc ctaaccctcc cgatggcgga tccacttccc ctgacagtgg tttgatcaga   1260

aacaatgcat cggatccatc cagaaatggt ccgagctcat tattaccaga tggaattgac   1320

tggttgcgtg gacttaccct tcttgggtat gaagacacgg aaagatttgc atctgccatg   1380

agtgatttta gaaggataac tggaccaagc caatatggtg catcggcttc atcatcgaat   1440

cctccaaatc tcgagtcaac atttgacaga actcatgttg ttgcagcacc ttctgcagac   1500

caagcatcta actcaagcac tgctgcagtg atacaggggg atgctggtat ctctgagagt   1560

gcaggagaac caagtaacgc ggggtcatca agatccctga ggaggagagg gaggagcagt   1620

gccctgggtt ctttggatgc tgatggcggg ggcctccaac ggaacaagag gcgaaggata   1680

aactga                                                              1686
```

<210> SEQ ID NO 62
<211> LENGTH: 1443
<212> TYPE: DNA
<213> ORGANISM: Oryza sativa

<400> SEQUENCE: 62

```
atggtgggag gagagcttgt gctggctgct ctggtgatcc tgcttgcttt gctgctgacc     60

ctggtgctga gccacttcct gcctttgctc ctgaatccca aggctcccaa gggaagcttt    120

gggtggcctc tccttggtga gacgctgagg ttcctcagtc ctcatgctag caacaccctg    180

ggcagcttcc tggaggatca ctgctccagg tatgggaggg tgtttaagtc ccatctgttc    240

tgcaccccca ccatagtgtc ctgtgaccag gagctgaacc acttcatcct tcagaatgag    300

gagaggctgt ttcagtgcag ctaccccagg ccaattcatg gcattctggg caagtcctcc    360

atgttagtgg tcctagggga ggaccacaag aggctcagga accttgctct agcactggtc    420

acctccacaa agctcaagcc cagctacctt ggcgacattg agaagattgc actgcatata    480

gttgggtcat ggcatggcaa gagcaaggac aaggggatgg tcaatgtcat cgccttctgc    540

gaggaggcaa gaaagtttgc attcagtgta atagtgaagc aggtgctggg gctatcacca    600
```

```
gaggagccgg tcactgccat gatacttgaa gatttcctcg ccttcatgaa gggtctcatc    660

tctttccctc tctacatccc agggacgccc tatgccaaag ctgtgcaggc cagagcgagg    720

atatcaagca ctgtgaaggg tattattgag gagaggagga atgctggctc cagcaacaag    780

ggtgatttcc ttgatgtgct gctttcaagc aatgagctct ctgatgagga gaaagtgagc    840

tttgtgctgg attccttact gggaggatat gagaccacct cactcttgat ctccatggtt    900

gtgtatttcc ttgggcagtc agctcaagat ctggaactag tgaagaggga gcatgaaggc    960

ataagatcga agaaagagaa ggacgagttc ttgagctctg aagactataa gaagatggaa   1020

tatacccaac atgttatcaa tgaggcactg agatgtggca acattgtcaa gtttgtccac   1080

aggaaggctc tcaaagatgt cagatacaaa gagtatctga ttccttctgg ttggaaggtc   1140

ctacctgttt tcagtgctgt tcatttgaac cccttacttc atggaaatgc ccaacaattt   1200

cagccctgca gatgggaggg tgcaagccaa gggacaagca agaagtttac gccgttcggc   1260

ggtggccccc ggctctgccc tggatcagag cttgcaaaag tagaggctgc tttcttcctc   1320

catcaccttg tgctcaatta tagatggaga atcgatggcg atgacattcc gatggcatac   1380

ccgtacgtgg agttccagag aggtctgccc atagaaatcg agccactttg ctctgaatcc   1440

tga                                                                 1443
```

<210> SEQ ID NO 63
<211> LENGTH: 2433
<212> TYPE: DNA
<213> ORGANISM: Oryza sativa

<400> SEQUENCE: 63

```
atggcgacgc tgccggacct gggtgtgtcc gccttcatca acatcttggg cgccttcgtc     60

ttcctcctca tcttcgccgc cctccgcctc cagcccatca acgaccgcgt ctacttcccc    120

aagctctacc tcactggcca gcgacgccac caccctcacc ctcatggctt cgtcaacctc    180

gacctctgct cctacctccg cttcctcgcc tgggtccccg gcgccctccg catgtcccag    240

cccgacctca tccaccacgc cggcctcgac tccgccgtct acctccgaat ctacacgctc    300

ggcctcaaga tatttttgcc catcatgact gtcgccttgc tggttcttat tccagttaat    360

gtctctggtg gcacgttact taatttacga aaagaaattg tctttagtga tattgataag    420

ctttccatat caaatgtcaa ccctggatcc aacaggttct ttatccatct attaatggca    480

tatgtgttca ctttttggac ttgctttatg ctatacaaag agtatagcaa tgtggcattt    540

atgagattgc acttcctggc ttctcagaag cgttgtgctg atcagttcac tgtgattgtt    600

agaaacatac ctcatgtttc aagccattca acatctgaaa cagtggatga attcttccgt    660

aggaatcatc cagaccacta tcttggtcag caggctgttt ataacgcaaa caggtatgct    720

aaacttgtga agaaaaaaga gaggcttcaa aactggttgg attactacca gctgaagttt    780

gaaaggcatc ctggaaaaag accaattgga aggacagggt gccttggttt ctgcggtaga    840

gaagtggatc aaatcgacta ttaccgtgct agaatcagcg agcttgataa gaagcttgca    900

tctgagcgtc aaagagttct caatgaccca aaagctgtta tgccagttgc ttttgtgaca    960

tttgactcga gatggggagc tgctgtatgt gcacagacac aacagtcaaa gaatcctacc   1020

caatggctaa ctgattgggc tcctgaaccg cgggatgtat attggcagaa tcttgccatt   1080

ccattttct ctctcagtat ccgcaagttc ctgatatcca ttgcagtttt tgctctggtg   1140

ttcttctaca tgatacctat agcttttgtg caatcacttg ccaatcttga gggtattgaa   1200

aaagttgcac ctttcctaag gcctgtgata gacacaccag tggtgaaatc cttcctgcag   1260
```

```
ggtttccttc cgggtttggc tttgaagatt tttctgtata tcctcccaac ggttttgatg   1320
attatgtcaa aggttgaagg ttatgtgtct ttatcatctc tggaaaggag ggctgcttca   1380
aaatattact acttcatgct ggtgaatgta tttcttggaa gcataatcgc tggcacagct   1440
tttgaacagc taaatgcatt tttccatcag ccaccttcac aaataccaag gaccattgga   1500
gtagctatac caatgaaagc tacatttttt atgacataca taatggttga cgggtgggct   1560
ggcatcgcga acgagattct tcgagtgaag ccgctggtga tataccacct gaagaacatg   1620
tttattgtga agacggagcg ggacagggag agggcaatgg atccgggcag cattgggctt   1680
gcagagaacc tcccatcact gcagctgtat ttttcttcttg ggcttgtgta tgctgtggtc  1740
acccccattc tcctcccttt cattatcatc ttctttgcct tcgctttcct cgtgtacaga   1800
caccagatca tcaacgtgta caaccaagaa tacgagagtg ctgctgcgtt ttggcctcag   1860
gtgcactctc gcataatagc gagcttgctg atctcgcatg taactctgtt tgggctgatg   1920
agcaccatga aggctgccta ctccaccccg ctgcttatct ttctgccact cctcaccata   1980
tggttccaca agtactgcaa gagccgtttc gagcctgctt tccgcaagta ccctctagag   2040
gaagcgatgg agaaggacaa tctggagcgc acgtcggagc caaacctgaa cctcaaatcg   2100
tacctgcaga acgcttacct gcaccccatt ttccacatgt ttgagcagca gcagcagcag   2160
gagcaggagc agcaacggga ggagaaggta gaggtgcgaa tcgacaaggc gcagcaacat   2220
catcatcggc aggtagagga ggaagaggag gagagcaaga gcagccaggc tacaacacac   2280
tactaccacc atcaccatga gcagaccaca acgacgacac accaccatta ccatcagcat   2340
gagcatatga gccactacca catgggcccc tccgacacag ctgactcacc ctcgccgccg   2400
cactttgtct accattatgg cgtcgaccct tga                                2433
```

<210> SEQ ID NO 64
<211> LENGTH: 882
<212> TYPE: DNA
<213> ORGANISM: Oryza sativa

<400> SEQUENCE: 64

```
atggagatga ccagaagcct tacgctcgtg ccgctcccgg cgacgctccg gccggcatcc     60
gcggcctgtc gccggcggcg gaggcggcga gggcttccct tcggtgcact cttctcacca    120
tcgcctcctt cgaaccagca gcagcaggaa atgcacatca gggcgctgca gccgcggcag    180
gattgggtgg gggagtgggt ccggagcaac gacacgctag tccgcggcct gcccatcctc    240
ggcggcggcg cctccctgct cgccgtcctc ctcaaccgtg cggtttccgg cattgcagct    300
gtcgccgacg cctccagttc gcagtcaagg gctgacatac tgactcttgc tctctccgta    360
actgatattc ttgctggcct tgtttggttg tccatccggc cgaaatccat ttctcctgtt    420
gttcctcgag gtgtcgagtg caaacgggta ggaacgggtg tattggactc ggctcttcgt    480
gaactacttt ggacatggga ttcccttaca actgcaactt gttgcaaatc cttggttgtt    540
gtgtatggag gtaattgtgt tcttcaaatt ggggttgctg ctggctctcc agaggatggt    600
aatgcagtta tggtggatgc acagaagttc atgcaaggtt ccctttatag aagtgccatg    660
gaatccaaga agcaatctta cctagcaaat cttgccttat atcctggaag gactgaacta    720
ccattcttgc cagctaacac gcaggcccta atattgcaac caattggtga taaaggaatt    780
gcagttattg gtggtgacac tataaggggg ttcactaatc ttgatcaggc atggattgca    840
atgatagcag ataaactgga tgctacattg tcaaagtcgt aa                       882
```

<210> SEQ ID NO 65
<211> LENGTH: 468
<212> TYPE: DNA
<213> ORGANISM: Oryza sativa

<400> SEQUENCE: 65
atggcatcat cagttgcagg ctcagtgact cgtcgtcctc ctcccgtgct gctggcttgc 60
cgatcgcgac caaataatcg tcgcctcatc agattgttac cgctcctctt cgccgtcgtc 120
gtcttgcttg ctcttcttcc accatgcgtt catggagctc gtgctctgaa tgatgccaaa 180
gaagccaaag ttgcagaggc cagcgaccag acgacgacga cgacgcacgc cgcggcggcg 240
gcggtggctc ggtggtctgt caccgtgagg gaaggaggag gtggtggtgg tcacggcagc 300
ggccatgccg gcgccggcca cggccacggc agcggccacg gcaggccgga gccagccgag 360
caccacacgg gcaggcgcag cgcggcggcc ggatccgtgc gccctcccat ggcggcctcc 420
tgcgccgccc tccttgtcgc cgccgtcgtc gctctgcttc gcttctga 468

<210> SEQ ID NO 66
<211> LENGTH: 375
<212> TYPE: DNA
<213> ORGANISM: Oryza sativa

<400> SEQUENCE: 66
atggagagtg caaagagatc ttgccttgct atctccctca tcctactcct actccttgtt 60
ccaagtatcc atggagcaag gcatgttgct gcagctatca agggtacagg cgccgacagc 120
gagatggtgg tgacggagag gacggccggc ggcggcggcg gacatggacg cggttacaca 180
agccaccggt cgcacaaccc caacaatccc aacgacggtg gctccggcac gccggtggtg 240
gacccgcaca atgtcgccac caggggccac caccaccgcg gcgcggcgac gaggacggcc 300
gccggcggcg acccccgcct ggcagcctgc atgcttcgtc tgggagcgac cttcttcctg 360
ctggttcttg gctga 375

<210> SEQ ID NO 67
<211> LENGTH: 1257
<212> TYPE: DNA
<213> ORGANISM: Oryza sativa

<400> SEQUENCE: 67
atggcgggcg ttggattcgt ggaggacatg ctgcgggagc agagcctcct ggaggcgacc 60
tgcggcgacc tcttcgacca catcgacgac ctgctcgact tccccaagga ggagtcggcc 120
gccgacgtgc tcctgctcga cgcgccggcg ccagggagcc cgctgtcctc gcgcatcatc 180
ggcggccacg ccaccatggc ggcggcgccg ccaccgccgc cgcagatgat ggcgctcccc 240
ccgccgccgg cccccgcgaa ggacgacgcg tcggcgctgt tcgacgcggc cggcgcgctc 300
ggcgccgagg tgttcgaccg caaggacgcc cacattggcc cgtgtgatga gctggacatg 360
gacatggcgc agctggagtg gctgtcgggg ctgttcgacg atggaaccat cccgcacgag 420
ccgagttttc cgggcgtcaa ctgcgcggcg ccgatcaagg cgtcggcgct gacggcgaac 480
gccggcgtcg tgctgccgga caaggcggag gaggcgctgt tccgcagctc cagccccatc 540
tccgtgctgg agcacagcgg cttcaacgtg gcaaccaatg gggctcctc ctcgtcgtcc 600 tcctcgtcgg cgtcctcctc gtcggagtcg ttctccggca gcggccgcgc gtggtccgcg 660
cccgtgtcgc cgcgcccgga gccgcccgtg ctcgtcatcc cggcgcgcgc gcgcagcaaa 720
cggtctaggc cgtccgcgtt cccggctgtc cgcggcgcgc cggcggcgac ggagaccacc 780
atcctggtgc cgacgccaat gtactcgtcc acctcgtcgc actcggatcc cgagagcatt 840

```
gccgagtcca acccgcaccc gccgccgatg aagaagaaga agaaggccaa gaagccggcc     900

gctccggccg ccgcctctga cgccgaggcc gacgccgacg cggcggacgc cgactacgag     960

gaaggcggcg cgctcgcgct cccgccgggc accgtgcggc ggtgcacgca ttgccagatc    1020

gagaagacgc cgcagtggcg cgcgggcccg ctcggcccca agacgctctg caacgcgtgc    1080

ggcgtccgct acaagtccgg ccgcctcttc ccggagtacc gcccggcggc gagccccacc    1140

ttcatgccgt ccatccattc caactcccac aagaaggtgg tggagatgcg ccagaaggca    1200

acccggaccg ccgacccgtc ctgcgacctc ctgcagtaca tccgccgccg ggattaa       1257


<210> SEQ ID NO 68
<211> LENGTH: 1329
<212> TYPE: DNA
<213> ORGANISM: Oryza sativa

<400> SEQUENCE: 68

atgggcgggt acgagctcgt caggagcgac gacgccgcgg cggccggccc gccagatctc      60

gagctcggcg gcagcggcag ctgcaacggc ggcggcgtct cggccaagtc ccggcctccg     120

tcatcgccgc cgtcgcaggg cggcgcgcgg cagcggctcg tctccctcga cgtcttccgc     180

gggatcaccg tgctgcttat gatcattgtc gatgatgctg gagcttttct cccagcactg     240

aaccactctc catgggacgg cgtaaccatt gcagatttcg tcatgccatt cttccttttc     300

atggttggga tctctctaac gctcgcgtac aagagggtgc cggacaaatt ggaggctact     360

aagaaggctg tactacgtgc cctcaagttg ttctgccttg gccttgttct ccaaggcggt     420

tttttccatg gtgtccgcag tctcactttt ggtgttgata ttacaaaaat acggttgatg     480

ggtatacttc agagaattgc tatagcttat cttttggctg caatctgtga aatttggctc     540

aagggagatg atgatgtaga ttgtggactc gatgtgatac ggagataccg ttaccaattg     600

gttgtagcat tgctcctgtc aaccatgtat actgttattt taaacggtgt ctacgttcca     660

gactgggaat accagatatc aggtcctggt tccacagaga aatcattctc tgtgagatgt     720

ggagtaagag gagacactgg tccagcttgc aatgccgttg gaatgcttga ccgtacaatc     780

ttggggatcg atcatctcta cagacgaccg gtttatgcgc gtacaaagca atgtagtata     840

aactatccgc aaaatgggcc ccttccacct gatgctccat catggtgtca ggctccattt     900

gatcctgaag gcctcctcag ctctgttatg gcaattgtca catgcttgat tgggctgcag     960

tttggacata taattataca ttttgagaaa cacaagggaa ggataataaa ttggctaatt    1020

ccttccttca gcatgttagc actggccttc tcaatggact tcattgggat tcgtatgaac    1080

aagccgctgt acacgataag ttacgccttg gctacctctg gtgctgcagg gcttcttttt    1140

gctgggatct acacactggt ggacgtgtat ggattcagga aacttaccat ccccatggag    1200

tggatgggta agcacgcgct gatgatctac gtgctagtgg catgcaacat cctgcccatt    1260

ttcatccatg gtttctattg gagggagccc aagaacaacc ttttgaagtt catcggagtt    1320

ggggcatga                                                            1329


<210> SEQ ID NO 69
<211> LENGTH: 1467
<212> TYPE: DNA
<213> ORGANISM: Oryza sativa

<400> SEQUENCE: 69

atggccgcga ctggcggcgc cgccggggag aagacggcca gcagcctcct gctcggcgtc      60

cggggctaca cgtccaccct caagaacgcc tccaccgcca gctgcaggtt gagcgccggc     120
```

```
catcccatcg aggtgacttt gtgggaggcg tccccgcctg ccctctccca cttctccgtc    180

cactgccccg atctcccatc cttcaatggc aatctgcttg gcgcgcctaa agccatcgcc    240

gccgccgtcg acgacgccga cggccagctc ctcctcctcc tccgagtccc catcgatcag    300

cttggtgccc cgcatgacaa cgactacttg gtctaccatc cggatccccc gtctccgaaa    360

ctggatctgc tccccaaccc gcctccccct accctcggtg accaccagct cgccatactc    420

agctgcggcg acgaccgcta cgtcgtggcc gccctccacg tctggagtga gttcacttcc    480

acgctgcgcc tgtacagatc ttcttgttcg tctgggagtt ggacatcgga ggaggtgtcc    540

gtggaggagc cggtgaggga caggctgtgc ccgatcccgg actcagccaa gaggcagctg    600

taccacgtca ccaccaagac catcacgctc ggaggtgcga agggcaccgt gggctgggtt    660

gatctctggc gcggcatcct cctctgcgac gtgctcgacg aaatgtctcc aaggaagctc    720

cgcgacatgc cgctgccgtg gccggccaag ggcaattgga ggatgtacct caatggagat    780

gtgtcctttt gtcgggacat cgccatcagc caacacaagg attccatcaa gtatctggag    840

atggagatcg tttcaccaag aacggtgacc accaccatac ccacctccac ctctgcagat    900

cctacttcat accttgaatg ggttcgccgc agcagagaac ctcagccgac acggcgacgc    960

tccgtgttcc accctggttc gtggagaatc actacatgga gcatgcctat cccggtcact   1020

tcatgggacg actggcgccg tgactgcact gctgaatcgc gtgaagtcca tcttgacacc   1080

aacccaagtc accattacga gttgcttcat agcctcatgc tcagcaacag cggtgatgaa   1140

cacagggagg aggctcaagg tcaaggggca acctcttcct tgtccctagg tcgcctgcgt   1200

ttgtgttacc cggccttgag ttgcatcgat gatgatgttg tttacctctt gggcaacgct   1260

gctggcaggg gtgctaagac gggaggaatg atggtcgctg ttgacgtcag gaacaaggag   1320

ctgcgaggag tggccaagct tgaccccgaa aagaacaccc tctactccat gcgatgctac   1380

cttgcaactg ggatctccaa acgcctcaac actaccacag acacaagagt tggacgacct   1440

gaggaggatg cagaagccgc cgagtag                                        1467
```

```
<210> SEQ ID NO 70
<211> LENGTH: 504
<212> TYPE: DNA
<213> ORGANISM: Oryza sativa

<400> SEQUENCE: 70

atggcgaact accaccacca ggagtactac cagatggcgg cggcggcagc ggtggcgtgg     60

ccgagggagc cggacagccc gcagctgagc atcatgagcg gctgcagctc cctcttctcc    120

atctccaccc tgagggacga cgacgacggc ggcggcgtcc gcctcgccgg cgccgcgctg    180

cccgccacgc cggtgtcgct cgccgggatc gccggcggcg ccagtacccc cggcggcgac    240

gaggtggaca tggaggtgcg gcagcagagc ggcggcagcg gcgacgaccg gaggaccatc    300

cggatgatga ggaaccggga gtccgcgctt cgctccaggg cgcgcaagag ggcgtacgtt    360

gaagagctag agaaagaggt tcgccggctg gtggatgaca acttgaatct caagaagcag    420

tgcaaagagc tgaaacagga ggttgctgca ctggtgatgc ctacaaagag ctcactgcga    480

cgaacttcat caactcaatt ctga                                           504

<210> SEQ ID NO 71
<211> LENGTH: 933
<212> TYPE: DNA
<213> ORGANISM: Oryza sativa

<400> SEQUENCE: 71
```

```
atggcagaga aaaagaagaa gaagaagaag aagaagccgc aatcactcct agtccttaca     60
agctggagat cgatcgggat ggggaggggt cgggtggagc tgaagaggat cgagaacaag    120
atcaaccggc aggtgacgtt cgccaagcgc aggaatggcc tgctcaagaa ggcgtacgag    180
ctctccgtcc tctgcgacgc cgaggtcgcc ctcatcatct tctccaaccg cggcaagctc    240
tacgagttct gcagcaccca gagcatgact aaaacgcttg agaagtatca gaaatgcagt    300
tacgcaggac ccgaaacagc tgtccaaaat agagaaagtg agcaattgaa agctagccgc    360
aatgaatacc tcaaactgaa ggcaagggtt gaaaatttac aacggactca aaggcaatac    420
tacaaatcta aacataggct gtgtttagtt cggtccaaag tttggaattt ggttaaaatt    480
agagacgatg tgactgaaaa gttgtgtatg tatgaaagaa atttgctggg tgaagatctt    540
gattcattag gcataaaaga gctcgagagc ctagagaagc agcttgattc atccctgaag    600
cacgtcagaa ctacaaggac aaaacatctg gttgaccaac tgacggagct tcagagaaag    660
gaacaaatgg tttctgaagc aaatagatgc cttaggagaa aactggagga aagcaaccat    720
gttcgcgggc agcaagtgtg ggagcagggc tgcaacttaa ttggctatga acgtcagcct    780
gaagtgcagc agcctcttca cggcggcaat gggttcttcc atccacttga tgctgctggt    840
gaacccaccc ttcagattgg gtaccctgca gagcatcatg aggcgatgaa cagtgcgtgc    900
atgaacacct acatgccccc atggctacca tga                                 933
```

<210> SEQ ID NO 72
<211> LENGTH: 612
<212> TYPE: DNA
<213> ORGANISM: Oryza sativa

<400> SEQUENCE: 72

```
atggagggag gagggaggag gaggaagagg gggaaggtgg agctgcggcg gatagaggac     60
cggacgagcc ggcaggtgcg attctcgaag cggcggagcg ggctgttcaa gaaggcgtac    120
gagctgtccg tgctctgcga cgcccaggtc gccctcctcg tcttctcccc cgccggccgc    180
ctctacgagt tcgcctcttc cacctccagc attgatacaa tttttggtcg gtattgggac    240
cttctggaca caacaattga tctcaatatt gaagcaaggg aatctcgggt tgattgcaat    300
atacaggtct ggatacggag acaaatcgtc cacggagggc tagctccttt gttggttgga    360
gatgcagctc ctccatttag ggtgttggt gtggctcctc gcctagccct ttgtatttat    420
gacgacactc cacctaggat caaggtggca aaagctggtg gcatggaagg tggcatgatg    480
gacgtcaatg atgggttgca agagtttggg ctgcatctca tgattgcctt agtgtggtat    540
tttatgcgac aaggctcgtt aggcaacaaa ggatcaatct ctggcacgac gatcatcaaa    600
gtttctaagt aa                                                        612
```

<210> SEQ ID NO 73
<211> LENGTH: 435
<212> TYPE: DNA
<213> ORGANISM: Oryza sativa

<400> SEQUENCE: 73

```
atgggtttga ggtgggacaa ggcggagagg tcaacgagaa gggcaaggag cgcaccgacg     60
agggagaaga ggccggagaa ggggaagtcc cgccagaggc gtcgcgtggc aacgacgcag    120
tcggcggcgg cggcactgcc aagcgtgcgc cgcgctggcg gtgagacgcc ggtgctgatg    180
agcggcacga ggcacgacgc gatggcgatg gtgaggctga caaaggtcag gatgctgttc    240
gtgcggtgcg gtggcagcgt gaggcactcg tcggaggagt ctgtgttgga cgacgacatc    300
```

tgggccgccg cgaggaagaa ggggaaaaga aaagaagaga gagagaggaa gaacagtgtc 360
aaaggtgggc gggctaaggt gagatcaagg ctaagacgag agtgccatca aacgtcgaat 420
tcttcgtctg gctag 435

<210> SEQ ID NO 74
<211> LENGTH: 804
<212> TYPE: DNA
<213> ORGANISM: Oryza sativa

<400> SEQUENCE: 74
atgagcttcg cggatctgga ggccggcgcg gtgcgggcgc ccaggagggc gcggggcccc 60
gacgccacgc gcgcgctcgt cttccagatc accaccgccg tggcctccta ccgccgcctc 120
ctcaactcgc tcgggacgcc caaggacacc cccgcccttc gtgaccagct gcagaagact 180
agtcataaca ttcttcaatt ggcaaaggat gcgaaggaga agctcaggag agctgctgag 240
gcagacaaga acgccgatac tagtgcagac aagagggttg ctgacatgaa gcttgccaag 300
gattttgcca cgacgatgga ggagtatgga aaacttcaaa atcttgcgat tcaaagggag 360
atggcatata agccagttgt tccccagaca tctcagccaa actatactac aggtggtata 420
gaagccaggg attctggtaa aattcctgaa cagcatgcgc tactcgcaga atcaaagagg 480
caagaggtgc tgcaattgga taatgaaatt gttttcaatg aagctatcat tgaggaaagg 540
gagcaagcta ttcaagatat tcaacaacag attggtgaag tacatgaagc atttaaggat 600
cttgctacac ttgtgcatat tcaaggagtt acaatcgagg aaatcgatac aaacattgag 660
aattctgcag cagcaaccaa agaggcaaag acagaactcg cgaaagcgtc caagactcag 720
aaatcgaatt catcactgct ctgcattctt ctggtgatct tcggggttgt cttgctaatt 780
gtgataatag ttttggcaac ttga 804

<210> SEQ ID NO 75
<211> LENGTH: 318
<212> TYPE: DNA
<213> ORGANISM: Oryza sativa

<400> SEQUENCE: 75
atgtgtgtgc tcgcacaaga gaaagagaga agaggtaaca atgcacttgc tgcagaatgg 60
tttccagcaa ggatattatg catgtactgg agtacaccaa gtttcaggaa gatgtcaatg 120
cgtggcaagg agaatcggtt ggtaggaggt aacactgtat accatcgtag cggatcacgt 180
ggcttattag ggactcgaca attcctaaag accaaaaatg gagttgatcc tgggcaggca 240
ggagcatggc atcatcaaca ccgaatggaa catgacgggc caagagggct ctgctgtgag 300
aaaactgcta ttttttag 318

<210> SEQ ID NO 76
<211> LENGTH: 3345
<212> TYPE: DNA
<213> ORGANISM: Oryza sativa

<400> SEQUENCE: 76
atgcgtgcgg cggcggcggc ctccaaggcg gcggggaagg agaagagcag gaggaagggc 60
ggcggcggag gagcaggagg aggaggaggc gagcagctgc tcaccgacca ggtcctctcc 120
ctccgcgccc gcctccacct cgccctcgcg ctcggcctcg ccaagtctga tggaggtcca 180
aagaaatggc agtctactga tgctggaata cagtctcatg tgctcaaagc agcatcagcc 240
tttcttggct gtttgaccaa tgagatgctg cggcttcctc ctataaagga gtcaatttcg 300

```
gatatactca tagcactgga aggtattctt cagtccaaga atgtgtcggt tctgatccaa    360
gcaactgatg ttagcttgaa gttagtttcc agtgtaggaa atttagctcg ccaatacccg    420
gttttagaga tcgttacatg cctcgcgagt cagctttctg caaaccagat aactatagct    480
gtctcatctg caagtacatt gaactgcata ctgaacaccc tagcaacagc gagaagttcg    540
attcatgcag aaatttggga agctttggag aaaaccgatg cagttacaag tgtcattgga    600
gctctgcaga attactcccc tgatgtccat ccattaaact atctgatgga aatgatgtct    660
ctgctaagaa ttatactgtg gatttggcct tcttcgagat accatgtatg gagtaactgc    720
aacttgatgg ggaagctagc acaatactgt gttgcctctg aaatggatgt tgctgttaga    780
gtcctcaagc tatatgctgc tttagcttta tgtgggaatg gtgcaatggt ccttctgaat    840
aatgaagact tgatggctaa ggttggtgcg cttttgggga agtcaaatcc atctattgct    900
agaattgaag cattgaaatt ctatcagatt cttttgcgat cttcaaaagg gtgcgatctg    960
ttaatggctg cacactatca acacattatt gaaggcacaa tcaacgcaat gtctagagat   1020
gatgaaagat tgttaacaat agagggctgc cgcactgcac tgctggtcct tcgttatgct   1080
ggggatcatc atcggctctt ttggtctcat gctattgatg atgtattata taagattctt   1140
actggtggct gcacctcttc acataaagcc aatcagattt tgtgccacga caagcttttt   1200
aatatggttt ccgagaactt tatggatata cattcttatg tgtgggatat acttggaaat   1260
ctagcagtac attgcaaaaa tgagtatctc tctgttagga aagggcaaga ctctgccttg   1320
caggcactaa tacattgtat ttgctcactt gcagcagatg ctatgcagaa aagcaacacc   1380
atgaaattat ccaaggatgt gcatgagcca gctttgaggg ctgttctgat gatgcttctc   1440
tcacccagtg gatacatttt gtctgaggca agttctaaac tcttacatgt tttaccttta   1500
ggtgatgact gtttgaatat tctgttcacg tcgttagaat caaatactac aagaagcatt   1560
actgcatctt ttgacaatgt caaaattatg tccaacctca tgagcctagc gggcatgagc   1620
atcaattttg tttgtatcca ctgtaaaagg aatttggatg tggggattgt gtgcaatgat   1680
tgcagagatc attatagtga aggtctgatt agagttcttc aaaatgcgtc atgtcaaaac   1740
ttgagcccag gaccgaagtt gtacatttca cgtatactga gtttgtttgg cctatgcggt   1800
tttccaagca agttgggagg aaagatgaga agggccttag atgataatga gctagctgat   1860
ctggaactgt tgctttcaaa tggtgaatct ttaaaagctc atacagccat catttcagta   1920
aggtgtccaa agttgttgcc atctgcaaaa tcccttggta gtgatggaaa aattactgat   1980
gaatggggca gatcatttta tcatgttcga atgtctgatc gtgttgatag ttgtggcttg   2040
aagaaaattt tggaatacac atacacaaat tctgtcatgg tagatgatga caacattaag   2100
ccagtaagga cacttgcgaa gtattgtcac ttgaaatcat tacaagagat gcttcaaaaa   2160
gagcagccta ggtggaactc tgattgtcct agatatgatc ttactgcagc acttgaacca   2220
gttaaatgtt cattctcctt ctcagaagtt atcaatgttc cactggggtg gcaagcgctg   2280
aacaaactga tccactggtt ctactcaggc gagctaccca agatcgaccc cgattgccga   2340
tggcgaaacc tgaacagcga ggagcagctt tctcagctgc ggccttacgc cgagctgtca   2400
tccctgtctg aattctggtt cctggaggga gtgaaggagg agagcctgtc agtggtcacc   2460
tcctgcctga gttccaccag cacggccgcc tccgtcgagt tcgtcgtctt cgcggcgcag   2520
ctgggtcagt gggagatggt ggaggccgcc gtcggcagcg tcgcccatct gtaccccaag   2580
ctgcgggact ccggtcagct ggagcagctt gatgatgatg tgctcaacat gctgcggaca   2640
gagtatgtca gacgcacgca aagaacggga gttggctcgg cggcggcgca ggcgggggcc   2700
```

```
agagtggtga cggcggtgta caggcggggg cagagggcag attattggca aagtggtggt   2760

tttggagata attggaattt tcaaatggtg attcttaatg cctcggaaga gcattgccgg   2820

gagtccaaat ttgatacaat tggagtttgt aaagctcgtt tcttgtacgg gaaggtttct   2880

aggggattta gattgcgtac ctcgggtata aacaaagagg gaggcccaag agggggtaca   2940

gtaatttata gcaggtcgtc aggagggctg cctccctggt gtggtgcagg aagtcacgac   3000

gcattggcag ccgtcagatg gccgtcactt ccaggcttgg agtcgcatca gacggcgcag   3060

gtgataaggc gaggcgcagg gcgcagaggc gaggggagag acgtaaacgt aaccaagcaa   3120

agcaacgcgc ccatgcggcc gcccgagacg atgcaacgcg agcagccgca gagcagagca   3180

agagccaacg gtaggaaatg gccaccacca cgacgatgga gatccggaat tcgcgaggag   3240

cagggggtgc caagtgcaaa ggcgtggcag gagaagagga agaggacaca gcaacagcgt   3300

tgcgcactgc ctgctgccat tgctgcctcg cgtttacagc tatag                   3345
```

<210> SEQ ID NO 77
<211> LENGTH: 1239
<212> TYPE: DNA
<213> ORGANISM: Oryza sativa

<400> SEQUENCE: 77

```
atggcctccg ccgtcgcgag taacttgcct gcagctgcgc ccgcggctgt catgccgttc     60

ggtggatggc atggtccgcg tgtctcgttc agccgcgacg ccgccggggc tgaggaggct    120

gccgcggtgg tcgtgtgttc ttcgcccctg gccgccgcgg cggcggtggc gacgacgacg    180

acgccggagc cggcgatatc caaggacttc atcgacttcg agttcagcct cgggggctcc    240

gccaccatgc tcccggcgga cgagctcttt gccgacggga agctgctccc gcttcggaag    300

gcggcggctg tgccggagat ggatgcggcg gcgccacggc cgccgcagcc tgaggcaatg    360

ccggcgcctt cggagccgat gaagccacta cgggcggcta ccgccgcggt tgacgccgcc    420

gacccgtacg ttttctctcc taaggcgccc agctgctcga gccggtggcg ggagttgctc    480

gggctgaaga gagcggcagc gcagagcccg aagccatcgc cgtcgtctgc gcccgcgaga    540

acccccggga gagcgatgaa ctcgacggcg gcgaggtcgc tgaagctgct gctccaacgg    600

aacaacggcc gctcgtccgg ggcctccgcg tcggagctcg cctctgcgcc gctcctccgc    660

gacagctccg actcggaggc gtctctctcc ctcgcctcct cccgcttctc cctctcgtcg    720

tcgtcgtctt cctccggcca cgaccacgac gacatcccgc gcctctccct cgactccgcc    780

gctgacccca acccgccccg catccgcctc gtccgttcct cccaccgcca ctccacctcc    840

tcatcctcct catcccgcgc cggccgaagc cccgcgcgcc gccgcccctc cccgccgccg    900

ccgccgcgct gcctctccgt cgactccccg cgcatgaact cctccggcaa gatcgtgttc    960

cagggcctgg agcgcagctc cagctcaccg tgcaccctcc acgccgcggc gaagccacgc   1020

tcccgcgccg tcgaccggtc atactcctcc ggcgtccgcg tggcgccggt ggtgctgaac   1080

gtgccggtgt gctcgcggcc ggtgttcggg ttcttcaagg acaagaagga cgcggcggcg   1140

aaggacgcca tggcggcgag gacgaggtcg tcgctggggc ggaagacgac ggcggcgccg   1200

caagggtgga gcggcgagct ggggagatct tgtgggtaa                          1239
```

<210> SEQ ID NO 78
<211> LENGTH: 2292
<212> TYPE: DNA
<213> ORGANISM: Oryza sativa

<400> SEQUENCE: 78

```
atgaaaatca gcggacttct gacctctgct ggcatcaata tcgctctttc tgtgctgttt     60
atatcgctct attctgttct gaggaagcag ccagccaatg tcagggtcta ctttgggagg    120
aggattgccg aggagcataa tcggctccga gaagctttta tcttggagag atttgtacca    180
tctactggct ggatagtaaa agccctgcag tgtaccgagg aagagatctt ggctgctgct    240
gggctagatg ctgttgtttt caatagaatt ctagtattca gcttacgcat cttctctcta    300
gctgccattc tgtgtgtgtt tggaattcta ccactgaact actttgggca agatatacat    360
catgttcgga ttccttcaga atcattggat atctttacaa ttgggaatgt gaaagtgaga    420
tcaagatggc tttgggtcca ttgtgtagcc ttgtacataa tatcaggagt agcttgcatt    480
ctcctatatc ttgagtacaa gcacattgct aggctgaggc tccgtcatct tacttgtgca    540
atgcccaatc caagccattt tactgtcctt gttcgtggaa taccaaagga aaccaaagaa    600
tcatgcagta atgctattga tgatttcttc accaagtacc atggatcaag ctacctgttc    660
catcaagttg tttacaaagt tggaaaagtt cagaagataa tgactggtgc taagaaggca    720
tacaggaaat tcaaacattt tacagacagc actattgatc agaggtgtcg agcaatttca    780
taccggtgct gtctgtgcgg agcctcatct aattctttcc agctgttggc aactgggctt    840
gagcagaatc aggggaaatc tgaccttcaa gattccagct tgaaactaga tgatcaggaa    900
tgtgcagctg cttttgtata tttcagaact cggtatgctg ctcttgttgc ctcagaaata    960
ctccaaacat ctaaccctat gaaatgggtt actgatctag ctccagaacc agatgatgtg   1020
tattggtcaa atctttggct accttataag cagctttgga ttcgccgaat agctacgctc   1080
cttggttcaa ttgtttttat gttattcttt ctgataccag tgacatttat acaaggacta   1140
tctcagctag agcagttgca gcagaggctt cctttcctga aggggatact ggagaagaaa   1200
tacatgagcc agcttgtaac tgggtacctt cccagtgtca tactgcaaat atttttatat   1260
gccgttgcac cgataatgat attattttct acattagagg ggcctatatc tcacagtgaa   1320
aggaagagga gtgcttgctg taaagtgctg tacttcactg tttggaacat attctttgga   1380
aatgtactat ctggtactgt cataagccaa ttgaatgtgt tatcaagccc aaaggacatc   1440
cctgtccagc ttgctagagc tatacctgtc caggctacct tctttatcac ctatgttctg   1500
acatcaggat gggccagttt atcatctgaa cttatgcaat tatttggttt aatatggaac   1560
tttgtgagga aatatattct acgtatgcca gaagacacag agtttgttcc ctcattccca   1620
tatcacacag aagtgccaaa agttttgctg ttcggactac tgggcttcac atgctctgta   1680
ctggcacctt tgatcttacc ttttctgtta gtgtacttct tccttggtta catcgtgtac   1740
cgcaatcagt tgctcaatgt ttaccgcaca agatatgaca cagggggttt gtactggcca   1800
atcgcacaca acgcagtgat attctctctc gtgctcacac agattatctg ccttggtgta   1860
tttggcctga aagaatcacc agtagctgca ggcttcacca tacctcttat catcctcact   1920
ctgttattca atcagtattg cagaaatcga cttctcccat tattcagaac taccccagca   1980
caggatttaa ttgacatgga cagggaagac gaacggtcag gaagaatgga tgaaattcac   2040
caccggcttc attctgccta ttgtcagttc cacgacactg aagatatacc cttggagaaa   2100
attcagactg tcgggagcga tgaggaacaa gggtgtagct ctgataagtc gaatggaaaa   2160
gaaagcttcg aggaacccag agcggagttg tctcacccaa cactgaatgg actcccagtt   2220
agccgtcttc ggcatgctgt gaagtcgatt actttccttg tcagattgca gaaaagaggt   2280
ttgtcagaat ag                                                       2292
```

<210> SEQ ID NO 79
<211> LENGTH: 2106
<212> TYPE: DNA
<213> ORGANISM: Oryza sativa

<400> SEQUENCE: 79

```
atggcggggg cggcggaggg agggagagcg aaccctacca cgaggcgcca ccagaggacg     60
gcgatcaaca tatctcctcc tccacggcat ggcgtggtgg cgcctcgccg gagtgcgcgg    120
cggcgcgtag gcgtagcagc tcagcttagg cttcgcccta actctcgatc ccaatcccca    180
tgcggcgtct ctacctctac caatcaggtc aggctccgat ccccattcgc tcgtgctctc    240
gtcggcgtgg aacaacaggt gcaagaagct gggcaggctg gccaagatgt ccagcgccga    300
cgtggaaggg gccgagaagg cttagatggg cctgagtggg aatgcgactc tctcttctgg    360
ttgggccaga acagtatcaa tgacatacat gcggcccata tttattgggc cggaacggga    420
ttgctacttc gtgcggcggt cgcgctcctc ccaaaccatc tccgcggcct cttcgtctgc    480
ctcaatgaat cgtgcctcca tggcttcttc gcccgtccct cgccgccggc caccatcccc    540
ggcatcgacc tcgactacga cctggacgac gatgccacca tcgaagtcca ctgcaacggc    600
ctcctcttgc tcgatcgcca catcgtcaac ccggccacac gccagtggat gcgtctacct    660
cctgtccccc cgtacgcctc actgcccaac ataatgtacg gtgatcgggg cctcgtcttc    720
gacccagcag cgtcaccaca ctacgacgtc ctctggatgc cctacctgat tcttcatcga    780
ctccctgctg cgtctctgtc ggatcagtgg ccgccgtcgc cgttcatcct gcacgtcttc    840
tcctccacga cggggcgatg ggaggagaag tcgtttctcc gggaaggcga cgccaccatg    900
ggcaccatgg ctgatgtatc cttggcaagg gtaccttacc actgcaagac tcactccgtc    960
tacctccggg gagcgctcta catgcattgc cagaatgatt gcgtcatcaa gatcacactt   1020
aacgaccaca agtatcgggt catcagattg cctggcgact ctgcatcaaa cagaaagact   1080
agggaccctt tcctaggaaa atcaaaagac agagtgtgct acgtattggt caccggtcta   1140
agtcgactcc aaatttggct cctcaacgaa acttcttctt cttcttcttc ttcttcttca   1200
tacgacgaca acgagtgggt gctcaagcat ggtgttgacc tagggccaat aatacaaagc   1260
taccccctgca accatggtcg tcagcaatgg atatggcata atgctgacac taaacaagac   1320
aaaaccaggg aattaccagc tgtaaatgat atggaggaat ttgaatgggc tatcgataag   1380
gactctgatg acattattag tggtgccaat gaaagcatcc accataatgg agaatacatc   1440
tccgctgtac tcggatttca tccttttaaa gacatcgtct tcttgcacga tacaaattta   1500
agagttgttg catatgacta caacaaggca aaggttcaag acttgggtat gatgttccta   1560
taccataata cagatagagt gccgtcggat ggaaaggctc agggttcaca gcacgtgagg   1620
cccatgtcac cttcctcctc ccatctcatt ctcatctcac catcccacgc ttttggactc   1680
ccaaacgacg ctgttgcctt tcgtcaaccc ccacttctcc ttccccgccg ccgccgctcg   1740
ccgcccgccc gcccgcccgc catggatgag gagtacgacg tgatcgtgct ggggacgggc   1800
ctcatggagt gcatcctcag cggcctcctc tccgtcgacg gcctcaagcc gcactcggat   1860
gagctgctgc tggttgcttt ttttttttta cctcgccatt tgatcgctgc acagagatcg   1920
aagggagggc ctgccatggc cgctcaacgt actcccgccc cctctccgcc ctccactgcc   1980
ttctacacat cggctcctcc ctctccactc ccccgctttt gcacccacca ccgcatcccc   2040
cgcccggaga ccggcaacga cggagggtta gcttcgacga gcgaccgacc acgagatatg   2100
atatga                                                              2106
```

```
<210> SEQ ID NO 80
<211> LENGTH: 909
<212> TYPE: DNA
<213> ORGANISM: Oryza sativa

<400> SEQUENCE: 80

atggcgccgc ctaatgacgc cggagatggc gacgacgaca agcccgagat gccggtggtg      60

ctcatcaccg gctgcgccaa cggcggcatc ggctacgagt actgcaaggc cttcgcctcc     120

ctcggctgcc gcgtcgtcgc caccgacgtc cccgaccgcg tgcccgacct cgccggcctc     180

gacgccgacc acctcccgct cgacgtcacc tccgacgaga gcgtcgaggg cgccgtggcg     240

cgcgtcctcg ccgagcacgg gcgcgtcgac gtgctggtga acaacgccgg catcgggtgc     300

accggcccgc tcgccgagct ccgcggcgag gccgtgcgtc gcgccatgga cgtcaacttc     360

ctcggccagc tccggatggt gcgcgccgtg gcgccgcaca tggcgtcgcg gcgttccggg     420

cgcgtggtga acgtgggcag cgtggtgggc acggcggcga cgccgtgggc cggcccctac     480

tgcgcgtcga aggcggcggt gcacgcggcg acggacgcgc tgcgggtgga gctgcggccg     540

ttcggcgtgc acgtggtgaa ggtggtgccc cgccgcggcg aggtccgggc tgggccacgc     600

caacacggcg cagctcgccg gagggcaggc ggagtggcgg ctgtaccggg agttcgcggc     660

ggcgatcgcg gagagggcgc gggcgtcgca ggcgggggc gcgacggacg gcggcgtgtt      720

cgcggcgcac gtggctcggc gggtgatgag cgcgcggccg ccgcgggaga tcgtgtacgg     780

gaacatgacg ttgctgttcg cggcgctggc ggcggcgccg ctgtgggcgc gcgacgcctt     840

cttcgccaag cgcttcggcc tcgacaagat gctaccaccg cgctagagaa gaagaagaag     900

ccatcatga                                                             909


<210> SEQ ID NO 81
<211> LENGTH: 744
<212> TYPE: DNA
<213> ORGANISM: Oryza sativa

<400> SEQUENCE: 81

atggtggagc tctctatcgc cgacgccagc gccagtgatc tgtgcggcgg cacgctgggg      60

cagatggtgg agctcgtctg cgaggcgagg ctacgagtga gggaggagta tgtgagatca     120

acagtggact tgatggcgtt gctgcgtggg cgcggcatgg tgttcgacgg ggtgtacgtg     180

gtgtcgaacc tgacgcggct cttcgcggag ctggactttg ggcgcgggga gtgggtggtt     240

agcggcatgg cacagccgat gctggcaacg ttcctggtga cgtgcaggaa cggcgacgac     300

gaggacgcgg tggcggcatc gatgctgttg ccgcctccgg tgaagttgag gtttgcagag     360

gagcttgctg ggctgatgat gagcatgccg cacggcggcg ctgccctatg ccccgcaccg     420

gcgagtacgt acctccctct tagcatgcgt ggaagacggt ggctacacat cccggagggg     480

tactacggca acgcactcgc atactccatc accgatgcca gtgccagcga tctgtgcggc     540

gcgacgctgg cccagatgat ggagctggtc tgcgaggcga ggctacgggt gacggaggag     600

tacgggagat cgacagtgga cttgatggcg tcgctccgtg ggcacgacac ggtgttcgat     660

ggggtgtacg tggtgtcgga cctgggtgcg gggagtgggt ggtcagcggc atggcctagc     720

cgatgctggc gacgttcctg gtga                                            744


<210> SEQ ID NO 82
<211> LENGTH: 435
<212> TYPE: DNA
<213> ORGANISM: Oryza sativa

<400> SEQUENCE: 82
```

atgaatcaac aacaccaaag atcaatcgag cactgctcga tcggttgctt tctggcctcg 60
ccgccgcctc ggttcttccc agctcggact cgatcggctc ccggcgagct tcgaatgaag 120
ctcgtcgtgt tcttgattcg aggctgtccc ggcgaagttt tgctgagacc aatcgtcccg 180
gcaaaagagg ggctgcgaac cagaacgaaa tggcacatat tgcagaggtt ttgcaaactt 240
gaaataataa gtatagagac agaaacgatg atcacgatct cgagtcgatc gatcatcaaa 300
tcgagatgta aaaagtcaaa taaaaagatt ttggttttct ttttatctat gtcagtgaaa 360
tttctgctca tcacaaccag aagatctttg tcagtacaga agagatcttc cacgttctcc 420
caacttttgc attag 435

<210> SEQ ID NO 83
<211> LENGTH: 285
<212> TYPE: DNA
<213> ORGANISM: Oryza sativa

<400> SEQUENCE: 83
atgtgcatgg accgagctgc cgtgccggtg aagagggtgt ggctcggcct cgccgcgcgc 60
ctcggcctcc ggcgaaccag cgggctgggg aagctgaaga aggaggtgag gacgtgcgag 120
taccacgacg tgcacatcat gtgggagatg ctgaggaaga cggacgcgcc ggtgcccatg 180
gcggagaagg aggccgccgc cgccgcggcc gtcgcggcgg ccgccggcgc ccggaggagg 240
aaggcggcgt ggagacggtt cctctactac tgctgcgcgt tctaa 285

<210> SEQ ID NO 84
<211> LENGTH: 912
<212> TYPE: DNA
<213> ORGANISM: Oryza sativa

<400> SEQUENCE: 84
atggcgacgt cccgcaagct ggcccgcgtc gacatcgccg agctgaagca gcggctggtg 60
aagcggctgg ggcggcagcg cgccgggcag tacttcgcgc acctcaccag gctgctgaat 120
ctgaagctca ccaaggtgga gttcgacaag ctctgctacg ccaccatcgg gagggaaaac 180
atcgctctgc acaacgccct gattaggggg atcatcagca atgcgctgtc cggggtgccc 240
ccgcccagcc gccaggcggt gacggggcag tccgggacga ccacggctcc cagcgggcag 300
tgcgtcggca tcgcgctaca gagcgcccga aatgtagggg ccgtggtgga ttcgggcgat 360
ggggactttg cgagggaacg ggcggttgcc ggcaaggtgt tgtcggtgga ggatggggag 420
gaggtggagc aggttaggtc tgctccatgt gtgcagagcc gaagcccgat aactgcccca 480
ttggggattt cgactacgcc aacctatggt gcaaggacat ggaggttgga tgatccaatg 540
gtgtcgtgtt acgattccca ccatctgctg gacactggtt ctctgttcaa gggtttgcag 600
cgtcggttgg agagtgatgg cattggagtg tcggtgcagg gtgttgaagt tttaaatcgt 660
ggattagatg agtttttgcg gaggttgatt aaaccatgca tggaattgtc caggtcaagg 720
tccagcggta gaagagttac caaaggcaat gctatgtttg cagctaggat gaatggcttg 780
caacaagcca atcatggtca ttgtacaaca ctacaagatt ttgctgtcgc tatggaatct 840
gatccacatt tgcttgggac caattggcct acacagcttg aaaagataca ggcaacgtcg 900
tttggtgaat ga 912

<210> SEQ ID NO 85
<211> LENGTH: 561
<212> TYPE: DNA
<213> ORGANISM: Oryza sativa

<400> SEQUENCE: 85
atggcgtctc ctcgctgcgc cgccgtcgcc ctcctccatc ccgccggagt cgccgccggc 60
ggcggagctc gccggcgtgt cctcctcctc gaccaagagc ggccgttgtg ggggactgag 120
gtgcgccggc gccggcgccg gcgtttctcg agcctcgaga cgccgccgcg gtgcagcaag 180
atgtacgtac ccggcttcgg agagggatcg ccggagaaga aggcagcaag aaacctgcag 240
cacttcttca actacattgc tgtcagggtt gtgctcacac agcttgagag ttacaaccgg 300
gaagcatatg gtgagctgat ggatttcgtg aaccgaaact ccctcaacga cgctgatact 360
ttctgcaaga agttgatccg cgagtctcca aggcacaagc agctagcaat gaggatcttg 420
gaggtccgat ctgcttatgt caagcatgat ttcgagtggg ataatctgaa aaggttatct 480
ttcaagatgg ttgatgaggc caacacaaag ctcatgaggg actatgtctt ggagaccagc 540
cacatcgaag acgataactg a 561

<210> SEQ ID NO 86
<211> LENGTH: 1044
<212> TYPE: DNA
<213> ORGANISM: Oryza sativa

<400> SEQUENCE: 86
atggacatca ccggcgcggg cgctatggga ggaggatcca cggccgccac cgccgccgcg 60
gcggcggggg ccgggtggaa gacgccggtg tcgatggtgc tggtgcagct gttcatcacg 120
gggcagatcc tgctgtccaa ggtgtccatc ggcggtggca tgttgatctt cgtgctgctt 180
gcgtacaaca gcttcttcgc cgtcgtcttc ctcctcccct tcgcgctcat cttcgagaga 240
ggcaagtgga gggacatgga ttggggtgca ttcggatgga tctttctcaa tgcgttcatt 300
gggtactctg tgccaatgag cctctactac tatggcctca aggataccac atcatcctat 360
tccgttatct ttcttaatat aactcccctg ttcaccttca tcctctcact tatgttcagg 420
ttggaggcat tcaaacttag aagcatacct ggagtactga aaatagcgag catactgctt 480
tccattggag ggacaatgct tataagcctt tacaaaggca agtcattgca tctctgggat 540
tctatcatac aacaccaaaa tgaacacaag tcagcaacca atcagctaag aggaacaatt 600
ctattggttg gcagcagctt caccttttgct tgctggtttc ttattcagtc aaagattctc 660
aaagtgtatc catacaaata ttggtcgtcc atggtgacat gcttggttgg agtatttcaa 720
accgcattgg tcggaatcat attaaggaga gacaagagtg catgggagct aggatggaat 780
ctcaaccttg ttaccatcgt gtacacgggg gcacttgcaa cagccgggaa atatatattg 840
aattcatggg caataactaa gcgaggccca acctatccca caatgttcag tccattatca 900
gtcgtcttca ctgttgtgtt ggattcagtc cttctaggaa atgatattac aattggaagt 960
cttctaggca cagcattggt gattgtcggg ctctaccttt ttctctgggc caaagcacga 1020
gaaataccta agaagtcaac atag 1044

<210> SEQ ID NO 87
<211> LENGTH: 528
<212> TYPE: DNA
<213> ORGANISM: Oryza sativa

<400> SEQUENCE: 87
atggctcggc gcgctgcgga aaaagaggcg gcgctccgcc agggtctcac cgccggtgac 60
ggcgaggcgc gacggacagg tgcattgtgg cggacagatg cgtggcggca gcgggcagct 120
gctagtgcgg ctgcagcgtc ggtggtgcgg acttggccga gctctgcgcc gtggctgcgg 180

```
tttgagctgg atccatggcg acgggtctgt ggagaacagg acctgcagac cgcggcctgc    240

ggcggcggcg acggcgccgt ggggctcagc ttcgagacgc accacggcgg cagcgtggcg    300

ccttcgccgg agttcgcggc gtgcgcggcg agctcttgca gcgcggaact catggtcttg    360

ctggtcctgc agcgcggcga gctcctggtg cgccatgacc ggccgagcca tcaccaccgc    420

cgtcgcttcc caacgccgca accagccgaa gccgccgccg cagttgaagt tggatgggga    480

tttcagaatc ccagagatgc aatgacttgc ctttgtaaag gcttataa                 528
```

```
<210> SEQ ID NO 88
<211> LENGTH: 921
<212> TYPE: DNA
<213> ORGANISM: Oryza sativa

<400> SEQUENCE: 88

atgggcagcg gcggcggtgg ctgcggcagg aacggcgctg tgaggcagta catcaggtcc     60

aaggtgccga ggctgaggtg gaccggggag ctccactgca gcttcgtcca agccatcgaa    120

ttcctcggtg gccaagacaa ggctacacct aagctcattc ttcagctcat gggggtgaag    180

gggctgacca tatctcatgt caagagccac ctccagatgt acagatgctc caggctcggc    240

tcccatggca cgggaaggag atcagagatg caaccacagc tgcaaaggaa gcactcatgt    300

ggtgctgatg agcaagtccc cagagaattc ctgtgccccc ctctgaaaag gaccaggatg    360

gggacagaag ccacatacaa aggcatgcaa ggaagccaag gaatcagtga gatgaggact    420

actggcaccc agtactgcat tgatgattac atgcaagcca tggcaatgga gaggagaata    480

aaggaggagg gcctcagatg gcagagggat gctgctgctg ctgctgctgc agatggtggt    540

gctgctgctt ccaacctcca aaccgtggga tgttcggtgc aagaatctga ccccttttaag    600

atcatcaaac cagaagtgca ccatcttggt cccgtgttga agctgcaatg ctccaaggtg    660

gagaacagtg gattcatctc cagcagcacc ggcacggctg caagggatca accggagccg    720

ccgccgctgg agaaatgttc gctgtcactc tccctcggtc cagaccccaa atgcatgccg    780

gcgatcgcct cgtcgccgag cgaaagcagc tgcatcctct cgtcgtcgtc caggagcttc    840

agcgactgct ccgggaactc aggttgtctt gttgccccgg gtgtgaactt ggaactctcc    900

atgtccatct gtggatctta g                                               921
```

```
<210> SEQ ID NO 89
<211> LENGTH: 564
<212> TYPE: DNA
<213> ORGANISM: Oryza sativa

<400> SEQUENCE: 89

atggctgccg ccgaccagcc cgcctacggc gatcgccggc cgtcccggcg cacgtacaag     60

ccggaccagc cggagggcct caccatctcg ttccgcgagc tctacgacct gccgacctcg    120

ccggagttcc tgttccacga ggaggcgctc cgcagccgcc gcacctgtgg cgaggacctc    180

acgttctaca ccggctgcgg ctacctcgtc ggccgggcgg cgggggcggc cgcggggctg    240

aagcgcgcgg cggaggaggc ggagcgcggc gagtcgatga agctgcgggg gcagccgcgt    300

cctcaaccag tgcggctccc tcgggcgcgc gtacggcaac cggctcggcg tcgtcgcgct    360

gctcttcgtg gggatcgaga gcaccgtggg gggcctccgc gacgccgacg gctgggccaa    420

caccgtcgcc gccgggatcg gtaccggcgc gctctaccgc gcggctgccg gcccgcgggc    480

ggcgatcgtc ggcagctccg tcggggggct catggccggc gcggtggtcg tggggaggca    540

agcgctgacg agatacgcgc ctaa                                            564
```

<210> SEQ ID NO 90
<211> LENGTH: 1275
<212> TYPE: DNA
<213> ORGANISM: Oryza sativa

<400> SEQUENCE: 90
atggacatgc cgcccacgcc ccttccgccg gagaccgcca acacctcgcc cgctcccaac 60
ggcgccaccg ccggaatccg ggttgagaac tgctacgtct tcaagagccg gctgcaagag 120
tatgcacaga aaaccggcct ccagactcca gagtatcata ccttcaagga gggaccttcc 180
cacgagcctg tcttcaagtc cacagtggtg attaataata ccagctatga ctccctgccc 240
ggattcttca acagaaaggc tgcagaacag tctgctgctg aagttgccct catggaaatt 300
gtcaagtcca taccagccaa cgcaaatatc ccagctgttc aagagactgg gctgtgcaag 360
aatcttcttc aggagtatgc acagaagatg aattatgcca ttccatctta tatttgcacc 420
aaatcagcct caggcttagc tcctttcata tgcactgtag agattggtgg aatacaatat 480
attggtgctg cagccaggac aaagaaagat gcagagataa aagctgcccg aactgctctt 540
ctggcaatcc aaggtcaatc agagggttcg gcaaatggtg caacaaaata tattgtagtt 600
cctggtaaaa gggtaggtaa ggaggtagag aaaaggccaa ttgaaacacc gaaaccactt 660
aaagtaaaga aaggtggttt caagaagaaa tggaacaaga ggaaattcat gaagaaggat 720
ggtcaagctg ttgatgtgga aaaggatgaa gctagagtgg ctggagatgc tcacgattct 780
gatgtcctaa tgcagccaac agtaataaca caggaggcat cttgtggcac tctgttcctg 840
caaccttgtg aggaagctaa aagagtagaa gctgagccac ctagagatat tgaaatggta 900
cagcctgata aggagaacca acacagtgac gctgcattgg tgcaacctga tgatgaagct 960
agagtagaac aggagccatc cagagatatt tcagtggtgc aacctaatga ggaagctata 1020
agtggtaagc aggaaccatc catcgatgct gcaattctgc aacctaaaga ggaagcttca 1080
agtgtaaagc aggagccatt catcgatact gcaatgctgc aagcttgtaa ggaagctgga 1140
agtgtagaac ttgggccagc cagagatact gtaatttccc aacttaatga gcaagatagg 1200
gctgtaaagc aggagccagc tggtgacatt gtagtgccac aacctgacgt gcacgctagg 1260
gtcgtaaagg agtag 1275

<210> SEQ ID NO 91
<211> LENGTH: 4080
<212> TYPE: DNA
<213> ORGANISM: Oryza sativa

<400> SEQUENCE: 91
atggcattgg gggatctcat ggcctccagg ctcgtccact cctcctcctc ctccgccgcg 60
ccatccgccg ccctgcccaa tcaccatacc aaccacctcg tcgatgacca cctccccgtg 120
gagaatggac cggaccccag gagggacgtg cccgacgagg agccgccgcc cccgccgccg 180
ccgcaggtcg ccttgctgcc ccaggtggtc gtgctgtgcg agcagcggca cgaggggttc 240
gacgaggccg ccgctgcggc ggccgggccc tccaccagcg ggcccgtctc caaatggcgc 300
cccaaagacc ggatgaaaac tggctgtgtg gcacttgtgt tgtgtttaaa cattagtgtt 360
gatccgccgg atgtgatcaa aatctcccct tgtgcaagaa aggagtgctg gatagatcca 420
ttttctatgg cacctccaaa agcccttgaa actattggga aaacattaca ctcacaatat 480
gagcgctggc agccaaaggc tcgttacaag cttcagctgg atccgacatt agaggaagtt 540
aagaagctat gtaatacttg ccgtaaattt gctagaacag agagagtcct ttttcattac 600

```
aatggtcatg gtgtaccaaa gcctacagct aatggggaga tttgggtatt taacaagagt    660
tacacacagt atattccgct tcctattact gatcttgatt catggctgaa aacaccctct    720
atatatgttt ttgactgctc agcagctgga atgatcgtga aagcttttct ggagcgccta    780
gactggagtt ctagctcgtc tgcatcttca tcgaaggact gcattctcct tgcggcctgt    840
gaggcacatc aaactctccc acagagcgca gaatttcctg ctgatgtgtt cacagcttgc    900
ctcaccacac ccatcaaaat ggcactgcac tggttttgta accgatcgtt actccgtgat    960
tccatggaac acaatcttat cgaccaaatt cctggaaggc aaaatgaccg caaaactctt   1020
ctaggggagt tgaactggat tttcactgct atcacagaca ctattgcatg gaatgttctt   1080
cctcatgatc tattccaaag acttttcagg caggatcttt tggttgctag tctctttcgc   1140
aacttcttac ttgctgagag aatcatgcgg tccgcaaatt gttccccaat ttcataccct   1200
ttgttgccac caactcatca gcaccatatg tgggatgcat gggacatggc tgcagagatc   1260
tgcctttcta agcttcctca attaattgct gatcctaatg cagagtttca gccgagtcca   1320
tttttcacgg agcaattgac agcatttgaa gtttggcttg atcatggctc tgaagacaag   1380
aaacccccag aacagctacc tattgttctt caggttttgc ttagtcagtc acacagattt   1440
agagcacttg ttctgcttgg aagatttctt gacatgggac cttgggcagt tgatttggct   1500
ttgtccgttg gcatcttccc ttatgtactt aaactgcttc aaacaagtgc aatggagttg   1560
cgccaaattc ttgtgttcat atggacaaaa attctctctc ttgataagtc atgccaggtt   1620
gacttggtga aagatggagg gcatgcatac tttatcaggt ttcttgacag tttggatgct   1680
tacccagagc agcgtgcaat ggctgctttc gttttagccg ttattgtgga tgggcatagg   1740
attggtcaag aggcttgtgc taatgcaggg cttatagatg tctgcctgag acatctgcaa   1800
cctgaaaatc cgaatgatgc tcagacagag cctttgctct tgcaatggct ttgtttatgc   1860
cttggcaaac tttgggaaga tttccctgag gctcagttac ttggtctgca atcaaacgca   1920
ccggaaattg ttatatgctt attgtcagag cctcaacctg aagtcagagc ttctgctgtt   1980
tttgcacttg gaaatcttgt ggatattgga tctccatcac tgaatggagc tgacgacgat   2040
tctgatgatg atgaaaaggt gagagctgaa ataaatgttg tccgaagcct tctgcagatc   2100
tcttcagatg gtagccctct tgttagatct gaggttgccg tagcgcttac ccgctttgca   2160
atggggcaca ataaacatat caaatctgtt gccgccgagt actggaaacc tcaaaccaat   2220
tcactgctca agtcattacc atcgttggct aatattaatt cgagcaatgt ttacagtccc   2280
agcagcttaa tacaaggtag cagtggcctt gcctcacata ttggtcctgt tttaagggtt   2340
ggcagtgata acagtgccac tgctcgtgat ggaagaatct ctacgagcag cccgattgca   2400
acaaatagca tcatgcatgg ttctccacag tcagatgatt cttcccaaca ctctgattca   2460
ggcatattac tgagagagaa tgcaagtaat ggtggtctca actactcaag atcgaggcct   2520
attgataatg ggatctattc ccaatttata gcaactatgt gcaatgttgc taaagatcct   2580
tacccaagaa ttgcaagtat tgggaaaagg gcattgtccc tcataggtgt tgagcaagta   2640
agcatgagaa acagtagact tagcaatgga ggtgcacacc caggagagac atctgtgccc   2700
ccttcatcaa actttggaat ggcacgctcc tcttcctggt ttgatatgaa ctctggaaat   2760
ttctcggtgg cctttaggac tcctcctgtt agtcccccct agcatgacta cctcacagga   2820
ttgcgccgag tgtgctcgat ggagttcaga ccacatgttt tgaactcacc tgatggctta   2880
gctgatccgc ttttaagctc cagtgcagcc cccagcaaca tggggctcta tatacttccc   2940
caatcattaa tttacagatg gagttgtggt cacttttcta ggccacttct aactggttct   3000
```

```
gatgataacg aggaagcaaa tgctagaaga gaagagcgag aacgaattgc aatggattgc   3060

attgctaaat gccaacgatc atcttgcaag atgaccagcc aaattgctag ctgggatacg   3120

aggtttgagt tgggtacaaa agcatcattg ttgttgccat tttctcctat tgttgttgct   3180

gcggatgaaa atgagcaaat acgagtatgg aactatgacg atgcgctgcc agtgaatact   3240

tttgaaaacc acaagttatc tgacagaggc ctatctaaac ttttgctgat caatgagctt   3300

gatgatagct tgttgttagt tggctcaagt gatggaaatg tccgcatatg gagaaactat   3360

actcaaaagg gaggacaaaa acttgtaact gctttttcat cagttcaagg ctatcgaagt   3420

gctggtcgca gtattgtatt tgattggcag caacagtcgg gttatctgta tgcatctggt   3480

gacatgtcct ctatccttgt atgggatctt gacaaggaac aagtcaacac catccagtca   3540

actgctgata gcgggatttc agctctttct gcatctcagg ttcgatgtgg ccaattcgct   3600

gctggttttc ttgatgcatc tgttaggata tttgacgtgc gtacacctga taggctagta   3660

tatacagcaa gaccacatgc cccaagatca gaaaaggttg ttggtatagg atttcagcct   3720

gggtttgatc cctacaagat tgtaagtgca tctcaagctg gagacattca gttccttgat   3780

gttagaaggg catctgaacc ctacctcact attgaagcac ataggggttc attaacggca   3840

ttagctgttc atcggcatgc cccagttatt gcaagcggct cagccaagca gatgatcaaa   3900

gtgtttagtc ttgaaggaga acagttgaca ataattcgct accagccatc ttttatgggt   3960

caacgaatag gcagcgtaaa ctgcctttct ttccaccgat acaaatcact ccttgccgct   4020

ggtgctggtg ataatgctct tgtttctatc tacgcggagg acaattacca agtacgatga   4080
```

<210> SEQ ID NO 92
<211> LENGTH: 702
<212> TYPE: DNA
<213> ORGANISM: Oryza sativa

<400> SEQUENCE: 92

```
atgggtgcca gcggaaggct gatctccatt tacccagagg atctcacttt cctatttgag     60

ctagataagc catgctattg caatctcaag gtggtgaaca acagcgagca tcatgttgca    120

tttaaggtca agacgacatc accgaggaag tattttgtcc ggccgaacgc gagcatcatc    180

cagccatggg attcttgcac aataacaatt acgctccagg cgcagaaaga gtacccacca    240

gatatgcaat gcaaggataa attcttgatc cagagcacca aggtagctgc cagtactgac    300

atggacgaga tccccccctaa cacgttcaac aaggaagtcg ataaggtgat tgaggaaatg    360

aagcttaagg ttgtttatac agttcccagt ggaagttctg acgactctgg tattacatct    420

ttaggcagca ggagcttcaa attggggtct gacgatctca cgatgctgaa gaatgcaagc    480

attgaaaaga tacagacaat acaacgccta aaagacgaac gagacaccac cctgcagcaa    540

aatcagcaaa tgcaacgtga attggatgtg atcaggaggc gtagaagccg caaaagcgat    600

gcgggtttct ccttaacgtt tgctgctttt gctgggctca taggtgtcct gattgggctc    660

ttgatgagcc tcatcttccc tcgcccacag gctgctgctt aa                       702
```

<210> SEQ ID NO 93
<211> LENGTH: 2820
<212> TYPE: DNA
<213> ORGANISM: Oryza sativa

<400> SEQUENCE: 93

```
atgggggtga tgaacccgct gatggcaaag ctcaccacgc tcatgggcga cgagtacaag     60

aagctcaagg ggctcaggaa gcaggtctcc ttcctcaagg atgagctcac caccatgagc    120
```

```
gctttcctcg agaagctcgc gctcatggat gatgatgatg atggtgagct cgatcctctg    180
gccaaggact ggaggaacca cgtcagggag atggcctatg acatggaaga ctgcattgat    240
gattacttca caagtcatct tgatcatcgt tactcttcct cagatgcagg gttaatccgc    300
aagatagctc gccgtctcag ggcattgcgg gtgcgtcatc gcatagccag ccagatcaat    360
gagctcaagg ctcgtgtggt cgaggcaaat gagcgtcgcg tgagatacag gcttgatgac    420
tgtaacaaca aacatggtgt ttctgccaat cctgctatag atccacggat aacatcgctc    480
taccaaaatg ccgggagtct tgtgggtatt gatggcccaa gccaagaact aatccagctg    540
ttgtcgttag atcgtgatac cgatcaacga caactcaaag tggtgtccgt cgtgggattt    600
ggaggtctcg gtaaaacaac tcttgcaaaa tatgtgtacg acaagatcgg gcatcaattc    660
gattgcacgg cattcgtctc agtatcccac aaacctgaca taacaaggat cctcagtagc    720
atccaatcca agcttgacat agggggcacg tctcaagctt gcgacgacgt gcaacaactc    780
atcgacgaca tacgagccta tctggagcat gaaaggtata ttattatagt cgatgacctg    840
tggaaacaag aagcatgggt tattattagt tgtgcctttc caaacaatgg caaaggtagc    900
agagtgatag taaccacacg agtgaaagat gtggccaggt tggcatgtgg caaggatgga    960
caaatttaca aaatacagcc tctgaacaat aaggactcaa gaaagttatt cttcgataga   1020
gtatttaggc ctgaagatag ttgtgtcctg cagtatgaag aaatttcaac tgaaatctta   1080
aagaagtgta gtggcttgcc acttgcaatt gttactgtag ggagcctctt agcctgtcga   1140
ccaagaacaa tggaagaatg gaagagcata cgggattctt tgggtgcccc gtttgacaaa   1200
aacaagagct tggaaggcat gaggaatatt ttaaacctga gttacaagaa tcttcctctt   1260
catctcaaaa catgcctcct atatattggt aaatatccag aggactatga gatcgggagg   1320
gatgaactag ttacggagtg gatagctgaa ggtattatgg gtaaccctca tggggaaaac   1380
ttggaggcta ctggtaatgg ctacttcagt gagcttatca acaggggctt gattcaacca   1440
gagagcaccg gctatggtgg ggaggtgttg agttgcaagg tgcatgatat gatgcttgat   1500
ctgatcctca tcaagtgtgc agaagataat tttgtcagcg ttgcacacag ttgtaaagac   1560
tacatgcgca tggctatgca ccatgagcgg agttgcaata aggtccgtcg gctatccctg   1620
cagtgcaagg ctgcaagatc agattgcgca attgagggca gcgtcatttc tacaagcatg   1680
gctcgtgctc gatcagtttc agtgtttggt gagtgttcac gtgggctccc atttctgatg   1740
ctatccaagt atatacgggt ggtgcacatc gaattggaag gccatggcgg tcaagtcgac   1800
ctcactgcca ttagccatgt gcttcaattg aggtatttga gagtggagac gcctggttgt   1860
gagatagatc tccccagcaa aatatgtggg ctcgtgcatt tggagacatt gtcaatattt   1920
tcccataaag ctgtaagtcg gctcccttca gatattagca gtcttccccg cttgtcagtc   1980
ctgtccctgg tggttccatg ggctacaagg ctacccaaca agttaaacaa gctaaaaggg   2040
tcactacgca gtctcaccat actattcaat cccccggatg cgttaggcat ggaggccatt   2100
ggtgagctga aaaatctaag ggacctaaac atctctgtta acaggtggcg ggacgatgag   2160
atccttagcc tttatgctct ggggtcttcc attggaaaac tggatgaact caggagtttg   2220
caaattcatg tcccacctgc taccttaggt gatgttgacc tgctgggctc attacccatt   2280
tttcctcaaa gtatcgagag actaatacta cacggttggt gcttctccaa agtacctcga   2340
tggatcaacg gtactctccg taacctccaa catgtgttgc tggaggtatc ggagacatcg   2400
agtagcgagg ttgaccttct tggtgaacta ccctccctcg ccgacctcga gctgagagta   2460
ggactcaaga caagagatgt catcgcgttc ggtggcacta gagcatcatt attccctgct   2520
```

ctcctgaaac tcaagctgcg tgtgggtgaa cacgttgcct caaggctgca gttccaggca 2580
ggggtgatgc ccaagctcca aagcctccat ctgtggttcc ggaattgtga gtcgggcatt 2640
cacgtaacac cggagggtat gcagcacctc ctgagcctcc aaagcatctg cgtggagata 2700
tacctccggg atgaggagct gaaagcaact tatccatggg acgccatgga gcgtgcgttc 2760
agggaaatca ctggagcaaa ccccaaccgg ccttccttca aatttgtcaa gcaagtctga 2820

<210> SEQ ID NO 94
<211> LENGTH: 1014
<212> TYPE: DNA
<213> ORGANISM: Oryza sativa

<400> SEQUENCE: 94
atggagtgcg agccggagga gctgcaattc ctgggcatgg tgggtatcta cagggaggcg 60
gcgtccatcc tgcgcgccca ccggccgctc ttcgcccgca tcgccgccgc cttcgtcctc 120
ccgctctccc tcctcttcct cctccacatc gccatctccc acgccctctt ctcccacatc 180
gactccgacg actccgccct cgactccgcc gccccgggca cccccgccca gcgccgcctc 240
ctccaccgcc tcgccgacga ctggctcgcc ctcctcctct tcaaggccgc ctacctcctc 300
gccctcctcc tcttctccct cctctccacc gccgccgccg tcttctccgt cgcctccgtc 360
tactccgcca agcacgacgc cctctccttc cccagggtcc tctccgtcgt cccccgcgtc 420
tggcgccgcc tcgccgccac cttcctcgcc gccttcctcc tcctcttcgc ctaccacctc 480
ctcttcgtcg ccgtcttcgt cgccctcctc gtcgccgccg actccggatc gggcctcgcc 540
gcgctgctcg ccttcctcct cgccctcgcc tacatcgcgg gcctcgtcta cctcagcgtc 600
gtctggcacc tcgccagcgt cgtctccgtc ctcgaggact acaagggatt cgaggccatg 660
cgcaagagca aggcgctcat acagggcaag ctctggaccg cctccgccat cttcttcgtc 720
ctcaacgtcg tcttcatcgt cgtcgaggtc gccttccggg cgtgggtggt gcgcggggcc 780
acccacggcc tcggcgccgg ctcaaggctc ctcctgggcc tcgccatgct cgccgcgctc 840
tgcgctgtcg tgatgctggc gctcgtggtg cagacggtgg tgtacctggt gtgcaagagc 900
taccaccacg agagcatcga caagagcaac ctctccgacc acctcgaggt ctacctcggc 960
gagtacgtcc cgctcaaggc cagcgacgtc cagatggagc aattcaacct ctga 1014

<210> SEQ ID NO 95
<211> LENGTH: 936
<212> TYPE: DNA
<213> ORGANISM: Oryza sativa

<400> SEQUENCE: 95
atggcgtcct cctccgccct cgcttcctcc cccttcctcc cgcccctctc aaccccaaac 60
cctagggccc tctccctccg cctccccgct cgccgcctcc ccgtggcgtc ctccgcggct 120
ccctcgggcg ctgccgctgc ggcgtcggcg agggagcgcc gccgcttcct ggagcggtac 180
ggcctcaacc ccgacgactt cgaggacgat gccgaggcgg aacccaggga agagaggaga 240
agggataggc ggaaccggcg gtcgggtaga ggggaggcgg aggatgctcc ggcgaaggcg 300
gcggctgagc ctcgggagac gcataaaatg cttcaggtgt taggaggaaa agtacgcaga 360
agaaaattac tttcaccaaa agataggaat gttcgtccaa tgatggaagt tgtacgaggg 420
gcagcctttg acattttaca gtcagctggt ggttttccgg cttcgcttag acctggtcga 480
tggttagact tgtatagtgg tactggatct gttggaattg aggctatgag ccgtggatgt 540
tcagaggcac attttgttga gatggatcct tgggttgttt ctgaggtcct taaaccgaat 600

```
ctggagtgta ctggatttct tgatgtttcg cacatacata tgatccgcgt cgaaaacttc    660

ttggccaatg ctgaaaaatc tagtggtaaa tatccttctt ttgattatat tagtgtaaca    720

ccgccatatc ttgaggtaaa ctacagtaca ctactcgatc aacttgcaag gtcaccattg    780

gttggagaag attgcttcat tctcgttgaa tacccactga aaacagacat ggccgaatca    840

tgtggaagcc ttataaaagt agctgacagg aggtttggta ggacaaactt gctaatttat    900

gggccaacct gggctgagaa gaagaggaga tcttga                              936
```

<210> SEQ ID NO 96
<211> LENGTH: 936
<212> TYPE: DNA
<213> ORGANISM: Oryza sativa

<400> SEQUENCE: 96

```
atgaacgacc tcatgaccaa gtcgttcatg agctacgtcg acctgaagaa ggcggcgatg     60

aaggacctgg aggcgggcgg ggatggcgtg gagctccccg aggtgggcgt caccgacgag    120

cgcctcaagg ggttcttcca ggagacggag gcggtggagg aggagatggc cgccatccgc    180

gacgcgctgg cgaggctcaa cgccgccaac gaggagggca agtcgctgca ccagcccgac    240

gccctccgcg cgctccgcgg ccgcgtcaac gccgacatca tcgccgtgct ccgccgcgcg    300

cgcgacatcc gcgccaggct cgaggccatg gaccgcgcca acgcggcgca gcgcaggctc    360

tccgcgggct gccgcgaggg caccccgctc gaccgcaccc gcaccgcgct caccgccgcg    420

ctccggaaga agctcaagga cctcatgctc gacttccagg ccctgcggca gcggatcatg    480

tccgagtaca aggacaccgt cgagcgccgc tactacaccc tcaccggcga ggtccccgag    540

gaggaggtga tcgagcgcat catctccgag ggacgcagcg aggagctcct gtgcgccgcc    600

gtggcggagc acggcaaggg cgcggtgctg gccacggtgc acgagatcca ggaccgccac    660

gacgccgccc gcgaggtgga gcgcagcctc ctggagctcc accaggtgtt cctcgacatg    720

gccgtggtgg tggagtccca gggggagcag ctcgacgaca tcgagcgcca cgtcaacagc    780

gccaccacct acgtccaggg cggcaacaag gagctacgca aggcccgcga gcaccagcgc    840

agcagccgca agtggctctg catcggcatc atcatcctgc tgctcctcgt cctcctcgtc    900

atcgtgccca tcgccaccag cttcaagaga tcgtga                              936
```

<210> SEQ ID NO 97
<211> LENGTH: 564
<212> TYPE: DNA
<213> ORGANISM: Oryza sativa

<400> SEQUENCE: 97

```
atggcgatgg aggggaagag caggaggttc gcggtggcgt gcggggtgct cagccagtac     60

gtgagggcgg agcagaagat ggcggcggcg gcgggggcgg caccggcgag ggcggtgacg    120

acgctgagcc tgatgcctgg ggcggaggtg gtcgtcgagg aggaggagcg gagggaggtt    180

ggggaggagg aggcggggcc agcgacggcg ccggccgcgc cgctgaccat cttctacggt    240

gggaggatgg tcgtcttcga ggacttcccc gcggacaagg cggcggaggt gatgcgcatg    300

gcctcctccg ggatggcggc ggcgccggct cagcgggagg gcgccgcgct cgcggacatg    360

cccatcatga ggaaggcgtc gctgcagcgg ttcttcgcca agcgcaagga ccgcctcgcg    420

gcgaccaccc cctacgcccg cccgtcgccg gcggagacca aggcctccga gccggaggag    480

aagaagacgc ccacctcatg gctggacctc gccgcctccg cctccgccgc cgcgcgccgt    540

gacagcctca ccatcgcgct gtga                                           564
```

<210> SEQ ID NO 98
<211> LENGTH: 3402
<212> TYPE: DNA
<213> ORGANISM: Oryza sativa

<400> SEQUENCE: 98

```
atgtcgtcgc tgagccggga gctggtattc ctcatcctgc agttcctcga tgaggagaag     60
ttcaaggaga ctgttcacaa gcttgagcag gagtctgggt tctacttcaa catgaagtac    120
ttcgaagacg aggtgatcaa tgggaattgg gatgaggttg agcgctacct cggtggcttt    180
accaaggttg atgacaaccg ctactcgatg aagatattct ttgagatccg caaacagaag    240
tatcttgagg cccttgataa gcatgatcgt tcgaaggcgg ttgaaatctt ggtcaaggac    300
ctgaaggtct tcgcgtcctt taacgaggag ttgtttaagg agatcacaca gcttttgacg    360
ttggaaaact ttagggaaaa tgagcaactc tccaaatacg gtgatacaaa atctgccaga    420
gcaataatgc ttgttgaact aaagaagctg attgaagcta atcccttgtt ccgtgacaag    480
cttcagtttc caaatctgaa gagctccaga ttgcggacac ttataaacca gagcttaaac    540
tggcagcacc agctttgcaa aaatcctaga cctaaccctg atatcaagac tctgtttgtt    600
gatcattctt gtggacaacc aaatggtgct cgtgctccat cgccagcaaa caatccatta    660
cttggatcta taccaaaacc tggaggtttc cccccattgg gtgctcacgc gccatttcaa    720
cctgcaccta cacctgtccc acctctggct ggctggatgt caaaccctcc agcagtaaca    780
catcctgctg tgtctggtgg agctattgga tttggtactc ctacaaatcc tgctgctata    840
ttaaaacatc ctagaacacc aacaactgcc aatccttcta tggattatcc atcaggagat    900
tctgatcacg tctccaagag aacgagacca gttgggatgt ctgaggaggt gaatcttcca    960
gtgaatatgt tacctgtgac atatccacag agtcatagtt acccgcaaga tgattttcat   1020
aaaaatgttg cacggacatt gagccaagga tcaactccaa tgagcatgga cttccatcca   1080
gttcagcaaa ctctccttct tgttggtacc aatgttggtg acattggatt atgggatgtc   1140
ggtaccaagg aacgacttgt tttaagaaac ttcaaggttt gggatcttac aaaatgctca   1200
atggccctcc aggcatcact tgtcaaagac cctactgtct cagttaaccg cataaatatgg  1260
agtcctgatg gaaccttgtt tggtgttgct tattcaaggc atattgtaca gatctattca   1320
taccatggcg gtgatgatat caggcagcac ttggagattg atgcgcatgt cggtggtgta   1380
aatgacattg catttgccca tccaaataag cagctatgta taataacctg cggagatgac   1440
aagacaatta aggtctggga ggccactagt ggagcaaagc aatttacatt tgaaggtcat   1500
gaagctcctg tttactctgt ttgtccacat tataaggaaa atattcagtt catcttctca   1560
actgctttgg atggaaagat aaaggcttgg ctatatgata atttgggatc cagagttgac   1620
tatgatgcgc caggacattg gtgcacaaca atggcatata gtgcagatgg ttcaaggtta   1680
ttttcttgtg ggactagcaa ggatggcgaa tcacatctag tggaatggaa tgaaagtgaa   1740
ggagctgtca agagaactta ccagggattt cgcaagcgat cgatgggtgt tgtccaattt   1800
gataccacac ggaacaggtt tttggctgct ggagatgaat tcttgattaa gatatgggac   1860
atggacaaca caagtcttct gactaccatt gatgccgatg gtggtcttcc tgcaagtcca   1920
cgggtccgat tcaacaagga aggtactctg ctggctgttt ctacccatga aaatggtatc   1980
aagatcttag caaatgctga tggagtacgg ttgctgcgca cattggaaaa tcgttcattt   2040
gatgcttctc ggagtgcgtc tgagactgta acaaagcccc taatgaatcc attgactgct   2100
gctgctgctg cggcggcgtc agctgctgct gccgggacta gttcaggaaa tgctgctcca   2160
```

```
ccggcaataa ctgcactgaa tggggatagc cgaagcttgg ttgatgtaaa gcctagaata   2220

gctgatgagc cattggataa atcaaaagtc tggaaactta tggagataac cgagtcaagt   2280

cagtgcagat cattgaaatt aacagataat atgaggacaa gcaagatttc aagacttatt   2340

tacacaaatt ctggtgtcgc tatcttggct ttagcttcaa atgctgttca tctgctctgg   2400

aaatggcctc gcaatgaccg aaactcaagt ggaaaggcta ctgcaagtgt ttctcctcaa   2460

ttatggcaac ctccaagcgg catcctcatg actaatgaca taactgacaa ccctgaagaa   2520

gctgtccatt gctttgcttt gtcaaagaat gattcatatg tcatgtctgc atctggaggg   2580

aaaatatctc tgttcaacat gatgactttt aagacgatga caacttttat gcctccgccg   2640

ccggcggcaa cgtttcttgc tttccatcct caagataaca acattatagc aattggaatg   2700

gatgactcaa ccatccaaat ctacaatgtt cgaattgatg aggtcaaaag caaacttcga   2760

gggcactcta agaaaattac tggacttgct ttttcaaatg tattaaatgt gttagtctct   2820

tctggagctg atgcgcagat atgtgtgtgg agcacagatg ggtgggataa attaaagagc   2880

agaatgttac agataccatc aagtcgtcca tcatctataa tcttagacac acgtgttcag   2940

ttccatcagg atcaattgca ctttcttgtt gtgcatgaga cccagattgc catatatgaa   3000

actacaaaat tagaacccgt gaagcagtgg cctgtccggg agaactcttc tccaataacg   3060

catgccatgt tctcctgcga tagtcaattg atttatgcaa gctttctgga tgccactgtt   3120

tgcatattta atgcatcgag tttgagactc caatgtcgaa ttcttccagc atcctatctt   3180

cctcagaata tcagctcaaa tgtttatcct gtcgttgtgg cggcacatcc ttcggaagca   3240

aatcagtttg ctctaggcct gactgatggt ggtgtttatg tattggaacc cttggaatct   3300

gagagaaaat ggggaaatcc tccaccagca gagaatggat caaccagcgc tttgtccaca   3360

cctcctaatg gagcatcaag ttctgatcaa ccagaaagat aa                      3402
```

```
<210> SEQ ID NO 99
<211> LENGTH: 158
<212> TYPE: PRT
<213> ORGANISM: Oryza sativa

<400> SEQUENCE: 99

Met Pro Arg His Ala Cys Leu Leu Gln Ser Asp Arg Ile Phe Phe Ile
1               5                   10                  15

Ala Thr Glu Glu Cys Arg Arg Arg Arg Arg Gln Gly Gly Ala Asp Ala
            20                  25                  30

Gly Ala Gly Gly Arg Gly Gly Gly Arg Arg Cys Trp Ala Glu Ala Ala
        35                  40                  45

Glu Ala Ala His Met Ala Ala Ala Ala Ala His Arg Ala Ala Ala Val
    50                  55                  60

His Arg Ala Ala Cys Gly Ser Ser Thr Val Ala Val Gly Leu Arg Glu
65                  70                  75                  80

Leu His Arg Arg Arg Leu Cys Ser Thr Cys Thr Gly Asp Gly Asp Gly
                85                  90                  95

Asp Arg Met Leu Met Gln Arg Asn Asp Ser Ser Asn Ser Lys Trp Met
            100                 105                 110

Leu Ser Arg Arg Ala Phe Ser Pro Phe His Val Ser Ala Lys Phe Ala
        115                 120                 125

Trp Glu Val Gln Glu Ser Leu Leu Asp Gly Gly Ser Thr Trp Phe Cys
    130                 135                 140

Leu Gly Ser Ser Ala Tyr Phe Val Ala Val Lys Tyr Asp Trp
145                 150                 155
```

<210> SEQ ID NO 100
<211> LENGTH: 117
<212> TYPE: PRT
<213> ORGANISM: Oryza sativa

<400> SEQUENCE: 100

```
Met Gly Thr Tyr Lys Cys Cys Ile Phe Phe Thr Arg Arg Phe Ala Leu
1               5                   10                  15

Ser Asp Ala Ser Thr Pro Gly Asp Val Arg Met Leu Phe Thr Arg His
            20                  25                  30

Ala Gly Gly Ala Pro Tyr Met Gly Ile Asp Glu Leu Arg Arg Tyr Leu
        35                  40                  45

Ala Ala Ser Gly Glu Ala His Val Asp Ala Asp Thr Ala Glu Arg Ile
    50                  55                  60

Ile Asp Arg Val Leu Gln Glu Arg Ser Arg Thr Pro Arg Phe Gly Lys
65                  70                  75                  80

Pro Ser Leu Thr Ile Asp Asp Phe Gln Tyr Phe Leu Phe Ser Glu Asp
                85                  90                  95

Leu Asn Pro Pro Ile Cys His Ser Lys Glu Glu Ser Phe Asp Ala Met
            100                 105                 110

Glu Lys Leu Glu Val
        115
```

<210> SEQ ID NO 101
<211> LENGTH: 490
<212> TYPE: PRT
<213> ORGANISM: Oryza sativa

<400> SEQUENCE: 101

```
Met Gln Val His His Asp Met Asn Ala Pro Leu Ser His Tyr Phe Ile
1               5                   10                  15

Tyr Thr Gly His Asn Ser Tyr Leu Thr Gly Asn Gln Leu Ser Ser Asp
            20                  25                  30

Cys Ser Asp Ile Pro Ile Ile Lys Ala Leu Gln Ile Gly Val Arg Val
        35                  40                  45

Ile Glu Leu Asp Met Trp Pro Asn Ser Ser Lys Asp Asp Val Asp Ile
    50                  55                  60

Leu His Gly Arg Thr Leu Thr Ala Pro Val Ser Leu Ile Lys Cys Leu
65                  70                  75                  80

Lys Ser Ile Lys Glu Tyr Ala Phe Val Ala Ser Pro Tyr Pro Val Ile
                85                  90                  95

Ile Thr Leu Glu Asp His Leu Thr Ser Asp Leu Gln Ala Lys Val Ala
            100                 105                 110

Lys Met Val Leu Glu Val Phe Gly Asp Thr Leu Tyr Tyr Pro Glu Ser
        115                 120                 125

Lys His Leu Gln Glu Phe Pro Ser Pro Glu Ala Leu Arg Gly Arg Val
    130                 135                 140

Ile Leu Ser Thr Lys Pro Pro Lys Glu Tyr Leu Glu Ser Lys Gly Gly
145                 150                 155                 160

Thr Met Lys Asp Arg Asp Ile Glu Pro Gln Phe Ser Lys Gly Gln Asn
                165                 170                 175

Glu Glu Ala Val Trp Gly Thr Glu Val Pro Asp Ile Gln Asp Glu Met
            180                 185                 190

Gln Thr Ala Asp Lys Gln His Glu Asn Asp Ile Leu Tyr Thr Gln Arg
        195                 200                 205
```

```
Asp Val Glu Glu Asp Asp Glu Lys Lys Met Cys Gln His His Pro Leu
    210                 215                 220

Glu Tyr Lys His Leu Ile Thr Ile Lys Ala Gly Lys Pro Lys Gly Ala
225                 230                 235                 240

Val Val Asp Ala Leu Lys Gly Asp Pro Asp Lys Val Arg Arg Leu Ser
                245                 250                 255

Leu Ser Glu Gln Glu Leu Ala Lys Val Ala Ala His His Gly Arg Asn
            260                 265                 270

Ile Val Ser Phe Thr His Lys Asn Leu Leu Arg Ile Tyr Pro Lys Gly
        275                 280                 285

Thr Arg Phe Asn Ser Ser Asn Tyr Asn Pro Phe Leu Gly Trp Val His
    290                 295                 300

Gly Ala Gln Met Val Ala Phe Asn Met Gln Gly Tyr Gly Arg Ser Leu
305                 310                 315                 320

Trp Leu Met His Gly Phe Tyr Lys Ala Asn Gly Gly Cys Gly Tyr Val
                325                 330                 335

Lys Lys Pro Asp Phe Met Met Gln Thr Cys Pro Asp Gly Asn Val Phe
            340                 345                 350

Asp Pro Lys Ala Asp Leu Pro Val Lys Lys Thr Leu Lys Val Lys Val
        355                 360                 365

Tyr Met Gly Glu Gly Trp Gln Ser Asp Phe Lys Gln Thr Tyr Phe Asp
    370                 375                 380

Thr Tyr Ser Pro Pro Asp Phe Tyr Ala Lys Val Gly Ile Ala Gly Val
385                 390                 395                 400

Pro Ser Asp Ser Val Met Gln Lys Thr Lys Ala Val Glu Asp Ser Trp
                405                 410                 415

Val Pro Val Trp Glu Glu Glu Phe Val Phe Pro Leu Thr Val Pro Glu
            420                 425                 430

Ile Ala Leu Leu Arg Val Glu Val His Glu Tyr Asp Val Ser Glu Asp
        435                 440                 445

Asp Phe Gly Gly Gln Thr Ala Leu Pro Val Ser Glu Leu Arg Pro Gly
    450                 455                 460

Ile Arg Thr Val Pro Leu Phe Asp His Lys Gly Leu Lys Phe Lys Ser
465                 470                 475                 480

Val Lys Leu Leu Met Arg Phe Glu Phe Val
                485                 490


<210> SEQ ID NO 102
<211> LENGTH: 211
<212> TYPE: PRT
<213> ORGANISM: Oryza sativa

<400> SEQUENCE: 102

Met Ala Met Gly Ala Ala Ala Ala Pro Trp Tyr Gly Ala Ile Gly Gly
1               5                   10                  15

Gly Gly Ser Arg Arg Ala Arg Val Arg Ala Gln Ala Ala Ala Pro Trp
            20                  25                  30

Ala Gly Gly Ala Glu Glu Leu Val Arg Ser Gly Ala Val Arg Ala Val
        35                  40                  45

Arg Ala Arg Glu Ala Ala Gly Ala Met Ser Ala Glu Gly Phe Arg Leu
    50                  55                  60

Leu Asp Val Arg Pro Glu Trp Glu Arg Ala Arg Ala Ala Val Arg Gly
65                  70                  75                  80

Ser Ala His Ala Pro Leu Phe Val Gly Asp Asp Asp Thr Gly Pro Val
                85                  90                  95
```

```
Thr Leu Leu Lys Lys Trp Val His Phe Gly Tyr Ile Gly Leu Trp Thr
            100                 105                 110

Gly Gln Ser Phe Thr Lys Met Asn Asp Arg Phe Leu Asp Asp Val Ala
        115                 120                 125

Ala Ala Ala Gly Glu Gly Lys Asp Ala Lys Leu Leu Val Ala Cys Gly
    130                 135                 140

Glu Gly Leu Arg Ser Leu Ile Ala Val Arg Met Leu Tyr Asp Asp Gly
145                 150                 155                 160

Tyr Lys Asn Leu Ala Trp Leu Ala Gly Gly Phe Ser Lys Cys Val Asp
                165                 170                 175

Gly Asp Phe Ala Asp Val Glu Gly Glu Ser Lys Leu Gln Tyr Ala Thr
            180                 185                 190

Val Gly Gly Val Ser Tyr Ile Phe Leu Gln Ile Leu Leu Leu Leu Arg
        195                 200                 205

Val Val Lys
    210


<210> SEQ ID NO 103
<211> LENGTH: 315
<212> TYPE: PRT
<213> ORGANISM: Oryza sativa

<400> SEQUENCE: 103

Met Ala Ala Ala Ala Gln Arg Arg Arg Ser Ser Ser Ala Ser Pro Glu
1               5                   10                  15

Phe Arg Phe Trp Pro Leu Asp Ala Asp Pro Ala Ala Ser Pro Ser Cys
            20                  25                  30

Ala Asp Glu Leu Phe Ser Gly Gly Val Leu Leu Pro Leu Gln Pro Leu
        35                  40                  45

Pro Tyr Pro Arg Arg Asp Ala Asp Leu Ser Met Ser Leu Ala Val Ala
    50                  55                  60

Asp Asp Asp Asp Asp Glu Asp Glu Glu Glu Glu Glu Val Gln Pro Gly
65                  70                  75                  80

Ala Ala Val Ala Ser Arg Ala Pro Pro Thr Ala Ala Val Ala Ala Ser
                85                  90                  95

Gly Gly Gly Gly Gly Gly Ser Lys Arg Trp Thr Asp Ile Phe Ala Lys
            100                 105                 110

Lys Gln Gln Gln Pro Ala Ala Glu Glu Lys Glu Lys Asp Gln Pro Thr
        115                 120                 125

Arg Arg Arg Arg Pro Ala Gly Gly Gly Gly Gly Ser Glu Leu Asn Ile
    130                 135                 140

Asn Ile Trp Pro Phe Ser Arg Ser Arg Ser Ala Gly Gly Gly Gly Val
145                 150                 155                 160

Gly Ser Ser Lys Pro Arg Pro Pro Pro Arg Lys Ala Ser Ser Ala Pro
                165                 170                 175

Cys Ser Arg Ser Asn Ser Arg Gly Glu Ala Ala Ala Val Ala Ser Ser
            180                 185                 190

Leu Pro Pro Pro Pro Arg Arg Trp Ala Ala Ser Pro Gly Arg Ala Gly
        195                 200                 205

Gly Gly Val Pro Val Gly Arg Ser Ser Pro Val Trp Gln Ile Arg Arg
    210                 215                 220

Pro Pro Ser Pro Ala Ala Lys His Ala Ala Ala Asp Arg Arg Pro Pro
225                 230                 235                 240

His His Lys Asp Lys Pro Thr Gly Gly Ala Lys Lys Pro His Thr Thr
                245                 250                 255
```

```
Ser Ala Thr Gly Gly Gly Gly Ile Arg Gly Ile Asn Leu Ser Ile Asn
            260                 265                 270

Ser Cys Ile Gly Tyr Arg His Gln Val Ser Cys Arg Arg Ala Asp Ala
        275                 280                 285

Gly Val Ala Arg Ala Ser Ala Gly Gly Gly Gly Gly Gly Gly Leu Phe
    290                 295                 300

Gly Ile Lys Gly Phe Phe Ser Lys Lys Val His
305                 310                 315


<210> SEQ ID NO 104
<211> LENGTH: 306
<212> TYPE: PRT
<213> ORGANISM: Oryza sativa

<400> SEQUENCE: 104

Met Gln Gln Lys Pro Ala Ala Glu Ala Met Glu Glu Glu Leu Lys Gly
1               5                   10                  15

Glu Ala Val Gly Pro Arg Arg Pro Gly Leu Gly Leu Trp Leu Ala Ala
            20                  25                  30

Arg Arg Arg Leu Ala Pro Asp Asp Pro Phe Phe Ala Ala Gly Asp Met
        35                  40                  45

Glu Arg Glu Leu Leu Ala Lys Gln Val Ala Leu Asp Leu Ser Glu Asp
    50                  55                  60

Glu Arg Tyr Gln Leu Glu Arg Met Glu Val Ala Ser Ala Asn Ala Leu
65                  70                  75                  80

Leu Cys Pro Ile Ser Gly Cys Gly Ala His Leu Asp Cys Leu Glu Asn
                85                  90                  95

Phe Glu Asp His Tyr Arg Thr Arg His Thr Ala Ser Cys Ser Val Cys
            100                 105                 110

Trp Arg Val Tyr Pro Thr Ser Arg Leu Leu Ser Ile His Ile Ser Glu
        115                 120                 125

Ala His Asp Ser Phe Phe Gln Ala Lys Val Ala Arg Gly Phe Pro Met
    130                 135                 140

Tyr Glu Cys Leu Val Glu Gly Cys Gly Val Lys Leu Lys Ser Tyr Lys
145                 150                 155                 160

Ser Arg Gln Gln His Leu Leu Asp Lys His Gln Phe Pro Lys Ser Phe
                165                 170                 175

Glu Phe Phe Lys Lys Ala Arg Pro Ser Gln Arg Gln Arg Asn Lys Asn
            180                 185                 190

Gln Lys Gln Arg Gln Thr Val His Lys Gly Asp Glu Thr Ser Glu Thr
        195                 200                 205

Leu Met Asp Val Asp Gly Lys Lys Ser Ser Arg Tyr Met Asn Ser Arg
    210                 215                 220

Tyr Arg Pro Lys Gln His Asp Gly Lys Glu Ser Lys Glu Asn Glu His
225                 230                 235                 240

Ser Ser Cys Lys Glu Ala Lys Asn Asn Glu Met Glu Val Asp Lys Gln
                245                 250                 255

Val Asp Glu Leu Ala Ser Ala Val Ser Arg Leu Ser Thr Ala Asp Ser
            260                 265                 270

Thr Pro Ser Ser Ile Ser Phe Gly His Arg Arg Ser Arg Gly Leu Ala
        275                 280                 285

Phe Val Pro Arg Ser Ile Arg Gln Asn Lys Gln Val Ser Gln Thr Glu
    290                 295                 300

Pro Lys
305
```

<210> SEQ ID NO 105
<211> LENGTH: 328
<212> TYPE: PRT
<213> ORGANISM: Oryza sativa

<400> SEQUENCE: 105

```
Met Gly Gly Gly Gly Gly Ala Glu Glu Glu Leu Thr Ala Gln Glu Thr
1               5                   10                  15

Ala Leu Tyr Asp Arg Gln Ile Arg Val Trp Gly Val Asp Ala Gln Lys
            20                  25                  30

Arg Leu Ser Lys Ala His Val Leu Val Cys Gly Met Asn Gly Thr Thr
        35                  40                  45

Thr Glu Phe Cys Lys Asn Ile Val Leu Ala Gly Val Gly Ser Leu Ser
    50                  55                  60

Leu Met Asp Asp His Leu Val Thr Glu Asp Asp Leu Asn Ala Asn Phe
65                  70                  75                  80

Leu Ile Pro His Asp Glu Ser Ile Tyr Gly Gly Arg Ser Arg Ala Glu
                85                  90                  95

Val Cys Cys Glu Ser Leu Lys Asp Phe Asn Pro Met Val Arg Val Ala
            100                 105                 110

Val Glu Lys Gly Asp Pro Ser Leu Ile Asp Gly Glu Phe Leu Asp Lys
        115                 120                 125

Phe Asp Ile Ile Val Val Ser Cys Ala Pro Ile Lys Thr Lys Leu Leu
    130                 135                 140

Ile Asn Asp Asn Cys Arg Lys Arg Ser Lys His Ile Ala Phe Tyr Ala
145                 150                 155                 160

Ile Glu Cys Lys Asp Ser Cys Gly Glu Ile Phe Val Asp Leu Gln Asn
                165                 170                 175

His Ser Tyr Val Gln Lys Val Gly Gly Glu Pro Lys Pro Lys Glu Leu
            180                 185                 190

Ala Tyr Pro Ser Leu Gln Glu Ala Ile Ser Val Pro Trp Lys Asn Leu
        195                 200                 205

Pro Arg Lys Thr Thr Lys Leu Tyr Phe Ala Met Arg Val Leu Glu Asn
    210                 215                 220

Tyr Glu Ser Ser Glu Gly Arg Asn Ala Cys Glu Ala Ser Leu Ser Asp
225                 230                 235                 240

Arg Pro Ala Val Leu Ala Leu Arg Lys Asp Met Cys Asp Lys Met Ser
                245                 250                 255

Leu Ser Glu Ser Gln Ile Pro Thr Ala Leu Leu Glu Arg Leu Leu Ala
            260                 265                 270

Ala Gly Lys Lys Gln His Pro Pro Val Cys Ala Ile Leu Gly Gly Ile
        275                 280                 285

Leu Gly Gln Glu Val Ile Lys Ser Ile Ser Gly Lys Gly Asp Pro Ile
    290                 295                 300

Lys Asn Phe Phe Tyr Tyr Asp Ala Ala Asp Gly Lys Gly Ile Ala Glu
305                 310                 315                 320

Asp Ile Pro Pro Leu Ser Ser Asp
                325
```

<210> SEQ ID NO 106
<211> LENGTH: 301
<212> TYPE: PRT
<213> ORGANISM: Oryza sativa

<400> SEQUENCE: 106

```
Met Ala Met Pro Leu Pro Pro Pro Pro Pro Pro Arg Pro Pro Leu Gly
```

```
1               5                   10                  15

Arg Gly Arg Leu Val Gly Val Gly Pro Ala Pro Ala Pro Ala Thr Ala
            20                  25                  30

Ser Gln Ser Asn Arg Pro Val Pro Pro Leu Gln Leu Pro Arg Cys Arg
        35                  40                  45

Cys His Arg Ser Glu Gly Pro Trp Arg Thr Thr Ala Ala Ala Asn Gly
    50                  55                  60

Arg Arg Arg Trp Trp Ser Asp Glu Asp Met Glu Glu Glu Asp Asp Glu
65                  70                  75                  80

Glu Gly Tyr Gly Tyr Asp Asp Gly Gly Ala Pro Gly Gly Ser Ala Gln
                85                  90                  95

Glu Leu Phe Gly Glu Pro Trp Phe Ser Lys Leu Phe Arg Ala Tyr Gly
            100                 105                 110

Tyr Val Leu Pro Leu Leu Leu Ala Ser Met Leu Val Ala Thr Gly Pro
        115                 120                 125

Arg Ala Phe Leu Met Ala Met Ala Leu Pro Leu Ala Gln Ser Ala Ile
    130                 135                 140

Ser Trp Val Val Ser Phe Phe Thr Thr Arg Ser Arg Arg Gln Gln Glu
145                 150                 155                 160

Glu Glu Glu Ser Tyr Gly Tyr Asp Tyr Asp Asp Asp Pro Ala Phe Gln
                165                 170                 175

Arg Arg Glu Glu Asp Asp Asp Asp Gly Asp Tyr Tyr Asp Ala Gly Ala
            180                 185                 190

Trp Gln Trp Arg Ser Arg Ser His Gln Gln Ser Thr Glu Ser Gly Ser
        195                 200                 205

Gly Phe Gly Gly Trp Asp Asp Leu Leu Tyr Asp Asp Glu Glu Lys Lys
    210                 215                 220

Glu Gln Glu Ser Ser Gly Lys Lys Arg Thr Pro Pro Glu Pro Asp Thr
225                 230                 235                 240

Ala Ala Ala Ala Ala Ala Ser Asp Leu Gly Leu Gly Leu Arg Ala Arg
                245                 250                 255

Arg Gly Pro Arg Arg Ser Asn Gly Gly Met Ser Arg Gly Arg Ser Ser
            260                 265                 270

Ser Ser Met Arg Tyr Asn Gln Ala Pro Leu Leu Thr Arg Leu Leu Val
        275                 280                 285

Ala Leu Phe Pro Phe Leu Gly Ser Trp Phe Arg Ile Leu
    290                 295                 300


<210> SEQ ID NO 107
<211> LENGTH: 406
<212> TYPE: PRT
<213> ORGANISM: Oryza sativa

<400> SEQUENCE: 107

Met Arg Gly Ser Leu Glu Val His Ala Ile Gly Arg His Ala Ala Ser
1               5                   10                  15

Pro Cys Ala Leu Arg Leu Lys Ala Leu Pro Ala Leu Asp Met Met Arg
            20                  25                  30

Tyr Gln Arg Leu Ser Pro Asp Cys Leu Pro Leu Ala Asn Gly Gly Gly
        35                  40                  45

Gly Gly Ser Gly Ser Val Thr Arg Lys Pro Ala Ser Arg Ser Cys Lys
    50                  55                  60

Asp Asp Asp Gly Gly Met Ala Val Ala Ala Asp Ser Ser Arg Leu Ser
65                  70                  75                  80

Ser Tyr Leu Pro Ser Ser Gln Leu Asp Ser Lys Pro Leu Arg Ala Arg
```

```
                85                  90                  95

Ala Pro Gln Pro Ser Ser Ser Ser Ala Ala Ala Trp Ser Pro Ala Arg
            100                 105                 110

Asp His Ala His Ala His His Asn His His His His His His Pro Ser
        115                 120                 125

Asp Ser Ser Asp Thr Ala Ser Pro Ser Ser Asn Gly Ala Gly Thr Gly
    130                 135                 140

Gly Asp Val Leu Leu Gln Trp Gly His Asn Lys Arg Ser Arg Cys Arg
145                 150                 155                 160

Arg Asp Ala Ser Ser Ser Ala Asn Ala Ala Pro Ser Ser Ser Gln Arg
                165                 170                 175

Arg Gln Thr Ala Ser Ala Ala Gly Lys Ile Leu Arg Arg Ser Ser Ala
            180                 185                 190

Pro Ala Glu Lys Leu Met Pro Pro Pro Pro Pro Ser Thr Thr Thr Gly
        195                 200                 205

Ser Tyr Thr Arg Gly Ser Asn Leu Arg Ser Ala Ser Ser Phe Pro Thr
    210                 215                 220

Arg Ser Ala Ala Ala Ala Ala Val Gly Asp Ala His His His Arg Ser
225                 230                 235                 240

Ala Val Glu Glu Arg Ser Gly Gly Gly Tyr Lys Arg Ser Pro Asp Lys
                245                 250                 255

Ala His Lys Ser Ala Leu Asp Ala Ala Leu His Met Asp Ser Lys Asn
            260                 265                 270

Asn His His His His His His Asp Ser Ser Val Thr Ala Asn Gly Gly
        275                 280                 285

Ala Gly Ala Gly Glu Lys Ile Gly Ser Glu Arg Phe Glu Leu Pro Arg
    290                 295                 300

Ile Tyr Ile Ser Leu Ser Arg Lys Glu Lys Glu Asp Asp Phe Leu Ile
305                 310                 315                 320

Met Lys Gly Thr Lys Leu Pro Gln Arg Pro Lys Lys Arg Ala Lys Asn
                325                 330                 335

Val Asp Lys Thr Leu Gln Tyr Val Phe Pro Gly Met Trp Leu Ser Asp
            340                 345                 350

Leu Thr Arg Gly Arg Tyr Glu Val Arg Glu Lys Lys Cys Val Lys Lys
        355                 360                 365

Val Tyr Ser Thr Leu His Leu Ala Phe Ser Val His Ala Phe Cys Val
    370                 375                 380

Phe Leu Gln Thr Arg Arg Gly Lys Leu Pro Arg Phe Arg Ala Ser Val
385                 390                 395                 400

Thr Gln Ile Gly Trp Val
                405


<210> SEQ ID NO 108
<211> LENGTH: 203
<212> TYPE: PRT
<213> ORGANISM: Oryza sativa

<400> SEQUENCE: 108

Met Ala Thr Thr Ala Ser Leu Leu Pro Pro Leu Leu Pro Ala Pro Ser
1               5                   10                  15

Ser Ser Pro Arg His Leu His Pro Ser Pro Arg His Leu Arg Pro Leu
            20                  25                  30

Pro Pro Ile Arg Leu Leu Arg Ala Ala Arg Arg Arg His Pro Asp Ala
        35                  40                  45

Val Val Val Val Pro Asp Ala Arg Pro Trp Val Gly Asp Leu Ser Gly
```

```
    50                  55                  60

Ala Ala Ala Ser Tyr Arg Asp Gly Arg Glu Glu Asp Asp Asp Asp Ala
65                  70                  75                  80

Gly Glu Glu Asp Asp Glu Asn Asp Asp Asp Asp Glu Asp Arg Ser Leu
                85                  90                  95

Asp Leu Leu Val Arg Phe Leu His Ser Val Phe Arg Lys Val Ser Arg
            100                 105                 110

Arg Ala Arg Arg Ala Ala Arg Ser Val Leu Pro Pro Ser Val Pro Ala
        115                 120                 125

Glu Leu Val Lys Phe Ser Val Asn Gly Val Leu Val Leu Thr Phe Leu
    130                 135                 140

Trp Val Leu Lys Gly Leu Leu Glu Val Val Cys Thr Phe Gly Ser Met
145                 150                 155                 160

Val Phe Val Thr Ile Leu Leu Val Arg Gly Ile Trp Ser Gly Val Thr
                165                 170                 175

Tyr Ile Arg Glu Asn Arg Tyr Ser Tyr Ile Arg Gln Ile Asp Asn Asp
            180                 185                 190

Asp Asn Arg Trp Ser Arg Val Gln Thr Ala Gly
        195                 200


<210> SEQ ID NO 109
<211> LENGTH: 809
<212> TYPE: PRT
<213> ORGANISM: Oryza sativa

<400> SEQUENCE: 109

Met Lys Leu Arg Leu Arg Ser Met Asp Gln Arg Gly Gly Ala Gly Gly
1               5                   10                  15

Ala Ala Glu Thr His Arg Val Gln Leu Pro Asp Thr Ala Thr Leu Ser
            20                  25                  30

Asp Val Lys Ala Phe Leu Ala Thr Lys Leu Ser Ala Ala Gln Pro Val
        35                  40                  45

Pro Ala Glu Ser Val Arg Leu Thr Leu Asn Arg Ser Glu Glu Leu Leu
    50                  55                  60

Thr Pro Asp Pro Ser Ala Thr Leu Pro Ala Leu Gly Leu Ala Ser Gly
65                  70                  75                  80

Asp Leu Leu Tyr Phe Thr Leu Ser Pro Leu Pro Ser Pro Ser Pro Pro
                85                  90                  95

Pro Gln Pro Gln Pro Gln Ala Gln Pro Leu Pro Arg Asn Pro Asn Pro
            100                 105                 110

Asp Val Pro Ser Ile Ala Gly Ala Ala Asp Pro Thr Lys Ser Pro Val
        115                 120                 125

Glu Ser Gly Ser Ser Ser Ser Met Pro Gln Ala Leu Cys Thr Asn Pro
    130                 135                 140

Gly Leu Pro Val Ala Ser Asp Pro His His Pro Pro Pro Asp Val Val
145                 150                 155                 160

Met Ala Glu Ala Phe Ala Val Ile Lys Ser Lys Ser Ser Leu Val Val
                165                 170                 175

Gly Asp Thr Arg Glu Met Glu Asn Val Gly Gly Ala Asp Gly Thr Val
            180                 185                 190

Ile Cys Arg Leu Val Val Ala Leu His Ala Ala Leu Leu Asp Ala Gly
        195                 200                 205

Phe Leu Tyr Ala Asn Pro Val Gly Ser Cys Leu Gln Leu Pro Gln Asn
    210                 215                 220

Trp Ala Ser Gly Ser Phe Val Pro Val Ser Met Lys Tyr Thr Leu Pro
```

```
225                 230                 235                 240

Glu Leu Val Glu Ala Leu Pro Val Val Glu Glu Gly Met Val Ala Val
                245                 250                 255

Leu Asn Tyr Ser Leu Met Gly Asn Phe Met Met Val Tyr Gly His Val
            260                 265                 270

Pro Gly Ala Thr Ser Gly Val Arg Arg Leu Cys Leu Glu Leu Pro Glu
        275                 280                 285

Leu Ala Pro Leu Leu Tyr Leu Asp Ser Asp Glu Val Ser Thr Ala Glu
    290                 295                 300

Glu Arg Glu Ile His Glu Leu Trp Arg Val Leu Lys Asp Glu Met Cys
305                 310                 315                 320

Leu Pro Leu Met Ile Ser Leu Cys Gln Leu Asn Asn Leu Ser Leu Pro
                325                 330                 335

Pro Cys Leu Met Ala Leu Pro Gly Asp Val Lys Ala Lys Val Leu Glu
            340                 345                 350

Phe Val Pro Gly Val Asp Leu Ala Arg Val Gln Cys Thr Cys Lys Glu
        355                 360                 365

Leu Arg Asp Leu Ala Ala Asp Asp Asn Leu Trp Lys Lys Lys Cys Glu
    370                 375                 380

Met Glu Phe Asn Thr Gln Asp Thr Cys Gly Cys Met Met Cys Lys Cys
385                 390                 395                 400

Ile Tyr Ser Asp Gln Arg Lys Asp Ile Val Leu Ala Asp Lys Tyr Thr
                405                 410                 415

Cys Gly Asn Tyr Met Gln Lys Pro Val Thr Gln Pro Gly Arg Trp Leu
            420                 425                 430

Ile Ile Leu Val Tyr His Ser Leu Leu Cys Gln Tyr Ile Thr Ile Gly
        435                 440                 445

Leu Ser Leu Leu Trp Tyr His Leu Val Asp Leu Val Gln Asp Ala Pro
    450                 455                 460

Ala Ala Gly Ile His Phe Asp Cys Ile Ile Pro Leu Pro Ile Asn Pro
465                 470                 475                 480

Tyr Gln Leu Pro Pro Ser Ala Gly Ala Cys Cys Ser Thr Thr Gln Ala
                485                 490                 495

Ser Ala Ser Ala Lys Asp Gly Gly Asn Met Tyr Ser Pro Pro Cys Ser
            500                 505                 510

Ala Ala Ala Ser Ser Gln Gly His Cys Phe Ala Val Gly Ala Asn Gln
        515                 520                 525

Leu Ala Ser Leu Asp Leu Ala Met Asp Phe Asp Glu Pro Ile Leu Phe
    530                 535                 540

Pro Val His Asn Ala Ser Leu Gln Glu Gly Ile Gln Phe Tyr Asn Pro
545                 550                 555                 560

Thr Gly Asp Thr Gln Leu Ser Arg Asn Met Ser Ile Asp Lys Cys Leu
                565                 570                 575

Lys Gly Ser Lys Arg Lys Gly Ser Gly Glu Gly Ser Ser Ser Leu His
            580                 585                 590

Ser Gln Glu Glu Thr Gly Glu Met Pro Gln Arg Glu Leu Ser Met Glu
        595                 600                 605

His Ala Gly Glu Lys Ala Gly Asp Ala Asp Ala Ser Arg Glu Glu Tyr
    610                 615                 620

Val His Val Arg Ala Lys Arg Gly Gln Ala Thr Asn Ser His Ser Leu
625                 630                 635                 640

Ala Glu Arg Phe Arg Arg Glu Lys Ile Asn Glu Arg Met Lys Leu Leu
                645                 650                 655
```

```
Gln Asp Leu Val Pro Gly Cys Asn Lys Ile Thr Gly Lys Ala Met Met
            660                 665                 670

Leu Asp Glu Ile Ile Asn Tyr Val Gln Ser Leu Gln Arg Gln Val Glu
        675                 680                 685

Phe Leu Ser Met Lys Leu Ser Thr Ile Ser Pro Glu Leu Asn Ser Asp
    690                 695                 700

Leu Asp Leu Gln Asp Ile Leu Cys Ser Gln Asp Ala Arg Ser Ala Phe
705                 710                 715                 720

Leu Gly Cys Ser Pro Gln Leu Ser Asn Ala His Pro Asn Leu Tyr Arg
                725                 730                 735

Ala Ala Gln Gln Cys Leu Ser Pro Pro Gly Leu Tyr Gly Ser Val Cys
            740                 745                 750

Val Pro Asn Pro Ala Asp Val His Leu Ala Arg Ala Gly His Leu Ala
        755                 760                 765

Ser Phe Pro Gln Gln Arg Gly Leu Ile Trp Asn Glu Glu Leu Arg Asn
    770                 775                 780

Ile Ala Pro Ala Gly Phe Ala Ser Asp Ala Ala Gly Thr Ser Ser Leu
785                 790                 795                 800

Glu Asn Ser Asp Ser Met Lys Val Glu
                805


<210> SEQ ID NO 110
<211> LENGTH: 467
<212> TYPE: PRT
<213> ORGANISM: Oryza sativa

<400> SEQUENCE: 110

Met Ala Ala Ala Ala Gly Ala Gly Glu Pro Ser Pro Tyr Ala Glu Ala
1               5                   10                  15

Ala Gly Ser Asp Leu Ala Asn Ala Arg Ala Pro Ser Pro Val Val Gly
            20                  25                  30

Lys His Leu Pro Ser Gly Ala Val Pro Arg His Ala Tyr Val Phe Asp
        35                  40                  45

Gly Glu Gly Gly Phe Ala Asp Ala Ala Trp Asp Val Ala Ala Ala Ala
    50                  55                  60

Pro Gly Ala Phe Thr Trp His His Ile Glu Leu Pro Arg Gln Gln Pro
65                  70                  75                  80

Gly Gly Ala Ala Ala Lys Pro Leu His His Ala Gln Ala Leu Ile Glu
                85                  90                  95

Leu Leu Cys Pro Pro Leu Thr Leu Gln Glu Ile Leu Ala Phe Val Ala
            100                 105                 110

Thr Gly Pro His Cys Gly Val Val Asp Gly Gly Gly Gly Gly Gly Ala
        115                 120                 125

Gly Ala Leu Leu Leu Arg Val Ser Ser Pro Gly Pro Val Gly Ser Ala
    130                 135                 140

Phe Ala Leu Arg Leu Ala Ala Arg Val Thr Asp Ser Ser Val Val Thr
145                 150                 155                 160

Val Ser Val Gly Gly Val Pro Arg Leu Ala Phe Gly Thr Thr Gln Ala
                165                 170                 175

Ser Leu Leu Ser Glu Val Pro Leu Gly Val Thr Ala Ser Leu Ser Asp
            180                 185                 190

Glu Gly His Gly Gly Gly Arg Ala Val Glu Gly Gly Val Val Ile Glu
        195                 200                 205

Glu Arg Leu Leu Glu Ser Leu Leu Ala Met Asn His Ala Asp Gly Ala
    210                 215                 220
```

```
His Thr Asp Asn Pro Val Pro Arg Thr Val Ser Asn Leu Leu Val His
225                 230                 235                 240

Val Leu Gly Thr His Val Asp His Val His Asp Ile Val Thr Arg Leu
                245                 250                 255

Glu Met Glu Leu Asp Ser Ile Glu Leu His Leu Asp Lys Gly Gly His
            260                 265                 270

Phe Met Arg Lys Leu Leu Leu Asp Gly Arg Arg Phe Pro Lys Met His
        275                 280                 285

Leu Asp Leu Gln Arg Leu Leu Gln Val Val Ser His Gly Asp Gln Val
    290                 295                 300

Phe Pro Arg Val Lys Glu Lys Cys Ala Ser Lys Ser Trp Phe Ala Ser
305                 310                 315                 320

Glu Asp Ile Val Ala Leu Glu Asp Leu Ile Gly Arg Leu Arg Arg Leu
                325                 330                 335

Lys Glu Asn Leu Gly Phe Ile Thr Asn Arg Val Thr Thr Leu Gln Ala
            340                 345                 350

Ser Leu Asp Ser Trp Gln Ser Glu Gln Ile Asn Lys Ser Leu Tyr Tyr
        355                 360                 365

Leu Ser Phe Leu Ser Ile Ile Phe Leu Pro Leu Ser Ile Val Thr Gly
    370                 375                 380

Val Phe Gly Met Asn Val Gly Gly Val Pro Trp Thr Glu Gln Lys Asn
385                 390                 395                 400

Pro Ala Asn Leu Asp Gly Phe Phe Asn Val Met Leu Ile Cys Val Val
                405                 410                 415

Ile Leu Leu Ile Leu Leu Leu Cys Phe Leu Phe Pro Ser Leu Tyr Ser
            420                 425                 430

His Val Ser Ala Trp Arg Thr Arg Arg Ala Leu Ala Arg Ser Ser Ser
        435                 440                 445

Gln Asn Lys Arg His Leu Lys Leu Phe Lys Gly His Lys Asp Gly Tyr
    450                 455                 460

Met Arg Leu
465
```

<210> SEQ ID NO 111
<211> LENGTH: 147
<212> TYPE: PRT
<213> ORGANISM: Oryza sativa

<400> SEQUENCE: 111

```
Met Gln Asp Gln Leu Ile Cys Ser Gly Cys Arg Arg Val Val Gln Tyr
1               5                   10                  15

Arg Arg Gly Val Ala Gly Val Cys Cys Pro Gly Cys Asn Thr Leu Thr
            20                  25                  30

Ala Val Asn Pro Ser Ala Val Ala Asp Met Ser Glu Leu Ile Cys Ser
        35                  40                  45

Gly Cys Pro Thr Leu Leu Phe Tyr Asn Arg Gly Ala Ser Asn Ile Arg
    50                  55                  60

Cys Pro Ser Cys Asn Arg Leu Asn Ser Thr Arg Ser Ala Asn Gln Ile
65                  70                  75                  80

Ala His Leu Thr Cys Gly Gln Cys Arg Thr Thr Leu Met His Pro Pro
                85                  90                  95

Gly Ala Ser Thr Val Gln Cys Ala Thr Cys Arg Tyr Val Asn His Val
            100                 105                 110

Arg Asp Ala Arg Pro Gln Thr Val Leu Val Glu Asn Pro Lys Thr Leu
        115                 120                 125
```

```
Asp Asp Lys Gly Lys Leu Val Ser Asn Val Val Val Gly Val Thr Ser
    130                 135                 140

Trp Lys Arg
145


<210> SEQ ID NO 112
<211> LENGTH: 266
<212> TYPE: PRT
<213> ORGANISM: Oryza sativa

<400> SEQUENCE: 112

Met Arg Gly Ala Val Ala Ile Phe Asn Glu Phe Lys Arg Arg Gly Leu
1               5                   10                  15

Asn Ile Ser Ile Thr Gly Ile Pro Lys Thr Val Asp Asn Asp Ile Gly
            20                  25                  30

Ile Ile Asp Arg Ser Phe Gly Phe Gln Thr Ala Val Glu Ile Ala Gln
        35                  40                  45

Gln Ala Ile Asp Ala Ala His Val Glu Ala Val Ser Ala Val Asn Gly
    50                  55                  60

Ile Gly Leu Val Lys Leu Met Gly Arg Ser Thr Gly His Ile Ala Leu
65                  70                  75                  80

His Ala Thr Leu Ser Ser Arg Asp Val Asp Cys Cys Leu Ile Pro Glu
                85                  90                  95

Val Asp Phe Tyr Leu Glu Gly Lys Gly Gly Leu Phe Glu Phe Leu Tyr
            100                 105                 110

Glu Arg Ile Lys Gln Lys Gly His Ala Val Val Val Val Ala Glu Gly
        115                 120                 125

Ala Gly Gln Glu Leu Ile Pro Arg Thr Asp Asp Gln Lys Arg Glu Gln
    130                 135                 140

Asp Glu Ser Gly Asn Ile Val Phe Leu Asp Val Gly Pro Trp Leu Lys
145                 150                 155                 160

Ser Glu Leu Gly Lys Trp Trp Lys Arg Glu His Pro Ser Glu Leu Phe
                165                 170                 175

Thr Val Lys Tyr Ile Asp Pro Thr Tyr Met Ile Arg Ala Val Pro Ala
            180                 185                 190

Asn Ala Thr Asp Asn Leu Tyr Cys Thr Leu Leu Ala His Ser Ala Ile
        195                 200                 205

His Gly Ile Met Ala Gly Tyr Thr Gly Phe Val Pro Gly Pro Ile Asn
    210                 215                 220

Gly Asn Tyr Ser Tyr Ile Pro Leu Glu Asp Val Ala Val Ala Lys Asn
225                 230                 235                 240

Pro Val Asp Val Asn Asp His Lys Trp Ala Trp Val Arg Ser Val Thr
                245                 250                 255

Asn Gln Pro Asp Phe Met Lys Pro Lys Tyr
            260                 265


<210> SEQ ID NO 113
<211> LENGTH: 595
<212> TYPE: PRT
<213> ORGANISM: Oryza sativa

<400> SEQUENCE: 113

Met Val Glu Ser Ala Ser Met Val Asn Glu Asn Ser Glu Asn Pro Tyr
1               5                   10                  15

Trp Lys Ala Ile Gly Tyr Arg Val Glu Glu Pro Arg Arg Asp Arg Ala
            20                  25                  30

Glu Ser Met Pro Ser Pro Ser Pro Ser Pro Val Ser Arg Arg Pro Leu
```

```
        35                  40                  45

Asp Asn Gly Val Val Glu Thr Arg Ala Leu Thr Asp Thr Thr Leu Leu
    50                  55                  60

Arg Ser Leu Ala Ala Lys Gly Leu Ala Val Arg Pro Gly Ala Ser Asp
65                  70                  75                  80

Glu His His Thr Val Arg Cys Asp Ala Val Ile Val Gly Ser Gly Cys
                85                  90                  95

Gly Gly Gly Val Ala Ala Ala Val Leu Ala Ser Ala Gly Tyr Lys Val
            100                 105                 110

Val Val Val Glu Lys Gly Asp Tyr Phe Thr Lys Glu Asp Tyr Ser Ser
        115                 120                 125

Ile Glu Gly Pro Ser Met Glu Arg Leu Phe Glu Arg Gly Gly Val Phe
    130                 135                 140

Cys Thr Ser Asn Val Thr Thr Met Ile Phe Thr Gly Ala Thr Val Gly
145                 150                 155                 160

Gly Gly Ser Ala Val Asn Trp Ser Ala Ser Ile Arg Thr Pro Ala Gly
                165                 170                 175

Val Met Gln Glu Trp Ser Arg Glu His Gly Leu Ala Val Phe Ala Ser
            180                 185                 190

Pro Gly Tyr Ala Arg Ala Met Asp Ala Val Cys Glu Arg Leu Gly Val
        195                 200                 205

Thr Asp Ala Cys Arg Glu Glu Gly Phe Gln Asn Lys Val Val Arg Arg
    210                 215                 220

Gly Cys Asp Ala Leu Gly Leu Arg Ala Asp Ala Val Pro Arg Asn Ser
225                 230                 235                 240

Ser Glu Gly His Phe Cys Gly Ser Cys Asn Phe Gly Cys Pro Thr Gly
                245                 250                 255

Asp Lys Lys Gly Thr Asp Thr Thr Trp Leu Val Asp Ala Val Glu Arg
            260                 265                 270

Gly Ala Val Ile Leu Thr Gly Cys Lys Ala Glu His Phe Ile Val Glu
        275                 280                 285

Ser Asn Gly Gly Gly Gly Gly Arg Ser Lys Arg Cys Val Gly Leu Val
    290                 295                 300

Ala Thr Cys Met Ser Asn Gly Ile Thr Lys Lys Leu Arg Val Glu Ala
305                 310                 315                 320

Lys Val Ser Ile Ser Ala Ser Gly Ala Leu Met Thr Pro Pro Leu Leu
                325                 330                 335

Arg Asn Ser Gly Leu Lys Asn Arg His Ile Gly Arg Asn Leu His Leu
            340                 345                 350

His Pro Val Ser Met Ala Trp Gly Tyr Phe Pro Asp Asn Thr Pro Glu
        355                 360                 365

Pro His Ile Pro Gly Lys Cys Tyr Glu Gly Gly Ile Ile Thr Ser Met
    370                 375                 380

His Arg Val Thr Glu Arg Thr Ile Ile Glu Thr Pro Ala Leu Gly Pro
385                 390                 395                 400

Gly Ala Phe Ala Ala Leu Val Pro Trp Glu Ser Gly Arg Asp Met Lys
                405                 410                 415

Glu Arg Met Arg Arg Tyr Ala Arg Thr Ala His Ala Phe Ala Leu Val
            420                 425                 430

Arg Asp Arg Gly Ala Gly Ser Val Asp Gly Glu Gly Arg Val Arg Tyr
        435                 440                 445

Ala Pro Ser Arg Asp Asp Ala Glu Glu Leu Arg Ala Gly Leu Arg Arg
    450                 455                 460
```

```
Ala Leu Arg Ile Leu Val Ala Ala Gly Ala Ala Glu Val Gly Thr His
465                 470                 475                 480

Arg Ser Asp Gly Ala Arg Leu Arg Cys Lys Gly Ala Arg Asp Ala Asp
                485                 490                 495

Val Glu Ala Phe Leu Asp Glu Val Thr Val Glu Lys Gly Pro Met His
            500                 505                 510

Ser Thr Thr Asp Lys Trp Ser Val Leu Cys Ser Ala His Gln Met Gly
        515                 520                 525

Ser Cys Arg Met Gly Ala Ser Pro Arg Asp Gly Ala Val Asp Val Ala
    530                 535                 540

Gly Glu Ser Trp Glu Ala Glu Gly Leu Tyr Val Cys Asp Gly Ser Leu
545                 550                 555                 560

Leu Pro Thr Ala Val Gly Val Asn Pro Met Ile Thr Ile Gln Ser Ile
                565                 570                 575

Ala Tyr Cys Val Ala Lys Gly Ile Ala Asp Ser Met Ala His Gly Lys
            580                 585                 590

Glu Gln Arg
        595


<210> SEQ ID NO 114
<211> LENGTH: 177
<212> TYPE: PRT
<213> ORGANISM: Oryza sativa

<400> SEQUENCE: 114

Met Ala Pro His Pro Leu Leu Arg Gly Gly Ala Arg Arg Gly Arg Lys
1               5                   10                  15

Tyr Ala His Gly Met His Pro Ala Gln Met Glu Ala Leu Arg Ala Met
            20                  25                  30

Cys Gly Ala Leu Ile Pro Ser Leu Pro Val Asp Ala Asp Gly Gly Asp
        35                  40                  45

Gly Gly Arg Arg Pro Gly Asp Lys Asp Leu Glu Arg Phe Tyr Leu Ala
    50                  55                  60

Ser Ala Ala Asp Ser Ser Ile Pro Asp Glu Val Ala Glu Leu Leu Val
65                  70                  75                  80

Thr Arg Cys Ile Trp Glu Ala Val Ala Leu Thr Trp Val Val Leu Trp
                85                  90                  95

Ala Leu Ser Thr Arg Ala Gly Thr Leu Leu Leu Cys Gly Arg Asp Ser
            100                 105                 110

Val Ala Ala Val Asp Gly Gly Gly Phe Pro Phe Val Ser Val Arg Arg
        115                 120                 125

Phe Ala Asp Met Pro Ala Ala Arg Arg Glu Ala Ala Leu Trp Arg Trp
    130                 135                 140

Ser Gly Ala Arg Trp Leu Phe Phe Pro Leu Arg Ile Ala Phe Ala Ile
145                 150                 155                 160

Ala Lys Ile Leu Cys His Tyr Val Phe Tyr Ser Met Ile Leu Val Ser
                165                 170                 175

Ala


<210> SEQ ID NO 115
<211> LENGTH: 477
<212> TYPE: DNA
<213> ORGANISM: Oryza sativa

<400> SEQUENCE: 115

atgcccaggc acgcatgtct gctgcagtct gaccgaattt ttttcatagc cactgaagag      60
```

```
tgcagacgga ggcgacgcca aggaggtgcc gacgccggcg ctggaggcag aggcggaggg    120

cgccggtgct gggcggaggc ggcggaggcg gcgcacatgg cggcggcggc ggcgcatagg    180

gcggcggcgg tgcacagggc ggcctgcggt agctccaccg tcgccgtcgg gctgcgggag    240

ctccaccggc gtcgtctctg cagcacctgc acgggggatg gggatgggga taggatgctt    300

atgcagagaa atgacagtag caatagcaaa tggatgttgt cacggagggc attttcgcct    360

tttcacgtga gtgctaaatt tgcatgggag gtacaggaat cgcttctgga tggagggagt    420

acctggttct gtttaggatc tagtgcgtac tttgtcgcag tcaaatacga ttggtga       477
```

<210> SEQ ID NO 116
<211> LENGTH: 354
<212> TYPE: DNA
<213> ORGANISM: Oryza sativa

<400> SEQUENCE: 116

```
atggggacgt acaagtgctg catcttcttc acccgcaggt tcgcgctgag cgacgcgtcc     60

acgccgggcg acgtgcgcat gctgttcacc cgccacgccg gcggcgcgcc ctacatgggc    120

atcgacgagc tccggcgcta cctcgccgcc agcggggagg cccacgtcga cgccgacacg    180

gcggagcgga tcatcgaccg ggtcctgcag gagcgcagcc gcaccccgcg cttcgggaag    240

ccgtcgctca ccatcgacga tttccagtac ttcctcttct ccgaggacct caacccgccc    300

atctgccatt ccaaggaaga aagttttgat gcgatggaaa agttggaagt ttga          354
```

<210> SEQ ID NO 117
<211> LENGTH: 1473
<212> TYPE: DNA
<213> ORGANISM: Oryza sativa

<400> SEQUENCE: 117

```
atgcaggtcc atcacgacat gaatgcacca ttatcgcact acttcatata cactggacac     60

aactcgtatc tgacgggcaa tcaacttagc agtgactgca gtgatattcc catcattaag    120

gcactgcaaa taggcgtccg tgtaattgaa ctggacatgt ggccaaattc ttctaaagat    180

gatgttgata ttctccatgg aaggacactg actgccccag tatcacttat caaatgcttg    240

aaatccatca aagaatatgc ctttgttgcg tctccctacc ctgttattat aacattagaa    300

gaccacctta catctgatct tcaggcgaaa gtagctaaga tggttcttga agtatttgga    360

gataccctat attatcccga gtcaaaacat cttcaagaat ttccttcacc cgaagcactg    420

aggggacgtg tcatcctctc aacaaaaccc ccaaaggagt accttgaatc aaaaggtggt    480

actatgaaag acagagacat tgagcctcag tttagcaaag gacaaaatga agaagctgtc    540

tggggaacag aagtcccaga tattcaggat gagatgcaaa ccgccgacaa gcagcatgag    600

aatgatatac tatacaccca aagagatgtg gaagaagatg atgagaagaa aatgtgccag    660

catcacccac tagagtataa acaccttatt actattaagg caggaaagcc aaagggtgct    720

gtagttgatg ccttaaaggg tgatccagat aaagttagac gcctcagttt gagtgagcag    780

gaacttgcaa aagtggcagc gcatcatggt cgtaacatcg tgagctttac acataaaaat    840

cttctgagaa tatacccaaa gggcactcgc ttcaattctt cgaactataa tccgtttctt    900

ggttgggtgc atggtgcaca aatggtggca tttaatatgc aggggtatgg aagatctctt    960

tggctaatgc acggattcta caaggccaac ggtggctgcg gttatgtgaa gaagccagat   1020

ttcatgatgc aaacttgtcc agatggaaat gtttttgacc cgaaagcaga tttacctgtg   1080

aagaaaacac tcaaggtcaa agtatacatg ggcgaaggtt ggcagagcga cttcaagcag   1140
```

```
acatacttcg acacgtattc ccctccagac ttctacgcaa aggtgggcat tgccggggtt   1200

ccgtcggact cggtgatgca gaagacgaaa gccgtggagg acagctgggt tcccgtgtgg   1260

gaggaggagt tcgtgttccc gctgaccgtc ccggagatcg cgctgctccg cgtggaggtg   1320

cacgagtacg acgtgagcga ggacgacttc ggcgggcaga cggcgctccc ggtgtcggag   1380

ctgcggccgg ggatccgcac cgtgccgctc ttcgaccaca aggggctcaa gttcaagagc   1440

gtcaagctcc tcatgcggtt cgagttcgtc tag                                1473
```

```
<210> SEQ ID NO 118
<211> LENGTH: 636
<212> TYPE: DNA
<213> ORGANISM: Oryza sativa

<400> SEQUENCE: 118

atggcgatgg gagccgcggc ggcgccatgg tacggcgcca tcggcggcgg tggctcgcgg     60

cgcgcgcggg tgagggcgca ggcggcggcg ccgtgggcag gaggcgcgga ggagctggtg    120

cggtcgggcg cggtgcgggc ggtgcgggcg agggaggcgg cgggggcgat gtccgcggag    180

gggttccggc tgctggacgt ccggccggag tgggagcgcg cgcgcgccgc cgtgcggggc    240

tcggcgcacg cgccgctgtt cgtcggggac gacgacacgg gccccgtcac gctgctcaag    300

aagtgggtcc acttcggcta catcggcctc tggaccggcc agtccttcac caagatgaac    360

gaccgcttcc tcgacgacgt cgccgccgcc gccggcgaag gcaaggacgc caagctgctc    420

gtcgcctgcg gcgaaggcct ccggtcgttg atcgcggtga ggatgctgta cgacgacggg    480

tacaagaacc tggcgtggct cgccggaggg ttcagcaagt gcgtcgacgg cgacttcgcc    540

gacgtggagg gggagagcaa gctgcagtat gccaccgtgg gtggggtgtc ctacatcttc    600

ctccagatcc tgcttctgct gcgggtagtc aagtga                              636
```

```
<210> SEQ ID NO 119
<211> LENGTH: 948
<212> TYPE: DNA
<213> ORGANISM: Oryza sativa

<400> SEQUENCE: 119

atggccgcag cagcgcagag gcggcggagc agcagcgcct ccccggagtt ccgcttctgg     60

cccctcgacg ccgaccccgc cgcatccccc tcctgcgccg acgagctctt ctccggcggc    120

gtcctcctcc ccctccaacc cctcccctac ccccgccgcg acgccgacct ctccatgtcc    180

ctcgccgtcg cggatgatga tgatgatgag gacgaggagg aggaggaggt gcagcctggt    240

gcggccgtcg cgtccagggc gccgcccact gctgcggtgg cggcgtcggg tggtggtggt    300

ggtgggtcga agaggtggac ggatatattc gccaagaagc agcagcagcc ggcggcggag    360

gagaaggaga aggatcagcc gacgaggcgg cggagaccgg cgggaggcgg aggcggatcg    420

gagctgaaca ttaacatctg gccgttctcc cggagccgct ccgccggcgg gggcggcgtg    480

gggtcgtcga agccccgccc gccgccgcgg aaggccagta gcgccccgtg ctcccgcagc    540

aactcccgcg gcgaggcggc ggcggtggcg tcgtcccttc ctcctcctcc tcgccgctgg    600

gccgccagcc ccggccgcgc aggcggcggc gtgccggtgg gccggtctag cccggtctgg    660

cagatcaggc gcccgccatc gccggcggcg aagcacgccg ccgcggacag gaggccgccg    720

caccacaagg acaagccaac cggcggcgcc aagaaacccc acaccacctc cgccaccggc    780

ggcggcggga tacgcggcat caacctgagc atcaactcct gcatcgggta ccgccaccag    840

gtgagctgcc gccgcgccga cgccggagtc gcccgcgcct ccgccggcgg cggcggcggc    900
```

```
ggcgggctct tcggcatcaa ggggttcttc tccaagaagg tgcattga              948


<210> SEQ ID NO 120
<211> LENGTH: 921
<212> TYPE: DNA
<213> ORGANISM: Oryza sativa

<400> SEQUENCE: 120

atgcagcaga agcccgcggc ggaggccatg gaggaggagt tgaaggggga ggccgtgggg     60

ccccgccgcc ccgggctagg gttatggttg gcggcgcggc ggcggctggc cccgacgac     120

cccttcttcg ccgccgggga catggagcgc gagctcctcg ccaagcaagt tgctctggat    180

ctctccgaag atgaacggta ccagcttgag aggatggaag tggcgagtgc caatgcccctt   240

ttatgcccaa tttctggctg tggtgctcat ctagattgcc tggagaactt tgaggaccac    300

tatcgcaccc gtcatactgc ttcatgctct gtatgttgga gagtgtatcc aacttcaagg    360

ctgctgagta ttcatatttc tgaggcacat gattcctttt ttcaagcaaa agttgcccgt    420

ggttttccaa tgtatgagtg tttggtggag ggttgtgggg tgaagttgaa gagctacaaa    480

agtcggcagc agcatcttct tgataagcac cagtttccca agtcatttga attcttcaaa    540

aaagcacgcc cttcgcaacg ccagcggaac aagaaccaga agcaacggca aacagttcac    600

aagggagacg agacaagcga aacactaatg gatgttgatg ggaagaagag ctcaaggtac    660

atgaattcca gatatcggcc aaagcaacat gatggaaaag agtcaaaaga aaatgagcat    720

agtagctgta aggaggccaa gaacaacgaa atggaggttg acaagcaggt tgatgagctt    780

gcttcggccg tatcaagact gagcacagcg gattcaactc cttctagcat aagctttggt    840

catcgtcgct ctcgcggtct tgcttttgtc cctaggtcga ttcggcaaaa caagcaggtt    900

tctcagacag aaccaaaatg a                                              921


<210> SEQ ID NO 121
<211> LENGTH: 987
<212> TYPE: DNA
<213> ORGANISM: Oryza sativa

<400> SEQUENCE: 121

atgggcggcg gcggcggcgc ggaggaggag ctgacggcgc aggagacggc gctctacgac     60

cgccagatcc gcgtctgggg cgttgacgcc cagaagaggc taagtaaagc tcatgtgctc    120

gtgtgcggca tgaatggtac tactactgag ttctgcaaga atattgttct agcaggagtt    180

ggcagtttat ccttgatgga tgatcattta gtcacagagg atgatctcaa tgcaaatttc    240

ttaattcctc atgatgagag catatatggt ggtagatcac gagctgaggt ttgctgtgag    300

tccctgaaag atttcaatcc aatggtccga gttgcagtcg aaaagggtga tccatcatta    360

attgatggag aattccttga caagtttgac ataattgtag ttagctgtgc gcctattaaa    420

acaaagttgt taattaacga caactgccgg aagagaagca agcatattgc attctacgcc    480

attgagtgca aggattcctg tggtgaaata tttgttgatt tgcagaacca tagctatgtt    540

cagaaggttg gaggtgaacc caaaccaaag gagttggcat atccaagtct ccaggaagct    600

atctccgtac cctggaagaa tttaccaaga aaaacaacta aactgtactt tgccatgaga    660

gtactggaga attatgagtc atctgaaggc cgcaatgctt gtgaggcatc actttctgat    720

cgacctgcag ttttggctct gaggaaggac atgtgtgata aaatgtcttt aagtgagtct    780

caaattccta ctgctctcct ggaacggctt ttagcagctg gaaagaagca acatcctcct    840

gtatgtgcaa tccttggcgg cattcttggt caggaggtga ttaagtcaat atctggtaag    900
```

```
ggtgatccga tcaagaattt cttctattac gacgccgctg atggtaaagg gatcgctgaa    960

gacattcctc ccctttcttc agactga                                        987


<210> SEQ ID NO 122
<211> LENGTH: 906
<212> TYPE: DNA
<213> ORGANISM: Oryza sativa

<400> SEQUENCE: 122

atggctatgc cgctgccgcc gccgccgccg cctcgtcctc ctcttggacg gggacggctc     60

gtcggagtag gaccagctcc agcaccagca acggcctccc aatccaaccg cccagtgccc    120

cccctgcagc tgcctcgctg ccgctgccat cgctcggagg gaccctggag gacgacggcg    180

gcggcgaacg ggaggaggcg gtggtggtcc gacgaggaca tggaggaaga ggacgacgag    240

gagggatacg gatacgacga cggcggcgcg ccaggcgggt cagcgcagga gctgttcggc    300

gagccatggt tttccaagct cttccgtgcg tacggctacg tgctgccgct gctgctggcg    360

tccatgctgg tggccacggg gcccagagct ttcctcatgg ccatggcgct gccgctcgcc    420

cagtccgcca tctcctgggt cgtctccttc ttcaccacca ggagtcgtcg gcagcaggag    480

gaggaggagt cgtacggata cgactacgat gacgatcccg ccttccaacg ccgagaggaa    540

gacgacgacg acggcgacta ctatgatgcc ggggcatggc aatggcggag caggagccac    600

cagcaatcga ccgaatccgg ctccggtttt ggaggatggg atgacctcct ctacgacgat    660

gaggagaaga aggagcagga gagctcaggg aagaagagga cgccaccgga gcccgacacg    720

gcggcggctg ctgccgcctc cgatctggga ctgggattgc gggcgaggag aggtccacga    780

cgcagcaatg gcggcatgtc gcgaggaaga agcagcagca gcatgaggta taaccaggcg    840

ccactgctga cgcgccttct cgtggcactc ttccccttcc tcggctcatg gttcaggata    900

ctctaa                                                               906


<210> SEQ ID NO 123
<211> LENGTH: 1221
<212> TYPE: DNA
<213> ORGANISM: Oryza sativa

<400> SEQUENCE: 123

atgcgtggct ccctggaggt ccacgcgatt ggcagacacg ccgcgtcgcc gtgcgccctg     60

agactgaaag ccctcccggc attggacatg atgaggtacc aaaggcttag cccggactgc    120

ctcccgctag ccaacggcgg cggcggagga agcggtagcg tgacacggaa gccggcgtcg    180

agatcctgca aggacgacga tggcggcatg gccgtcgccg cggacagctc ccgcctctcg    240

tcgtacctcc cgtcgtcaca gctcgattcc aagccgctgc gcgctcgggc gccgcagccg    300

tcgtcctcgt cggccgccgc ctggagcccg gcgcgcgacc acgcgcacgc ccaccacaac    360

caccaccacc accaccaccc gtccgactcc tccgacacgg cctcgccgag ctccaacggc    420

gcgggcaccg gtggcgacgt gctgctgcag tgggggcaca acaagcggtc ccgctgccgg    480

cgcgacgcgt cctcctcggc caacgcggct ccctcctcct cgcagcgccg ccagaccgcc    540

tccgccgccg gcaagatcct gcgccgctcg tcggcgccgg cggagaagct catgccgccg    600

ccgcccccat ccaccaccac cgggtcgtac acgcgcgggt ccaacctgag gtccgcttcg    660

tccttcccga cgcggtccgc cgccgccgcc gccgtcggag acgcacacca ccacaggtcc    720

gccgtggagg agcgatcagg cggcgggtac aagcggtcgc cggacaaggc gcacaagtcc    780

gccctggacg cggcgctgca catggattcc aagaacaacc accatcacca ccaccacgac    840
```

```
tcgtcggtga ccgcaaacgg cggcgccggc gccggcgaga agatcggctc cgagcggttt    900

gagctgcccc ggatctacat ctcgctgtcg cgcaaggaga aggaggacga cttcttgatc    960

atgaagggca ccaagctgcc tcagaggccc aagaagaggg ccaagaacgt ggacaagacc   1020

ctccaatatg tattccctgg gatgtggctt tcagacttga cgagaggacg gtatgaggtg   1080

cgagagaaga aatgtgtgaa gaaggtatac tccactctgc acctggcatt ttcagttcat   1140

gcattctgtg tatttttaca gacaagaaga ggaaaattac ctagatttag ggcatcagtg   1200

acccagattg gttgggtcta a                                             1221
```

<210> SEQ ID NO 124
<211> LENGTH: 612
<212> TYPE: DNA
<213> ORGANISM: Oryza sativa

<400> SEQUENCE: 124

```
atggcgacca ccgcctccct cctccctcct ctcctcccgg ccccttcctc ctccccccgc     60

cacctccacc cctcccctcg ccacctccgc cccttgccac cgatccgcct cctccgcgcc    120

gcccgccgcc gccaccccga cgccgtcgtc gtcgtcccgg acgcccgccc ctgggtcggc    180

gacctctcgg gcgccgccgc gtcctaccgg gacggcaggg aagaggacga cgacgacgcg    240

ggggaggagg atgacgaaaa cgacgacgac gacgaggacc gcagcctgga cctcctggtc    300

cgcttcctgc actcggtgtt caggaaggtc tcccgccgcg cgcgccgcgc cgccaggtcc    360

gtgctgccgc cttccgtccc cgctgagctg gtgaagttct cggtcaacgg cgtgcttgtt    420

ctcacgtttc tatgggtcct aaaggggcta cttgaggtgg tgtgcacatt tggaagtatg    480

gtgttcgtga ccatccttct tgttcgtgga atatggtctg gagtgactta cataagagaa    540

aaccgatata gctatattcg ccagattgat aatgatgaca accgatggag cagagtacag    600

actgctggct aa                                                        612
```

<210> SEQ ID NO 125
<211> LENGTH: 2431
<212> TYPE: DNA
<213> ORGANISM: Oryza sativa

<400> SEQUENCE: 125

```
atgaagcttc ggttgcgatc catggaccag cgcggcggcg ccggcggcgc cgccgagacc     60

caccgcgtgc agctgccgga cacggccacg ctctccgacg tcaaggcctt cctcgccacc    120

aagctgtccg cggcgcagcc cgtgcccgcc gagtcggtgc gcctcaccct caaccgctcc    180

gaggagctcc tcacccccga cccctccgct accctcccgg ccctcgggct cgcgtccggt    240

gatctcctct acttcacgct ctcccccctc ccgtcgccct cgcctccgcc gcagccgcag    300

ccacaggccc aaccctgccc cgtaacccta accctgatgt cccctcgatc gcgggagctg    360

ctgacccgac caaatctcct gtggagtctg gtagtcctcg tcgatgccgc aagctttgtg    420

cacgaatcct ggcttacctg tcgcatccga tccgcatcat cctccaccgg atgtggtgat    480

ggcggaggcc ttcgccgtga tcaagagcaa gtcgagtctc gtcgtcgggg atacgaagag    540

agagatggag aatgtcggtg gtgcggatgg aaccgtcatc tgtcgccttg tcgtggcgct    600

gcatgcggcc ttgctcgatg ccggcttcct ctatgcaaac ccggtggggt cttgccttca    660

gctgccacag aattgggcgt caggttcttt tgtccccgta tcgatgaagt acaccctgcc    720

agagcttgta gaagcgttac ctgtggttga ggaggggatg gtggcagtgc tgaactactc    780

cttgatgggg aattttatga tggtgtatgg gcatgtgcct ggggcaacat cgggggtgcg    840
```

```
aaggttgtgc ttggagctgc cggagcttgc gcctttgttg tacttggata gtgatgaggt    900

gagcacagca gaggagaggg aaattcatga gctgtggagg gtcctgaagg atgagatgtg    960

cttgcctctg atgatatcgt tgtgtcaact gaacaatttg agcttgccac cgtgcttgat   1020

ggcgctgcca ggtgatgtca aggcaaaggt cctggagttt gttcctgggg tggatcttgc   1080

aagggttcaa tgcacgtgca aggaattgag ggatcttgct gcagatgata atctttggaa   1140

gaagaagtgt gagatggagt tcaatactca agatacatgc ggttgtatga tgtgtaaatg   1200

catttactct gaccaaagga aggatatcgt actagctgat aagtatacct gtggtaatta   1260

tatgcagaag cccgtcacac aacctggtag gtggcttatt atattagtct accattccct   1320

actttgccag tacatcacta ttgggttgag tttgctgtgg tatcatttgg ttgatttggt   1380

tcaggatgct cctgcagcag gcattcactt tgactgtatt attccactgc caatcaatcc   1440

ttaccagctt cccccatctg ctggtgcctg ctgctcaaca actcaagctt cagcatcagc   1500

aaaagatggt ggcaatatgt attcccctcc ctgcagtgct gctgcaagca gccaagggca   1560

ttgtttcgcg gtcggagcta accagcttgc ttcgcttgac cttgccatgg acttcgacga   1620

gcctatcctt tttcctgtgc ataatgcaag tttgcaagag gggattcagt tttacaatcc   1680

taccggcgat actcagctaa gtagaaacat gagcattgac aagtgtttga agggcagtaa   1740

aaggaagggc tcaggcgagg gcagttcatc gctacattcc caagaggaaa ccggtgaaat   1800

gcctcagaga gaactcagca tggagcatgc cggagagaag gcgggtgatg ctgacgctag   1860

cagggaggag tacgtgcatg tccgggcaaa acgcggccag gcgaccaaca gccacagcct   1920

tgcagaaaga tttcgaaggg agaagataaa cgaaaggatg aagcttctgc aggacctcgt   1980

cccaggatgc aacaagatta cagggaaggc catgatgctc gacgagatca taaactacgt   2040

ccagtctctg cagcgacagg tggagttcct ctcgatgaag ctctcgacaa tcagtcctga   2100

gttgaactct gacctcgacc tgcaagatat cctttgttca caagatgctc gctccgcatt   2160

tctgggatgc agcccgcaat tgagcaatgc ccatcctaac ctttacaggg cggctcagca   2220

atgcctctca cctcctggct tgtacgggag tgtgtgtgtc ccaaatcccg cagatgttca   2280

tttggcaagg gccggtcact tggcttcgtt tcctcagcag agaggcctca tctggaacga   2340

ggaacttcgc aacattgctc cggccggttt cgcttcagac gccgctggca ccagtagctt   2400

agagaactct gattcgatga aagtggagta g                                  2431
```

<210> SEQ ID NO 126
<211> LENGTH: 1404
<212> TYPE: DNA
<213> ORGANISM: Oryza sativa

<400> SEQUENCE: 126

```
atggcggccg cggccggcgc cggcgagccg tcgccgtacg cggaggcggc gggatccgac     60

ctcgcgaatg cgcgggcgcc gtctcccgtg gtcggcaagc acctcccgtc gggcgccgtg    120

ccgcgccacg cgtacgtgtt cgacggcgag ggggggttcg ccgacgcggc gtgggacgtc    180

gcggcggcgg cgccgggggc gttcacgtgg caccacatcg agctcccgcg gcagcagccc    240

gggggcgccg ccgcgaagcc gctccaccac gcgcaggcgc tgatcgagct gctctgcccg    300

ccgctcacgc tgcaggagat cctcgcgttc gtcgccacgg gcccgcactg cggcgtcgtg    360

gacggcggcg gcggcggcgg ggcgggcgcg ctccttctcc gcgtgagctc gccggggccg    420

gtggggagcg cgttcgcgct ccgcctcgcc gcgcgcgtca cggacagctc cgtggtgacc    480

gtgtccgtgg gcggcgtccc gcgcctcgcg ttcgggacca cgcaggcgtc gctcctctcc    540
```

```
gaggtgccgc tcggggtgac cgcgtcgctc tccgacgagg gccacggcgg cgggcgcgcc    600

gtcgagggcg gggtggtgat cgaggagcgg ctgctcgagt cgctgctcgc catgaaccac    660

gccgacggcg cgcacaccga caaccccgtg ccgcggaccg tgtccaacct cctcgtgcac    720

gtcctgggaa cgcacgtaga ccacgtccac gacatcgtca cgcgcctcga gatggagctc    780

gacagcatcg agctgcatct cgacaagggt ggtcacttta tgaggaaact tttgttggat    840

ggaaggagat tccccaaaat gcatcttgat ctacagcgcc tgcttcaggt tgtttctcat    900

ggtgaccaag tattcccccg tgtaaaggaa aaatgtgcga gcaagagttg gtttgcgagt    960

gaagatattg ttgctcttga agatctgata ggccgtctta ggaggctgaa ggaaaatctt   1020

ggatttataa cgaatagggt gactacactt caagctagtc tagatagctg gcaatctgag   1080

cagataaaca aaagcttgta ctatctttca tttttgtcca taatattcct tcctctatcc   1140

attgtcactg gagtttttgg gatgaatgtt ggtggtgtgc catggactga gcagaaaaac   1200

cctgcaaatc tagatggctt cttcaatgtc atgttaatat gcgtcgtgat cttgttgatc   1260

ctgctgcttt gtttcttatt tccttcattg tattcacacg tgtcggcatg gagaacccgc   1320

cgtgcactgg cccggagcag ttctcagaac aagagacatc tgaaactctt taagggtcac   1380

aaagatggtt acatgcgcct ctga                                          1404
```

<210> SEQ ID NO 127
<211> LENGTH: 444
<212> TYPE: DNA
<213> ORGANISM: Oryza sativa

<400> SEQUENCE: 127

```
atgcaggacc agctgatctg cagcggctgc aggcgcgtcg tccagtacag gagaggggtc     60

gccggcgtct gctgcccggg ctgcaacacg ctcaccgccg tcaacccgtc agcggtggcc    120

gacatgtcgg agctcatctg cagcggctgc cccacgctgc tgttctacaa ccgcggcgcc    180

tccaacatcc gctgccccag ctgcaacagg ctcaactcca ccagatcagc caaccagatt    240

gcacacctga catgcgggca gtgccggacg actctgatgc acccacctgg agcctcaact    300

gtgcagtgtg caacctgcag atatgttaac catgtcaggg atgctcggcc tcaaactgtc    360

cttgtagaga atcctaagac actggatgat aagggcaagc tggtgagcaa tgtggttgtt    420

ggtgtcacct catggaaaag atga                                           444
```

<210> SEQ ID NO 128
<211> LENGTH: 801
<212> TYPE: DNA
<213> ORGANISM: Oryza sativa

<400> SEQUENCE: 128

```
atgagaggag ctgtggccat cttcaacgag tttaagcgcc gtggtttgaa catttctatt     60

acagggatcc cgaaaactgt ggacaatgat atcggcatca tagacaggtc atttgggttc    120

caaaccgcag tggagattgc tcagcaggca atcgacgcag cacatgtcga ggctgtgagc    180

gccgtgaatg gcattggact tgtcaaactt atgggcagga gcacaggcca cattgctctt    240

catgccaccc tgagcagccg cgatgttgac tgctgtttga ttcctgaggt tgatttctat    300

cttgaaggaa agggggcct gtttgagttc ttgtatgaaa ggataaaaca gaagggacat    360

gctgttgtcg ttgttgctga aggtgctggt caggaattga ttccaaggac tgacgatcaa    420

aagcgggagc aggacgagtc cggcaacatt gtgttccttg atgtgggtcc ctggttaaaa    480

tctgagctgg gtaaatggtg gaagagagaa cacccaagcg agttgttcac tgtgaagtat    540
```

```
atcgatccca cttacatgat acgagctgtt ccagcaaatg ccactgacaa tctgtactgt    600

acattgttgg cacattcggc gatccatggg atcatggctg ggtacactgg cttcgtccct    660

ggcccgatta atggaaacta tagctacata ccgctggaag atgttgctgt ggcgaagaac    720

ccggtggatg tgaatgatca caaatgggca tgggttagat cagtcacaaa ccaaccagat    780

ttcatgaagc caaaatacta a                                              801
```

<210> SEQ ID NO 129
<211> LENGTH: 1788
<212> TYPE: DNA
<213> ORGANISM: Oryza sativa

<400> SEQUENCE: 129

```
atggttgaaa gtgcaagcat ggtgaacgag aactcggaga atccatactg gaaagcaata     60

ggatacagag tggaagagcc ccgacgtgat cgagcagagt cgatgccgtc gccgtcgcca    120

tcgccggtat cgcggcggcc actggacaac ggcgtcgtgg agacgagggc gctgacggac    180

accaccctcc tccggtcgct cgcggcgaag ggcctcgccg tgaggcccgg cgcgtcggac    240

gagcaccaca cggtgcggtg cgacgccgtc atcgtcggct ccggctgcgg cggcggcgtg    300

gccgccgcgg tgctcgcgtc cgccgggtac aaggtggtcg tcgtcgagaa gggcgactac    360

ttcaccaagg aggattacag ctcgatcgag ggcccgtcca tggagcgcct cttcgagagg    420

ggcggcgtct tctgcacgtc caacgtcacg acgatgatat tcaccggcgc gacggtcggc    480

ggcgggtcgg cggtgaactg gtcggcgagc atccgcacgc cggcgggcgt gatgcaggag    540

tggtcgcgcg agcacgggct ggcggtgttc gcgagccccg ggtacgcgcg ggccatggac    600

gcggtgtgcg agcgcctcgg tgtgaccgac gcgtgccggg aggaagggtt ccagaacaag    660

gtggtgcgcc gcgggtgcga cgcgctcggg ctgcgcgccg acgccgtgcc gcgcaactcg    720

tcggaggggc acttctgcgg cagctgcaac ttcgggtgcc ccaccggcga caagaagggc    780

accgacacga cgtggctcgt cgacgccgtc gagcgcggtg cggtcatcct gaccgggtgc    840

aaggccgaac acttcatcgt cgagagcaac ggcggtggcg gcggccggag caagaggtgc    900

gtcggcctgg tggcgacgtg catgagcaac ggcatcacca agaagctccg cgtcgaggcg    960

aaggtgtcca tctcggcgag cggcgcgctc atgacgccgc cgctgctgcg caacagcggg   1020

ctcaagaacc gccacatcgg ccggaacctg cacctccacc cggtgtccat ggcgtggggc   1080

tacttcccgg acaacacgcc ggagccgcac atcccgggga agtgctacga gggcggcatc   1140

atcaccagca tgcaccgcgt cacggagcgc accatcatcg agacgccagc gctcggcccg   1200

ggcgccttcg ccgccctggt gccctgggag tccggccgcg acatgaagga gcggatgcgc   1260

cggtacgcgc gcacggcgca cgcgttcgcg ctggtgcgcg accgcggcgc cgggtccgtc   1320

gacggcgagg gccgcgtccg ctacgccccg agccgcgacg acgccgagga gctccgcgcc   1380

ggcctccgcc gcgcgctgcg catcctggtg gccgccggcg ccgccgaggt gggcacgcac   1440

cgcagcgacg gggcccgcct ccgatgcaag ggcgcgcgcg acgcggacgt ggaggcgttc   1500

ctcgacgagg tgaccgtgga gaaggggccg atgcactcga cgacggacaa gtggtcggtg   1560

ctctgctcgg cgcaccagat ggggagctgc cggatgggcg cgagccccccg cgacggcgcc   1620

gtcgacgtcg ccggcgagag ctgggaggcg gaggggctct acgtctgcga cggcagcctg   1680

ctcccgacgg cggtgggcgt gaacccgatg atcaccatac agtccatcgc ctactgcgtc   1740

gccaagggca tagccgactc gatggcacac ggcaaggagc agcgctag                1788
```

<210> SEQ ID NO 130

<211> LENGTH: 534
<212> TYPE: DNA
<213> ORGANISM: Oryza sativa

<400> SEQUENCE: 130

```
atggcgccgc acccgctgct gaggggaggg gcgaggcggg ggaggaagta cgcgcacggg     60
atgcaccccg cgcagatgga ggcgctgcgc gccatgtgcg gcgcgctcat cccgtcgctg    120
cccgtggacg cggacggcgg cgacggcggg cgccgccccg gcgacaagga cctcgagcgg    180
ttctacctcg cctccgccgc cgactcctcc atccccgacg aggtggcgga gctgctggtg    240
acgcgttgca tatgggaggc ggtggcgctg acgtgggtgg tgctgtgggc gctgagcacg    300
cgggcgggca cgctgctgct gtgcggccgg gacagcgtcg ccgccgtcga cggcggcggg    360
ttcccgttcg tgtccgtgcg ccgcttcgcc gacatgccgg cggcgaggcg ggaggcggcg    420
ctgtggcggt ggagcggcgc gcggtggctc ttcttcccgc tccgcatcgc cttcgccatc    480
gccaagatcc tctgccacta cgtcttctac tccatgatac tcgtatcagc ctaa          534
```

<210> SEQ ID NO 131
<211> LENGTH: 4029
<212> TYPE: DNA
<213> ORGANISM: Oryza sativa

<400> SEQUENCE: 131

```
attgctgcta ctctctctcc ccttctcttc tccggttctc cctctcctcc tcccacctca     60
gccgccgctt accggcggcg ccgcctgcta atctgccggc gtgagcaccg gcggagatgt    120
gttactgcta cccaacctat aacgcagctc tcccgcgcag tgcctctgtc tctagctagg    180
gttttcctct tgggggagac gacctactat ggtaaggtgg ggagctgaag ccggcgacct    240
ggtgctgtcc ggaggaagct ggagctcgtc gccgtcggat ggacgccgat gaggccgcgg    300
ggagtagcag gaggatggat ctgaacctct accttggcct cccacgcgcc ccgcgcccgc    360
gccgctccga cctcggctcc gacctcgccc tcagcacccc gatgccctcc tccccgtcct    420
cctccgcagc ctccgtcgac gcgccgccgc caccgcccga gctgtcgcat cccccgtact    480
ccccctctca cgccgacctt tcccctccgc tgcaggaggt ctactccctg tacaaccccg    540
acgacccgcc tgcttccgag acgcacctgc cgccgtatgc gccgcctccg gctccggtgg    600
tctcggagct ccctgacgac ctcgagtttg gcctccaccc cccgccgccg ctggtgcgtg    660
ccagcgaact gctaggttgg gaggaccggc cgtcttcgtc gacggcatcg tcctctttcc    720
tccctgacac cgcagcccgt tactggcggc ttctcgagca gactggaagc agatggctcc    780
gtgcgaggcg gtttaggtcg gaccttccgc cactcagttc tgaagcttac ccagctgggc    840
gtgatgctgc cgcagtccca gtgctgcagc atgaaccgat gaatgatact gttgaacata    900
ataaggtagc tgccgatggc gcggaagtag gcgcctccga ggaatcggag gagcagggca    960
ggagcgctgc cacatttgag tgtaatatat gcttcgatat ggccagcgag ccggtggtca   1020
cctcttgtgg ccatctcttc tgctggcctt gcttgtacca atggctcaat gtttattcca   1080
atcacaagga atgcccagtc tgcaaaggcg aggtgactga ggcgaatatt actccgatct   1140
atgggagagg gaattcatgt ttggatgccg agaaggctgt ggaaggtggg aaacaaacag   1200
gtcctactat cccaccaaga ccacatggaa atcggctcga aagcttcagg cagcagtttc   1260
accatttgcg accgatctca agaaggcttg gtgaggctca tgggttattg tcatcatgga   1320
ggcgccttct ggaccaacag attatgaata ctgcgagtag gtttgaaggt ccgcctgaat   1380
cagctgtgca ggaaatggtt gacactgctc acgctcagca caccagtcgc ctaagtagat   1440
```

```
tggcgtcaag gatgagagca agacggttgc tgagagaagc agacaaccct aaccctcccg   1500
atggcggatc cacttcccct gacagtggtt tgatcagaaa caatgcatcg gatccatcca   1560
gaaatggtcc gagctcatta ttaccagatg gaattgactg gttgcgtgga cttacccttc   1620
ttgggtatga agacacggaa agatttgcat ctgccatgag tgattttaga aggataactg   1680
gaccaagcca atatggtgca tcggcttcat catcgaatcc tccaaatctc gagtcaacat   1740
ttgacagaac tcatgttgtt gcagcacctt ctgcagacca agcatctaac tcaagcactg   1800
ctgcagtgat acagggggat gctggtatct ctgagagtgc aggagaacca agtaacgcgg   1860
ggtcatcaag atccctgagg aggagaggga ggagcagtgc cctgggttct ttggatgctg   1920
atggcggggg cctccaacgg aacaagaggc gaaggataaa ctgaacattc tgtgttgtgg   1980
tgttgatcta aactctgcat gccatgctcg ctgattttca actattgcat ttcatttctt   2040
cgggtgatgt ctcctgtgtt gtagtgtaac atttttttctt ctcttttcat tttcccccgt   2100
aggttgcact gaaatgttta tctgtttagt tctcatgtag cctgtacctg tttaatttat   2160
ggaaagttat tgatcaagac atttttgcat tcgaaaggta atgaatggtt caactgcatt   2220
tccatgacaa taaattggat gctgaaatgt gcatccaaca caatggtatt cttgtgcatc   2280
aaataatagg cataaacatt gtgtttttat ttgtgtcaat aagctccttc agacatatag   2340
aaaactaaca ggtcaataat gtagtatatt gaagttggaa ggaataccca gagaatggat   2400
ccatggacac aattgtcttt tgttgcttgg gagaaggtac atagcctgat ctttagtcct   2460
tgtttatcct ccaatgaaaa tactcacgca ttgattgttt caatagacaa ggtaaacttt   2520
gccatcgccg tgaattttat gatccatgga agctgtttca ttgagcagtg gtgggtgtaa   2580
ctgtgataac ctttatatta cttgcttgct tttaaggaat agcacacttt ttgtggggat   2640
gggattactc cccttttttgg aactacatat tgaggaacgg atttaacata gaaagagctt   2700
aatacattta agtactgatt gtgtgcatag aaaggggttt attatttgga acaaaattgc   2760
ttagctcgta gtaataagga agttcatagt attgaacttt atatgacatg tgagttatat   2820
atatcatgtt tgtctttggt cacttctatt ttatgaccat gtaacattta tttcatgtgg   2880
aacttggcag aagagaattt gaagagattt cttctgattg atttccattt cggacaaaat   2940
acaaagctcc cagaccagct gtcacaaaga ggtctggttg attttccaga tttgtatgcc   3000
tgtctctagc cgagagtaac aggtattttt ctgcatctat gactggcatg gatagtagat   3060
tggcatatgg aaacaaactc ggaagggttt gggtggtgct taggtgctct tggcagggaa   3120
gggagacaac tctgtgtttt tgggttttca gtacatctat cctacatatc ttccaaaagc   3180
tcacacataa gccagttaat tgtttttttt tttggcttgc agaattacct caataacttc   3240
catgtaaata ttttactctt ttgcagtatt acatgaacag attcaatgct atttttctgc   3300
agaactgccc caagatgtaa aatgaaaatg cattgagtct gttcaattag aaaacacaag   3360
atcactgtgt atactgttca aagaatgtgc taaacatatt atagaaccaa acacagttca   3420
tctcaacatt gttgcttttt gtcttagttg tcacaactat ttaaacggat gaaacagtgg   3480
aatctctaag caaagctgtg aagagcttca gggctacctc ctggcgcgaa atgaaggtgc   3540
tattgcaagc tgctgcagct ctactgggtg aacaattact cacatgtcac cagaactcta   3600
gcaatgaagc agcatattgg aacctgaaaa gatttggatc tcaccaatgt ggacaacgag   3660
gctcatgagt tatgactgct atgatgatga tgatgaagat ctgcttcagc aagctcatgt   3720
tatggatgta ctactttagt atgctttgct ttgttgattg ggagctgcat cagatcctgt   3780
ttgactgctc aatcaattgc accatcttac tctcacctac tgttggatga gggtggggct   3840
```

ttgctgtatg ctcaatgttc ttgaactctt gcatatgaca gtaatgatgt tccgtcctta 3900
agaaattgta cttatgtagt gcagcagttg atcatccagg atttaaccca agttctaggt 3960
gatacaatat aggttgtaca tgacctaata aatttctaaa tagaaggtaa atccatgttg 4020
attttcagg 4029

<210> SEQ ID NO 132
<211> LENGTH: 5036
<212> TYPE: DNA
<213> ORGANISM: Oryza sativa

<400> SEQUENCE: 132
tcgcatatcc cgttaccttt gccgccgcgg cgccgccgcc ctcttccgct cgccgccggc 60
cgagggcgcc cgtcgcgcgc cgtggagcga gcctagccgc acgagctgaa agcacctaaa 120
aggtcagcgc gtcccctccc cctttcctct cctttcgccg ctcccgcagc agccacagga 180
cacctgagac gggtctgggg gtgcaggtcg cgcctggagg aatccctagg ggctagggga 240
ggtggctgga gatggctggt gggagctgcg acgtgtgcaa ggaggcgccg tccaagtaca 300
agtgctccgc ttgccgcacg ccatagtaag tccagccacc ggatatctcc acccttctgt 360
gcttacagct tccatgggta gcgtcgtcgc ataccactgt ccttaaaatt tgggaaatcg 420
cttcgatcat ggtgctcagt aatggcctac tagctagcat aacaattgaa ttgaagaaca 480
cttgttacgg ttttagtgca atgtcctact tgctgtgttc acatcgatta cttcactgct 540
tactgcttga aaagagagta cgggtttgct aggtcaatag agtagattga tgattaatgg 600
ttggaagcat tagcttcttt ttagaatatg agcctacatc agaattagct tgatatattt 660
tgggtttgac tcggtagctt gctgctggag tggttttgca tgagtaaaaa aaaaaaaagg 720
cagcagcaaa acaagacatg taaacctttc tcctgatatc tggtgtcagt gttggttttg 780
gtactaagct gtattgaatt agtattcaga ggcaaacgtc catcattcaa taatctgtaa 840
tactttgctt attttttctt gaatacgcaa gagaattaca tatcatactt tatgacttct 900
cttgcacaat tgtttcaagg atgtaacctt aggattgcca aatatgatta tctaaacaaa 960
ctgtttttca agattccctg aaactaaatg gactactgaa ctaacatacc tgttcagcga 1020
tgcaatcacg gttggacatc ttctatgtgt cctgtagatt tgtttggtaa aattgctctt 1080
ttgccctaaa gttgaatggc attggctcat ttgccacagt ccggtgtatg acaactgggg 1140
ccagggctac atgttataca cacatatgtg gcaaaagagc acatgtcata ttgtagacca 1200
attaagagca tggtccgttc aatttctctg gcttcttttt ctctattgtg taatgcagtt 1260
gggccttaca aacggtttca ttatcccttg cagttgctcg gtggcatgct ttaaaaatca 1320
caaaggtact cagtgctatc ctttggtagt ttctaaatat agctctagtg ctgcgatctg 1380
aaagtagctc aagtagcgcg agggggctgt agcaaactgc cgtgttccct ctgttgcttc 1440
ttagttgtgt attttaaatc aacaagcttc cctgtactgc cttttctctc tttggccagc 1500
gttctttgcc agccgcattt ttaaacatag ctcaataaac caaacgtctt aaaaaaatat 1560
agcaagtgat aaactgctta tcacactcca agtgtccaag tctgcggggg accttttgtt 1620
ttgaaatttt ggcaatttta ctattgtact tggtttgaga ttagggaaag gctgaacagt 1680
actaaacaca gcacaaatta taactatcat ttatgcattg cctttatgca aacaaaaatg 1740
gccaccaaat atcttcatct cccttttttta gaggaatata tttattatct tgatagccag 1800
tatttgtgct aaatatcgtt ttgccaacag ataaattttg ccagaagaca atacctctgg 1860
aagaagttag caagtcatct cttcaggagg aaatttgtaa gtgctctagc ttttggtgac 1920

-continued

```
tcaatacagt tgtttgcaac agctatatag tcctgctata tatggaaatt gagttgaaac   1980
catgatcatt aaaatagagg ggtcctacat aaaattacat caatatactg taaatgagca   2040
tttgactgtg tacacctaaa agtcctgcag ggcatgtact tgcccatata taagggcctg   2100
aattatctta tcatatagtc attcattaaa ttgtcaattg ttctgtccta ctaacatgtt   2160
tctaaaataa tctactggaa tttacagttg tgccttctat tgttttcagc aaggaactct   2220
aggtcactgg aagaagcaac aaattgtcct aatgacaagg atcaaacccc gtctttatgt   2280
aaaaatgcac catacttatc tctgttgtta actctccatt tcttctattt ggttttcact   2340
aataattgat tgaactcaaa actttataga tcatgactac cttcagttgt aaacaatgta   2400
accatatgct atcctcgcaa aaaaagaaga agaagtaacc atatgctatg ctttttaatc   2460
aataatttaa attagtttct ctagaattta ttataagggc tataatatta ttcattgtga   2520
atcttgaagg ccaagaaaat ttatgttaag ctcaattttt tgtctgtagt atcggacacg   2580
acttgtccca cacaatatcc aaacacattg cactctgcaa aatctcttga agttgaggat   2640
ccaagctggc ttgttgacaa gaatggatta agatctttag gtattgccta tgtttgacta   2700
tttcatacca tgatttgtgt tttttaaaaa ggaatccttt gcttttactt gatttctggc   2760
tttatttgtt agctgaaaca aatgtctcca tgttagtata gtccagcatt tcaacccaag   2820
aatatcgact tcaatttcat aattatctga acctaatccc aatcctacag acctacagta   2880
taggagtaaa atattggcat gcacatttag taatggggaa tttaactatt tgccactttt   2940
ataaatggct actctccgtt tgccattctt acatttctct acggatttgc caccagagag   3000
aaggtttctt aatcatttgc cactttcacc tattaagcat gctagtgagg acagccaatg   3060
tggacaagag acacaaaaag tccattttac ccatggccct tcccttgtgt tccccccctct   3120
ctccctttcc ttttcagatt tgagctcacc tccgccgctg tttctcgtcc atcttctgca   3180
ctgctgtgta gtgacaagcc attaggtagc agtaacactt aggtgcgtgc atggatgttc   3240
tttggctgct attgattgcg gatgtacctt ctccttgtgg ctgtcgatga caaccttcaa   3300
ccttgcggat gtaccttctc cttgtacctc aacgtgctcc tcacttgccg gccttgccat   3360
caatgaaccg catgacgacc tgcaccgggg tgctccgcca tcctcccagt gagtttgagg   3420
gcctcgcggt tatctggcct gccgaagaag atgatgcaga tgcagtgcac aaccttcttg   3480
ccgctgacac atgattgacg aggcttgatg agacagcgtg gctggtgtgg ccgcggatgg   3540
tctcaatgag gaggtgaccc cgcaagcagg aagccagaag catacgtgca ccgctgtgga   3600
tgatctcaat gagatgaagg ggagtggcag gggcaaaaag gacattcacg tcctcagtcc   3660
atgctggtat gccacatcgg tgaaaggggc aaattgttaa gaaaatttct ctccggtggc   3720
aaaaatgtaa ggacaatcgt aagtggcatt tggagagtgg ttattcgtaa gagttgacaa   3780
atagttagta aggatagtac tgtaagcaga atatgggctt catgctagtc aattttgtat   3840
attggttcca catccctccc tgtacaaatt tcataacctg ctagcatttc taccttattt   3900
aattaatcat agtaatactc atcgtcttgt ctcgcaaaaa gaaataaaca tcatcaatta   3960
actcattgct tgatttttgt atccatgcca gcggaatcta atgagatccg agatgctctg   4020
aaagattgta agcttcagca aatgctactt aagattgatg gctctgcaga gccagaaaag   4080
gtaattctct actcttgtga taactgcaag tttatttaac aagttaacta tgtttgcaat   4140
ttctgtccgg ctgctcaaat aacatgcaca taatatgcca atacctattg aggacaatgg   4200
tttgcagtaa tgaacattgt cactgttata gtacaacact tctgtttctt attccaccat   4260
catgacttca ttttcctacc agtagttgag aagcttcaaa tgggcacgtt cgatgaatta   4320
```

```
attcctttta ctatagtctg ctgaatactg atacgaatat aacttttctc acttacattt   4380

atttttttcc tctctctacc acctttattt tatgatgccc actccctcat taattcatcc   4440

tcaggaatta gagaaattga tggaaggaca agtttttcaa cagttcacca ataaggtttc   4500

tctttccgtt gcatttgctc ttctatccac aagatattcc ttgttaactc taagttaatt   4560

aaccagacac ttgcacgttt ttgtttcctc tgtgtttgca gattcttgac attgttagcc   4620

cacaacaatg aacaccaact ttctggtgga gctattcagc agaagagtgc acgcatcggg   4680

gcaaatgaca acatgtagag caacttacct cagatgctgt tttcctacca tgatgagatt   4740

gcctataccc gtgacatttc cttctactac tttgagaaag ttttgtcgtc caatatggtg   4800

ctagtatttt accatggcat ctctggctca atcaacaact gttcaatttg tctacatccg   4860

tgacatcttc tttggctaat ggctactgtg agagttttgt tgtccattat gttttttttg   4920

tggtatactc cctccagttt taggttttgt tgttcagttt tgtggtttac caaagtcaaa   4980

ctactttaag tttgactaac gttatagaca aatacaataa tattcacatt accaaa       5036
```

<210> SEQ ID NO 133
<211> LENGTH: 2503
<212> TYPE: DNA
<213> ORGANISM: Oryza sativa

<400> SEQUENCE: 133

```
atgcccaggc acgcatgtct gctgcaggta gccaaaactg aaacttagaa atccgtgtac     60

gcgtcgctta agtgcttcgg cttaaggatg ggcattcggt caggctgaaa aattcggtct    120

cggtttttag tttttggtt agttcggttt ttgaaaactc aggaccgaat ttcatcacaa    180

aaatctcata actgataaat tcggtctcgg tttcggtctc agtctgaccg aatttttttc    240

atagccactg aagagtgcag acggaggcga cgccaaggag gtgccgacgc cggcgctgga    300

ggcagaggcg gagggcgccg gtgctgggcg gaggcggcgg aggcggcgca catggcggcg    360

gcggcggcgc atagggcggc ggcggtgcac agggcggcct gcggtagctc caccgtcgcc    420

gtcgggctgc gggagctcca ccggcgtcgt ctctgcagca cctgcacggg ggatggggat    480

ggggataggg tatggatgga gagatgcttg tggtggtggg tggataaggt tttctttttg    540

ctgtggtctg tggaggtatt gggcctaatg ggccaatgca atatttcggt tttttgtcaa    600

ttcggttaac cgagccaaaa aaccgaattg accgaactaa atttggttag ctgaaactgc    660

tgaccgaatt tgtgaccgaa tttttcagtc tcggttagtt cggtttcggt ctcggttatt    720

ttggttcggt ttttcggttc ggcctttttt cccaccccta ctgcggagaa tgcagcgcga    780

tgggcctcca atctttgtcc tgcctagctc gcggcggatg tgtagttgca tgatccgagc    840

agatttgtcg tggcggcgtg cggtcaatat cgggatcagc gcagtggccg acggcgcgga    900

caccggcaga acgtagcggc cagcgggttc gcggttgatc aaacggctgg gggtgcccgg    960

tccacgtctc tttgacggta tacgtacata ttcataatat catatatttc atttgatatt   1020

tttccctctg tttcatatta taattctatt tgactctttt tttaaagtca tttttttcta   1080

aatttgatta agtttatgta aaaatttagt aacatttaca acacgaaatt aatttcattt   1140

aaactaacat ttaatatatt tgataatatt tatgttttat gtcaaaaata ttgtcaaatt   1200

tttctataaa tttaatcgtt cttaaaaaaa attaattaga aaaaaaatca aaacaactta   1260

aaacgaagtt tgaaactgag gaagtacatt atcatatttt aagacggtaa tagttactac   1320

gaaagagcag cccgattaac ggaaaagcaa tagagaagaa cgtacgaacg tcgcgtgcgc   1380

gaaaggagga cagaaagaaa gatcgatcga tcgatggatc ggccaacgcg agcgaaacgt   1440
```

cgtacacatg tacacacaga tcacgagttc acggctcatg ggtgtcggcc cttcttttgt 1500
cgaaaagaaa aattgttgcg tgactgaatg gagatttcag atttctgcgt gctcggttag 1560
ttgattacaa gtactagtta ctagtatacg caacagagac gtacgtcgtc tgctgcgatc 1620
tcaatatctc atgctcacgt ttggtggtgg ttgctgttcg atcgtccagg tattaattgt 1680
cgagccatgc atccacgtgc acagggtatc atgtttaatt cgtgacttac atgtccttta 1740
tggttgatgt ctcattggat tgatcatttt cctgggagat aattaattac ttactcctac 1800
tccctcggtc ccagaaagag acgatttctg gaggggagga tttgtccaaa aaaaagcaat 1860
tcctctacag aaatcaagaa aacttcaagt atatcgtatc attatgggcc caagtggata 1920
gcgaattctt tttctctcgt tcacattcac cccacaagaa tcttatcgcc tgcccgtctc 1980
tcgcagtctc gcatttctct ctttttctct cacgtttctc tcccgttccc aaatcgattg 2040
catcgatgtg gcggcggcgg aggcgacggg gagacgcggc ttcgtcggcg gcggcggaga 2100
cgcggaggcc acgaggagac gtggcgtcgt cggaggcgga ggcaacaaat ggatgctgct 2160
tcgtcggcgg cgggggcttg tatgcctaac tgcttatcat ccccggaaga agatctgatg 2220
cggttgcctg atgcacgagc tgcgttgttc ttgtgttcat tgtgttcatg cactgcattt 2280
ctttttcttt gggttcttgc catgttcatg cgtgcgtcag atgcttatgc agagaaatga 2340
cagtagcaat agcaaatgga tgttgtcacg gagggcattt tcgccttttc acgtgagtgc 2400
taaatttgca tgggaggtac aggaatcgct tctggatgga gggagtacct ggttctgttt 2460
aggatctagt gcgtactttg tcgcagtcaa atacgattgg tga 2503

<210> SEQ ID NO 134
<211> LENGTH: 567
<212> TYPE: DNA
<213> ORGANISM: Oryza sativa

<400> SEQUENCE: 134
atggggacgt acaagtgctg catcttcttc acccgcaggt tcgcgctgag cgacgcgtcc 60
acgccgggcg acgtgcgcat gctgttcacc cgccacgccg gcggcgcgcc ctacatgggc 120
atcgacgagc tccggcgcta cctcgccgcc agcggggagg cccacgtcga cgccgacacg 180
gcggagcgga tcatcgaccg ggtcctgcag gagcgcagcc gcaccccgcg cttcgggaag 240
ccgtcgctca ccatcgacga tttccagtac ttcctcttct ccgaggacct caacccgccc 300
atctgccatt ccaaggaagt aagcaaacta cccgctcgat ccccaatttc ccaaatgctg 360
ttagattcat cgtcattccg tgataatcct gccgttgcac aatgcggtga aatggcgtaa 420
tttgctagga ttcagaaggg gattcttggg gtttgtttag ttcacattaa aattaaaagt 480
ttggttaaaa ttggaatgat gtgacgaaaa gttagaagtt tgtgtgtgca ggaaagtttt 540
gatgcgatgg aaaagttgga agtttga 567

<210> SEQ ID NO 135
<211> LENGTH: 2684
<212> TYPE: DNA
<213> ORGANISM: Oryza sativa

<400> SEQUENCE: 135
atgcaggtaa tgaattgaat ttccatacaa cattctgctc tcctaagaaa ttacgcttac 60
aagttcactt ggatattgct aaactccatt ttgatattac ttagtgtgta ctgaatgatc 120
taagatgtga gttgatggta gatctcgtgc tctcaggtcc atcacgacat gaatgcacca 180
ttatcgcact acttcatata cactggacac aactcgtatc tgacgggcaa tcaacttagc 240

-continued

```
agtgactgca gtgatattcc catcattaag gcactgcaaa taggcgtccg tgtaattgaa    300
ctggacatgt ggccaaattc ttctaaagat gatgttgata ttctccatgg aaggtatgca    360
tgagaattgc tcacttgaag acatttttgt tctgcactgg aggccattcg atatgctatg    420
accttattcc aaactatttg cttctttggt aggacactga ctgccccagt atcacttatc    480
aaatgcttga aatccatcaa agaatatgcc tttgttgcgt ctccctaccc tgttattata    540
acattagaag accaccttac atctgatctt caggcgaaag tagctaaggt aattgcattt    600
tcctcgtatg atcaataatt tggtgcagtt gattctgttg tagctagtta tgaaattttc    660
tttagatggt tcttgaagta tttggagata ccctatatta tcccgagtca aaacatcttc    720
aagaatttcc ttcacccgaa gcactgaggg gacgtgtcat cctctcaaca aaacccccaa    780
aggagtacct tgaatcaaaa ggtggtacta tgaaagacag agacattgag cctcagttta    840
gcaaaggaca aaatgaagaa gctgtctggg gaacagaagt cccagatatt caggatgaga    900
tgcaaaccgc cgacaaggtt ctactggttt taacatttgt tgtttcttgt ttcttagcat    960
atggtgtatg tccatcactg ttgtattggc tttattccct agcagcatga gaatgatata   1020
ctatacaccc aaagagatgt ggaagaagat gatgagaaga aaatgtgcca gcatcaccca   1080
ctagagtata aacaccttat tactattaag gcaggaaagc caaagggtgc tgtagttgat   1140
gccttaaagg gtgatccaga taaagttaga cgcctcagtt tgagtgagca ggaacttgca   1200
aaagtggcag cgcatcatgg tcgtaacatc gtgaggttcg tttagcaaat atactgaatt   1260
tcgtagcaaa gtattttcta tcattgcacc agagctctct atgtccattg accttaactt   1320
cattctgttt attcaaagca gctttacaca taaaaatctt ctgagaatat acccaaaggg   1380
cactcgcttc aattcttcga actataatcc gtttcttggt tgggtgcatg gtgcacaaat   1440
ggtggcattt aatatgcagg tacatttcta acatgacact cctctgctac atcatattgg   1500
cctgaatgcc tgatacattt ttcttcgcag ggtatggaa gatctctttg gctaatgcac    1560
ggattctaca aggccaacgg tggctgcggt tatgtgaaga agccagattt catgatgcaa   1620
acttgtccag atggaaatgt ttttgacccg aaagcagatt tacctgtgaa gaaaacactc   1680
aaggtaggtt tgtggcatat gtttcttcct ttcattttca tctctgaaat tcaggaatcg   1740
agctacttac agcttgcctg tttgtctacc aggtcaaagt atacatgggc gaaggttggc   1800
agagcgactt caagcagaca tacttcgaca cgtattcccc tccagacttc tacgcaaagg   1860
tacatcgaat tttacgctga tgccaaacgc caacaaattt gcaaatgcaa aacggagctt   1920
tgaaaaaaca tgtatatatg tataactttt acatatggag tgagatgaag acaaacttta   1980
tatcaaaatt gtagagctcc atgagttcta cgacgttctt attgactagt ccatcgttcc   2040
atcatcataa caggtgggca ttgccggggt tccgtcggac tcggtgatgc agaagacgaa   2100
agccgtggag gacagctggg ttcccgtgtg ggaggaggag ttcgtgttcc cgctgaccgt   2160
cccggagatc gcgctgctcc gcgtggaggt gcacgagtac gacgtgagcg aggacgactt   2220
cggcgggcag acggcgctcc cggtgtcgga gctgcggccg gggatccgca ccgtgccgct   2280
cttcgaccac aaggggctca agttcaagag cgtcaagctc ctcatgcggt tcgagttcgt   2340
ctagcaaatt cagtaggcat atcactcgct catgtgtgtt gtatacttag catgatgatc   2400
tatttctcta gtagcaagat tagattttta cttatgtgtg ttgtatacgt agtatgatga   2460
tattttctag caagatcaga attttggact acctgttttt ctaggaaaaa acagattatt   2520
tggacatcgg tgaccagaat tttggactag caagatagat ttggactgct ttgatctgca   2580
gatcggtgga catttttcta gcaagattag aatattagat tatggtttga ttagatttaa   2640
```

gaacttgttt tggtctctat gtagatcgga gaatcagttc catc 2684

<210> SEQ ID NO 136
<211> LENGTH: 1012
<212> TYPE: DNA
<213> ORGANISM: Oryza sativa

<400> SEQUENCE: 136
atggcgatgg gagccgcggc ggcgccatgg tacggcgcca tcggcggcgg tggctcgcgg 60
cgcgcgcggg tgagggcgca ggcggcggcg ccgtgggcag gaggcgcgga ggagctggtg 120
cggtcgggcg cggtgcgggc ggtgcgggcg agggaggcgg cgggggcgat gtccgcggag 180
gggttccggc tgctggacgt ccggccggag tgggagcgcg cgcgcgccgc cgtgcggggc 240
tcggcgcacg cgccgctgtt cgtcggggac gacgacacgg gccccgtcac gctgctcaag 300
aagtgggtcc acttcggcta catcggcctc tggaccggcc agtccttcac caagatgaac 360
gaccgcttcc tcgacgacgt cgccgccgcc gccggcgaag gcaaggacgc caagctgctc 420
gtcgcctgcg gcgaaggcct ccggtaatta atctaatcac actgaagcta ctgagaattt 480
ttatctgttt agtgtgtaat acaacgtggc aattaagctt ctggatcggt tgcatgcatc 540
cgaactaggg ctgctttccg aactactaaa cggtgtgttt tttgtaaaaa aattctatag 600
gaaagttgtt ttaaaaaatc atattaatcc atttttaaag tttaaaataa ttaatactca 660
attaatcatg tactaatggc tcacctcgtt ttacgtatct tcccaatctc ctctatctcc 720
tcctcctcaa acacaggtcg ttgatcgcgg tgaggatgct gtacgacgac gggtacaaga 780
acctggcgtg gctcgccgga gggttcagca agtgcgtcga cggcgacttc gccgacgtgg 840
agggggagag caagctgcag tatgccaccg tgggtggggt gtcctacatc ttcctccaga 900
tcctgcttct gctgcgggta gtcaagtgat gatcatgtaa catcaggaca tgcatccgag 960
tatccgacca atgttgcagt ggaatatgct gccaagtccc aaatattctc cc 1012

<210> SEQ ID NO 137
<211> LENGTH: 1186
<212> TYPE: DNA
<213> ORGANISM: Oryza sativa

<400> SEQUENCE: 137
atctccaaga agcagtctcc acgccgatcc gagatggccg cagcagcgca gaggcggcgg 60
agcagcagcg cctccccgga gttccgcttc tggcccctcg acgccgaccc cgccgcatcc 120
ccctcctgcg ccgacgagct cttctccggc ggcgtcctcc tccccctcca acccctcccc 180 taccccccgcc gcgacgccga cctctccatg tccctcgccg tcgcggatga tgatgatgat 240
gaggacgagg aggaggagga ggtgcagcct ggtgcggccg tcgcgtccag ggcgccgccc 300
actgctgcgg tggcggcgtc gggtggtggt ggtggtgggt cgaagaggtg gacggatata 360
ttcgccaaga agcagcagca gccggcggcg gaggagaagg agaaggatca gccgacgagg 420
cggcggagac cggcgggagg cggaggcgga tcggagctga acattaacat ctggccgttc 480
tcccggagcc gctccgccgg cgggggcggc gtggggtcgt cgaagccccg cccgccgccg 540
cggaaggcca gtagcgcccc gtgctcccgc agcaactccc gcggcgaggc ggcggcggtg 600
gcgtcgtccc ttcctcctcc tcctcgccgc tgggccgcca gccccggccg cgcaggcggc 660
ggcgtgccgg tgggccggtc tagcccggtc tggcagatca ggcgcccgcc atcgccggcg 720
gcgaagcacg ccgccgcgga caggaggccg ccgcaccaca aggacaagcc aaccggcggc 780
gccaagaaac cccacaccac ctccgccacc ggcggcggcg ggatacgcgg catcaacctg 840
agcatcaact cctgcatcgg gtaccgccac caggtgagct gccgccgcgc cgacgccgga 900
gtcgcccgcg cctccgccgg cggcggcggc ggcggcgggc tcttcggcat caaggggttc 960
ttctccaaga aggtgcattg agccatggaa gcctttcttt caccttagct agagatccaa 1020
ataactttta attttctcct ctcttttta ccctcctttt tttactttc ttttttttt 1080 taccttttgt aactttttg tttaaccttt ggggtgcttg tgatcatgat gatgatgatg 1140
atggctgtta attacatgta attaagccaa taacctgttt ttgtaa 1186

<210> SEQ ID NO 138
<211> LENGTH: 3363
<212> TYPE: DNA
<213> ORGANISM: Oryza sativa

<400> SEQUENCE: 138
aaaaacgaaa aaaaaaaatc aaaatccttc cccctttcaa attcgaaatt tcgaatcaaa 60
cacgcgcacg ctcctctctc ctctcccctc tcgatcgagg cacgcttctc cgcggcggcg 120
gcgcgcgacc ggatcacggc ggcgggggag gggaggggag gggaggatgc agcagaagcc 180
cgcggcggag gccatggagg aggagttgaa gggggaggcc gtggggcccc gccgccccgg 240
gctagggtta tggttggcgg cgcggcggcg gctggccccc gacgacccct tcttcgccgc 300
cggggacatg gagcgcgagc tcctcgccaa gcaagtgcgt tctcttcccc tttcacctcc 360
cttccttctg ctcgcttaat ttgggcgctt tagcttcttc gattttacgg ggattttttt 420
tgttagctgt attgagctgg aacccgtgga aaagatgaaa tagagatagt aaaatcagcc 480
atgataacct ttgattttgc agaaattcag ctgtactgta cataagagga aaagcttttg 540
cccttctttg aaaaaaaaaa gagagaagaa attcagctgc acttagcatc agttaggtgg 600
gaattcctta atgctctgca atacttgttt ctttgatttc ttgaacggat catggccgat 660
tagctcagat accctgccct gatgtgaaaa gtgtagatga actgtgcttt tactcaacaa 720
gtcccctata ctccactgtt tttttaggtg tctgatgttt tcttgtttag gttgctctgg 780
atctctccga agatgaacgg taccagcttg agaggatgga agtggcgagt gccaagtaag 840
agattgatct ttacttatgc ttactctttg gattgatgat tatttatcct ttccgtttca 900
cgccgaatta gggggggggg ggggttagtc cctgtcacat cagatgtttg gacactaatt 960
tgaagtatta aacgtagact attgacaaaa cccactccat aaccttggac taattcgcga 1020
gacgaatcta ttgagccaaa ttaatccatg attagcctat gtgatgctac agtcaacatg 1080
tgctaattat ggattaatta ggcttaaaaa aaatttcacg tgaattagct ctcatttatg 1140
taattagttt tgtaagtagt ctatgtttaa tactctaagg gccccttga atcgtagaaa 1200 tgaaaaaacg gaggaatagg aaaaacatag gattcgacag gaatataagt gtaaaacaga 1260
ggattgcaaa acacagggaa aacacatgaa tgatcgtttg attggaccag aggaaaaaca 1320
caagaatcgg atgagagaga tagactcaaa ggattttttc caagaggttg gacctcttgc 1380
taagtttcct ccaaaaccta tatgccataa gccattccat aggaattttg taggatttgg 1440
aaaacttcaa tcctttcaat caaagagcta tataggaaaa tttcctacag gatttcaatt 1500
ctatgaaatt ccttcataat ttcatttgat tcaaaggggc ccttaattag tgtctaaaca 1560
tccgatgtgc cagggactac agtttagtcc ctagatccaa acaccccta acataccctc 1620 tctacagatt taaaacagca tgttaatgta ctgtttttct gcatccccat aacaccataa 1680
atttcttcgc tgtagctaag gaagtccctg aaccagtggt ccacacccca cagtgactaa 1740
agtctgagaa aatgacaact ggatgtcttg aactaaatta ttgtacgagt tctctagaac 1800

```
ctataattca aaatgattgg cgagtattcc atcctgacac ctgctaaatc atgtcacctt   1860
ttgcagttgt atgttctctg tgttgtgtta gtactgcaag ttttggtctc attctgttta   1920
tttgatcata tatactactg caagtttatg tcaccttttg cagttgtatg ttctttgtgt   1980
tgtgttagta ctgcaagttt tggtctcatt ctgtttattt gatcatatat actactgcaa   2040
gttttggtct tatctgttcg atttatttga tcatatgtct taagctcttg cagtgccctt   2100
ttatgcccaa tttctggctg tggtgctcat ctagattgcc tggagaactt tgaggaccac   2160
tatcgcaccc gtcatactgc ttcatgctct gtatgttgga gagtgtatcc aacttcaagg   2220
ctgctgagta ttcatatttc tgaggcacat gattcctttt ttcaagcaaa agttgcccgt   2280
ggttttccaa tggtaataaa ttcataatct atccatgccc ccagttcttt aattggttta   2340
attttgtggc atcatgcaca ctagccaatt ttatgcaaac ccagaacttc cagtggactg   2400
tgcctgctgg ccagtttaaa attactactc aatgtcttag cattagttag cattacatgg   2460
ttttctggtc ccgctaatga agctttccaa tttccacatg tcacctttac tggcatctga   2520
ttcttgtata aatttacata gtagtaagtg atacttttat attccctcaa ctttctatag   2580
caattcacat tgtgtatgct atttttgaaa cagtatgagt gtttggtgga gggttgtggg   2640
gtgaagttga agagctacaa aagtcggcag cagcatcttc ttgataagca ccagtttccc   2700
aagtcatttg aattcttcaa aaaagcacgc ccttcgcaac gccagcggaa caagaaccag   2760
aagcaacggc aaacagttca caagggagac gagacaagcg aaacactaat ggatgttgat   2820
gggaagaaga gctcaaggta catgaattcc agatatcggc caaagcaaca tgatggaaaa   2880
gagtcaaaag aaaatgagca tagtagctgt aaggaggcca agaacaacga aatggaggtt   2940
gacaagcagg ttgatgagct tgcttcggcc gtatcaagac tgagcacagc ggattcaact   3000
ccttctagca taagctttgg tcatcgtcgc tctcgcggtc ttgcttttgt ccctaggtcg   3060
attcggcaaa acaagcaggt ttctcagaca gaaccaaaat gacagcattt gataccatct   3120
ttctcttcat tgctgatctc ggatgcatca acaatcctga atgtgctgtt tcctgtacct   3180
ggacattcac cgaatccact aatatacatt cttgtagttg tatcacgaga tatgtcttct   3240
agctggttat ccttgcttat ggatgtactg agcttcctgt tactgccatg tagtagaaca   3300
atttttctga agcggcaaat atgaagtgca aaatacaaga cagttcttgt ggttgatcga   3360
ttt                                                                  3363
```

<210> SEQ ID NO 139
<211> LENGTH: 6316
<212> TYPE: DNA
<213> ORGANISM: Oryza sativa

<400> SEQUENCE: 139

```
gaaagccatc atctactagc agcagcgaaa gccaagaacg ccaaaaaccc tcgctttgct     60
gctgctcctc ccccttctcc ttcggctgct gatcggattc gcggcgtccc aggctaggga    120
tccgggcggt ggcggcgatg ggcggcggcg gcggcgcgga ggaggagctg acggcgcagg    180
agacggcgct ctacgaccgc cagatccgcg tctggggcgt tgacgcccag aagaggtatc    240
cccggctccg cctctctctc tctctctctc tctctctctc tctctctctc tctctctctt    300
cccctaaaag tcccgggttt tctttcgctc ttcgcttatg tggaggaaat tttgttgagt    360
tgatgcttct tctttttctt ctcttttaat cgcaggttgt ttcttgcaga aaaggaagaa    420
aagaaaatca ttcttttggg ggatttcatg gtttatgtta gaacgaatgg ctgttgtttg    480
tttctttaaa agaaaaactt gagcccgaag tgtttgtatt tttgaagtga agacagagat    540
```

```
atccgctgtt ttcgtatctt gtgtctgcta ttgaattttc ctaaatcttt ttttttgagc    600
ttgtttggtg ctttccttga atttctcgta actttcaccc ccaaattatt cttccattcc    660
atcgtatttg ttagcttcgg aaccaaaact tttgatgtct ttcatctgtt tttgactact    720
gaatctgtgc tgcttggaac aggctaagta aagctcatgt gctcgtgtgc ggcatgaatg    780
gtactactac tgaggtaggt attttaagat tttcctctcc aattgttgcg ttttgtttgt    840
agtttacacc gcgtgggcat tcaaagcatt gaaacgaagt tgcattgagt tatggagtaa    900
taggggttag tttcatgggc caaattgccc atgtttacct gttgctttta gttcgttatt    960
ataactcatt agttttctgg gcatttgatt attgctctgt tgttcttgta gactttctag   1020
tgctatggat gcattgcctg cgagataaaa tctcaatgtt cttatttact ttttaggctg   1080
gctttttctc ttttgtagga cccctgttgt accatctgtt aaagttaatt gcttttagtt   1140
ctcaacgttt aggctcaatt ttctgtagat aaattctttc atttatttat gctagcttac   1200
gttgttccaa tatatgtcta tttatccttt tcttttacag tcatatccca tgattatctg   1260
atcaatgcac ttcgctttgt taagaatatg attgctatta tactatttac tacttccttc   1320
gtttcatatt ataagacttt ctggcattgc ctacattcat atatatgtta atgaatctag   1380
acatatatgt gtgcctagat tcattaacat ctatatgaat atgggcaatg ctagaaagtc   1440
ttataacctg aaacggaggt agtagttaaa gtatatgcct tagaaactag atttctgtag   1500
tcatagagta tcataagcag ctgcatcctg actcaattgt atattcatct aggtacttaa   1560
gtacctcagt tcttctggat atattgataa agcttaactc ataatcgaag gcagccttat   1620
acactaaatg ccatttctct cttaccctgt agttctgcaa gaatattgtt ctagcaggag   1680
ttggcagttt atccttgatg gatgatcatt tagtcacaga ggatgatctc aatgcaaatt   1740
tcttaattcc tcatgatgag agcatatatg gtggtagatc acgagctgag gtttgctgtg   1800
agtccctgaa agatttcaat ccaatggtcc gagttgcagt cgaaaagggt gagcctagtc   1860
tggttttctt cattggtttg ggtgtcagaa ttagaagtac ataaagtagg atgccttctt   1920
gcattcttga attgctctcg tcctaatggt taatctttga ataaaatgtt aaagaagaga   1980
ttctatttca atttgtaatc ttacactttt agctgcactt taacaaggaa agttcttgta   2040
agaaatcatt taattttagt aacaggcaca tgttactata gtgtatcatt gtaccaagaa   2100
atcagcatat atgttactga gagaattctg atatatctgt ggccataaca atgactaatt   2160
ctttggatct tcacagcata ttctaaaaac aaatttctta ctgtttctgc tatttccttt   2220
aggtgatcca tcattaattg atggagaatt ccttgacaag tttgacataa ttgtagttag   2280
ctgtgcgcct attaaaacaa aggtgtgtat tcttctcccg tttagttctt catcctattg   2340
caagttccaa gtcactcagt gtcttttaaa ctaaaattct gcaacaaatt tctctttatt   2400
gcgctcagtt ctcacaacat ttctgcatgt gttgtactgc tttagttgtt aattaacgac   2460
aactgccgga agagaagcaa gcatattgca ttctacgcca ttgagtgcaa ggattcctgt   2520
ggtgaaatat ttgttgattt gcagaaccat agctatgttc aggtatgggc atatatgaca   2580
tgctatatgt tctgttgatt tttcagttta atttttttcc agcagtccac atatatatct   2640
gtaagcacta agcatcgcgc agatgtctta aattggttta ttttctccat aatgtttctc   2700
atatactgct tccaatattc cttcctgtgt acatgcatgt ggtttgtgta cttgttagta   2760
cttttcttca tgtactctag aggcactcat tttttttcta tgatatgttt gaactcaaaa   2820
ttgatgtcat tatgtcagac tgttcatgtt aacatattaa atctgatgta cttagcctga   2880
tgaaggtgcc attaaggatg agaattgcaa aggagcacgt acttttttt ggtaataaaa   2940
```

```
tgtagtgtac taatctgctc tcactgactg gttttcaacc aagttattgt atctgttcct   3000
tttctgcatc attgaaatgg tgatacaaag aaaggttact tagttttggt gcttaaaata   3060
tggtaatgtg acactttcta gcatattaag ttttgtaatt tgtaccaagg attcatcttg   3120
caatgctagt tttggttcaa tcgctatgaa tatataagca cttatgcttt ggaaatcatg   3180
atcactagaa tgtttcagga attattttct ttgttcagta gtttgggccc tggatacttt   3240
tttgaagggg tatgtgtttt ttttttttctc agaaggttgg aggtgaaccc aaaccaaagg   3300
agttggcata tccaagtctc caggtaaatg acttgttaag ctgatctttt ttttatatgt   3360
ttgagaggaa gctgatccaa cttgagataa catctttcat ttaatattac atgttttgta   3420
ttgcccctgt agtttgttct ctcttggctg ccataaatgt agctgtggaa tatttatgat   3480
gcaccttata caagctacat ggtatatata catgaaaacc atttaacctg aaaaaataaa   3540
caatttgaat agtgtcttca tgttttaata atagtaaact tatgttttcc tctgaaaaaa   3600
atgattttct gtaagacaaa aaaataaata gacaaaatgc ttactctgct gttttttttgt   3660
tttgactatc agaatgccag agtgcttatt tattcgaata aatgtgtatc atatattata   3720
tttttacaat actaagaaca gtcatcttca atctaaaaca aagtaaaacc atatcagccg   3780
gcaatctaca tgtatacatg tgccaatttg cagttaatca aatcctaaaa aggacatact   3840
tatttacata gatattgacg gagatcagtg tagcatacca acaccatctc cttactcctt   3900
ttaaggagta ggtaaactaa gtatgattga caatctggat aagacttgaa tacgtagata   3960
catctacaga agattgatgt agagcacagc aacactatta ccaaatcctc ttttcacggc   4020
atagaaaaat acacttattt atgctcatgt agcccagcct tactattgga ggtcttcatt   4080
tcatgtggta attaaattgg ttccacagaa atccccttttc tgggttatag gtgtttttgg   4140
aataattttg taagagttca aatctacact agacaatgtg ctgatgcttt ctggtttgtt   4200
cattttgcat acatccctag aagaatggag tagcgtagca tgttgacctt gactttttag   4260
ctttctttat gtgtatcatc acttaaatat gtgttcaatt tgttgccata tgccaccata   4320
tatcaccatt ttggatgctt cagtttggaa tgttacagtt tgtttatcat tggaaatgat   4380
cttttataca ggaagctatc tccgtaccct ggaagaattt accaagaaaa acaactaaac   4440
tgtactttgc catgagaggt gaggatgtca gacttttgca gcactgttga agattcatta   4500
gtgcagtttt atctccccaa atactcaaac aaatcagcca gctttctaac ttgtttttcc   4560
ctgcccctgc gcatatgtcc tcttgaaatg tccttttgca gtactggaga attatgagtc   4620
atctgaaggc cgcaatgctt gtgaggcatc actttctgat cgacctgcag ttttggctct   4680
gaggaaggac atgtgtgata aaatggtata taagtttttg tgttccttaa tttcaatcat   4740
gttctttaag atttttttca tggtgtggta aataaactgc agtctttaag tgagtctcaa   4800
attcctactg ctctcctgga acggctttta gcagctggaa agaagcaaca tcctcctgta   4860
tgtgcaatcc ttggcggcat tcttggtcag gtaggtacca atgttccatt acttgaatgt   4920
gaaaattgag tatatgtggt tgaactagat ggcaattaag gatttaccct ctagtagatg   4980
gtaattgaag taaactacta acttcacaat aaccatttcc cccaaaagaa aaaaataaac   5040
tcctcaacaa atactatgca tccacatttt actcctgcag taattcactt aaaccacatt   5100
acttgggtcc atgaacttag gaactacata ttaaggtcct tagtgggtct tttcggacat   5160
attgaaagac aacttaattt ataatcatga atgatggccc ctggctgagg gtgccttgct   5220
tgtcctggtt gtgggtctca cagcctccag gcccaattcc catgacagac actttgccca   5280
gacatgtgct gaagtttgac tatccttttg ctacgtaaga tcgatgtaaa gctagcagaa   5340
```

gtgctgtgtc ctctaattat cagttatgat tccctagctc agccatacaa ttttgggagc 5400
atgaatgtgt agttctcagt ccaggggccc aagatgcata cttggatatt gtgttgccac 5460
aattagatga tagttacaca tggaattgga tcggtactct cactggacac cttcaaagat 5520
gtaaatattt tatctacagc cttttggtgg aatacggatt ttgtattgat ggttcaagga 5580
attatacaca atgaaagaac tagcacaaga aagatttgaa cattctgtag caatgtaaaa 5640
ttttctgaat tatttagcaa cctcaactca gtgatgtctg aaaggagtcc aaaagtagta 5700
atattccttt ttttgccaag aaaagtattc tgtactttgt caaatgttaa tcttcaaaag 5760
cagcaggaac ttaattttgt tctgttccaa acaggaattt catctgtgtt tatgcacagt 5820
tctcattgtt ttgcactctg tttttgccta acaggaggtg attaagtcaa tatctggtaa 5880
gggtgatccg atcaagaatt tcttctatta cgacgccgct gatggtaaag ggatcgctga 5940
agacattcct cccctttctt cagactgaac cagttaactg ctcgactccc attcagcctg 6000
gcttcactaa tccctgtacc cattaattag cttcaaatta gattagcagt caatttaagt 6060
ctgagagata cttagaactc tactatttgt tatttaagtt gtgccagctt agaaatggta 6120
tcagatagaa attttacatt ttgtgccaac aatttcaaag ctgaaaccag gaaaggtttt 6180
gtgctgattg aaagattaaa tgtgttgctc tgtattctct tccaatgatg tgcctacaac 6240
tatgccatgc ccgtgtacta atctacccct ttgttctaaa atataatcat ttatgtgcgt 6300
tttccaatat ccagat 6316

<210> SEQ ID NO 140
<211> LENGTH: 1614
<212> TYPE: DNA
<213> ORGANISM: Oryza sativa

<400> SEQUENCE: 140
cttcaaactt ccaacttttc catcacatca aaactttcct acatacataa acttctaaca 60
ttttcgtcac atcgttccaa tttcaatcaa actttcaatt ttaacgtgaa ctaaacacac 120
cagttgtgtt tgtttgtaga ccctgttaca gctgctgcat tcttggttca aactattgga 180
agggaaaaat gtcaagctga tgcaaggttt gctatatttc gttgtgatga attagagcag 240
cgaaaagacc ttactaacct cctgcttgtc ttgtccactc cagtccacac agccactcga 300
tcgttatccc ttgtccgtct tgccttgcct tgtcgtaagc taggcaatgg ctatgccgct 360
gccgccgccg ccgccgcctc gtcctcctct tggacgggga cggctcgtcg gagtaggacc 420
agctccagca ccagcaacgg cctcccaatc caaccgccca gtgccccccc tgcagctgcc 480
tcgctgccgc tgccatcgct cggagggacc ctggaggacg acggcggcgg cgaacgggag 540
gaggcggtgg tggtccgacg aggacatgga ggaagaggac gacgaggagg gatacggata 600
cgacgacggc ggcgcgccag gcgggtcagc gcaggagctg ttcggcgagc catggttttc 660
caagctcttc cgtgcgtacg gctacgtgct gccgctgctg ctggcgtcca tgctggtggc 720
cacggggccc agagctttcc tcatggccat ggcgctgccg ctcgcccagt ccgccatctc 780
ctgggtcgtc tccttcttca ccaccaggag tcgtcggcag caggaggagg aggagtcgta 840
cggatacgac tacgatgacg atcccgcctt ccaacgccga gaggaagacg acgacgacgg 900
cgactactat gatgccgggg catggcaatg gcggagcagg agccaccagc aatcgaccga 960
atccggctcc ggttttggag gatgggatga cctcctctac gacgatgagg agaagaagga 1020
gcaggagagc tcagggaaga agaggacgcc accggagccc gacacggcgg cggctgctgc 1080
cgcctccgat ctgggactgg gattgcgggc gaggagaggt ccacgacgca gcaatggcgg 1140

```
catgtcgcga ggaagaagca gcagcagcat gaggtataac caggcgccac tgctgacgcg   1200

ccttctcgtg gcactcttcc ccttcctcgg ctcatggttc aggatactct aaatttgaga   1260

agaagaagaa aaactgagag atttcagcat tcagaatgga ttgattcatc gtcagttcgt   1320

cagactctta tcacaatttc cttctcccgg tcaggtgcac tttgcctctt ttttgtcttg   1380

gtcatgttca cctgacaatc acaactcaca acttcatgca aatcaaaaca aaaaaaaaat   1440

cacttggttt cttcaggaac caaaccatga aaattgagat gaaatttctg gccttgttgt   1500

ctactgatag caagaagcat cagacgctga tgtggacagg cagaagaact gaccttcttc   1560

tccttctcct tctattcctt cgccgtgctg gcgctgttgt tctgcctact cttt         1614
```

```
<210> SEQ ID NO 141
<211> LENGTH: 6053
<212> TYPE: DNA
<213> ORGANISM: Oryza sativa

<400> SEQUENCE: 141

atcgccattg ctgccctcct ctccgtcttc ctcctccctc ctctgtcgcc tgttcttctt     60

cttctcacga tttttttccc ctgtaaattt cccggcggct tctcgcatct cgttcatcgt    120

cgtcgtctgc tcgcgacttg acggacgagg aggaggaaga agggagcgat tggtttggac    180

ggtaagaaag ggagggacgc gcgggcggcc ggagccggtg gccgacggcc atttttttcat   240

gcgtggctcc ctggaggtcc acgcgattgg cagacacgcc gcgtcgccgt gcgccctgag    300

actgaaagcc ctcccggcat tggacatgat gaggtagacg gcagatctcc aggccctcga    360

gcctctcgtc cttgttcggt tgttcctgcg gttcctcgtt tcttgctctc ttctgtgtca    420

gatcgctatg ttgtttctat ggttcgcgtt cggttttgtt ttcctctttc ggtttttttgt   480

tcggctggtg aagcgatttg gttgatttgc ttgcctgccg gccggtgatg gccggcctcc    540

ttgtcgaatt gctgtccttt gtgattctac ttgttaatct gtctgatggt tttgttctgt    600

tcgtttgatt tttggatttc atggtgttgc tgctgttgcg gttcgattga tctctacttg    660

actgtttcta tgccggtttc gctaattcgc gtggaattcg tgcgtctcgt tttgacccga    720

tttcattctc tccgtatttc gcagtcttct gctcataatc tcagtataat cgtcttttgc    780

ttttcttggt tcctctctgg ctgttttaga gtctgggtac aaaagcatcg gatcgtttgg    840

tcgttttgca accatgggta ctctttctgg gatgatgaga gccatagttc atgtcagttt    900

gttcatgttc tttgtggccg tgttcccttt caagaactgg ttggtttgtt gtcaaatttt    960

cggtcatttt ggtgcctcct gttcaaccct gcttctgttg catctgcaga gttcgatctg   1020

ttcgttttat ttccattcca tgtgatggtc tgagaaggcc cgatttgcga ctcgcatttt   1080

gtagcagatc tctttcctcc gatcaaatcg ctaatcggcg cgttttgatt cactgcaggt   1140

accaaaggct tagcccggac tgcctcccgc tagccaacgg cggcggcgga ggaagcggta   1200

gcgtgacacg gaagccggcg tcgagatcct gcaaggacga cgatggcggc atggccgtcg   1260

ccgcggacag ctcccgcctc tcgtcgtacc tcccgtcgtc acagctcgat tccaagccgc   1320

tgcgcgctcg ggcgccgcag ccgtcgtcct cgtcggccgc cgcctggagc ccggcgcgcg   1380

accacgcgca cgcccaccac aaccaccacc accaccacca cccgtccgac tcctccgaca   1440

cggcctcgcc gagctccaac ggcgcgggca ccggtggcga cgtgctgctg cagtgggggc   1500

acaacaagcg gtcccgctgc cggcgcgacg cgtcctcctc ggccaacgcg gctccctcct   1560

cctcgcagcg ccgccagacc gcctccgccg ccggcaagat cctgcgccgc tcgtcggcgc   1620

cggcggagaa gctcatgccg ccgccgcccc catccaccac caccgggtcg tacacgcgcg   1680
```

```
ggtccaacct gaggtccgct tcgtccttcc cgacgcggtc cgccgccgcc gccgccgtcg   1740
gagacgcaca ccaccacagg taacacacgc ctcctacctc ctcctctccg tctcgtctca   1800
tatcgatgtc gtggggaaga tgacgtcctt cctttttcct cgcctgcatt tcgctcggcg   1860
actttttttc tgtttccgct tttgcccctc cgcggaaact accgggccgc gcgctctcat   1920
attcctcgtt ggagtcgtgg tggctcttgc gtttgttttg ttttgttggg ttcgtgagtt   1980
cgtgtcttcg ccgcgttatt tattcgcttc gggttttttt ttgggtcttc gggtttgggt   2040
ctcttttgtt tctgagctgt accgctccgt agagagaagg gtgggttgag tttgataaaa   2100
gattcttttc tcctttttac ttcacacact tttgtttcta ttaaaaaatt ggagcaggtt   2160
ctcacctgat ctagatctct tcgtctctcc ccgaattttc gtggtattta taacccttt   2220
aatttttatt tacaatattt ttcggaggat gttgtgtgtc cggatctggt gtgtggtaca   2280
ttgaggtggt aactttacct tcctcttcct tgactaatct gtaacccaag tcgtaaggtc   2340
ataggcagca gcacccgtat ttgtcacacg ttgcatgatg catggggacc cccatcgaga   2400
tctccatatc tcgctgaaat tcgttgatgg tcatggtggt actccttggt tagggcagct   2460
ttaatttggg aggatcgttt ggtcgatctg gttaatttgg ggtgttggga tgatgatgat   2520
catcatcata tgaatttgca gcatcaagag gagggagagc ttgtagtact gcttgtaggg   2580
tagatggtta taaatatatc cacatcacag ctcccctctc ttttctttct gggcatcaac   2640
aatagtagta tagcttttgc tcatagtgca tccatcttgt tgtggtagga gtctccagca   2700
gaccagttgt actactagtg agtaaccaat ccaccctacc caccccttct tccccttac   2760
cctttctctc aacctcccaa ccacctccaa gtccatcatc accaccacta gcacctgcaa   2820
caatccccat gattaacgtc ttgttttctt tctctggtgg tatgatcagg tccgccgtgg   2880
aggagcgatc aggcggcggg tacaagcggt cgccggacaa ggcgcacaag tccgccctgg   2940
acgcggcgct gcacatggat tccaagaaca accaccatca ccaccaccac gactcgtcgg   3000
tgaccgcaaa cggcggcgcc ggcgccggcg agaagatcgg ctccgagcgg tttgagctgc   3060
cccggatcta catctcgctg tcgcgcaagg agaaggagga cgacttcttg atcatgaagg   3120
gcaccaagct gcctcagagg cccaagaaga gggccaagaa cgtggacaag accctccaag   3180
tatgccaatc tttgctccgc aaaccggcct gatcttatct gctccgatcc attcttgcat   3240
ctgttctgat cacagagcta acatgtgtct cgtgttgccc ccgatgtgat gtgcagtatg   3300
tattccctgg gatgtggctt tcagacttga cgagaggacg gtatgaggtg cgagagaaga   3360
aatgtgtgaa gaaggtatac tccactctgc acctggcatt ttcagttcat gcattctgtg   3420
tatttttaca gacaagaaga ggaaaattac ctagatttag ggcatcagtg acccagattg   3480
gttgggtcta atgcaaaaat aaagccgaag agtaggtgaa ttacttgccc ttttctttta   3540
gtttggcccc ttctccctca catggggccc atgactcgtg atgctccgtg tcctcattga   3600
tgacggcacg gcactgattt atttggctca gctttattgc tgtggacgtg gagatgcaag   3660
cgaacgatca ttctattgcc cttacctaaa ggagtcttct tgttctacgt ttagttggat   3720
ccattcgttc atctttctac atttgtcatg tgctttccca ggcaaatctc attcaagaac   3780
actacagtca caactcacaa caaaccagag tgtgccacat gtcatagcag aaagaacaaa   3840
aaaaagtctt ggcctctttc agtatggggc ccagctgtca gcctcttatc gtccttagct   3900
aagcatgaga aagaactgta gcattattac tacttaggtg gtgttagttc agtgcttagc   3960
tgcgggtgcg agattgttga caacttgatt attccggacc ttgaaggctt gaatgcaagt   4020
cgtcgtcgct gacaagtagg gaagggccaa cgtggagaca tgtatctgtg tcttttgtta   4080
```

```
ggaccacatg ataatgtctg gatagagctt ggaatcataa ccatcgaaaa agagaagaaa   4140

aagaaatggt acaaagggtt ggaaaagaaa ttgtggtgct gtcttttgat ctactagtct   4200

gtttttcacc ttttccgtga tagggtcttc aactcattcc ctttgttatt aggagcattc   4260

aagcatgctg tagtttaatg agctcctgta acatactaac atgcatatat tttccaatag   4320

taacaaggcc agctcgaatc ttgtaacatg aactctacta gtattgttta gctgactggc   4380

agctattaaa aacccctgat ggttaggttg tgcttgaggg gtgctagatt ctccacaaga   4440

attaggctca gcacatgcac ctaatcacct agtagtatct ccatccatca aggtttctgc   4500

ttaatctcgg gcactaaccg aaaactcctg tttctgacta tgcagaggcg tagagggctg   4560

aaagggatgg agagcatgga cagtgactcg gagtgacggc agctggaggt caagcgaggc   4620

acccaaagcg aaaggagcaa taagattgga gtggatggag attgggccat tgcaatcaaa   4680

gtggatgggg ggagaagaag taagggcaag ccaaagggaa ggcgaaggcg aagagtgttt   4740

tttgtgtaaa tggagaggaa aaagaagagg aggatgtgcc gagggcagga ggtgcacgcg   4800

taacgcgttt gcctcacaca ccctcctcga ggcgcccggc ccagcggaag tggtggcttg   4860

agacgacgac gacgactatg ccccggggtg aatttttttc gtttctttcg ggttttgtca   4920

gagccggcca cctgctcgca cgtcgtcgca gcggcgcaca acttggtgcc gcgtttttct   4980

ccccgcgaga ggccattttg tggtgtaatt ttttgggtgg gctccgttgg cccggccggc   5040

ctcgccttcc tgtgagcttt tgcggtttgg tttggttgga atggttaccc ggtgactctt   5100

gtgcatagtt ctttactatt agtactagta ccattttttt tcttcttctt tctcccattc   5160

attcacgttg ggcaagtctt cggaacacca aaagtattct gaaaaggtta aaaaaaaaag   5220

aaagaatcat tgtgcagtcg caatgaggca ggagattctg aatggattca gtatgggcca   5280

gggccagggc tgatggaggc tgcttcgatg ggcctggcgc gtcgcggtca cctgcaaagt   5340

gcggtagtcc cttgtgacga gctgacaaac gttcggcatg ccggacggac gggggctgag   5400

atatctaacg aggatcttct acgtcatata tgatggaaga atctgttaca gaagtttggc   5460

atggctcgtc tatcagccgt gcgattacac cgaatattgg acacgtgtcg gcatctcgcg   5520

tgatcaactt gaccactatt tcctttggct tcttccttcg tccatcagtt gtgtgtacag   5580

tactgttgtg gaagaggcga tgattaaact ctccaatcat gtattcatgt gctgatgcgt   5640

atatgtatgt gcacgtcaca tgtgggcgag tatgggaggg ccgtgagggc gaggaaagcg   5700

tggttgaaaa acgccagcga ccacgatttt ccatacgcaa cgccggccat tgctggtgaa   5760

gtagctcttt tttccccttt tctttggaaa accctgtact actctttacc cagtttgcaa   5820

tattttaggg tggaggagta ctccgtattt agtttagggg cggagaattt gaggctttgt   5880

tgttcggaca tggtacgagt ggcgaactgg cggcgatggc agccataaac aggaacacaa   5940

ttgtctgtct gtctgtatgt ttactacaga ctgtttacgg tctcatgtcc agctgtttga   6000

attttgtacc tgaatgtttt tttctttgga caaaaagatg gagtatttga ata          6053
```

```
<210> SEQ ID NO 142
<211> LENGTH: 3348
<212> TYPE: DNA
<213> ORGANISM: Oryza sativa

<400> SEQUENCE: 142

acacctgctt tccaatcgca gctgcctccc atggcgacca ccgcctccct cctccctcct     60

ctcctcccgg ccccttcctc ctcccccgc cacctccacc cctcccctcg ccacctccgc     120

cccttgccac cgatccgcct cctccgcgcc gcccgccgcc gccaccccga cgccgtcgtc    180
```

```
gtcgtcccgg acgcccgccc ctgggtcggc gacctctcgg gcgccgccgc gtcctaccgg    240
gacggcaggg aagaggacga cgacgacgcg ggggaggagg atgacgaaaa cgacgacgac    300
gacgaggacc gcagcctgga cctcctggtc cgcttcctgc actcggtgtt caggaaggtc    360
tcccgccgcg cgcgccgcgc cgccaggtcc gtgctgccgc cttccgtccc cgctgagctg    420
gtccgttcaa cccttccgtt tctccccttt ggtttcaatc ttcttcttgt tcaaattgag    480
cggatccttc tctgtattgt gtgatctggc cttgatatgt ttagtttatg cttgtgcagg    540
tgaagttctc ggtcaacggc gtgcttgttc tcacgtttct atgggtccta aaggggctac    600
ttgaggtgag caattcattt gtctgaggct tgtttcaaaa ttgtgagctg attgtgatca    660
tgcccttgat atgaactact aagtgttaca ctgtgatact atccagtgga ggattcagga    720
atttcttga  gcctggtcaa acctagtgat gtataacaag tacataaaaa atcagtatag    780
ctccatactt ccatagacca tatactatga acgcaagcaa aaccgacagc tgccaagttg    840
tgatttagga agagcaaaac cagtacgtac gagagattat atcgttgaga tgatggctgt    900
ctattgccaa tgggctagac tatggggcta ttatcatcct gacaaatgtg gtgatgagtg    960
ctagcttaga gttgtgtcgg tttgaccctc gtgcagcaaa cattcaaacc ggcatatcaa   1020
gtagtttgct tggttggttt ggctcccatt cgaaccagca gatcaagtag taattgatgg   1080
agtgctgtct tgctcatgtg ctgatcgcag agcctggaga ccagccacag ttgctggggc   1140
ttggctcctc cgctgatact aacagtgaca tataatggaa taacattata tgtccagaga   1200
acaaacattg tgcatgcttc tgaatttcat gtatgtccag agaacaaatg ggtgttctac   1260
cttcgttgtc attcgcttag agagtgaaga agacaatcag tgtctgatta catgctgata   1320
tgacactttt aaatgtttga tttgagtttt ttcccttcat tctgatgtct cgtaaatttg   1380
gttttcaaat tttggtcaac caagtttgat gaacatggat gagaaccaga caagtgtata   1440
tgataccaca aaaaagattg tccttttctc taactgtcac gtgtagatga gaatcctcac   1500
tttgttgaag tgatgccctc ttttcccttg tactagatgc ttgctcccag ttttgagcat   1560
aaaacaaaaa catgttctag tacagagtat ataataatgt gcatatatac tcagagtagg   1620
gaatggtgca catcagcaca tggttcaatc attccttatt gattgtctac tctttgattg   1680
gagtcatgct tatgatcaat aaacagttat gctttcaatt cagaaaatta taaaaaaaaa   1740
ttgtgatgaa ataacaaata ctccacatgc attacaagta caagtttgtt tctgggagac   1800
atacaagtag tttagaatca tgagattact taatgcttat aatggcgttt tcgatggatg   1860
aattcagacc aaatgagaat gaatcttgta ttcttttgca ctgacacttt cagcaaattt   1920
catttcttag cattctggta gtttggtcat gtgatttacc tctggtgctt ttggaatacg   1980
agttttttat tcgttgtaac atttcctatt gataatagat ggaaatggtt cgtcttatta   2040
agatgattct ctttagtgaa attatgaatt ctgtttagta gagaaagagc ctactgctac   2100
tgctgtcaag tttgatccca tacccacccc aacccccagc gtctggcggg cttccccttc   2160
tggatgagct cggtccaccg ctatcctcca caaggtcgtg ccattgtcct ccgtcgcttc   2220
ccctccctcc actcctgtcg cttgccttcc ccttccttcc gtcgatctga aggcagtgag   2280
cagagaggcc aaggtggtgg ctgcaaggag tagatggcga tgtcgcctgg atccaagaga   2340
gagagaaggg gtaagaagga atatatgctg gcaaatgggg acagtcggat tttgtaaaat   2400
tatttcataa tcttgctgag tggattgcca tgtgaccaaa ttaacaccat gtagtatcaa   2460
aaccactccg tttttttgcca ggggggtaat ttgtccagat tcaatagctt ggaggtgtca   2520
aatgtccggt attgtagtgt agttcgcgca gggcgggtgg gtgtggggtg taaatcgtac   2580
```

ggtcctaacc cttataattg catacaagct taaactacac cctggttctc aagcagggct 2640
actgagtact gactgttact ctcttcaact gacaccccta cacactgtct tctagtgcca 2700
tgcctttcct tcagtaactg tttatattgt ttgtgctcag gtggtgtgca catttggaag 2760
tatggtgttc gtgaccatcc ttcttgttcg tggaatatgg tctggagtga cttacataag 2820
agaaaaccga tatagctata ttcgccagat tgataatgat gacaaccgat ggagcagagt 2880
acagactgct ggctaatcat ttgatttcct tgactacata catacacttt gcaccaaagg 2940
gatcatcagt aaacctttcc tcactgttaa gacagcatgc taccagttca gcaccaactg 3000
ccaacagctg ttgctataca gcagagttga acaagaacaa aaggaatccc atgtattcgt 3060
cgaataagtg gaattttctt cctctgcaca aatgcaggag ggatggttga gctgaacaag 3120
attaatacgc gtgtaaaaca atccagcaca ctgatgaatg agagctgctg ctgtgatgca 3180
ttttctgcta ctcttttctt gaagagatgt atcggtcctt attagtgtat gtattgttcc 3240
atgctgttac aactagccgg tgtagaaaaa ctcatgtttg ttgtattgaa aggtggtgca 3300
cgataccttt ttggttaaaa agtgaatatc atttcgattt catttgaa 3348

<210> SEQ ID NO 143
<211> LENGTH: 8998
<212> TYPE: DNA
<213> ORGANISM: Oryza sativa

<400> SEQUENCE: 143
ggtagacacc gcttcagcct ctgcccatcc aactcgcaaa aattccccac gattccacga 60
aagtaggaac catgaagctt cggttgcgat ccatggacca gcgcggcggc gccggcggcg 120
ccgccgagac ccaccgcgtg cagctgccgg acacggccac gctctccgac gtcaaggcct 180
tcctcgccac caagctgtcc gcggcgcagc ccgtgcccgc cgagtcggtg cgcctcaccc 240
tcaaccgctc cgaggagctc ctcacccccg accccctccgc taccctcccg gccctcgggc 300
tcgcgtccgg tgatctcctc tacttcacgc tctccccct cccgtcgccc tcgcctccgc 360
cgcagccgca gccacaggcc caacccctgc cccgtaaccc taaccctgat gtcccctcga 420
tcgcgggagc tgctgacccg accaaatctc ctgtggagtc tggtagctcc tcgtcgatgc 480
cgcaagcttt gtgcacgaat cctggcttac ctgtcgcatc cgatccgcat catcctccac 540
cggatgtggt gatggcggag gccttcgccg tgatcaagag caagtcgagt ctcgtcgtcg 600
gggatacgaa gagagagatg gagaatgtcg gtggtgcgga tggaaccgtc atctgtcgcc 660
ttgtcgtggc gctgcatgcg gccttgctcg atgccggctt cctctatgca aacccggtgg 720
ggtcttgcct tcagctgcca cagaattggg cgtcaggttc ttttgtcccc gtatcgatga 780
agtacaccct gccagagctt gtagaagcgt tacctgtggt tgaggagggg atggtggcag 840
tgctgaacta ctccttgatg gggaatttta tgatggtgta tgggcatgtg cctggggcaa 900
catcgggggt gcgaaggttg tgcttggagc tgccggagct tgcgcctttg ttgtacttgg 960
atagtgatga ggtgagcaca gcagaggaga gggaaattca tgagctgtgg agggtcctga 1020
aggatgagat gtgcttgcct ctgatgatat cgttgtgtca actgaacaat ttgagcttgc 1080
caccgtgctt gatggcgctg ccaggtgatg tcaaggcaaa ggtcctggag tttgttcctg 1140
gggtggatct tgcaagggtt caatgcacgt gcaaggaatt gagggatctt gctgcagatg 1200
ataatctttg gaagaagaag tgtgagatgg agttcaatac tcaaggtgag agttctcagg 1260
tgggcaggaa ctggaaggaa aggtttggag cagcctggaa ggtttctaac aataagggcc 1320
agaagaggcc cagtcctttt tttaactatg gctggggtaa tccttatagt ccacatggct 1380

```
ttccggtgat tggtggggat tcagacatgc tcccgtttat cgggcatccc aatctccttg   1440
ggcgcagctt tggaaatcag cgcaggaaca tctcacccag ctgcagtttt ggtggacacc   1500
atcgcaactt tcttggttaa gtcatttcgt gggttttgct agtatgttaa gaatatttca   1560
tctgaaaagc tacatataac atattgtaca tattttatag ttggcacttt atgcatgttc   1620
agttgttaac tgtattactg tactcgtaat cttttctttc tttgttgata tatcctatat   1680
tttcttgtag taccagtgtt atgcatgcct taatcatggt aaagtatcgt ctgtttaatt   1740
ctctgtgcta caatatgcat ttcaaacact tgtaacttgt aagtctcatt tgttggatgc   1800
ctttagtcaa tctgattatt tcatccatca acggagaaac aagatactgg tcatgttata   1860
taccatcatg atctgctgat gagattgaaa ctgtcacttg tttctaaagt ttgcgtgaaa   1920
taactggaag caggtggtgt ctttctttgg taaaagaaaa gtattgtcct tatcatctct   1980
ttgttctttt cgttttatat gctatgaaaa gatatattca tcccatattc cgataatttg   2040
gaatacttgc ttgccttttg tgctatggca acttatgcat attattttgt tatttttatg   2100
ttcgtggggg gttgtagcct cacaggttgt agcctccata ctgaatcgtg caaaactgct   2160
atcctacaaa gaaggacaaa caaactggat aggctgtact cattaatcaa tgtctaagct   2220
agtgcgatta acttgggcag catatggtcc gaaaacaaag aaggaaaagg tgaacatata   2280
tcaggaacag atcaatagac ttatcacgag actataacca ctggtgccaa acgaattagc   2340
aaacagataa taccttagaa tttttgtatt tggcaataaa atctagtaag aatttgttga   2400
gctgcactac aaacatgtat agataagaaa tagcatccaa ggcgaggatg atatgttgtt   2460
aagacatact atcgagcaaa tcctgtggca ggtttctctt acaccaggtt ttacctatgg   2520
tttgtaagtt tctacctgat tttcattgta tatattattt tgtgattaca cgaatcaatt   2580
gtttccttct atatattgct gaaaccgagc tgccctgttt aaatgcatta gttaatgtta   2640
tacgttatct gtgtttgata aaaagcttct atgaaactat gaccactgtt tgcttttgtt   2700
ttgatcaagc tttcagtgca aggacttttg gttgtgcaca cgtatgtgac atttagtgga   2760
ttttttaaaa tcaaatacat tatcagtact tggggctgga gcaatctgtt ccctggggat   2820
acttttagca ggaacatgac tgaaacatta tcagtttaaa acaatatgac tgattgtcat   2880
ttccttatta ttgtaattgt atttagcagg aacatgattc tgaaacttgt gtcttgatga   2940
tcagatacat gcggttgtat gatgtgtaaa tgcatttact ctgaccaaag gaaggatatc   3000
gtactagctg ataagtatac ctgtggtaat tatatgcaga agcccgtcac acaacctggt   3060
aggtgagtaa tatatataag cactctgggg aactatttat ttctttctag aaatattctg   3120
aatagttgtt atgttacctg catgcctaag ttaatttctt attccctttg tgtccttttt   3180
gtgtttgtct gttactttat tttgtacaat gtttcgcaga tcgtcaatat tctcgtggct   3240
tgcatctcaa ttggatttct ccaactgatg cttcctccta acatatccat ttttggttgc   3300
gcgtacttgt tttatgataa aggagaataa aggagtcatc cttttttttt tcacttcgac   3360
ttacgaatat ggtttatttt cttggttgtc gatgcaccac tttatgaatc tgactgtagt   3420
atttgctttt acttttattt ttccttcgca ataggtggct tattatatta gtctaccatt   3480
ccctactttg ccagtacatc actattgggt tgagtttgct gtggtatcat ttggttgatt   3540
tggttcaggt ataatttttt aagagatttt agtcttttgt cctaagtgaa tatgggttgc   3600
aggatctata tgacaataaa gttcttgatt ttatacagaa gcttcacatt tacactgcag   3660
tcactacttg aattatcaac atttctcact atacatatat aatcagctga acgcctgaac   3720
cttttgagat atttgagtta tgactagagg caaaaatgga tagtttcttt gtaaaacgat   3780
```

```
atataacaat caataatggt ttttcatgga cttctgaagc aactcgacat tgatgttccc   3840
ataccatatt tttcttgagg ctatgatggt tgagtgaacc atatagctct tctctctcca   3900
tagtccattg gagtcttaga cctgggggc caaagattgc tccattttct taaagtgggc    3960
tttatattga ccgcagggag aaatatcact tttttggtgt aggcgtgcat ctatctactt   4020
tgcctacaca tgttctattg actattggac tcatctgtct ttatgttgca taattaaacc   4080
atgaaatatc tttcatgaga tttaactttt tgatcacttc tctttggact gagactgaac   4140
caccgttacg atactcaaat gggagctgta cggagtgtca cggagtccaa gaaaagctac   4200
aactttcagt aaggggagta ctctttgctt gtggcttggt gcactgaaaa gattgtgggg   4260
gaaggagtat gggaagaaag agtttataaa tccaaatggg taagaatttg agtgttttac   4320
tgccaggata tctcaatgct atgattggtg atctaaatta tggttaaacg ttactctgtg   4380
gttccatgaa ctttggctgc tctatgaaaa gtatttagtt tcagttccgt gccaaataca   4440
gcatttgagt ttcagttatg tggcaactac cgttcatacg cagccttata tattttcctc   4500
attgttcctt ttaccaatag tcctgtaaac ccgaattctt ctgtttcaca ttcaactttg   4560
tcctgcatac agtatgtttt acgttctcag cctgtgctat tattgaaagg ctattgcatt   4620
gcagtggagg acctgaagcg atactgcatc ccagcgaccc agctcaattc acgcatccag   4680
ttctgttagc ctcggaacaa tagtactcct acagatagct ggctgatact gcacaagcta   4740
caggcagcct cagcggagta agtacaagaa tccaattcgc tgccaacaca cgtctgcctg   4800
ccgctggcag gatgctcctg cagcaggcat tcactttgac tgtattattc cactgccaat   4860
caatccttac cagcttcccc catctgctgg tgcctgctgc tcaacaactc aagcttcagc   4920
atcagcaaaa gatggtggca atgtactcca gattccaaag cctcttgaag tgaaacagca   4980
cagtgatgaa cttctatgat tgacacttgg gcaccctgct ttgagctttg ccttttgctc   5040
tctcatctgc tactagtagc atgctggacc ttatccttat gcaacacaag taatatacta   5100
acaggtattg cttgttggag aaggcctaac caggaccgat ttttaagcca aggtggatag   5160
gataatcttg tggcaattga aatctgcaaa tgtgcaacta gtcttcttca tgaagggaag   5220
ttgtacttct gctatgctta caccgaggtg taatcaaata aagacactgg gaagctggtg   5280
gaagcagcag tggtggcctt ctagtatctt ttatttcacc cctcctgtcc tagccacatg   5340
tctctgcatg cagccactac atggtgaaca ctattcgttc taccataggc tggtgagtaa   5400
ctaacacctc tgatcaagag aggtggagca gagaaagtgg cagcagccct cacccccgac   5460
tggtaataag aactctcccc ttccatccta aatatatatc ttgttcaata ttttctacat   5520
caattttatg cattttggca gaatagtttc tttgtagaca gtgcattgtt ttttcccttg   5580
atgaaactac agcacaagaa cattattagc tgtttgctca ttaagtgcca acagcctttt   5640
tactgaacgg tttctgtgct ccatccaagt ccttttgcct ctcctcaatc tacacattaa   5700
agaaagggga gaagtttcaa cgttgtacta acccttgtcc ttgcatctgg gatcaatcaa   5760
tttctccctt ctgaatttcg agatagccct taaactgtca tggtagaagc tctgaattgg   5820
tgagtagtac gaagtgtcga cagcctgtgt aaaatcgggc agtcattgtc gtgcttgaca   5880
gatcatttac agtgccagca ccaaattcgg atgatggtat gtacgatact cactgttgag   5940
agccgaagaa tccctctgct ttgctactga taacaatcag ctctcttttt aacttttatc   6000
gatcatagaa cctaatcact tccctggttt ctctgatgat ttcatcgaag ctttgcacat   6060
tcttagctgt tgctgtcttt gttgttctgt ggatctgatt ctacagaacg aacttctgac   6120
atttccattc agatttcaga gcgacagttt gaactgtgta acaactaacc ttctgtcctt   6180
```

```
gttacctcta gcctcacatc caccccagtg aatacgcaat ctgagtcttt gtgttggaga   6240

tttcgtttaa ttacaaatta aaaagagagg actaaggttt agtctgtaac attaattacc   6300

acacttgaaa cgacgcctta catctaggca ctgccactga aaggtgggtt cccttttctc   6360

ctcttatgca agaattgttg aacatgttaa gaataagact ttgaaactaa aaacttgtaa   6420

gttgggttta tcagaaaaaa atggtgaaga agggtattaa tccagtagta caaaatttaa   6480

gagggtttaa ggctttaagc aaagatggat ctggttcatt aattaatcat taaccttatt   6540

ctgggctggc ccatacagtg gatgacaata gcatctgttc tttggtttgg tcttcatttt   6600

acagtaccac ctgcaattta tcttaattca gagaatttta ttctgattca tggatgtgat   6660

ccagctggtg catggttgtt agcagtaccg acaattctat tccaggactg tggtttccac   6720

ctttgccctt gcgtttgtct attgcattag gcttacttaa cttttcactt tggacaatct   6780

ttatgtaagg ctgcaagggt tagttgttcc ttgttgagcc ttgcaagaaa ttgactgcca   6840

cagctcccga tctaccctac cctttaagta aagcccattc acttgtcaaa gctgacaatt   6900

tagaaggcca tcacgcattt cttaaaatga ttgcaatatc accctgagat caagtatcag   6960

gcacaaggtt ggtggcttgt ttaatttctt catatgtatg ttcttgggag ttgggaacta   7020

gcatctatct aatctagtac acactagatg acttatctca gagagttgtg atataatggt   7080

catcatgtga ttgatcatcg tttcttctgc agatgtattc cctccctgc agtgctgctg   7140

caagcagcca agggcattgt ttcgcggtcg gagctaacca gcttgcttcg cttgaccttg   7200

ccatggactt cgacgagcct atcctttttc ctgtgcataa tgcaagtttg caagagggga   7260

ttcagtttta caatcctacc ggcggtatgt ctctctcgtt acctatgttc tattttcaag   7320

gataaccaca gtatcctcct ctcttttttt ttttcaatta gataaccaca gtttcttaat   7380

ttgtgaagtt cctaactatt acagtttccg tgttccaact ccccagatac tcagctaagt   7440

agaaacatga gcattgacaa gtgtttgaag ggcagtaaaa ggaagggctc aggcgagggc   7500

agttcatcgc tacattccca agtaacaagt taattagaag ctctctttgc ttagcttcat   7560

cgggtgggag cacgtttcat cgtgaaaatc gtactactgc aggaggaaac cggtgaaatg   7620

cctcagagag aactcagcat ggagcatgcc ggagagaagg cgggtgatgc tgacgctagc   7680

agggaggagt acgtgcatgt ccgggcaaaa cgcggccagg cgaccaacag ccacagcctt   7740

gcagaaagag taattgatct ctccaacatt aatggaagat ctttctgtgt atagattttc   7800

ttgctcacac agcttcacca tctgaatgca gtttcgaagg gagaagataa acgaaaggat   7860

gaagcttctg caggacctcg tcccaggatg caacaaggta gcaacgaaat caataactct   7920

ttgagtctgt gatggtgtgg tgtgctctaa cctgtgtgaa catgttgctc ttgacaaagc   7980

agattacagg gaaggccatg atgctcgacg agatcataaa ctacgtccag tctctgcagc   8040

gacaggtgga ggtaagtgtc ccgaaattac acatcttgtc aacaagaatt tacacttctc   8100

aatgccaatc actgactgaa ctatccatga agtgcttatc cgtgccgggt tttgcagttc   8160

ctctcgatga agctctcgac aatcagtcct gagttgaact ctgacctcga cctgcaagat   8220

gtaagatgaa aaaactccaa ctctgaagaa caaataactc atctatcacc attgctacac   8280

cttgatcctt tctttttcac tgccatacag atcctttgtt cacaagatgc tcgctccgca   8340

tttctgggat gcagcccgca attgagcaat gcccatccta acctttacag ggcggctcag   8400

caatgcctct cacctcctgg cttgtacggg agtgtgtgtg tcccaaatcc cgcagatgtt   8460

catttggcaa gggccggtca cttggcttcg tttcctcagg tctacatcta actccagtga   8520

atacagtagt tcaaatcctt cagaacagcc gagagttatt catgttttct ttgctgcagc   8580
```

```
agagaggcct catctggaac gaggaacttc gcaacattgc tccggccggt ttcgcttcag   8640

acgccgctgg caccagtagc ttagagaact ctggtatttt tcagagctcc actgccctac   8700

ttgctttttt taaatacatt tcttctgcag ctgaaattct ggcgatcgtg atgctgcaga   8760

ttcgatgaaa gtggagtagc tagtcagcag ctggtgatga acaattgaca cgcctgaaag   8820

tcctgaaatg atcgcgcgtt ggactgctaa tggagggatg cactctttca ggtttgcaaa   8880

ggctgcacac aggtttccat tggggtgagc gaatttggtg gtcgtcgaag ttctcgagga   8940

aaactctgta gcctaatcat tgtacagttt gactaatcga aaagatgaaa gtttgaga     8998
```

<210> SEQ ID NO 144
<211> LENGTH: 2611
<212> TYPE: DNA
<213> ORGANISM: Oryza sativa

<400> SEQUENCE: 144

```
atggcggccg cggccggcgc cggcgagccg tcgccgtacg cggaggcggc gggatccgac     60

ctcgcgaatg cgcgggcgcc gtctcccgtg gtcggcaagc acctcccgtc gggcgccgtg    120

ccgcgccacg cgtacgtgtt cgacggcgag gggggggttcg ccgacgcggc gtgggacgtc   180

gcggcggcgg cgccgggggc gttcacgtgg caccacatcg agctcccgcg gcagcagccc    240

gggggcgccg ccgcgaagcc gctccaccac gcgcaggcgc tgatcgagct gctctgcccg    300

ccgctcacgc tgcaggagat cctcgcgttc gtcgccacgg gcccgcactg cggcgtcgtg    360

gacggcggcg gcggcggcgg ggcgggcgcg ctccttctcc gcgtgagctc gccggggccg    420

gtggggagcg cgttcgcgct ccgcctcgcc gcgcgcgtca cggacagctc cgtggtgacc    480

gtgtccgtgg gcggcgtccc gcgcctcgcg ttcgggacca cgcaggcgtc gctcctctcc    540

gaggtgccgc tcggggtgac cgcgtcgctc tccgacgagg gccacggcgg cgggcgcgcc    600

gtcgagggcg gggtggtgat cgaggagcgg ctgctcgagt cgctgctcgc catgaaccac    660

gccgacggcg cgcacaccga caaccccgtg ccgcggaccg tgtccaacct cctcgtgcac    720

gtcctgggaa cgcacgtaga ccacgtccac gacatcgtca cgcgcctcga gatggagctc    780

gacagcatcg agctgcatct cgacaagggt aggtggaggt tgctttcttg actagtaatc    840

gcatataaac ataaatcaaa ttattagggt tctaagaaca tctccattcg ttagacaaag    900

ttggtgccct ttttttccct tttctggtga tgttgttagg taggacgaac tagcttcttc    960

gttacgtctg ttgttcatga ttatgcacga gagaaattta ttgtgctttg ctttgttcta   1020

tgggctcatt ggattacact aaactggaag tctaaaaatt gggaatttgt cgaaaattat   1080

cgattctgtt gtgattgtcc atccgcattg gggcggcaac ttgatgaaaa actcctatga   1140

ttggaaggag gttgctgatg ctattgaatt gattcttgat tgttactgtt ccatggagaa   1200

gttccaattc catattcgtg cttaaattga ttctgaagcg gtgtatttcc ttttagaggt   1260

gatttcgggt gtgtttagtt cccaccaaaa ttggaagttt ggttgaaatt ggaacgatgt   1320

gacggaaaag ttggaagttt gtatgtgtag gaaagttttg atgtgatgga aaagatggaa   1380

gtttgaagaa aaactttgga actaaaccca gccaataaat tataaatttg gggtgaagta   1440

aggtcagaga agaaggaaag gtcatcaatt tatagtttgt tatgtatggt ggaatgaaat   1500

ttctgaatgt catgttggca gcaaccgtat ttcctgaaat gccatgatta tattgctagc   1560

tgtgattcca gatgggattc atttcacatg atcagtatgt gcaacagaat attttctgag   1620

atggatttct cacgtagtct atggatatct gttctacttc tacataggtt aatgtcaatg   1680

gaagtcaatg tgaagtctag tttatttact actagccaaa cttatgctca aatttgttat   1740
```

```
agcattctgc agatgttatt ctttctctta atgggctttg aaggtattta tgatatttct   1800
gtgaatcttg cttgcaggtg gtcactttat gaggaaactt ttgttggatg gaaggagatt   1860
ccccaaaatg catcttgatc tacagcgcct gcttcaggta ttttctgaga tttatctcaa   1920
attgctaaaa tggagttcaa tgtatgagta tgttattgtt cactggatcg ggaacgcata   1980
atagaagtca tgggctttaa tgatttcttg cctaggttgt ttctcatggt gaccaagtat   2040
tcccccgtgt aaaggaaaaa tgtgcgagca agagttggtt tgcgagtgaa gatattgttg   2100
ctcttgaaga tctgataggc cgtcttagga ggctgaagga aaatcttgga tttataacga   2160
atagggtgac tacacttcaa gctagtctag atagctggca atctgagcag ataaacaaaa   2220
gcttgtacta tctttcattt ttgtccataa tattccttcc tctatccatt gtcactggag   2280
gtatgttccc atgcgtattt ctgatgccat ttattgctta aggtctccaa tttacatgat   2340
ctgctgcaat gtttgtgcag tttttgggat gaatgttggt ggtgtgccat ggactgagca   2400
gaaaaaccct gcaaatctag atggcttctt caatgtcatg ttaatatgcg tcgtgatctt   2460
gttgatcctg ctgctttgtt tcttatttcc ttcattgtat tcacacgtgt cggcatggag   2520
aacccgccgt gcactggccc ggagcagttc tcagaacaag agacatctga aactctttaa   2580
gggtcacaaa gatggttaca tgcgcctctg a                                 2611
```

<210> SEQ ID NO 145
<211> LENGTH: 2561
<212> TYPE: DNA
<213> ORGANISM: Oryza sativa

<400> SEQUENCE: 145

```
accgtggagc actcgatctc caagctcatc tagctcttct tgcttcagct tcttcctctc     60
tctcacagtt catcacactt ggctttttga gtcaggtgct tgttcttcct gctgttcttg    120
ccttggtaat gctcttgatc tcttcttaga tgtaatcttg ggttagctag catgcagttc    180
ttggggttta tctcatcttt ctgtagttta gtgtgtcagg tttagtagta attgttcgtc    240
gagaaaacaa aatgatatat gggttggatg aatggagaag aatgtggttc agttcagtgt    300
gatcatcttc ttgttgtggc tctgaatcga atgagctgtg aatttggtga atttgcaggc    360
atatgcagga ccagctgatc tgcagcggct gcaggcgcgt cgtccagtac aggagagggg    420
tcgccggcgt ctgctgcccg ggctgcaaca cgctcaccgc cgtcaacccg tcagcggtgg    480
ccgacatgtc ggagctcatc tgcagcggct gccccacgct gctgttctac aaccgcggcg    540
cctccaacat ccgctgcccc agctgcaaca ggctcaactc caccagatca ggtgaatgat    600
catatttttg cacatactat atctttctct gaaaagatca tatttgcagc tgattcagag    660
ctgcaaattg ggatgaaatt aatctactga aatctgagct gatcatggat ggttttattt    720
ggtggttcag ccaaccagat tgcacacctg acatgcgggc agtgccggac gactctgatg    780
cacccacctg gagcctcaac tgtgcagtgt gcaacctgca gatatgttaa ccatgtcagg    840
gtatgttctc atctctgaat gtttctaccc tctatatttc tcgcatcgcg cattcgctct    900
ccggtttcgc tctctggtag taatcatcgt cggctcatcg gctcggtgat aaccagggtt    960
ggaaattccg aaacgaaatt tccgaaattt cggacatttt agacctctct gatatgatat   1020
tatttcggcc aaattttttt attttttaa tttttcgtg aactttggta atatttgttc   1080
aaattcaact aaattttatt caaaatttcg gaaatttcag accgaaattt caaaaaattt   1140
ggcatttcca tgaggaccga tcaaatcggc taaaccgaaa ggtttaaccc tggtgataaa   1200
tagttagtgt gttcttgaat gatctttcca caactgaaca gcaacctgag ttgatcaact   1260
```

-continued

```
ggaaagatgg aataaccttt taactttgcc tagaatatca gtagtcggca caggtttttc   1320

tgaagctgaa aatatggaat tttcaattag attttctcat ttctgtgaac aaaatttcat   1380

gggaccattg actgaacaaa ccagcacttg cttttatctt taattttgca tcaactaggg   1440

gatgcatatg gttctcctct tcttaaaaaa gatgacaact ttggtaggtt cagcttgctc   1500

catggttttt catggaatca gttctcaaag taggcatgta cctatgatta gccagcagaa   1560

ctcgatgcct cggccaagat ttttatcttc caattccgtt atcaggacaa tgaaactaaa   1620

tgatgatggt ccattgggac aaatgaaaca atctgaatct tatgtgatgt caaatgttcc   1680

atgatgacga tgctagcttt gttctctgaa tttccttttc tttctcctac ttgcaggatg   1740

ctcggcctca aactgtcctt gtagagaatc ctaagacact ggatgataag ggcaagctgg   1800

taagcctcat ctctaggcta tatatctcta ctatctacta ctttaaaaga cgcagtcctc   1860

ccatcccacc ctaccgcacg cagcacgaga aaatcttgta ataaaccgaa ccggcccacc   1920

caccgcaccc tccttcccgc accgcgtgag agaaaaaaaa agtgcacgtc cgacttccat   1980

gtcgtcttct cgctagaaaa accgagtttc agtatcagac aaaaatatga tagttgtttt   2040

tatgggtcca ttgcaacgcc tagacattta actagtagta ccctaaaacc aaaatttcct   2100

tctgaatttt tttcttggaa tagcagaaag tttcacttct gaaatgatag ctgaagagta   2160

catgtatttc agctctgaaa tgtccagttg attgactgtt ctgttttgtt atggtatagg   2220

tgagcaatgt ggttgttggt gtcacctcat ggaaaagatg atgaacaggg gctcatctag   2280

ggtttaatcc caagggtcta tggatgattg ataccccttgg tggatttgta tcattactac   2340

aaagctattg ttaaatcaag tgtgttttga agcttgatat aaacaagaga aaaacaatag   2400

ggcaaaaaat gaagaaaaaa atatatccga aatgtgccat gtttgtgctt cttttgtgag   2460

aaaaaaaaat gtaaatatgc tggctatggt gctagcctat gtgcttttta gcaaaaagga   2520

atggaaatga gatgagcagc attgtgtcct ggaattttta t                       2561
```

<210> SEQ ID NO 146
<211> LENGTH: 2377
<212> TYPE: DNA
<213> ORGANISM: Oryza sativa

<400> SEQUENCE: 146

```
ccccttcatt ttctcgaagc gcttcccttc ccttcgcttc cccgcacaat ctgcaaacgc     60

gccacccgtc gctcataaac ccctctccct ctctctctgg ccgacacatg gaccccaccg    120

ctcccaactc cggcgacgcc aacggcggcg cggccgccga cgccaccgcc ccgtccaaca    180

ccaccgtcac cctcccgccg ctcaccctcc gagacgtgcc cctgctcccg tcggcggcgg    240

cggcgaccga cacgatcccc aacccgatct cccgccaccc ctacttccac ccgccggcca    300

ccttctacat ctccccgggt gacgtctccc tccgccacgc cttcttcgac ctcgcctccg    360

cgtcgccgtc cccgctcgtc gcctaccgcc cgcgcggggc cgcgcgcggg ggtcgccgtg    420

gaccccgccc gcgcgcgcgc cgcggtcgtc acctgcgggg ggctctgccc gggcctcaac    480

accgtcctca gggagctcgt cgtcggcctc cgggagctct acggcgtccg cgacgtcttc    540

ggcgtcgccg ccggctaccg cgggttctac ggccccgacg ccgaccacgc ccgcctggac    600

ctggccgccg tcgacgactg gcacaagaag ggcggcaccg tgctcaagac cacccgtggt    660

ggctttgatc tcaacaagat cgttgacggc atcgtcgcgc gcgggtatac gcaggtgaga    720

gcaaaccccct accgttttta gagttttcag gttttatgta tttttttggc aaatagctaa    780

agtttaaact gatctcacaa atcatgtgca cgtggaaacc cctaagcttc tttttacgcc    840
```

aagctggcaa atgaaagctg gccaattttg ttaagattag aagcacaaga aacatgttac 900
aggtatttgc aagtgtacaa tgtgtcatct gaattggcaa ggatactatc ttggtgctac 960
aaatttgctt tagacatttt agtatgttgg tgtacaatca tgggggttgt tctgaattga 1020
catggagtag tacttattat gttaggtgtc attatggaag aattatctca aagaatttgt 1080
ctgtccagaa tttttctttg tcagtagagt ttctttttcc accgggctct ttgtcggtta 1140
gagtggtcaa gtactcaagt ggttgaagtc ttactgattt gatcgatcag cgttgagtcg 1200
tcttgctagt tcaacatgct aatttgtttc agttattgct tgtattttgg cttattaaag 1260
tgtctgacct caaacacttt ttatcatgac tatatcttgc tgaaggttta tgcaattgga 1320
ggggatggaa caatgagagg agctgtggcc atcttcaacg agtttaagcg ccgtggtttg 1380
aacatttcta ttacagggat cccgaaaact gtggacaatg atatcggcat catagacagg 1440
tcatttgggt tccaaaccgc agtggagatt gctcagcagg caatcgacgc agcacatgtc 1500
gaggctgtga gcgccgtgaa tggcattgga cttgtcaaac ttatgggcag gagcacaggc 1560
cacattgctc ttcatgccac cctgagcagc cgcgatgttg actgctgttt gattcctgag 1620
gttgatttct atcttgaagg aaagggggc ctgtttgagt tcttgtatga aaggataaaa 1680
cagaagggac atgctgttgt cgttgttgct gaaggtgctg gtcaggaatt gattccaagg 1740
actgacgatc aaaagcggga gcaggacgag tccggcaaca ttgtgttcct tgatgtgggt 1800
ccctggttaa aatctgagct gggtaaatgg tggaagagag aacacccaag cgagttgttc 1860
actgtgaagt atatcgatcc cacttacatg atacgagctg ttccagcaaa tgccactgac 1920
aatctgtact gtacattgtt ggcacattcg gcgatccatg ggatcatggc tgggtacact 1980
ggcttcgtcc ctggcccgat taatggaaac tatagctaca taccgctgga agatgttgct 2040
gtggcgaaga acccggtgga tgtgaatgat cacaaatggg catgggttag atcagtcaca 2100
aaccaaccag atttcatgaa gccaaaatac taagaccaaa agtgctgtta ctggacatgg 2160
ttgtatgact ttttctccct ggagccttga cacgttaagc ttgatttctt tctatccagt 2220
ttcttctctt gttatgccga tctatctata agatgttagg tattctgatc tccctggttt 2280
gtgtttgtgt gcacttgaaa tcgtgttagc aggtattgct gtaaatctgt agtacataaa 2340
taaatgaagt ggcaggaaat gttgttctcc attggcg 2377

<210> SEQ ID NO 147
<211> LENGTH: 2411
<212> TYPE: DNA
<213> ORGANISM: Oryza sativa

<400> SEQUENCE: 147
atggttgaaa gtgcaagcat ggtaatttgt gtgattaaac aaatttacac actacgttag 60
tactctctcc atttcacatt ataagtcgtc ttgtaggagt actaactact ccctccgtcc 120
caaaatataa gaacttaaag accataaggg atattaggaa cttaaagacc ggaaatgtcc 180
catccggttc tagattctta tattttgaga cggagagaat aatatcttat aatgtgaaac 240
agagaaaata cttcttcctt aatgaaacaa ctgtgcaaac tctaaattaa taacaaaaaa 300
aaagaccgat taatatctga atgaatgatc aaagaacaaa tgtatctgca aatcaaacga 360
tcatttctgt aacttgcaaa tttcctttgt ccatcatgca ggtgaacgag aactcggaga 420
atccatactg gaaagcaata ggatacagag tggaagagcc ccgacgtgat cgagcagagt 480
cgatgccgtc gccgtcgcca tcgccggtat cgcggcggcc actggacaac ggcgtcgtgg 540
agacgagggc gctgacggac accaccctcc tccggtcgct cgcggcgaag ggcctcgccg 600

-continued

```
tgaggcccgg cgcgtcggac gagcaccaca cggtgcggtg cgacgccgtc atcgtcggct    660

ccggctgcgg cggcggcgtg gccgccgcgg tgctcgcgtc cgccgggtac aaggtggtcg    720

tcgtcgagaa gggcgactac ttcaccaagg aggattacag ctcgatcgag ggcccgtcca    780

tggagcgcct cttcgagagg ggcggcgtct tctgcacgtc caacgtcacg acgatgatat    840

tcaccggcgc gacggtcggc ggcgggtcgg cggtgaactg gtcggcgagc atccgcacgc    900

cggcgggcgt gatgcaggag tggtcgcgcg agcacgggct ggcggtgttc gcgagccccg    960

ggtacgcgcg ggccatggac gcggtgtgcg agcgcctcgg tgtgaccgac gcgtgccggg   1020

aggaagggtt ccagaacaag gtggtgcgcc gcgggtgcga cgcgctcggg ctgcgcgccg   1080

acgccgtgcc gcgcaactcg tcggaggggc acttctgcgg cagctgcaac ttcgggtgcc   1140

ccaccggcga caagaagggc accgacacga cgtggctcgt cgacgccgtc gagcgcggtg   1200

cggtcatcct gaccgggtgc aaggccgaac acttcatcgt cgagagcaac ggcggtggcg   1260

gcggccggag caagaggtgc gtcggcctgg tggcgacgtg catgagcaac ggcatcacca   1320

agaagctccg cgtcgaggcg aaggtgtcca tctcggcgag cggcgcgctc atgacgccgc   1380

cgctgctgcg caacagcggg ctcaagaacc gccacatcgg ccggaacctg cacctccacc   1440

cggtgtccat ggcgtggggc tacttcccgg acaacacgcc ggagccgcac atcccgggga   1500

agtgctacga gggcggcatc atcaccagca tgcaccgcgt cacggagcgc accatcatcg   1560

agacgccagc gctcggcccg ggcgccttcg ccgccctggt gccctgggag tccggccgcg   1620

acatgaagga gcggatgcgc cggtacgcgc gcacggcgca cgcgttcgcg ctggtgcgcg   1680

accgcggcgc cgggtccgtc gacggcgagg gccgcgtccg ctacgccccg agccgcgacg   1740

acgccgagga gctccgcgcc ggcctccgcc gcgcgctgcg catcctggtg gccgccggcg   1800

ccgccgaggt gggcacgcac cgcagcgacg gggcccgcct ccgatgcaag ggcgcgcgcg   1860

acgcggacgt ggaggcgttc ctcgacgagg tgaccgtgga gaaggggccg atgcactcga   1920

cgacggacaa gtggtcggtg ctctgctcgg cgcaccagat ggggagctgc cggatgggcg   1980

cgagcccccg cgacggcgcc gtcgacgtcg ccggcgagag ctgggaggcg gaggggctct   2040

acgtctgcga cggcagcctg ctcccgacgg cggtgggcgt gaacccgatg atcaccatac   2100

agtccatcgc ctactgcgtc gccaagggca tagccgactc gatggcacac ggcaaggagc   2160

agcgctagta aaatcttttt cctcttttgt tcatgcataa attgcaaatt tgcaatgtcc   2220

ctgcttgtta atcaactgta atagtgatga taaatcacga gcatatttca gcagatgatt   2280

catatgggaa aataattcta agggatttag agatctgttt agagtctttc agagacgaca   2340

tgggcctcaa gataaatatg gtaaaggttc aaatggccgg aatgagaagc tgaaatgtct   2400

gcccgtatta a                                                        2411
```

```
<210> SEQ ID NO 148
<211> LENGTH: 1278
<212> TYPE: DNA
<213> ORGANISM: Oryza sativa

<400> SEQUENCE: 148

atggcgccgc acccgctgct gaggggaggg gcgaggcggg ggaggaagta cgcgcacggg     60

atgcaccccg cgcagatgga ggcgctgcgc gccatgtgcg gcgcgctcat cccgtcgctg    120

cccgtggacg cggacggcgg cgacggcggg cgccgccccg gcgacaagga cctcgagcgg    180

ttctacctcg cctccgccgc cgactcctcc atccccgacg aggtcggtcg gtcggtcgat    240

cggtcgaaca ccccatgcgc gcgagttctt tcttgtttat aatctctaat ctggcggcgg    300
```

```
ccgcggcgac cgcggcgtgg cgtggcgtgc aggtggcgga gctgctggtg acgcgttgca    360

tatgggaggc ggtggcgctg acgtgggtgg tgctgtgggc gctgagcacg cgggcgggca    420

cgctgctgct gtgcggccgg gacagcgtcg ccgccgtcga cggcggcggg ttcccgttcg    480

tgtccgtgcg ccgcttcgcc gacatgccgg cggcgaggcg ggaggcggcg ctgtggcggt    540

ggagcggcgc gcggtggctc ttcttcccgc tccgcatcgc cttcgccatc gccaagatcc    600

tctgccacta cgtcttctac tccatggtac gtacgtctcc tcttcctcct cctcctcctc    660

ctctcgaccg actcacgaat cagaatcacc atgcagcagc acggcatcac ataccccgtg    720

cttttcaaat ttcaaccaca taaaaatctg acaaatctaa aattctgtaa gaaatcgatc    780

aattatcgtc aaaatttagc agagatcgaa tttccataca agtatacaac agtcctacac    840

cgaagcacgc aggtgcacca tgttaacaaa caacagcagg gtttttaatt tcgaaattgg    900

atttttggc aagggggac tggaattact gaaatttcgg aaatatcagt aatttcgttt    960

tttttgccaa aattatttga aattttgact attttgaatg aatttgaata aaatttgatc   1020

aaattcacaa aaagttgcaa aaaaccaaaa atttcggacg agatttgagc atgctggtgg   1080

ggggtgaaat caccaaaatt tcaaaccctg aacaacagta caaacaccag ccagtcactc   1140

gcagcagctg caccgtagac ttcttgttct tggagctacc taggaaccgg tttagagaat   1200

tttttattta taattcgtct gttttcagca tatgcgtatt ctgcatttgt tcaaattcag   1260

atactcgtat cagcctaa                                                 1278

<210> SEQ ID NO 149
<211> LENGTH: 455
<212> TYPE: PRT
<213> ORGANISM: Oryza sativa

<400> SEQUENCE: 149

Met Glu Trp Asp Leu Lys Met Pro Pro Ala Ala Ser Trp Glu Leu Ala
1               5                   10                  15

Asp Glu Leu Glu Asn Ser Gly Gly Gly Gly Val Pro Ala Ala Val Ser
            20                  25                  30

Ser Ser Ser Ala Ala Val Gly Gly Gly Val Asn Ala Gly Gly Gly Gly
        35                  40                  45

Arg Gln Glu Cys Ser Val Asp Leu Lys Leu Gly Gly Leu Gly Glu Phe
    50                  55                  60

Gly Gly Gly Gly Ala Gln Pro Arg Val Ala Val Ala Gly Glu Pro Ala
65                  70                  75                  80

Lys Gly Lys Gly Pro Ala Ala Ala Ala Thr Gly Ala Ala Ala Ala Ala
                85                  90                  95

Ser Ser Ala Pro Ala Lys Arg Pro Arg Gly Ala Ala Ala Ala Gly Gln
            100                 105                 110

Gln Gln Cys Pro Ser Cys Ala Val Asp Gly Cys Lys Glu Asp Leu Ser
        115                 120                 125

Lys Cys Arg Asp Tyr His Arg Arg His Lys Val Cys Glu Ala His Ser
    130                 135                 140

Lys Thr Pro Leu Val Val Val Ser Gly Arg Glu Met Arg Phe Cys Gln
145                 150                 155                 160

Gln Cys Ser Arg Phe His Leu Leu Gln Glu Phe Asp Glu Ala Lys Arg
                165                 170                 175

Ser Cys Arg Lys Arg Leu Asp Gly His Asn Arg Arg Arg Arg Lys Pro
            180                 185                 190

Gln Pro Asp Pro Met Asn Ser Ala Ser Tyr Leu Ala Ser Gln Gln Gly
        195                 200                 205
```

```
Ala Arg Phe Ser Pro Phe Ala Thr Pro Arg Pro Glu Ala Ser Trp Thr
    210                 215                 220

Gly Met Ile Lys Thr Glu Glu Ser Pro Tyr Tyr Thr His His Gln Ile
225                 230                 235                 240

Pro Leu Gly Ile Ser Ser Arg Gln Gln His Phe Val Gly Ser Thr Ser
                245                 250                 255

Asp Gly Gly Arg Arg Phe Pro Phe Leu Gln Glu Gly Glu Ile Ser Phe
            260                 265                 270

Gly Thr Gly Ala Gly Ala Gly Gly Val Pro Met Asp Gln Ala Ala Ala
        275                 280                 285

Ala Ala Ala Ala Ser Val Cys Gln Pro Leu Leu Lys Thr Val Ala Pro
    290                 295                 300

Pro Pro Pro Pro His Gly Gly Gly Gly Ser Gly Gly Gly Lys Met Phe
305                 310                 315                 320

Ser Asp Gly Gly Leu Thr Gln Val Leu Asp Ser Asp Cys Ala Leu Ser
                325                 330                 335

Leu Leu Ser Ala Pro Ala Asn Ser Thr Ala Ile Asp Val Gly Gly Gly
            340                 345                 350

Arg Val Val Val Gln Pro Thr Glu His Ile Pro Met Ala Gln Pro Leu
        355                 360                 365

Ile Ser Gly Leu Gln Phe Gly Gly Gly Gly Gly Ser Ser Ala Trp Phe
    370                 375                 380

Ala Ala Arg Pro His His Gln Ala Ala Thr Gly Ala Ala Ala Thr Ala
385                 390                 395                 400

Val Val Val Ser Thr Ala Gly Phe Ser Cys Pro Val Val Glu Ser Glu
                405                 410                 415

Gln Leu Asn Thr Val Leu Ser Ser Asn Asp Asn Glu Met Asn Tyr Asn
            420                 425                 430

Gly Met Phe His Val Gly Gly Glu Gly Ser Ser Asp Gly Thr Ser Ser
        435                 440                 445

Ser Leu Pro Phe Ser Trp Gln
    450                 455
```

<210> SEQ ID NO 150
<211> LENGTH: 1368
<212> TYPE: DNA
<213> ORGANISM: Oryza sativa

<400> SEQUENCE: 150

```
atggagtggg atctcaagat gccgccggcg gcgagctggg agctagccga cgagctggag     60

aacagcggcg gcgggggtgt accggcggcg gtatcgtcgt catcggctgc ggttggtggc    120

ggcgtcaatg cgggggtgg tggcaggcag gagtgctcgg tcgacctcaa gctcggcggg    180

ttgggggagt tcggcggcgg cggcgcgcag ccgcgggtcg ccgtggcggg cgagccggcc    240

aaggggaagg ggccagcggc cgccgccacg ggagcagcag cagcagcgtc gtcggcgccg    300

gcgaagcggc cgcgcggtgc ggcggcggcg gggcagcagc agtgcccgtc gtgcgcggtg    360

gacgggtgca aggaggacct gagcaagtgc cgcgactacc atcgccggca caaggtgtgc    420

gaggcccact ccaagacccc cctcgtcgtc gtctccggcc gcgagatgcg cttctgccag    480

cagtgcagca ggtttcactt gcttcaggag tttgatgagg ccaagcgcag ctgtagaaag    540

cgactagatg ggcacaaccg tcgccgcagg aagccacagc cagatcccat gaactctgca    600

agttatcttg caagccaaca aggggcaaga ttctcaccgt tcgcgacgcc gagaccggag    660

gcaagctgga cagggatgat caaaaccgag gagagcccat actacacgca ccaccaaatc    720
```

```
cctcttggca tcagcagcag gcagcagcat ttcgttggct ccacctctga cggcggccgc    780

cgcttccctt tcctccagga aggcgagatc agcttcggca ccggcgccgg cgccggcggc    840

gtgccaatgg atcaggcagc agctgctgct gctgcttcag tgtgccagcc acttctgaag    900

acggtagctc ctcctcctcc tcctcatggc ggcggcggca gcggcggcgg caagatgttc    960

tccgatggtg ggttgacaca agtgctcgac tccgattgtg ctctctctct tctgtcagct   1020

ccggcgaact ccacggccat cgacgtcggc ggtggccggg tggtcgtcca gccgaccgag   1080

cacatcccca tggcgcagcc tctcatctct ggccttcagt tcggcggcgg cggcggcagc   1140

tcagcctggt tcgcggcgcg gccgcatcat caggcggcca ccggcgccgc cgccaccgcc   1200

gtcgtcgtct cgacggccgg tttctcctgc ccggtggtgg agagcgagca gctgaacaca   1260

gtcctgagct ccaatgacaa tgagatgaac tacaatggga tgtttcacgt cggcggcgaa   1320

ggctcatcgg atggcacgtc gtcgtctctg ccgttctcat ggcagtag                1368
```

<210> SEQ ID NO 151
<211> LENGTH: 5052
<212> TYPE: DNA
<213> ORGANISM: Oryza sativa

<400> SEQUENCE: 151

```
acagctcaag cttacgcggg agctaagctg agctacagcg agcggcggcg gcggccatgg     60

agtgggatct caagatgccg ccggcggcga gctgggagct agccgacgag ctggagaaca    120

gcggcggcgg gggtgtaccg gcggcggtat cgtcgtcatc ggctgcggtt ggtggcggcg    180

tcaatgcggg gggtggtggc aggcaggagt gctcggtcga cctcaagctc ggcgggttgg    240

gggagttcgg cggcggcggc gcgcagccgc gggtcgccgt ggcgggcgag ccggccaagg    300

ggaaggggcc agcggccgcc gccacgggag cagcagcagc agcgtcgtcg gcgccggcga    360

agcggccgcg cggtgcggcg gcggcggggc agcagcagtg cccgtcgtgc gcggtggacg    420

ggtgcaagga ggacctgagc aagtgccgcg actaccatcg ccggcacaag gtgtgcgagg    480

cccactccaa gacccccctc gtcgtcgtct ccggccgcga gatgcgcttc tgccagcagt    540

gcagcaggta accccccccc cccccccca accattgtct ccttccttcc cgccaaattc    600

actgcaaaac aaaaaaaaaa tcgtagccca aaacacccca agacgtcatg gcaattcgca    660

tcaagaactg catatatcaa tttctccact tcttttcagc gtcactgtct ctgatcattc    720

tctttgctga acaaaagaaa aagaagataa gcaagagttt ttctcttttt tttgctcctt    780

tttttttgg ctttgcacaa tctcttcttg cttccagttg caactgacca ttgtgcagta    840

catgcatctg catctactga ttctaatttc tacgctactt cggatcaaaa ttaattcagt    900

actgcaaagc acaatttcat tgatccattt catccagcct cggactttgt tcatcatcat    960

ctatctgtct cttacttcct ttccattggg agcatactat ccggctgtct cgtttcaggg   1020

acgcacagct ttgcctttaa tggcatgcct tttcagcctt ccctcatgct atcctttagc   1080

tcggcaactc gtattacccc aaattattac ctctttgctc gcctttagat ttattactat   1140

catcttttct tttcttttt atatctcttc ttcaccagta gctgcactgt ttttgcactg   1200

ctcaagagca aagcagctgc tgtagttgtt cagtgtttgt tgcttactga gaaaaaaaag   1260

tgatagagac agaaaaaaaa gtgagggaga gaaaaaaaaa aaaacagaac tgacgcctga   1320

atctcatcag ccagagatca cattaggcaa tttaccacca gactgttatg atattatttt   1380

cagtgtcctc ctgtctgaat atgaccgtct gcttcctcta acaagaacaa taaatcagca   1440

cctagttcag tactaactaa ttttctcatg aataaataaa taaatatagt cactgtaatt   1500
```

-continued

```
agtgacacta ctagcacggt agcacctggt ttagtggtta acaatacttg gttcttgcac   1560
ttctccctgt cgatgttttt tcgcgtgggg gctagctatc gattgattga ttcctcaact   1620
atggcatcga aactggaaga acatatgcat actgggacac acaccctgct tgctttctga   1680
atttctgatt tctcctcaag gcagctggcc taccacatat atctgactga gctgtgctgc   1740
ttcttgccat gagagctaag ctaccttagc ttagctacta ctaccactta ctacgccgtc   1800
tgttttggaa gggaaaggca gatgtggatg cccaaaccta gaaagatggt tgtaccactg   1860
aaagagagag tttgtggatg tgatctgcac taaagcaccc ctgtacaggg aaaggaccat   1920
gtagccctac tacaagttca ccatttacac ctctgttcct aaggttgggc cacacatata   1980
tgaagctttt aatgtctcgg tttgttggaa agggttttgc attgccatta caagccagca   2040
cagtggatac agatagccag ggtgctctct attggagaag aaaaaaaatg gagccctgaa   2100
caccctgatt ggatctcact attgcatgaa agaatgatga gatttcttgt cttataattt   2160
ttaaagattt tttttctaaa gtcagtctta gttacattca tttgttatat tccagtttca   2220
gacttattgg tactaggttc tgtgagatct tttttttttt ttacatcgtt tgagtatcat   2280
agggtgattc agtaccacct tgacccctgt ttttatcaga gctctaaact tctaacacca   2340
cttctaactt ttgagctagt cttctaacct tgctgttttc tgaacaaaga tgtatactca   2400
agattggtca tagatggaga tattctgtga acagaactaa cataatagca ccaaattagt   2460
cagacatact ctttacaaaa ttactttgga gtttgttgtc cactccttga actagtacaa   2520
tattgtccta ctgaatgcct tcctgccttt caacttgaaa gttccctatt ttatctgtta   2580
gttcttttat aaaatgtaac tgcacattgt cagaaggatt tgcatcttat ttcactttgc   2640
gccagtttta agtaatacat ggtatattgg cataagacca gactctacca tttttttatct   2700
tgcagagaca tagcaaacaa ctaagtactt tttattgtgg tgtgctcctt tacacagtag   2760
cacaacttgt aggatgctta tgtgattgtc tcatcaatta ttctctttat ctttaaaaag   2820
agaatgatac aaaaaatctc tttatctgag aatacacatt acccagtggg gacagtcttt   2880
caatgatttg attacttcgt cagtgtttgc aaactgggaa gatcattatg ctgctgcatg   2940
cagactttat aaattaagtg atcttcagag tcagaacaag atgttagctt tctataccta   3000
tggatccaca tccactgtat tgtggtccat gtacaagtgg ggttaaaata tttttctgcc   3060
gttgacagaa cttcagttca ataaatttat ctaagatgaa gtatccaagc acggaaagag   3120
ctaattaact gatgaaattc ctgtggtccc ttgtgttggt atatgagtat tctaagagag   3180
aatatggaga cagtatatta aattattctg agaatactta tcctgacgtt tctttagtga   3240
gaactgtggt gcatcgttac aaaacttcag atcatgtttc aggagtattt tatcatgtaa   3300
gaattttaaa aagacgtaca tcctaggtac agtcatttct taaggtttca tggtactgaa   3360
tgattaaatt acttcttctg gattgggttt caagcatcat ttggctaatt tcaatgcagt   3420
taaatgatca taagcttttc tttcttcagg tttcacttgc ttcaggagtt tgatgaggcc   3480
aagcgcagct gtagaaagcg actagatggg cacaaccgtc gccgcaggaa gccacagcca   3540
gatcccatga actctgcaag ttatcttgca agccaacaag gtattttctt gtttattatt   3600
accactctat gatatcgcag ttcatataag attaactggg atatagtcat tcagacttcc   3660
taactattgt tagactagga aaaaaactat gaaacatgct aatagcatag ataagtcatg   3720
gtaaaaaaaa agtaaaagaa aatgaaactg tggttaaaaa aaaacgcaaa tattagggaa   3780
tgacctaata tcaaataatt agaaggagtg aggcttcgaa cccaggtcgt ctagcccatc   3840
acctttttgaa gctagccaga aaacccctgg gcgtttctca gaactgtggt tcagctatga   3900
```

```
ctctgttctt tcaatcctga catcttgtaa catgtaatgc attctagtat acatctaatg   3960

cattgaacca tatcttatgt actaatttgt gctgatatat caaacatcgc atcaaaattc   4020

aggggcaaga ttctcaccgt tcgcgacgcc gagaccggag gcaagctgga cagggatgat   4080

caaaaccgag gagagcccat actacacgca ccaccaaatc cctcttggca tcagcagcag   4140

gcagcagcat ttcgttggct ccacctctga cggcggccgc cgcttccctt tcctccagga   4200

aggcgagatc agcttcggca ccggcgccgg cgccggcggc gtgccaatgg atcaggcagc   4260

agctgctgct gctgcttcag tgtgccagcc acttctgaag acggtagctc ctcctcctcc   4320

tcctcatggc ggcggcggca gcggcggcgg caagatgttc tccgatggtg ggttgacaca   4380

agtgctcgac tccgattgtg ctctctctct tctgtcagct ccggcgaact ccacggccat   4440

cgacgtcggc ggtggccggg tggtcgtcca gccgaccgag cacatcccca tggcgcagcc   4500

tctcatctct ggccttcagt tcggcggcgg cggcggcagc tcagcctggt tcgcggcgcg   4560

gccgcatcat caggcggcca ccggcgccgc cgccaccgcc gtcgtcgtct cgacggccgg   4620

tttctcctgc ccggtggtgg agagcgagca gctgaacaca gtcctgagct ccaatgacaa   4680

tgagatgaac tacaatggga tgtttcacgt cggcggcgaa ggctcatcgg atggcacgtc   4740

gtcgtctctg ccgttctcat ggcagtagtt ttttcagtaa ctgtatgttg ctgccttagt   4800

ttcagtagag ttggttcttc atttcttttc agtgatcaaa ttattgtttc tgttcttttc   4860

tgccatggta agttcctttt ttttttcttc ttcttgcctt catttgagtt aattacagca   4920

ttgatttgtg tgaacaaaat tcatcataaa tcagttcctc gcgagatcat tggtctcaac   4980

atgatggtgc caagtgagaa ctgcagtatt gtgcagtttt cagttttgag tctaagttgt   5040

ataaacttgc ag                                                       5052
```